(12) United States Patent
Pennell

(10) Patent No.: US 7,214,789 B2
(45) Date of Patent: May 8, 2007

(54) PROMOTER, PROMOTER CONTROL ELEMENTS, AND COMBINATIONS, AND USES THEREOF

(75) Inventor: Roger Pennell, Malibu, CA (US)

(73) Assignee: Ceres, Inc., Thousand Oaks, CA (US)

( * ) Notice: Subject to any disclaimer, the term of this patent is extended or adjusted under 35 U.S.C. 154(b) by 0 days.

(21) Appl. No.: 11/172,703

(22) Filed: Jun. 30, 2005

(65) Prior Publication Data

US 2007/0042387 A1    Feb. 22, 2007

Related U.S. Application Data

(60) Provisional application No. 60/583,691, filed on Jun. 30, 2004, provisional application No. 60/583,609, filed on Jun. 30, 2004.

(51) Int. Cl.
*C07H 21/04* (2006.01)
*C12N 15/09* (2006.01)
*A01H 9/00* (2006.01)

(52) U.S. Cl. .................... 536/24.1; 435/320.1; 800/295

(58) Field of Classification Search ............. 435/320.1; 800/295
See application file for complete search history.

(56) References Cited

FOREIGN PATENT DOCUMENTS

WO    WO 02/06487    1/2002

OTHER PUBLICATIONS

Nature, 408, pp. 816-820, Dec. 14, 2000, Sequences and Analysis of Chromosome 1 of the Plant *Arabidopsis thaliana*.

Rognes, Sven Erik et al., "Transcriptional and biochemical regulation of a novel . . . ," Plant Molecular Biology, 2002, 51, pp. 281-294.

Kuusk, Sandra et al., "STY1 and STY2 promote the formation of apical . . . ," Development, 2002, 129, pp. 4707-4717.

Jinn, Tsung-Luo et al., "HAESA, an Arabidopsis leucine-rich repeat receptor . . . ," Genes & Development, 2000, 14, pp. 108-117.

Nazoa, Patricia et al., "Regulation of the nitrate transporter . . . ," Plant Molecular Biology, 2003, 52, pp. 689-703.

Schunnmann et al., "Characterization of promoter expression patterns . . . ," Journal of Experimental Botany, 2004, vol. 55, No. 398, pp. 855-865.

Hong, Seung-Beom et al., "Analysis of Gene Promoters for Two Tomato . . . ," Plant Physiology, 2000, vol. 123, pp. 869-881.

*Primary Examiner*—Celine Qian
*Assistant Examiner*—Tara L. Garvey
(74) *Attorney, Agent, or Firm*—Birch Stewart Kolasch & Birch, LLP

(57) ABSTRACT

The present invention is directed to promoter sequences and promoter control elements, polynucleotide constructs comprising the promoters and control elements, and methods of identifying the promoters, control elements, or fragments thereof. The invention further relates to the use of the present promoters or promoter control elements to modulate transcript levels.

6 Claims, 1 Drawing Sheet

PROMOTER, PROMOTER CONTROL ELEMENTS, AND COMBINATIONS, AND USES THEREOF

Figure 1:
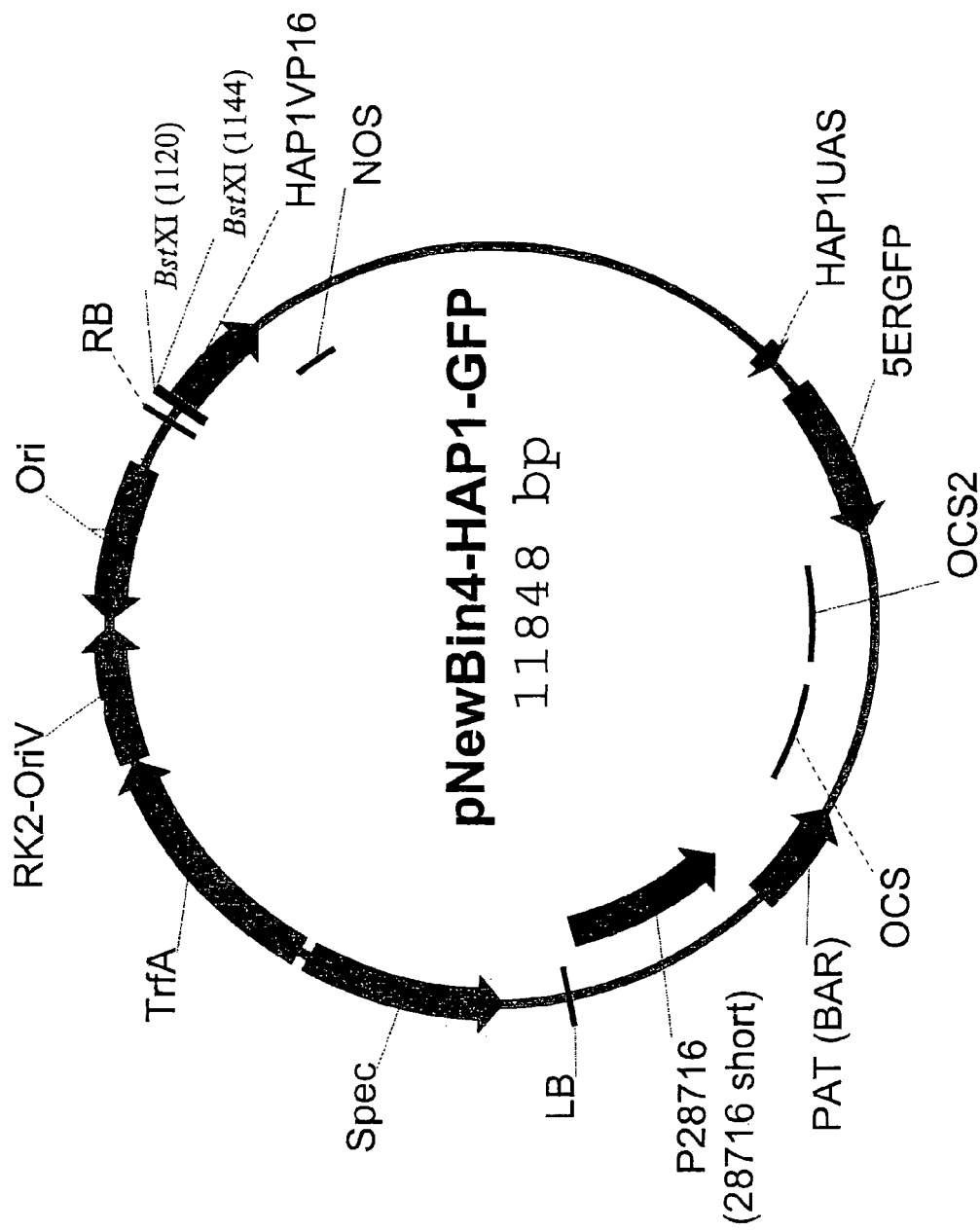

This Nonprovisional application claims priority under 35 U.S.C. § 119(e) on U.S. Provisional Application Nos. 60/583,691 and 60/583,609 both filed on Jun. 30, 2004, the entire contents of which are hereby incorporated by reference.

FIELD OF THE INVENTION

The present invention relates to promoters and promoter control elements that are useful for modulating transcription of a desired polynucleotide. In order to modulate in vivo and in vitro transcription of a polynucleotide such promoters and promoter control elements can be included in polynucleotide constructs, expression cassettes, vectors or inserted into the chromosome or exist in the plant cell as an exogenous element. Host cells with polynucleotides comprising the promoters and promoter control elements of the present invention which have desired traits or characteristics resulting therefrom are also a part of the invention. This includes plant cells and plants regenerated therefrom.

BACKGROUND OF THE INVENTION

This invention relates to the field of biotechnology and in particular to specific promoter sequences and promoter control element sequences which are useful for the transcription of polynucleotides in a host cell or transformed host organism.

One of the primary goals of biotechnology is to obtain organisms such as plants, mammals, yeast and prokaryotes that have particular desired characteristics or traits. Examples of these characteristics or traits abound and in plants may include, for example, virus resistance, insect resistance, herbicide resistance, enhanced stability, enhanced biomass, enhanced yield or additional nutritional value.

Recent advances in genetic engineering have enabled researchers in the field to incorporate polynucleotide sequences into host cells to obtain the desired qualities in the organism of choice. This technology permits one or more polynucleotides from a source different than the organism of choice to be transcribed by the organism of choice. If desired, the transcription and/or translation of these new polynucleotides can be modulated in the organism to exhibit a desired characteristic or trait. Alternatively, new patterns of transcription and/or translation of polynucleotides endogenous to the organism can be produced. Both approaches can be used at the same time.

SUMMARY OF THE INVENTION

The present invention is directed to isolated polynucleotide sequences that comprise promoters and promoter control elements from plants, especially *Arabidopsis thaliana, Glycine max, Oryza sativa* and *Zea mays*, and other promoters and promoter control elements that function in plants.

It is an object of the present invention to provide isolated polynucleotides that are promoter sequences. These promoter sequences comprise, for example, (1) a polynucleotide having a nucleotide sequence as set forth in the Sequence Listing or a fragment thereof, (2) a polynucleotide having a nucleotide sequence having at least 80% sequence identity to a sequence as set in the Sequence Listing or a fragment thereof, and (3) a polynucleotide having a nucleotide sequence which hybridizes to a sequence as set forth in in the Sequence Listing under a condition establishing a Tm-20° C.

It is another object of the present invention to provide isolated polynucleotides that are promoter control element sequences. These promoter control element sequences comprise, for example, (1) a polynucleotide having a nucleotide sequence as set forth in the Sequence Listing or a fragment thereof, (2) a polynucleotide having a nucleotide sequence having at least 80% sequence identity to a sequence as set forth in the Sequence Listing or a fragment thereof, and (3) a polynucleotide having a nucleotide sequence which hybridizes to a sequence as set forth in the Sequence Listing under a condition establishing a Tm-20° C.

Promoter or promoter control element sequences of the present invention are capable of modulating preferential transcription.

In another embodiment, the present promoter control elements are capable of serving as or fulfilling the function of, for example, a core promoter, a TATA box, a polymerase binding site, an initiator site, a transcription binding site, an enhancer, an inverted repeat, a locus control region, or a scaffold/matrix attachment region.

It is yet another object of the present invention to provide a polynucleotide that includes at least a first and a second promoter control element. The first promoter control element is a promoter control element sequence as discussed above and the second promoter control element is heterologous to the first control element. Moreover, the first and second control elements are operably linked. Such promoters may modulate transcript levels preferentially in a tissue or under particular conditions.

In another embodiment, the present isolated polynucleotide comprises a promoter or a promoter control element as described above, wherein the promoter or promoter control element is operably linked to a polynucleotide to be transcribed.

In another embodiment of the present vector, the promoter and promoter control elements of the instant invention are operably linked to a heterologous polynucleotide that is a regulatory sequence.

It is another object of the present invention to provide a host cell comprising an isolated polynucleotide or vector as described above or a fragment thereof. Host cells include, for instance, bacterial, yeast, insect cells, mammalian cells and plant cells. The host cell can comprise a promoter or promoter control element exogenous to the genome. Such a promoter can modulate transcription in cis- and in trans-orientation to the polynucletide.

In yet another embodiment, the present host cell is a plant cell capable of regenerating into a plant.

It is yet another embodiment of the present invention to provide a plant comprising an isolated polynucleotide or vector described above.

It is another object of the present invention to provide a method of modulating transcription in a sample that contains either a cell-free system of transcription or a host cell. This method comprises providing a polynucleotide or vector according to the present invention as described above and contacting the sample of the polynucleotide or vector with conditions that permit transcription.

In another embodiment of the present method, the polynucleotide or vector preferentially modulates (a) constitutive transcription,
(b) stress induced transcription,
(c) light or shade induced transcription,
(d) dark induced transcription,
(e) leaf transcription,
(f) root transcription,
(g) stem or shoot transcription,
(h) silique or seed transcription,
(i) callus transcription,
(j) flower transcription,
(k) immature bud and inflorescence-specific transcription, or
(l) senescence induced transcription
(m) germination transcription.

Other and further objects of the present invention will be made clear or become apparent from the following description.

BRIEF DESCRIPTION OF THE TABLES AND FIGURES

Table 1

Table 1 consists of the Expression Reports for each promoter of the invention and provides the nucleotide sequence for each promoter as well as details for GFP expression driven by each of the nucleic acid promoter sequences as observed in transgenic plants. The results are presented as summaries of the spatial expression, which provides information as to gross and/or specific expression in various plant organs and tissues. The observed expression pattern is also presented, which gives details of expression during different generations or different developmental stages within a generation. Additional information is provided regarding the associated gene, the GenBank reference, the source organism of the promoter and the vector and marker genes used for the construct. The following symbols are used consistently throughout the Table:

T1: First generation transformant
T2: Second generation transformant
T3: Third generation transformant
(L): low expression level
(M): medium expression level
(H): high expression level Each row of the table begins with heading of the data to be found in the section. The following provides a description of the data to be found in each section:

| Heading in Table 1 | Description |
| --- | --- |
| Promoter Expression Report | Identifies the particular promoter report |
| Promoter tested in | Identifies the organism used for analysis |
| Spatial expression summary: | Identifies the organs and tissues where expression was observed and estimates the strength of expression |
| Observed expression pattern: | Presents expression pattern observed for various generations of plants and developmental stages |
| Expected expression pattern: | Identifies the pattern expected from other experiments |
| Selection Criteria: | Provides details on cloning the polynucleotide |

-continued

| Heading in Table 1 | Description |
| --- | --- |
| Gene: | Provides information concerning the gene modulated by the promoter |
| GenBank: | This field gives the Locus Number of the gene as well as the accession number. |
| Source Promoter Organism: | Identifies the organism from which the promoter was cloned. |
| Vector: | Identifies the vector into which the promoter was cloned. |
| Marker Type: | Identifies the type of marker linked to the promoter. The marker is used to determine patterns of gene expression in plant tissue. |
| Generation screened:<br>☐Ti Mature<br>☐T2 Seedling<br>☐T2 Mature<br>☐T3 Seedling | Identifies the plant generation(s) used in the screening process. T1 plants are those plants subjected to the transformation event while the T2 generation plants are from the seeds collected from the T1 plants and T3 plants are from the seeds of T2 plants. |
| Plant Expression | Identifies the generation and developmental stage of the plants analyzed |
| Events Screened<br>Events Expressing | Provides the number of independent transformation events analyzed and the number which expressed the marker gene |
| GFP Expression Detected | This section lists the various organs analyzed and, where expression was observed, indicates the strength of the expression |
| X in the . . . | This field summarizes the expression pattern from digital images of the cells |
| Promoter Utility: | Identifies a specific function or functions that can be modulated using the promoter cDNA. |
| Trait-Subtrait Area: | Provides information as to what agronomic traits could be altered |
| Construct: | Provides the Ceres identifier number for the construct |
| Promoter Candidate I.D.: | Provides the Ceres identifier number for the promoter isolated |
| cDNA ID: | Provides the Ceres identifier number associated with the cDNA that corresponds to the endogenous cDNA sequence of the promoter. |
| T1 lines expressing (T2 seed): | Provides the identifier numbers for the events analyzed |
| Sequence | Provides the nucleotide sequence for the promoter described in the report |

Table 2

Table 2 provides a partial summary of the expression for some of the constructs of the invention.

FIG. 1

FIG. 1 is a schematic representation of the vector pNew-Bin4-HAP1-GFP. The definitions of the abbreviations used in the vector map are as follows:

Ori—the origin of replication used by an *E. coli* host
RB—sequence for the right border of the T-DNA from pMOG800
BstXI—restriction enzyme cleavage site used for cloning
HAP1VP16—coding sequence for a fusion protein of the HAP1 and VP16 activation domains
NOS—terminator region from the nopaline synthase gene
HAP1UAS—the upstream activating sequence for HAP1
5ERGFP—the green fluorescent protein gene that has been optimized for localization to the endoplasmic reticulum OCS2—the terminator sequence from the octopine synthase 2 gene OCS—the terminator sequence from the octopine synthase gene p28716 (a.k.a 28716 short)—promoter used to drive expression of the PAT (BAR) gene PAT (BAR)—a marker gene conferring herbicide resistance LB—sequence for the left border of the T-DNA from pMOG800

Spec—a marker gene conferring spectinomycin resistance

TrfA—transcription repression factor gene

RK2-OriV—origin of replication for *Agrobacterium*

DETAILED DESCRIPTION OF THE INVENTION

1. Definitions

Chimeric: The term "chimeric" is used to describe polynucleotides or genes, as defined supra, or constructs wherein at least two of the elements of the polynucleotide or gene or construct are heterologous to each other, such as the promoter and the polynucleotide to be transcribed and/or other regulatory sequences and/or filler sequences and/or complements thereof.

Constitutive Promoter: Promoters referred to herein as "constitutive promoters" actively promote transcription under most, but not necessarily all, environmental conditions and is essentially all cells in the vegetative stage and/or flowers and essentially all states of cell differentiation. Examples of constitutive promoters include the cauliflower mosaic virus (CaMV) 35S transcript initiation region and the 1' or 2' promoter derived from T-DNA of *Agrobacterium tumefaciens* as well as other transcription initiation regions from various plant genes known to those of skill in the art, such as the maize ubiquitin-1 promoter.

Core Promoter: This is the minimal stretch of contiguous DNA sequence that is sufficient to direct accurate initiation of transcription by the RNA polymerase II machinery (for review see: Struhl, 1987, *Cell* 49: 295–297; Smale, 1994, In *Transcription: Mechanisms and Regulation* (eds R. C. Conaway and J. W. Conaway), pp 63–81/Raven Press, Ltd., New York; Smale, 1997, *Biochim. Biophys. Acta* 1351: 73–88; Smale et al., 1998, *Cold Spring Harb. Symp. Quant. Biol.* 58: 21–31; Smale, 2001, *Genes & Dev.* 15: 2503–2508; Weis and Reinberg, 1992, *FASEB J.* 6: 3300–3309; Burke et al., 1998, *Cold Spring Harb. Symp. Quant. Biol* 63: 75–82). There are several sequence motifs, including the TATA box, initiator (Inr), TFIIB recognition element (BRE) and downstream core promoter element (DPE), that are commonly found in core promoters. Not all of these elements, however, occur in all promoters. That is, there are no universal core promoter elements (Butler and Kadonaga, 2002, *Genes & Dev.* 16: 2583–2592).

Domain: Domains are fingerprints or signatures that can be used to characterize protein families and/or parts of proteins. Such fingerprints or signatures can comprise conserved (1) primary sequence, (2) secondary structure, and/or (3) three-dimensional conformation. A similar analysis can be applied to polynucleotides. Generally, each domain has been associated with either a conserved primary sequence or a sequence motif. Generally these conserved primary sequence motifs have been correlated with specific in vitro and/or in vivo activities. A domain can be any length, including the entirety of the polynucleotide to be transcribed. Examples of amino acid domains include, without limitation, AP2, helicase, homeobox, zinc finger, etc. Examples of nucleotide domains include, without limitation, TATA box, CAAT box, etc.

Endogenous: The term "endogenous" within the context of the current invention refers to any polynucleotide, polypeptide or protein sequence which is a natural part of a cell or organism regenerated from said cell. In the context of promoter, the term "endogenous coding region" or "endogenous cDNA" refers to the coding region that is naturally operably linked to the promoter.

Enhancer/Suppressor: An "enhancer" is a DNA regulatory element that can increase the steady state level of a transcript, usually by increasing the rate of transcription initiation. Enhancers usually exert their effect regardless of the distance, upstream or downstream location, or orientation of the enhancer relative to the start site of transcription. In contrast, a "suppressor" is a corresponding DNA regulatory element that decreases the steady state level of a transcript, again usually by affecting the rate of transcription initiation. The essential activity of enhancer and suppressor elements is to bind a protein factor(s). Such binding can be assayed, for example, by methods described below. The binding is typically in a manner that influences the steady state level of a transcript in a cell or in an in vitro transcription extract.

Exogenous: As referred to within, "exogenous" is any polynucleotide, polypeptide or protein sequence, whether chimeric or not, that is introduced into the genome of a host cell or organism regenerated from said host cell by any means other than by a sexual cross. Examples of means by which this can be accomplished are described below and include *Agrobacterium*-mediated transformation (of dicots—e.g. Salomon et al. EMBO J. 3:141 (1984); Herrera-Estrella et al. EMBO J. 2:987 (1983); of monocots, representative papers are those by Escudero et al., *Plant J.* 10:355 (1996), Ishida et al., Nature Biotechnology 14:745 (1996), May et al., Bio/Technology 13:486 (1995)), biolistic methods (Armaleo et al., Current Genetics 17:97 1990)), electroporation, in planta techniques and the like. Such a plant containing the exogenous nucleic acid is referred to here as a $T_0$ for the primary transgenic plant and $T_1$ for the first generation transformant. The term "exogenous" as used herein is also intended to encompass inserting a naturally found element into a non-naturally found location.

Gene: The term "gene," as used in the context of the current invention, encompasses all regulatory and coding sequence contiguously associated with a single hereditary unit with a genetic function (see SCHEMATIC 1). Genes can include non-coding sequences that modulate the genetic function that include, but are not limited to, those that specify polyadenylation, transcriptional regulation, DNA conformation, chromatin conformation, extent and position of base methylation and binding sites of proteins that control all of these. Genes encoding proteins are comprised of "exons" (coding sequences), which may be interrupted by "introns" (non-coding sequences). In some instances complexes of a plurality of protein or nucleic acids or other molecules, or of any two of the above, may be required for a gene's function. On the other hand a gene's genetic function may require only RNA expression or protein production, or may only require binding of proteins and/or nucleic acids without associated expression. In certain cases, genes adjacent to one another may share sequence in such a way that one gene will overlap the other. A gene can be found within the genome of an organism, in an artificial chromosome, in a plasmid, in any other sort of vector, or as a separate isolated entity.

Heterologous sequences: "Heterologous sequences" are those that are not operatively linked or are not contiguous to each other in nature. For example, a promoter from corn is considered heterologous to an *Arabidopsis* coding region sequence. Also, a promoter from a gene encoding a growth factor from corn is considered heterologous to a sequence encoding the corn receptor for the growth factor. Regulatory element sequences, such as UTRs or 3' end termination sequences that do not originate in nature from the same gene as the coding sequence originates from, are considered heterologous to said coding sequence. Elements operatively linked in nature and contiguous to each other are not heterologous to each other.

Homologous: In the current invention, a "homologous" gene or polynucleotide or polypeptide refers to a gene or polynucleotide or polypeptide that shares sequence similarity with the gene or polynucleotide or polypeptide of interest. This similarity may be in only a fragment of the sequence and often represents a functional domain such as, examples including without limitation a DNA binding domain or a domain with tyrosine kinase activity. The functional activities of homologous polynucleotide are not necessarily the same.

Inducible Promoter: An "inducible promoter" in the context of the current invention refers to a promoter the activity of which is influenced by certain conditions such as light, temperature, chemical concentration, protein concentration, conditions in an organism, cell, or organelle, etc. A typical example of an inducible promoter, which can be utilized with the polynucleotides of the present invention, is PARSK1, the promoter from an *Arabidopsis* gene encoding a serine-threonine kinase enzyme which is induced by dehydration, abscissic acid and sodium chloride (Wang and Goodman, Plant J. 8:37 (1995)). Examples of environmental conditions that may affect transcription by inducible promoters include anaerobic conditions, elevated temperature, the presence or absence of a nutrient or other chemical compound and/or the presence of light.

Modulate Transcription Level: As used herein, the phrase "modulate transcription" describes the biological activity of a promoter sequence or promoter control element. Such modulation includes, without limitation, up- and down-regulation of initiation of transcription, rate of transcription and/or transcription levels.

Mutant: In the current invention "mutant" refers to a heritable change in a mutation sequence at a specific location. Mutant genes of the current invention may or may not have an associated identifiable phenotype.

Operable Linkage: An "operable linkage" is a linkage in which a promoter sequence or promoter control element is connected to a polynucleotide sequence(s) in such a way as to place transcription of the polynucleotide sequence under the influence or control of the promoter or promoter control element. Two DNA sequences (such as a polynucleotide to be transcribed and a promoter sequence linked to the 5' end of the polynucleotide to be transcribed) are said to be operably linked if induction of promoter function results in the transcription of mRNA encoded by the polynucleotide and if the nature of the linkage between the two DNA sequences does not (1) result in the introduction of a frame-shift mutation, (2) interfere with the ability of the promoter sequence to direct the expression of the protein, antisense RNA or ribozyme or (3) interfere with the ability of the DNA template to be transcribed. Thus, a promoter sequence would be operably linked to a polynucleotide sequence if the promoter was capable of effecting transcription of that polynucleotide sequence.

Optional Promoter Fragments: The phrase "optional promoter fragments" is used to refer to any sub-sequence of the promoter that is not required for driving transcription of an operationally linked coding region. These fragments comprise the 5' UTR and any exon(s) of the endogenous coding region. The optional promoter fragments may also comprise any exon(s) and the 3' or 5' UTR of the gene residing upstream of the promoter (that is, 5' to the promoter). Optional promoter fragments also include any intervening sequences that are introns or sequence that occurs between exons or an exon and the UTR.

Orthologous: "Orthologous" is a term used herein to describe a relationship between two or more polynucleotides or proteins. Two polynucleotides or proteins are "orthologous" to one another if they serve a similar function in different organisms. In general, orthologous polynucleotides or proteins will have similar catalytic functions (when they encode enzymes) or will serve similar structural functions (when they encode proteins or RNA that form part of the ultrastructure of a cell). Generally it is believed that orthologous structures share a common evolutionary origin.

Percentage of sequence identity: "Percentage of sequence identity," as used herein, is determined by comparing two optimally aligned sequences over a comparison window, where the fragment of the polynucleotide or amino acid sequence in the comparison window may comprise additions or deletions (e.g., gaps or overhangs) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman *Add. APL. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci.* (*USA*) 85: 2444 (1988), by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by inspection. Given that two sequences have been identified for comparison, GAP and BESTFIT are preferably employed to determine their optimal alignment. Typically, the default values of 5.00 for gap weight and 0.30 for gap weight length are used. The term "substantial sequence identity" between polynucleotide or polypeptide sequences refers to polynucleotide or polypeptide comprising a sequence that has at least 80% sequence identity, preferably at least 85%, more preferably at least 90% and most preferably at least 95%, even more preferably, at least 96%, 97%, 98% or 99% sequence identity compared to a reference sequence using the programs.

Query nucleic acid sequences were searched against subject nucleic acid sequences residing in public or proprietary databases. Such searches were done using the Washington University Basic Local Alignment Search Tool Version 1.83 (WU-Blast2) program. The WU-Blast2 program is available on the internet from Washington University. A WU-Blast2 service for *Arabidopsis* can also be found on the internet. Typically the following parameters of WU-Blast2 were used: Filter options were set to "default," Output format was set to "gapped alignments," the Comparison Matrix was set to "BLOSUM62," Cutoff Score (S value) was set to "default," the Expect (E threshold) was set to "default," the Number of best alignments to show was set to "100," and the "Sort output" option was set to sort the output by "pvalue."

Plant Promoter: A "plant promoter" is a promoter capable of initiating transcription in plant cells and can modulate transcription of a polynucleotide. Such promoters need not be of plant origin. For example, promoters derived from plant viruses, such as the CaMV35S promoter or from *Agrobacterium tumefaciens* such as the T-DNA promoters, can be plant promoters. A typical example of a plant promoter of plant origin is the maize ubiquitin-1 (ubi-1) promoter known to those of skill in the art.

Plant Tissue: The term "plant tissue" includes differentiated and undifferentiated tissues or plants, including but not limited to roots, stems, shoots, cotyledons, epicotyl, hypocotyl, leaves, pollen, seeds, tumor tissue and various forms of cells in culture such as single cells, protoplast, embryos, and callus tissue. The plant tissue may be in plants or in organ, tissue or cell culture.

Preferential Transcription: "Preferential transcription" is defined as transcription that occurs in a particular pattern of cell types or developmental times or in response to specific stimuli or combination thereof. Non-limitive examples of preferential transcription include: high transcript levels of a desired sequence in root tissues; detectable transcript levels of a desired sequence in certain cell types during embryogenesis; and low transcript levels of a desired sequence under drought conditions. Such preferential transcription can be determined by measuring initiation, rate, and/or levels of transcription.

Promoter: A "promoter" is a DNA sequence that directs the transcription of a polynucleotide. Typically a promoter is located in the 5' region of a polynucleotide to be transcribed, immediately upstream to the transcriptional start site of such polynucleotide. More typically, promoters are defined as the region upstream of the first exon; more typically, as a region upstream of the first of multiple transcription start sites; more typically, as the region downstream of the preceding gene and upstream of the first of multiple transcription start sites; more typically, the region downstream of the polyA signal and upstream of the first of multiple transcription start sites; even more typically, about 3,000 nucleotides upstream of the ATG of the first exon; even more typically, 2,000 nucleotides upstream of the first of multiple transcription start sites. The promoters of the invention comprise at least a core promoter as defined above. Frequently promoters are capable of directing transcription of genes located on each of the complementary DNA strands that are 3' to the promoter. Stated differently, many promoters exhibit bidirectionality and can direct transcription of a downstream gene when present in either orientation (i.e. 5' to 3' or 3' to 5' relative to the coding region of the gene). Additionally, the promoter may also include at least one control element such as an upstream element. Such elements include UARs and optionally, other DNA sequences that affect transcription of a polynucleotide such as a synthetic upstream element.

Promoter Control Element: The term "promoter control element" as used herein describes elements that influence the activity of the promoter. Promoter control elements include transcriptional regulatory sequence determinants such as, but not limited to, enhancers, scaffold/matrix attachment regions, TATA boxes, transcription start locus control regions, UARs, URRs, other transcription factor binding sites and inverted repeats.

Public sequence: The term "public sequence," as used in the context of the instant application, refers to any sequence that has been deposited in a publicly accessible database prior to the filing date of the present application. This term encompasses both amino acid and nucleotide sequences. Such sequences are publicly accessible, for example, on the BLAST databases on the NCBI FTP web site (accessible via the worldwide web). The database at the NCBI FTP site uses "gi" numbers assigned by NCBI as a unique identifier for each sequence in the database, thereby providing a non-redundant database for sequence from various databases, including GenBank, EMBL, DBBJ, (DNA Database of Japan) and PDB (Brookhaven Protein Data Bank).

Regulatory Sequence: The term "regulatory sequence," as used in the current invention, refers to any nucleotide sequence that influences transcription or translation initiation and rate, or stability and/or mobility of a transcript or polypeptide product. Regulatory sequences include, but are not limited to, promoters, promoter control elements, protein binding sequences, 5' and 3' UTRs, transcriptional start sites, termination sequences, polyadenylation sequences, introns, certain sequences within amino acid coding sequences such as secretory signals, protease cleavage sites, etc.

Related Sequences: "Related sequences" refer to either a polypeptide or a nucleotide sequence that exhibits some degree of sequence similarity with a reference sequence.

Specific Promoters: In the context of the current invention, "specific promoters" refers to a subset of promoters that have a high preference for modulating transcript levels in a specific tissue or organ or cell and/or at a specific time during development of an organism. By "high preference" is meant at least 3-fold, preferably 5-fold, more preferably at least 10-fold still more preferably at least 20-fold, 50-fold or 100-fold increase in transcript levels under the specific condition over the transcription under any other reference condition considered. Typical examples of temporal and/or tissue or organ specific promoters of plant origin that can be used with the polynucleotides of the present invention, are: PTA29, a promoter which is capable of driving gene transcription specifically in tapetum and only during anther development (Koltonow et al., Plant Cell 2:1201 (1990); RCc2 and RCc3, promoters that direct root-specific gene transcription in rice (Xu et al., Plant Mol. Biol. 27:237 (1995); and TobRB27, a root-specific promoter from tobacco (Yamamoto et al., Plant Cell 3:371 (1991)). Examples of tissue-specific promoters under developmental control include promoters that initiate transcription only in certain tissues or organs, such as root, ovule, fruit, seeds, or flowers. Other specific promoters include those from genes encoding seed storage proteins or the lipid body membrane protein, oleosin. A few root-specific promoters are noted above. See also "Preferential transcription".

Stringency: "Stringency" as used herein is a function of probe length, probe composition (G+C content) and salt concentration, organic solvent concentration and temperature of hybridization or wash conditions. Stringency is typically compared by the parameter $T_m$, which is the temperature at which 50% of the complementary molecules in the hybridization are hybridized, in terms of a temperature differential from $T_m$. High stringency conditions are those providing a condition of $T_m-5°$ C. to $T_m-10°$ C. Medium or moderate stringency conditions are those providing $T_m-20°$ C. to $T_m-29°$ C. Low stringency conditions are those providing a condition of $T_m-40°$ C. to $T_m-48°$ C. The relation ship of hybridization conditions to $T_m$ (in °C.) is expressed in the mathematical equation $$T_m = 81.5 - 16.6(\log_{10}[Na^+]) + 0.41(\% G+C) - (600/N) \quad (1)$$

where N is the length of the probe. This equation works well for probes 14 to 70 nucleotides in length that are identical to the target sequence. The equation below for $T_m$ of DNA—DNA hybrids is useful for probes in the range of 50 to greater than 500 nucleotides, and for conditions that include an organic solvent (formamide).

$$T_m = 81.5 + 16.6 \log\{[Na^+]/(1+0.7[Na^+])\} + 0.41(\% G+C) - 500/L 0.63 (\% \text{ formamide}) \quad (2)$$

where L is the length of the probe in the hybrid (P. Tijessen, "Hybridization with Nucleic Acid Probes" in *Laboratory Techniques in Biochemistry and Molecular Biology*, P. C. vand der Vliet, ed., c. 1993 by Elsevier, Amsterdam.) The $T_m$ of equation (2) is affected by the nature of the hybrid; for DNA-RNA hybrids $T_m$ is 10–15° C. higher than calculated, for RNA—RNA hybrids $T_m$ is 20–25° C. higher. Because the $T_m$ decreases about 1° C. for each 1% decrease in homology when a long probe is used (Bonner et al. (1973) J. Mol. Biol. 81:123), stringency conditions can be adjusted to favor detection of identical genes or related family members.

Equation (2) is derived assuming equilibrium and therefore, hybridizations according to the present invention are most preferably performed under conditions of probe excess and for sufficient time to achieve equilibrium. The time required to reach equilibrium can be shortened by inclusion of a hybridization accelerator such as dextran sulfate or another high volume polymer in the hybridization buffer.

Stringency can be controlled during the hybridization reaction or after hybridization has occurred by altering the salt and temperature conditions of the wash solutions used. The formulas shown above are equally valid when used to compute the stringency of a wash solution. Preferred wash solution stringencies lie within the ranges stated above; high stringency is 5–8° C. below $T_m$, medium or moderate stringency is 26–29° C. below $T_m$ and low stringency is 45–48° C. below $T_m$.

Substantially free of: A composition containing A is "substantially free of" B when at least 85% by weight of the total A+B in the composition is A. Preferably, A comprises at least about 90% by weight of the total of A+B in the composition, more preferably at least about 95% or even 99% by weight. For example, a plant gene can be substantially free of other plant genes. Other examples include, but are not limited to, ligands substantially free of receptors (and vice versa), a growth factor substantially free of other growth factors and a transcription binding factor substantially free of nucleic acids.

Suppressor: See "Enhancer/Suppressor"

TATA to start: "TATA to start" shall mean the distance, in number of nucleotides, between the primary TATA motif and the start of transcription.

Transgenic plant: A "transgenic plant" is a plant having one or more plant cells that contain at least one exogenous polynucleotide introduced by recombinant nucleic acid methods.

Translational start site: In the context of the present invention, a "translational start site" is usually an ATG or AUG in a transcript, often the first ATG or AUG. A single protein encoding transcript, however, may have multiple translational start sites.

Transcription start site: "Transcription start site" is used in the current invention to describe the point at which transcription is initiated. This point is typically located about 25 nucleotides downstream from a TFIID binding site, such as a TATA box. Transcription can initiate at one or more sites within the gene and a single polynucleotide to be transcribed may have multiple transcriptional start sites, some of which may be specific for transcription in a particular cell-type or tissue or organ. "+1" is stated relative to the transcription start site and indicates the first nucleotide in a transcript.

Upstream Activating Region (UAR): An "Upstream Activating Region" or "UAR" is a position or orientation dependent nucleic acid element that primarily directs tissue, organ, cell type, or environmental regulation of transcript level, usually by affecting the rate of transcription initiation. Corresponding DNA elements that have a transcription inhibitory effect are called herein "Upstream Repressor Regions" or "URR"s. The essential activity of these elements is to bind a protein factor. Such binding can be assayed by methods described below. The binding is typically in a manner that influences the steady state level of a transcript in a cell or in vitro transcription extract.

Untranslated region (UTR): A "UTR" is any contiguous series of nucleotide bases that is transcribed, but is not translated. A 5' UTR lies between the start site of the transcript and the translation initiation codon and includes the +1 nucleotide. A 3' UTR lies between the translation termination codon and the end of the transcript. UTRs can have particular functions such as increasing mRNA message stability or translation attenuation. Examples of 3' UTRs include, but are not limited to polyadenylation signals and transcription termination sequences.

Variant: The term "variant" is used herein to denote a polypeptide or protein or polynucleotide molecule that differs from others of its kind in some way. For example, polypeptide and protein variants can consist of changes in amino acid sequence and/or charge and/or post-translational modifications (such as glycosylation, etc). Likewise, polynucleotide variants can consist of changes that add or delete a specific UTR or exon sequence. It will be understood that there may be sequence variations within sequence or fragments used or disclosed in this application. Preferably, variants will be such that the sequences have at least 80%, preferably at least 90%, 95, 97, 98, or 99% sequence identity. Variants preferably measure the primary biological function of the native polypeptide or protein or polynucleotide.

2. Introduction

The polynucleotides of the invention comprise promoters and promoter control elements that are capable of modulating transcription.

Such promoters and promoter control elements can be used in combination with native or heterologous promoter fragments, control elements or other regulatory sequences to modulate transcription and/or translation.

Specifically, promoters and control elements of the invention can be used to modulate transcription of a desired polynucleotide, which includes without limitation:
  (a) antisense;
  (b) ribozymes;
  (c) coding sequences; or
  (d) fragments thereof.

The promoter also can modulate transcription in a host genome in cis- or in trans-.

In an organism such as a plant, the promoters and promoter control elements of the instant invention are useful to produce preferential transcription which results in a desired pattern of transcript levels in particular cells, tissues or organs or under particular conditions.

3. Table of Contents

The following description of the present invention is outlined in the following table of contents.

A. Identifying and Isolating Promoter Sequences of the Invention
(1) Cloning Methods
(2) Chemical Synthesis
B. Isolating Related Promoter Sequences
(1) Relatives Based on Nucleotide Sequence Identity
(2) Relatives Based on Coding Sequence Identity
(3) Relatives Based on Common Function
C. Identifying Control Elements
(1) Types of Transcription Control Elements
(2) Those Described by the Examples
(3) Those Identifiable by Bioinformatics
(4) Those Identifiable by In Vitro and In Vivo Assays
(5) Non-Natural Control Elements
D. Constructing Promoters and Control Elements
(1) Combining Promoters and Promoter Control Elements
(2) Number of Promoter Control Elements
(3) Spacing Between Control Elements
E. Vectors
(1) Modification of Transcription by Promoters and Promoter Control Elements
(2) Polynucleotide to be Transcribed
(3) Other Regulatory Elements
(4) Other Components of Vectors
F. Insertion of Polynucleotides and Vectors Into a Host Cell
(1) Autonomous of the Host Genome
(2) Integrated into the Host Genome
G. Utility A. Identifying and Isolating Promoter Sequences of the Invention The promoters and promoter control elements of the present invention are presented in the Sequence Listing and were identified from *Arabidopsis thaliana* or *Oryza sativa*. Additional promoter sequences encompassed by the invention can be identified as described below.

(1) Cloning Methods

Isolation from genomic libraries of polynucleotides comprising the sequences of the promoters and promoter control elements of the present invention is possible using known techniques.

For example, polymerase chain reaction (PCR) can amplify the desired polynucleotides utilizing primers designed from sequences in the row titled "Sequences". Polynucleotide libraries comprising genomic sequences can be constructed according to Sambrook et al., *Molecular Cloning: A Laboratory Manual*, 2$^{nd}$ Ed. (1989) Cold Spring Harbor Press, Cold Spring Harbor, N.Y.), for example.

Other procedures for isolating polynucleotides comprising the promoter sequences of the invention include, without limitation, tail-PCR and 5' rapid amplification of cDNA ends (RACE). For tail-PCR see, for example, Liu et al. (1995) Plant J 8(3): 457–463; Liu et al. (1995) Genomics 25: 674–681; Liu et al. (1993) Nucl. Acids Res. 21(14): 3333–3334; and Zoe et al. (1999) BioTechniques 27(2): 240–248; for RACE see, for example, *PCR Protocols: A Guide to Methods and Applications*, (1990) Academic Press, Inc.

(2) Chemical Synthesis

In addition, the promoters and promoter control elements described in the Sequence Listing can be chemically synthesized according to techniques in common use. See, for example, Beaucage et al. (1981) Tet. Lett. 22: 1859 and U.S. Pat. No. 4,668,777.

Such chemical oligonucleotide synthesis can be carried out using commercially available devices, such as Biosearch 4600 or 8600 DNA synthesizer by Applied Biosystems, a division of Perkin-Elmer Corp. (Foster City, Calif., USA) and Expedite by Perceptive Biosystems (Framingham, Mass., USA).

Synthetic RNA, including natural and/or analog building blocks, can be synthesized on the Biosearch 8600 machines (see above).

Oligonucleotides can be synthesized and then ligated together to construct the desired polynucleotide.

B. Isolating Related Promoter Sequences

Included in the present invention are promoter and promoter control elements that are related to those described in the Sequence Listing. Such related sequences can be isolated using
(a) nucleotide sequence identity,
(b) coding sequence identity or
(c) common function or gene products.

Relatives can include both naturally occurring promoters and non-natural promoter sequences. Non-natural related promoters include nucleotide substitutions, insertions or deletions of naturally-occurring promoter sequences that do not substantially affect transcription modulation activity. For example, the binding of relevant DNA binding proteins can still occur with the non-natural promoter sequences and promoter control elements of the present invention.

According to current knowledge, promoter sequences and promoter control elements exist as functionally important regions, such as protein binding sites and spacer regions. These spacer regions are apparently required for proper positioning of the protein binding sites. Thus, nucleotide substitutions, insertions and deletions can be tolerated in the spacer regions to a certain degree without loss of function.

In contrast, less variation is permissible in the functionally important regions since changes in the sequence can interfere with protein binding. Nonetheless, some variation in the functionally important regions is permissible so long as function is conserved.

The effects of substitutions, insertions and deletions to the promoter sequences or promoter control elements may be to increase or decrease the binding of relevant DNA binding proteins to modulate transcript levels of a polynucleotide to be transcribed. Effects may include tissue-specific or condition-specific modulation of transcript levels of the polypeptide to be transcribed. Polynucleotides representing changes to the nucleotide sequence of the DNA-protein contact region by insertion of additional nucleotides, changes to identity of relevant nucleotides, including use of chemically-modified bases, or deletion of one or more nucleotides are considered encompassed by the present invention.

(1) Relatives Based on Nucleotide Sequence Identity

Included in the present invention are promoters exhibiting nucleotide sequence identity to those described in the Sequence Listing.

Definition

Typically, such related promoters exhibit at least 80% sequence identity, preferably at least 85%, more preferably at least 90%, and most preferably at least 95%, even more preferably, at least 96%, 97%, 98% or 99% sequence identity compared to those shown in the Sequence Listing. Such sequence identity can be calculated by the algorithms and computers programs described above.

Usually, such sequence identity is exhibited in an alignment region that is at least 75% of the length of a sequence shown in the Sequence Listing or corresponding full-length sequence; more usually at least 80%; more usually, at least 85%, more usually at least 90%, and most usually at least 95%, yet even more usually, at least 96%, 97%, 98% or 99% of the length of a sequence shown in the Seqeunce Listing.

The percentage of the alignment length is calculated by counting the number of bases of the sequence in the region of strongest alignment, e.g. a continuous region of the sequence that contains the greatest number of bases that are identical to the bases between two sequences that are being aligned. The number of bases in the region of strongest alignment is divided by the total base length of a sequence in the Sequence Listing.

These related promoters generally exhibit similar preferential transcription as those promoters described in the Sequence Listing and as described in the "observed expression pattern" and "expected expression pattern" fields of the reports of Table 1.

Construction of Polynucleotides

Naturally occurring promoters that exhibit nucleotide sequence identity to those shown in the Sequence Listing can be isolated using the techniques as described above. More specifically, such related promoters can be identified, for example, with typical hybridization procedures such as Southern blots or probing of polynucleotide libraries using varying stringencies (see above).

Non-natural promoter variants of those shown in the Sequence Listing can be constructed using cloning methods that incorporate the desired nucleotide variation. For example see Ho et al. (1989) Gene 77:51–59, which describes a site directed mutagenesis procedure using PCR.

Any related promoter showing sequence identity to those shown in the Sequence Listing can be chemically synthesized as described above.

Also, the present invention includes non-natural promoters that exhibit the above-sequence identity to those in the Sequence Listing.

The promoters and promoter control elements of the present invention may also be synthesized with 5' or 3' extensions to facilitate additional manipulation, for instance.

Testing of Polynucleotides

Polynucleotides of the invention were tested for activity by cloning the sequence into an appropriate vector, transforming plants with the construct and assaying for marker gene expression. Recombinant DNA constructs were prepared which comprise the polynucleotide sequences of the invention inserted into a vector suitable for transformation of plant cells. The construct can be made using standard recombinant DNA techniques (Sambrook et al. 1989) and can be introduced to the species of interest by *Agrobacterium*-mediated transformation or by other means of transformation as referenced below.

The vector backbone can be any of those typical in the art such as plasmids, viruses, artificial chromosomes, BACs, YACs and PACs and vectors of the sort described by
(a) BAC: Shizuya et al. (1992) Proc. Natl. Acad. Sci. USA 89: 8794–8797; Hamilton et al. (1996) Proc. Natl. Acad. Sci. USA 93: 9975–9979;
(b) YAC: Burke et al. (1987) Science 236:806–812;
(c) PAC: Sternberg N. et al. (1990) Proc Natl Acad Sci USA. 87(1):103–7;
(d) Bacteria-Yeast Shuttle Vectors: Bradshaw et al. (1995) Nucl Acids Res 23: 4850–4856;
(e) Lambda Phage Vectors: Replacement Vector, e.g., Frischauf et al. (1983) J. Mol Biol 170: 827–842; or Insertion vector, e.g., Huynh et al., In: Glover N M (ed) DNA Cloning: A practical Approach, Vol. 1 Oxford: IRL Press (1985); T-DNA gene fusion vectors: Walden et al. (1990) Mol Cell Biol 1: 175–194; and
(g) Plasmid vectors: Sambrook et al., infra.

Typically, the construct comprises a vector containing a sequence of the present invention operationally linked to any marker gene. The polynucleotide was identified as a promoter by the expression of the marker gene. Although many marker genes can be used, Green Fluroescent Protein (GFP) is preferred. The vector may also comprise a marker gene that confers a selectable phenotype on plant cells. The marker may encode biocide resistance, particularly antibiotic resistance, such as resistance to kanamycin, G418, bleomycin, hygromycin or herbicide resistance, such as resistance to chlorosulfuron or phosphinotricin. Vectors can also include origins of replication, scaffold attachment regions (SARs), markers, homologous sequences, introns, etc.

Promoter Control Elements of the Invention

The promoter control elements of the present invention include those that comprise a sequence shown in the Sequence Listing or fragments thereof. The size of the fragments can range from 5 bases to 10 kilobases (kb). Typically, the fragment size is no smaller than 8 bases; more typically, no smaller than 12; more typically, no smaller than 15 bases; more typically, no smaller than 20 bases; more typically, no smaller than 25 bases; even more typically, no more than 30, 35, 40 or 50 bases.

Usually, the fragment size is no larger than 5 kb bases; more usually, no larger than 2 kb; more usually, no larger than 1 kb; more usually, no larger than 800 bases; more usually, no larger than 500 bases; even more usually, no more than 250, 200, 150 or 100 bases.

Relatives Based on Nucleotide Sequence Identity

Included in the present invention are promoter control elements exhibiting nucleotide sequence identity to those described in the Sequence Listing or fragments thereof.

Typically, such related promoters exhibit at least 80% sequence identity, preferably at least 85%, more preferably at least 90%, and most preferably at least 95%, even more preferably, at least 96%, 97%, 98% or 99% sequence identity compared to those shown in the Seqeunce Listing. Such sequence identity can be calculated by the algorithms and computers programs described above.

Promoter Control Element Configuration

A common configuration of the promoter control elements in RNA polymerase II promoters is described in "Models for prediction and recognition of eukaryotic promoters", T. Werner (1999) Mammalian Genome 10, 168–175.

Promoters are generally modular in nature. Promoters can consist of a basal promoter which functions as a site for assembly of a transcription complex comprising an RNA polymerase, for example RNA polymerase II. A typical transcription complex will include additional factors such as $TF_{II}B$, $TF_{II}D$ and $TF_{II}E$. Of these, $TF_{II}D$ appears to be the only one to bind DNA directly. The promoter might also contain one or more promoter control elements such as the elements discussed above. These additional control elements may function as binding sites for additional transcription factors that have the function of modulating the level of transcription with respect to tissue specificity, of transcriptional responses to particular environmental or nutritional factors and the like.

One type of promoter control element is a polynucleotide sequence representing a binding site for proteins. Typically, within a particular functional module, protein binding sites constitute regions of 5 to 60, preferably 10 to 30, more preferably 10 to 20 nucleotides. Within such binding sites, there are typically 2 to 6 nucleotides which specifically contact amino acids of the nucleic acid binding protein.

The protein binding sites are usually separated from each other by 10 to several hundred nucleotides, typically by 15 to 150 nucleotides, often by 20 to 50 nucleotides.

Further, protein binding sites in promoter control elements often display dyad symmetry in their sequence. Such elements can bind several different proteins and/or a plurality of sites can bind the same protein. Both types of elements may be combined in a region of 50 to 1,000 base pairs.

Binding sites for any specific factor have been known to occur almost anywhere in a promoter. For example, functional AP-1 binding sites can be located far upstream, as in the rat bone sialoprotein gene where an AP-1 site located about 900 nucleotides upstream of the transcription start site suppresses expression (Yamauchi et al. (1996) Matrix Biol. 15, 119–130). Alternatively, an AP-1 site located close to the transcription start site plays an important role in the expression of Moloney murine leukemia virus (Sap et al. (1989) Nature 340, 242–244.

(2) Those Identifiable by Bioinformatics

Promoter control elements from the promoters of the instant invention can be identified utilizing bioinformatic or computer driven techniques.

One method uses a computer program AlignACE to identify regulatory motifs in genes that exhibit common preferential transcription across a number of time points. The program identifies common sequence motifs in such genes. See, Roth et al. (1998) Nature Biotechnol. 16: 949–945; Tavazoie et al. (1999) Nat Genet Jul;22 (3):281–5;

Genomatix also makes available a GEMS Launcher program and other programs to identify promoter control elements and configuration of such elements. Genomatix is located in Munich, Germany.

Other references also describe detection of promoter modules by models independent of overall nucleotide sequence similarity. See, for instance, Klingenhoff et al. (1999) Bioinformatics 15: 180–186.

Protein binding sites of promoters can be identified as reported in "Computer-assisted prediction, classification, and delimitation of protein binding sites in nucleic acids", Frech et al. (1993) Nucleic Acids Research 21(7): 1655–1664.

Other programs used to identify protein binding sites include, for example, Signal Scan (Prestridge et al. (1996) Comput. Appl. Biosci. 12: 157–160); Matrix Search (Chen et al. (1995) Comput. Appl. Biosci. 11: 563–566), available as part of Signal Scan 4.0; MatInspector (Ghosh et al. (1993) Nucl. Acid Res. 21: 3117–3118) available via the internet; ConsInspector (Frech et al. (1993) Nucl. Acids Res. 21: 1655–1664), available via the internet; TFSearch and TESS.

Frech et al. (1997) "Software for the analysis of DNA sequence elements of transcription", Bioinformatics & Sequence Analysis, Vol. 13, no. 1, 89–97 is a review of different software for analysis of promoter control elements. This paper also reports the usefulness of matrix-based approaches to yield more specific results.

For other procedures, see Fickett et al. (2000) Curr. Op. Biotechnol. 11: 19–24 and Quandt et al. (1995) Nucleic Acids Res. 23: 4878–4884.

(3) Those Identifiable by In-Vitro and In-Vivo Assays

Promoter control elements can also be identified with in-vitro assays such as transcription detection methods and with in-vivo assays such as enhancer trapping protocols.

In-Vitro Assays

Examples of in-vitro assays include detection of binding of protein factors that bind promoter control elements. Fragments of the instant promoters can be used to identify the location of promoter control elements. Another option for obtaining a promoter control element with desired properties is to modify known promoter sequences. This is based on the fact that the function of a promoter is dependent on the interplay of regulatory proteins that bind to specific, discrete nucleotide sequences ("motifs") in the promoter. Such interplay subsequently affects the general transcription machinery and regulates transcription efficiency. These regulatory proteins are positive regulators or negative regulators (repressors) and one protein can have a dual role depending on the context (Johnson and McKnight, (1989) Annu. Rev. Biochem. 58:799–839).

One type of in-vitro assay uses a known DNA binding factor to isolate DNA fragments that bind. If a fragment or promoter variant does not bind, then a promoter control element has been removed or disrupted. For specific assays, see, for instance, Luo et al. (1997) J. Mol. Biol. 266:470, Chusacultanachai et al. (1999) J. Biol. Chem. 274:23591, Fabbro et al. (1995) Biochem. Biophys. Res. Comm. 213: 781).

Alternatively, a DNA fragment suspected of conferring a particular pattern of expression can be examined for the ability to bind transcription factors responsible for generating the particular pattern using methods such as DNA footprinting (e.g. Cousins et al. (2000) Immunology 99:101 and V. Kolla et al. (1999) Biochem. Biophys. Res. Comm. 266:5) or "mobility-shift" assays (Fabiani et al. (2000) J. Biochem. 347:147 and Sugiura et al. (2000) J. Biochem 347:155) or fluorescence polarization (e.g. Royer et al. U.S. Pat. No. 5,445,935). Both mobility shift and DNA footprinting assays can also be used to identify portions of large DNA fragments that are bound by proteins in unpurified transcription extracts prepared from tissues or organs of interest.

Cell-free transcription extracts can be prepared and used to directly assay in a reconstitutable system (Narayan et al. (2000) Biochemistry 39:818).

In-Vivo Assays

Promoter control elements can be identified with reporter genes in in-vivo assays with the use of fragments of the instant promoter, polynucleotides or variants thereof. That is, a fragment(s) comprising a basal or "core" promoter operably linked to a reporter sequence can be inserted into a vector. When transcribed, a detectable label is produced. Examples of reporter genes include those encoding luciferase, green fluorescent protein, GUS, neo, cat and bar. Alternatively, the transcribed reporter sequence can be detected with AFLP and microarray techniques.

In promoter probe vector systems, genomic DNA fragments are inserted upstream of the coding sequence of a reporter gene which is expressed only when the cloned fragment contains DNA having transcription modulation activity (Neveet al. (1979) Nature 277:324–325). No transcription occurs when control elements are present in the fragment or when control elements present are disrupted. Probe vectors have been designed for assaying transcription modulation in E. coli (An et al. (1979) J. Bact. 140:400–407)

and other bacterial hosts (Band et al. (1983) Gene 26:313–315 and Achen (1986) Gene 45:45–49), yeast (Goodey et al. (1986) Mol. Gen. Genet. 204:505–511) and mammalian cells (Pater et al. (1984) J. Mol. App. Gen. 2:363–371).

A different design of a promoter/control element trap includes packaging into retroviruses for more efficient delivery into cells. One type of retroviral enhancer trap was described by von Melchner et al. (Genes Dev. (1992); U.S. Pat. No. 5,364,783). The basic design of this vector includes a reporter protein coding sequence engineered into the U3 portion of the 3' LTR. No splice acceptor consensus sequences are included, limiting its utility to work as an enhancer trap only. A different approach to a gene trap using retroviral vectors was pursued by Friedrich and Soriano (Genes Dev. 1991) who engineered a lacZ-neo fusion protein linked to a splicing acceptor. LacZ-neo fusion protein expression from trapped loci allows not only for drug selection, but also for visualization of β-galatactosidase expression using the chromogenic substrate, X-gal.

A general review of tools for identifying transcriptional regulatory regions of genomic DNA is provided by J. W. Fickett et al. (Curr. Opn. Biotechnol (2000) 11:19).

(4) Non-Natural Control Elements

Non-natural control elements can be constructed by inserting, deleting or substituting nucleotides into the promoter control elements described above. Such control elements are capable of transcription modulation that can be determined using any of the assays described above.

C. Constructing Promoters with Control Elements (1) Combining Promoters and Promoter Control Elements The promoter polynucleotides and promoter control elements of the present invention, both naturally occurring and synthetic, can be combined with each other to produce the desired preferential transcription. In addition, the polynucleotides of the invention can be combined with other known sequences to generate promoters useful for modulating, for example, tissue-specific transcription or condition-specific transcription. Such preferential transcription can be determined using the techniques or assays described above.

The relatives, fragments and variants as well as full-length sequences shown in the Sequence Listing are useful alone or in combination.

The location and relation of promoter control elements within a promoter can affect the ability of the promoter to modulate transcription. The order and spacing of control elements is a factor when constructing promoters.

(2) Number of Promoter Control Elements

Promoters can contain any number of control elements. For example, a promoter can contain multiple transcription binding sites or other control elements. One element may confer tissue or organ specificity, another element may limit transcription to specific time periods, etc. Typically, promoters will contain at least a basal or core promoter as described above. Any additional element can be included as desired. For example, a fragment comprising a basal or "core" promoter can be fused with another fragment with any number of additional control elements.

(3) Spacing Between Control Elements

Spacing between control elements or the configuration or control elements can be determined or optimized to permit the desired polynucleotide or protein-polynucleotide interactions to occur.

For example, if two transcription factors bind to a promoter simultaneously or relatively close in time, the binding sites are spaced to allow each factor to bind without steric hinderance. The spacing between two such hybridizing control elements can be as small as a profile of a protein bound to a control element. In some cases, two protein binding sites can be adjacent to each other when the proteins bind at different times during the transcription process.

Further, when two control elements hybridize the spacing between such elements will be sufficient to allow the promoter polynucleotide to form a hairpin or loop so as to permit the two elements to bind. The spacing between two such hybridizing control elements can be as small as a t-RNA loop, to as large as 10 kb.

Typically, the spacing is no smaller than 5 bases, more typically no smaller than 8, more typically no smaller than 15 bases, more typically no smaller than 20 bases, more typically no smaller than 25 bases, even more typically no more than 30, 35, 40 or 50 bases.

Usually, the fragment size in no larger than 5 kb bases, more usually no larger than 2 kb, more usually no larger than 1 kb, more usually no larger than 800 bases, more usually no larger than 500 bases, even more usually no more than 250, 200, 150 or 100 bases.

Such spacing between promoter control elements can be determined using the techniques and assays described above.

(4) Other Promoters

The following are promoters that are induced under stress conditions and can be combined with those of the present invention: ldh1 (oxygen stress, tomato see Germain and Ricard (1997) Plant Mol Biol 35:949–54), GPx and CAT (oxygen stress, mouse, see Franco et al. (1999) Free Radic Biol Med 27:1122–32), ci7 (cold stress, potato, see Kirch et al. (1997) Plant Mol Biol. 33:897–909), Bz2 (heavy metals, maize, see Marrs and Walbot (1997) Plant Physiol 113: 93–102), HSP32 (hyperthermia, rat, see Raju and Maines (1994) Biochim Biophys Acta 1217:273–80); MAPKAPK-2 (heat shock, *Drosophila*, see Larochelle and Suter (1995) Gene 163:209–14).

In addition, the following promoters are examples those induced by the presence or absence of light and can be used in combination with those of the present invention: Topoisomerase II (pea, see Reddy et al. (1999) Plant Mol Biol 41:125–37), chalcone synthase (soybean, see Wingender et al. (1989) Mol Gen Genet 218:315–22), mdm2 gene (human tumor, see Saucedo et al. (1998) Cell Growth Differ 9:119–30), Clock and BMAL1 (rat, see Namihira et al. (1999) Neurosci Lett 271:1–4), PHYA (*Arabidopsis*, see Canton and Quail 1999 Plant Physiol 121:1207–16), PRB-1b (tobacco, see Sessa et al. (1995) Plant Mol Biol 28:537–47) and Ypr10 (common bean, see Walter et al. (1996) Eur J Biochem 239:281–93).

The promoters and control elements of the following genes can be used in combination with the present invention to confer tissue specificity: for roots MipB (iceplant, Yamada et al. (1995) Plant Cell 7:1129–42) and SUCS (root nodules, broadbean, Kuster et al. (1993) Mol Plant Microbe Interact 6:507–14), for leaves OsSUT1 (rice, Hirose et al. (1997) Plant Cell Physiol 38:1389–96), for siliques Msg (soybean, Stomvik et al. (1999) Plant Mol Biol 41:217–31) and for inflorescence (*Arabidopsis*, Shani et al. (1997) Plant Mol Biol 34(6):837–42) and ACT11 (*Arabidopsis*, Huang et al. (1997) Plant Mol Biol 33:125–39).

Still other promoters are affected by hormones or participate in specific physiological processes, which can be used in combination with those of present invention. Some examples are the ACC synthase gene that is induced differently by ethylene and brassinosteroids (mung bean, Yi et al. (1999) Plant Mol Biol 41:443–54), the TAPG1 gene that is active during abscission (tomato, Kalaitzis et al. (1995) Plant Mol Biol 28:647–56) and the 1-aminocyclopropane-1-carboxylate synthase gene (carnation, Jones et al. (1995) Plant Mol Biol 28:505–12) and the CP-2/cathepsin L gene (rat, Kim and Wright (1997) Biol Reprod 57:1467–77), which are both active during senescence.

E. Vectors

Vectors are a useful component of the present invention. In particular, vectors can deliver the present promoters and/or promoter control elements to a cell. For the purposes of this invention, such delivery ranges from randomly introducing the promoter or promoter control element alone into a cell to integrating the vector containing the promoter or promoter control element into a cell's genome. Thus, a vector need not be limited to a DNA molecule such as a plasmid, cosmid or bacterial phage that has the capability of replicating autonomously in a host cell. All other manner of delivery of the promoters and promoter control elements of the invention are envisioned. The various T-DNA vector types are preferred vectors for use with the present invention. Many useful vectors are commercially available.

It may also be useful to attach a marker sequence to the present promoter and promoter control element in order to determine activity of such sequences. Marker sequences typically include genes that provide antibiotic resistance, such as tetracycline resistance, hygromycin resistance or ampicillin resistance, or provide herbicide resistance. Specific selectable marker genes may be used to confer resistance to herbicides such as glyphosate, glufosinate or broxynil (Comai et al. (1985) Nature 317: 741–744; Gordon-Kamm et al. (1990) Plant Cell 2: 603–618; and Stalker et al. (1988) Science 242: 419–423). Other marker genes exist which provide hormone responsiveness.

(1) Modification of Transcription by Promoters and Promoter Control Elements

The promoter or promoter control element of the present invention may be operably linked to a polynucleotide to be transcribed. In this manner, the promoter or promoter control element modifys transcription by modulating transcript levels of that polynucleotide when inserted into a genome.

The promoter or promoter control element need not be linked, operably or otherwise, to a polynucleotide to be transcribed before being inserted into a genome. For example, the promoter or promoter control element can be inserted into the genome in front of a polynucleotide already present therein. Here, the promoter or promoter control element modulates the transcription of a polynucleotide that was already present in the genome. This polynucleotide may be native to the genome or inserted at an earlier time.

Alternatively, the promoter or promoter control element can simply be inserted into a genome or maintained extrachromosomally as a way to divert the transcription resources of the system to itself. See, for example, Vaucheret et al. (1998) Plant J 16: 651–659. This approach may be used to downregulate the transcript levels of a group of polynucleotide(s).

(2) Polynucleotide to be Transcribed

The nature of the polynucleotide to be transcribed is not limited. Specifically, the polynucleotide may include sequences that will have activity as RNA as well as sequences that result in a polypeptide product. These sequences may include, but are not limited to antisense sequences, ribozyme sequences, spliceosomes, amino acid coding sequences and fragments thereof.

Specific coding sequences may include, but are not limited to endogenous proteins or fragments thereof, or heterologous proteins including marker genes or fragments thereof.

Promoters and control elements of the present invention are useful for modulating metabolic or catabolic processes. Such processes include, but are not limited to secondary product metabolism, amino acid synthesis, seed protein storage, oil development, pest defense and nitrogen usage. Some examples of genes, transcripts, peptides or polypeptides participating in these processes which can be modulated by the present invention: are tryptophan decarboxylase (tdc), strictosidine synthase (str1), dihydrodipicolinate synthase (DHDPS), aspartate kinase (AK), 2S albumin, alpha-, beta-, and gamma-zeins, ricinoleate, 3-ketoacyl-ACP synthase (KAS), *Bacillus thuringiensis* (Bt) insecticidal protein, cowpea trypsin inhibitor (CpTI), asparagine synthetase and nitrite reductase. Alternatively, expression constructs can be used to inhibit expression of these peptides and polypeptides by incorporating the promoters in constructs for antisense use, co-suppression use or for the production of dominant negative mutations.

(3) Other Regulatory Elements

As explained above, several types of regulatory elements exist concerning transcription regulation. Each of these regulatory elements may be combined with the present vector if desired.

(4) Other Components of Vectors

Translation of eukaryotic mRNA is often initiated at the codon that encodes the first methionine. Thus, when constructing a recombinant polynucleotide for expressing a protein product according to the present invention, it is preferable to ensure that no intervening codons encoding a methionine are contained within the linkage between the polynucleotide to be transcribed, or a functional derivative thereof, and the 3' portion of the promoter, preferably including the TATA box.

The vector of the present invention may contain additional components. For example, an origin of replication that allows for replication of the vector in a host cell may be added. In addition, homologous sequences flanking a target location in the genome may be added to allow for site-specific recombination of a specific sequence contained in the vector. T-DNA sequences also allow for insertion of a specific sequence randomly into a target genome, but in a random manner.

The vector may also contain a plurality of restriction sites for insertion of the promoter and/or promoter control elements of the present invention as well as any polynucleotide to be transcribed. The vector can additionally contain selectable marker genes. The vector can also contain a transcriptional and translational initiation region and/or a transcriptional and translational termination region that functions in the host cell. The termination region may be native with the transcriptional initiation region, may be native with the polynucleotide to be transcribed or may be derived from another source. Convenient termination regions are available from the Ti-plasmid of *A. tumefaciens*, such as the octopine synthase and nopaline synthase termination regions. See also, Guerineau et al. (1991) Mol. Gen. Genet. 262:141–144; Proudfoot (1991) Cell 64:671–674; Sanfacon et al. (1991) Genes Dev. 5:141–149; Mogen et al. (1990) Plant Cell 2:1261–1272; Munroe et al. (1990) Gene 91:151–158; Ballas et al. (1989) Nucleic Acids Res. 17:7891–7903; Joshi et al. (1987) Nucleic Acid Res. 15:9627–9639.

Where appropriate, the polynucleotide to be transcribed may be optimized for increased expression in a certain host cell. For example, the polynucleotide can be synthesized using preferred codons for improved transcription and translation. See U.S. Pat. Nos. 5,380,831, 5,436, 391 and Murray et al. (1989) Nucleic Acids Res. 17:477–498.

Additional sequence modifications include elimination of sequences encoding spurious polyadenylation signals, exon intron splice site signals, transposon-like repeats and other such sequences well characterized as deleterious to expression. The G–C content of the polynucleotide may be adjusted to the average levels for a given cellular host, as calculated by reference to known genes expressed in the host cell. The polynucleotide sequence may be modified to avoid hairpin secondary mRNA structures.

A general description of expression vectors and reporter genes can be found in Gruber et al., "Vectors for Plant Transformation", in Methods in Plant Molecular Biology & Biotechnology (1993) Glich et al. eds., pp. 89–119, CRC Press). Moreover GUS expression vectors and GUS gene cassettes are available from Clonetech Laboratories, Inc. (Palo Alto, Calif.) while luciferase expression vectors and luciferase gene cassettes are available from Promega Corp. (Madison, Wis.). GFP vectors are available from Aurora Biosciences.

F. Polynucleotide Insertion Into A Host Cell

The polynucleotides according to the present invention can be inserted into a host cell. A host cell includes but is not limited to a plant, mammalian, insect, yeast and prokaryotic cell, preferably a plant cell.

The method of insertion into the host cell genome is chosen based on convenience. For example, the insertion into the host cell genome may either be accomplished by vectors that integrate into the host cell genome or by vectors which exist independent of the host cell genome.

(1) Polynucleotides Autonomous of the Host Genome

The polynucleotides of the present invention can exist autonomously or independent of the host cell genome. Vectors of these types are known in the art and include, for example, certain types of non-integrating viral vectors, autonomously replicating plasmids, artificial chromosomes and the like.

Additionally, in some cases transient expression of a polynucleotide may be desired.

(2) Polynucleotides Integrated into the Host Genome

The promoter sequences, promoter control elements or vectors of the present invention can be transformed into host cells. These transformations can be into protoplasts or isolated cells or intact tissues. Preferably, expression vectors are introduced into intact tissue. General methods of culturing plant tissues are provided for example by Maki et al. ("Procedures for Introducing Foreign DNA into Plants" in Methods in Plant Molecular Biology & Biotechnology (1993) Glich et al. eds., pp. 67–88 CRC Press) and by Phillips et al. "Cell-Tissue Culture and In-Vitro Manipulation" in Corn & Corn Improvement, 3rd Edition 10Sprague et al. (1998) eds. pp. 345–387) American Society of Agronomy Inc. et al.

Methods of introducing polynucleotides into plant tissue include the direct infection or co-cultivation of a plant cell with *Agrobacterium tumefaciens* (Horsch et al. (1985) Science 227:1229). Descriptions of *Agrobacterium* vector systems and methods for *Agrobacterium*-mediated gene transfer are provided by Gruber et al. supra.

Alternatively, polynucleotides are introduced into plant cells or other plant tissues using a direct gene transfer method such as microprojectile-mediated delivery, DNA injection, electroporation and the like. More preferably, polynucleotides are introduced into plant tissues using the microprojectile media delivery with the biolistic device. See, for example, Tomes et al., "Direct DNA transfer into intact plant cells via microprojectile bombardment" In: Plant Cell, Tissue and Organ Culture: Fundamental Methods (1995) Gamborg and Phillips eds. Springer Verlag, Berlin.

In another embodiment of the current invention, expression constructs can be used for gene expression in callus culture for the purpose of expressing marker genes encoding peptides or polypeptides that allow identification of transformed plants. Here, a promoter that is operatively linked to a polynucleotide to be transcribed is transformed into plant cells and the transformed tissue is then placed on callus-inducing media. If the transformation is conducted with leaf discs, for example, callus will initiate along the cut edges. Once callus growth has initiated, callus cells can be transferred to callus shoot-inducing or callus root-inducing media. Gene expression will occur in the callus cells developing on the appropriate media: callus root-inducing promoters will be activated on callus root-inducing media, etc. Examples of such peptides or polypeptides useful as transformation markers include, but are not limited to barstar, glyphosate, chloramphenicol acetyltransferase (CAT), kanamycin, spectinomycin, streptomycin or other antibiotic resistance enzymes, green fluorescent protein (GFP) and β-glucuronidase (GUS), etc. Some of the promoters in the Seqeunce Listing will also be capable of sustaining expression in some tissues or organs after the initiation or completion of regeneration. Examples of these tissues or organs are somatic embryos, cotyledon, hypocotyl, epicotyl, leaf, stems, roots, flowers and seed.

Integration into the host cell genome also can be accomplished by methods known in the art such as by homologous sequences or T-DNA discussed above or by using the cre-lox system (Vergunst et al. (1998) Plant Mol. Biol. 38:393).

G. Utility

Common Uses

In yet another embodiment, the promoters of the present invention can be used to further understand developmental mechanisms. For example, promoters that are specifically induced during callus formation, somatic embryo formation, shoot formation or root formation can be used to explore the effects of overexpression, repression or ectopic expression of target genes, or for isolation of trans-acting factors.

The vectors of the invention can be used not only for expression of coding regions but may also be used in exon-trap cloning, or promoter trap procedures to detect differential gene expression in various tissues. See Lindsey et al (1993) "Tagging Genomic Sequences That Direct Transgene Expression by Activation of a Promoter Trap in Plants," Transgenic Research 2:3347 and Auch et al. "Exon Trap Cloning: Using PCR to Rapidly Detect and Clone Exons from Genomic DNA Fragments," Nucleic Acids Research, 18:674.

Entrapment vectors, first described for use in bacteria (Casadaban and Cohen (1979) Proc. Nat. Aca. Sci. U.S.A. 76: 4530 and Casadaban et al. (1980) J. Bacteriol. 143: 971) permit selection of insertional events that lie within coding sequences. Entrapment vectors can be introduced into pluripotent ES cells in culture and then passed into the germline via chimeras (Gossler et al. (1989) Science 244: 463 and Skarnes (1990) Biotechnology 8: 827). Promoter or gene trap vectors often contain a reporter gene, e.g. lacZ, lacking its own promoter and/or splice acceptor sequence upstream.

That is, promoter gene traps contain a reporter gene with a splice site but no promoter. If the vector lands in a gene and is spliced into the gene product, then the reporter gene is expressed.

Recently, the isolation of preferentially-induced genes has been made possible with the use of sophisticated promoter traps (e.g. IVET) that are based on conditional auxotrophy complementation or drug resistance. In one IVET approach, various bacterial genome fragments are placed in front of a necessary metabolic gene that is coupled to a reporter gene. The DNA constructs are inserted into a bacterial strain otherwise lacking the metabolic gene and the resulting bacteria are used to infect the host organism. Only bacteria expressing the metabolic gene survive in the host organism. Consequently, inactive constructs can be eliminated by harvesting only bacteria that survive for some minimum period in the host. At the same time, constitutively active constructs can be eliminated by selecting only bacteria that do not express the reporter gene under laboratory conditions. The bacteria selected by such a method contain constructs that are selectively induced only during infection of the host. The IVET approach can be modified in plants to identify genes induced in either the bacteria or the plant cells upon pathogen infection or root colonization. For information on IVET see the following articles: Mahan et al. (1993) Science 259:686–688, Mahan et al. (1995) PNAS USA 92:669–673, Heithoff et al. (1997) PNAS USA 94:934–939, and Wang et al. (1996) PNAS USA. 93:10434.

Constitutive Transcription

Promoters and control elements providing constitutive transcription are desired for modulation of transcription in most cells of an organism under most environmental conditions. In a plant, for example, constitutive transcription is useful for modulating genes involved in defense, pest resistance, herbicide resistance, etc.

Constitutive up-regulation and down-regulation of transcription are useful for these applications. For instance, genes, transcripts and/or polypeptides that increase defense, pest and herbicide resistance may require constitutive up-regulation of transcription. In contrast, constitutive down-regulation of transcriptional may be desired to inhibit those genes, transcripts, and/or polypeptides that lower defense, pest and herbicide resistance.

Typically, promoter or control elements that provide constitutive transcription produce transcription levels that are statistically similar in many tissues and environmental conditions observed.

Calculation of P-value from the different observed transcript levels is one means of determining whether a promoter or control element is providing constitutive up-regulation. P-value is the probability that the difference of transcript levels is not statistically significant. The higher the P-value, the more likely the difference of transcript levels is not significant. One formula used to calculate P-value is as follows:

$\int \phi(x) \, dx$, integrated from a to $\infty$, where $\phi(x)$ is a normal distribution;

$$\text{where } a = \frac{|Sx - \mu|}{\sigma(\text{all Samples except } Sx)};$$

where Sx=the intensity of the sample of interest where μ=is the average of the intensities of all samples except Sx, $$= \frac{\left(\sum S1 \ldots Sn\right) - Sx}{n - 1}$$

where σ(S1 . . . S11, not including Sx)=the standard deviation of all sample intensities except Sx.

The P-value from the formula ranges from 1.0 to 0.0.

Usually, each P-value of the transcript levels produced by the promoter or control element and observed in a majority of cells, tissues or organs under various environmental conditions is greater than $10^{-8}$; more usually, greater than $10^{-7}$; even more usually, greater than $10^{-6}$; even more usually, greater than $10^{-5}$ or $10^{-4}$.

For up-regulation of transcription, promoter and control elements produce transcript levels that are above background of the assay.

Stress Induced Preferential Transcription

Promoters and control elements providing modulation of transcription under oxidative, drought, oxygen, wound and methyl jasmonate stress are particularly useful for producing host cells or organisms that are more resistant to biotic and abiotic stresses. For example, in a plant modulation of genes, transcripts and/or polypeptides in response to oxidative stress can protect cells against damage caused by oxidative agents such as hydrogen peroxide and other free radicals.

Drought induction of genes, transcripts and/or polypeptides are useful to increase the viability of a plant, for example when water is a limiting factor. In contrast, genes, transcripts and/or polypeptides induced during oxygen stress can help the flood tolerance of a plant.

The promoters and control elements of the present invention can modulate the plant's response to stresses. Examples of some genes involved in stress condition responses are VuPLD1 (drought stress, Cowpea; Pham-Thi et al. (1999) Plant Mol. Biol 1257–65), pyruvate decarboxylase (oxygen stress, rice; Rivosal et al. (1997) Plant Physiol. 114(3): 1021–29), and the chromoplast specific carotenoid gene (oxidative stress, *Capsicum*; see Bouvier et al. (1998) J Biol Chem 273: 30651–59).

Promoters and control elements providing preferential transcription during wounding or that are induced by methyl jasmonate can produce a defense response in host cells or organisms. In a plan, preferential modulation of genes, transcripts and/or polypeptides under such conditions is useful to induce a defense response to mechanical wounding, pest or pathogen attack or treatment with certain chemicals.

Promoters and control elements of the present invention also can trigger a response similar to those described for cf9 (viral pathogen, tomato; O'Donnell et al. (1998) Plant J 14(1): 137–42), hepatocyte growth factor activator inhibitor type 1 (HAI-1), which enhances tissue regeneration (tissue injury, human; Koono et al. (1999) J Histochem Cytochem 47: 673–82), copper amine oxidase (CuAO) induced during ontogenesis and wound healing (wounding, chick-pea; Rea et al. (1998) FEBS Letters 437: 177–82), proteinase inhibitor II (wounding, potato; Pena-Cortes et al. (1988) Planta 174: 84–89), protease inhibitor II (methyl jasmonate, tomato; Farmer and Ryan (1990) Proc Natl Acad Sci USA 87: 7713–7716) and two vegetative storage protein genes VspA and VspB (wounding, jasmonic acid and water deficit; soybean; Mason and Mullet (1990) Plant Cell 2: 569–579).

Up-regulation and down-regulation of transcription are useful for these applications. For instance, genes, transcripts and/or polypeptides that increase oxidative, flood or drought tolerance may require up-regulation of transcription. In contrast, transcriptional down-regulation may be desired to inhibit those genes, transcripts and/or polypeptides that lower such tolerance.

Typically, promoter or control elements which provide preferential transcription in wounding or under methyl jasmonate induction produce transcript levels that are statistically significantly altered as compared to cell types, organs or tissues under other conditions.

For preferential up-regulation of transcription, promoter and control elements produce transcript levels that are above background of the assay.

Light Induced Preferential Transcription

Promoters and control elements providing preferential transcription when induced by light exposure can be utilized to modulate growth, metabolism and development to increase drought tolerance and to decrease damage from light stress for host cells or organisms. In a plant, modulation of genes, transcripts and/or polypeptides in response to light is useful (1) to increase the photosynthetic rate;
(2) to increase storage of certain molecules in leaves or green parts only, e.g. silage with high protein or starch content;
(3) to modulate production of exogenous compositions in green tissue, e.g. certain feed enzymes;
(4) to induce growth or development, such as fruit development and maturity, during extended exposure to light;
(5) to modulate guard cells to control the size of stomata in leaves to prevent water loss, or
(6) to induce accumulation of beta-carotene to help plants cope with light induced stress.

The promoters and control elements of the present invention can also trigger responses similar to those described for: abscisic acid insensitive3 (ABI3) (dark-grown *Arabidopsis* seedlings, Rohde et al. (2000) Plant Cell 12: 35–52), asparagine synthetase (pea root nodules, Tsai, Coruzzi, (1990) EMBO J 9: 323–32) and mdm2 gene (human tumor; Saucedo et al. (1998) Cell Growth Differ 9: 119–30).

Up-regulation and down-regulation of transcription are useful for these applications. For instance, genes, transcripts and/or polypeptides that increase drought or light tolerance may require up-regulation of transcription. In contrast, transcriptional down-regulation may be desired to inhibit those genes, transcripts and/or polypeptides that lower such tolerance.

Typically, promoter or control elements which provide preferential transcription in cells, tissues or organs exposed to light produce transcript levels that are statistically significantly altered as compared to cells, tissues or organs under decreased light exposure (intensity or length of time).

For preferential up-regulation of transcription, promoter and control elements produce transcript levels that are above background of the assay.

Dark Induced Preferential Transcription

Promoters and control elements providing preferential transcription when induced by dark or decreased light intensity or decreased light exposure time can be utilized to time growth, metabolism and development and to modulate photosynthesis capabilities for host cells or organisms. In a plant, modulation of genes, transcripts and/or polypeptides in response to dark is useful (1) to induce growth or development, such as fruit development and maturity, despite lack of light;
(2) to modulate genes, transcripts and/or polypeptide active at night or on cloudy days; or
(3) to preserve the plastid ultra structure present at the onset of darkness.

The present promoters and control elements can also trigger response similar to those described in the section above.

Up-regulation and down-regulation of transcription are useful for these applications. For instance, genes, transcripts and/or polypeptides that increase growth and development may require up-regulation of transcription. In contrast, transcriptional down-regulation may be desired to inhibit those genes, transcripts and/or polypeptides that modulate photosynthesis capabilities.

Typically, promoter or control elements which provide preferential transcription under exposure to dark or decreased light intensity or decreased exposure time produce transcript levels that are statistically significantly altered.

For preferential up-regulation of transcription, promoter and control elements produce transcript levels that are above background of the assay.

Leaf Preferential Transcription

Promoters and control elements providing preferential transcription in a leaf can modulate growth, metabolism and development or modulate energy and nutrient utilization in host cells or organisms. In a plant, preferential modulation of genes, transcripts and/or polypeptide in a leaf is useful (1) to modulate leaf size, shape, and development;
(2) to modulate the number of leaves; or
(3) to modulate energy or nutrient usage in relation to other organs and tissues.

Up-regulation and down-regulation of transcription are useful for these applications. For instance, genes, transcripts and/or polypeptides that increase growth may require up-regulation of transcription. In contrast, transcriptional down-regulation may be desired to inhibit energy usage in a leaf and to redirect it to the fruit instead, for instance.

Typically, promoter or control elements which provide preferential transcription in the cells, tissues, or organs of a leaf produce transcript levels that are statistically significantly altered as compared to other cells, organs or tissues.

For preferential up-regulation of transcription, promoter and control elements produce transcript levels that are above background of the assay.

Root Preferential Transcription

Promoters and control elements providing preferential transcription in a root can modulate growth, metabolism, development, nutrient uptake, nitrogen fixation or modulate energy and nutrient utilization in host cells or organisms. In a plant, for example, preferential modulation of genes, transcripts, and/or in a leaf, is useful (1) to modulate root size, shape, and development;
(2) to modulate the number of roots, or root hairs;
(3) to modulate mineral, fertilizer, or water uptake;
(4) to modulate transport of nutrients; or
(4) to modulate energy or nutrient usage in relation to other organs and tissues.

Up-regulation and down-regulation of transcription are useful for these applications. For instance, genes, transcripts and/or polypeptides that increase growth may require up-regulation of transcription. In contrast, transcriptional down-regulation may be desired to inhibit nutrient usage in a root and to redirect it to the leaf instead, for instance.

Typically, promoter or control elements which provide preferential transcription in cells, tissues or organs of a root produce transcript levels that are statistically significantly altered as compared to other cells, organs or tissues.

For preferential up-regulation of transcription, promoter and control elements produce transcript levels that are above background of the assay.

Stem/Shoot Preferential Transcription

Promoters and control elements providing preferential transcription in a stem or shoot can modulate growth, metabolism and development or modulate energy and nutrient utilization in host cells or organisms. In a plant, preferential modulation of genes, transcripts and/or a polypeptide in a stem or shoot is useful
(1) to modulate stem/shoot size, shape, and development; or
(2) to modulate energy or nutrient usage in relation to other organs and tissues Up-regulation and down-regulation of transcription are useful for these applications. For instance, genes, transcripts and/or polypeptides that increase growth may require up-regulation of transcription. In contrast, transcriptional down-regulation may be desired to inhibit energy usage in a stem/shoot and to redirect it to the fruit instead, for instance.

Typically, promoter or control elements which provide preferential transcription in the cells, tissues or organs of a stem or shoot produce transcript levels that are statistically significant as compared to other cells, organs or tissues.

For preferential up-regulation of transcription, promoter and control elements produce transcript levels that are above background of the assay.

Fruit and Seed Preferential Transcription

Promoters and control elements providing preferential transcription in a silique or fruit can time growth, development, or maturity; or modulate fertility; or modulate energy and nutrient utilization in host cells or organisms. In a plant preferential modulation of genes, transcripts and/or polypeptides in a fruit is useful
(1) to modulate fruit size, shape, development, and maturity;
(2) to modulate the number of fruit or seeds;
(3) to modulate seed shattering;
(4) to modulate components of seeds, such as, storage molecules, starch, protein, oil, vitamins, anti-nutritional components, such as phytic acid;
(5) to modulate seed and/or seedling vigor or viability;
(6) to incorporate exogenous compositions into a seed, such as lysine rich proteins;
(7) to permit similar fruit maturity timing for early and late blooming flowers; or
(8) to modulate energy or nutrient usage in relation to other organs and tissues.

Up-regulation and down-regulation of transcription are useful for these applications. For instance, genes, transcripts, and/or polypeptides that increase growth may require up-regulation of transcription. In contrast, transcriptional down-regulation may be desired to inhibit late fruit maturity, for instance.

Typically, promoter or control elements which provide preferential transcription in the cells, tissues or organs of siliques or fruits produce transcript levels that are statistically significantly altered as compared to other cells, organs or tissues.

For preferential up-regulation of transcription, promoter and control elements produce transcript levels that are above background of the assay.

Callus Preferential Transcription

Promoters and control elements providing preferential transcription in a callus can be useful to modulating transcription in dedifferentiated host cells. In a plant transformation, for example, preferential modulation of genes or transcript in callus is useful to modulate transcription of a marker gene, which can facilitate selection of cells that are transformed with exogenous polynucleotides.

Up-regulation and down-regulation of transcription are useful for these applications. For instance, genes, transcripts and/or polypeptides that increase marker gene detectabilitymay require up-regulation of transcription. In contrast, transcriptional down-regulation may be desired to increase the ability of the calluses to differentiate, for instance.

Typically, promoter or control elements which provide preferential transcription in callus produce transcript levels that are statistically significantly altered as compared to other cell types, tissues, or organs. Calculation of P-value from the different observed transcript levels is one means of determining whether a promoter or control element is providing such preferential transcription.

Usually, each P-value of the transcript levels observed in callus as compared to at least one other cell type, tissue or organ, is less than $10^{-4}$; more usually, less than $10^{-5}$; even more usually, less than $10^{-6}$; even more usually, less than $10^{-7}$ or $10^{-8}$.

For preferential up-regulation of transcription, promoter and control elements produce transcript levels that are above background of the assay.

Flower Specific Transcription

Promoters and control elements providing preferential transcription in flowers can modulate pigmentation or modulate fertility in host cells or organisms. In a plant, preferential modulation of genes, transcripts and/or polypeptides in a flower is useful,
(1) to modulate petal color; or
(2) to modulate the fertility of pistil and/or stamen.

Up-regulation and down-regulation of transcription are useful for these applications. For instance, genes, transcripts and/or polypeptides that increase pigmentation may require up-regulation of transcription. In contrast, transcriptional down-regulation may be desired to inhibit fertility, for instance.

Typically, promoter or control elements which provide preferential transcription in flowers produce transcript levels that are statistically significantly altered as compared to other cells, organs or tissues.

For preferential up-regulation of transcription, promoter and control elements produce transcript levels that are above background of the assay.

Immature Bud and Inflorescence Preferential Transcription

Promoters and control elements providing preferential transcription in an immature bud or inflorescence can time growth, development or maturity or modulate fertility or viability in host cells or organisms. In a plant, preferential modulation of genes, transcripts, and/or polypeptide in an immature bud or inflorescence is useful,
(1) to modulate embryo development, size, and maturity;
(2) to modulate endosperm development, size, and composition;
(3) to modulate the number of seeds and fruits; or
(4) to modulate seed development and viability.

Up-regulation and down-regulation of transcription is useful for these applications. For instance, genes, transcripts and/or polypeptides that increase growth may require up-regulation of transcription. In contrast, transcriptional down-regulation may be desired to decrease endosperm size, for instance.

Typically, promoter or control elements which provide preferential transcription in immature buds and inflorescences produce transcript levels that are statistically significantly altered as compared to other cell types, organs or tissues.

For preferential up-regulation of transcription, promoter and control elements produce transcript levels that are above background of the assay.

Senescence Preferential Transcription

Promoters and control elements providing preferential transcription during senescence can be used to modulate cell degeneration, nutrient mobilization and scavenging of free radicals in host cells or organisms. Other types of responses that can be modulated include, for example, senescence associated genes (SAG) that encode enzymes thought to be involved in cell degeneration and nutrient mobilization (*Arabidopsis*; Hensel et al. (1993) Plant Cell 5: 553–64), and the CP-2/cathepsin L gene (rat; Kim and Wright (1997) Biol Reprod 57: 1467–77). Both of these genes are induced during senescence.

In a plant, preferential modulation of genes, transcripts and/or polypeptides during senescencing is useful to modulate fruit ripening.

Up-regulation and down-regulation of transcription are useful for these applications. For instance, genes, transcripts and/or polypeptides that increase scavenging of free radicals may require up-regulation of transcription. In contrast, transcriptional down-regulation may be desired to inhibit cell degeneration, for instance.

Typically, promoter or control elements which provide preferential transcription in cells, tissues or organs during senescence produce transcript levels that are statistically significantly altered as compared to other conditions.

For preferential up-regulation of transcription, promoter and control elements produce transcript levels that are above background of the assay.

Germination Preferential Transcription

Promoters and control elements providing preferential transcription in a germinating seed can time growth, development or maturity or modulate viability in host cells or organisms. In a plant, preferential modulation of genes, transcripts and/or polypeptide in a germinating seed is useful
(1) to modulate the emergence of they hypocotyls, cotyledons and radical; or
(2) to modulate shoot and primary root growth and development;

Up-regulation and down-regulation of transcription is useful for these applications. For instance, genes, transcripts and/or polypeptides that increase growth may require up-regulation of transcription. In contrast, transcriptional down-regulation may be desired to decrease endosperm size, for instance.

Typically, promoter or control elements which provide preferential transcription in a germinating seed produce transcript levels that are statistically significantly altered as compared to other cell types, organs or tissues.

For preferential up-regulation of transcription, promoter and control elements produce transcript levels that are above background of the assay.

Results

GFP Experimental Procedures and Results

Procedures

The polynucleotide sequences of the present invention were tested for promoter activity using Green Fluorescent Protein (GFP) assays in the following manner.

Approximately 1–2 kb of genomic sequence occurring immediately upstream of the ATG translational start site of the gene of interest was isolated using appropriate primers tailed with BstXI restriction sites. Standard PCR reactions using these primers and genomic DNA were conducted. The resulting product was isolated, cleaved with BstXI and cloned into the BstXI site of an appropriate vector, such as pNewBin4-HAP1-GFP (see FIG. 1).

Transformation

The following procedure was used for transformation of plants

1. Stratification of WS-2 Seed.
   Add 0.5 ml WS-2 (CS2360) seed to 50 ml of 0.2% Phytagar in a 50 ml Corning tube and vortex until seeds and Phytagar form a homogenous mixture.
   Cover tube with foil and stratify at 4° C. for 3 days.

2. Preparation of Seed Mixture.
   Obtain stratified seed from cooler.
   Add seed mixture to a 1000 ml beaker.
   Add an additional 950 ml of 0.2% Phytagar and mix to homogenize.

3. Preparation of Soil Mixture.
   Mix 24 L SunshineMix #5 soil with 16 L Therm-O-Rock vermiculite in cement mixer to make a 60:40 soil mixture.
   Amend soil mixture by adding 2 Tbsp Marathon and 3 Tbsp Osmocote and mix contents thoroughly.
   Add 1 Tbsp Peters fertilizer to 3 gallons of water and add to soil mixture and mix thoroughly.
   Fill 4-inch pots with soil mixture and round the surface to create a slight dome.
   Cover pots with 8-inch squares of nylon netting and fasten using rubber bands.
   Place 14 4-inch pots into each no-hole utility flat.

4. Planting.
   Using a 60 ml syringe, aspirate 35 ml of the seed mixture.
   Exude 25 drops of the seed mixture onto each pot.
   Repeat until all pots have been seeded.
   Place flats on greenhouse bench, cover flat with clear propagation domes, place 55% shade cloth on top of flats and subirrigate by adding 1 inch of water to bottom of each flat.

5. Plant Maintenance.
   3 to 4 days after planting, remove clear lids and shade cloth.
   Subirrigate flats with water as needed.
   After 7–10 days, thin pots to 20 plants per pot using forceps.
   After 2 weeks, subirrigate all plants with Peters fertilizer at a rate of 1 Tsp per gallon water.
   When bolts are about 5–10 cm long, clip them between the first node and the base of stem to induce secondary bolts.
   6 to 7 days after clipping, perform dipping infiltration.

6. Preparation of *Agrobacterium*.
   Add 150 ml fresh YEB to 250 ml centrifuge bottles and cap each with a foam plug (Identi-Plug).
   Autoclave for 40 min at 121° C.
   After cooling to room temperature, uncap and add 0.1 ml each of carbenicillin, spectinomycin and rifampicin stock solutions to each culture vessel.
   Obtain *Agrobacterium* starter block (96-well block with *Agrobacterium* cultures grown to an $OD_{600}$ of approximately 1.0) and inoculate one culture vessel per construct by transferring 1 ml from appropriate well in the starter block.

Cap culture vessels and place on Lab-Line incubator shaker set at 27° C. and 250 RPM.

Remove after *Agrobacterium* cultures reach an $OD_{600}$ of approximately 1.0 (about 24 hours), cap culture vessels with plastic caps, place in Sorvall SLA 1500 rotor and centrifuge at 8000 RPM for 8 min at 4° C.

Pour out supernatant and put bottles on ice until ready to use.

Add 200 ml Infiltration Media (IM) to each bottle, resuspend *Agrobacterium* pellets and store on ice.

7. Dipping Infiltration.

Pour resuspended *Agrobacterium* into 16 oz polypropylene containers.

Invert 4-inch pots and submerge the aerial portion of the plants into the *Agrobacterium* suspension and let stand for 5 min.

Pour out *Agrobacterium* suspension into waste bucket while keeping polypropylene container in place and return the plants to the upright position.

Place 10 covered pots per flat.

Fill each flat with 1-inch of water and cover with shade cloth.

Keep covered for 24 hr and then remove shade cloth and polypropylene containers.

Resume normal plant maintenance.

When plants have finished flowering cover each pot with a ciber plant sleeve.

After plants are completely dry, collect seed and place into 2.0 ml micro tubes and store in 100-place cryogenic boxes.

Recipes:

0.2% Phytagar
2 g Phytagar
1 L nanopure water
Shake until Phytagar suspended
Autoclave 20 min YEB (for 1 L)
5 g extract of meat
5 g Bacto peptone
1 g yeast extract
5 g sucrose
0.24 g magnesium sulfate
While stirring, add ingredients, in order, to 900 ml nanopure water
When dissolved, adjust pH to 7.2
Fill to 1 L with nanopure water
Autoclave 35 min Infiltration Medium (IM) (for 1 L)
2.2 g MS salts
50 g sucrose
5 ul BAP solution (stock is 2 mg/ml)
While stirring, add ingredients in order listed to 900 ml nanopure water
When dissolved, adjust pH to 5.8.
Volume up to 1 L with nanopure water.
Add 0.02% Silwet L-77 just prior to resuspending *Agrobacterium*

High Throughput Screening—T1 Generation

1. Soil Preparation. Wear gloves at all times.
    In a large container, mix 60% autoclaved SunshineMix #5 with 40% vermiculite.
    Add 2.5 Tbsp of Osmocote, and 2.5 Tbsp of 1% granular Marathon per 25 L of soil.
    Mix thoroughly.

2. Fill Com-Packs With Soil.
    Loosely fill D601 Com-Packs level to the rim with the prepared soil.
    Place filled pot into utility flat with holes, within a no-hole utility flat.
    Repeat as necessary for planting. One flat set should contain 6 pots.

3. Saturate Soil.
    Evenly water all pots until the soil is saturated and water is collecting in the bottom of the flats.
    After the soil is completely saturated, dump out the excess water.

4. Plant the Seed.

5. Stratify the Seeds.
    After sowing the seed for all the flats, place them into a dark 4° C. cooler.
    Keep the flats in the cooler for 2 nights for WS seed. Other ecotypes may take longer. This cold treatment will help promote uniform germination of the seed.

6. Remove Flats From Cooler and Cover With Shade Cloth. (Shade cloth is only needed in the greenhouse)
    After the appropriate time, remove the flats from the cooler and place onto growth racks or benches.
    Cover the entire set of flats with 55% shade cloth. The cloth is necessary to cut down the light intensity during the delicate germination period.
    The cloth and domes should remain on the flats until the cotyledons have fully expanded. This usually takes about 4–5 days under standard greenhouse conditions.

7. Remove 55% Shade Cloth and Propagation Domes.
    After the cotyledons have fully expanded, remove both the 55% shade cloth and propagation domes.

8. Spray Plants With Finale Mixture. Wear gloves and protective clothing at all times.
    Prepare working Finale mixture by mixing 3 ml concentrated Finale in 48 oz of water in the Poly-TEK sprayer.
    Completely and evenly spray plants with a fine mist of the Finale mixture.
    Repeat Finale spraying every 3–4 days until only transformants remain. (Approximately 3 applications are necessary.)
    When satisfied that only transformants remain, discontinue Finale spraying.

9. Weed Out Excess Transformants.

Weed out excess transformants such that a maximum number of five plants per pot exist evenly spaced throughout the pot.

GFP Assay

Tissues are dissected by eye or under magnification using INOX 5 grade forceps and placed on a slide with water and coversliped. An attempt is made to record images of observed expression patterns at earliest and latest stages of development of tissues listed below. Specific tissues will be preceded with High (H), Medium (M), Low (L) designations.

| | |
|---|---|
| Flower | Pedice, I receptacle, nectary, sepai, petal, filament, anther, pollen, carpel, style, papillaec, vascular, epidermis, stomata, trichome |
| Silique | Stigma, style, carpel, septum, placentae, transmitting tissue, vascular, epidermis, stomata, abscission zone, ovule |

-continued

| | |
|---|---|
| Ovule | Pre-fertilization: inner integument, outer integument, embryo sac, funiculus, chalaza, micropyle, gametophyte<br>Post-fertilization: zygote, inner integument, seed coat, primordial, chalaza, micropyle, early endosperm, mature endosperm, embryo |
| Embryo | Suspensor, preglobular, globular, heart, torpedo, late, mature, provascular, hypophysis, radicle, cotyledons, hypocotyl |
| Stem | epidermis, cortex, vascular, xylem, phloem, pith, stomata, trichome |
| Leaf | Petiole, mesophyll, vascular, epidermis, trichome, primordial, stomata, stipule, margin |

T1 Mature: These are the T1 plants resulting from independent transformation events. These are screened between stage 6.50–6.90 (means the plant is flowering and that 50–90% of the flowers that the plant will make have developed) which is 4–6 weeks of age. At this stage the mature plant possesses flowers, siliques at all stages of development, and fully expanded leaves. We do not generally differentiate between 6.50 and 6.90 in the report but rather just indicate 6.50. The plants are initially imaged under UV with a Leica Confocal microscope. This allows examination of the plants on a global level. If expression is present, they are imaged using scanning laser confocal micsrocopy.

T2 Seedling: Progeny are collected from the T1 plants giving the same expression pattern and the progeny (T2) are sterilized and plated on agar-solidified medium containing M&S salts. In the event that there was no expression in the T1 plants, T2 seeds are planted from all lines. The seedlings are grown in Percival incubators under continuous light at 22° C. for 10–12 days. Cotyledons, roots, hypocotyls, petioles, leaves, and the shoot meristem region of individual seedlings were screened until two seedlings were observed to have the same pattern. Generally found the same expression pattern in the first two seedlings. However, up to 6 seedlings were screened before "no expression pattern" was recorded. All constructs are screened as T2 seedlings even if they did not have an expression pattern in the T1 generation.

T2 Mature: The T2 mature plants were screened in a similar manner to the T1 plants. The T2 seeds were planted in the greenhouse, exposed to selection and at least one plant screened to confirm the T1 expression pattern. In instances where there were any subtle changes in expression, multiple plants were examined and the changes noted in the tables.

T3 Seedling: This was done similar to the T2 seedlings except that only the plants for which we are trying to confirm the pattern are planted.

Image Data:

Images are collected by scanning laser confocal microscopy. Scanned images are taken as 2-D optical sections or 3-D images generated by stacking the 2-D optical sections collected in series. All scanned images are saved as TIFF files by imaging software, edited in Adobe Photoshop, and labeled in Powerpoint specifying organ and specific expressing tissues.

Instrumentation:

Microscope

Inverted Leica DM IRB

Fluorescence filter blocks:

Blue excitation BP 450–490; long pass emission LP 515.

Green excitation BP 515–560; long pass emission LP 590

Objectives

HC PL FLUOTAR 5x/0.5

HCPL APO 10x/0.4 IMM water/glycerol/oil

HCPL APO 20x/0.7 IMM water/glycerol/oil

HCXL APO 63x/1.2 IMM water/glycerol/oil

Leica TCS SP2 Confocal Scanner

Spectral range of detector optics 400–850 nm.

Variable computer controlled pinhole diameter.

Optical zoom 1–32x.

Four simultaneous detectors:

Three channels for collection of fluorescence or reflected light.

One channel for transmitted light detector.

Laser sources:

Blue Ar 458/5 mW, 476 nm/5 mW, 488 nm/20 mW, 514 nm/20 mW.

Green HeNe 543 nm/1.2 mW

Red HeNe 633 nm/10 mW

Results

The section in Table 1 entitled "The spatial expression of the promoter-marker-vector" presents the results of the GFP assays as reported by their corresponding cDNA ID number, construct number and line number. Unlike the microarray results, which measure the difference in expression of the endogenous cDNA under various conditions, the GFP data gives the location of expression that is visible under the imaging parameters. Table 3 summarizes the results of the spatial expression results for each promoter.

Explanation of Table 1

Table 1 includes various information about each promoter or promoter control element of the invention including the nucleotide sequence, the spatial expression pattern associated with each promoter and the corresponding results from different expression experiments.

TABLE 1

Promoter Expression Report # 1

Promoter Tested In: Arabidopsis thaliana, WS ecotype
Spatial expression summary:
Flower        (M)upper part of receptacle, (M)base of ovary
Flower        (M)pedicel, (M)receptacle, silique, (M)carpel

TABLE 1-continued

Promoter Expression Report # 1

Stem                    (H)cortex, (H)pith
Hypocotyl               (M)cortex
Primary Root            (H)vascular, (M)cap Observed expression pattern: T1 mature: Expression was specific to the top of the receptacle and base of gynoecium of immature flowers. Not detected in any other organs. T2 seedlings: No expression observed. Appended Notes: T2 mature: In addition to the original expression observed in T1 mature plants, expression is observed in pith cells near the apex of the inflorescence meristem and stem-pedicel junctions. T3 seedling: Expressed at cotyledon-hypocotyl junction, root vascular, and root tip epidermis. This expression is similar to the original 2-component line CS9107 (see T3 seedling, expression).
Expected expression pattern: The candidate was selected from a 2-component line with multiple inserts. The target expression pattern was lateral root cap and older vascular cells, especially in hypocotyls.
Appended notes: T2 mature and T3 seedling expression similar to original 2-component line.
Selection Criteria: Arabidopsis 2-component line CS9107 (J1911) was selected to test promoter reconstitution and validation. T-DNA flanking sequences were isolated by TAIL-PCR and the fragment cloned into pNewBin4-HAP1-GFP vector to validate expression.
Gene: 2 kb seq. is in 7 kb repeat region on Chr.2 where no genes are annotated.
Appended Notes: Alignment of promoter sequence to genome reveals that it is approximately 2 kb upstream of gene "At2g23300"product= "putative receptor-like protein kinase"
GenBank: NM 127894 Arabidopsis thaliana leucine-rich repeat transmembrane protein kinase, putative (At2g23300) mRNA, complete cds gi|18400232|ref|NM 127894.1|[18400232]
Source Promoter Organism: Arabidopsis thaliana WS
Vector:                 pNewBin4-HAP1-GFP
Marker Type:            X GFP-ER
Generation Screened:    X T1 Mature X T2 Seedling   X T2 Mature X T3 Seedling T1 Mature Plant Expression   Organs/Tissues screened Events Screened: n =3        Events Expressing: n =2
GFP Expression Detected
X Flower      ☐pedicel M receptacle ☐nectary ☐sepal ☐petal ☐filament ☐anther ☐pollen ☐carpel ☐style
              ☐papillae ☐vascular ☐epidermis ☐stomata ☐trichome
X Silique     ☐stigma ☐style M carpel ☐septum ☐placentae ☐transmitting tissue ☐vascular ☐epidermis
              ☐stomata ☐abscission zone
☐ Ovule       Pre-fertilization: ☐inner integument ☐outer integument ☐embryo sac
              ☐funiculus ☐chalaza ☐micropyle ☐gametophyte
              Post-fertilization: ☐zygote ☐seed coat ☐primordia ☐chalaza ☐micropyle ☐early endosperm
              ☐mature endosperm
☐Embryo       ☐suspensor ☐preglobular ☐globular ☐heart ☐torpedo ☐late ☐mature ☐provascular
              ☐hypophysis ☐radicle ☐cotyledons ☐hypocotyl
☐Stem         ☐epidermis ☐cortex ☐vascular ☐xylem ☐phloem ☐pith ☐stomata ☐trichome
☐Leaf         ☐petiole ☐mesophyll ☐vascular ☐epidermis ☐trichome ☐primordia ☐stomata ☐stipule
              ☐margin
X in Sepal (Se), Receptacle (Re), Pedicel (Pd) in the upper part of the receptacle of the flower T2 Seedling Expression       Tissues Screened Events Screened:             Events Expressing
No GFP Expression Detected
☐Hypocotyl                   ☐epidermis ☐cortex ☐vascular ☐xylem ☐phloem ☐stomata
☐Cotyledon                   ☐mesophyll ☐vascular ☐epidermis ☐trichome ☐margin ☐stomata
☐Rosette Leaf                ☐mesophyll ☐vascular ☐epidermis ☐trichome ☐petiole ☐primordia
                             ☐stomata ☐stipule ☐margin
☐Primary Root                ☐epidermis ☐trichoblast ☐atrichoblast ☐cortex ☐endodermis
                             ☐vascular ☐xylem ☐phloem ☐pericycle ☐quiescent ☐columella ☐cap
                             ☐root hairs
☐Lateral root                ☐epidermis ☐initials ☐flanking cells ☐vascular ☐cap
☐Shoot apical meristem       ☐SAM ☐epidermis T2 Mature Plant Expression T2 Expression Frequency: Plants expressing / Plants screened
Event-01: 1/1   Event-02: 1/1 stronger expression seen in this line.
☐Scheduled
☐T2 Mature tissue expressions similar to T1 expression data (data not shown).
X T2 Mature tissue expression (if different expression pattern).
Original expression pattern observed and new expression not observed in previous generation.
X Flower    M pedicel M receptacle ☐nectary ☐sepal ☐petal ☐filament ☐anther ☐pollen ☐carpel
            ☐style ☐papillae ☐vascular ☐epidermis ☐stomata ☐trichome
X Silique   ☐stigma ☐style M carpel ☐septum ☐placentae ☐transmitting tissue ☐vascular ☐epidermis
            ☐stomata ☐abscission zone
☐Ovule      Pre-fertilization: ☐inner integument ☐outer integument ☐embryo sac
            ☐funiculus ☐chalaza ☐micropyle ☐gametophyte
            Post-fertilization: ☐zygote ☐seed coat ☐primordia ☐chalaza ☐micropyle ☐early
            endosperm ☐mature endosperm
☐Embryo     ☐suspensor ☐preglobular ☐globular ☐heart ☐torpedo ☐late ☐mature ☐provascular
            ☐hypophysis ☐radicle ☐cotyledons ☐hypocotyl

TABLE 1-continued

Promoter Expression Report # 1

X Stem     ☐epidermis H cortex ☐vascular ☐xylem ☐phloem H pith ☐stomata ☐trichome
☐Leaf     ☐petiole ☐mesophyll ☐vascular ☐epidermis ☐trichome ☐primordia ☐stomata ☐stipule
    ☐margin
X in Pedicel (Pd) and Stem (Sm) in the inflorescence meristem
X in Epidermis (Ep), Pedicel (Pd) and Stem (Sm) in the pedicel junction of the stem
X in the flower T3 Seedling Expression Events Screened:     Events Expressing:
T3 seedling expression frequency: Plants expressing / Plants screened
Event-01: 1/1   Event-02: 1/1 stronger expression seen in this line.
☐Scheduled
☐T3 Seedling tissue expressions similar to T2 seedling expression (data not shown)
☐T3 Seedling tissue expression (if different expression pattern than T2 seedling).
GFP Expression Detected
X Hypocotyl     ☐epidermis H cortex ☐vascular ☐xylem ☐phloem ☐stomata
☐Cotyledon     ☐mesophyll ☐vascular ☐epidermis ☐trichome ☐margin ☐stomata
☐Rosette Leaf     ☐mesophyll ☐vascular ☐epidermis ☐trichome ☐petiole ☐primordia
    ☐stomata ☐stipule ☐margin
X Primary Root     ☐epidermis ☐trichoblast ☐atrichoblast ☐cortex ☐endodermis
    H vascular ☐xylem ☐phloem ☐pericycle ☐quiescent ☐columella
    H cap ☐root hairs
☐Lateral root     ☐epidermis ☐initials ☐flanking cells ☐vascular ☐cap
☐Shoot apical meristem     ☐SAM ☐epidermis Expression is similar to original Two component line CS9107 (J1911).

X in the junction of the Cotyledons (Co), the Cotyledons and the Hypocotyl (Hy)
X in the vasculature of the root
X in the Epidermis of the root tip Promoter utility Trait-Subtrait Area:     Among other uses this promoter sequence is useful to improve:
    PG&D-abscission, plant size
    Nutrients-nitrgen utilization
Utility: Promoter useful in fruit abscission. Sinces expression overlaps the base of the gynoecium, it
will be useful to overexpress genes thought to be important in supplying nutrients to the gynoecium or
genes important in development of carpel primordia.

Construct:     YP0001
Promoter Candidate I.D:     13148168 (Old ID: C59107-1)
cDNA I.D:     12736079
T1 lines expressing (T2 seed): SR00375-01,-02,-03,-04,-05

Sequence (SEQ ID NO: 1):

```
CTGCATTCACACATATTTTGGGCTCTCACGTGTTTGTGAATTTAATATATT
TGACTACACGATCTTTCAACGTATGAAAAAGTTTTATACTACTATTTTCGT
TTGAGTGGGAAATAAACAAATGATAGCTACAGTTATCTATATGGTATAATT
TTACACTTTTATAACTAATAATGATGAGTGATGACAATCGAGTGTCGGATA
TAACAGGCCAACAAGTGGAATGGACTTATGTAACTTTTTAATCACGGGATT
AAATCACGTAACCCAATGTCCTAATTGGTATTTAATTTTGATTATCTCGAT
GCTACATATTGTCATAGGACTCATATCTTTGATCACGTGCCGCTACCAATC
CAGACATTTTAGTATACAAAAAAAAGAAGATACAAACTTAAGATATGGAA
TATATATCAGAACTATCAGTTTTAGACTTTAATAATTCGAATTGAATAACT
ACGATCAATATATAAATTGGCAAATAGATTGGTCAATTGTAGTGCAAGAA
TTTGTGAACTTTATTACAGTACGAAGAGAGTAAGAGAAGCAAGATCCGGTT
TTTAGGCAACAAGTAACATTTTTGAGTTCAGAGAGTTTGCTTCTTACTTTA
AGTTACGTCACTACAAAAGCCAAGTTCCTACTTCTTAGGTCTAAAGTCAAT
TTTCGAATATTCAGAAAAATTGTACTCTACTAGATCGAATAGTTTTCACCG
GTGAAACGATATATAAATGAAGACTACAATATTTTTTAATTTTTTTAAGCG
TATGAGTTCTAGACCTTTGGCACGTAAATTTCTCCGGTACCTGGGACCAAT
CGTTGATAATATCACGTTTAAGATTTAATCATCCATCCCAAGTAGAGTTGA
ACTAGTAACCTTGAGCACTTTTTCTCGAGACAACTAAACCATCATCCACTT
AGTGCAATAAAGCGTCATTCTTTTTTTCTTTTCAAAAATTCGTATTTAAT
TTTAATTTATTAAAAATATTTCTTTTGTTTTAAATTGGGACAGAATTATCA
TTTAACATATTTAAAATTTATATTTTTAATTAAAAATAGGGTAAAATATAT
TTTTCAAACAAAAATTCAAAAATAGGGCAATTTTCAAAATCATCCATTCTT
AAATCTAAAGTCGGCTACAGTCTTTTCGTTGTTTTGTTGCTAATTTCAATT
TATATACATGCAAATTACAAAATATAATAGTTTTTGGGGGATAATTATCTT
CTTGCGCCTTTTTATTAAATTAATATGCTCATATATGCAGTTCTTACAATTA
ATATAACTAGGGTTTTAAATTTCAATATCGAGTTGACAAAATGAATTGTTT
```

-continued

ACAAGTTTTTTCTTTTCAATATGCATTGTTCATCACGTATTCGTAGTGAT

GCAAAAACAAACTATAAATTATAATTGCACTAGTGAGATTAGCAAGAAGTG

TTATAAATTAGAATAAACGGAACTATCAAACTGTGTTATGTACACCATTTA

TTTTTGTTAAAGAATATGTGTAGTAGTTAGAAAACTGATCAAATTAAACTG

AAAATTCACATTACGGAGATCAAGTTACATTGTCTATTGATGAAAAAAACA

AAATAAATCCAAATGGCACTAAAAGTTGTAGAAATTGAAAGAAGAAAATAG

ATTTTTGTCTAGGAATAAAAGTCAAAATGGGAAAGACAAAAAAAAGAGAGG

-continued

CAAATAAGCAGTGATGGAGCTAAAGCAACGCTTTACTCTTTTAATTATGAA

TTATTTGATTTGACCTCCACTCGCCTGGCTTTTTTTGGTTGTTCTTTATAG

AAAAGTAAAATAACACAATTAGCACATAACATGAGTTATCGAGAAACCAAT

TCTCTTTGTGGTGTTTTAGTTAATTTCTATAACTTATGAAACCATTTTCTC

AGTTTATCATGATAATTGATCCTCTATTTAAAACCCTAAAGTTTATATTTT

GTTTGTTCAAACACAGTCGCCATTGCACTGGGATCCAACAATGTCCTCCGA

CTCGTCCAAGATCAAGAGGAAGCGGAACCGCATnCCTTTAACGAAGGCGA

| Promoter Expression Report # 2 | |
|---|---|
| Promoter Tested In: Arabidopsis thaliana, WS ecotype | |
| Spatial expression summary: | |
| Ovule | Pre-fertilization: (H)inner integument |
| | Post-fertilization: (M)seed coat, (M)endothelium |
| Root | (H)epidermis, (H)atrichoblast |
| Cotyledons | (L)epidermis |
| Observed expression pattern: T1 mature: GFP expression exists in the inner integument of ovules. T2 seedling: Expression exists in root epidermal atrichoblast cells. Appended notes: T2 mature: Same expression exists as T1 mature. T3 seedlings: Same expression, plus additional weak epidermal expression was observed in cotyledons. | |
| Expected expression pattern: flower buds, ovules, mature flower, and silique | |
| Selection Criteria: Arabidopsis 2-component line CS9180(J2592). | |
| Gene: | water channel-like protein "major intrinsic protein (MIP) family |
| GenBank: | NM 118469 Arabidopsis thaliana major intrinsic protein (MIP) family (At4g23400) mRNA, complete cds gi|30686182|ref|NM 118469.21|[30686182] |
| Source Promoter Organism: Arabidopsis thaliana WS | |
| Vector: | pNewBin4-HAP1-GFP |
| Marker Type | X GFP-ER |
| Generation Screened: | X T1 Mature    X T2 Seedling   X T2 Mature  X T3 Seedling |

| T1 Mature Plant Expression Organs/Tissues screened | |
|---|---|
| Events Screened: n =5     Events Expressing: n =3 | |
| GFP Expression Detected | |
| ☐Flower | ☐pedicel ☐receptacle ☐nectary ☐sepal ☐petal ☐filament ☐anther ☐pollen ☐carpel ☐style ☐papillae ☐vascular ☐epidermis ☐stomata ☐trichome |
| X Silique | ☐stigma ☐style ☐carpel ☐septum ☐placentae ☐transmitting tissue ☐vascular ☐epidermis ☐stomata ☐abscission zone H ovule |
| X Ovule | Pre-fertilization: H inner integument ☐outer integument ☐embryo sac ☐funiculus ☐chalaza ☐micropyle ☐gametophyte |
| | Post-fertilization: ☐zygote ☐inner integument ☐outer integument M seed coat ☐primordia ☐chalaza ☐micropyle ☐early endnsperm ☐mature endosperm ☐embryo |
| Embryo | ☐suspensor ☐preglobular ☐globular ☐heart ☐torpedo ☐late ☐mature ☐provascular ☐hypophysis ☐radicle ☐cotyledons ☐hypocotyl |
| ☐Stem | ☐epidermis ☐cortex ☐vascular ☐xylem ☐phloem ☐pith ☐stomata ☐trichome |
| ☐Leaf | ☐petiole ☐mesophyll ☐vascular ☐epidermis ☐trichome ☐primordia ☐stomata ☐stipule ☐margin |
| X in the Endosperm (En) and Inner integument (Ii) of the fertilized Ovule (Ov) | |

| T2 Seedling Expression | Tissues Screened |
|---|---|
| Events Screened: n =5     Events Expressing: n =1 | |
| GFP Expression Detected | |
| ☐Hypocotyl | ☐epidermis ☐cortex ☐vascular ☐xylem ☐phloem ☐stomata |
| ☐Cotyledon | ☐mesophyll ☐vascular ☐epidermis ☐trichome ☐margin ☐stomata |
| ☐Rosette Leaf | ☐mesophyll ☐vascular ☐epidermis ☐trichome ☐petiole ☐primordia ☐stomata ☐stipule ☐margin |
| X Primary Root | H epidermis ☐trichoblast H atrichoblast ☐cortex ☐endodermis ☐vascular ☐xylem ☐phloem ☐pericycle ☐quiescent ☐columella ☐cap ☐root hairs |

Promoter Expression Report # 2

☐Lateral root  ☐epidermis ☐initials ☐flanking cells ☐vascular ☐cap
☐Shoot apical meristem  ☐SAM ☐epidermis
X in the root transition zone of the Root (Rt).
X in Atrichoblast (At) within the root differentiation zone of the root.

T2 Mature Plant Expression

Plants expressing / Plants screened
Event-01: Did not growEvent-02: 1/1
☐Scheduled
X T2 Mature tissue expressions similar to T1 expression data.
☐T2 Mature tissue expression (if different expression pattern).
X in the Inner Integument (Ii) of developing ovules at approximately late heart stage embryo
X in the Endothelium (Ed) which is derived from the inner integuments during the seed maturation stage.

T3 Seedling Expression

Events Screened: n = 1    Events Expressing: n =1
Seedlings expressing / Seedlings screened
Event-01: Not screened    Event-02: 1/1
☐Scheduled
☐T3 Seedling tissue expressions similar to T2 seedling expression (data not shown).
X T3 seedling tissue expression (if different expression pattern).
Weak epidermal expression in cotyledons was not observed in T2 seedling screen

Promoter utility

Trait-subtrait Area:    Among other uses this promoter sequence is useful to improve:
   Seed- seed size, seed enhancement
   Yield- total yield
   Water use efficiency- heat, water potential, drought, moisture stress
   Nutrients- nitrogen efficiency, phosphate efficiency
Utility: Promoter could be used to misexpress any genes playing a role in seed size. It also has utility in misexpressing genes important in root hair initiation to try to get the plant to generate more or fewer root hairs to enhance nutrient utilization and drought tolerance.
Notes: Pigment deposition occurring in the endothelium gives Arabidopsis seeds their characteristic brown color. Seed coat pigments in Arabidopsis are predominantly flavonoids or proanthocyanidins. Proanthocyanidins (PAs) accumulate as colorless compounds during the early steps of embryogenesis and have been shown to participate in the maintenance of seed coat imposed dormancy as well as in seed longevity during storage. Nesi, N, et.al., The Plant Cell, Vol. 14, 2463-2479, October 2002.

Construct:    YP0007
Promoter Candidate I.D:    13148318 (Old ID: CS9180-3 )
cDNA I.D:    12703041 (Old I.D: 12332468)
T1 lines expressing (T2 seed): SR00408-01,-02,-05

Sequence (SEQ ID NO: 2):

```
AGCAGAACAACTATATTTATTGTGTCACATAAATCTGAGATCATTTATAAC
CACCAAAGAACCTATACACAGTAAATGACAAATGTATCTCCCTCTATCTCT
ATTGCCCATATGTAGATGCTAAAGTAAGATTTCTCTTTTTTTTAATGTACT
TTTTTTTGTATAAAGTATATTCCATAAGAAAAAGGAAAAGCTTGTTTATGG
ATCAATTGACCCCAAAAAAAGTTTTTAGATCAAAGCCCAATATAAAAAAAA
AACACAGTAGTGACACAAAGGAACTTAAATAAACCATGAATTGATCTATAA
ACAGTAGAGATCGATAAGGCGAACATTTTCCATGTGAAGTGTCTTCTTTCA
TCTATAATATTTTTGACATCCAATAATTTCCTCTATAATATCATTCACATA
ATTGATAGAAACATTATGTTAGAATTGTCCACATCATTTGAGCTGTAATAT
ATTCTGTTTTAACAAATTATATGGTAGTTGCTTAATCTTATGTCCATCTTC
TTCTATGCATCGTTTTCGCGCCTAGTTGTCCAGTCCATTTCAACTACCTAC
CTCTAATTCTTATCTTAAAACAACATTTTTTAATTTAAGTATTATGCTCAA
AGACTAACTAGATAGAAAACCGTTATTAAACATTAAACGAATTAAAAGTCT
TACATGGAAAATGTAGGTTTATAAACCACGAGTTATGATTGACAATAAAAA
AAATGCAAATCATCAATCAAAAGAGACTTGAGTGCGACTCTATATCAACCA
TTGCAATTAAAATTATCTATCACAAAAATTTTAGACAGATTAAGTTAATTT
AGTCTAAATTCACTAATTTATTTTCTATAATTAGTAATTAACTATATTTAT
TTATTTACACATTTTCTGATAATTTAGAAATTTGCATGAATAACAAATATA
AGATTTTGGAAATTAGTAGCAAATTTAATTAATAATTATTTTTGCCTAAAT
GAACCAAACTATAAAACCTCCACATACACCAGTCATCAAATTTACAGAGAC
AACAAACTAAAGTTGGTGGTGATAGAGTGAGAGAGAAACACCATTGCACTG
GGATCCAACAATGTCCTCCGACTCGTCCAAGATCAAGAGGAAGCGGAACCG
CATCCCG
```

| Promoter Expression Report # 3 |
|---|

Promoter Tested In: Arabidopsis thaliana, WS ecotype
Spatial expression summary:
| | |
|---|---|
| Leaf | (L)vascular |
| Hypocotyl | (L)epidermis |
| Primary Root | (H)epidermis, (H)cap |
| Lateral root | (H)epidermis, (H)cap |

Observed expression pattern: T1 mature: Low GFP expression was detected throughout the vasculature of leaves of mature plants. T2 seedling: No expression was detected in the vasculature of seedlings. Appended observations: T2 mature: Transformation events which expressed as T1 plants were screened as T2 plants and no expression was detected. This line was re-screened as T1 plants and leaf expression was not detected in 3 independent events. T3 seedling: New expression was observed in T3 seedlings which was not observed in T2 seedlings. Strong primary and lateral root tip expression and weak hypocotyl epidermal expression exists.

| | |
|---|---|
| Expected expression pattern: | High in leaves. Low in tissues like roots or flowers |
| Selection Criteria: | Arabidopsis Public; Sauer N. EMBO J 1990 9:3045-3050 |
| Gene: | Glucose transporter (Sugar carrier) STP1 |
| GenBank: | NM 100998Arabidopsis thaliana glucose transporter (At1g11260) mRNA, complete cds, gi|30682126|ref|NM 100998.2|[30682126] |
| Source Promoter Organism: | Arabidopsis thaliana WS |
| Vector: | pNewBin4-GFP Direct fusion construct |
| Marker Type: | X GFP-ER |
| Generation Screened: | X T1 Mature X T2 Seedling X T2 Mature XT3 Seedling |

| T1 Mature Plant Expression | Organs/Tissues screened |
|---|---|

First T1 Screen: Events Screened: n = 5   Events Expressing: n = 5 (old protocol)
Second T1 screen: Events Screened: n = 3  Events Expressing: n = 0 (new protocol)
GFP Expression Detected
☐Flower    ☐pedicel ☐receptacle ☐nectary ☐sepal ☐petal ☐filament ☐anther ☐pollen ☐carpel
           ☐style ☐papillae ☐vascular ☐epidermis ☐stomata ☐trichome
☐Silique   ☐stigma ☐style ☐carpel ☐septum ☐placentae ☐transmitting tissue ☐vascular ☐epidermis
           ☐stomata ☐abscission zone
☐Ovule     Pre-fertilization: ☐inner integument ☐outer integument ☐embryo sac
           ☐funiculus ☐chalaza ☐micropyle ☐gametophyte
           Post-fertilization: ☐zygote ☐seed coat ☐primordia ☐chalaza ☐micropyle ☐early
           endosperm ☐mature endosperm
☐Embryo    ☐suspensor ☐preglobular ☐globular ☐heart ☐torpedo ☐late ☐mature ☐provascular
           ☐hypophysis ☐radicle ☐cotyledons ☐hypocotyl
☐Stem      ☐epidermis ☐cortex ☐vascular ☐xylem ☐phloem ☐pith ☐stomata ☐trichome
X Leaf     ☐petiole ☐mesophyll L vascular ☐epidermis ☐trichome ☐primordia ☐stomata ☐stipule
           ∞margin X in the Vascular (Vs) of the leaf

| Table 2. T2 Seedling Expression | Tissues Screened |
|---|---|

Seedlings expressing/ Seedlings screened:
Event-01: No data    Event-02: No data
No GFP Expression Detected
| | |
|---|---|
| ☐Hypocotyl | ☐epidermis ☐cortex ☐vascular ☐xylem ☐phloem ☐stomata |
| ☐Cotyledon | ☐mesophyll ☐vascular ☐epidermis ☐trichome ☐margin ☐stomata |
| ☐Rosette Leaf | ☐mesophyll ☐vascular ☐epidermis ☐trichome ☐petiole ☐primordia |
| | ☐stomata ☐stipule ☐margin |
| ☐Primary Root | ☐epidermis ☐trichoblast ☐atrichoblast ☐cortex ☐endodermis |
| | ☐vascular ☐xylem ☐phloem ☐pericycle ☐quiescent ☐columella |
| | ☐cap ☐root hairs |
| ☐Lateral root | ☐epidermis ☐initials ☐flanking cells ☐vascular ☐cap |
| ☐Shoot apical meristem | ☐SAM ☐epidermis |

T2 Mature Plant Expression

Seedlings expressingf Seedlings screened:
Event-01: 0/4    Event-02: 0/2
☐Scheduled
☐T2 Mature tissue expressions similar to T1 expression data (data not shown).
☐T2 Mature tissue expression (if different expression pattern).
X No expression detected T3 Seedling Expression Seedlings expressing/ Seedlings screened:
Event-01: 2/3    Event-02:1/3
X Scheduled
☐T3 Seedling tissue expressions similar to T2 seedling expression (data not shown).
X T2 Seedling tissue expression (if different expression pattern).

Promoter Expression Report # 3

NEW- Expression pattern not observed in previous generation.
Expression detected
X Hypocotyl                L epidermis ☐cortex ☐vascular ☐xylem ☐phloem ☐stomata
☐Cotyledon                 ☐mesophyll ☐vascular ☐epidermis ☐trichome ☐margin ☐stomata
☐Rosette Leaf              ☐mesophyll ☐vascular ☐epidermis ☐trichome ☐petiole ☐primordia
                           ☐stomata ☐stipule ☐margin
X Primary Root             H epidermis ☐trichoblast ☐atrichoblast ☐cortex ☐endodermis
                           ☐vascular ☐xylem ☐phloem ☐pericycle ☐quiescent ☐columella
                           H cap ☐root hairs
X Lateral root             H epidermis ☐initials ☐flanking cells ☐vascular H cap
☐Shoot apical meristem    ☐SAM ☐epidermis
X in the Epidermis of the Hypocotyl (Hy)
X in the Vasculature (Vs) of the root
X in the root tip and lateral root tip Promoter utility Trait-subtrait Area:   Among other uses this promoter sequence could be useful to improve:
                       Source- C/N partitioning, transport of amino acids, source enhancement
                       Yield- Total yield
                       Quality- Amino acids, carbohydrates, Optimize C3-C4 transition
Utility: Sequence most useful to overexpress genes important in cascular maintenance and transport
in and out of the phloem and xylem.
Notes: Some weak vascular expression was observed in T1 that was not present in T2. The
expression was also not observed in new T1 lines that were screened. The seedlings in the T3 do
show some epidermal expression particulary in the root tip.

Construct:                  G0013
Promoter Candidate I.D.:    1768610 (Old ID: 35139302)
cDNA ID:                    12679922 (Old IDs:123282 10, 4937586.)
T1 lines expressing (T2 seed): G00013-01,-02,-03,-04,-05

Sequence (SEQ ID NO: 3):

ATCTTGTGATACACAATTTATTACTATTTGGTACATTTTGAAGTATTTGTT

TTTGCATGATATATGACGTTAATTTGAACTGATATTAGTCAATTTATGGGT

ACAAAAGTTGAAAGTTTAGAGCACTATGTTGGATTTATTAAAAATGATATC

ATACAATGGTTCAATATATATATATTTTTTTCCACGTTTTTAATAACATTT

TTGTAAACAAGTCTTCTACTATTGTCTTTATTGTTAATGAGTTTCTAGTAC

CTAATTAGGAATTTTGAGGATATACGATACATTAATGAGTTACATTATCCC

GAAAACAAATCTTGAAAACGAACAAAGATAATTTGGACATTACTCGTTAT

GTATACGTATGGAATTGGATAGAGCCGTTGAACCATCAAGTGGGTCTTCAA

GTCAACGAACTGAATTTGATTTTACACTCATGTACATCGGCCACAATTTTA

TTCACACACTACTAACACCTCTGGTGTCCACTTTTTTCTTTCTCTAGATTG

ATGTGTTAAGATTTTTGTTGCAATTCATTTATTCAGGTATTTTTATATATA

TATATATATAAATTAGAATAAACTAATTTAAAGAAAGATATAGCAATTATG

TTTCACATTTTAACATTCTCAATCATTTATAAAACTAATGTGGTGATGAAT

GGTATATATATATATATATATATATATATACATATATATATTTTGTTGT

GAACTAATGGTAAATATTTAAAATAAGACATACGTACATAAATCCACGGGC

TCTTAAAGTCATGATGCGGTTAATAAATGTTCACATAACGGTAACCAAGTG

GCTCAAAATCATGAAACAACGTCACATAATTTATCTTATAATGTGGATAAT

TAGTACCGCATTATTTGTAAGAAAATTAAATTAATTATAGATTCACAGCTA

AGAAAATACGAAAAGACAGCTCAACACTTTTCCACTTCTATTCCCCACTGT

CTATATAACTCTGATAAATAATCTCTGATCTCTCCACCATTGCACTGGTCC

AGGAGATAAACAAGA

Promoter Expression Report # 4

Promoter Tested In: Arabidopsis thaliana, WS ecotype
Spatial expression Summary:
Flower            (H)sepal, (L)epidermis
Embryo            (H)suspensor, (H)preglobular, (H)globular, (M)heart, (M)torpedo, (L)late, (L)mature,
                  (L)hypophysis
Ovule             Pre fertilization: (M)outer integument, (I1)funiculus
                  Post fertilization: (M)outer integument, (H)zygote
Embryo            (H)hypocotyl, (H)epidermis, (H)cortex, (H)stipules, (L)lateral root, (H)initials,
                  (H)lateral rootcap -continued

| Promoter Expression Report # 4 |
| --- |

Stem                     (L)epidermis
Observed expression patterns: T1 Mature: Strong expression was seen in 4-cell through heart stage embryo with decreasing expression in the torpedo stage; preferential expression in the root and shoot meristems of the mature embryo. Strong expression was seen in the outer integument and funiculus of developing seed. T2 Seedling: Strong expression was seen in epidermal and cortical cells at the base of the hypocotyl. Strong expression was seen in stipules flanking rosette leaves. Low expression was seen in lateral root initials with increasing expression in the emerging lateral root cap. T2 Mature-Same expression patterns were seen as T1 mature plants with weaker outer integument expression in second event. Both lines show additional epidermal expression at the inflorescence meristem, pedicels and tips of sepals in developing flowers (T2 Mature Plant Expression). T3 seedling expression - same expression

| | |
|---|---|
| Expected expression pattern: | Expression in ovules |
| Selection Criteria: | Greater than 50x up in pi ovule microarray |
| Gene: | Lipid transfer protein-like |
| GenBank: | NM 125323 Arabidopsis thaliana lipid transfer protein 3 (LTP 3) (At5g59320) mRNA, complete cds, gi\|30697205\|ref\|NM 125323.2\|[30697205] |

Source Promoter Organism: Arabidopsis thaliana WS
Vector:                 pNewbin4-HAP1-GFP
Marker Type:       X GFP-ER
Generation Screened:    X T1 Mature    X T2 Seedling    X T2 Mature    X T3 Seedling T1 Mature Plant Expression   Organs/Tissues Screened Events Screened: n = 3     Events Expressing: n = 2
GFP Expression Detected

| | |
|---|---|
| ☐Flower | ☐pedicel ☐receptacle ☐nectary ☐sepal ☐petal ☐filament ☐anther ☐pollen ☐carpel ☐style ☐papillae ☐vascular ☐epidermis ☐stomata ☐trichome |
| ☐Silique | ☐stigma ☐style ☐carpel ☐septum ☐placentae ☐transmitting tissue ☐vascular ☐epidermis ☐stomata ☐abscission zone |
| X Ovule | Pre-fertilization: ☐inner integument H outer integument ☐embryo sac H funiculus ☐chalaza ☐micropyle ☐gametophyte Post-fertilization: ☐zygote ☐seed coat ☐primordia ☐chalaza ☐micropyle ☐early endosperm ☐mature endosperm |
| X Embryo | H suspensor ☐preglobular H globular H heart M torpedo M late L mature ☐provascular H hypophysis ☐radicle ☐cotyledons ☐hypocotyl |
| ☐Stem | ☐epidermis ☐cortex ☐vascular ☐xylem ☐phloem ☐pith ☐stomata ☐trichome |
| ☐Leaf | ☐petiole ☐mesophyll ☐vascular ☐epidermis ☐trichome ☐primordia ☐stomata ☐stipule ☐margin |

X in the Embryo (Em) and Suspensor (Su) of the four day embryo
X in the globular Embryo (Em), the heart stage embryo and the torpedo stage embryo
X in the Embryo (Em) and Outer Integument (Oi) of the ovule
X in the Funiculus (Fn) and Placenta (Pl) of the ovary T2 Seedling Expression    Tissues Screened Seedlings expressing/ Seedlings screened:
Event-01:    2/3  Event-02:1/3
GFP Expression Detected

| | |
|---|---|
| X Hypocotyl | H epidermis H cortex ☐vascular ☐xylem ☐phloem ☐stomata |
| ☐Cotyledon | ☐mesophyll ☐vascular ☐epidermis ☐trichome ☐margin ☐stomata |
| X Rosette Leaf | ☐mesophyll ☐vascular ☐epidermis ☐trichome ☐petiole ☐primordia ☐stomata H stipule ☐margin |
| ☐Primary Root | ☐epidermis ☐trichoblast ☐atrichoblast ☐cortex ☐endodermis ☐vascular ☐xylem ☐phloem ☐pericycle ☐quiescent ☐columella ☐cap ☐root hairs |
| X Lateral root | ☐epidermis H initials ☐flanking cells ☐vascular H cap |
| ☐Shoot apical meristem | ☐SAM ☐epidermis |

X in the Epidermis (Ep) of the hypocotyl
X in the Cotyledon (Co)
X in the Stipules (Ss)
X in the lateral root initial
X in the lateral root cap T2 Mature Plant Expression Plants expressing/ plants screened:
Event-01: 2/3    Event-02: 1/3 weaker line; weak outer integument expression.
Original expression pattern observed including new expression not observed in previous generation.
☐Scheduled
☐T2 Mature tissue expression similar to T1 expression data (data not shown).
☐T2 Mature tissue expression (if different expression pattern).
GFP Expression Detected

| | |
|---|---|
| X Flower | ☐pedicel ☐receptacle ☐nectary H sepal ☐petal ☐filament ☐anther ☐pollen ☐carpel ☐style ☐papillae ☐vascular L epidermis ☐stomata ☐trichome |
| X Silique | ☐stigma ☐style ☐carpel H septum H placentae ☐transmitting tissue ☐vascular ☐epidermis ☐stomata ☐abscission zone H ovule |

| Promoter Expression Report # 4 | |
|---|---|
| X Ovule | Pre-fertilization: ☐inner integument L outer integument ☐embryo sac ☐funiculus ☐chalaza ☐micropyle ☐gametophyte<br>Post-fertilization: H zygote ☐inner integument M outer integument ☐seed coat ☐primordia ☐chalaza ☐micropyle ☐early endosperm ☐mature endosperm |
| X Embryo | H suspensor H preglobular H globular M heart M torpedo L late L mature ☐provascular ☐hypophysis ☐radicle ☐cotyledons D hypocotyl |
| X Stem | L epidermis ☐cortex ☐vascular ☐xylem ☐phloem ☐pith ☐stomata ☐trichome |
| ☐Leaf | ☐petiole ☐mesophyll ☐vascular ☐epidermis ☐trichome ☐primordia ☐stomata ☐stipule ☐margin |
| X in the Epidermis (Ep) of the inflorescence meristem | |
| X in the Epidermis (Ep) of the flower | |
| X in the Epidermis (Ep) of the flower primordial | |
| X in the Epidermis (Ep) of the stem | |
| X in the Placenta (Pl), Embryo (Em) and Funiculus (Fn) of the ovary | |
| X in the Embryo (Em) and Outer Integument (Qi) of the ovule | |
| X in the Mature Embryo | |

T3 Seedling Expression

Seedlings expressing/ Seedlings screened:
Event-01: 1/3   Event-02: 2/3
Same expression pattern observed as in previous generation.
X Scheduled
X T3 Seedling tissue expressions similar to T2 seedling expression (data not shown).
☐T2 Mature tissue expression (if different expression pattern).

Promoter utility

| Trait-subtrait Area: | Among other uses this promoter sequence is useful to improve:<br>Water use efficiency- Moisture stress, water use efficiency, ovule/seed abortion Seed- test weight, seed size Yield- harvest index, total yield. Quality- amino acids, carbohydrate, protein total oil, total seed composition |
|---|---|

| Construct: | YP0097 |
|---|---|
| Promoter Candidate I.D: | 11768657 (Old ID: 35139702) |
| cDNA ID | 12692181 (Old IDs: 12334169, 1021642) |
| T1 lines expressing (T2 seed): | SR00706-01,-02 |

Sequence (SEQ ID NO: 4):

TTCATCTTTATATTTAAGAGTTTAAAAACTGCAACTTTTGTTTTTCTTTCA

CTAAGTCTTATGGCCACAGTTAATTAAAAGCAGATGAAAGGTGGTCCAATG

GAAAAGGAGAATGTGATTGGGCTAGTTGGGAGAGTTCTGATGTCTAGTGTT

GGGTACACGTGTCCGTCAGTTACACATAGCATTAAATCAGACGGCATGTCA

TTATTCAAATCTAGTTCACATAGTACGACTAATAGCTGATAAATTAATGAT

TATACAGCATATGAATTATGAATTCAAAAAAAAAAAAAAATTGAAAATGTT

AAGGAGATGCTATATTTTACAAAATTCATCGCAATGCTTTCTACTAATTTG

CTAAGTGGTCTTCTCCAGTTAGTCTTGTCGATTCCAAGCGATATTATTAAA

TCTTGAAGCATCGCTCAAAGCATTATAGCTTAAGATAACCAAATTGTTATT

AAAAACACCTAGTGAAATTTTTAAATTAAAACAATTTTGATATCTTTGTAA

TATCTAATACTACTCTTTCTGTGTCTAAAAGGATTAATTTTCAAAAATTTC

ACACATATTAAAAAAAAAAAAAAATTACTAGCTAAACAATTTTCAATAATC

ATAAAACAATAGTAACTTAATAATTTTTTTTATTTTCAAAATAGTCCTTC

AAGTTTACAATTCATTTTAGTATTATAATCAACAAAATTTGTATTAAAAAG

TTGGAAAATTAATCTTTGTGGAACAAAAAAATCTAGAAATCATTTTTTAGA

-continued
ATTAGAGAGAGGTTTGATAAAAAAAAATAAAAAAAAATAGAGAGAGGTAGT

ACATACTAAACGATGTGATACTACTATTGACAAAATCTTAATTCTCAGTTT

AGTAGAATAAACTAGAAGGAATGAATGAAGTAAATGCGAATCCAACTACTA

ACAAACCCTACTTAGTCATCATATTTTCCCATATGAAATCCCTATATAAAC

CCATCATCATCTCCCACTTTTTTCATATCCA

| Promoter Expression Report #5 | |
|---|---|
| Spatial expression summary: | |
| Ovule | Pre-fertilization: (L)inner integument<br>Post-fertilization: (H)inner integument, (M)endothelium |
| Primary Root | (H)endodermis |
| Observed expression pattern: | |

GFP is expressed in the endosperm of developing seeds and pericycle cells of seedling roots. GFP level rapidly increases following fertilization, through mature endosperm cellularization. GFP is also expressed in individual pericycle cells.
Appended observations: T1 and T2 mature:

Same expression pattern was observed in T1 and T2 mature plants. Closer examination of the images reveals that GFP is expressed in the endothelium of ovules which is derived from the inner most layer of the

Promoter Expression Report #5 inner integuments. Lower levels of expression can be seen in the maturing seeds which is consistent with disintegration of the endothelium layer as the embryo enters maturity.

T2 seedling:

Expression appears to be localized to the endodermis which is the third cell layer of seedling root not pericycle as previously noted.

T3 seedlings:

Low germination. No expression was observed in the few surviving seedlings.

| | |
|---|---|
| Expected expression pattern: | Expression in ovules |
| Selection Criteria: | Greater than 50× up in pi ovule microarray |
| Gene: | palmitoyl-protein thioesterase |
| GenBank: | NM_124106 *Arabidopsis thaliana* palmitoyl protein thioesterase precursor, putative (At5g47350) mRNA, complete cds gi\|30695161\|ref\|NM_124106.2\| [30695161] |
| Source Promoter Organism: | *Arabidopsis thaliana* WS |
| Vector: | pNewbin4-HAP1-GFP. |
| Marker Type: | (X) GFP-ER |
| Generation Screened: | (X) T1 Mature   (X) T2 Seedling |
| | (X) T3 Mature   (X) T3 Seedling |
| Marker Intensity: | (X) High   ☐ Med   ☐ Low |

T1 Mature Plant Expression    Organs/Tissues Screened
Events Screened: n = 3    Events Expressing: n = 2
GFP Expression Detected

| | |
|---|---|
| ☐Flower | ☐pedicel ☐receptacle ☐nectary ☐sepal ☐petal ☐filament ☐anther ☐pollen ☐carpel ☐style ☐papillae ☐vascular ☐epidermis ☐stomata ☐trichome |
| ☐Silique | ☐stigma ☐style ☐carpel ☐septum ☐placentae ☐transmitting tissue ☐vascular ☐epidermis ☐stomata ☐abscission zone |
| X Ovule | Pre-fertilization: L inner integument ☐outer integument ☐embryo sac ☐funiculus ☐chalaza ☐micropyle ☐gametophyte |
| | Post-fertilization: H inner integument ☐outer integument M endothelium ☐seed coat ☐primordia ☐chalaza ☐micropyle ☐early endosperm ☐mature endosperm ☐zygote |
| ☐Embryo | ☐suspensor ☐preglobular ☐globular ☐heart ☐torpedo ☐late ☐mature ☐provascular ☐hypophysis ☐radicle ☐cotyledons ☐hypocotyl |
| ☐Stem | ☐epidermis ☐cortex ☐vascular ☐xylem ☐phloem ☐pith ☐stomata ☐trichome |
| ☐Leaf | ☐petiole ☐mesophyll ☐vascular ☐epidermis ☐trichome ☐primordia ☐stomata ☐stipule ☐margin |

X in the Endosperm (En) and Seed Coat (Sc) of ovules

T2 Seedling Expression    Tissues Screened
Events Screened: n = 2    Events Expressing: n = 2
Seedlings expressing/Seedlings screened
Event-01: No data
Event-02: No data
GFP Expression Detected

| | |
|---|---|
| ☐Hypocotyl | ☐epidermis ☐cortex ☐vascular ☐xylem ☐phloem ☐stomata |
| ☐Cotyledon | ☐mesophyll ☐vascular ☐epidermis ☐trichome ☐margin ☐stomata |
| ☐Rosette Leaf | ☐mesophyll ☐vascular ☐epidermis ☐trichome ☐petiole ☐primordia ☐stomata ☐stipule ☐margin |
| X Primary Root | ☐epidermis ☐trichoblast ☐atrichoblast ☐cortex H endodermis ☐vascular ☐xylem ☐phloem ☐pericycle ☐quiescent ☐columella ☐cap ☐root hairs |
| ☐Lateral root | ☐epidermis ☐initials ☐flanking cells ☐vascular ☐cap |
| ☐Shoot apical meristem | ☐SAM ☐epidermis |

X in the Endodermis (Ed), Epidermis (Ep), Lateral root primordium (Lr) of the root
X in the Pericycle (EP, PE) of the Stele (St)

T2 Mature Plant Expression
Plants expressing/Plants screened
Event-01: 2/2    Event-02: 1/1 Stronger expressing line.
X Scheduled
X T2 Mature tissue expressions similar to T1 expression data (additional images taken).
☐T2 Mature tissue expression (if different expression pattern).
GFP Expression Detected

| | |
|---|---|
| ☐Flower | ☐pedicel ☐receptacle ☐nectary ☐sepal ☐petal ☐filament ☐anther ☐pollen ☐carpel ☐style ☐papillae ☐vascular ☐epidermis ☐stomata ☐trichome |
| ☐Silique | ☐stigma ☐style ☐carpel ☐septum ☐placentae ☐transmitting tissue ☐vascular ☐epidermis ☐stomata ☐abscission zone |
| X Ovule | Pre-fertilization: L inner integument ☐outer integument ☐embryo sac ☐funiculus ☐chalaza ☐micropyle ☐gametophyte |
| | Post-fertilization: L inner integument ☐outer integument ☐zygote ☐seed coat ☐primordia ☐chalaza ☐micropyle ☐early endosperm ☐mature endosperm |
| ☐Embryo | ☐suspensor ☐preglobular ☐globular ☐heart ☐torpedo ☐late ☐mature ☐provascular ☐hypophysis ☐radicle ☐cotyledons ☐hypocotyl |
| ☐Stem | ☐epidermis ☐cortex ☐vascular ☐xylem ☐phloem ☐pith ☐stomata ☐trichome |
| ☐Leaf | ☐petiole ☐mesophyll ☐vascular ☐epidermis ☐trichome ☐primordial ☐stomata ☐stipule ☐margin |

X in the Inner Integument (Ii) of developing seed
X in the maturing seed

T3 Seedling Expression
Plants expressing/Plants screened
Event-01: 0/3 Low germination: 3 of 9 seedlings
Event-02: 0/1 Low germination: 1 of 10 seedlings
X Scheduled
☐T3 Seedling tissue expressions similar to T2 seedling expression (data not shown).
☐T2 Mature tissue expression (if different expression pattern).
No GFP Expression Detected Promoter utility
Trait - Sub-trait Area:

Among other uses this promoter sequence is useful to improve:
Seed - ovule/seed abortion, seed size, test weight, total seed
Composition - amino acids, carbohydrate, protein to oil composition
Utility:

Promoter useful for increasing endosperm production or affecting compositional changes in the developing seed. Should also have utility in helping to control seed size.
Notes:

Endothelium is the location of pigment deposition, and it is this deposition that gives *Arabidopsis* seeds their characteristic brown color. Seed coat pigments in *Arabidopsis* are predominantly flavonoids or proanthocyanidins. Proanthocyanidins (PAs) accumulate as colorless compounds during the early steps of embryogenesis and have been shown to participate in the maintenance of seed coat-imposed dormancy as well as in seed longevity during storage. Nesi, N, et.al., Plant Cell, 14 2463–2479 2002.

Promoter Expression Report #5

| | |
|---|---|
| Construct: | YP0111 |
| Promoter Candidate I.D: | 11768845 (Old ID: 4772159) |
| cDNA ID | 13619323 (Old IDs: 12396169, 4772159) |
| T1 lines expressing (T2 seed): | SR00690-01,-02 |

Sequence (SEQ ID NO: 5):

CGATTGGATTTAGTCTATACATTATAGGGCGCAAGTTTGTGGATTTAAGAA

TTATATAAAAACTTGAAATATATAGTTTTTATGCATTCTCCTCTTGTGTAA

TACATAAACCAAATATGAGATAGGTTAATCTGTATTTCAGATAATATTAAA

TTCCAAACAATATTTTTACTTGTTATAAGAAGGCAATTAATATCTCTCTGT

TAATGGCAAGTGGTACCAAGTAGTATTAAACTATTAATGCAATGGAAGAGT

ACTGTTGGAAATTATAATCCTCTATCACACATTCAAACAGATCTCCTGAAA

TCTTCTCTTCCAAACTTGTACTTCTCTGATCCAAATGTAGGCTCCAAATA

TAGACATTTACCATTTACTAAGTCCACAACTCCTTTCTTGTCTCCTTCAAA

AATGACTCTTGTGTAACCACCATATGACTCCGACAGTTCGGCATTGCCATG

ATGAGAGCTTAAAAATTCACCTTCCTGAGCATTTCAAGTCTTCACTCCCTT

AGCTTGACCTGAACCAAGATAAAATGCCTTTGTCGTCCCGTAATATCCATC

CTGCTTTGGACGGCATCATAGTTACATTCGATCCATCCTATTTACAATGTT

ATTTTAGTATTAAAAACATGACAATAAATTTGTTGTTAAACATATTCAAAT

ACAATATGATTGGATTTATAAGTAATTGTAATATGAAATGTCCTTAGTAAT

ATGTTAAAAAATACATAGATACACACACGTACTAAAAGAGGCAACGCGGGA

GATGTCATTAGAGGAAGAACTAGGAAGCAGAGCGTTCATGCAAAATGCTAC

CAAAAACGTTAATGCAATATCTCAACTAATCAGCACAGTCCATTTCATACT

GAGAATGTAAAAACCAATCAGCATCGTCCATTTTTTCATCTAATTATTTGT

TAACTCTTAATTGGCCACAACTTCCAACCACATGACGCTCTTTCTATTCCC

TTTATATATTCCCATCTCAAATGTTCTTGGAGACACAAAATATCATAAACA

TATAAACATAAACGCCAATCGCAGCTTTTGTACTTTTGGCGGTTTACA

Promoter Expression Report #6

| | |
|---|---|
| Promoter Tested In: | *Arabidopsis thaliana*, WS ecotype |
| Spatial expression summary: | |
| Stem | (H)epidermis, (H)cortex |
| Hypocotyl | (H)epidermis, (H)cortex |
| Silique | (H)style, (H)carpel, (H)septum, (H)epidermis |
| Leaf | (M)mesophyll, (M)epidermis |

Observed expression patterns:

Strong GFP expression exists throughout stem epidermal and cortical cells in T1 mature plants. GFP expression exhibits polarity in T2 seedling epidermal cells. First, it appears in the upper part of the hypocotyl near cotyledonary petioles, increasing toward the root, and in the abaxial epidermal cells of the petiole. An optical section of the seedling reveals GFP expression in the cortical cells of the hypocotyl.
T2 mature:

Same expression pattern was seen as in T1 mature with extension of cortex and epidermal expression through to siliques. No expression was seen in placental tissues and ovules. Additional expression was observed in epidermis and mesophyll of cauline leaves.
T3 seedling:

Same as T2.

| | |
|---|---|
| Expected expression pattern: | Expression in ovules |
| Selection Criteria: | Greater than 50× up in pi ovule microarray |
| Gene: | cytochrome P450 homolog |
| GenBank: | NM_104570 *Arabidopsis thaliana* cytochrome P450, putative (At1g57750) mRNA, complete cds, gi\|30696174\|ref\|NM_104570.2\| [30696174] |
| Source Promoter Organism: | *Arabidopsis thaliana* WS |
| Vector: | pNewbin4-HAP1-GFP |
| Marker Type: | X GFP-ER |
| Generation Screened: | X T1 Mature    X T2 Seedling |
| | X T3 Mature    X T3 Seedling |

Inductions completed: ABA, Drought

| Treatment: | Age: | Generation | Time points: | Response: |
|---|---|---|---|---|
| I. ABA- | | | | |
| 100 uM Submerged | 10–14d. | T3 | 8 Hr | Yes |
| 100 uM Spray | 14d. | T2 | 1 Hr, 6 Hr | Inconclusive |
| II. Drought- | | | | |
| Soil Extracted Wilt | 14d. | T2 | 3 Hr, 6 Hr | No |

Observed expression:

(Yellow arrows point to areas of potential response):
I. ABA (100 uM)

High expression in hypocotyl epidermal cells of in multiple seedlings of experimental line YP0104-01-02 when compare to control. The second event, YP0104-01-02, shows similar expression pattern and higher GFP expression than in control.
High GFP expression in few guard cells of rosette leaves in line-02 6 Hr after ABA when compared to control. Line -01 shows similar weak expression.
II. Drought:

Hypocotyl expression, same as control, no observable significant differences.

T1 Mature Plant Expression    Organs/Tissues screened
Events Screened: n = 3    Events Expressing: n = 3
GFP Expression Detected

| | |
|---|---|
| ☐Flower | ☐pedicel ☐receptacle ☐nectary ☐sepal ☐petal ☐filament ☐anther ☐pollen ☐carpel ☐style ☐papillae ☐vascular ☐epidermis ☐stomata ☐trichome |
| ☐Silique | ☐stigma ☐style ☐carpel ☐septum ☐placentae ☐transmitting tissue ☐vascular ☐epidermis ☐stomata ☐abscission zone |
| ☐Ovule | Pre-fertilization: ☐inner integument ☐outer integument ☐embryo sac ☐funiculus ☐chalaza ☐micropyle ☐gametophyte Post-fertilization: ☐zygote ☐seed coat ☐primordia ☐chalaza ☐micropyle ☐early endosperm ☐mature endosperm |
| ☐Embryo | ☐suspensor ☐preglobular ☐globular ☐heart ☐torpedo ☐late ☐mature ☐provascular ☐hypophysis ☐radicle ☐cotyledons ☐hypocotyl |
| X Stem | H epidermis H cortex ☐vascular ☐xylem ☐phloem ☐pith ☐stomata ☐trichome |
| ☐Leaf | ☐petiole ☐mesophyll ☐vascular ☐epidermis ☐trichome ☐primordia ☐stomata ☐stipule ☐margin |

-continued

Promoter Expression Report #6

X in the Pedicel (Pd) of the inflorescence meristem
X in the stem

T2 Seedling Expression   Tissues Screened
Events Screened: n = 2   Events Expressing: n = 2
Seedlings expressing/Seedlings screened
Event-01: No data   Event-02: No data
GFP Expression Detected

| | |
|---|---|
| X Hypocotyl | H epidermis H cortex ☐vascular ☐xylem ☐phloem ☐stomata |
| ☐Cotyledon | ☐mesophyll ☐vascular ☐epidermis ☐trichome ☐margin ☐stomata |
| ☐Rosette Leaf | ☐mesophyll ☐vascular ☐epidermis ☐trichome ☐petiole ☐primordia ☐stomata ☐stipule ☐margin |
| ☐Primary Root | ☐epidermis ☐trichoblast ☐atrichoblast ☐cortex ☐endodermis ☐vascular ☐xylem ☐phloem ☐pericycle ☐quiescent ☐columella ☐cap ☐root hairs |
| ☐Lateral root | ☐epidermis ☐initials ☐flanking cells ☐vascular ☐cap |
| ☐Shoot apical meristem | ☐SAM ☐epidermis |

X in the Epidermis (Ep) of the hypocotyl
X in the Epidermis (Ep) of the cotyledon petiole
X in the Epidermis (Ep) and Cortex (Cr) of the hypocotyl T2 Mature Plant Expression
Plants expressing/Plants screened
Event-01: 1/1   Event-02: 1/2.
Original T1 mature expression pattern was observed including new expression pattern not observed in previous generation.
☐Scheduled
☐T2 Mature tissue expressions similar to T1 expression data (data not shown).
☐T2 Mature tissue expression (if different expression pattern).
Expression detected

| | |
|---|---|
| ☐Flower | ☐pedicel ☐receptacle ☐nectary ☐sepal ☐petal ☐filament ☐anther ☐pollen ☐carpel ☐style ☐papillae ☐vascular ☐epidermis ☐stomata ☐trichome |
| X Silique | ☐stigma H style H carpel H septum ☐placentae ☐transmitting tissue ☐vascular H epidermis ☐stomata ☐abscission zone ☐ovule |
| ☐Ovule | Pre-fertilization: ☐inner integument ☐outer integument ☐embryo sac ☐funiculus ☐chalaza ☐micropyle ☐gametophyte<br>Post-fertilization: ☐zygote ☐inner integument ☐outer integument ☐seed coat ☐primordia ☐chalaza ☐micropyle ☐early endosperm ☐mature endosperm ☐embryo |
| ☐Embryo | ☐suspensor ☐preglobular ☐globular ☐heart ☐torpedo ☐late ☐mature ☐provascular ☐hypophysis ☐radicle ☐cotyledons ☐hypocotyl |
| ☐Stem | ☐epidermis ☐cortex ☐vascular ☐xylem ☐phloem ☐pith ☐stomata ☐trichome |
| X Leaf | ☐petiole M mesophyll ☐vascular M epidermis ☐trichome ☐primordial ☐stomata ☐stipule ☐margin |

T3 Seedling Expression
Plants expressing/Plants screened
Event-01: 2/2   Event-02: 0/1   Low germination.
☐Scheduled
X T3 Seedling tissue expressions similar to T2 seedling expression (data not shown).
☐T2 Mature tissue expression (if different expression pattern).
GFP Expression Detected Induction Screens I. ABA (100 uM)

ABA
X (low) in the hypocotyl of the YP0104-01-02. 8Hr.H.CTRL T3 Seedling
X (high) in the hypocotyl of the YP0104-01-02. 8Hr.ABA T3 Seedling
X (low) in the VP0104-02-02.8hr ABA CTRL T3 Seedling
X (high) in the YP0104-02-02.8hr ABA T3 Seedling
ABA:
X in the YP0104-01 1 Hr. CTRL
X in the YP0104.02 6 hrs CTRL
X in the YP0104.02 6 hrs- Rosette leaf guard cells Promoter utility
Trait - Sub-trait Area:

Among other uses this promoter sequence is useful to improve:
Water use efficiency - moisture stress, water use efficiency, ovule/seed abortion
Seed - test weight, seed size
Yield - harvest index, total yield
Composition - amino acids, carbohydrate, protein total oil, total seed
Utility:

Useful when expression is predominantly desired in stems, in particular, the epidermis.

| | |
|---|---|
| Construct: | YP0104 |
| Promoter Candidate ID: | 11768842 |
| cDNA ID: | 13612879 (Old IDs: 12371683, 1393104) |
| T1 lines expressing (T2 seed): | SR00644-01,-02,-03 |

Sequence (SEQ ID NO: 6):

TTTATTTTATTTTTTGAATGAAAATGTCTTCTTTATTCGTAATTTTAAACT

CACTGGTGGTGGATATATTGTTATGTCCCCAATTCGTCTGGCAACTCTCGT

ATATTAGTGAGAAAAATTTGTCCATTATTTACTGCACTATTACCCCTGTGT

TAATTTTTTGTATTGAAATTGTTTTTTTAGTAATTCACGTCATATAGCGAA

TGATTCTTTAATTTTAAAAATTCAGTCTTAAGTTTACAAATTAAATAACGC

TACTGTAACCAACTCTGTACGACCAACATGTTCGAGTTTTTGTATATACGG

CCATATATGTACATATTTTACTATAAAGCGAAAAAATCCATAAATTATTTA

ATTAATATATAAAGGTGCCATTCTATTTCCAATGTGCTTAGGAAAATGCAG

AACCTCGTGCTATATCTCTGTCGCCACGTGCAAATATAACAATATGAAATA

GAACTAGCAAATCTTGAAATCTAACTCTTAAGACTAATTCAAGCACATACG

TAGAGAAAGTTGACCAACGGTTATCAGCATTTTAACATGGACCTTATCAAC

ATTTTAACAAAGTCCACAAACAACCAGTCTTACAATCGCATTGGTACAAGA

TAATCGAATTCATCTTCCATATAACAAAACCTAAACCTTGGTGTGAAAAGG

AGAAGATATGTATGTTAAAGGCCGCCTATGCCTCTGGTTTGGGGTATATGA

TTCTAAGATTAGGGTTTGAATATTTTCGTTAGCCTGCCATGAGATATATTT

ATGTGATAATTTAGAGCCTCTTATGCATTAATGCATAACCGACTAGATCCA

TGTGGTATTCAGCTAATCAGTACACACAAGACAAAGTAGTAAATGAGTTTG

ATGAAGACTGTGGTCTGATAATTCCTATCAACGTTAAATCTGTCGGGGCCA

GGCAGCCAGCAACATTTTGCCTACCAACGCTCTGAATTCAATTGAACCTAG

GCTATATAATAGCAGGCTAACTTAACTAAGAGTT

Promoter Expression Report #7

| | |
|---|---|
| Promoter Tested In: | *Arabidopsis thaliana*, WS ecotype |
| Spatial expression summary: | |
| Flower | (L)sepal, (L)petal, (L)silique, (L)vascular, (H)stomata, (L)pedicel |
| Silique | (L)vascular, (L)epidermis |
| Cotyledon | (H)stomata, (L)root hair |
| Observed expression patterns: | |

GFP expressed in the vasculature and guard cells of sepals and pedicels in mature plants. GFP expressed in the guard cells of seedling cotyledons.
T2 mature:

Stronger expression extended into epidermal tissue of siliques in proximal-distal fashion.
T3 seedling:

Weak root hair expression was observed which was not observed in T2 seedlings; no guard cell expression observed. All epidermal tissue type expression was seen with the exception of weak vasculature in siliques.

| | |
|---|---|
| Expected expression pattern: | Drought induced |
| Selection Criteria: | Expression data (cDNAChip), > 10 fold induction under drought condition. Screened under non-induced condition. |
| Gene: | Unknown protein; At5g43750 |
| GenBank: | NM_123742 *Arabidopsis thaliana* expressed protein (At5g43750) mRNA, complete cds, gi\|30694366\|ref\|NM_123742.2\| [30694366] |
| Source Promoter Organism: | *Arabidopsis thaliana* WS |
| Vector: | pNewbin4-HAP1-GFP |
| Marker Type: | X GFP-ER |
| Generation Screened: | X T1 Mature   X T2 Seedling X T3 Mature   X T3 Seedling |

T1 Mature Plant Expression    Organs/Tissues screened
Events Screened: n = 3    Events Expressing: n = 2
GFP Expression Detected

| | |
|---|---|
| X Flower | L pedicel □receptacle □nectary □sepal □petal □filament □anther □pollen □carpel □style □papillae □vascular □epidermis H stomata □trichome |
| X Silique | □stigma □style □carpel □septum □placentae □transmitting tissue L vascular □epidermis □stomata □abscission zone |
| □Ovule | Pre-fertilization: □inner integument □outer integument □embryo sac □funiculus □chalaza □micropyle □gametophyte Post-fertilization: □zygote □seed coat □primordia □chalaza □micropyle □early endosperm □mature endosperm |
| □Embryo | □suspensor □preglobular □globular □heart □torpedo □late □mature □provascular □hypophysis □radicle □cotyledons □hypocotyl |
| □Stem | □epidermis □cortex □vascular □xylem □phloem □pith □stomata □trichome |
| □Leaf | □petiole □mesophyll □vascular □epidermis □trichome □primordia □stomata □stipule □margin |

X in the Guard cell (Gc) and Vasculature (Vs) of the petal and sepal in the flower
X in the Lateral vasculature (Lv) and Medial vasculature (Mv), of the silique
X in the Guard cell (Gc) of the pedicel T2 Seedling Expression    Tissues Screened
Events Screened: n = 2    Events Expressing: n = 2
GFP Expression Detected

| | |
|---|---|
| □Hypocotyl | □epidermis □cortex □vascular □xylem □phloem □stomata |
| X Cotyledon | □mesophyll □vascular □epidermis □trichome □margin H stomata |
| □Rosette Leaf | □mesophyll □vascular □epidermis □trichome □petiole □primordia □stomata □stipule □margin |
| □Primary Root | □epidermis □trichoblast □atrichoblast □cortex □endodermis □vascular □xylem □phloem □pericycle □quiescent □columella □cap □root hairs |
| □Lateral root | □epidermis □initials □flanking cells □vascular □cap |
| □Shoot apical meristem | □SAM □epidermis |

X in the Guard cell (Gc), that define the Stomata (So) of the cotyledon

T2 Mature Plant Expression
Plants expressing/Plants screened
Event-01: 1/2    Event-02: 1/1
SAME PLUS- Original expression pattern was observed including new expression not observed in previous generation.
□Scheduled
□T2 Mature tissue expressions similar to T1 expression data (data not shown).
X T2 Mature tissue expression (if different expression pattern).
Expression detected

| | |
|---|---|
| □Flower | □pedicel □receptacle □nectary □sepal □petal □filament □anther □pollen □carpel □style □papillae □vascular □epidermis □stomata □trichome |
| X Silique | □stigma □style □carpel □septum □placentae □transmitting tissue □vascular L epidermis H stomata □abscission zone □ovule |
| □Ovule | Pre-fertilization: □inner integument □outer integument □embryo sac □funiculus □chalaza □micropyle □gametophyte Post-fertilization: □zygote □inner integument □outer integument □endothelium □seed coat □primordia □chalaza □micropyle □early endosperm □mature endosperm □embryo |
| □Embryo | □suspensor □preglobular □globular □heart □torpedo □late □mature □provascular □hypophysis □radicle □cotyledons □hypocotyl |
| □Stem | □epidermis □cortex □vascular □xylem □phloem □pith □stomata □trichome |
| □Leaf | □petiole □mesophyll □vascular □epidermis □trichome □primordia □stomata □stipule □margin |

X in the Epidermis (Ep), Guard Cells (Gc) and Vasculature (Vs) of the proximal, mid and distal siliques
X in the Epidermis (Ep) and Guard cells (Gc) of the mid region of the siliques and the stem T3 Seedling Expression
Plants expressing/Plants screened
Event-01: 2/3 Event-02: 0/2
NEW- Expression pattern not observed in previous generation.
□Scheduled
□T3 Seedling tissue expressions similar to T2 seedling expression (data not shown)
X T2 Mature tissue expression (if different expression pattern).
GFP Expression Detected Weak expression in a few root hairs. No guard cell expression observed Promoter utility
Trait - Subtrait Area:

Among other uses this promoter sequence is useful to improve:
Water use efficiency - Heat

Promoter Expression Report #7

Notes:

The GFP expression pattern si similar to promoters that are 100% exonic.

Construct: YP0075
Promoter Candidate I.D: 11768626 (Old ID: 35139358)
cDNA ID: 13612919 (Old IDs: 12694633, 5672796)
T1 lines expressing (T2 seed): SR00554-01,-02

Sequence (SEQ ID NO: 7):

TGGATTACAAATCATTAAGCTAATATCTTCGATGAATTAAGAAGATAAGTG

GATAACAAGTACCTAACCGCAATAGTCCATAAATTAAAACATTAATGTATT

TGTCGTTGAAAATTTGGCCGACTTTTATTTGTTATTCTAGTTTCCACATCA

AAAATGTTTGTACTTCGTAGCAATCCATCCACCTAAACCCCAAATCTTAAT

TTATATTTGTTGCGTTTAAATTTGGGTGAGATTTGATTCTAAGTAGTTGAG

ATAAATTGATATTCTATTCATTAGTAAAATGATAGAGAAATTGGTTTATAA

TAATTTTACCCTAGAACATGACATGATATTGGTAACCATTAATCAAAGAAA

GAGCAAAGCATTTAATTTACCCTACTCTCCAACCACTCCAGCCTTTATTAG

TTGCAGTTGGGAATCATTTCTTTATGATTCTTATGTCATTGTCTCCTAAAT

CAATGAAGTGCCTTGACCTTGTTACTAATTCGAACATAGCAAAGCCAACTA

CATAGATCCTTTACAAAGTTCTAAAAACAGGTTGTTTAGGCGTCTAGACAA

ACAAAACCATTTTGTACGATTCAACAAATTGGTCCATAGAATGTTATTGAT

CTTTCTTGTTTAGGCATTCGATAAATCGGCTAATACATTATTTTTTGTTT

TGCTTTTTCCTTATTAAAAATATGCAAAGTATTATGATGTTTAACCTGAAC

TGAATTTTACATTTAACTGGATATAGGAAAATATTGGGTTGAATTTAATAA

TTAAGCAATTGTCACGTAAATCAAATTGGGCTTAATATATATTGTTGATTT

CAGCAAAGACAAAGTTGGGCCGTTTCAATAGTCTTCACGCGATGTAAGCGT

TCACTAACCAACTAGAGAAGACAATCAAATGAATACGTTCCACGTGACGCT

TACGAACTTGTCAGTCACTTTGGTAATATGACAGACAGTAACCAGTAAACT

ACTAATCTCTTTCGCTAACGAACACACAAAA

Promoter Expression Report #8

Promoter Tested In: *Arabidopsis thaliana*, WS ecotype
Spatial expression summary:
Flower (L)receptacle, (L)vascular
Leaf (H)vascular, (H)epidermis
Root (M)phloem
Cotyledon (M)vascular, (M)hydathode
Primary Root (L)epidermis, (M)vascular
Observed expression patterns:

Expression was seen at the receptacle and vasculature of immature flower and leaf, and phloem of seedling root.
T2 mature:

Similar to T1 expression. Strong expression was seen in vascular tissues on mature leaves. Vascular expression in flowers was not observed as in T1.

Promoter Expression Report #8

T3 seedling:

Similar to T2 seedling expression.
Expected expression pattern:

Vascular tissues; The SUC2 promoter directed expression of GUS activity with high specificity to the phloem of all green tissues of *Arabidopsis* such as rosette leaves, stems, and sepals.
Selection Criteria: *Arabidopsis* public; Planta 1995; 196:564–70
Gene: "Sugar Transport" SUC2
GenBank: NM_102118 *Arabidopsis thaliana* sucrose transporter SUC2 (sucrose-proton transporter) (At1g22710) mRNA, complete cds, gi|30688004|ref|NM_102118.2| [30688004]
Source Promoter Organism: *Arabidopsis thaliana* WS
Vector: Newbin4-HAP1-GFP
Marker Type: X GFP-ER
Generation Screened: X T1 Mature  X T2 Seedling
X T3 Mature  X T3 Seedling T1 Mature Plant Expression   Organs/Tissues screened
Events Screened: n = 5   Events Expressing: n = 5
GFP Expression Detected

| | |
|---|---|
| X Flower | ☐pedicel L receptacle ☐nectary ☐sepal ☐petal ☐filament ☐anther ☐pollen ☐carpel ☐style ☐papillae ☐vascular ☐epidermis ☐stomata ☐trichome |
| ☐Silique | ☐stigma ☐style ☐carpel ☐septum ☐placentae ☐transmitting tissue ☐vascular ☐epidermis ☐stomata ☐abscission zone |
| ☐Ovule | Pre-fertilization: ☐inner integument ☐outer integument ☐embryo sac ☐funiculus ☐chalaza ☐micropyle ☐gametophyte Post-fertilization: ☐zygote ☐seed coat ☐primordia ☐chalaza ☐micropyle ☐early endosperm ☐mature endosperm |
| ☐Embryo | ☐suspensor ☐preglobular ☐globular ☐heart ☐torpedo ☐late ☐mature ☐provascular ☐hypophysis ☐radicle ☐cotyledons ☐hypocotyl |
| ☐Stem | ☐epidermis ☐cortex ☐vascular ☐xylem ☐phloem ☐pith ☐stomata ☐trichome |
| X Leaf | ☐petiole ☐mesophyll H vascular ☐epidermis ☐trichome ☐primordia ☐stomata ☐stipule ☐margin |

X X in the Receptacle (Re) and Vasculature (Vs) of the flower
X in the Phloem (Ph) of the leaf T2 Seedling Expression   Tissues Screened
Events Screened: n = No data   Events Expressing: n = 1
GFP Expression Detected

| | |
|---|---|
| ☐Hypocotyl | ☐epidermis ☐cortex ☐vascular ☐xylem ☐phloem ☐stomata |
| ☐Cotyledon | ☐mesophyll ☐vascular ☐epidermis ☐trichome ☐margin ☐stomata |
| ☐Rosette Leaf | ☐mesophyll ☐vascular ☐epidermis ☐trichome ☐petiole ☐primordia ☐stomata ☐stipule ☐margin |
| X Primary Root | ☐epidermis ☐trichoblast ☐atrichoblast ☐cortex ☐endodermis ☐vascular ☐xylem (M) phloem ☐pericycle ☐quiescent ☐columella ☐cap ☐root hairs |
| ☐Lateral root | ☐epidermis ☐initials ☐flanking cells ☐vascular ☐cap |
| ☐Shoot apical meristem | ☐SAM ☐epidermis |

X in the Phloem (Ph) of the root differentiation zone

T2 Mature Plant Expression
Plants expressing/Plants screened
Event-01: 1/1   Event-02: 0/3

Promoter Expression Report #8

☐Scheduled
X T2 Mature tissue expressions similar to T1 expression data (additional images taken).
☐T2 Mature tissue expression (if different expression pattern).
Expression detected

| | |
|---|---|
| ☐Flower | ☐pedicel ☐receptacle ☐nectary ☐sepal ☐petal ☐filament ☐anther ☐pollen ☐carpel ☐style ☐papillae ☐vascular ☐epidermis ☐stomata ☐trichome |
| ☐Silique | ☐stigma ☐style ☐carpel ☐septum ☐placentae ☐transmitting tissue ☐vascular ☐epidermis ☐stomata ☐abscission zone ☐ovule |
| ☐Ovule | Pre-fertilization: ☐inner integument ☐outer integument ☐embryo sac ☐funiculus ☐chalaza ☐micropyle ☐gametophyte Post-fertilization: ☐zygote ☐inner integument ☐outer integument ☐endothelium ☐seed coat ☐primordia ☐chalaza ☐micropyle ☐early endosperm ☐mature endosperm ☐embryo |
| ☐Embryo | ☐suspensor ☐preglobular ☐globular ☐heart ☐torpedo ☐late ☐mature ☐provascular ☐hypophysis ☐radicle ☐cotyledons ☐hypocotyl |
| ☐Stem | ☐epidermis ☐cortex ☐vascular ☐xylem ☐phloem ☐pith ☐stomata ☐trichome |
| X Leaf | ☐petiole ☐mesophyll H vascular H epidermis ☐trichome ☐primordia ☐stomata ☐stipule ☐margin |

X in the hydathode region of mature leaves. Hydathode is a highly modified region of vascular and ground tissue that permits release of water through a pore in the epidermis.

T3 Seedling Expression
Plants expressing/Plants screened
Event-01: 2/2   Event-02: 1/2
☐Scheduled
X T3 Seedling tissue expressions similar to T2 seedling expression (additional images taken).
☐T2 Mature tissue expression (if different expression pattern).
GFP Expression Detected

| | |
|---|---|
| ☐Hypocotyl | ☐epidermis ☐cortex ☐vascular ☐xylem ☐phloem ☐stomata |
| X Cotyledon | ☐mesophyll M vascular ☐epidermis ☐margin ☐stomata M hydathode |
| ☐Rosette Leaf | ☐mesophyll ☐vascular ☐epidermis ☐trichome ☐petiole ☐primordia ☐stomata ☐stipule ☐margin |
| X Primary Root | ☐epidermis ☐trichoblast ☐atrichoblast ☐cortex ☐endodermis M vascular ☐xylem ☐phloem ☐pericycle ☐quiescent ☐columella ☐root cap ☐root hairs |
| ☐Lateral root | ☐epidermis ☐trichoblast ☐atrichoblast ☐cortex ☐endodermis ☐initials ☐flankin cells ☐vascular ☐lateral root cap |
| ☐Shoot apical meristem | ☐SAM ☐epidermis |

X in the Epidermis (Ep) of the root transition zone of the hypocotyl
X in the Vasculature (Vs) of the root
X in the Hydathode (Hd) and Vasculature (Vs) of the root Promoter utility
Trait - Sub-trait Area:

Among other uses this promoter sequence could be useful to improve:
Source - Source enhancement, C/N partitioning
Utility:

Useful for loading and unloading phloem.
Notes:

Good vascular expression.
  1: Gottwald JR. Krysan PJ. Young JC.   Related Articles, Links
     Evert RF. Sussman MR.

Genetic evidence for the in planta role of phloem-specific plasma membrane sucrose transporters. Proc Natl Acad Sci U S A. 2000 Dec 5;97(25):13979–84. PMID: 11087840 [PubMed - indexed for MEDLINE]
  2: Truenit E. Sauer N.   Related Articles, Links
     The promoter of the *Arabidopsis thaliana* SUC2 sucrose-H+ symporter gene directs expression of beta-glucuronidase to the phloem: evidence for phloem loading and unloading by SUC2. Planta. 1995;196(3):564–70.
     PMID: 7647685 [PubMed - indexed for MEDLINE]
  3. Sauer N. Stolz J.   Related Articles, Links
     SUC1 and SUC2: two sucrose transporters from *Arabidopsis thaliana*; expression and characterization in baker's yeast and identification of the histidine-tagged protein. Plant J. 1994 Jul;6(1):67–77. PMID: 7920705 [PubMed - indexed for MEDLINE]

| | |
|---|---|
| Construct: | YP0016 |
| Promoter Candidate I.D: | 11768612 (Old ID: 35139304) |
| cDNA ID | 13491988 (Old IDs: 6434453, 12340314) |
| T1 lines expressing T2 seed : | SR00416-01,-02,-03,-04,-05 |

Sequence (SEQ ID NO: 8):

AAACATGTTTTATGTAACTACTTTGCTTATGTGATTGCCTGAGGATACTAT

TATTCTCTGTCTTTATTCTCTTCACACCACATTTAAATAGTTTAAGAGCAT

ATAAATTAATTATCTTCAAAAAGGTGATTATATGCATGCAAAATAGCACAC

CATTTATGTTTATATTTTCGAATTATTTAATACATTTCAATATTTCATAAG

TGTGATTTTTTTTTTTTTGTCAATTTCATAAGTGTGATTTGTCATTTGTA

TTAAACAATTGTATCGCGCAGTACAAATAAACAGTGGGAGAGGTGAAAATG

CAGTTATAAAACTGTCCAATAATTTACTAACACATTTAAATATCTAAAAAG

AGTGTTTCAAAAAAAATTCTTTTGAAATAAGAAAAGTGATAGATATTTTA

CGCTTTCGTCTGAAAATAAAACAATAATAGTTTATTAGAAAAATGTTATCA

CCGAAAATTATTCTAGTGCCACTCGCTCGGATCGAAATTCGAAAGTTATAT

TCTTTCTCTTTACCTAATATAAAAATCACAAGAAAAATCAATCCGAATATA

TCTATCAACATAGTATATGCCCTTACATATTGTTTCTGACTTTTCTCTATC

CGAATTTCTCGCTTCATGGTTTTTTTTTAACATATTCTCATTTAATTTTCA

TTACTATTATATAACTAAAAGATGGAAATAAAATAAAGTGTCTTTGAGAAT

CGAACGTCCATATCAGTAAGATAGTTTGTGTGAAGGTAAAATCTAAAAGAT

TTAAGTTCCAAAAACAGAAAATAATATATTACGCTAAAAAAGAAGAAAATA

ATTAAATACAAAACAGAAAAAAATAATATACGACAGACACGTGTCACGAAG

ATACCCTACGCTATAGACACAGCTCTGTTTTCTCTTTTCTATGCCTCAAGG

CTCTCTTAACTTCACTGTCTCCTCTTCGGATAATCCTATCCTTCTCTTCCT

ATAAATACCTCTCCACTCTTCCTCTTCCT

Promoter Expression Report #9

Promoter Tested In: *Arabidopsis thaliana*, WS ecotype
Spatial Expression summary:
Flower   (L)inflorescence, (H)pedicel, (H)vascular
Stem     (L)phloem

Promoter Expression Report #9

Leaf (L)vascular
Ovule Pre fertilization: (H)chalaza end of embryo sac
Hypocotyl (M)vascular, (M)phloem
Cotyledon (M)vascular, (M)phloem
Root (H)vascular, (H)pericycle, (H)phloem
Observed expression patterns: GFP expressed in the stem, pedicels and leaf vasculature of mature plants and in seedling hypocotyl, cotyledon, petiole, primary leaf and root.
Expected expression pattern: Phloem of the stem, xylem-to-phloem transfer tissues, veins of supplying seeds, vascular strands of siliques and in funiculi. Also expressed in the vascular system of the cotyledons in developing seedlings. T2 mature: Same as T1 mature, no images were taken. T3 seedling: Same as T2 seedling, additional images were taken.
Selection Criteria Arabidopsis public PNAS 92, 12036–12040 (1995)
Gene: AAP2 (X95623)
GenBank: NM_120958 *Arabidopsis thaliana* amino acid permease 2 (AAP2) (At5g09220) mRNA, complete cds, gi|30682579|ref|NM_120958.2|[30682579]
Source Promoter Organism: *Arabidopsis thaliana* WS
Vector: pNewbin4-HAP1-GFP
Marker Type: X GFP-ER
Generation Screened: X T1 Mature X T2 Seedling X T3 Mature X T3 Seedling
T1 Mature Plant Expression Organs/Tissues screened
Event Screened: n = 3 Events Expressing: n = 2
GFP Expression Detected
X Flower L pedicel □receptacle □nectary □sepal □petal □filament □anther □pollen □carpel □style □papillae L vascular □epidermis □stomata □trichome
□ Silique □stigma □style □carpel □septum □placentae □transmitting tissue □vascular □epidermis □stomata □abscission zone
X Ovule Pre-fertilization: □inner integument □outer integument □embryo sac □funiculus H chalaza □micropyle □gametophyte
Post-fertilization: □zygote □seed coat □primordia □chalaza □micropyle □early endosperm □mature endosperm
□ Embryo □suspensor □preglobular □globular □heart □torpedo □late □mature □provascular □hypophysis □radicle □cotyledons □hypocotyl
X Stem □epidermis □cortex L vascular □xylem □phloem □pith □stomata □trichome
X Leaf □petiole □mesophyll L vascular □epidermis □trichome □primordia □stomata □stipule □margin
X in the Phloem (Ph) of the Inflorescence meristem (Im), the stem and the mature leaf
X in the Chalaza (Ch) of the Embryo (Em) of the developing seed
T2 Seedling Expression Tissues Screened
Event Screened: n = 2 Events Expressing: n = 2
Seedlings expressing/Seedlings screened
Event-01: No data. Event-02: No data.
GFP Expression Detected
X Hypocotyl □epidermis □cortex M vascular □xylem M phloem □stomata
X Cotyledon □mesophyll M vascular □epidermis □trichome □margin □stomata M phloem
□ Rosette Leaf □mesophyll □vascular □epidermis □trichome □petiole □primordia □stomata □stipule □margin
X Primary Root □epidermis □trichoblast □atrichoblast □cortex □endodermis H vascular □xylem H phloem H pericycle □quiescent □columella □cap □root hairs
□ Lateral root □epidermis □initials □flanking cells □vascular □cap
□ Shoot apical meristem □SAM □epidermis
X in the Phloem (Ph) of the Hypocotyl (Hy) root elongation zone and primary leaf
X in the Phloem (Ph) and Pericycle (Pr) of the root differentiation zone and the Lateral root (Lr) initial
T2 Mature Plant Expression
Plants expressing/Plants screened
Event-01: 1/3 very weak line Event-02: 2/2 same as T1
X Scheduled X Completed
X T2 Mature tissue expressions similar to T1 expression data (data not shown) see Table 1.
□ T2 Mature tissue expression (if different expression pattern).
Expression detected
T3 Seedling Expression
Plants expressing/Plants screened
Event-01: 1/3 Event-02: 2/2
□ scheduled
X T3 Seedling tissue expressions similar to T2 seedling expression ()
□ T2 Mature tissue expression (if different expression pattern).
GFP Expression Detected
X in the root vasculature of the mature seedling

| Treatment: | Age: | Generation: | Time points: | Response: |
|---|---|---|---|---|
| Total Nitrogen Minus N. to Low 50 uM N. High 240 mM | 7–10 d. | T2 | 2 Hr, 6 Hr | Possible |

Nitrogen
Minus N CONTROL
2 Hr - Low N; No expression.
6 Hr - Low N
X in the vasculature (Vs) of seedlings and seedling roots
2 Hr - High N
Expression observed
6 Hr High N
Expression observed

| ID | Treatment | # Screened | # Expressing |
|---|---|---|---|
| YP0094-02 | minus N | 5 | 1 |
| YP0094-02 | 2 Hr - Low N | 6 | 0 |
| YP0094-02 | 2 Hr - High H | 4 | 2 |
| YP0094-03 | 6 Hr - minus N | 6 | 0 |
| YP0094-03 | 6 Hr - Low N | 5 | 3 |
| YP0094-03 | 6 Hr High N | 5 | 3 |

Promoter utility

Trait - Sub-trati Area: Among other uses this promoter sequence could be useful to improve:
Trait Area: Seed - Seed enhancement
Source - transport amino acids
Yield - harvest index, test weight, seed size,
Quality - amino acids, carbohydrate, protein, total seed composition Sequence (SEQ ID NO: 9):

```
TAAAGATCAGAAGAGGAAGGTTTCGCCGCGGCGGTTGCATCTTCACCGTCG
ATTTCATCGTTACAGCGACGCCGGTAATTCCTAGGTTGCTTAGTTCCCATT
CTCTCTCTAAAATTAGGGCTCGAAATGAATTGTTGAACAAGATAGAGATCT
TTTTCTGATCCCCGTCGAACATTTATTCAAGGCCAAAAAAAGCACACGGGA
ATTTAGAGTACCAATACATATCAAAACCTAATGGGCTTTGAATGGTTGCAT
GTGTGTGTTTATTTCTGATATGCAAAGCGATCGATAGTCTTTTCCATACAA
GTGTAAACTGTAAACAACGTAATTAAGCATAACAATACAACTCTTTCTTCT
CTTTTTTTTTGTAAACACAAAATAAAATTACATCAATTCATGCTTTTCCTA
GTTCATCTGACATTTTCCAAAATTCATGTTCCATTGAGTCCCTAATACTTG
TTCATATTCATATTAGGGTACATGAATAAAAGTTATCATTCTTGAAACTAC
TAAATTTTCATAGTTTATTTTTCTTCTTTTCGTTTCACTTTCGAACAAAAC
ACTACGCGTGGCATTTGCAATGAATTCCACATTATATGGAATAACACCATG
ATGAACATTCTACATATATAATTATTATGTTTAAGCACTTAGACAGCATAA
ATTCTTTCTAATTATATAAATCTAACCTTGTTACATTGTACATCTATAAAT
```

```
TACTTGAAGAAATAACGAGTTCTATTTCTTTTTAAAAATTAAAAATACTAT

ACCATATCTCAGTGATTAAGTTGAACCAAAAGGTACGGAGGAGAAACAAGC

ATTTGATTCTTCCTTATTTTATTTTATTCATCTCTCACTAATGATGGTGGA

GAAAAAAGAAAATACCTAACAAACAAATATATATTGTCATACAAAAATAT

TTCTATATTTTTAGTTAATTAGTTTATATTCCTCACTTTTCAGGGCTTATA

TAAGAAAGTGAGCAAACACAAATCAAAATGC
```

| Promoter Expression Report #10 |
|---|

Promoter Tested In: *Arabidopsis thaliana*, WS ecotype
Spatial expression summary:
Flower       (L)sepal, (L)pedicel, (L)vascular
Silique       (H)stomata
Hypocotyl   (M)epidermis
Primary Leaf (H)stomata
Root        (H)epidermis, (H)root hairs
Observed expression pattern: T1 mature: GFP expression was seen in the guard cells of pedicels and mature siliques. Weak expression was seen in floral vasculature. T2 seedling; Strong expression observed in epidermis and root hairs of seedling roots (not in lateral roots) and guard cells of primary leaves. T2 mature: Similar to T1 plants. T3 seedling: Similar to T2 seedling. Screened under non-induced conditions.
Expected expression pattern: As described by literature. Expressed preferentially in the root, not in mature stems or leaves of adult plants (much like AGL 17); induced by KNO3 at 0.5 hr with max at 3.5 hr
Selection Criteria: *Arabidopsis* Public; Science 279, 407–409 (1998)
Gene: ANR1, putative nitrate inducible MADS-box protein;
GenBank: NM—126990*Arabidopsis thaliana* MADS-box protein ANR1 (At2g14210) mRNA, complete cds
gi|22325672|ref|NM_126990.2|[22325672]
Source Promoter Organism: *Arabidopsis thaliana* WS
Vector: pNewbin4-HAP1-GFP
Marker Type: X GFP-ER
Generation Screened: X T1 Mature X T2 Seedling X T2 Mature X T3 Seedling
T1 Mature Plant Expression  Organs/Tissues screened
Events Screened: n = 3   Events Expressing: n = 2
GFP Expression Detected
X Flower    L pedicel ☐receptacle ☐nectary L sepal ☐petal ☐filament ☐anther ☐pollen ☐carpel ☐style ☐papillae L vascular ☐epidermis H stomata ☐trichome
X Silique    ☐stigma ☐style ☐carpel ☐septum ☐placentae ☐transmitting tissue ☐vascular ☐epidermis H stomata ☐abscission zone
☐ Ovule    Pre-fertilization: ☐inner integument ☐outer integument ☐embryo sac ☐funiculus ☐chalaza ☐micropyle ☐gametophyte
             Post-fertilization: ☐zygote ☐seed coat ☐primordia ☐chalaza ☐micropyle ☐early endosperm ☐mature endosperm
☐ Embryo  ☐suspensor ☐preglobular ☐globular ☐heart ☐torpedo ☐late ☐mature ☐provascular ☐hypophysis ☐radicle ☐cotyledons ☐hypocotyl
☐ Stem     ☐epidermis ☐cortex ☐vascular ☐xylem ☐phloem ☐pith ☐stomata ☐trichome
☐ Leaf     ☐petiole ☐mesophyll ☐vascular ☐epidermis ☐trichome ☐primordia ☐stomata ☐stipule ☐margin
X in the Vasculature (Vs) of the sepal of the flower
X in the Guard cell (Gc) of the pedicel
X in the Guard cell (Gc) of the silique
T2 Seedling Expression  Tissues Screened
Events Screened: n = 2  Events Expressing: n = 2
GFP Expression Detected
X Hypocotyl  M epidermis ☐cortex ☐vascular ☐xylem ☐phloem ☐stomata
☐ Cotyledon  ☐mesophyll ☐vascular ☐epidermis ☐trichome ☐margin ☐stomata
X Rosette Leaf ☐mesophyll ☐vascular ☐epidermis ☐trichome ☐petiole ☐primordia H stomata ☐stipule ☐margin
X Primary   H epidermis ☐trichoblast ☐atrichoblast ☐cortex

| Promoter Expression Report #10 |
|---|

Root         ☐endodermis ☐vascular ☐xylem ☐phloem ☐pericycle ☐quiescent ☐columella ☐cap H root hairs
☐ Lateral root  ☐epidermis ☐initials ☐flanking cells ☐vascular ☐cap
☐ Shoot apical  ☐SAM ☐epidermis
meristem
X in the Guard cells (Gc) of the leaf
X in the Root hair (Rh) and Epidermis (Ep) of the root transition zone between hypocotyl and root
X in the Atrichoblast and Trichoblast (Tr) of the root differentiation zone
T2 Mature Plant Expression
Plants expressing / Plants screened
Event-01: 1/2    Event-02: 1/3
☐ Scheduled
X T2 Mature tissue expressions similar to T1 expression data (data not shown).
☐ T2 Mature tissue expression (if different expression pattern).
Expression detected
T3 Seedling Expression
Plants expressing / Plants screened
Event-01: 1/3    Event-02: 2/3
☐ Scheduled
X T3 Seedling tissue expressions similar to T2 seedling expression (data not shown).
☐ T2 Mature tissue expression (if different expression pattern).
GFP Expression Detected
Promoter utility
Trait - Sub-trait Area:   Among other uses this promoter sequence is useful to improve:
                           Yield - Heterosis, general combining ability, specific combining ability
Notes: Has GFP expression pattern of exonic promoter.
References:
☐ 3: Zhang H. Forde BG.

An Arabidopsis MADS box gene the controls nutrient-induced changes in root architecture.
Science. Jan. 16, 1998; 279(5349):407–9.
PMID: 9430595 [PubMed - indexed for MEDLINE]
Construct: YP0033
Promoter Candidate I.D.: 13148205 (Old ID: 35139684)
cDNA ID: 12370148 (Old IDs: 7088230, 12729537)
T1 lines expressing (T2 seed): SRXXXXX-01, Sequence (SEQ ID NO: 10):

```
GTCGATTGGAACTTCCAATTTCTAAACGGATGCAATAAGAACTTACATATT

CTCTTTCATTAGTCATTTATTGGCCAGATTTATTAAAAAAAGTTTTACTCA

ATGACCAAGGATTAGAGTTAAAGATAATATAGATTATTACATATATTATTC

GAAAAAATATACCCATGTCCGACTTTTTAAACCTCAAAAATATCAAAACCA

GAAAAGATGATACAACACAAAAAAACAATAAAATAATAAGTGGAAGAGATA

TCATCGGACAACAGTACAAGTACAGCACCAGCTCTGCCAAAAGCCAAAACC

ATTTGTCAATTACAGAAAGATACTAATGTTTGAAATTACTAAATTACCCCT

CGGACTTTACAAAAGCATCTCTAACTTATCCACGTGTCAGTCATCTATTGA

TTGTTTCAATACCACCTTGTATTAACGCCCCACGATTCGTGGTTGGGTACA

CCTGATAGTCCGAGGATATTTAAATCTCACGCGCTCGTGTCTATAATTCGA

CTGTACTCGCTTTTCTTGCTCGTGATTTTAGCAATTTACGAAGTCAAATGTT

TGACTCAATCAGACTTGCGCATAGGAGAGCGAGTATAAATGTTTACTATAC

TCACGCAAGTGGGGCTTTATTGAAACTACTCTTTTGTAATAAAACCAGCAG

TGGTTTTGTTCTGAATCCGCTCTCTTGC
```

Promoter Expression Report #11

| | |
|---|---|
| Promoter Tested In: | *Arabidopsis thaliana*, WS ecotype |
| Spatial expression summary: | |
| Flower | (H)epidermis, (H)sepal, (H)petal, (H)vascular |
| Stem | (L)vascular |
| Hypocotyl | (L)epidermis, (H)phloem |
| Cotyledon | (L)epidermis, (M)stomata, (L)vascular |
| Root | (H)phloem |

Observed expression pattern:

Strong GFP expression was seen in the epidermal layer and vasculature of the sepals and petals of developing flowers in mature plants and seedlings.

T2 mature:

Expression was similar to T1 mature plants. Vascular expression in the stem was not observed in T1 mature.

T3 Seedling:

Same expression seen as T2 seedling expression

| | |
|---|---|
| Expected expression pattern: | Predominantly expressed in the phloem. |
| Selection Criteria: | *Arabidopsis* public: Deeken, R. The Plant J.(2000) 23(2),285–290 Geiger, D. Plant Cell 2002 14,1859–1868 |
| Gene: | potassium channel protein AKT3 |
| GenBank: | NM_118342 *Arabidopsis thaliana* potassium channel (K+ transporter 2)(AKT2) (At4g22200) mRNA, complete cds, gi\|30685723\|ref\|NM_118342.2\| [30685723] |
| Source Promoter Organism: | *Arabidopsis thaliana* WS |
| Vector: | pNewbin4-HAP1-GFP |
| Marker Type: | X GFP-ER |
| Generation Screened: | X T1 Mature   X T2 Seedling |
| | X T3 Mature   X T3 Seedling |

T1 Mature Plant Expression    Organs/Tissues screened
Events Screened: n = 3   Events Expressing: n = 3
GFP Expression Detected

| | |
|---|---|
| X Flower | ☐pedicel ☐receptacle ☐nectary H sepal H petal ☐filament ☐anther ☐pollen ☐carpel ☐style ☐papillae H vascular H epidermis ☐stomata ☐trichome |
| ☐Silique | ☐stigma ☐style ☐carpel ☐septum ☐placentae ☐transmitting tissue ☐vascular ☐epidermis ☐stomata ☐abscission zone |
| ☐Ovule | Pre-fertilization: ☐inner integument ☐outer integument ☐embryo sac ☐funiculus ☐chalaza ☐micropyle ☐gametophyte Post-fertilization: ☐zygote ☐seed coat ☐primordia ☐chalaza ☐micropyle ☐early endosperm ☐mature endosperm |
| ☐Embryo | ☐suspensor ☐preglobular ☐globular ☐heart ☐torpedo ☐late ☐mature ☐provascular ☐hypophysis ☐radicle ☐cotyledons ☐hypocotyl |
| ☐Stem | ☐epidermis ☐cortex ☐vascular ☐xylem ☐phloem ☐pith ☐stomata ☐trichome |
| ☐Leaf | ☐petiole ☐mesophyll ☐vascular ☐epidermis ☐trichome ☐primordia ☐stomata ☐stipule ☐margin |

X in the Sepal (Se) and Pedicel (Pd) of the flower
X in the Epidermis (Ep) and Phloem (Ph) of the sepal
X in the Epidermis (Ep) and Phloem (Ph) of the petal T2 Seedling Expression   Tissues Screened
Events Screened: n = 2   Events Expressing: n = 2
GFP Expression Detected

| | |
|---|---|
| X Hypocotyl | L epidermis ☐cortex ☐vascular ☐xylem ☐phloem ☐stomata |
| X Cotyledon | ☐mesophyll ☐vascular ☐epidermis ☐trichome ☐margin M stomata |
| ☐Rosette Leaf | ☐mesophyll ☐vascular ☐epidermis ☐trichome ☐petiole ☐primordia ☐stomata ☐stipule ☐margin |
| X Primary Root | ☐epidermis ☐trichoblast ☐atrichoblast ☐cortex ☐endodermis ☐vascular ☐xylem H phloem ☐pericycle ☐quiescent ☐columella ☐cap ☐root hairs |
| ☐Lateral root | ☐epidermis ☐initials ☐flanking cells ☐vascular ☐cap |
| ☐Shoot apical meristem | ☐SAM ☐epidermis |

X in the Phloem (Ph) and Epidermis (Ep) of the hypocotyl
X in the Phloem (Ph) of the root transition zone of the hypocotyl
X in the Guard cells (Gc) of the primary leaf
X in the Phloem (Ph) and Epidermis (Ep) of the Cotyledon (Co)
X in the Phloem Ph of the root elongation zone and root differentiation zone T2 Mature Plant Expression
Plants expressing/Plants screened
Event-01: 1/1   Event-02: 1/1
☐Scheduled
X T2 Mature tissue expressions similar to T1 expression data.
☐T2 Mature tissue expression (if different expression pattern).
Expression detected

| | |
|---|---|
| X Stem | ☐epidermis ☐cortex L vascular ☐xylem ☐phloem ☐pith ☐stomata ☐trichome |

X in the Vasculature (Vs) of the stem

T3 Seedling Expression
Plants expressing/Plants screened
Event-01: 1/6   Weak line   Event-02: 1/1
☐Scheduled
X T3 Seedling tissue expressions similar to T2 seedling expression (data not shown).
☐T2 Mature tissue expression (if different expression pattern).
GFP Expression Detected Promoter Utility
Trait - Sub-trait Area:

Among other uses this promoter sequence is useful to improve:
Nutrient - Low nitrogen tolerance; Nitrogen use efficiency; Nitrogen utilization
References:

1: Deeken R. Geiger D. Fromm J.   Related Articles, Links
Koroleva O, Ache P. Langenfeld-Heyser R. Sauer N. May ST. Hedrich R.
Loss of the AKT2/3 potassium channel affects sugar loading into the phloem of *Arabidopsis*. Planta. 2002 Dec;216(2):334–44. Epub 2002 Sep 21.
PMID: 12447548 [PubMed - indexed for MEDLINE]

2: Geieer D. Becker D. Lacombe B.   Related Articles, Links
Hedrich R.
Outer pore residues control the H(+) and K(+) sensitivity of the *Arabidopsis* potassium channel AKT3.
Plant Cell. 2002 Aug;14(8):1859–68. Erratum in: Plant Cell 2002 Nov;14(11):2975. PMID: 12172027 [PubMed - indexed for MEDLINE]

| | |
|---|---|
| Construct: | YP0049 |
| Promoter Candidate I.D: | 11768643 (Old ID: 6452796) |
| cDNA ID | 12660077 (Old IDs: 7095446, 6452796) |
| T1 lines expressing (T2 seed): | SR00548-01,-02,-03 |

Sequence (SEQ ID NO: 11):

TTCCAAATTCTTATGGTTCTCTAGTGTCATGATTTTGAGAATCACTCAACT

CCAAAAATATAATCCACGATCCCGTGTTAATTATTGAAGAATCAATCGTTT

TTAATTTCTCACCAATAGATGTTGCTCTTATTACTTAAAACAAATTGTTCG

```
GACAAATGTAGCAAGTGTGATACTTTGTGGGATCTTAAAGACGATTTCTCC

TATAACAGAGGACAAAACAGGTCGGTCAATTACAATGTCATCCCTCTTTGC

CCTGTCTTTTTTTTCTTCTTAAAACCTAACCATTTGATTGTTTCTAAAGG

TATTTCAAGAATATATGATCAATCTAGATGAATACTATACCGACGATGACT

ACACACACAAGGAAATATATATATCAGCTTTCTTTTCACCTAAAAGTGGTC

CCGGTTTAGAATCTAATTCCTTTATCTCTCATTTTCTTCTGCTTCACATTC

CCGCTAGTCAAATGTTAATAAGTGCACACAACGTTTTCTCGAAGCATTAGA

ATGTCCTCCTCTTAATTAATCTCCTTCTGATTAGATTCTCAATAGAGTTTA

AATTTGTTAATGGAGAGATATATTGGGACCCTCAAGGCTTCTAATTATACC

ACGTTTGGCATAATTCTCTATCGTTTGGGGCCACATCTTTCACACTTCATT

ACCTTATCACCAAAACATAAAATCAATCAACTTTTTTTTGCCTTATTGATT

GTGTTGGATCCCTCCAAAATTAAAACTTGTGTTCCCCACAAAAGCTTACCC

AATTTCACTTCAATCTTAACAAATAGGACCACCACTACCACGTACGGTTTG

CATCATACAAACCACAAACTCCTTCTTCATTACAATTATTATATCATCTAC

TAAAACCTCTTTCTCCCTCTCTCTTTCTTGTTCTTAGTGCTAAATTTTCTT

TGTTCAGGAGAAATATCCATTGCACTGGGATCCAACAATGTCATCCGACTC

GTCCAAGATCAAGAGGAAAGCGG
```

Promoter Expression Report #12

| | |
|---|---|
| Promoter Tested In: | *Arabidopsis thaliana*, WS ecotype |
| Spatial expression summary: | |
| Flower | (L)pedicel, (L)sepal, (L)vascular |
| Leaf | (M)petiole, (M)vascular |
| Cotyledon | (H)stomata, (M)petiole, (H)vascular |
| Primary Leaf | (L)vascular, (L)petiole |
| Root | (H)root hair |

Observed expression pattern:

GFP expression was detected in the vasculature of sepals, pedicel, and leaf petiole of immature flowers. Also weak guard cell expression existed in sepals. Strong GFP expression was seen in guard cells and phloem of cotyledons, and upper root hairs at hypocotyl root transition zone.
T2 mature:

Same as T1 mature.
T3 seedling:

Same as T2 seedling.

| | |
|---|---|
| Expected expression pattern: | Shoot apical meristems |
| Selection Criteria: | Greater than 5× down in stm microarray |
| Gene: | AP2 domain transcription factor |
| GenBank: | NM_129594 *Arabidopsis thaliana* AP2 domain transcription factor, putative(DRE2B) (At2g40340) mRNA, complete cds, gi\|30688235\|ref\|NM_129594.2\| [30688235] |
| Source Promoter Organism: | *Arabidopsis thaliana* WS |
| Vector: | pNewbin4-HAP1-GFP |
| Marker Type: | X GFP-ER |
| Generation Screened: | X T1 Mature   X T2 Seedling |
| | X T3 Mature   X T3 Seedling |

T1 Mature Plant Expression   Organs/Tissues screened
Lines Screened:  n = 3   Lines Expressing:  n = 2

Promoter Expression Report #12

GFP Expression Detected

| | |
|---|---|
| X Flower | L pedicel ☐receptacle ☐nectary L sepal ☐petal ☐filament ☐anther ☐pollen ☐carpel ☐style ☐papillae L vascular ☐epidermis ☐stomata ☐trichome |
| ☐Silique | ☐stigma ☐style ☐carpel ☐septum ☐placentae ☐transmitting tissue ☐vascular ☐epidermis ☐stomata ☐abscission zone |
| ☐Ovule | Pre-fertilization: ☐inner integument ☐outer integument ☐embryo sac ☐funiculus ☐chalaza ☐micropyle ☐gametophyte Post-fertilization: ☐zygote ☐seed coat ☐primordia ☐chalaza ☐micropyle ☐early endosperm ☐mature endosperm |
| ☐Embryo | ☐suspensor ☐preglobular ☐globular ☐heart ☐torpedo ☐late ☐mature ☐provascular ☐hypophysis ☐radicle ☐cotyledons ☐hypocotyl |
| ☐Stem | ☐epidermis ☐cortex ☐vascular ☐xylem ☐phloem ☐pith ☐stomata ☐trichome |
| X Leaf | L petiole ☐mesophyll L vascular ☐epidermis ☐trichome ☐primordia ☐stomata ☐stipule ☐margin |

X in the Guard Cells (Gc) and Vasculature (Vs) of the sepals of the flower
X in the Vasculature (Vs) of the Pedicel (Pd)
X in the Vasculature (Vs) of the petiole T2 Seedling Expression   Tissues Screened
Events Screened: n = 2   Events Expressing: n = 2
Seedlings expressing/Plants screened
Event-01: No data.   Event-02: No data.
GFP Expression Detected

| | |
|---|---|
| ☐Hypocotyl | ☐epidermis ☐cortex ☐vascular ☐xylem ☐phloem ☐stomata |
| X Cotyledon | ☐mesophyll M vascular ☐epidermis ☐trichome ☐margin H stomata M petiole |
| X Rosette Leaf | ☐mesophyll M vascular ☐epidermis ☐trichome ☐petiole ☐primordia ☐stomata ☐stipule ☐margin |
| X Primary Root | ☐epidermis ☐trichoblast ☐atrichoblast ☐cortex ☐endodermis ☐vascular ☐xylem ☐phloem ☐pericycle ☐quiescent ☐columella ☐cap H root hairs |
| ☐Lateral root | ☐epidermis ☐initials ☐flanking cells ☐vascular ☐cap |
| ☐Shoot apical meristem | ☐SAM ☐epidermis |

X in the Guard Cells (Gc) and Vascular (Vs) tissue of the Cotyledon (Co)
X in the Phloem (Ph) of the petiole
X in the Vascular (Vs) tissue of the primary leaf
X in the Root hair (Rh) of the root transition zone T2 Mature Plant Expression Plants expressing/Plants screened
Event-01: 1/1 Event-02: 1/1
☐Scheduled
X T2 Mature tissue expressions similar to T1 expression data (data not shown).
☐T2 Mature tissue expression (if different expression pattern).
Expression detected

T3 Seedling Expression

Plants expressing/Plants screened
Event-01: 1/3 Event-02: 0/3 No expression
☐Scheduled
X T3 Seedling tissue expressions similar to T2 seedling expression (data not shown).
☐T2 Mature tissue expression (if different expression pattern).
GFP Expression Detected

Promoter Expression Report #12

| | |
|---|---|
| Promoter utility | |
| Trait Area: | Among other uses this promoter sequence is useful to improve: Cold, PG & D, |
| Sub-trait Area: | Cold germination & vigor, plant size, growth rate, plant development |

| | |
|---|---|
| Construct: | YP0060 |
| Promoter Candidate I.D: | 11768797 (Old ID: 35139885) |
| cDNA ID: | 13613553 (Old IDs: 4282588, 12421894) |
| T1 lines expressing (T2 seed): | SR00552-02,-03 |

Sequence (SEQ ID NO: 12):

TGGAGCTTTATTGAAATGCAAGAAAGTAAACAAAGGAAGATCTTTAGATTG

TCACCAAGAGTGGTCTGAAACTCTCATAACACTCAATCCTCCTCCTCCTCA

TCACCACCACTACAAAATATTATATTCTCTATCTCTCAATCTATGAGGAGA

TGTATTCTATCAAGCATTTGAAATGATAAGAAACTGGCGATCATCCTCTAC

GTCACCATCACTCCAAAATTATCCTCTTTCTAGGTTTAAGTTTTGTAATGA

TCGCCTTTATTTGTTGAGATCTCTAACTTCTCGCATTTCCAAAATGTTAAG

TCCAATAACTGCATTGGTTAAGTTGGGGCGTTACTAGTCGGCTTAAATCCA

AATATGGATTTGATTCCATATGTATGTGACAGTTTCTTAACGTTCATATTA

CAATGAATGATGGATCCTTGACTAGACAAAGAGAAAATGGATTGTCACTTC

GTAGGAAAAATAGAAATTCTCCACGAAGGCTGGTCTCCTTTATTTAACGAC

AAATTCACTCATAGTCTCATTCACAATTTGAACTTGTCTAACACAATGTGT

TATATACTCGCAAAAGAAGCATAATAGGCTCTTAAGGGTAATCCACGAAA

CCAAAACACATATAAAACATTAATATTTTTCTCTAAATTTATTCATATCAA

TAATAAAGTTTACAAAAAATATAAAACAATAATCCATACTTAGCCCATAGC

TTCGTGTGGAAGAAGACTTGATTTTTGACTAGTCAACGAAAATGAGTAAAT

GACGTATTCAGCTATAGTAAAAGGGATCATAAGCGGAAATTACAAAGAAGC

TTTGAGGGTAAACTAGTCAAAAAGCATAATCAGAAATAACTTAGGCCCAAA

GCAAAAAGGAAAGGGCTCTGGATCCAGCCGCAAATCAGAATCTGGTAAGTT

CGAACGCCACGTCATCACCTAAATATCTGAAATATCTAATTAAGACTTGTC

TATATATAAAGGCTTCTCCTTTCACAATCCC

Promoter Expression Report #13

| | |
|---|---|
| Promoter Tested In: | Arabidopsis thaliana, WS ecotype |
| Spatial expression summary: | |
| Ovule Post-fertilization: | (H)endothelium, (H)micropyle, (H)chalaza |
| Observed expression pattern: T1 and T2 mature: | |

Strong expression was seen in the mature inner integument cell layer, endothelium, micropyle and chalaza ends of maturing ovules. Expression was not detected in earlier stage ovules.
T2 and T3 seedling expression:

None
Expected expression pattern: Primarily in developing seeds
Selection Criteria: Arabidopsis public; Mol. Gen. Genet. 244, 572–587 (1994)

Promoter Expression Report #13

| | |
|---|---|
| Gene: | plasma membrane H(+)-ATPase isoform AHA10; |
| GenBank: | NM_101587 Arabidopsis thaliana ATPase 10, plasma membrane-type (proton pump 10) (proton-exporting ATPase), putative (At1g17260) mRNA, complete cds, gi\|18394459\| |
| Source Promoter Organism: | Arabidopsis thaliana WS |
| Vector: | pNewbin4-HAP1-GFP. |
| Marker Type: | X GFP-ER |
| Generation Screened: | X T1 Mature   X T2 Seedling<br>X T3 Mature   X T3 Seedling |

| T1 Mature Plant Expression | Organs/Tissues screened |
|---|---|
| Events screened:   n = 3 | Events expressing:   n = 3 |
| No GFP Expression Detected | |
| ☐Flower | ☐pedicel ☐receptacle ☐nectary ☐sepal ☐petal ☐filament ☐anther ☐pollen ☐carpel ☐style ☐papillae ☐vascular ☐epidermis ☐stomata ☐trichome |
| ☐Silique | ☐stigma ☐style ☐carpel ☐septum ☐placentae ☐transmitting tissue ☐vascular ☐epidermis ☐stomata ☐abscission zone |
| X Ovule | Pre-fertilization: ☐inner integument ☐outer integument ☐embryo sac ☐funiculus chalaza micropyle ☐gametophyte<br>Post-fertilization: ☐zygote L seed coat ☐primordia H chalaza H micropyle ☐early endosperm ☐mature endosperm |
| ☐Embryo | ☐suspensor ☐preglobular ☐globular ☐heart ☐torpedo ☐late ☐mature ☐provascular ☐hypophysis ☐radicle ☐cotyledons ☐hypocotyl |
| ☐Stem | ☐epidermis ☐cortex ☐vascular ☐xylem ☐phloem ☐pith ☐stomata ☐trichome |
| ☐Leaf | ☐petiole ☐mesophyll ☐vascular ☐epidermis ☐trichome ☐primordia ☐stomata ☐stipule ☐margin |

X in the endothelium layer surrounding the embryo of mature ovules. Inner integument cell layers can still be distinguished at micropllar pole.
X in the Inner integument (Ii)

| T2 Seedling Expression | Tissues Screened |
|---|---|
| Events Screened: n = 2 | Events Expressing: n = 2 |
| Seedlings expressing/Plants screened | |
| Event-01: No data Event-02: No data | |
| ☐Scheduled | |
| GFP Expression Detected | |
| ☐Hypocotyl | ☐epidermis ☐cortex ☐vascular ☐xylem ☐phloem ☐stomata |
| ☐Cotyledon | ☐mesophyll ☐vascular ☐epidermis ☐margin ☐stomata ☐hydathode |
| ☐Rosette Leaf | ☐mesophyll ☐vascular ☐epidermis ☐trichome ☐petiole ☐primordia ☐stomata ☐stipule ☐margin |
| ☐Primary Root | ☐epidermis ☐trichoblast ☐atrichoblast ☐cortex ☐endodermis ☐vascular ☐xylem ☐phloem ☐pericycle ☐quiescent ☐columella ☐root cap ☐root hairs |
| ☐Lateral root | ☐epidermis ☐trichoblast ☐atrichoblast ☐cortex ☐endodermis ☐initials ☐flanking cells ☐vascular ☐lateral root cap |
| ☐Shoot apical meristem | ☐SAM ☐epidermis |

T2 Mature Plant Expression
Plants expressing/Plants screened
Event-01: 1/1 Event-02: 1/1
☐Scheduled
X T2 Mature tissue expressions similar to T1 expression data (data not shown).
☐T2 Mature tissue expression (if different expression pattern).
Expression detected

Promoter Expression Report #13

T3 Seedling Expression
Plants expressing/Plants screened
Event-01: 0/3 Event-02: 0/3
☐ Scheduled
X T3 Seedling tissue expressions similar to T2 seedling expression (data not shown).
☐ T2 Mature tissue expression (if different expression pattern).
GFP Expression detected Promoter utility
Trait Area:

Among other uses this promoter sequence could be useful to improve:
Seed - Endosperm cell number and size, endosperm granule number/size, seed enhancement
Yield - harvest index, test weight, seed size
Quality - protein, total oil, total seed composition, composition
Notes:

Endothelium is the location of pigment deposition which gives *Arabidopsis* seeds their characteristic brown color. Seed coat pigments in *Arabidopsis* are predominantly flavonoids or proanthocyanidins. Proanthocyanidins (PAs) accumulate as colorless compounds during the early steps of embryogenesis and have been shown to participate in the maintenance of seed coat-imposed dormancy as well as in seed longevity during storage. Nesi, N, et. al., The Plant Cell, Vol. 14, 2463–2479, October 2002.
References:

1: Harper JF. Manney L. Sussman MR. Related Articles, Links The plasma membrane H(+)-ATPase gene family in *Arabidopsis*; genomic sequence of AHA10 which is expressed primarily in developing seeds. Mol Gen Genet. 1994 Sep 28; 244(6): 572–87.

| | |
|---|---|
| Construct: | YP0092 |
| Promoter Candidate I.D: | 13148193 (Old ID: 35139598) |
| cDNA ID | 12661844 (Old ID: 4993117) |
| T1 lines expressing (T2 seed : | SR00639-01,-02,-03 |

Sequence (SEQ ID NO: 13):

AAAGATTGAGTTGAGAGAGATGGTGGAGACGCAGAACAGACAAAGGGAGTT

TACCATATAGTGCTCTAAAGGGCAATGAGATTGCAGTGATGTGGCTATCCG

GGGAATCATCGCAGGTTATTCCTTCCCATGAGCAACAATCAATGGATGGT

TCCAATTCAGAGGAGAAACAGAAGAAGAAACGTTTCCAGAGAACCACAGTA

GGGATTCTCGATCTTGCGAGTTGCAGAGAGCCTCTGAAACTGCAATAGAAA

GGACACTGATGAAAAGAACACACTGAAGGAGTATGCCAATCATGTGAAAAC

TCAGAGCTTGTATTGGTCTTGTGGTTGATGAAGTTCTCACAAAACCTTTGG

CTTTGAATCTCCCCTCATTAGTCATGGTGAGAACAAGAACAAGACGAGAAA

CAGACAAAGAAGATGAAAAAACTTGTTGGCCAGTGTTGACTAAGGGGAAT

AGCCCCAGACATAACAAAATTAGACTTGTCGTACATCTTTAATATTTTTT

ATCTGTTTCTTTGTCCTGACGCTTTCATTATTCCTGTGATCAATTTTCTCA

TACCATTGGTCCATCGTTAATCCTTTCTTAATTTCATTTTCTACGTAACAT

GAGAGGAGACCAAGTCCTATGAGAACAGTTGACGTAACAGTGGTTGTTAAG

TTAAGTTAAAAAGAGGAAGCTAGTGAGAGTGACCGTTAGGTAGAGAAGTGA

GATCTTTAACCACTCTTCTTTCTCTCTCTCTGCTTTTTTCGTCGTCTTT

CACATCTACTGTTCGCAAACTCTCTTATGCTTCCAATAATGGTGATACCAA

TTGAGACTTGCAGGAGAATCTCCTCTTCTCCACACTCTATCAACTGGTCAG

CCATGGAATGGTCGTTTCAGTTTCAATATTCCTGGATTCTTTTTAAGGATT

CCTGTTTCTCTTCTGTTCCTGGTATATTCTTAACGACGAAATTAGTATCGG

ATCCTGGTAATACATTTTGAAGCTTTTAAGTACCATTGCACTGGGATCCAA

CAATGTCCTCCGACTCGTCCAAGATCAAGAGGAAGCGGAACCGCATCCC

Promoter Expression Report #14

| | |
|---|---|
| Promoter Tested In: | *Arabidopsis thaliana*, WS ecotype |
| Spatial expression summary: | |
| Flower | (L)silique |
| Silique | (L)medial vasculature, (L)lateral vasculature |
| Observed expression pattern: | |

GFP expressed in the medial and lateral vasculature of pre-fertilized siliques. Expression was not detected in the older siliques or in T2 seedlings.
T2 mature:

Weak silique vasculature expression was seen in one of two events.
T3 seedling:

Same as T2 seedling.

| | |
|---|---|
| Expected expression pattern: | Expression in ovules |
| Selection Criteria: | Greater than 50× up in pi ovule microarray |
| Gene: | expressed protein; protein id: At4g15750.1, hypothetical protein |
| GenBank: | NM_117666 *Arabidopsis thaliana* expressed protein (At4g15750) mRNA, complete cds gi\|18414516\|ref\|NM_117666.1\| [18414516] |
| Source Promoter Organism: | *Arabidopsis thaliana* WS |
| Vector: | pNewbin4-HAP1-GFP |
| Marker Type: | X GFP-ER |
| Lines Screened: | n = 3 |
| Lines Expressing: | n = 3 |
| Generation Screened: | X T1 Mature    X T2 Seedling |
| | X T3 Mature    X T3 Seedling |

T1 Mature Plant Expression    Organs/Tissues screened
Events screened: n = 3    Events expressing: n = 3
GFP Expression Detected

| | |
|---|---|
| X Flower | ☐pedicel ☐receptacle ☐nectary ☐sepal ☐petal ☐filament ☐anther ☐pollen ☐carpel ☐style ☐papillae ☐vascular ☐epidermis ☐stomata ☐trichome L silique |
| X Silique | ☐stigma ☐style ☐carpel ☐septum ☐placentae ☐transmitting tissue L vascular ☐epidermis ☐stomata ☐abscission zone |
| ☐Ovule | Pre-fertilization: ☐inner integument ☐outer integument ☐embryo sac ☐funiculus ☐chalaza ☐micropyle ☐gametophyte Post-fertilization: ☐zygote ☐seed coat ☐primordia ☐chalaza ☐micropyle ☐early endosperm ☐mature endosperm |
| ☐Embryo | ☐suspensor ☐preglobular ☐globular ☐heart ☐torpedo ☐late ☐mature ☐provascular ☐hypophysis ☐radicle ☐cotyledons ☐hypocotyl |
| ☐Stem | ☐epidermis ☐cortex ☐vascular ☐xylem ☐phloem ☐pith ☐stomata ☐trichome |
| ☐Leaf | ☐petiole ☐mesophyll ☐vascular ☐epidermis ☐trichome ☐primordia ☐stomata ☐stipule ☐margin |

Promoter Expression Report #14

X in the Lateral vasculature (Lv) and Medial vasculature (Mv) of the silique

T2 Seedling Expression   Tissues Screened
Events Screened: n = 2   Events Expressing: n = 0
Seedlings expressing/Plants screened
Event-01: 0/6 Event-02: 0/6
No GFP Expression Detected

| | |
|---|---|
| ☐Hypocotyl | ☐epidermis ☐cortex ☐vascular ☐xylem ☐phloem ☐stomata |
| ☐Cotyledon | ☐mesophyll ☐vascular ☐epidermis ☐trichome ☐margin ☐stomata |
| ☐Rosette Leaf | ☐mesophyll ☐vascular ☐epidermis ☐trichome ☐petiole ☐primordia ☐stomata ☐stipule ☐margin |
| ☐Primary Root | ☐epidermis ☐trichoblast ☐atrichoblast ☐cortex ☐endodermis ☐vascular ☐xylem ☐phloem ☐pericycle ☐quiescent ☐columella ☐cap ☐root hairs |
| ☐Lateral root | ☐epidermis ☐initials ☐flanking cells ☐vascular ☐cap |
| ☐Shoot apical meristem | ☐SAM ☐epidermis |

T2 Mature Plant Expression
Plants expressing/Plants screened
Event-01: 0/4 Event-02: 1/3
☐Scheduled
X T2 Mature tissue expressions similar to T1 expression data.
☐T2 Mature tissue expression (if different expression pattern).
Expression detected
X in the Medial vasculature (Mv) of the silique T3 Seedling Expression
Plants expressing/Plants screened
Event-01: 0/1; 1 of 12 seedlings germinated. Event-02: 0/12
☐Scheduled
☐T3 Seedling tissue expressions similar to T2 seedling expression (data not shown).
☐T2 Mature tissue expression (if different expression pattern).
No GFP Expression Detected Promoter utility
Trait - Sub-trait Area:

Among other uses this promoter sequence could be useful to improve:
Water use efficiency - Moisture stress at seed set, Moisture stress at seed fill, water use efficiency, Ovule/seed abortion
Seed - test weight, seed size
Yield - harvest index, , total yield
Quality - amino acids, carbohydrate, protein, total oil, total seed composition

| | |
|---|---|
| Construct: | YP0113 |
| Promoter Candidate I.D: | 13148162 (Old ID: 35139698) |
| cDNA ID: | 12332135 (Old ID: 5663809) |
| T1 lines expressing (T2 seed): | SR00691-01,-03 |

Sequence (SEQ ID NO: 14):

TATGAAGAAATTATAATAGACTCTCATAAAAATAGTGTTACAACTTACATT
CTCTTATATAGAAATTAGGATAAACAGAAATGTAAATAATATATTTCGAAA
TAATGTTAAATTTCCTAAATTCTAATATTAATATTTATAAATGGTCATTTA
ACTTTTTCGTACCGGTTCGATGGGACATGTGTTATATTCAGTTAAGGTTAC
CACCATGCGCCAACTTGGCCTCTACCAAGTCAACATGGATATGGACCTTAT
GGTTACATGCCGCCTCCGCCTCCACCGCTACCGGGATATGGATACAGAGGT
CCGCCACCTCAGCAACCGACGAGGAATGAAACAAGGCAATAATATATTGAT
GCTATTGTGGATTTAGTTACTGATAATTAGTGCCTTAGTGACAGTTCAAAA
ATGTTGTTCATCAATAATCTACAATTTAAGGTTTGTGTTGTGGAATGTTTC
ATGATTTTATGAAGTCTTGCTTATCAAAAAGTATGATGATTAAGAATTTGA
CTTCATGGCATATTCATTTGAGTTAGCAAAACTTTTTTGTGTTGCACCTTC
AAATTTATAAATTTATGATTTTTAACCATCGAAATTATATATTTGAAAAGA
CTATCTCTACAAGCCAAACCCACTGGGCCACCAATATGGGTTTATCTGCGA
AATCTGTGAACCTTAGAAAATCAAAGCCCATATCCACTTTGCTGGAACTTT
GCTGGAATGTAGGTTAGACAAAACCTTAAGACGCAGCTACAAGTCTCTTAT
GTGGCAGATGTCAAAATTAATGAGCAGCTATAATTTACCCAAGAGGAGCAA
AATAAGATTAGCAGCTTAAATTAATTGTGTTGGATTAAATGAAACTTGCAC
TATGAATGGCAAAAAAGAGGTTACAATCTAGCAACCACCTCATAAACCCTC
ATTAATGAGATACTGCATCGTGAACCAATCAAATCTCAAGTTTCGTAGTTT
AAATAAGTAGTAAACACCTCCTGATCAAAGCATCACCACCACCAAATATCA
AACGCAAAAACCTATTATCAAAAGAACTAGGGAGGAAATGACTAATCCCCA
TGATCATGGTTATGCTGTTGTTGTTTCTTGTGATGTCGACTAGAGCAGACG
AAGAGCTGATTAAGACAGAGTGTAATCACACAGAATACCAAAACGTATGCC
TCTTCTGTCTTGAAGCCGATCCCAATCTCCTTCAATATCGGACCGTGCTGG
ACTTGTCAACCATCATTAATACACTGTCTCGGGATCTCAACTTGATGTTCT
TATCAAGTAAGTTTCACCATGTACACCATTAATCATTATTGTACAAATAAT
AATATTTTTAATGTGTTTTCACAAAATTAATATTACCTCTTTTTTGTAAAC
TAATATGCTACGAAAATTAACATACTACGAAAAATGTGAATTAATATTACT
TTGCCTGTAAATTTTTACCTCCATAATAATATTAGCATACCACGAAAAAAT
GTAACGTATTTCTTTTGGTGTAATGTGAATTTTGCTACGGTAAACTTACTT
TACAAAGAAAGAAGAGCGTTTTCCAAGTGGAAAATAATACATTTTGCGGTT
TATATATTATAGGAACGACTATTGATTTGTTTTTTTGGTTGTACCATTGCA
CTGGGATCCAACAATGTCCTCCGACTCGTCCAAGATCAAGAGGAAGCGGAA
CCGC

Promoter Expression Report #15

| | |
|---|---|
| Promoter Tested In: | *Arabidopsis thaliana*☐, WS ecotype |
| Spatial expression summary: | |
| Flower | (L)silique |
| Silique | (L)medial vasculature, (L)lateral vasculature, (H)guard cells |
| Rosette leaf | (H)guard cell |
| Observed expression pattern: | |

GFP expressed in the medial and lateral vasculature of pre-fertilized siliques. Expression was not detected in older siliques. Guard cell expression was seen throughout pre-fertilized and fertilized siliques.
T2 seedling:

No expression was seen.
T2 mature expression:

Similar to T1 mature expression.

Promoter Expression Report #15

T3 seedling:

Guard cell expression not seen in T2 seedlings, however it is in the same tissue type observed in mature plants of previous generation.
Expected expression pattern:

Strong activity in the inner endosperm tissue of developing seeds and weak activity in root tips.

| | |
|---|---|
| Selection Criteria: | *Arabidopsis* public; Plant Mol. Biol. 39, 149–159 (1999) |
| Gene: | Alanine aminotransferase, AlaAT |
| GenBank: | AAK92629 Putative alanine aminotransferase [*Oryza sativa*] gi\|15217285\|gb\|AAK92629.1\| AC079633_9[15217285] |
| Source Promoter Organism: | Rice |
| Vector: | pNewbin4-HAP1-GFP. |
| Marker Type: | X GFP-ER |
| Generation Screened: | X T1 Mature   X T2 Seedling  X T3 Mature   X T3 Seedling |

T1 Mature Plant Expression   Organs/Tissues screened
Events screened: n = 3   Lines Expressing: n = 2

| | |
|---|---|
| ☐Flower | ☐pedicel ☐receptacle ☐nectary ☐sepal ☐petal ☐filament ☐anther ☐pollen ☐carpel ☐style ☐papillae ☐vascular ☐epidermis ☐stomata ☐trichome |
| X Silique | ☐stigma ☐style ☐carpel ☐septum ☐placentae ☐transmitting tissue L vascular ☐epidermis H stomata ☐abscission zone |
| ☐Ovule | Pre-fertilization: ☐inner integument ☐outer integument ☐embryo sac ☐funiculus ☐chalaza ☐micropyle ☐gametophyte Post-fertilization: ☐zygote ☐seed coat ☐primordia ☐chalaza ☐micropyle ☐early endosperm ☐mature endosperm |
| ☐Embryo | ☐suspensor ☐preglobular ☐globular ☐heart ☐torpedo ☐late ☐mature ☐provascular ☐hypophysis ☐radicle ☐cotyledons ☐hypocotyl |
| ☐Stem | ☐epidermis ☐cortex ☐vascular ☐xylem ☐phloem ☐pith ☐stomata ☐trichome |
| ☐Leaf | ☐petiole ☐mesophyll ☐vascular ☐epidermis ☐trichome ☐primordia ☐stomata ☐stipule ☐margin |

X in the Guard cell (Gc), Lateral vasculature (Lv) and Medial vasculature (Mv) of the silique T2 Seedling Expression   Tissues Screened
Events screened: n = 2   Lines Expressing: n = 0
Plants expressing/Plants screened
Event-01: 0/4 Event-02: 0/2
No GFP Expression Detected

| | |
|---|---|
| ☐Hypocotyl | ☐epidermis ☐cortex ☐vascular ☐xylem ☐phloem ☐stomata |
| ☐Cotyledon | ☐mesophyll ☐vascular ☐epidermis ☐trichome ☐margin ☐stomata |
| ☐Rosette Leaf | ☐mesophyll ☐vascular ☐epidermis ☐trichome ☐petiole ☐primordia ☐stomata ☐stipule ☐margin |
| ☐Primary Root | ☐epidermis ☐trichoblast ☐atrichoblast ☐cortex ☐endodermis ☐vascular ☐xylem ☐phloem ☐pericycle ☐quiescent ☐columella ☐cap ☐root hairs |
| ☐Lateral root | ☐epidermis ☐initials ☐flanking cells ☐vascular ☐cap |

T2 Mature Plant Expression
Plants expressing/Plants screened
Event-01:1/1   Event-02: 1/2
☐Scheduled
X T2 Mature tissue expressions similar to T1 expression data (data not shown).

☐T2 Mature tissue expression (if different expression pattern).
Expression detected T3 Seedling Expression
Plants expressing/Plants screened
Event-01:1/3   Event-02: 2/3
☐Scheduled
☐T3 Seedling tissue expressions similar to T2 seedling expression (data not shown).
X T2 Mature tissue expression (if different expression pattern).
GFP Expression Detected Promoter utility
Trait Area:

Among other uses this promoter sequence could be useful to improve:
Seed, source, yield, quality
Sub-trait Area:

Seed enhancement, transport amino acids, harvest index, test weight, seed size, amino acids, carbohydrate, protein, total seed composition

| | |
|---|---|
| Construct: | YP0095 |
| Promoter Candidate ID: | 13148198 (Old ID: 35139658) |
| cDNA ID: | 6795099 in rice |
| T1 lines expressing (T2 seed:) | SR00642-02,-03 |

Sequence (SEQ ID NO: 15):

TTCCTCGACCATGCCGTTGCCGGAACCGGCTAGCGCGGCCGGCCGGCGGCG

GCGGGGAGGCCGCAGTGGGACGACGGGTGAAGGATCCTCCAGCTGCGGAAG

GAGGTGGTCCTCGAGGCCGAAGGGGAGAGGCTACGGAGATGGAGGGAAGCC

GAAGAGAAGGGAGGCTGCTGCTGCTGCTGCATTTGGGAGACGAGAACTCGA

CTCGAGCCATGGCGGCAGATTGGTGTTTCACGGCGGAATGCTAACTAGATC

CAGCATCTCCATAGCAAAGGTAGAATGGTAGATTGAGGTGAGTTTTTTTTC

CCCTCTTCTGCAGTTTTGATGTATTATTACTGCCCTCATCTGATCTGGGTA

ACATATTTCTGAGCTCAGTAGAACTGTTAAAAAAAGGCAGAAATGCACAAA

CTCTTCTCACAAAACAACATACAAATGCTTATATTTTGGAGCGGAGGCAAT

ACATGGTATATTTTTTAAAGTGAAAAAAACAATCAGACACATGGTATTGAG

TGATAGCAAAGCTGGGTGACCACAGAAAATACCTCCTGCTTTAAATACTTT

ATACCTGGGCTGTCAATCCTCGGAGTTCCTCCCAATGTAATGTCTGAGGAA

GAAGTATTGCAGCTAAATTTTAAGGGTTTCTTGTACGAAACAGGGACAATC

AGAGATTAAGAAACTCTATGTGGAAAAGGCCATGCGCATTTTGTTATGTGA

TTCAACAAATAAGATGAGGAGGCAAAGTCATGGTTCTGTTCTAATTAACAA

ATCTACTATGGGGCCGTTGCTCCCTATTGTCCACGCTCCTTTTCTTCATT

TCTCTCCTGCAGGATATCTTGTCTTTTGATTCTTCATTTTAGGTCTTATAA

ATATCACGTGGTTCAGGCCTCCAATGTCAAATTATCATTACGTGGAACTCT

CTTAGATGCTTGAGAAAAGTTAGCTCTTACCTGTCCATAGAAGCTCCAAGG

AAGCGAGAATAGTAGATACTTTGGTTGGCC

Promoter Expression Report #16

| | |
|---|---|
| Promoter Tested In: | *Arabidopsis thaliana*, WS ecotype |
| Spatial expression summary: | |
| Ovule | Pre-fertilization: (M)gametophyte, (M)embryo sac |
| Root | (H)epidermis, (M)pericycle, (H)root hairs |
| Lateral root | (H)flanking cells |
| Observed expression patterns: | |

GFP expressed in the egg cell and synergid cell of female gametophyte in early ovule development. It expressed in polarizing embryo sac in later stages of pre-fertilized ovule development. No expression was seen in fertilized ovules. GFP expressed throughout the epidermal cells of seedling roots. It also expressed in flanking cells of lateral root primordia.

T2 mature:

Same as T1 mature.

T3 seedling:

Same as T2 seedling

| | |
|---|---|
| Expected expression pattern: | Expression in ovules |
| Selection Criteria: | Greater than 50× up in pi ovule microarray |
| Gene: | Senescence-associated protein homolog |
| GenBank: | NM_119189 *Arabidopsis thaliana* senescence-associated protein family (At4g30430) mRNA, complete cds, gi\|18417592\|ref\|NM_119189.1\| [18417592] |
| Source Promoter Organism: | *Arabidopsis thaliana* WS |
| Vector: | pNewbin4-HAP1-GFP |
| Marker Type: | X GFP-ER |
| Generation Screened: | X T1 Mature   X T2 Seedling |
| | X T3 Mature   X T3 Seedling |

T1 Mature Plant Expression    Organs/Tissues screened
Lines Screened: n = 3   Lines Expressing: n = 2
GFP Expression Detected

| | |
|---|---|
| ☐Flower | ☐pedicel ☐receptacle ☐nectary ☐sepal ☐petal ☐filament ☐anther ☐pollen ☐carpel ☐style ☐papillae ☐vascular ☐epidermis ☐stomata ☐trichome |
| ☐Silique | ☐stigma ☐style ☐carpel ☐septum ☐placentae ☐transmitting tissue ☐vascular ☐epidermis ☐stomata ☐abscission zone |
| X Ovule | Pre-fertilization: ☐inner integument ☐outer integument M embryo sac ☐funiculus ☐chalaza ☐micropyle M gametophyte Post-fertilization: ☐zygote ☐seed coat ☐primordia ☐chalaza ☐micropyle ☐early endosperm ☐mature endosperm |
| ☐Embryo | ☐suspensor ☐preglobular ☐globular ☐heart ☐torpedo ☐late ☐mature ☐provascular ☐hypophysis ☐radicle ☐cotyledons ☐hypocotyl |
| ☐Stem | ☐epidermis ☐cortex ☐vascular ☐xylem ☐phloem ☐pith ☐stomata ☐trichome |
| ☐Leaf | ☐petiole ☐mesophyll ☐vascular ☐epidermis ☐trichome ☐primordia ☐stomata ☐stipule ☐margin |

X in the Female gametophyte (Fgm) of early pre-fertilized ovules
X in the Embryo sac (Es) of pre-fertilized ovules T2 Seedling Expression    Tissues Screened
Events Screened: n = 2   Events Expressing: n = 2
Seedlings expressing/Plants screened
Event-01: 1/3   Event-02: 2/3

| | |
|---|---|
| ☐Hypocotyl | ☐epidermis ☐cortex ☐vascular ☐xylem ☐phloem ☐stomata |
| ☐Cotyledon | ☐mesophyll ☐vascular ☐epidermis ☐trichome ☐margin ☐stomata |
| ☐Rosette Leaf | ☐mesophyll ☐vascular ☐epidermis ☐trichome ☐petiole ☐primordia ☐stomata ☐stipule ☐margin |

Promoter Expression Report #16

| | |
|---|---|
| X Primary Root | H epidermis ☐trichoblast ☐atrichoblast ☐cortex ☐endodermis ☐vascular ☐xylem ☐phloem M pericycle ═quiescent ☐columella ☐cap H root hairs |
| X Lateral root | ☐epidermis ☐initials H flanking cells ☐vascular ☐cap |
| ☐Shoot apical meristem | ☐SAM ☐epidermis |

X in the Epidermis (Ep), Lateral root initial (Lri) and Root hair (Rh) of the hypocotyl-root
X in the Epidermis (Ep), Lateral root initial (Lri) and Pericycle (Pr) of the lateral root initial
X in the root epidermis
X in the Pericycle (Pr) of the lateral root primordial
X in the Pericycle (Pr) of the lateral root T2 Mature Plant Expression
Plants expressing/Plants screened
Event-01: 1/1   Event-02: 1/1
☐Scheduled
X T2 Mature tissue expressions similar to T1 expression data (data not shown).
☐T2 Mature tissue expression (if different expression pattern).
Expression detected T3 Seedling Expression
Plants expressing/Plants screened
Event-01: 2/3   Event-02: 1/3
☐Scheduled
X T3 Seedling tissue expressions similar to T2 seedling expression (data not shown).
☐T2 Mature tissue expression (if different expression pattern).
GFP Expression Detected Promoter utility
Trait Area:

Among other uses this promoter sequence could be useful to improve: Water use efficiency, seed, yield
Sub-trait Area:

Moisture stress, water use efficiency, ovule/seed abortion, harvest index, test weight, seed size, total yield, amino acids, carbohydrate, proteintotail oil, total seed composition

| | |
|---|---|
| Construct: | YP0102 |
| Promoter Candidate I.D: | 11768651 (Old ID: 35139696) |
| cDNA ID: | 13613954 (Old IDs: 12329268, 1382001) |
| T1 lines expressing (T2 seed): | SR00643-01,-02 |

Sequence (SEQ ID NO: 16):

ATTTGGTTGATAACGTTTTCACTCGACTAATTATATACTTCAGAAGGATAG

TAATAGAATACCAAAATAATTAAATGATTGGTTAGTGCCTTAGTGGAGACT

TTTTAACCGATTCTAATAGACTAATGATGTAGCTAAGCATTTATTTGGGAT

CATCACTGTTTGAAAACGTGAAATGTGATAAAAGTTATGAAACGATTAAAA

TATAAAATAACCGTACAAAACATTATGTACCGTTTTTTTCTCTGTTCTTTT

GGCGATTTGGTTTAGTTCGTTACACTCTAAATGTTATTGCAGATATATATA

TAATGATGCATTTGCATCTGAGGAACATATAATTCCGGTTAACACTTCCAA

ATCTTATATCCGTCTAGGTAGGGATTTTATAAATCATTTGTGTCATCATGC

GTTATGCTTGTCGGCTTTGACCATAACGCAGAGATATAGAACTAGCTTTTA

CTTAACTTTTAGATTTATTATTTGATCTAGAGTTAAGTGGAGATATATAGT

GTTTTTGTTAGATTATTGGTGGATGTGAGAGTTTGTCTTTAGTTTCAAGTT

-continued
```
GAGAATATAAGGCAAGAGGAGACTCTGAGGCAATCAGAGGTTTTGATTGGC

AAAATATCCAAAAGGCCCAAACCAAGTCGAAGCCCATCTCGTACAAAAAAA

GAAAGAGATCTGTAAGAAAAAATATTCTTTGATATTCTTACAAAAATAAGT

GTAAAACTTTTATTAGTCAAAATCTTCAATCTTTAAAAACTCTCATCACTC

CTACGAAAGCGCGTGAGAGTTATGAGACATTCCTTAATAGCATTACTCACA

AGTCACAAGTTCAAAACGTCTGACTGAAACAGAAACAAGCCTTTGTTGAAG

TCTTGAAGAAGAGACATTAGTACTCGTCGTATAGCCATAAAAGGTAATATA

CGAAATTTCTTCGCTAATCTCTTCACCTTCCTCTACGCGTTTCACTTTCAC

TTTATAAATCCAAATCTCCCTTCGAAAACAT
```

| Promoter Expression Report #17 | |
|---|---|
| Promoter Tested In: | *Arabidopsis thaliana*, WS ecotype |
| Spatial expression summary: | |
| Ovule | Pre-fertilization: (H)inner integument |
| | Post-fertilization: (H)inner integument, (M)outer integument, (M)seed coat |
| Primary Root | (L)root hair |
| Observed expression pattern: | |

GFP expressed in the inner integuments of pre-fertilized and fertilized ovules. Female gametophyte vacuole seen as dark oval.
T2 mature:

Same expression was seen as T1 with additional expression observed in similar tissue. GFP expressed in the outer integument and seed coat of developing ovules and seed.
T3 seedling expression:

GFP expression was seen in a few root hairs

| | |
|---|---|
| Expected expression pattern: | Expression in ovules |
| Selection Criteria: | Greater than 50× up in ovule microarray |
| Gene: | putative protease inhibitor |
| GenBank: | NM_129447 *Arabidopsis thaliana* protease inhibitor - related (At2g38900) mRNA, complete cds, gi│30687699│ref│NM_129447.2│ [30687699] |
| Source Promoter Organism: | *Arabidopsis thaliana* WS |
| Vector: | pNewbin4-HAP1-GFP |
| Marker Type: | X GFP-ER |
| Generation Screened: | X T1 Mature    X T2 Seedling |
| | X T3 Mature    X T3 Seedling |

T1 Mature Plant Expression    Organs/Tissues screened
Lines Screened: n = 3    Lines Expressing: n = 3
GFP Expression Detected

| | |
|---|---|
| ☐Flower | ☐pedicel ☐receptacle ☐nectary ☐sepal ☐petal ☐filament ☐anther ☐pollen ☐carpel ☐style ☐papillae ☐vascular ☐epidermis ☐stomata ☐trichome |
| ☐Silique | ☐stigma ☐style ☐carpel ☐septum ☐placentae ☐transmitting tissue ☐vascular ☐epidermis ☐stomata ☐abscission zone |
| X Ovule | Pre-fertilization: H inner integument ☐outer integument ☐embryo sac ☐funiculus ☐chalaza ☐micropyle ☐gametophyte Post-fertilization: ☐zygote ☐seed coat ☐primordia ☐chalaza ☐micropyle ☐early endosperm ☐mature endosperm |
| ☐Embryo | ☐suspensor ☐preglobular ☐globular ☐heart ☐torpedo ☐late ☐mature ☐provascular ☐hypophysis ☐radicle ☐cotyledons ☐hypocotyl |

| Promoter Expression Report #17 | |
|---|---|
| ☐Stem | ☐epidermis ☐cortex ☐vascular ☐xylem ☐phloem ☐pith ☐stomata ☐trichome |
| ☐Leaf | ☐petiole ☐mesophyll ☐vascular ☐epidermis ☐trichome ☐primordia ☐stomata ☐stipule ☐margin |

X in the Female gametophyte (Fgm), Inner integument (Ii), and the Micropyle (Mp) in the pre-fertilized ovule
X in the Inner integument (Ii) of the fertilized ovule T2 Seedling Expression    Tissues Screened
Events Screened: n = 2    Events Expressing: n = 0
Seedlings expressing/Plants screened
Event-01: 0/3    Event-02: 0/3
☐Scheduled
No GFP Expression Detected

| | |
|---|---|
| ☐Hypocotyl | ☐epidermis ☐cortex ☐vascular ☐xylem ☐phloem ☐stomata |
| ☐Cotyledon | ☐mesophyll ☐vascular ☐epidermis ☐margin ☐stomata ☐hydathode |
| ☐Rosette Leaf | ☐mesophyll ☐vascular ☐epidermis ☐trichome ☐petiole ☐primordia ☐stomata ☐stipule ☐margin |
| ☐Primary Root | ☐epidermis ☐trichoblast ☐atrichoblast ☐cortex ☐endodermis ☐vascular ☐xylem ☐phloem ☐pericycle ☐quiescent ☐columella ☐root cap ☐root hairs |
| ☐Lateral root | ☐epidermis ☐trichoblast ☐atrichoblast ☐cortex ☐endodermis ☐initials ☐flanking cells ☐vascular ☐lateral root cap |
| ☐Shoot apical meristem | ☐SAM ☐epidermis☐☐ |

T2 Mature Plant Expression
Plants expressing/Plants screened
Event-01: 2/3 Event-02: 1/3
☐Scheduled
☐T2 Mature tissue expressions similar to T1 expression data
(data not shown).
X T2 Mature tissue expression (if different expression pattern).
Expression detected

| | |
|---|---|
| X Ovule | Pre-fertilization: M inner integument ☐outer integument ☐embryo sac ☐funiculus ☐chalaza ☐micropyle ☐gametophyte Post-fertilization: ☐zygote M inner integument M outer integument ☐endothelium M seed coat ☐primordia ☐chalaza ☐micropyle ☐early endosperm ☐mature endosperm ☐embryo |

X in the outer integument(Oi) of the developing ovules
X in the seed coat (Sc) of the developing seed T3 Seedling Expression
Plants expressing/Plants screened
Event-01: 2/2    Event-02: 0/0 No germination.
☐Scheduled
☐T3 Seedling tissue expressions similar to T2 seedling expression
(data not shown).
X T2 Mature tissue expression (if different expression pattern).
GFP Expression Detected

| | |
|---|---|
| X Primary Root | ☐epidermis ☐trichoblast ☐atrichoblast ☐cortex ☐endodermis ☐vascular ☐xylem ☐phloem ☐pericycle ☐quiescent ☐columella ☐root cap L root hairs |

GFP expressed in a few root hairs.

Promoter utility
Trait Area:

Among other uses this promoter sequence is useful to improve:
Water use efficiency, seed, yield

Promoter Expression Report #17

Sub-trait Area:

Moisture stress, water use efficiency, ovule/seed abortion, harvest index, test weight, seed size, total yield, amino acids, carbohydrate, proteintotail oil, total seed composition.

| | |
|---|---|
| Construct: | YP0103 |
| Promoter Candidate I.D: | 13148199(Old ID: 35139718) |
| cDNA ID: | 4905097 (Old ID: 12322121, 1387372) |
| T1 lines expressing (T2 seed): | SR00709-01,-02,-03 |

Sequence (SEQ ID NO: 17):

GTTTTGAAGAACAATCTGGATCGAAATCTAACATAAGGTCATCGTATTCAA

GTTACGCAGTCAAGGACTTGACATCATCCTACTCTGGTCTGAGGTTACCAC

TTCCAAAGATGGGATTTTTCGACTCGGTATGCTTCCTAAGAAATTCGTTTT

ATTGAACCTAGCAAATATCTTGTAATGTAAGATTCCTGAGATGATGAAGAA

AAAACAAACTTTTGTTACAGCAGGAGAACGGAGAGAAAGAAAACAGAGAAC

CAAATGCTCTTGAAGCAAACAGAAGAAGAAGACACAAATCCAAACTTGAGA

CTTCTTCTACACCAGAAACCGCAGCATTCTGGGACAACGCAAAACACGAA

AGTGAAACGGGCAATGATATATATGTCTTGGGTGCGTTACAAGGCATCGTT

TGCAACTGTTGAGTTGGATAAGTCAACTGTCTTCTTTTCCTTTGGTTGTAG

TAGCTGCCTTTTTTTTCCTTTGTTGCTTTAAGAAATAGCCCGAAAAAAAGA

ATGTTCTACATTTCGGAGCAGAAAACTAACCGAATGAGTTTTTGGTCGGAT

CATCGGATCGATCAGATATATTTTGAGTTACGAACTGTTATAAAAAAAGCC

ATAATTTTGTGTTGAGTTTGCAAAATACCTTATAACTTGTTATTTGAGATT

GCACCTCCATATATATTAATTCGTAAGAGTATTTATTAAGTAAGCTTTAGT

ATAAATCCTTTTTTCCTTTAAAGTAAGTTAATGTTCTACTAAATAATAGTA

AAGTTGAAGAACCGCTCCGTTTTTACACCATGCACGTGTTATCTAACAAAG

AAAATATGGTACACCTAATGGCTAATGCAAAGGACAACACAATGAAACTAA

CTTGACTCTGTGTTATAGAAACCCATAGACATCTGCATACATCCTAGTATT

TGTATAAATTGGACTCAAATTCCTGAGGACAATCATAGCAAACAATCACAT

CATCGCAATATACATAAACAAAAGAGGAAGAAAAA

Promoter Expression Report #18

| | |
|---|---|
| Promoter Tested In: | *Arabidopsis thaliana*, WS ecotype |
| Spatial expression summary: | |
| Embryo | (H)mature, (H)late |
| Ovule | (H)endothelium |
| Primary root | (L)root hair |
| Observed expression pattern: | |

Low levels of GFP expression were detected in late torpedo stage with highest levels in the mature and late embryo. High GFP expression was detected in late endosperm stage in endothelium layer of developing seed.
T2 mature:

Same as T1 mature.

T3 seedling:

GFP was detected in a few root hairs not observed in T2 seedlings.

| | |
|---|---|
| Expected expression pattern: | Embryo and seed |
| Selection Criteria: | *Arabidopsis* public; Rossak, M. Plant Mol. Bio. 2001.46:717 |
| Gene: | fatty acid elongase 1; FAE1 |
| GenBank: | NM__119617 *Arabidopsis thaliana* fatty acid elongase 1 (FAE1) (At4g34520) mRNA, complete cds, gi\|30690063\|ref\|NM__119617.2\| [30690063] |
| Source Promoter Organism: | *Arabidopsis thaliana* WS |
| Vector: | pNewbin4-HAP1-GFP |
| Marker Type: | X GFP-ER |
| Generation Screened: | X T1 Mature   X T2 Seedling |
| | X T2 Mature   X T3 Seedling |

T1 Mature Plant Expression    Organs/Tissues screened
Lines Screened: n = 3    Lines Expressing: n = 2
GFP Expression Detected

| | |
|---|---|
| ☐Flower | ☐pedicel ☐receptacle ☐nectary ☐sepal ☐petal ☐filament ☐anther ☐pollen ☐carpel ☐style ☐papillae ☐vascular ☐epidermis ☐stomata ☐trichome |
| ☐Silique | ☐stigma ☐style ☐carpel ☐septum ☐placentae ☐transmitting tissue ☐vascular ☐epidermis ☐stomata ☐abscission zone |
| ☐Ovule | Pre-fertilization: ☐inner integument ☐outer integument ☐embryo sac ☐funiculus ☐chalaza ☐micropyle ☐gametophyte
Post-fertilization: ☐zygote ☐inner integument ☐outer integument ☐seed coat ☐primordia ☐chalaza ☐micropyle ☐early endosperm ☐mature endosperm H endothelium |
| X Embryo | ☐suspensor ☐preglobular ☐globular ☐heart ☐torpedo H late H mature ☐provascular ☐hypophysis ☐radicle ☐cotyledons ☐hypocotyl |
| ☐Stem | ☐epidermis ☐cortex ☐vascular ☐xylem ☐phloem ☐pith ☐stomata ☐trichome |
| ☐Leaf | ☐petiole ☐mesophyll ☐vascular ☐epidermis ☐trichome ☐primordia ☐stomata ☐stipule ☐margin |

X in the mature embryo
X in the Endosperm (En)
X in the Endothelium (Ed)

T2 Seedling Expression    Tissues Screened
Events Screened: n = 2    Events Expressing: n = 0
Seedlings expressing/Plants screened
Event-01: 0/6 Event-02: 0/3
☐Scheduled
No GFP Expression Detected

| | |
|---|---|
| ☐Hypocotyl | ☐epidermis ☐cortex ☐vascular ☐xylem ☐phloem ☐stomata |
| ☐Cotyledon | ☐mesophyll ☐vascular ☐epidermis ☐margin ☐stomata ☐hydathode |
| ☐Rosette Leaf | ☐mesophyll ☐vascular ☐epidermis ☐trichome ☐petiole ☐primordia ☐stomata ☐stipule ☐margin |
| ☐Primary Root | ☐epidermis ☐trichoblast ☐atrichoblast ☐cortex ☐endodermis ☐vascular ☐xylem ☐phloem ☐pericycle ☐quiescent ☐columella ☐root cap ☐root hairs |
| ☐Lateral root | ☐epidermis ☐trichoblast ☐atrichoblast ☐cortex ☐endodermis ☐initials ☐flanking cells ☐vascular ☐lateral root cap |
| ☐Shoot apical meristem | ☐SAM ☐epidermis☐☐ |

Promoter Expression Report #18

T2 Mature Plant Expression
Plants expressing/Plants screened
Event-01: 2/3   Event-02: 0/3 No expression.
☐Scheduled
X T2 Mature tissue expressions similar to T1 expression data.
☐T2 Mature tissue expression (if different expression pattern).
Expression detected
X first detected in late torpedo stage of embryo Promoter utility
Trait - Sub-trait Area:

Among other uses this promoter sequence is useful to improve:
Seed - Ovule/seed abortion, seed enhancement, seed size
Yield
Reference:

1: Rossak M. Smith M. Kunst L.   Related Articles, Links
Expression of the FAE1 gene and FAE1 promoter activity in developing seeds of *Arabidopsis thaliana*.
Plant Mol Biol. 2001 Aug; 46(6):717–25.
PMID: 11575726 [PubMed - indexed for MEDLINE☐

| | |
|---|---|
| Construct: | YP0107 |
| Promoter Candidate I.D: | 13148252 (Old ID: 35139824) |
| cDNA ID: | 12656458 (Old ID: 1815714) |
| T1 lines expressing (T2 seed): | SR00646-01,-02 |

Sequence (SEQ ID NO: 18):

TAACAATCCTTGGGAACATTGCATCCATAGATATCCGGTTAAGATCGATCT

TTGAACTCATAAAAACTAGTAGATTGGTTGGTTGGTTTCCATGTACCAGAA

GGCTTACCCTATTAGTTGAAAGTTGAAACTTTGTTCCCTACTCAATTCCTA

GTTGTGTAAATGTATGTATATGTAATGTGTATAAAACGTAGTACTTAAATG

ACTAGGAGTGGTTCTTGAGACCGATGAGAGATGGGAGCAGAACTAAAGATG

ATGACATAATTAAGAACGAATTTGAAAGGCTCTTAGGTTTGAATCCTATTC

GAGAATGTTTTTGTCAAAGATAGTGGCGATTTTGAACCAAAGAAAACATTT

AAAAAATCAGTATCCGGTTACGTTCATGCAAATAGAAAGTGGTCTAGGATC

TGATTGTAATTTTAGACTTAAAGAGTCTCTTAAGATTCAATCCTGGCTGTG

TACAAAACTACAAATAATCTATTTTAGACTATTTGGGCCTTAACTAAACTT

CCACTCCATTATTTACTGAGGTTAGAGAATAGACTTGCGAATAAACACATT

CCCCGAGAAATACTCATGATCCCATAATTAGTCGGAGGGTATGCCAATCAG

ATCTAAGAACACACATTCCCTCAAATTTTAATGCACATGTAATCATAGTTT

AGCACAATTCAAAAATAATGTAGTATTAAAGACAGAAATTTGTAGACTTTT

TTTTGGCGTTAAAAGAAGACTAAGTTTATACGTACATTTTATTTTAAGTGG

AAAACCGAAATTTTCCATCGAAATATATGAATTTAGTATATATATTTCTGC

AATGTACTATTTTGCTATTTTGGCAACTTTCAGTGGACTACTACTTTATTA

CAATGTGTATGGATGCATGAGTTTGAGTATACACATGTCTAAATGCATGCT

TTGTAAAACGTAACGGACCACAAAAGAGGATCCATACAAATACATCTCATA

GCTTCCTCCATTATTTTCCGACACAAACAGAGCA

Promoter Expression Report #19

| | |
|---|---|
| Promoter Tested In: | *Arabidopsis thaliana*, WS ecotype |
| Spatial expression summary: | |
| Ovule | Pre-fertilization: (M)gametophyte, (M)embryo sac |
| | Post-fertilization: (H)zygote |

Observed expression pattern:

GFP expressed in the developing female gametophyte of unfertilized ovules and the degenerated synergid cell of the fertilized ovule hours after fertilization. No expression was observed in T2 seedlings.
T2 mature:

Similar expression as T1 mature.
T3 seedling:

Root expression in one of two events was not observed in T2 seedlings. No expression was observed in the second line which is consistent with T2 seedling expression.

| | |
|---|---|
| Expected expression pattern: | Expression in ovules |
| Selection Criteria: | Greater than 50× up in pi ovule microarray |
| Gene: | Hypothetical protein |
| GenBank: | NM_112033 *Arabidopsis thaliana* expressed protein (At3g11990) mRNA, complete cds gi\|18399438\|ref\|NM_112033.1 [18399438] |
| Source Promoter Organism: | *Arabidopsis thaliana* WS |
| Vector: | pNewbin4-HAP1-GFP |
| Marker Type: | X GFP-ER |
| Generation Screened: | X T1 Mature   X T2 Seedling |
| | X T3 Mature   X T3 Seedling |

T1 Mature Plant Expression   Organs/Tissues screened
Lines Screened: n = 3   Lines Expressing: n = 2
GFP Expression Detected

| | |
|---|---|
| ☐Flower | ☐pedicel ☐receptacle ☐nectary ☐sepal ☐petal ☐filament ☐anther ☐pollen ☐carpel ☐style ☐papillae ☐vascular ☐epidermis ☐stomata ☐trichome |
| ☐Silique | ☐stigma ☐style ☐carpel ☐septum ☐placentae ☐transmitting tissue ☐vascular ☐epidermis ☐stomata ☐abscission zone |
| X Ovule | Pre-fertilization: ☐inner integument ☐outer integument M embryo sac ☐funiculus ☐chalaza ☐micropyle M gametophyte |
| | Post-fertilization: H zygote ☐seed coat ☐primordia ☐chalaza ☐micropyle ☐early endosperm ☐mature endosperm |
| ☐Embryo | ☐suspensor ☐preglobular ☐globular ☐heart ☐torpedo ☐late ☐mature ☐provascular ☐hypophysis ☐radicle ☐cotyledons ☐hypocotyl |
| ☐Stem | ☐epidermis ☐cortex ☐vascular ☐xylem ☐phloem ☐pith ☐stomata ☐trichome |
| ☐Leaf | ☐petiole ☐mesophyll ☐vascular ☐epidermis ☐trichome ☐primordia ☐stomata ☐stipule ☐margin |

X in the Embryo sac (Es) of the pre-fertilized ovule
X in the Degenerated synergid cell (dSn) of the fertilized ovule T2 Seedling Expression   Tissues Screened
Events Screened: n = 2   Events Expressing: n = 0
Seedlings expressing/Plants screened
Event-01: 0/4 Event-02: 0/3
☐Scheduled
No GFP Expression Detected

| | |
|---|---|
| ☐Hypocotyl | ☐epidermis ☐cortex ☐vascular ☐xylem ☐phloem ☐stomata |
| ☐Cotyledon | ☐mesophyll ☐vascular ☐epidermis ☐margin ☐stomata ☐hydathode |

| Promoter Expression Report #19 | |
|---|---|
| ☐Rosette Leaf | ☐mesophyll ☐vascular ☐epidermis ☐trichome ☐petiole ☐primordia ☐stomata ☐stipule ☐margin |
| ☐Primary Root | ☐epidermis ☐trichoblast ☐atrichoblast ☐cortex ☐endodermis ☐vascular ☐xylem ☐phloem ☐pericycle ☐quiescent ☐columella ☐root cap ☐root hairs |
| ☐Lateral root | ☐epidermis ☐trichoblast ☐atrichoblast ☐cortex ☐endodermis ☐initials ☐flanking cells ☐vascular ☐lateral root cap |
| ☐Shoot apical meristem | ☐SAM ☐epidermis |

T2 Mature Plant Expression
Plants expressing/Plants screened
Event-01: 1/1 Event-02: 1/1
☐Scheduled
X T2 Mature tissue expressions similar to T1 expression data
☐T2 Mature tissue expression (if different expression pattern).
☐No expression detected T3 Seedling Expression
Plants expressing/Plants screened
Event-01: 2/2* Event-02: 0/2
☐Scheduled
☐T3 Seedling tissue expressions similar to T2 seedling expression (data not shown).
X T2 Seedling tissue expression (if different expression pattern).
GFP Expression Detected

*Event 01: Root expression in one of two events not observed in T2 seedlings. No expression observed in second line which is consistent with T2 seedling expression.

Promoter utility
Trait Area:

Among other uses this promoter sequence is useful to improve:
Water use efficiency, seed, yield
Sub-trait Area:

Moisture stress, water use efficiency, ovule/seed abortion, harvest index, test weight, seed size, total yield, amino acids, carbohydrate, proteinotail oil, total seed composition.

| Construct: | YP0110 |
|---|---|
| Promoter Candidate I.D: | 13148212 (Old ID: 35139697) |
| cDNA ID: | 13604221 (Old IDs: 12395818, 4772042) |
| T1 lines expressing (T2 seed): | SR00689-02,-03 |

Sequence (SEQ ID NO: 19):

```
GGGATGCGGTTCCGCTTCCTCTTGATCTTGGACGAGTCGGAGGACATTGTT
GGATCCCAGTGCAATGGTAATATAAAACAAGAAAACAAGAGATTTTATAGG
ACAATCACTAAATGACATTTAATTGATTAAACATTTATTCATTAATAATTG
TATGTTACTAACTTCAACATTTAATAATTTTGTTTAAGATACGTTTACATC
AGAGACTATTAATATTTTTACAGGTTGTAACTTTAAACTTTGTCTTGAATC
GAACATGACTATAGATTTTGGGCAAACTTAAAGATAACAACATTTCCGTTT
TTTTTCAAATTATTACAAATCAAACTGATATATTAGACACAACACGATTAC
ACGTAATGAAAAAGAAAAAGATAAAAAGATAAAAGAAGGGATCGATTCTG
TTTGGTCTGGTTTAGTGAGATTCAAAGTTAAGCTCTTCCTTTCAAGACATG
CCTTCTTAAACCGGAATGTGAACGTTTGTAATGTAGTCCGTCCAGTTAAT
GCTTCCAACATCAAATCCAAATTCTCTCTTCTCGTCCTCTGACATATTCTC
CATTAATCTCTGGGGTATTGCTGTTATCAAATCTGTAAAAGAAACCAAAAA
AAAAAGATGAAAACTTTGCGGGTACCGGTTTTGTCTGCTCTAAGAATTAGA
ATGTTAATGAGTTCTGTCTTACCTTCCACCATAGAAAGTGTATGGCTCATA
AATAGTAGCAAGGTGTTTGGCTTGTTCAACAGATTTCTTGCATATAAACTT
TAGCTTCTGCATCATCTTACTATCCACTGAACTCATACCACTCATCAACCC
ACTCCGTTCTTGAGCATCTCTCCACAAATGATCCGAGAAATCATCAACGGA
ATTGAAAAGTTTCATCAAACGCACCATAATAGGATCACCTTTAGAGTCCAT
GCATGGAGATGTTTTGTAGTGGTTATAAAGAAGCTCCGCTAAGTCTTCGAA
AACCAGCGGGTTTATCGCCGAAGAAGCGATCTGATACACGTTTATTTCAGG
TTCCGGATCTGACATTGCCATTCCATGCTTTGCTATAGCAGCTAACGTTCC
```

| Promoter Expression Report #20 | |
|---|---|
| Promoter Tested In: | *Arabidopsis thaliana*, WS ecotype |
| Spatial expression summary: | |
| Flower | (L)silique |
| Silique | (M)medial vasculature, (M)lateral vasculature, (M)guard cells |
| Observed expression pattern: | |

GFP expressed in the medial and lateral vasculature of pre-fertilized siliques. Expression was not detected in older siliques. Guard cell expression was seen throughout pre-fertilized and fertilized siliques.
T2 Mature:

Same as T1 Mature.
T2 seedling:

Same as T2 seedling.
| Expected expression pattern: | Expression in ovules |
|---|---|
| Selection Criteria: | Greater than 50× up in pi ovule microarray |
| Gene: | hypothetical protein |
| GenBank: | NM_104488 *Arabidopsis thaliana* hypothetical protein (At1g56100) mRNA, complete cds gi\|18405686\|ref\|NM_104488.1\| [18405686] |
| Source Promoter Organism: | *Arabidopsis thaliana* WS |
| Vector: | pNewbin4-HAP1-GFP |
| Marker Type: | X GFP-ER |
| Generation Screened: | X T1 Mature   X T2 Seedling X T2 Mature   X T3 Seedling |

T1 Mature Plant Expression   Organs/Tissues screened
Events screened: n = 3     Events expressing: n = 3
☐No GFP Expression Detected

| ☐Flower | ☐pedicel ☐receptacle ☐nectary ☐sepal ☐petal ☐filament ☐anther ☐pollen ☐carpel ☐style ☐papillae ☐vascular ☐epidermis ☐stomata ☐trichome |
|---|---|
| X Silique | ☐stigma ☐style ☐carpel ☐septum ☐placentae ☐transmitting tissue L vascular ☐epidermis H stomata ☐abscission zone |
| ☐Ovule | Pre-fertilization: ☐inner integument ☐outer integument ☐embryo sac ☐funiculus ☐chalaza ☐micropyle ☐gametophyte Post-fertilization: ☐zygote ☐seed coat ☐primordia ☐chalaza ☐micropyle ☐early endosperm ☐mature endosperm |
| ☐Embryo | ☐suspensor ☐preglobular ☐globular ☐heart ☐torpedo ☐late ☐mature ☐provascular ☐hypophysis ☐radicle ☐cotyledons ☐hypocotyl |

-continued

Promoter Expression Report #20

| ☐Stem | ☐epidermis ☐cortex ☐vascular ☐xylem |
| --- | --- |
| | ☐phloem ☐pith ☐stomata ☐trichome |
| ☐Leaf | ☐petiole ☐mesophyll ☐vascular |
| | ☐epidermis ☐trichome ☐primordia |
| | ☐stomata ☐stipule ☐margin |

X in the Medial vasculature (Mv), Lateral vasculature (Lv) and Guard cell (Gc) of the stigma
X in the Medial Guard cell (Gc) of the carpel T2 Seedling Expression    Tissues Screened
Events screened: n = 2    Events expressing: n = 0
Seedlings expressing/Seedlings screened
Event-01: 0/3    Event-02: 0/3
No GFP Expression Detected

| ☐Hypocotyl | ☐epidermis ☐cortex ☐vascular ☐xylem |
| --- | --- |
| | ☐phloem ☐stomata |
| ☐Cotyledon | ☐mesophyll ☐vascular ☐epidermis |
| | ☐trichome ☐margin ☐stomata |
| ☐Rosette Leaf | ☐mesophyll ☐vascular ☐epidermis |
| | ☐trichome ☐petiole ☐primordia |
| | ☐stomata ☐stipule ☐margin |
| ☐Primary Root | ☐epidermis ☐trichoblast ☐atrichoblast |
| | ☐cortex ☐endodermis ☐vascular ☐xylem |
| | ☐phloem ☐pericycle ☐quiescent |
| | ☐columella ☐cap ☐root hairs |
| ☐Lateral root | ☐epidermis ☐initials ☐flanking cells |
| | ☐vascular ☐cap |
| ☐Shoot apical meristem | ☐SAM ☐epidermis |

T2 Mature Plant Expression
Plants expressing/Plants screened
Event-01: 1/2    Event-02: 1/1
☐Scheduled
X T2 Mature tissue expressions similar to T1 expression data (data not shown).
☐T2 Mature tissue expression (if different expression pattern).
Expression detected T3 Seedling Expression
Plants expressing/Plants screened
Event-01: 0/2    Event-02: 0/1
☐Scheduled
☐T3 Seedling tissue expressions similar to T2 seedling expression (data not shown).
☐T2 Mature tissue expression (if different expression pattern).
No GFP Expression Detected Promoter utility
Trait Area:

Among other uses this promoter sequence is useful to improve:
Water use efficiency, seed, yield
Sub-trait Area:

Moisture stress at seed set, moisture stress at seed fill, water use efficiency, ovule/seed abortion, harvest index, test weight, seed size, total yield, amino acids, carbohydrate, protein, total oil, total seed composition, composition

| Construct: | YP0112 |
| --- | --- |
| Promoter Candidate I.D: | 13148226 (Old ID: 35139719) |
| cDNA ID: | 12321680 (Old ID: 5662775) |
| T1 lines expressing (T2 seed): | SR00710-01,-02,-03 |

Sequence (SEQ ID NO: 20):

TTATGTGCCCTGATGTCCTATGCAGATGGTGCAACTACTGCTTTTGGTGAG

AAGCTTCGCGAACAAGTTGAGGAAAGGCTAGAATTTTATGACAAAGGTGTT

GCCCCACGCAAGAACGTGGATGTAATGAAGGAGGTGATAGAGAATCTAAAG

CAAGGTATTTCTTGTAGCTGTTTTTTTTGGTTGTAATCAGAGTCCTCTTT

ATGATGGCAAACTCAGTGTTTTTTTATCTGTTCCTCCTTTAGAAGAGGAAG

GGAAGGAGCCAGTTGATGCCTCGGTGAAGAAAAGCAAGAAGAAGAAGGCAA

AGGGTGAAGAAGAAGAAGAGGTGGTGGCAATGGAGGAGGACAAGTCAGAGA

AAAAGAAGAAGAAAGAGAAGAGGAAGATGGAGACTGCAGAGGAGAACGAGA

AATCAGAGAAGAAGAAGACAAAGAAGAGTAAAGCTGGAGGAGAAGAGGAGA

CTGATGATGGTCACAGCACCAAGAAGAAGAAGAAGAAGTCTAAGAGCGCTG

AATAGAAAGGGATGCAACATTAACAAACCCTGTATTGTATTTTTTTTTGA

GCTAAATTAATGTCGTCTGTTTTTCGTAGTGAACATCGGAGAATTTTTGTT

TTGGTCTGGAAACGATTCAAGGTTTGGCAATATCTTAAGTTTGTTTAGGTT

TTCACTATTTTGACGTTTGCAACCGTGAAGGAGGCTCCTCCATTTTATAAA

ATACAATTACCAATTCCAGTGCTTTGCAAATGTTTCAATAATAGCTAAACT

AACTACCAAATTGGAAAACTAGCTTAACAAGTTTGTGAAAATGAATTTGGA

GCCATATGATTTATTATTTTACCCAAATGGAGTAATAGAAGAAGAGCAGCT

CGCGTTTGAATGGTCAGTTAACATTAACAAAAGGTAAAATTGAATAGATGT

TAAAACTTGTGTAAGTAAACAATAGAGCTACCTCCTTTTGAGAAGGATAGA

TAAACTCGTGACCAACCACATTCCCAGTCCCATATTCTTAGTACAAATAAG

AAATTCACACCCCTCAAAAGAAATATAACATAATCAATCATAGGAAATATA

CTTCGCATAATGACGATAATGATCAAGTTTCTCCTGTTAGCTCTGCTCGTG

ATCTCTCCGATTTGCGCCGAGAAGGACCTGATGAAAGAGGAATGCCATAAT

GCACAAGTTCCGACCATTTGCATGCAATGTCTTGAATCCGACCCAACCTCC

GTTCATGCAGACCGTGTTGGCATCGCCGAGATCATCATACACTGTCTCGAC

TCTCGTCTCGATATCATCACCAAGCAAGTTTTCCCTTCTAATAACCATACA

TATATATTAACTTAGATATATGACAATATTCTCTAACTAATATATCAATCT

TTTTATTGTTCTACCATTGCACTGGGATCCAACAATGTCCTCCGACTCGTC

CAAGATCAAGAGGAAGCGGAACCGC

| Promoter Expression Report #21 | |
|---|---|
| Promoter Tested In: | *Arabidopsis thaliana*, WS ecotype |

Spatial expression summary:
Silique (H)stigma, (H)transmitting tissue
Observed expression pattern:
GFP expression was seen in the stigma and pollen transmitting tract spanning the entire silique. T2 seedlings: No expression.
T2 Mature: Same as T1. T3 seedlings: No data

| | |
|---|---|
| Expected expression pattern: | Expression in ovules |
| Selection Criteria: | Greater than 50x up in pi ovule microarray |
| Gene: | putative drought induced protein |
| GenBank: | NM_105888 *Arabidopsis thaliana* drought induced protein - related (At1g72290) mRNA, complete cds gi\|18410044\|ref\|NM_105888.1\|[18410044] |
| Source Promoter Organism: | *Arabidopsis thaliana* WS |
| Vector: | pNewbin4-HAP1-GFP |
| Marker Type: | X GFP-ER |
| Generation Screened: | X T1 Mature   X T2 Seedling   X T3 Mature   X T3 Seedling |
| T1 Mature Plant Expression | Organs/Tissues screened |
| Events Screened: n = 3 | Events Expressing: n = 2 |

GFP Expression Detected

| | |
|---|---|
| ☐ Flower | ☐pedicel ☐receptacle ☐nectary ☐sepal ☐petal ☐filament ☐anther ☐pollen ☐carpel ☐style ☐papillae ☐vascular ☐epidermis ☐stomata ☐trichome |
| X Silique | H stigma ☐style ☐carpel ☐septum ☐placentae H transmitting tissue ☐vascular ☐epidermis ☐stomata ☐abscission zone |
| ☐ Ovule | Pre-fertilization: ☐inner integument ☐outer integument ☐embryo sac ☐funiculus ☐chalaza ☐micropyle ☐gametophyte Post-fertilization: ☐zygote ☐seed coat ☐primordia ☐chalaza ☐micropyle ☐early endosperm ☐mature endosperm |
| ☐ Embryo | ☐suspensor ☐preglobular ☐globular ☐heart ☐torpedo ☐late ☐mature ☐provascular ☐hypophysis ☐radicle ☐cotyledons ☐hypocotyl |
| ☐ Stem | ☐epidermis ☐cortex ☐vascular ☐xylem ☐phloem ☐pith ☐stomata ☐trichome |
| ☐ Leaf | ☐petiole ☐mesophyll ☐vascular ☐epidermis ☐trichome ☐primordia ☐stomata ☐stipule ☐margin |

X in the transmitting tract of the stigma
X in the Epidermis (Ep)
T2 Mature Plant Expression Plants expressing/Plants screened
Event-01: 1/1   Event-02: 1/1
☐ Scheduled
X T2 Mature tissue expressions similar to T1 expression data (data not shown).
☐ T2 Mature tissue expression (if different expression pattern).
Expression detected
T3 Seedling Expression Seedlings expressing/Seedlings screened
Event-01: No data   Event-02:
☐ Scheduled
☐ T3 Seedling tissue expressions similar to T2 seedling expression (data not shown).
☐ T2 Mature tissue expression (if different expression pattern).
GFP Expression Detected

| | |
|---|---|
| Utility: | Among other uses, this promoter sequence is useful to improve: Water use efficiency - Moisture stress at seed set, Moisture stress at seed fill, water use efficiency, Ovule/seed abortion |
| Construct: | YP0116 |
| Promoter Candidate I.D: | 13148262 (Old ID: 35139699) |
| cDNA ID: | 12325134 (Old ID: 6403538) |
| T1 fines expressing (T2 seed): | SR00693-02,-03 |

Sequence (SEQ ID NO: 21):

```
AAACGCCTCTTCGGTCCACGCTGTCGTTTTATTGAAGGAATTATATTTTAT
TTTAATTGGGCCTGCAGGCTAAACTATAAGTCCGTCTGATATGGGTCGGGT
TGGGCTTATGAGTTATGGGTCTGGTAGGGGTCAATTAGCTTAATTTCGATA
TGTGCCCTACTCTCGACCTAACGTTTTGAACACGTAAGAGAGAGTTTCTAA
TATTGAGTTGTCTAATTAACTCGATAGGCTTATACAAAGTGTTTCCGCATT
TTACCTTCTTAATAACTCATCATTCACTAACTAAGAAAAGTTTTACTCAGA
CCATATCTTCCGCTTCTTGATTATTGTCAATTTGTTGTCACTCAATTTATC
TCTTGCAAAATTTAGTTGAAATCATTTGGTTTCATCTTTGGCTCTTGAATA
GTTGCATGTGTGTATTTAGTAAGTTCTTTTCAATTAAGAAGGAAGAATAAA
ACAAATTGTGGCCAGAAACAATTATGTTGAGTTTTATCTCATACGTTGGCT
CACTCATCCCCATCTCTCTGCTTTTGAATCATTCTACTCCTCCCATTTTTT
```

```
GATCGTCCTTTTTTCTGCTTCTGAACATGGATCATTGTGCATGTTCGGATG

TTCCTCGATCGTGCTGAAACTCAAAGTCTGAATCGATTACCATAGACTCTC

AACCCATCTTTGATATATAAAAAAGAGCCTTAACCCATCTCTTCTACTCTC

CCTCTCTAGAAACAAACACATCACGTGATGATCTGTTTCCCCCCATACTTA

CGGGATGATCAGAATGTGGCATGAGGAAAAAGCCAAGAAATAAGTTGATAA

ATTTAAGGTTTAATTTAACAAAAATGAGAGATTAATCTTTTCATTTTAGGG

TCGCACGCGGTGTTTTGTGCAACCGCAGAAACTTCCTATAAATACCGATAC

AATGTGCATGCTTTCTACAACTCAACTCACTCAAACCAAAAAAAGAAACAT

CAAACCCCAAAACACACATAACAATCACAAACCATTGCACTGGGATCCAAC

AATGTCCTCCGACTCGTCCAAGATCAAGAGGAAGCGGAACCGCAnCCCGTT

TGGAAATCAGnCCG
```

| Promoter Expression Report #22 |
|---|

Promoter Tested In: *Arabidopsis thaliana*, WS ecotype
Spatial expression summary:

Flower      (H)pedicle
Silique     (M)vascular
Stem        (H)cortex
Ovule       Pre-fertilization: (H)outer integument, (M)chalaza
Hypocotyl   (H)cortex
Root        (H)epidermis, (H)atrichoblast, (H)cortex
Observed expression pattern:

Strong GFP expression was seen in the adaxial surface of the pedicel and secondary inflorescence meristem internodes. High magnification reveals expression in 2–3 cell layers of the cortex. GFP expressed in the vasculature of silique, inner integuments, and chalazal region of ovule. Expression was highest in the outer integuments of pre-fertilized ovules decreasing to a few cells at the micropylar pole at maturity. Specific expression was in the chalazal bulb region where mineral deposits are thought to be accumulated for seed storage. GFP expressed in 2 cortical cell layers of the hypocotyl from root transition zone to apex. At the apex, GFP is expressed at the base of the leaf primordial and cotyledon. Root expression is specific to the epidermis and cortex. T2 Mature: Same as T1 mature. T3 seedling: Same expression in event 01 as in T2 seedlings. Event 02 expression is different with weak root epidermal, weak hypocotyl and stronger lateral root expression. This expression is variable within siblings in this family. Other seedlings were more like event 01.

Expected expression pattern:   Expressed in ovules and different parts of seeds
Selection Criteria:            Greater than 50x up in pi ovule microarray
Gene:                          hypothetical protein T20K18.24
GenBank:                       NM_117358 *Arabidopsis thaliana* expressed protein (At4g12890)
                               mRNA, complete cds gi|30682271|ref|NM_117358.2|[30682271]
Source Promoter Organism:      *Arabidopsis thaliana* WS
Vector:                        pNewbin4-HAP1-GFP
Marker Type:                   X GFP-ER
Generation Screened:           X T1 Mature   X T2 Seedling   X T2 Mature   X T3 Seedling
T1 Expression   Mature plants screened
GFP Expression Detected X Flower      H pedicel □receptacle □nectary □sepal □petal □filament □anther □pollen □carpel
              □style □papillae □vascular □epidermis □stomata □trichome
X Silique     □stigma □style □carpel □septum □placentae □transmitting tissue
              M vascular □epidermis □stomata □abscission zone
X Ovule       Pre-fertilization: □inner integument H outer integument □embryo sac □funiculus
              M chalaza □micropyle □gametophyte
              Post-fertilization: □zygote □seed coat □primordia □chalaza □micropyle □early
              endosperm □mature endosperm
□ Embryo      □suspensor □preglobular □globular □heart □torpedo □late □mature □provascular
              □hypophysis □radicle □cotyledons □hypocotyl
X Stem        □epidermis H cortex □vascular □xylem □phloem □pith □stomata □trichome
□ Leaf        □petiole □mesophyll □vascular □epidermis □trichome □primordia □stomata □stipule
              □margin
X in the stem pedicel branch
X in the secondary Inflorescence meristem (Im)
X in the Lateral vasculature (Lv) and Medial vasculature (Mv) of the silique
X in the ovary
x in the Inner integument (Ii) and Micropyle (Mp) of the ovule
T2 Seedling Expression   Tissues Screened
Events Screened: n = 2   Events Expressing: n = 1
Seedlings expressing/Plants screened
Event-01: 1/6   Event-02: 2/3
X Hypocotyl              □epidermis H cortex □vascular □xylem □phloem □stomata

Promoter Expression Report #22

| | |
|---|---|
| ☐ Cotyledon | ☐mesophyll ☐vascular ☐epidermis ☐trichome ☐margin ☐stomata |
| ☐ Rosette Leaf | ☐mesophyll ☐vascular ☐epidermis ☐trichome ☐petiole ☐primordia ☐stomata ☐stipule ☐margin |
| X Primary Root | H epidermis ☐trichoblast H atrichoblast H cortex ☐endodermis ☐vascular ☐xylem ☐phloem ☐pericycle ☐quiescent ☐columella ☐cap ☐root hairs |
| ☐ Lateral root | ☐epidermis ☐initials ☐flanking cells ☐vascular ☐cap |
| ☐ Shoot apical meristem | ☐SAM ☐epidermis |

X in the Cortex (Cr) of the hypocotyl
X in the Epidermis (Ep) and Cortex (Cr) of the lateral root
X in the Epidermis (Ep) and Cortex (Cr) of the root differentiation zone T2 Mature Plant Expression Plants expressing/Plants screened
Event-01: 1/2    Event-02: 1/1
☐ Scheduled
X T2 Mature tissue expressions similar to T1 expression data (data not shown).
☐ T2 Mature tissue expression (if different expression pattern).
Expression detected T3 Seedling Expression Plants expressing/Plants screened
Event-01: 2/3    Event-02: 2/6
☐ Scheduled
☐ T3 Seedling tissue expressions similar to T2 seedling expression (data not shown).
X T2 Mature tissue expression (if different expression pattern).
GFP Expression Detected YP0117.02.T3 seedling
Event 01: weak lateral root, same as T2 seedling expression
Event 02: stronger lateral root expression, weak epidermal expression, cortex, vascular expression.
X in the Lateral root (Lr) of the hypocotyl root transition zone
X in the lateral root primordia
X in the Epidermis (Ep) and Vasculature (Vs) of the root Promoter utility

| | |
|---|---|
| Trait - Sub-trait Area: | Among other uses this promoter sequence is useful to improve: Water use efficiency - Moisture stress at seed set, Moisture stress at seed fill, water use efficiency, ovule/seed abortion<br>Seed - harvest index, test weight, seed size<br>Yield - total yield<br>Quality - amino acids, carbohydrate, protein, total oil, total seed composition |
| Construct: | YP0117 |
| Promoter Candidate I.D: | 11768655 (Old ID: 35139700) |
| cDNA I.D: | 13617054 (Old IDs: 12322571, 7074452) |
| T1 lines expressing (T2 seed): | SR00694-01,-02 |

Sequence (SEQ ID NO: 22):

GTCAGTGAGTCGATTGGATCACAGTCCTTTATGATAAAACAAACTCATAAT
TATTCCACCGACAACATGCGTTTTAAATTATTTTTTCTTAAATTATATTAT
ATTATATTGATATCAACCTAGCTAAAATAATTCGGATGGCGAAATCGGACA
ATTTTTAATAGAAAAAATGGGTATGAAGATAGTCTATGATTCCGTTCTTAG
CGACTAGAGGGACCTGCTCAAATCTCCCGGGTGATACGCGATGTCAAGCTC
AATAGAACCCCACAACCGACGAGACCGAGAAATCCTTGATTTGGGCTAGAA
GATTTTGAAATAAATTTAATATATTCTAAGTAACTTGCTTAAATTTTTTTT
CAAACTCTAAAGACATAACTAACATAAAGTAAAAAAAAAAAAGTTAATACA
TGGGAAGAAAAAAATTAAACTAATGATTAGCTCTCTAACGTGTTTAATCTC
GTATCAAGTTTTTTTTTAAAAATTATATTGCTATTAAAACATTGTACTATT
GTTTCTATTTTGTTTAGCTATTATTCTTGTGAAATGAAAAGTTGTGTTTAT
TCAATTACTAAATGGCAATATTTATCTTGGAAAACTATACCTCTAATTGGA
TTAGGCCCTAGACATCCTCTTTAGCTTATTGACGTTAAAATTATTCCCAAA
ACTATTAAAGTTTAGTAGTTTGAAAGATGCATCAAGACCTACTCAGATAGG
TAAAAGTAGAAAACTACAGTTAGTGTGATTATATTTTAAAATATATAAAAC
AATCTTATTAAACTAAATATTCAAGATATATACTCAAATGGAAGATAAAAA
CATTTAGTCTGTTACCACTACCAGCCTAGCTAGTCACTAATAGTCACTTTG
GAACTGAGTAGATATTTGCATCTTGAGTTACCATGGACTCAAAAGTCCAAA
AAGAGACCCCGAGTGAAAATGCTACCAACTTAATAACAAAGAAGCATTTAC
AGCGGTCAAAAAGTATCTATAAATGTTTACACAACAGTAGTCATAAGCACC
ATTGCACTGGGATCCAACAATGTCCTCCGACTCGTCCAAGATCAAGAGGAA
GCGGAACCGCATCCCGTTAAACGAAGGCG

| Promoter Expression Report #23 |
|---|

Promoter Tested In: *Arabidopsis thaliana*, WS ecotype
Spatial expression summary:

Flower     (L)silique
Silique     (L)carpel, (L)vascular

| | |
|---|---|
| Observed expression pattern: | Low levels of GFP expressed in the medial and lateral vasculature of developing pre-fertilized siliques. |
| T2 mature: | No Expression. |
| T3 seedling: | No Expression. |
| Expected expression pattern: | Expressed in ovules and different parts of seeds. |
| Selection Criteria: | Greater than 50x up in pi ovule microarray |
| Gene: | Putative vacuolar processing enzyme |
| GenBank: | NM_112912 *Arabidopsis thaliana* vacuolar processing enzyme/asparaginyl endopeptidase -related (At3g20210) mRNA, complete cds gi\|3068571\|ref\|NM_112912.2\|[30685671] |
| Source Promoter Organism: | *Arabidopsis thaliana* WS |
| Vector: | pNewbin4-HAP1-GFP |
| Marker Type: | X GFP-ER |
| Generation Screened: | X T1 Mature    X T2 Seedling    X T2 Mature    X T3 Seedling |

T1 Expression    Mature plants screened
GFP Expression Detected

Lines Screened: n = 3    Lines Expressing: n = 3

| | |
|---|---|
| X Flower | ☐pedicel ☐receptacle ☐nectary ☐sepal ☐petal ☐filament ☐anther ☐pollen ☐carpel ☐style ☐papillae ☐vascular ☐epidermis ☐stomata ☐trichome L silique |
| X Silique | ☐stigma ☐style L carpel ☐septum ☐placentae ☐transmitting tissue L vascular ☐epidermis ☐stomata ☐abscission zone |
| ☐ Ovule | Pre-fertilization: ☐inner integument ☐outer integument ☐embryo sac ☐funiculus ☐chalaza ☐micropyle ☐gametophyte<br>Post-fertilization: ☐zygote ☐seed coat ☐primordia ☐chalaza ☐micropyle ☐early endosperm ☐mature endosperm |
| ☐ Embryo | ☐suspensor ☐preglobular ☐globular ☐heart ☐torpedo ☐late ☐mature ☐provascular ☐hypophysis ☐radicle ☐cotyledons ☐hypocotyl |
| ☐ Stem | ☐epidermis ☐cortex ☐vascular ☐xylem ☐phloem ☐pith ☐stomata ☐trichome |
| ☐ Leaf | ☐petiole ☐mesophyll ☐vascular ☐epidermis ☐trichome ☐primordia ☐stomata ☐stipule ☐margin |

X in the Lateral vasculature (Lv) and Medial vasculature (Mv) of the carpels of the silique
T2 Seedling Expression      Tissue Screened
Events Screened: n = 2      Events Expressing: n = 0
Seedlings expressing/Plants screened
Event-01: No data      Events Expressing: n = 0
☐Scheduled
No GFP Expression Detected

| | |
|---|---|
| ☐ Hypocotyl | ☐epidermis ☐cortex ☐vascular ☐xylem ☐phloem ☐stomata |
| ☐ Cotyledon | ☐mesophyll ☐vascular ☐epidermis ☐margin ☐stomata ☐hydathode |
| ☐ Rosette Leaf | ☐mesophyll ☐vascular ☐epidermis ☐trichome ☐petiole ☐primordia ☐stomata ☐stipule ☐margin |
| ☐ Primary Root | ☐epidermis ☐trichoblast ☐atrichoblast ☐cortex ☐endodermis ☐vascular ☐xylem ☐phloem ☐pericycle ☐quiescent ☐columella ☐root cap ☐root hairs |
| ☐ Lateral root | ☐epidermis ☐trichoblast ☐atrichoblast ☐cortex ☐endodermis ☐initials ☐flanking cells ☐vascular ☐lateral root cap |
| ☐ Shoot Apical meristem | ☐SAM ☐epidermis ☐☐ |

T2 Mature Plant Expression

Plants expressing/Plants screened
Event-01: 0/3    Event-02: 0/2
☐ Scheduled
☐ T2 Mature tissue expressions similar to T1 expression data (data not shown).
☐ T2 Mature tissue expression (if different expression pattern).
No expression detected
T3 Seedling Expression Plants expressing/Plants screened
Event-01: 0/3    Event-02: 0/3
☐ Scheduled
☐ T3 Seedling tissue expressions similar to T2 seedling expression (data not shown).
☐ T2 Mature tissue expression (if different expression pattern).
No GFP Expression Detected
T3 Seedling Expression X Scheduled
☐ T3 Seedling tissue expressions similar to T2 seedling expression (data not shown).
☐ T2 Mature tissue expression (if different expression pattern).

Promoter Expression Report #23

Promoter utility

Trait Area: Among other uses this promoter sequence is useful to improve:
  Water use efficiency - Moisture stress at seed set, Moisture stress at seed fill, water use efficiency, ovule/seed abortion
  Seed - harvest index, test weight, seed size
  Yield - total yield
  Quality - amino acids, carbohydrate, protein, total oil, total seed composition
Construct: YP0118
Promoter Candidate I.D: 11768691 (Old ID: 35139754)
cDNA I.D: 12329827 (Old ID: 4908806)
T1 lines expressing (T2 seed): SR00711-01,-02,-03

Sequence (SEQ ID NO: 23):

```
AATTGAGAAAGGTGCCTCAATTTCAGTAGAACCTGACGCAAAATTTCGCGA
TCATGCATGACTCAAATTGGTTTATTCACTTAAATAAAAAAGTTGTTTCCC
TATCTAGTTGAAGTTCTCAATTCAAACGCAACTTCTTACTTTTTCTTTTTA
TTTATACTGGAATGAATTTTTCGTCAATGCTAGACCTCAATATTTGGTGAT
TAAGTCCAAAAAATTATAGCAATATTCATTAGTTAAATCATAATAATATTT
GTTATTTCTGCTAAATATATTAGTTTTAAATTGGTAAATATATCAGTCATC
ATACTTTATATATGTGCACAAGAAAAAGAGGAAAAAAAACTAACTTTTAAT
AAATTGAACGCTATCCTCTATATCTCGTCCTGGTCCAAATGTAAACTTCAA
TATCCTTTTGATTTTATTGCTGATTGCTTTAAAAAATTTCACAAACACTTT
TATCATTCTTTTATTCCACCAAAATCTACAGACATAATACTTTGTAATTTT
ATGTAAAAATCTTCAAAATTTGGGAAAAGAAAAATCATTTAAAATCAATTT
GCATTAACTGGATTTATTTCCAAAGGTGTGGTGTTGTGTTTATATATGTGG
AGTTGTTGGCTAGTAATATAATAAGGAAAAGAGTGAAACATATGTAGTATA
ACGTATTTCTAGTTTTTTTTCTCTGTATTAATGAATCACTAATTAAGTAGT
ATGCATTAATTGAATTATCAGAAGCTGGTCACAAAAGTCTACCAAAAAAAA
CAAAAAAATTGGTCGGAAGAAAATGAAAATAATGAGAATAAAAAAGGGAAA
AAAAATAAGAAGCTAGCAAACAAAGCAATTAACATTTCAAGGCAGTTAATT
CATCATGCAAGGTGCTTATGTGTGACAACGTCATGCGTTACTTTTTGCGTC
TACACTCATCTCTCTAACGCAATCCACTAATTCTGGTAATGGATTCTGCTA
TTTAGACCAACCAGTTTCTTCGTCTCTCAATC
```

Promoter Expression Report #24

Promoter Tested In: *Arabidopsis thaliana*, WS ecotype
Spatial expression summary:

Flower    sepal, petal, silique
Silique   epidermis
Leaf      mesophyll, vascular, epidermis, margin
Hypocotyl epidermis
Cotyledon mesophyll, vascular epidermis Observed expression pattern: Screened under non-induced conditions. Strong GFP expression was seen in epidermal and vasculature tissue of mature floral organs and leaves including photosynthetic cells. GFP is expressed in two cell layers of the margin and throughout mesophyll cells of mature leaf. GFP expressed in the epidermal cells of hypocotyl and cotyledons and mesophyll cells. GFP expression in the leaf is non guard cell epidermal specific.
Expected expression pattern: N induced, source tissue.
Selection Criteria: *arabidopsis* microarray-nitrogen
Gene: hypothetical protein, auxin-induced protein-like
GenBank: NM_120044 *Arabidopsis thaliana* auxin-induced (indole-3-acetic acid induced) protein, putative (At4g38840) mRNA, complete cds gi|18420319|ref|NM_120044.1|[18420319]
Source Promoter Organism: *Arabidopsis thaliana* WS
Vector: pNewbin4-Hap1-GFP
Marker Type: X GFP-ER
Generation Screened: X T1 Mature   X T2 Seedling   X T3 Mature   X T3 Seedling
T1 Expression   Mature plants screened
Events Screened: n = 3   Events Expressing: n = 2

Promoter Expression Report #24

GFP Expression Detected

X Flower  X pedicel ☐receptacle ☐nectary X sepal X petal ☐filament ☐anther ☐pollen ☐carpel ☐style ☐papillae X vascular ☐epidermis ☐stomata ☐trichome X silique
X Silique  ☐stigma ☐style ☐carpel ☐septum ☐placentae ☐transmitting tissue ☐vascular X epidermis ☐stomata ☐abscission zone
☐ Ovule  Pre-fertilization: ☐inner integument ☐outer integument ☐embryo sac ☐funiculus ☐chalaza ☐micropyle ☐gametophyte
Post-fertilization: ☐zygote ☐seed coat ☐primordia ☐chalaza ☐micropyle ☐early endosperm ☐mature endosperm
☐ Embryo  ☐suspensor ☐preglobular ☐globular ☐heart ☐torpedo ☐late ☐mature ☐provascular ☐hypophysis ☐radicle ☐cotyledons ☐hypocotyl
☐ Stem  ☐epidermis ☐cortex ☐vascular ☐xylem ☐phloem ☐pith ☐stomata ☐trichome
X Leaf  ☐petiole X mesophyll X vascular X epidermis ☐trichome ☐primordia ☐stomata ☐stipule X margin X in the Petal (Pe), Sepal (Se) and Silique (Si) of the flower
X in the Epidermis (Ep) and Vasculature (Vs) of the sepal
X in the Epidermis (Ep) of the petal
X in the Mesophyll (Me), Epidermis (Ep) and Vasculature (Vs) of the leaf
T2 Seedling Expression Tissues Screened
GFP Expression Detected X Hypocotyl              X epidermis ☐cortex ☐vascular ☐xylem ☐phloem ☐stomata
☐ Cotyledon              ☐mesophyll ☐vascular ☐epidermis ☐trichome ☐margin ☐stomata
X Rosette Leaf           X mesophyll X vascular X epidermis ☐trichome ☐petiole ☐primordia ☐stomata ☐stipule ☐margin
☐ Primary Root           ☐epidermis ☐trichoblast ☐atrichoblast ☐cortex ☐endodermis ☐vascular ☐xylem ☐phloem ☐pericycle ☐quiescent ☐columella ☐cap ☐root hairs
☐ Lateral root           ☐epidermis ☐initials ☐flanking cells ☐vascular ☐cap
☐ Shoot apical meristem  ☐SAM ☐epidermis X in the Epidermis (Ep) of the hypocotyl
X in the Epidermis (Ep), Mesophyll (Me), Cytoskeletal (Cy), Epidermal bodies (Eb), Guard cells (Gc), and Vasculature (Vs) of the rosette leaf
T2 Mature Expression X Scheduled
☐ T2 Mature tissue expressions similar to T1 expression data (data not shown).
☐ T2 Mature tissue expression (if different expression pattern).
T3 Seedling Expression X Scheduled
☐ T3 Seedling tissue expressions similar to T2 seedling expression (data not shown).
☐ T2 Mature tissue expression (if different expression pattern).
Promoter utility Trait - Sub-trait Area:  Among other uses this promoter sequence is useful to improve:
                         Source - Photosynthetic efficiency
                         Yield - seed size
Additional notes:        Expression seen in Epidermal bodies within epidermal cells thought to be involved in pathogen defense mechanisms.
Construct:               YP0126
Promoter Candidate I.D.: 11768662 (Old ID: 35139721)
cDNA ID:                 12713856 (Old IDs: 12580379, 4767659)
T1 lines expressing (T2 seed): SR00715-01,-02

Sequence (SEQ ID NO: 24):

```
CATTGTATCTGAGATGTGACTGTGAAGAACAAAGATTCATGACATGGTATT
GTTAAGCCGCCCATGTGGATGATCATAACCAAACTCTGTCCTCAGATTTAC
TCAACAGTGTGTGTGAAACAAAGGCTGGTTTAAGTATGAAACCGGCACCAC
ATATCTCTTCTTCTTCTGATCATTCTCTCCTACATAGACCGCCATGAATCC
TCTTGGTGTCGACGATGATTCCCTTCGAATAATTTGCTTAGCACCCAAGAA
ACTCCTCAAAAAAGCCATATTTTCCCTTATGTTTTCCTGAAGCTTAAATGT
TTCTTAGTCTTGGAGAAAGCTTTGAGATTTTAAAATTGGATCTTCTTTAGT
TTGTGAATCTAAAGGGGTTTAGTTACTTGGTATATAAACGAACGTATGAAA
GAAATGATTAAGGATTTTTGAGGTTTTTCTTTTTAATTACAGAGCACATGG
CTTTGGGTTGTAGATACTAAACCAAGAACAAATCAATAAATGGTGTCTGAG
AAGTTAGTGTCTAATGATGTCCTACATGATAACTTCATTGGGGCTTATTTG
TCTCAAAGACATCACATGCCCAAATCTCTCTATAGATTATGTAGGGACATG
AAGTTGTGTACCTAATGAACCACAAGTCTCTATCACTGATTAAGTCATACC
TTCTTCTCAATGATATTCAAAAGACAGGACCACATGATTTGATTATATACT
GACAAAGTCACAAAAGCCTTCAAAAAAATTCTGTGGCAAGAAAGGAAAATT
TGACTAGTTATAGTGTCTATCTAACAAACAAGTGGTCATATTGATTTCTAT
CTTCACATCAGAAATCATGAAGATTGATCACTATAGGGCCCTTACTTATCA
```

-continued

TGCCGTGGTCCGGCAAAGCCATGTGCTTGCTTGTTGGTGTAAAAATTTATG

AGCTGAAACTTTTGAAACCAATAAAGGGTTATCTACAAGTAATGTTCTTAT

-continued

CTATATATACTCATCACTGACTCCTTTCTGCTCTGCCATTGCACTGGGATC

CAACAATGTCCTCCGACTCGTCCAAGATCAAGAGGAAGCGGAACCGCATCC

CGCTC

| Promoter Expression Report #25 |
|---|

Promoter Tested In: *Arabidopsis thaliana*, WS ecotype
Spatial expression summary:

| | |
|---|---|
| Flower | (H)sepal, (H)anther |
| Silique | (M)vascular |
| Ovule | Post-fertilization: (M)inner integument, (M)chalaza, (M)micropyle |
| Stem | (H)Pith |
| Hypocotyl | (H)phloem |
| Cotyledon | (M)epidermis |
| Rosette Leaf | (H)hydathode |
| Primary Root | (H)phloem, (H)pericycle |
| Lateral root | (H)phloem |

Observed expression pattern: Expressed in the vasculature of sepal and connective tissue of anthers in pre-fertilized flowers, inner integuments restricted to micropyle region, and chalazal bulb of post-fertilized ovules. GFP expressed throughout the phloem of hypocotyl and root and in pericycle cells in root differentiation zone. Screened under non-induced conditions.
T2 mature: Same expression as observed in T1 mature. In addition, silique vascular expression was not observed in T1 mature. T3 seedling: Same expression as observed in T2 seedlings. In addition, expression was observed in cotyledon epidermal and rosette leaf hydathode secretory gland cells.

| | |
|---|---|
| Expected expression pattern: | nitrogen induced |
| Selection Criteria: | *Arabidopsis* microarray |
| Gene: | probable auxin-induced protein |
| GenBank: | NM_119918 *Arabidopsis thaliana* lateral organ boundaries (LOB) domain family (At4g37540) mRNA, complete cds gi|18420067|ref|NM_119918.1|[18420067] |
| Source Promoter Organism: | *Arabidosis thaliana* WS |
| Vector: | pNewBin4-HAP1-GFP |
| Marker Type: | X GFP-ER |
| Generation Screened: | X T1 Mature   X T2 Seedling   X T2 Mature   X T3 Seedling |

T1 Mature Plant Expression Organs/Tissues screened
Events Screened: n = 3     Events Expressing: n = 2
GFP Expression Detected X Flower   □pedicel □receptacle □nectary H sepal □petal □filament H anther □pollen
           □carpel □style □papillae H vascular □epidermis □stomata □trichome
□ Silique  □stigma □style □carpel □septum □placentae □funiculus □transmitting tissue
           □vascular □epidermis □stomata □abscission zone □ovule
X Ovule    Pre-fertilization: □inner integument □outer integument □embryo sac
           □funiculus □chalaza □micropyle □gametophyte
           Post-fertilization: □zygote M inner integument □outer integument seed coat
           □primordia M chalaza M micropyle □early endosperm □mature endosperm
           □embryo
□ Embryo   □suspensor □preglobular □globular □heart □torpedo □late □mature
           □provascular □hypophysis □radicle □cotyledons □hypocotyl
X Stem     □epidermis □cortex □vascular □xylem □phloem H pith □stomata □trichome
□ Leaf     □petiole □mesophyll □vascular □epidermis □trichome □primordia □stomata
           □stipule □margin
X in the inflorescence meristem
X in the vasculature (Vs) of the sepal
X in the stamen
X in the Micropyle (Mp), Funiculus (Fn), Inner integuement and Chalaza (Ch) of the ovule
T2 Seedling Expression   Tissues Screened
Events Screened: n = 3     Events Expressing: n = 2
Seedlings expressing/Seedlings screened
Event-01: 1/3   Event-02: 2/2
GFP Expression Detected X Hypocotyl        □epidermis □cortex □vascular □xylem H phloem □stomata
□ Cotyledon        □mesophyll □vascular □epidermis □trichome □margin □stomata
□ Rosette Leaf     □mesophyll □vascular □epidermis □trichome □petiole □primordia
                   □stomata □stipule □margin
X Primary Root     □epidermis □trichoblast □atrichoblast □cortex □endodermis □vascular
                   □xylem H phloem H pericycle □quiescent □columella □cap □root
                   hairs -continued Promoter Expression Report #25

X Lateral root   □epidermis □initials □flanking cells □vascular H phloem □cap
□ Shoot apical meristem   □SAM □epidermis
X in the Phloem (Ph) of the hypocotyl root (Rt) and Lateral root (Lr)
X in the Phloem (Ph) of the root
X in the Phloem (Ph) of the lateral root
X in the Phloem Ph and Pericycle (Pr) of the lateral root initial
T2 Mature Plant Expression Plants expressing/Plants screened
Event-01: 1/1    Event-02: 1/1
□ Scheduled
□ T2 Mature tissue expressions similar to T1 expression data (data not shown).
X T2 Mature tissue expression (if different expression pattern).
Expression detected
X Silique   □stigma □style □carpel □septum □placentae □transmitting tissue
          M vascular □epidermis □stomata □abscission zone □ovule
X in the Vasculature (Vs) of the silique
T3 Seedling Expression Plants expressing/Plants screened
Event-01: 2/3    Event-02: 2/3
□ Scheduled
□ T3 Seedling tissue expressions similar to T2 seedling expression (data not shown).
X T2 Mature tissue expression (if different expression pattern).
GFP Expression Detected X Cotyledon    □mesophyll □vascular M epidermis □margin □stomata
               □hydathode
X Rosette Leaf  □mesophyll □vascular □epidermis □trichome □petiole
                □primordia □stomata □stipule □margin H hydathode
X in the Epidermis (Ep) of the cotyledon
X in the Hydathode (Hy) of the rosette leaf
Promoter utility Trait - Sub-trait Area:   Among other uses this promoter sequence is useful to improve:
                          Source - Photosynthetic efficiency
                          Yield - seed size
Notes: Hydathodes are modified parts of leaves, usually located at leaf margins or tips, in which water
released from xylem is able to reach the surface of the leaf. It does so by passing through modified
mesophyll and leaving through openings in the epidermis. These openings are stomata that are
incapable of opening and closing movememts.
Construct:                YP0127
Promoter Candidate I.D:   13148197 (Old ID: 11768663)
cDNA I.D:                 13617784 (Old IDs: 12712729, 4771741)
T1 lines expressing (T2 seed): SR00716-01,-02

Sequence (SEQ ID NO: 25):

```
TCAGTGAGTCGATTGGAACGTTTAAAGTTGAGACATAACGCAGTGATTTC
AAATTTGTATTAGGGTGGTCTTATTGTGTGTCTAGCTACTAGCTAGAGAA
TACTAGAAGAAGAATACGTAGCAAGATACGCATAACATTTGGTCCTCTCT
TTTTTTTACTTTCTTTTAACACATTGTCCTCTTATGATTTGCTTATTGAT
TTCAGTATCTTTTTGTATCAATAATTCCCTCCAAATGATTAAACCCTAAA
AAAATGTGATTCATTCACCACCCGAAGATTAGCATCATCAAGTAACACAC
AATAACTACCAATAACCTAGTTTTCATTTTTCTATACTAAAATCCTAAAC
ATCCCATAAAAATACAAACAACTCTGAACCAATAATTTCCTCTAATCCAC
GTGCACCCCATCGTCTCCTGACGTAAGATTTGTCTATAACTTATCAAATC
CCAAATTCAGCTTTGTTTTCATTATATAGTACGTACTCTTATAAAAAGA
GAAGAGTACACATCTTTAATACTTTAACTTAAAAGAAGAAAGTAATACTA
ATATAAGAGGAGTCTGAGTCAGCGACAAGTGTTCGCGGAGAAACGGAAAC
GCTCTCTTTCTCTCTCTTCCCCCAACGCCAATACCTTTGGAATCCCTCCC
TAACTCTGTCCTGTCCTTTCGTCCTCACTTTCTCTCTTTTTACATTTTCT
ACACACCAATAAAATTGAAACCAGCAACTTATAAATCAACTCAAGTTTGA
ATTAATGATCGAAAAACTAGTTTATTTGTGTCAATATGACCCATTCTTTA
TTCACATAAGTATTTTAACTTTTCAAAATGTTATCTCAATCTCCTTTGAG
TTTCTGTCTTCCCCATAATAAATTTCAAATAATTAATACACATGGTTTTT
TAATTAGAAATAATGGAAAAGAAAGGACAAAGGAATAAAAAAGAAACACA
AGTTGGCACACTCTCTTTATTATTCACTCCCCTCTATAAATCTCATACTA
TCTTCTCTCATCTTCTT
```

| Promoter Expression Report #26 |
|---|

Promoter Tested In: *Arabidopsis thaliana*, WS ecotype
Spatial expression summary:

| | |
|---|---|
| Silique | (L)vascular |
| Rosette Leaf | (H)stipule |
| Primary Root | (H)trichoblast, (H)atrichoblast |
| Cotyledon | (L)hydathode |

Observed expression pattern: Weak expression in vasculature of pre-fertilized siliques. Expressed throughout epidermal cells of seedling root. T2 mature: Expression not confirmed. Event 01:0/4; Event 02: Not screened. No data. T3 seedlings: Same expression as observed in T2 seedlings. In addition, expression was observed in cotyledon epidermal and hydathode secretory gland cells.
Expected expression pattern: Inducible promoter - induced by different forms of stress e.g., drought, heat, cold).

| | |
|---|---|
| Selection Criteria: | *Arabidopsis* microarray-Nitrogen |
| Gene: | similar to SP|P30986 reticuline oxidase precursor (Berberine-bridge-forming enzyme; Tetrahydroprotoberberine synthase) contains PF01565 FAD binding domain" product = "FAD-linked oxidoreductase family" |
| GenBank: | NM_102808 *Arabidopsis thaliana* FAD-linked oxidoreductase family (At1g30720) mRNA, complete cds gi|30692034|ref|NM_102808.2|[30692034] |
| Source Promoter Organism: | *Arabidopsis thaliana* WS |
| Vector: | pNewBin4-HAP1-GFP |
| MarkerType: | X GFP-ER |
| Generation Screened: | XT1 Mature   X T2 Seedling   X T2 Mature   X T3 Seedling |
| T1 Mature Plant Expression | Organs/Tissues screened |
| Events Screened: n = 3 | Events Expressing: n = 2 |

GFP Expression Detected

| | |
|---|---|
| ☐ Flower | ☐pedicel ☐receptacle ☐nectary ☐sepal ☐petal ☐filament ☐anther ☐pollen ☐carpel ☐style ☐papillae ☐vascular ☐epidermis ☐stomata ☐trichome |
| X Silique | ☐stigma ☐style ☐carpel ☐septum ☐placentae ☐transmitting tissue L vascular ☐epidermis ☐stomata ☐abscission zone ☐ovule |
| ☐ Ovule | Pre-fertilization: ☐inner integument ☐outer integument ☐embryo sac ☐funiculus ☐chalaza ☐micropyle ☐gametophyte Post-fertilization: ☐zygote ☐inner integument ☐outer integument seed coat ☐primordia ☐chalaza ☐micropyle ☐early endosperm ☐mature endosperm ☐embryo |
| ☐ Embryo | ☐suspensor ☐preglobular ☐globular ☐heart ☐torpedo ☐late ☐mature ☐provascular ☐hypophysis ☐radicle ☐cotyledons ☐hypocotyl |
| ☐ Stem | ☐epidermis ☐cortex ☐vascular ☐xylem ☐phloem ☐pith ☐stomata ☐trichome |
| ☐ Leaf | ☐petiole ☐mesophyll ☐vascular ☐epidermis ☐trichome ☐primordia ☐stomata ☐stipule ☐margin |

X in the vasculature (Lv) and Medial vasculature (Mv) of the silique
T2 Seedling Expression   Tissues Screened
Events Screened: n = 3   Events Expressing: n = 2
Seedlings expressing/Plants screened
Event-01: 1/2   Event-02: 2/3
GFP Expression Detected

| | |
|---|---|
| ☐ Scheduled | |
| ☐ Hypocotyl | ☐epidermis ☐cortex ☐vascular ☐xylem ☐phloem ☐stomata |
| ☐ Cotyledon | ☐mesophyll ☐vascular ☐epidermis ☐trichome ☐margin ☐stomata |
| X Rosette Leaf | ☐mesophyll ☐vascular ☐epidermis ☐trichome ☐petiole ☐primordia ☐stomata H stipule ☐margin |
| X Primary Root | epidermis H trichoblast H atrichoblast cortex ☐endodermis ☐vascular ☐xylem ☐phloem ☐pericycle ☐quiescent ☐columella ☐cap ☐root hairs |
| ☐ Lateral root | ☐epidermis ☐initials ☐flanking cells ☐vascular ☐cap |

☐ Shoot apical meristem   ☐SAM ☐epidermis
X in the Epidermis (Ep) of the root transition zone of the hypocotyl
X in the Epidermis (Ep) of the root specialization zone
X in the stipules
X in the Epidermis (Ep), Atrichoblast (At) and Trichoblast (Tr) of the root differentiation zone
T2 Mature Plant Expression Plants expressing/Plants screened
Event-01: 0/4   Event-02: Not screened.
☐ Scheduled
☐ T2 Mature tissue expressions similar to T1 expression data (data not shown).
☐ T2 Mature tissue expression (if different expression pattern).
No GFP expression detected
T3 Seedling Expression Seedlings expressing/Seedlings screened
Event-01: 1/2   Event-02: 2/2
☐ Scheduled
☐ T3 Seedling tissue expressions similar to T2 seedling expression (data not shown).
☐ T2 Mature tissue expression (if different expression pattern).

Promoter Expression Report #26

GFP Expression Detected

X Cotyledon ☐mesophyll ☐vascular ☐epidermis ☐margin ☐stomata
        L hydathode
X in the Epidermis (Ep) of the cotyledon
X in the Epidermis (Ep) and Hydathode (Hy)

Promoter utility

Trait - Sub-trait Area:  Among other uses this promoter sequence is useful to improve:
                        Water use efficiency - Heat
Utility:                   This promoter is useful for root nutrient uptake.
Additional notes: Hydathodes are modified parts of leaves, usually located at leaf margins or tips, in which water released from xylem is able to reach the surface of the leaf. It does so by passing through modified mesophyll and leaving through openings in the epidermis. These openings are stomata that are incapable of opening and closing movememts.
Construct:              YP0128
Promoter Candidate I.D:  13148257 (Old ID: 11769664)
cDNA I.D:             13610584 (Old IDs: 12327909, 4807730)
T1 lines expressing (T2 seed): SR00717-01,-02

Sequence (SEQ ID NO: 26):

GATAAACTGATAATGGAAAAGAACAAAGAAACCAGTTTTTAACTATTTGC

ATATGTAATTTATTTGTTGCAAATTATATTTAGTTAAAATGTTTCCTCTA

TTTATATATATATATATCAGTCAAGCACTATGTATAAGAAATGTCAATTT

ATAAATTTTTACATGTCCTTTAACAGAAAGAAAATGAATTTTTACATGTC

ATTCATAGAGAGTCACTCGTTTATTTCTTATATAGAGAATAACACACTCA

CATGCATATGCATGCAATATGATACATTTTATGACAAAGATAATCAACGG

AAACGGTCAAGACATAATTTGATAAACAACTTGCACGATGCACAGATCTG

ATCAAATATATAACTCTTTAACATATCCAAAATATTCAAAAAGAAAAACT

CGATCCAAACTAGCAACATCACGCTCACGCGGTAGGCTAAAAATTTATTA

ATCTCCAAAAGTCTTTCTTATGAACACTGCAAACACAACAACTTGAAAAG

TCATATAGGTTTAGATGATGACGCGTATTGGCTATCGCTTACCGGAGTGG

CTCATAAATACAATAAACAATACGTAAAAGTCAAAGTCAAATATATTTAG

TCAACTATAACCATTAATCGGGCAAAACCTTTAGCTGTCAAAACAACGTG

AAAACGATATTTGTATATATCATCAAGAATCAGTAGATAAGAGAATGATT

TAATCCCCTGACTATTACAATTTTGGTGTAATAAACAGTCTCTATTGGTT

TTTATTCTTTGTTTTAATTTCTCATGACCTATAGAGAGAATTAGGTAGTT

TCGAAAATTGGCTAATCAACTTTTGAAAACTACTGTCTACTTTGCTTAAA

TTCTCTACACTTAGTTTCGGATAAGATAATTGTCGGACTAATAGTTAATC

CCTTGACAATCTTTGATATTATAAAAGGTTTAGTTAATCTCTTCTCTATA

TAAATATTCATACACCAGCTTTCAAAAATATATAATCCAAACACCAAAAA

CAAA

Promoter Expression Report #27

Promoter Tested In: *Arabidopsis thaliana*, WS ecotype
Spatial expression summary:

Flower          (L)stomata
Silique          (M)stomata
Stem            (L)stomata
Cotyledon     (L)mesophyll, (L)vascular, (M)hydathode
Rosette Leaf   (H)stomata, (H)hydathode
Primary Root  L root hairs
Observed expression pattern: Expression specific to upper root hairs at hypocotyl root transition zone and hydathode secretory cells of the distal cotyledon.
T1 mature: No T1 mature expression by old screening protocol.
T2 mature: Guard cell and Hydathode expression same as T1 mature expression, T2 and T3 seedling expression.
Note: Promoter lines up to YP0060 were screened for expression in the expected target tissue only. Expression

| Promoter Expression Report #27 |
|---| patterns in these lines may be found coincidentally. YP0060 and later promoter lines were screened for expression in all aerial tissues. This line was re-screened in newly selected T1 mature plants.
Expected expression pattern: Shoot and root meristem
Selection Criteria: Literature. Plant Cell 1998 10 231–243
Gene: CYP90B1, *Arabidopsis* steroid 22-alpha-hydroxylase (DWF4)
GenBank: NM_113917 *Arabidopsis thaliana* cytochrome p450, putative (At3g30180) mRNA, complete cds
gi30689806|ref|NM_113917.2|[30689806]
LM Aug. 24, 2004 Cloned promoter not predicted sequence.
NM_114926 DWF4 *Arabidopsis thaliana* steroid 22-alpha-hydroxylase (CYP90B1) (DWF4) (At3g50660) mRNA, complete cds
Source Promoter Organism: *Arabidopsis thaliana* WS
Vector: pNewBin4-HAP1-GFP
Marker Type: X GFP-ER
Generation Screened: XT1 Mature   X T2 Seedling   X T2 Mature   X T3 Seedling
T1 Mature Plant Expression Organs/Tissues screened
Events Screened: n = 5    Events Expressing: n = 0 (old protocol)
Events Screened: n = 2    Events Expressing: n = 2 (new protocol)
No GFP Expression Detected (old protocol)
GFP Expression Detected (new protocol)
X Flower        □pedicel □receptacle □nectary □sepal □petal □filament □anther □pollen □carpel
                □style □papillae □vascular □epidermis □stomata □trichome
X Silique       □stigma □style □carpel □septum □placentae □transmitting tissue □vascular
                □epidermis
                M stomata □abscission zone □ovule
□ Ovule         Pre-fertilization: □inner integument outer integument □embryo sac
                □funiculus □chalaza □micropyle □gametophyte
                Post-fertilization: □zygote □inner integument □outer integument seed coat
                □primordia □chalaza □micropyle □early endosperm □mature endosperm □embryo
□ Embryo        □suspensor □preglobular □globular □heart □torpedo □late □mature □provascular
                □hypophysis □radicle □cotyledons □hypocotyl
X Stem          □epidermis □cortex □vascular □xylem □phloem □pith L stomata □trichome
□ Leaf          □petiole □mesophyll □vascular □epidermis □trichome □primordia □stomata
                □stipule □margin
New T1 screen protocol. Weak guard cell expression in stems and flowers.
T2 Seedling Expression    Organs/Tissues Screened
Events Screened: n = 2    Events Expressing: n = 2
Seedlings expressing/Plants screened
Event-01: 2/2    Event-02: No data
GFP Expression Detected
□ Hypocotyl              □epidermis □cortex □vascular □xylem □phloem □stomata
X Cotyledon              □mesophyll □vascular □epidermis □trichome □margin □stomata
                         M hydathode
□ Rosette Leaf           □mesophyll □vascular □epidermis □trichome □petiole □primordia
                         H stomata □stipule □margin H hydathode
X Primary Root           □epidermis □trichoblast □atrichoblast □cortex □endodermis □vascular
                         □xylem □phloem □pericycle □quiescent □columella □cap L root hairs
□ Lateral root           □epidermis □initials □flanking cells □vascular □cap
□ Shoot apical meristem   □SAM □epidermis
X in the Root Hair (Rh) of the hypocotyl
X in the Hydathode (Hd) of the cotyledon adaxial surface
X in the Epidermis (Ep), Mesophyll (Me) and Vascular (Vs) of the cotyledon
X in the Hydathode and Guard cells of the rosette leaf
T2 Mature Plant Expression Plants expressing/Plants screened
Event-01: 2/2    Event-02: 2/2
□ Scheduled
X T2 Mature tissue expressions similar to T1 expression data
□ T2 Mature tissue expression (if different expression pattern).
Expression detected
T2 mature expression same as T1 mature, T2 seedling, and T3 seedling
X in the Guard cell (Gc) of the flower, silique and pedicle
X in the Guard cell (Gc) and Vasculature (Vs) of the leaf
T3 Seedling Expression Seedlings expressing/Seedlings screened
Event-01: 1/3    Event-02: 1/3
□ Scheduled
X T3 Seedling tissue expressions similar to T2 seedling expression (data not shown).
□ T2 Mature tissue expression (if different expression pattern).
GFP Expression Detected
Promoter utility Trait - Sub-trait Area:   Among other uses, this promoter sequence is useful to improve:
                          PG&D - Plant size, growth rate

Promoter Expression Report #27

| | |
|---|---|
| Utility: | Useful to increase biomass, root mass, growth rate, seed set |
| Additional notes: | Hydathodes are modified parts of leaves, usually located at leaf margins or tips, in which water released from xylem is able to reach the surface of the leaf. It does so by passing through modified mesophyll and leaving through openings in the epidermis. These openings are stomata that are incapable of opening and closing movements. |
| Construct: | YP0020 |
| Promoter Candidate I.D: | 11768639 (Old ID: 11768639) |
| cDNA I.D: | 12576899 (Old ID: 7104529) |
| T1 lines expressing T2 seed: | SR00490-01,-02,-03,-04 |

Sequence (SEQ ID NO: 27):

CAGAGCAGTGCATATTTTTTTTTTTTTTTTTGGTGTTAGTGCATATCT

ATATATATAGTACTATTATAATATATTTCAATATATATATTTTAAGAAAA

TATCTGATTCTTAAGTTTGGACTTATTTGTCAACAATAGCCAGTAAAAAA

CAAAAGCGAAGTTTCACTAACTTAAAAAATAACCACATTTGTATATTTCG

AATACATACTATAAATTAATAAATTTATCAAAACAACTATAGAAACTGTT

ATTTCCAATCAATTTCTTTATCAAGATTATATCTGAAATATATTTATTAA

AATTAATAGTTATTTACAAGAACTATTTTATGAAAGTGTAAGAACTCTC

TGAAAACTTGATAAGTCAATATTTTTTCTAACATCGTAAACATAAACTAG

ATTCAAATTCGAATCTAGTTATTCAAAAACTTATAAAAACATAAAAATGA

AATACTGTTACTTCAACAAAAAAACATTATTATTATTTTGTTTAAATATC

TAATTTATTCATCAACAGCAAAATATTTAAAAGAGTGGGAAACAAATAAA

AATTAAACTCTGTTTTGGTATGATAAAATTATTTACTAAACTAAACTCAA

TATATTTTTAGTATCACGGTTATAACTATAACAATAATCGAACTTTGTTA

TTTTCTTGGTACTGGTTTTAGTAGTATAGATAGATATTTTAGTCATAACT

CATAAGATACATGTACAAATATTTGCTATATATGATCAGTGATAACTGAA

TTTCGTGCTGAAAATTGCCATAGTTTGCTTATTTTACTCTTGAAACAATA

ACGATATGGTCGTTACTTAAAACAACATTTTAAAAACGAAGAAAATTAAA

CAGAGTTTGTTAAAATAAATTAAATACCATAAATTTCTCTTTGACTCTTC

ATATATAGTAAAATCTCTCATCCCCTTCTCTCTCTCTCATAGCATGTT

GGTCTTTAGGTTCCTATATAAACAACGCCACACACACCCATTTAGTCCCA

CCATTGCACTGGGATCCAACAATGTCCTCCGACTCGTCCAAGATCAAGAG

GAAGCGGAACCGCATCCCGTTAAACGAAGGC

Promoter Expression Report #28

Promoter Tested In: *Arabidopsis thaliana*, WS ecotype
Spatial expression summary:

| | |
|---|---|
| Flower | (L)pedicel, (M)vascular |
| Stem | (H)vascular, (H)pith |
| Silique | (H)septum, (H)vascular |
| Cotyledon | (H)vascular, (H)epidermis |
| Rosette Leaf | (H)vascular, (H)phloem |
| Primary Root | (H)vascular; (H)phloem |
| Lateral root | (H)vascular |

Observed expression pattern: T1 mature (old protocol- screened target tissue): No expression observed. T2 seedling: Strong expression throughout phloem of hypocotyl, cotyledons, primary rosette leaves and roots. Also found in epidermal cells of upper root hairs at root transition zone. GFP expressed in a few epidermal cells of distal cotyledon.
T1 mature: (new protocol-screened all tissues): High expression found in silique vasculature. T2 mature: Strong expression detected in inflorescence meristem and silique medial vasculature. T3 seedling: Same expression as T2 seedlings, however no cotyledon vascular expression was detected.

| | |
|---|---|
| Expected expression pattern: | Shoot and root meristem |
| Selection Criteria: | Plant Physiol. 2002 129: 1241–51 |
| Gene: | brassinosteroid-regulated protein (xyloglucan endotransglycosylase related protein |
| GenBank: | NM_117490 *Arabidopsis thaliana* xyloglucan endotransglycosylase (XTR7) (At4g14130) mRNA, complete cds gi\|30682721\|ref\|NM_117490.2\|[30682721] |
| Source Promoter Organism: | *Arabidopsis thaliana* WS |
| Vector: | pNewBin4-HAP1-GFP |

-continued

Promoter Expression Report #28

Marker Type: X GFP-ER
Generation Screened: X T1 Mature   XT2 Seedling   X T2 Mature   X T3 Seedling
T1 Mature Plant Expression Organs/Tissues screened
Events Screened: n = 5   Events Expressing: n = 0 (old protocol)
No GFP Expression Detected Events Screened: n = 3   Events Expressing: n = 2 (new protocol)
GFP Expression Detected ☐ Flower         ☐pedicel ☐receptacle ☐nectary ☐sepal ☐petal ☐filament ☐anther ☐pollen ☐carpel
                 ☐style ☐papillac ☐vascular ☐epidermis ☐stomata ☐trichome
X Silique        ☐stigma ☐style ☐carpel H septum ☐placentae ☐transmitting tissue H vascular
                 ☐epidermis ☐stomata ☐abscission zone ovule
☐ Ovule          Pre-fertilization: ☐inner integument outer integument ☐embryo sac
                 funiculus ☐chalaza ☐micropyle ☐gametophyte
                 Post-fertilization: ☐zygote ☐inner integument ☐outer integument funiculus
                 ☐chalaza ☐micropyle seed coat ☐primordia ☐early endosperm ☐mature endosperm
                 ☐embryo
☐ Embryo         ☐suspensor ☐preglobular ☐globular ☐heart ☐torpedo ☐late ☐mature ☐provascular
                 ☐hypophysis ☐radicle ☐cotyledons ☐hypocotyl
☐ Stem           ☐epidermis ☐cortex ☐vascular ☐xylem ☐phloem ☐pith ☐stomata ☐trichome
☐ Leaf           ☐petiole ☐mesophyll ☐vascular ☐epidermis ☐trichome ☐primordia ☐stomata
                 ☐stipule ☐margin
X in the Vasculature (Vs) of the pre-fertilized and fertilized silique
T2 Seedling Expression   Tissues Screened
Events Screened: n = 3   Events Expressing: n = 2
Seedlings expressing/Seedlings screened
Event-01: No data   Event-02: No data
GFP Expression Detected ☐ Hypocotyl              ☐epidermis ☐cortex ☐vascular ☐xylem ☐phloem ☐stomata
X Cotyledon              ☐mesophyll ☐vascular ☐xylem ☐phloem H epidermis ☐margin
                         ☐stomata ☐petiole
X Rosette Leaf           ☐mesophyll H vascular ☐xylem H phloem ☐epidermis ☐trichome
                         ☐petiole ☐primordia ☐stomata ☐stipule ☐margin
X Primary Root           ☐epidermis ☐trichoblast ☐atrichoblast ☐cortex ☐endodermis H
                         vascular ☐xylem H phloem ☐pericycle ☐quiescent ☐columella ☐cap
                         ☐root hairs
X Lateral root           ☐epidermis ☐initials ☐flanking cells H vascular ☐cap
☐ Shoot apical meristem   ☐SAM ☐epidermis
X in the Epidermis (Ep), Phloem (Ph) and Root hair (Rh) of the hypocotyl root zone
X in the Epidermis (Ep) and Vasculature (Vs) of the petiole leaf
X in the Epidermis (Ep), Phloem (Ph) and Vascular bundle (Vb) of the Cotyledon (Co)
X in the Phloem (Ph) of the Lateral root (Lr) and lateral root initial
X in the Phloem (Ph) and Vascular bundle (Vb) of the Root (Rt)
T2 Mature Plant Expression Plants expressing/Plants screened
Event-01: 1/2   Event-02: Not screened.
X Scheduled
☐ T2 Mature tissue expressions similar to T1 expression data.
☐ T2 Mature tissue expression (if different expression pattern).
X Flower         L pedicel ☐receptacle ☐nectary ☐sepal ☐petal ☐filament ☐anther ☐pollen ☐carpel
                 ☐style ☐papillae ☐vascular ☐epidermis ☐stomata ☐trichome
X Silique        ☐stigma ☐style ☐carpel H septum ☐placentae ☐transmitting tissue H vascular
                 ☐epidermis ☐stomata ☐abscission zone ovule
X Stem           ☐epidermis ☐cortex H vascular ☐xylem ☐phloem H pith ☐stomata ☐trichome
X in the Vasculature (Vs) of the inflorescence meristem and silique
X in the Guard cell (Gc) of the pedicle
X in the Septum (Sp) of the silique
T3 Seedling Expression Seedlings expressing/Seedlings screened
Event-01: 2/3   Event-02: 2/2
☐ Scheduled
X T3 Seedling tissue expressions similar to T2 seedling expression (data not shown).
☐ T2 Mature tissue expression (if different expression pattern).
Promoter utility Trait Area:   Among other uses this promoter sequence is useful to improve:
              PG&D - Plant size, growth rate
Utility:      Useful to increase biomass, root mass, growth rate
Construct:                YP0022
Promoter Candidate I.D:   11768614
cDNA I.D:                 12711515 (Old ID: 5674312)
T1 lines expressing (T2 seed): SR00492-02,-03

Sequence (SEQ ID NO: 28):

TAGTTCCATTACAATTTCCAAATGATTTGTTACAAAGCTACAAGATTATT

CGAAATAGGATTTCATCCATAAGAGAGAATGGTGTGGTCGACGCTACAAT

GTTGATTTATTGGTTGTGGTTTGCATCTTGGGGATGTCAAATCCTAAGTT

TCAAGTTCTTGTAAAAACGTTTTCAGGTTTCTTTAATATATTTTAATATT

AATGTAAAAAGAAAAGATATAGCTTTTGTACAAAAAAATTTGTTTAATCA

CTATGTAGGAGGATGCGATCAAATTCATGGAATGATGTATTATTAGCTTT

TCTATCCTCACTCTAAAAACAATACTATAGTGAGTTAAATAATTTGATCA

TTTCAATGTAGATTAAAATTTTATTAAAAGAAGAAAAATTTAAAAGCCTA

TAACAAAATAAAAAAGGAGGCTCGAGGTATGATGGGTGTAGCAGAAGAGC

TGGCAACAGCTATCGACTGAGTGATTACGAACTCAGTACTCAGTGTTCTC

AGCTCACACACTCTTTTTTTGTTCTCTTTCTTTTGGACAGCTTTCATTTT

CTCTTTTCTTTTTCTATTTTGTTTCAAAATTCCATCCATATTAAAATAAG

CCTGATCATGAGAATAAAGGAAATACTAATGATGAGTTTCTCAATAATGC

AATAAGATGCAATTATTATGAGCTATTTACTATTGAAAATGAGCAAATAA

ATGTCAAAACACAATCTGGTTAAGTTAGAGCAACTCCATTGTATAGGATT

CATGTAGTTTCTAAGAAAACAAAATGTATTAATATTTTACTTTTACATCC

AAAAAACCAAAAAACCAACTTATATGAGTAATAGAAACGATCCTCATATT

AGGAATTTTAGAGATTTTCTCTCATCTGTTTCTTAACTTTTCAATATTTT

TATTTTTTTAAATTGTATGAGTTTCTACTAAGAAACTACTGCTGGAGTTG

GTCTTAGCTTCCCAATGCTTCTCCACCTATATATATGCATATCTCCTTCT

TAAAACTCCATTGCACTGGGATCCAACAATGTCCTCCGACTCGTCCAAGA

TCAAGAGGAAGCGGAACCGCATCCCTTATACTAAAGGCGG

| Promoter Expression Report #29 | |
|---|---|
| Promoter Tested In: | *Arabidopsis thaliana*, WS ecotype |
| Spatial expression summary: | |
| Flower | (M)sepal, (L)stomata |
| Silique | (M)stomata |
| Rosette Leaf | (H)stomata |
| Primary Root | (H)epidermis, (H)trichoblast, (H)root hair |
| Observed expression pattern: | Strong GFP expression in stomata of primary rosette leaves and epidermal root hair trichoblast cells of seedlings. T1 mature: No expression observed. T2 seedling: Same as T2 seedling expression. T2 mature: Guard cell and weak vascular expression in flowers. |
| Expected expression pattern: | embryo |
| Selection Criteria: | Plant J 2000 21: 143–55 |
| Gene: | ABI3-interacting protein 2, AIP2 [*Arabidopsis thaliana*] |
| GenBank: | NM_122099 *Arabidopsis thaliana* zinc finger (C3HC4-type RING finger) protein family (At5g20910) mRNA, complete cds gi\|30688046\|ref\|NM_122099.2\|[30688046] |
| Source Promoter Organism: | *Arabidopsis thaliana*, WS |
| Vector: | pNewBin4-HAP1-GFP |
| Marker Type: | X GFP-ER |
| Generation Screened: | X T1 Mature   XT2 Seedling   X T2 Mature   X T3 Seedling |
| T1 Mature Plant Expression Organs/Tissues screened | |
| Events Screened: n = 5    Events Expressing: n = 0 | |
| No GFP Expression Detected | |
| ☐ Flower | ☐pedicel ☐receptacle ☐nectary ☐sepal ☐petal ☐filament ☐anther ☐pollen ☐carpel ☐style ☐papillae ☐vascular ☐epidermis ☐stomata ☐trichome |
| ☐ Silique | ☐stigma ☐style ☐carpel ☐septum ☐placentae ☐transmitting tissue ☐vascular ☐epidermis ☐stomata ☐abscission zone ☐ovule |
| ☐ Ovule | Pre-fertilization: ☐inner integument ☐outer integument ☐embryo sac ☐funiculus ☐chalaza ☐micropyle ☐gametophyte Post-fertilization: ☐zygote ☐inner integument ☐outer integument ☐seed coat ☐primordia ☐chalaza ☐micropyle ☐early endosperm ☐mature endosperm ☐embryo |
| ☐ Embryo | ☐suspensor ☐preglobular ☐globular ☐heart ☐torpedo ☐late ☐mature ☐provascular ☐hypophysis ☐radicle ☐cotyledons ☐hypocotyl |
| ☐ Stem | ☐epidermis ☐cortex ☐vascular ☐xylem ☐phloem ☐pith ☐stomata ☐trichome |
| ☐ Leaf | ☐petiole ☐mesophyll ☐vascular ☐epidermis ☐trichome ☐primordia ☐stomata ☐stipule ☐margin |
| T2 Seedling Expression   Organs/Tissues Screened | |
| Events Screened: n = 4    Events Expressing: n = 2 | |
| Seedlings expressing/Seedlings screened | |
| Event-01: No data.   Event-02: No data. | |

Promoter Expression Report #29

GFP Expression Detected

☐ Hypocotyl ☐epidermis ☐cortex ☐vascular ☐xylem ☐phloem ☐stomata
☐ Cotyledon ☐mesophyll ☐vascular ☐epidermis ☐trichome ☐margin ☐stomata
X Rosette Leaf ☐mesophyll ☐vascular ☐epidermis ☐trichome ☐petiole ☐primordia
H stomata ☐stipule ☐margin
X Primary Root H epidermis H trichoblast ☐atrichoblast ☐cortex ☐endodermis
☐vascular ☐xylem ☐phloem ☐pericycle ☐quiescent ☐columella ☐cap
H root hairs
☐Lateral root ☐epidermis ☐initials ☐flanking cells ☐vascular ☐cap
☐ Shoot apical meristem ☐SAM ☐epidermis
X in the Root hair (Rh) of the hypoctyl root zone and the roof
X in the Guard cells (Gc) of the leaf T2 Mature Plant Expression Plants expressing/Plants screened
Event-01: 2/2   Event-02: 1/2
☐ Scheduled
☐ T2 Mature tissue expressions similar to T1 expression data (data not shown).
X T2 Mature tissue expression (if different expression pattern).
☐ No expression detected
X Flower ☐pedicel ☐receptacle ☐nectary M sepal ☐petal ☐filament ☐anther ☐pollen ☐carpel
☐style ☐papillae ☐vascular ☐epidermis L stomata ☐trichome
X Silique ☐stigma ☐style ☐carpel ☐septum ☐placentae ☐transmitting tissue ☐vascular
☐epidermis
M stomata ☐abscission zone ☐ovule
X in the flower and silique T3 Seedling Expression Seedlings expressing/Seedlings screened
Event-01: 1/3   Event-02: 2/3
☐ Scheduled
X T3 Seedling tissue expressions similar to T2 seedling expression (data not shown).
☐ T2 Mature tissue expression if different expression pattern
GFP Expression Detected
Promoter utility

| | |
|---|---|
| Trait - Sub-trait Area: | Among other uses this promoter sequence is useful to improve: Water use efficiency - Drought, heat |
| Utility: | This promoter useful for enhancing recovery after growth under water deprivation Also useful for nutrition uptake |
| Construct: | YP0024 |
| Promoter Candidate I.D: | 11768616 |
| cDNA I.D: | 13614559 (Old IDs: 12324998, 5675795) |
| T1 Lines expressing (T2 seed): | SR00494-01,-03 |

Sequence (SEQ ID NO: 29):

TGTTAAGGGAAGGTTTGCACCTAAGAATTTTGAAGGAATTTTGCGGCGAT

ATATCAGTAAGTAACTTTCTTCTTAGTCTCAAAATTTAAGTTGCCATAAA

AGTATATCAGTTTGGAGTTGTTAACCTCTTGTTTTATTATTTCTCAGCTG

ACTACGTCATTTGCCTTGGTTGCAAGAGCCCAGACACCATTCTCTCCAAG

GAGAACCGTCTCTTCTTTCTGAGATGTGAAAAGGTATAAGTTAATCTAAT

TAGTCCTGATCTTGATATGCATTCCTTTGTTTCTGTTTTACAGTTTTACT

TTCTGCGCAACAAAGTAATAAAGTATTTTGTGTGTTTGAATTTGCTAATG

TGATTAACGAGTGGGCTACATGGTTTTTGCAGTGTGGATCTCAACGATCT

GTGGCTCCGATCAAAACAGGGTTTGTTGCTCGTGTTAGTCGCAGGAAGAC

TTGAGAAATTAGAAGGTGAAGTGACCTTGGTATGGAGTTTGGAGCTATTC

TACTGCTTCTGTATGAGTTTATGAGTTGAAGAAATACTTGTCTTGTTTTT

TTTATTTTGTTTTGGAATATGATTATGACTTGACTTTTAAAATGGGATAG

GATCAAAACCTTTTACTCTGTCAGGTTCATGTGGTCACCTTGAAGGTTGA

TTTAGTAAATCCATGGACTTCTTTTTTGTGTTAAGATTATTCTTAGTTCA

AAATTAATAGACTAATGATATTAACGTCCACAGGCATTGCGTTCAACATC

TCAAATTAAAGCGTGGAAGGCTCAGAAAGTCCAATATACACTATGTTTAT

CTACAGTTACAATCATACTACAAAAAACAAATAATGTATACGGTTTGGTC

TAATATAGCCGCATACGATTTCGTATTTACCACAAAAAATTGGTCTCAAA

CCAAACCGAACAATTGGTAATTAACAATTGTTCTTTTGGTCTTGAACCGA

ACCAAACCGAACTGAACTATATTAACCGACCGACTTCGTCCTTTCCTCCC

CATTGCACTGGGATCCAACAATGTCCTCCGACTCGTCCAAGATCAAGAGG

AAGCGGAACCGCATCCCnTTAAACGAAGGCG

---

Promoter Expression Report # 30

---

Promoter Tested In: *Arabidopsis thaliana*, WS ecotype
Spatial expression summary:

| | |
|---|---|
| Silique | (H)ovule |
| Ovule | Pre-fertilization: (H)outer integument, (H)funiculus |
| | Post-fertilization: (H)outer integument, (H)funiculus |
| Rosette Leaf | (H)vascular |
| Primary Root | (H)epidermis, (H)trichoblast, (H)root hair |
| Lateral root | (H)pericycle |

Observed expression pattern: Strong GFP expression in upper root hairs at root transition zone and in distal vascular bundle of cotyledon. Low expression in pericycle cells of seedling root. T1 mature: No expression observed. T3 seedling: Same as T2 seedling expression. T2 mature: GFP expression in funiculus of ovules as in connective tissue between locules of anther.

| | |
|---|---|
| Expected expression pattern: | Root vasculature |
| Selection Criteria: | Helariutta, et al. 2000 Cell 101: 555–567 |
| Gene: | SHR (Short-root gene) |
| GenBank: | NM_119928 *Arabidopsis thaliana* short-root transcription factor (SHR) (At4g37650) mRNA, complete cds gi|30691190|ref|NM_119928.2|[30691190] |
| Source Promoter Organism: | *Arabidopsis thaliana* WS |
| Vector: | pNewBin4-HAP1-GFP |
| Marker Type: | X GFP-ER |
| Generation Screened: | X T1 Mature   X T2 Seedling   X T2 Mature   X T3 Seedling |

T1 Mature Plant Expression     Organs/Tissues screened
Events Screened:   n = 5     Events Expressing:   n = 0
No GFP Expression Detected ☐ Flower     ☐ pedicel ☐ receptacle ☐ nectary ☐ sepal ☐ petal ☐ filament ☐ anther ☐ pollen ☐ carpel
              ☐ style ☐ papillae ☐ vascular ☐ epidermis ☐ stomata ☐ trichome
☐ Silique    ☐ stigma ☐ style ☐ carpel ☐ septum ☐ placentae ☐ transmitting tissue ☐ vascular
              ☐ epidermis ☐ stomata ☐ abscission zone ☐ ovule
☐ Ovule      Pre-fertilization: ☐ inner integument ☐ outer integument ☐ embryo sac
              ☐ funiculus ☐ chalaza ☐ micropyle ☐ gametophyte
              Post-fertilization: ☐ zygote ☐ inner integument ☐ outer integument ☐ seed coat
              ☐ primordia ☐ chalaza ☐ micropyle ☐ early endosperm ☐ mature endosperm ☐ embryo
☐ Embryo     ☐ suspensor ☐ preglobular ☐ globular ☐ heart ☐ torpedo ☐ late ☐ mature ☐ provascular
              ☐ hypophysis ☐ radicle ☐ cotyledons ☐ hypocotyl
☐ Stem       ☐ epidermis ☐ cortex ☐ vascular ☐ xylem ☐ phloem ☐ pith ☐ stomata ☐ trichome
☐ Leaf       ☐ petiole ☐ mesophyll ☐ vascular ☐ epidermis ☐ trichome ☐ primordia ☐ stomata
              ☐ stipule ☐ margin T2 Seedling Expression     Tissues Screened
Events Screened:   n = 2     Events Expressing:   n = 2
Seedlings expressing / Seedlings screened
Event-01: 1/3     Event-02: 1/2
GFP Expression Detected ☐ Hypocotyl              ☐ epidermis ☐ cortex ☐ vascular ☐ xylem ☐ phloem ☐ stomata
☐ Cotyledon              ☐ mesophyll ☐ vascular ☐ epidermis ☐ trichome ☐ margin ☐ stomata
X Rosette Leaf           ☐ mesophyll H vascular ☐ epidermis ☐ trichome ☐ petiole ☐ primordia
                         ☐ stomata ☐ stipule ☐ margin
X Primary Root           H epidermis H trichoblast atrichoblast ☐ cortex ☐ endodermis
                         ☐ vascular ☐ xylem ☐ phloem ☐ pericycle ☐ quiescent ☐ columella ☐ cap
                         H root hair
X Lateral root           ☐ epidermis ☐ initials ☐ flanking cells ☐ vascular ☐ xylem ☐ phloem
                         M pericycle ☐ cap
☐ Shoot apical meristem  ☐ SAM ☐ epidermis
X in the Root hair (Rh) of the hypocotyl root zone
X in the Vasculature (Vs) and Vascular bundle (Vb) of the leaf
X in the Pericycle (Pr) of the root and lateral root T2 Mature Plant Expression Plants expressing / Plants screened
Event-01: 1/1     Event-02: No germination
☐ Scheduled
☐ T2 Mature tissue expressions similar to T1 expression data (data not shown).
X T2 Mature tissue expression (if different expression pattern).
☐ No expression detected X Silique    ☐ stigma ☐ style ☐ carpel ☐ septum ☐ placentae ☐ transmitting tissue ☐ vascular
              ☐ epidermis ☐ stomata ☐ abscission zone H ovule
X Ovule      Pre-fertilization: ☐ inner integument H outer integument ☐ embryo sac
              H funiculus ☐ chalaza ☐ micropyle ☐ gametophyte
              Post-fertilization: ☐ zygote ☐ inner integument H outer integument ☐ seed coat
              ☐ primordia ☐ chalaza ☐ micropyle ☐ early endosperm ☐ mature endosperm ☐ embryo
              H funiculus
X in the Ovule (Ov) of the ovary and silique
X in the Funiculus (Fn) of the ovule primordia
X in the pre-fertilized and fertilized ovule

Promoter Expression Report # 30

T3 Seedling Expression

Seedlings expressing / Seedlings screened
Event-01: 2/3    Event-02: No seeds.
☐ Scheduled
X T3 Seedling tissue expressions similar to T2 seedling expression (data not shown).
☐ T2 Mature tissue expression (if different expression pattern).
GFP Expression Detected
Promoter utility

| | |
|---|---|
| Trait - Sub-trait Area: | Among other uses this promoter sequence is useful to improve:<br>Water use efficiency - Increase leaf water potential<br>PG & D - increase root biomass, plant size<br>Nutrient - nitrogen use efficiency, nitrogen utilization, low nitrogen tolerance |
| Utility: | This promoter is a good promoter for root nutrition uptake, root biomass. |
| Construct: | YP0028 |
| Promoter Candidate I.D: | 11768648 |
| cDNA I.D: | 12561142 (Old ID: 7093615) |
| T1 lines expressing (T2 seed): | SR00586-03,-04 |

Sequence (SEQ ID NO: 30):

GTCAGTGAAGTCGATTGGTAGTACTTGAAACACTTGGTTGGTTTCATGTA

TTTGGCCTATATATAAACAAACATCGTAATTATATACGGATTTTTTCGG

AATTTTACGCCATATCTGTAAGTATATATAACATGCATGTCGTTTTCAAA

TTCATATGATGAACAGTCCACGTAAGTGCTACTACTCCTACAATATTGCA

TGAGAGAGATATGTATTTATAAATTTTATTTTGAAGAAGAAATAAGAGGG

AAGGTTACTTGGGTGGATCGATGTGAAAACAAAGAAGAAAAAGCGAAAC

CCACTAAGCCATTACATGATATCGACCTTCTTATCTTTTTCCTCTTTATT

TTATTTTTCTCATCTTCTTTTTGTCAGGACTTTTTTCTACTTAATGAAAC

CTCCAAACTATCTAACTAATACACTCCCATGTAGAATAAAGAAAATTATA

TAAGATATTGTTGATATTTTGTAACTAGAAAATATATTTGCTCTGTAATT

TTTCGTAAGTTAAATCAACATTTTAAAGTAGAAACAAATATTACTGCAAA

AAGTAGGATCATTATTTTTGTCCAAAATCTCAGTTAGCTATAGGGTTGTA

GTAAAAACAAAACACATTCTTGATTTGCCCCAAAAAATAAAGAGAGAGAA

GAATATTGTTCAAAAGTGGTCTCTTCTCTCTCTAATTATGTTTTCACTAA

ACCCAATTAGATTCAAACAGTCTACAAAGTCCAAAAGATAAACATGGGAC

AACAATTCGATGCAAAAAATCCTCTTTTCATGCTCTTTTTTTATTCTCTA

GTCTTTTAAATTACTAATAAAAACTCACAAATCCACCAAACCCATTCTCT

ACAACTCACCTTCATCTAGATTACCCACTCCCACCGAGAAACACAAGAAA

AAAAATATACATATATAAATATACAAGACAACACATGATGCTGATGCAAT

ATACACAACAAAGTATTAAATCTTAGATATTGTGGGTCTCCCTTTCTTCT

ATTCATTTTCTTATTCATTAAAAAAAAAAA

Promoter Expression Report # 31

Promoter Tested In: *Arabidopsis thaliana*, WS ecotype
Spatial expression summary:

Flower          (L)stomata
Primary Root    (H)epidermis, (H)trichoblast, (H)atrichoblast, (H)root hairs
Observed expression pattern: Strong GFP expression specific to epidermal root hair trichoblast and atrichoblast cells throughout seedling root. Not expressed in lateral root.
T1 mature: No expression observed. T2 mature: Low guard cell expression in flower not observed in T1 mature.
T3 seedling expression: Same as T2 seedlings.
Expected expression pattern: localized to the lateral root cap, root hairs, epidermis and cortex of roots.
Selection Criteria: *Arabidopsis* public; The roles of three functional sulfate transporters involved in uptake and translocation of sulfate in *Arabidopsis thaliana*. Plant J. 2000 23:171-82

-continued

| Promoter Expression Report # 31 | |
|---|---|
| Gene: | Sulfate transporter |
| GenBank: | NM_116931 *Arabidopsis thaliana* sulfate transporter -related (At4g08620) mRNA, complete cds gi30680813\|refNM_116931.2[30680813] |
| Source Promoter Organism: | *Arabidopsis thaliana* WS |
| Vector: | pNewBin4-HAP1-GFP |
| Marker Type: | X GFP-ER |
| Generation Screened: | X T1 Mature   X T2 Seedling   X T2 Mature   X T3 Seedling |

T1 Mature Plant Expression   Organs/Tissues screened
Events Screened:   n = 5   Events Expressing:   n = 0
No GFP Expression Detected
☐ Flower   ☐ pedicel ☐ receptacle ☐ nectary ☐ sepal ☐ petal ☐ filament ☐ anther ☐ pollen ☐ carpel
            ☐ style ☐ papillae ☐ vascular ☐ epidermis ☐ stomata ☐ trichome
☐ Silique  ☐ stigma ☐ style ☐ carpel ☐ septum ☐ placentae ☐ transmitting tissue ☐ vascular
            ☐ epidermis ☐ stomata ☐ abscission zone ☐ ovule
☐ Ovule    Pre-fertilization: ☐ inner integument ☐ outer integument ☐ embryo sac
            ☐ funiculus ☐ chalaza ☐ micropyle ☐ gametophyte
           Post-fertilization: ☐ zygote ☐ inner integument ☐ outer integument ☐ seed coat
            ☐ primordia ☐ chalaza ☐ micropyle ☐ early endosperm ☐ mature endosperm ☐ embryo
☐ Embryo   ☐ suspensor ☐ preglobular ☐ globular ☐ heart ☐ torpedo ☐ late ☐ mature ☐ provascular
            ☐ hypophysis ☐ radicle ☐ cotyledons ☐ hypocotyl
☐ Stem     ☐ epidermis ☐ cortex ☐ vascular ☐ xylem ☐ phloem ☐ pith ☐ stomata ☐ trichome
☐ Leaf     ☐ petiole ☐ mesophyll ☐ vascular ☐ epidermis ☐ trichome ☐ primordia ☐ stomata
            ☐ stipule ☐ margin T2 Seedling Expression   Tissues Screened
Events Screened:   n = 3   Events Expressing:   n = 2
Seedlings expressing / Seedlings screened
Event-01: No data   Event-02: No data
GFP Expression Detected
☐ Hypocotyl           ☐ epidermis ☐ cortex ☐ vascular ☐ xylem ☐ phloem ☐ stomata
☐ Cotyledon           ☐ mesophyll ☐ vascular ☐ xylem ☐ phloem ☐ epidermis ☐ trichome
                      ☐ margin ☐ stomata
☐ Rosette Leaf        ☐ mesophyll ☐ vascular ☐ epidermis ☐ trichome ☐ petiole ☐ primordia
                      ☐ stomata ☐ stipule ☐ margin
X Primary Root        H epidermis H trichoblast H atrichoblast ☐ cortex ☐ endodermis
                      ☐ vascular ☐ xylem ☐ phloem ☐ pericycle ☐ quiescent ☐ columella ☐ cap
                      H root hairs
☐ Lateral root        ☐ epidermis ☐ initials ☐ flanking cells ☐ vascular ☐ xylem ☐ phloem
                      ☐ cap
☐ Shoot apical meristem   ☐ SAM ☐ epidermis
X in the Epidermis (Ep) and Root hair (Rh) of the hypocotyl root and root T2 Mature Plant Expression Plants expressing / Plants screened
Event-01: 1/1   Event-02: 1/1
☐ Scheduled
☐ T2 Mature tissue expressions similar to T1 expression data (data not shown).
X T2 Mature tissue expression (if different expression pattern).
☐ No expression detected
☐ Flower   ☐ pedicel ☐ receptacle ☐ nectary ☐ sepal ☐ petal ☐ filament ☐ anther ☐ pollen ☐ carpel
            ☐ style ☐ papillae ☐ vascular ☐ epidermis ☐ stomata ☐ trichome
X in the Guard cells of the flower T3 Seedling Expression Seedlings expressing / Seedlings screened
Event-01: 1/3   Event-02: 2/3
☐ Scheduled
X T3 Seedling tissue expressions similar to T2 seedling expression (data not shown).
☐ T2 Mature tissue expression (if different expression pattern).
GFP Expression Detected
Promoter utility

| Sub-trait Area: | Among other uses this promoter sequence is useful to improve: Water use efficiency - Water potential, drought, moisture stress at seed set and seed fill, water use efficiency Nutrient - nitrogen use efficiency |
|---|---|
| Utility: | This is good promoter for root nutrient uptake, increase root mass and water use efficiency |
| Construct: | YP0030 |
| Promoter Candidate I.D: | 11768642 |
| cDNA I.D: | 12664333 (Old ID: 7079065) |
| T1 lines expressing (T2 seed): | SR00545-01,-02 |

Sequence (SEQ ID NO: 31):

```
AGGTCAGTGAAGTCGATTGGTACTTGCCTCATGTGTTTGGATACGAGATT

ACTGAACGTTGTGGTGTATTTTATAGTCATGGGTTTGTTAATTGTTATCA

TGCTTGCCTACTTAACTAGCGTAATTATGTTTTTTGTACTACCTCGGAAG

TAGCTATTTTGTCGCTTATTGACAACGAGATACTTTAAGATGTTCCACAT

CCACGTCGTAATCGGTTGATCGAATGGTGCCTAATAGATCAAAGTTATCC

TCAACAAATATCGATGTGTAGTATATACGTGAATATATAGTAGTCTCTTG

CATGCATATCATATACAACTTAAATACTTTTTGTTTCAAAATAAATAATG

TTTTAGGAAAAAGATTATTTGTGTCAAATTAAGTGTTGGTCTATTCATCC

AAACAAGAAAGAAAAAAAATACGAATTTGTTTTATATATCATTGACGAAC

AATGTTTAGCTAATAATAAATAATTATTTATTTATAAAAATTAAAAGTTA

GATAGTTTCTTAATTTAGGTGCATATAAGTTCTTTAACAAAAAAAACATT

TAGGTGCATAAGTCTTAAATATCAAATATTTTGGAACAGTAATTTTATGT

ATAACTTTTTCGTACCTATCTTCACACCGCATAAATTGCCAAAGTCAAC

CTTTTGATATTTCATTCCTCACAAAACCATATTAATTTATACACCTCAAT

ATTGTTTAATAGTATTATCATGTTGGCTTTCGCTGAATTTATCAAAGTGC

AACATGTTTTATCTTACAAAAAAATAAAAAGAAATTCACGTTGTGTGATC

TTGAGAGTTTGACTTTTAAATATATCACAACTTATATAAATACGCAGCAA

CATTCCAATCTCTCAAGAAAATCTACAGTTCCTCCAAATAATAATACCCT

CCCTCTAAGGTTTAAAACTATACCTCATTAACACATTAAGAAGCTAGTCA

TTACTTTCATTTCTATATTTTAAATAATGTTTATTGATAACAATTTGCAG

GCAACTAATTTTCAGCAATCACCATTGCACTGGGATCCAACAATGTCCTC

CGACTCGTCCAAGATCAAGAGGAAGC
```

| Promoter Expression Report # 32 | |
|---|---|
| Promoter Tested In: *Arabidopsis thaliana*, WS ecotype | |
| Spatial expression summary: | |
| Cotyledon | (L)epidermis |
| Primary Root | (H)epidermis, (H)trichoblast, (H)atrichoblast |
| Observed expression pattern: | High GFP expression in epidermal cells of seedling root from hypocotyl root transition to differentiation zone. Not observed in root tip. Low GFP expression in epidermal cells of distal cotyledon. T1 mature: No expression detected. T2 mature: Guard cell expression in stem, pedicles. Low silique vascular expression. T3 seedling: Same as T2 seedlings. |
| Expected expression pattern: | predominantly expressed in the phloem |
| Selection Criteria: | Ceres microarray data |
| Gene: | putative glucosyltransferase [*Arabidopsis thaliana*] |
| GenBank: | BT010327 *Arabidopsis thaliana* At2g43820 mRNA, complete cds gi|33942050|gb|BT010327.1|[33942050] |
| Source Promoter Organism: | *Arabidopsis thaliana* WS |
| Vector: | pNewBin4-HAP1-GFP |
| Marker Type: | X GFP-ER |
| Generation Screened: | X T1 Mature   X T2 Seedling   X T2 Mature   X T3 Seedling |
| T1 Mature Plant Expression | Organs/Tissues screened |
| Events Screened:    n = 3 | Events Expressing:    n = 0 |
| No GFP Expression Detected | |
| ☐ Flower | ☐ pedicel ☐ receptacle ☐ nectary ☐ sepal ☐ petal ☐ filament ☐ anther ☐ pollen ☐ carpel ☐ style ☐ papillae ☐ vascular ☐ epidermis ☐ stomata ☐ trichome |
| ☐ Silique | ☐ stigma ☐ style ☐ carpel ☐ septum ☐ placentae ☐ transmitting tissue ☐ vascular ☐ epidermis ☐ stomata ☐ abscission zone ☐ ovule |
| ☐ Ovule | Pre-fertilization: ☐ inner integument ☐ outer integument ☐ embryo sac ☐ funiculus ☐ chalaza ☐ micropyle ☐ gametophyte Post-fertilization: ☐ zygote ☐ inner integument ☐ outer integument ☐ seed coat ☐ primordia ☐ chalaza ☐ micropyle ☐ early endosperm ☐ mature endosperm ☐ embryo |
| ☐ Embryo | ☐ suspensor ☐ preglobular ☐ globular ☐ heart ☐ torpedo ☐ late ☐ mature ☐ provascular ☐ hypophysis ☐ radicle ☐ cotyledons ☐ hypocotyl |
| ☐ Stem | ☐ epidermis ☐ cortex ☐ vascular ☐ xylem ☐ phloem ☐ pith ☐ stomata ☐ trichome |
| ☐ Leaf | ☐ petiole ☐ mesophyll ☐ vascular ☐ epidermis ☐ trichome ☐ primordia ☐ stomata ☐ stipule ☐ margin |
| T2 Seedling Expression | Organs/Tissues Screened |
| Events Screened:    n = 2 | Events Expressing:    n = 2 |
| Seedlings expressing /Plants screened | |
| Event-01: 2/2    Event-02: 1/2 | |
| GFP Expression Detected | |

Promoter Expression Report # 32

☐ Hypocotyl     ☐ epidermis ☐ cortex ☐ vascular ☐ xylem ☐ phloem ☐ stomata
☐ Cotyledon     ☐ mesophyll ☐ vascular L epidermis ☐ trichome ☐ margin ☐ stomata
☐ Rosette Leaf     ☐ mesophyll ☐ vascular ☐ epidermis ☐ trichome ☐ petiole ☐ primordia
               ☐ stomata ☐ stipule ☐ margin
☐ Lateral root     ☐ epidermis ☐ initials ☐ flanking cells ☐ vascular ☐ cap
☐ Shoot apical meristem     ☐ SAM ☐ epidermis
X in the Epidermis (Ep) of the hypocotyl root zone and cotyledon
X in the Epidermis (Ep) and Vascular bundle (Vb) of the root differentiation zone T2 Mature Plant Expression Plants expressing / Plants screened
Event-01: 1/1     Event-02: 1/2
☐ Scheduled
☐ T2 Mature tissue expressions similar to T1 expression data (data not shown).
X T2 Mature tissue expression (if different expression pattern).
Expression detected T3 Seedling Expression Seedlings expressing / Seedlings screened
Event-01: 2/3     Event-02: 1/3
☐ Scheduled
X T3 Seedling tissue expressions similar to T2 seedling expression.
☐ T2 Mature tissue expression (if different expression pattern).
GFP Expression Detected
X in the seedling root and root tip Promoter utility Trait - Sub-trait Area:    Among other uses this promoter sequence is useful to improve:
                       Nutrient - nitrogen and phosphate uptake and transport
                       Growth and Development - plant size, growth rate
Utility: Promoter useful where expression in the root epidermis is important. Expression appears to be in expanded or differentiated epidermal cells.
Construct:                YP0054
Promoter I.D:            13148233 (Old ID: 11768644)
cDNA I.D:               12348737 (Old ID: 1609253)
T1 lines expressing (T2 seed):    SR00549-01,-02

Sequence (SEQ ID NO: 32):

```
CTGATCTCTAGTCCAGTCGATTGGAGCTTATTTTGTTCTATTCTATCGTA
TTTGATTCTTCTTTCGTTTTTTTTTGTTTGACTTAAGAAACCGATTGTTT
ATAGTAGTAAACATTTGTTTTAATGTTGCTCGATTCCAGTGCACATGTC
CAGGCTAGACACTTGTCGTTATAAAGGTTGCTTTGGTTCAATATTGATCC
ACTAGAGATGTTACAACTATTTGTTGACATCTGAGATTTGTGTGATAAGA
AAATATGAAACTGGATTTAGTGAAAGTTACAATATATAATCATACATCAT
AGATAGGAAATAAGGAAATGTCAGATATACTTGAAGAATACATCAAATAG
ACAAGGTCCTTTTTCTTATTTGTCGACTATTATAGAGCCGTACAGAACCT
TTTCACGTCTTTAGTAATTAGTACATTCTCCATTTCGGCTCTCTCTTATT
TTTTTTCCATCTCTTTTTACTTCTCCAAATAATAACAATAAAAGCTTCGA
TTTTGTGTGTGTTTGTATTTACATCTTGACATCGATATTCTTTTCATCAA
TTTTTTACCAAAAATGTAATAAAAACAAAAAAAAACCAACGCTGAACACA
GACATGGTTTCTCCATCCGTTTATATTCATCGTTTGTATGTTTACTTAAC
AACTTATTTCAAAATAGTACATATCATGGTTGTGTTTTAAAAAAAGTAT
ACAGAACAGAAAAGCACATGGTAGACAAAATAATGAAGCCAAAATTAATA
CAAAGAAGAAGTTTCAACTTGTATTTATTAACACATTTTCTTTCCTTGTC
AAAGACATGCAAATTGGTTTTGTTTTCTTATTCCCATTTTTTTTTTATAA
TAAAAAGAAGAAGAGTAAAACAAAAAAACTATCATTTCTTCTTATCGCAA
AACTCTTATCTAAGCAAGAAACCGACAAAACCTATATCTACATATATTCT
CATCAACATCTTGAGACATATTCATTTTGGTTAAAGCAAAAGATTTTAAG
AGAGAAAGGGGGAGAAGTGAGAGAGACCATTGCACTGGGATCCAACAATG
TCCTCCGACTCGTCCAAGATCAAGAGGAAGCGGAACCGCATCCCnTTAAC
GAAGGCG
```

| Promoter Expression Report # 33 |
| --- |

Promoter Tested In: *Arabidopsis thaliana*, WS ecotype
Spatial expression summary:

Flower       (M)stomata
Stem        (M)stomata
Rosette leaf   (H)stomata
Observed expression pattern: GFP expression specific to stomata of primary rosette leaves. Not detected in other organs. Not detected in T1 mature. T2 mature: Expression in guard cells of flowers and stem not observed in T1 mature. T3 seedling: Same as T2 seedling expression.

| | |
|---|---|
| Expected expression pattern: | Root and seed development |
| Selection Criteria: | Full-length cDNA clustering with ABI3 interacting protein2 |
| Gene: | Pseudo-response regulator 1; protein id: |
| GenBank: | NM_125531 *Arabidopsis thaliana* pseudo-response regulator 1, APRR1 (APRR1/TOC1 family) (At5g61380) mRNA, complete cds gi|30697520|ref|NM_125531.2|[30697520] |
| Source Promoter Organism: | *Arabidopsis thaliana*, WS |
| Vector: | pNewBin4-HAP1-GFP |
| Marker Type: | X GFP-ER |
| Generation Screened: | X T1 Mature    X T2 Seedling    X T2 Mature    X T3 Seedling |

T1 Mature Plant Expression    Organs/Tissues screened
Events Screened:    n = 5      Events Expressing:    n = 0
No GFP Expression Detected ☐ Flower         ☐ pedicel ☐ receptacle ☐ nectary ☐ sepal ☐ petal ☐ filament ☐ anther ☐ pollen ☐ carpel
                  ☐ style ☐ papillae ☐ vascular ☐ epidermis ☐ stomata ☐ trichome
☐ Silique        ☐ stigma ☐ style ☐ carpel ☐ septum ☐ placentae ☐ transmitting tissue ☐ vascular
                  ☐ epidermis ☐ stomata ☐ abscission zone ☐ ovule
☐ Ovule         Pre-fertilization: ☐ inner integument ☐ outer integument ☐ embryo sac
                  ☐ funiculus ☐ chalaza ☐ micropyle ☐ gametophyte
                  Post-fertilization: ☐ zygote ☐ inner integument ☐ outer integument ☐ seed coat
                  ☐ primordia ☐ chalaza ☐ micropyle ☐ early endosperm ☐ mature endosperm ☐ embryo
☐ Embryo      ☐ suspensor ☐ preglobular ☐ globular ☐ heart ☐ torpedo ☐ late ☐ mature ☐ provascular
                  ☐ hypophysis ☐ radicle ☐ cotyledons ☐ hypocotyl
☐ Stem         ☐ epidermis ☐ cortex ☐ vascular ☐ xylem ☐ phloem ☐ pith ☐ stomata ☐ trichome
☐ Leaf          ☐ petiole ☐ mesophyll ☐ vascular ☐ epidermis ☐ trichome ☐ primordia ☐ stomata
                  ☐ stipule ☐ margin T2 Seedling Expression    Organs/Tissues Screened
Events Screened:    n = 4      Events Expressing:    n = 2
Seedlings expressing / Seedlings screened
Event-01: No data     Event-02: No data.
GFP Expression Detected ☐ Hypocotyl               ☐ epidermis ☐ cortex ☐ vascular ☐ xylem ☐ phloem ☐ stomata
☐ Cotyledon              ☐ mesophyll ☐ vascular ☐ epidermis ☐ trichome ☐ margin ☐ stomata
X Rosette Leaf           ☐ mesophyll ☐ vascular ☐ epidermis ☐ trichome ☐ petiole ☐ primordia
                             H stomata ☐ stipule ☐ margin
☐ Primary Root          epidermis ☐ trichoblast atrichoblast ☐ cortex ☐ endodermis ☐ vascular
                             ☐ xylem ☐ phloem ☐ pericycle ☐ quiescent ☐ columella ☐ cap ☐ root hairs
☐ Lateral root             ☐ epidermis ☐ initials ☐ flanking cells ☐ vascular ☐ cap
☐ Shoot apical meristem   ☐ SAM ☐ epidermis
X in the Guard cell (Gc) in the leaf T2 Mature Plant Expression Plants expressing / Plants screened
Event-01: 0/3     Event-02: 1/1
☐ Scheduled
☐ T2 Mature tissue expressions similar to T1 expression data (data not shown).
X T2 Mature tissue expression (if different expression pattern).
☐ No expression detected
X Flower         ☐ pedicel ☐ receptacle ☐ nectary ☐ sepal ☐ petal ☐ filament ☐ anther ☐ pollen ☐ carpel
                  ☐ style ☐ papillae ☐ vascular ☐ epidermis M stomata ☐ trichome
X Stem         ☐ epidermis ☐ cortex ☐ vascular ☐ xylem ☐ phloem ☐ pith M stomata ☐ trichome
X in the Guard cell (Gc) of the leaf and stem T3 Seedling Expression Seedlings expressing / Seedlings screened
Event-01: 1/3     Event-02: 1/3
☐ Scheduled
X T3 Seedling tissue expressions similar to T2 seedling expression (data not shown).
☐ T2 Mature tissue expression (if different expression pattern).
GFP Expression Detected
Promoter utility

| | |
|---|---|
| Trait Area: | Among other uses this promoter sequence can be useful to improve: Water Use Efficiency - Drought, heat |
| Construct: | YP0025 |
| Promoter Candidate I.D: | 11768641 |
| cDNA I.D: | 12322657 (Old ID: 11005502) |
| T1 lines expressing (T2 seed): | SR00495-03,-04 |

Sequence (SEQ ID NO: 33):

```
gtcagtgaagtcgattgggtCTCACCATGAGCCAATGAAAAGAAATAGTA
ATCCAGGTGATTGTTTCTCTTTGATGTCTCACTTTCTAATAGCTAGTCTC
TAAAAGAACCTTTGTTTTAGTGAATTCTAATATAGTAGGGGTTTTTGCAG
CGCAATTTTCTTCAGCACCGAAGAAAAGTAGATTGAAGATCGGAGAGTCC
TCTGCTTTTCTTTACATATGTCAAATCTACTGTCCTTAGAACTAACGGTC
AGGATCCTCCTCTTGTCGATGGAAATGGCTCACTTCATCTTCATCGGGGT
TTGGCGGAGAAGTTTCAAGTGGTGGCTAGTGAAGGGATCAACAACACCAA
ACAAGCACGCAGAGCAACACCAAAATCTACTGTCCTTAGAACTAACGGTC
AGGATCCTCCTCTTGTCAATGGAAATGGCTCACATCATCTTTCATCGGGG
TGCGGCGGAAAAGTTTCAAGTGGTGGCTAGTGAAGGGATCAACAACACCA
AACAAGCACACAGAAGTAGAGGGACCGAGCAATACCATTCTCAAGGAGAG
ACCTTGCAGAATGGCGCCAGCTATCCACATTCCCTTGAGCGGTCACGCAC
GCTTCCCACATCAATGGAATCTCATGGTAGGAACTACCAAGAGGGCAATA
TGAATATTCCCCAAGTTGCTATGAACAGAAGTAAAGATTCGTCTCAAGTT
GATGGATCGGGTTTCTCTGCACCAAATGCCTATCCTTACTATATGCATGG
GGTCATGAACCAAGTTATGATGCAATCAGCAGCCATGATGCCTCAATATG
GTCATCAAATTCCTCATTGCCAACCAAATCATCCGAATGGAATGACGGGA
TATCCTTACTACCACCACCCAATGAACACATCTTTGCAGCATAGTCAGAT
GTCTTTACAGAATGGTCAGATGTCTATGGTTCATCATTCTTGGTCACCGG
CAGGAAATCCGCCTTCTAATGAGGTGAGGGTAAATAAACTTGACAGAAGA
GAGGAAGCTCTGCTGAAatt
```

| Promoter Expression Report # 34 |
|---|

Promoter Tested In: *Arabidopsis thaliana*, WS ecotype
Spatial expression summary:

| | |
|---|---|
| Flower | (M)sepal, (M)style, (M)epidermis |
| Stem | (M)epidermis, (H)endodermis, (H)cortex |
| Leaf | (H)mesophyll, (H)epidermis |
| Hypocotyl | (H)epidermis, (H)vascular |
| Cotyledon | (H)epidermis, (H)mesophyll |
| Primary Root | (H)epidermis, (H)trichoblast, (H)atrichoblast, (H)vascular phloem, (H)Root cap, (H)root hairs |
| Lateral root | (H)vascular, (H)cap |

Observed expression pattern: GFP expressed in sepals, style of silique in immature flowers, mesophyll, and epidermis of mature leaves. GFP expressed throughout epidermal layers of seedling including root tissue. Also expressed in mesophyll and epidermal tissue in distal primary leaf, and vasculature of root. Specific expression in meristematic zone of primary and lateral root.
T2 Mature: Same expression as T1 mature: stem expression. T3 Seedling expression: Same as T2 seedling expression.

| | |
|---|---|
| Expected expression pattern: | Shoot apical meristem |
| Selection Criteria: | Greater than 5x down in stm microarray |
| Gene: | Fructose-bisphosphate aldolase |
| GenBank: | NM_118786 *Arabidopsis thaliana* fructose-bisphosphate aldolase, putative (At4g26530) mRNA, complete cds gi\|30687252\|ref\|NM_118786.2\|[30687252] |
| Source Promoter Organism: | *Arabidopsis thaliana* WS |
| Vector: | NewBin4-HAP1-GFP |
| Marker Type: | X GFP-ER |
| Generation Screened: | X T1 Mature   X T2 Seedling   X T2 Mature   X T3 Seedling |
| T1 Mature Plant Expression | Organs/Tissues screened |
| Events Screened:   n = 5 | Events Expressing:   n = 2 |
| X Flower | ☐ pedicel ☐ receptacle ☐ nectary M sepal ☐ petal ☐ filament ☐ anther ☐ pollen ☐ carpel M style ☐ papillae ☐ vascular M epidermis ☐ stomata ☐ trichome |
| X Silique | ☐ stigma ☐ style M carpel M septum ☐ placentae ☐ transmitting tissue ☐ vascular M epidermis ☐ stomata ☐ abscission zone ☐ ovule |
| ☐ Ovule | Pre-fertilization: ☐ inner integument ☐ outer integument ☐ embryo sac ☐ funiculus ☐ chalaza ☐ micropyle ☐ gametophyte Post-fertilization: ☐ zygote ☐ inner integument ☐ outer integument ☐ seed coat ☐ primordia ☐ chalaza ☐ micropyle ☐ early endosperm ☐ mature endosperm ☐ embryo |
| ☐ Embryo | ☐ suspensor ☐ preglobular ☐ globular ☐ heart ☐ torpedo ☐ late ☐ mature ☐ provascular ☐ hypophysis ☐ radicle ☐ cotyledons ☐ hypocotyl |
| ☐ Stem | epidermis ☐ endodermis ☐ cortex ☐ vascular ☐ xylem ☐ phloem ☐ pith ☐ stomata ☐ trichome |

-continued

Promoter Expression Report # 34

X Leaf ☐ petiole H mesophyll ☐ vascular H epidermis ☐ trichome ☐ primordia ☐ stomata ☐ stipule ☐ margin
X in the Sepal (Se)
X in the Carpel (Ca) and Style (Sy) in the silique
X in the Epidermis (Ep) and Mesophyll (Me) of the leaf
T2 Seedling Expression   Organs/Tissues Screened
Events Screened:  n = 1   Events Expressing:  n = 1
Seedlings expressing /Plants screened
Event-01: No data.   Event-02: Not plated.
GFP Expression Detected
X Hypocotyl           H epidermis ☐ cortex H vascular ☐ xylem ☐ phloem ☐ stomata
X Cotyledon           H epidermis H mesophyll ☐ vascular ☐ trichome ☐ margin ☐ stomata
☐ Rosette Leaf        ☐ mesophyll ☐ vascular ☐ epidermis ☐ trichome ☐ petiole ☐ primordia ☐ stomata ☐ stipule ☐ margin
X Primary Root        H epidermis H trichoblast H atrichoblast ☐ cortex ☐ endodermis H vascular ☐ xylem H phloem ☐ pericycle ☐ quiescent ☐ columella H cap H root hairs
X Lateral root        ☐ epidermis ☐ initials ☐ flanking cells H vascular H cap
☐ Shoot apical meristem    ☐ SAM ☐ epidermis
X in the Epidermis (Ep), Root hair (Rh), Root (Rt) and Vasculature (Vs) of the hypocotyl root zone
X in the Epidermis (Ep) and Vasculature (Vs) of the hypocotyl
X in the Epidermis (Ep) and Mesophyll (Me) in the cotyledon
X in the Guard cell (Gc), Epidermis (Ep) and Mesophyll (Me) in the primary leaf
X in the Epidermis (Ep), Cortex (Cr) and Phloem (Ph) in the lateral root
X in the lateral root tip
X in the primary Root cap (Rc),
T2 Mature Plant Expression Plants expressing / Plants screened
Event-01: 1/1   Event-02: 0/5
☐ Scheduled
X T2 Mature tissue expressions similar to T1 expression data
☐ T2 Mature tissue expression (if different expression pattern).
Expression detected
X Flower    ☐ pedicel ☐ receptacle ☐ nectary M sepal ☐ petal ☐ filament ☐ anther ☐ pollen ☐ carpel M style ☐ papillae ☐ vascular M epidermis ☐ stomata ☐ trichome
X Silique   ☐ stigma ☐ style M carpel M septum ☐ placentae ☐ transmitting tissue ☐ vascular M epidermis ☐ stomata ☐ abscission zone ☐ ovule
☐ Ovule     Pre-fertilization: ☐ inner integument ☐ outer integument ☐ embryo sac ☐ funiculus ☐ chalaza ☐ micropyle ☐ gametophyte
            Post-fertilization: ☐ zygote ☐ inner integument ☐ outer integument ☐ seed coat ☐ primordia ☐ chalaza ☐ micropyle ☐ early endosperm ☐ mature endosperm ☐ embryo
☐ Embryo    ☐ suspensor ☐ preglobular ☐ globular ☐ heart ☐ torpedo ☐ late ☐ mature ☐ provascular ☐ hypophysis ☐ radicle ☐ cotyledons ☐ hypocotyl
X Stem      M epidermis H endodermis H cortex ☐ vascular ☐ xylem ☐ phloem ☐ pith ☐ stomata ☐ trichome
X in the immature flower, the sepal and the silique pedicle
X in the Cortex (Cr), Endodermis (Ed) and Epidermis (Ep) in the stem
T3 Seedling Expression Seedlings expressing / Seedlings screened
Event-01: 0/3   Event-02: 1/3
☐ Scheduled
X T3 Seedling tissue expressions similar to T2 seedling expression
☐ T2 Mature tissue expression (if different expression pattern).
GFP Expression Detected
X in the root
X in the Epidermis (Ep) of the cotyledon
X in the rosette leaf
X in the root cap
Promoter utility Trait - Sub-trait Area:   Among other uses this promoter sequence is useful to improve:
                          PG & D - Plant size, growth rate, plant development
                          Water use efficiency -
Construct:                YP0050
Promoter Candidate I.D:   13148170 (Old ID:11768794)
cDNA I.D:                 4909806 (Old IDs: 12340148, 1017738)
T1 lines expressing (T2 seed):  SR00543-01,-02

Sequence (SEQ ID NO: 34):

aatctgatctctagtccagtcgattggtaCTTGAGGGAAACATCATATTT

TTAAACCTTGTCTCAGTAAGCTAACACACACCCCTTGTGATTACTTATCC

ATGTTTATCCACAAGAATGCAGTTGGATTGAGATATTTTCTTCTTTGTTG

AAATCAGGCCTCAAGGTGTTCATGTGGTCTGCAAAAAAATTCCCAAAAAT

AAAGATAGTGACATCTGAAATCGATAATGGATTAGACGAAGAGTTTCGTG

TTATTCCTTGGTATGGGCGGGTTTGGGGACAGATATTTTGGCACAGACGA

GGACTAGGCCACTGTGGTCCTGCAGCATTAGGTGTCCCTTCCATGTCCTG

CATTACATTTTATTGATGGATTCATCACCCTATCTACTACAACGGCTACA

CAAACTATGAAGAGTTTTGTTTACTAATAAATGCCCAAGTGAGGGTCGA

TCGAACCCGGGACACGTTTTTCAGTTTTACCATATAGAATTATCCTTGGA

ACCCTTGATACTCCATAGAACATCACCACCTCTGTTGTCATCTCAGGAAT

CCAGGTTCAAACCTAGTCTCTCTCTCCCTAGTGGGAGGTATATGGCCACT

GGGCCAATGATGACAAAATGCAAAAAAAATAAAATACATTTGGGTTCATT

ATCTAAAATATCTTGTGTTTGTAAGTTTTGGTTGCACACTCGTGTGGTTG

AAGTGTGTGTGAGAGGTACTATACAATACACTCTGCTTTTGTTTTGTACC

TATCTCTTTCTCTTCTCCACATATCCAAGACTTTGGGGATAAAGCTGAGA

TCATTGGTTGCCATTTGGTTGTGTAGAAGCAATCACCCATTTGCTTTATC

CGAGGTTGATAAATTTCCTCGGGTTCTCCTTCTGACACGTATGACAAATT

CTAATAGTATATTCCTCGTAGATATTACCTATATATTCTCAATAGTTGCA

GGTACTTAAGGCTTTGTCTTGGCATCCTCGTCCTCTTCAGCAAAACTCGT

CTCTCTTGCACTCCAAAAAGCAa

| Promoter Expression Report # 35 | |
|---|---|
| Promoter Tested In: *Arabidopsis thaliana*, WS ecotype | |
| Spatial expression summary: | |
| Flower | (H)pedicel, (H)anther, (H)pollen, (H)vascular, (H)epidermis |
| Stem | (H)cortex, (L)vascular |
| Hypocotyl | (H)epidermis, (H)vascular, (H)phloem |
| Cotyledon | (H)vascular |
| Primary Root | (H)vascular, (H)phloem, (H)pericycle |
| Observed expression pattern: High GFP expression throughout seedling vasculature including root. Low Expression at the base of hypocotyls. Not detected in rosette leaves. T1 mature: No expression observed. T3 seedling: Same as T2 seedling expression. T2 mature: Strong vascular and epidermal expression in floral pedicels and in developing pollen sacs of anthers. | |
| Expected expression pattern: xylem parenchyma cells of roots and leaves and in the root pericycles and leaf phloem. | |
| Selection Criteria: *Arabidopsis* public; The roles of three functional sulfate transporters involved in uptake and translocation of sulfate in *Arabidopsis thaliana*. Plant J. 2000 23:171–82 | |
| Gene: | Sulfate transport |
| GenBank: | NM_121056 *Arabidopsis thaliana* sulfate transporter (At5g10180) mRNA, complete cds<br>gi\|30683048\|ref\|NM_121056.2\|[30683048] |
| Source Promoter Organism: | *Arabidopsis thaliana* WS |
| Vector: | pNewBin4-HAP1-GFP |
| Marker Type: | X GFP-ER |
| Generation Screened: | X T1 Mature  X T2 Seedling  X T2 Mature  X T3 Seedling |
| T1 Mature Plant Expression | Organs/Tissues screened |
| Events Screened:   n = 3 | Events Expressing:   n = 0 |
| No GFP Expression Detected | |
| ☐ Flower | ☐ pedicel ☐ receptacle ☐ nectary ☐ sepal ☐ petal ☐ filament ☐ anther ☐ pollen ☐ carpel<br>☐ style ☐ papillae ☐ vascular ☐ epidermis ☐ stomata ☐ trichome |
| ☐ Silique | ☐ stigma ☐ style ☐ carpel ☐ septum ☐ placentae ☐ transmitting tissue ☐ vascular<br>☐ epidermis ☐ stomata ☐ abscission zone ☐ ovule |
| ☐ Ovule | Pre-fertilization: ☐ inner integument ☐ outer integument ☐ embryo sac<br>☐ funiculus ☐ chalaza ☐ micropyle ☐ gametophyte<br>Post-fertilization: ☐ zygote ☐ inner integument ☐ outer integument ☐ seed coat<br>☐ primordia ☐ chalaza ☐ micropyle ☐ early endosperm ☐ mature endosperm ☐ embryo |
| ☐ Embryo | ☐ suspensor ☐ preglobular ☐ globular ☐ heart ☐ torpedo ☐ late ☐ mature ☐ provascular<br>☐ hypophysis ☐ radicle ☐ cotyledons ☐ hypocotyl |
| ☐ Stem | ☐ epidermis ☐ cortex ☐ vascular ☐ xylem ☐ phloem ☐ pith ☐ stomata ☐ trichome |
| ☐ Leaf | ☐ petiole ☐ mesophyll ☐ vascular ☐ epidermis ☐ trichome ☐ primordia ☐ stomata<br>☐ stipule ☐ margin |
| T2 Seedling Expression | Organs/Tissues Screened |
| Events Screened:   n = 3 | Events Expressing:   n = 2 |

Promoter Expression Report # 35

Seedlings expressing / Seedlings screened
Event-01: No data.    Event-02: No data.
GFP Expression Detected
X Hypocotyl              H epidermis ☐ cortex H vascular ☐ xylem H phloem ☐ stomata
X Cotyledon              ☐ mesophyll H vascular ☐ epidermis ☐ trichome ☐ margin ☐ stomata
☐ Rosette Leaf           ☐ mesophyll ☐ vascular ☐ epidermis ☐ trichome ☐ petiole ☐ primordia
                         ☐ stomata ☐ stipule ☐ margin
X Primary Root           ☐ epidermis ☐ trichoblast atrichoblast ☐ cortex ☐ endodermis
                         H vascular ☐ xylem H phloem H pericycle ☐ quiescent ☐ columella
                         ☐ cap ☐ root hairs
☐ Lateral root           ☐ epidermis ☐ initials ☐ flanking cells ☐ vascular ☐ cap
☐ Shoot apical meristem  ☐ SAM ☐ epidermis
X in the Phloem (Ph) and Epidermis (Ep) of the hypocotyl
X in the Phloem (Ph) of the hypocotyl root zone
X in the Phloem (Ph) of the petiole, cotyledon and root
X in the Pericycle (Pr) of the root
T2 Mature Plant Expression Plants expressing / Plants screened
Event-01: Not screened.    Event-02: 1/5
☐ Scheduled
☐ T2 Mature tissue expressions similar to T1 expression data (data not shown).
X T2 Mature tissue expression (if different expression pattern).
Expression detected
X Flower     H pedicel ☐ receptacle ☐ nectary ☐ sepal ☐ petal ☐ filament H anther H pollen
             ☐ carpel ☐ style ☐ papillae H vascular H epidermis ☐ stomata ☐ trichome
X Stem       ☐ epidermis H cortex L vascular ☐ xylem ☐ phloem ☐ pith ☐ stomata ☐ trichome
X in the Epidermis (Ep) and Vasculature(Vs) of the inflorescence meristem
X in the Pollen (Po)
X in the Epidermis (Ep), Guard cell (Gc) and Cortex (Cr) of the stem
T3 Seedling Expression Seedlings expressing / Seedlings screened
Event-01: Not screened.    Event-02: 1/3
☐ Scheduled
X T3 Seedling tissue expressions similar to T2 seedling expression.
☐ T2 Mature tissue expression (if different expression pattern).
GFP Expression Detected
Promoter utility Trait Area:    Among other uses this promoter sequence is useful to improve:
               Water use efficiency -
               Nutrient - nitrogen use, Nutrient efficiency
               Plant Growth and Development - growth rate
Utility:       Useful for root nutrient uptake and metabolism manipulation
Construct:              YP0040
Promoter Candidate ID:  11768649
cDNA I.D:               12670159 (Old ID: 11020088)
T1 lines expressing (T2 seed): SR00588-01,-02,-03

Sequence (SEQ ID NO: 35):

```
CCCATCACATGTAACATCATTGGGCTATCCAAAAGTCTAACCAATAATGT
CAATCTATAAACCACATTAAGTAGTTCATTTTTTTTGTAGTCGTGTTTAG
CTTGTTAAACCTCATAAAATATGTTTTCACTTACGTTAACAAAACAAATA
TCTTCACGAAAAAAAATAAAATAAAATATCTTTTTGATACCGAAAAAATA
AAATAAAATAAAATAATTTTTCCCTTTCGATCATAAAATGCGTAGATAAG
AGAAACTGTGTTTGAGGCTCCATTTCATGTTCACCTACCAGTCTACCACG
TCATTTCTCAAAGACGCAAATTTTCTAATTAGGGATGTGCTCTTTTTACA
TATAGATCAATATCCTAAAAAAATTTTAAGATATTCATATTTTCGTACAT
ATATATCGAGTTTCCCGAAAAATCCATAAAAAGGGTATAATGATAGTCCT
TTTTCTCCTTTAATAATAATTTCTGAACAAAATTATATCATAATAAACTT
GTGATTTTATACAAAATTTATTTGTATATATAATTTTACTAAACAACGTG
AACGATAAAAATAATATTCTCATAAAATGTTGATTAAAAATTACTTAAAA
TAAATAATTATTTAGGATTATGTATTAGTAGTACTCGAACCATTTTTTTA
GTTATATCTGCATGAAGACCCTAATTTTTCACATATATCGAAACTAAAAC
TTTGGATATACACTGTAATTTGAAAACGCTTGGAACGGATAATGTAGTTA
CCTCACAAGATTTTGTACATCCCTGACATTTTATATTCATTAAAGTGTTT
TTTTCTTCAGAAAAGAAAACACTTTTTCTTTTTTTAGTAGTACTCGAACC
ATTTTTTTAGTTATCTGCATGAAGACCCTAATTTTTCACATATATCGAAA
CTAAAACTTTGGATATACACTGTAATTTGAAAACGCTTGGAACGGATAAT
GTAGTTACCTCACAAGATTTTGTACATCCCTGACATTTTATATTCATTAA
AGTGTGTTTTTTCTTCAGAAAAGAAAACACTTTTTCTTTTTGTGCTTTT
AGTTTTAAATTAACAAAAAAATGGACACCATGAGATTCCACTAACTCATG
```

-continued

```
TGTATATAACATTAGGGAAGCAGTCAATTCATTTCAGCATCCACACACAC

TTTGAATGCTCAATCAAAGCTTCTTCATAGTTAAACTTCCTCACAACGTC
```

-continued

```
AAAACTCGAGAAGAAGACCATTGCACTGGGATCCAACAATGTCCTCCGAC

TCGTCCAAGATCAAGAGGAAGCGGAACCGCATCCCTTTTnAACGAAGGCG
```

| Promoter Expression Report # 36 |
|---|

Promoter Tested In: *Arabidopsis thaliana*, WS ecotype
Spatial expression summary:

| | |
|---|---|
| Flower | (M)stomata |
| Silique | (M)vascular, (L)stomata |
| Stem | (H)stomata |
| Cotyledon | (M)stomata |
| Rosette Leaf | (M)stomata, (M)petiole |

Observed expression pattern: Stomata specific expression in T2 seedling leaves. Screened under non-induced condition. T1 mature, T2 mature, T3 seedlings: Expressed in guard cells.
Note: Promoter lines up to YP0060 were screened for expression in the expected target tissue only. Expression patterns in these lines may be found coincidentally. YP0060 and later promoter lines were screened for expression in all aerial tissues. This line was re-screened in newly selected T1 mature plants.
Expected expression pattern: Expression found predominantly in a very small number of cells immediately adjacent to the xylem in all organs. Strong expression was observed in pollen grains. Down-regulated by light.
Selection Criteria: *Arabidopsis* public; *Arabidopsis* actin-related protein 2 (AtARP2) promoter directs expression in xylem precursor cells and pollen. Plant Mol Biol. 1999 41:65–73

| | |
|---|---|
| Gene: | *Arabidopsis* actin-related protein 2 (AtARP2) |
| GenBank: | NM_113613 *Arabidopsis thaliana* expressed protein (At3g26990) mRNA, complete cds<br>gi\|30688587\|ref\|NM_113613.2\|[30688587] |
| Source Promoter Organism: | *Arabidopsis thaliana* WS |
| Vector: | pNewBin4-HAP1-GFP |
| Marker Type: | X GFP-ER |
| Generation Screened: | X T1 Mature  X T2 Seedling  X T2 Mature  X T3 Seedling |

T1 Mature Plant Expression    Organs/Tissues screened
Events Screened:   n = 5    Events Expressing:   n = 0 (old protocol)
No GFP Expression Detected
Events Screened:   n = 7    Events Expressing:   n = 3 (new protocol)
GFP Expression Detected

| | |
|---|---|
| X Flower | ☐ pedicel ☐ receptacle ☐ nectary ☐ sepal ☐ petal ☐ filament ☐ anther ☐ pollen ☐ carpel<br>☐ style ☐ papillae ☐ vascular ☐ epidermis M stomata ☐ trichome |
| X Silique | ☐ stigma ☐ style ☐ carpel ☐ septum ☐ placentae ☐ transmitting tissue M vascular<br>☐ epidermis L stomata ☐ abscission zone ☐ ovule |
| ☐ Ovule | Pre-fertilization: ☐ inner integument ☐ outer integument ☐ embryo sac<br>☐ funiculus ☐ chalaza ☐ micropyle ☐ gametophyte<br>Post-fertilization: ☐ zygote ☐ inner integument ☐ outer integument ☐ seed coat<br>☐ primordia ☐ chalaza ☐ micropyle ☐ early endosperm ☐ mature endosperm ☐ embryo |
| ☐ Embryo | ☐ suspensor ☐ preglobular ☐ globular ☐ heart ☐ torpedo ☐ late ☐ mature ☐ provascular<br>☐ hypophysis ☐ radicle ☐ cotyledons ☐ hypocotyl |
| X Stem | ☐ epidermis ☐ cortex ☐ vascular ☐ xylem ☐ phloem ☐ pith H stomata ☐ trichome |
| ☐ Leaf | ☐ petiole ☐ mesophyll ☐ vascular ☐ epidermis ☐ trichome ☐ primordia ☐ stomata<br>☐ stipule ☐ margin |

X in the vasculature Vs and Guard Cells Gc of the tem and flower
T2 Seedling Expression    Organs/Tissues Screened
Events Screened:   n = 2    Events Expressing:   n = 2
Seedlings expressing / Seedlings screened
Event-01: No data    Event-02: No data
GFP Expression Detected

| | |
|---|---|
| ☐ Hypocotyl | ☐ epidermis ☐ cortex ☐ vascular ☐ xylem ☐ phloem ☐ stomata |
| X Cotyledon | ☐ mesophyll ☐ vascular ☐ epidermis ☐ trichome ☐ margin M stomata |
| X Rosette Leaf | ☐ mesophyll ☐ vascular ☐ epidermis ☐ trichome M petiole ☐ primordia<br>M stomata ☐ stipule ☐ margin |
| ☐ Primary Root | ☐ epidermis ☐ trichoblast atrichoblast ☐ cortex ☐ endodermis ☐ vascular<br>☐ xylem ☐ phloem ☐ pericycle ☐ quiescent ☐ columella ☐ cap ☐ root hairs |
| ☐ Lateral root | ☐ epidermis ☐ initials ☐ flanking cells ☐ vascular ☐ cap |
| ☐ Shoot apical meristem | ☐ SAM ☐ epidermis |

X in the Guard cell (Gc) of the petiole, cotyledon and leaf
T2 Mature Plant Expression Plants expressing / Plants screened
Event-01: 1/1    Event-02: 1/2
☐ Scheduled
☐ T2 Mature tissue expressions similar to T1 expression data (data not shown).
X T2 Mature tissue expression (if different expression pattern).

| | |
|---|---|
| X Flower | ☐ pedicel ☐ receptacle ☐ nectary ☐ sepal ☐ petal ☐ filament ☐ anther ☐ pollen<br>☐ carpel ☐ style ☐ papillae ☐ vascular ☐ epidermis H stomata ☐ trichome<br>☐ silique |

Promoter Expression Report # 36

X Silique    ☐ stigma ☐ style ☐ carpel ☐ septum ☐ placentae ☐ transmitting tissue
                M vascular ☐ epidermis L stomata ☐ abscission zone ☐ ovule
X Stem      ☐ epidermis ☐ cortex ☐ vascular ☐ xylem ☐ phloem ☐ pith H stomata
                ☐ trichome
X in the developing flower and pedicle
T3 Seedling Expression Seedlings expressing / Seedlings screened
Event-01: 1/3     Event-02: 2/3
☐ Scheduled
X T3 Seedling tissue expressions similar to T2 seedling expression (data not shown).
☐ T2 Mature tissue expression (if different expression pattern).
Promoter utility Trait Area:    Among other uses this promoter sequence is useful to improve:
               Water use efficiency - Water potential, drought, moisture stress at seed set and seed
               fill, water use efficiency, ovule/seed abortion, Seed Yield
Utility:        Regulate transpiration during water stress
Construct:     YP0041
Promoter Candidate I.D:     13148154 (Old ID: 11768621)
cDNA I.D:                  12717822 (Old ID: 4962959, 12735348)
T1 lines expressing (T2 seed):    SR00537-01,-02

Sequence (SEQ ID NO: 36):

gggaTGCGGTTCCGCTTCCTCTTGATCTTTGGACGAGTCGGAGGACATTG

TTGGATCCCAGTGCAATGGTGCAACATCGAATCCAAATTCTCTTAACATC

ATAACACAGACTAAAATTTCAGGCTTTCGTGTTAAAAGAGAGAATATCAT

TGAACTTTTTCTCTTACCTTCATGATTCCTGCAAGAACAGCACCTCCGAG

GTATACCATGTGTTTCCTTCTCGGTGGATCTTCGATCCGCAATCTGAGTT

TCTGATTGATAAGAAAAACGAAGATAAATGTTAAAAGCTGAGCTAATGAC

TGACAGTGATCATGGCATTATCAGAATTATCTTTTTTACCTTCAAGCCAT

CTTTGTTTCCTTTTAGAACTGTGTCGAGATACCGATCCTGTATTTCTTTC

TCAAGACTAGAAACAAACAGAGAATAAAAGACATTGAAACATAAAACAAT

GGAACTTCTTGCTGGGTTTATGATAAACAAAAAATATACGAACCGGCTAG

GTAATCCTGGGTACATGGTGCTACCTCCGCTTAAAACTATGTGTTGGTAG

AGCTGTGAAAAAAGAGCAAAGGGTTTAAGACAGATACATGATtagttttg tTGGATCTGTCTTTGAAATACCAAGCAAGCGTAAGAGTCACACGTACCAT CATGcggttatcaatatccatttcttgaatacatcggaaaaccatgtctg ccattccatcaccttcaacatcaatgagttcctgaaaaaatatttggttg tgatcagcctcgagattcttggagggttgaaactattccaaaagagaaat tagcagaggacgcgatgaggtttaccggagtaaaaagcgcttcaggtgct tggaatctttcagtgcctactttgataaccctcccatctggaagctgatc acagttcaaaaacacaacgggttagtactctggaaaaaaaataatttggt gataatatcagctttagaggctgcaactggcacaagtatgaaactttatc gactatcggatgaaaaatcccaa

Promoter Expression Report # 37

Promoter Tested In: *Arabidopsis thaliana*, WS ecotype
Spatial expression summary:

Flower           (L)pedicel, (L)stomata
Stem             (L)stomata
Leaf              (L)vascular, (L)stomata
Cotyledon       (H)mesophyll, (H)vascular, (H)epidermis
Primary Root    (H)root hairs
Observed expression pattern: Low GFP expression in stomatal cells of stem, pedicels, and vasculature of leaves
in mature plants. High GFP expression in root hairs, epidermis and mesophyll cells of seedling cotyledon. Not
seen in rosette leaves.
T2 mature: Same as T1 mature expression.
T3 seedling: Same as T2 seedling expression.
Expected expression pattern:    Constitutively expressed in all green tissues

-continued

Promoter Expression Report # 37

| | |
|---|---|
| Selection Criteria: | *Arabidopsis* microarray |
| Gene: | Expressed protein [*Arabidopsis thaliana*] |
| GenBank: | NM_119524 *Arabidopsis thaliana* expressed protein (At4g33666) mRNA, complete cds gi\|30689773\|ref\|NM_119524.2\|[30689773] |
| Source Promoter Organism: | *Arabidopsis thaliana* WS |
| Vector: | pNewBin4-HAP1-GFP |
| Marker Type: | X GFP-ER |
| Generation Screened: | X T1 Mature   X T2 Seedling   X T2 Mature   X T3 Seedling |
| T1 Mature Plant Expression | Organs/Tissues screened |
| Events Screened:   n = 3 | Events Expressing:   n = 2 |
| X Flower | L pedicel ☐ receptacle ☐ nectary ☐ sepal ☐ petal ☐ filament ☐ anther ☐ pollen ☐ carpel ☐ style ☐ papillae ☐ vascular ☐ epidermis L stomata ☐ trichome |
| ☐ Silique | ☐ stigma ☐ style ☐ carpel ☐ septum ☐ placentae ☐ transmitting tissue ☐ vascular ☐ epidermis ☐ stomata ☐ abscission zone ☐ ovule |
| ☐ Ovule | Pre-fertilization: ☐ inner integument ☐ outer integument ☐ embryo sac ☐ funiculus ☐ chalaza ☐ micropyle ☐ gametophyte |
| | Post-fertilization: ☐ zygote ☐ inner integument ☐ outer integument ☐ seed coat ☐ primordia ☐ chalaza ☐ micropyle ☐ early endosperm ☐ mature endosperm ☐ embryo |
| ☐ Embryo | ☐ suspensor ☐ preglobular ☐ globular ☐ heart ☐ torpedo ☐ late ☐ mature ☐ provascular ☐ hypophysis ☐ radicle ☐ cotyledons ☐ hypocotyl |
| X Stem | ☐ epidermis ☐ cortex ☐ vascular ☐ xylem ☐ phloem ☐ pith L stomata ☐ trichome |
| X Leaf | ☐ petiole ☐ mesophyll L vascular ☐ epidermis ☐ trichome ☐ primordia L stomata ☐ stipule ☐ margin |

X in the Guard cell (Gc) of the stem and pedicel
X in the Vascular (Vs) of the leaf
T2 Seedling Expression    Organs/Tissues Screened
Events Screened:   n = 2    Events Expressing:    n = 1
Seedlings expressing / Seedlings screened
Event-01: 1/3    Event-02: 0/10
GFP Expression Detected

| | |
|---|---|
| ☐ Hypocotyl | ☐ epidermis ☐ cortex ☐ vascular ☐ xylem ☐ phloem ☐ stomata |
| X Cotyledon | H mesophyll H vascular H epidermis ☐ trichome ☐ margin ☐ stomata |
| ☐ Rosette Leaf | ☐ mesophyll ☐ vascular ☐ epidermis ☐ trichome ☐ petiole ☐ primordia ☐ stomata ☐ stipule ☐ margin |
| X Primary Root | epidermis ☐ trichoblast atrichoblast ☐ cortex ☐ endodermis ☐ vascular ☐ xylem ☐ phloem ☐ pericycle ☐ quiescent ☐ columella ☐ cap H root hairs |
| ☐ Lateral root | ☐ epidermis ☐ initials ☐ flanking cells ☐ vascular ☐ cap |
| ☐ Shoot apical meristem | ☐ SAM ☐ epidermis |

X in the Root hair (Rh) of the hypocotyl
X in the Epidermis (Ep) and Mesophyll (Me) of the cotyledon
X in the Vasculature (Vs) of the cotyledon
T2 Mature Plant Expression Plants expressing / Plants screened
Event-01: 1/1    Event-02: 0/3
☐ Scheduled
X T2 Mature tissue expressions similar to T1 expression data.
☐ T2 Mature tissue expression (if different expression pattern).
No expression detected
X in the inflorescence meristem
T3 Seedling Expression
Seedlings expressing / Seedlings screened
Event-01: 1/3 Strong    Event-02: 1/3 Very weak
☐ Scheduled
X T3 Seedling tissue expressions similar to T2 seedling expression.
☐ T2 Mature tissue expression (if different expression pattern).
☐ No GFP Expression Detected
X in the Cotyledon (Co) and Root hair (Rh)
Promoter utility

| | |
|---|---|
| Trait Area: | Among other uses this promoter sequence is useful to improve: PG & D |
| Sub-trait Area: | Plant size, growth rate, stay green, |
| Utility: | Useful for C/N partitioning, photosynthetic efficiency, source enhancement and seedling establishment |
| Construct: | YP0056 |
| Promoter Candidate I.D: | 11768645 |
| cDNA I.D: | 12396394 (Old ID: 7083850) |
| T1 lines expressing (T2 seed): | SR00550-01 |

Sequence (SEQ ID NO: 37):

ATAGGAATCTGCTTCGGTAGAAGATTCGAGAGAGGAGAGGAAGCATCGGT

GGTTTTGGAGTTCCTTATTCTTCTCTTCTTTCCAAAGTTTTGTCATTCGC

CAAGATTCCTTAAAAACTTGTTCACACATCATAATTATGCACCAATAGGT

TATAAATCATAATCCAACAAGTTAGTCATTGGCTTTAATTTTAAAAAATC

CCATAAGAGTAAAATCTTTTAGAAAGTTAATCAACCCACACATGGGCTAG

AAAACCAAAAACCCCACGAACATTGAGATTACAAGAAACATTTTTAAGTC

CTAAATGAGCCCAAGAGCATTGCTTAATGAAGAAGAACTGATATTAATTA

ACTAATATTAGGACACATAAAAAAATACGAAAACACCAATCTTCATGCCA

CAAAATCAAACAAAAACGAAAAAATCAATTTTCATGAAATGGATAAAGAG

AGAGCGTAATTATCAGGAATTTGATTGAGTACGGTTGTTATGATGATCAT

TCACAATTATCTTTGATCTTGAGATTTAGCAATAGTTAATTTTCGGATGT

TTTTTTGTTACTTGCTGCTCACTTCTTGTATGCAGATTAATTTATAAGAG

AGACCAGTTACAACTCTTTCTTATTTGAATAAGATTTTATAAGATGTAGT

GTGGCCATGTGGGTTTATTGCATGCAGCTCTCTGCGTTGGTCCCAAGTCC

ACGACAATAGAGAGTTTTCTGCACTTCACGGTATCGTCGTCGTCACAAGT

TCTTTACCTTATCATTGGCACAAGTTAGCCACCGTCTTTGCGCAAGTTAG

CATGTTGTGCTACATACGTGTCATGAACTGATTGGTCAAATTTGGATATA

TTTTATTCCCGTCGGTTATGTTTGGATAAAAATATAAAACGGAAATTTCT

GTTTCAGCCTTCCTTGGTCCCAAAGAAAAATACGCACACCTACTCCCTTC

ATTCTCTATCCTCTCCACTCATAATATATACATCTAAATGCAATCTCTCC

| Promoter Expression Report # 38 | |
|---|---|
| Promoter Tested In: | *Arabidopsis thaliana*, WS ecotype |

Spatial expression summary:

Primary root   (H)root hairs
Observed expression pattern: GFP expression specific to epidermal root hairs at hypocotyl root transition zone.
This line was not screened in T2 mature and T3 seedlings.

| | |
|---|---|
| Expected expression pattern: | Shoot apical meristem |
| Selection Criteria: | Greater than 5x down in stm microarray |
| Gene: | hypothetical protein |
| GenBank: | NM_118575 *Arabidopsis thaliana* RNA recognition motif (RRM)-containing protein (At4g24420) mRNA, complete cds gi\|18416342\|ref\|NM_118575.1\|[18416342] |
| Source Promoter Organism: | *Arabidopsis thaliana* WS |
| Vector: | pNewBin4-HAP1-GFP |
| Marker Type: | X GFP-ER |
| Generation Screened: | X T1 Mature   X T2 Seedling   T2 Mature   T3 Seedling |
| T1 Mature Plant Expression | Organs/Tissues screened |
| Events Screened:   n = 3 | Events Expressing:   n = 0 |

No GFP Expression Detected
☐ Flower       ☐ pedicel ☐ receptacle ☐ nectary ☐ sepal ☐ petal ☐ filament ☐ anther ☐ pollen ☐ carpel
               ☐ style ☐ papillae ☐ vascular ☐ epidermis ☐ stomata ☐ trichome
☐ Silique      ☐ stigma ☐ style ☐ carpel ☐ septum ☐ placentae ☐ transmitting tissue ☐ vascular
               ☐ epidermis ☐ stomata ☐ abscission zone ☐ ovule
☐ Ovule        Pre-fertilization: ☐ inner integument ☐ outer integument ☐ embryo sac
               ☐ funiculus ☐ chalaza ☐ micropyle ☐ gametophyte
               Post-fertilization: ☐ zygote ☐ inner integument ☐ outer integument ☐ seed coat
               ☐ primordia ☐ chalaza ☐ micropyle ☐ early endosperm ☐ mature endosperm ☐ embryo
☐ Embryo       ☐ suspensor ☐ preglobular ☐ globular ☐ heart ☐ torpedo ☐ late ☐ mature ☐ provascular
               ☐ hypophysis ☐ radicle ☐ cotyledons ☐ hypocotyl
☐ Stem         ☐ epidermis ☐ cortex ☐ vascular ☐ xylem ☐ phloem ☐ pith ☐ stomata ☐ trichome
☐ Leaf         ☐ petiole ☐ mesophyll ☐ vascular ☐ epidermis ☐ trichome ☐ primordia ☐ stomata
               ☐ stipule ☐ margin T2 Seedling Expression       Organs/Tissues Screened
Events Screened:   n = 2       Events Expressing:   n = 2
Seedlings expressing / Seedlings screened
Event-01: 2/3
Event-02: 1/3
GFP Expression Detected
☐ Hypocotyl          ☐ epidermis ☐ cortex ☐ vascular ☐ xylem ☐ phloem ☐ stomata
☐ Cotyledon          ☐ mesophyll ☐ vascular ☐ epidermis ☐ trichome ☐ margin ☐ stomata
☐ Rosette Leaf       ☐ mesophyll ☐ vascular ☐ epidermis ☐ trichome ☐ petiole ☐ primordia
                     ☐ stomata ☐ stipule ☐ margin

Promoter Expression Report # 38

X Primary Root  □ epidermis □ trichoblast atrichoblast □ cortex □ endodermis □ vascular
 □ xylem □ phloem □ pericycle □ quiescent □ columella □ cap H root hairs
□ Lateral root  □ epidermis □ initials □ flanking cells □ vascular □ cap
□ Shoot apical meristem  □ SAM □ epidermis
X in the collet root hairs only of the hypocotyl root zone
T2 Mature Plant Expression Plants expressing / Plants screened
Event-01: N/A   Event-02: N/A
□ Scheduled
□ T2 Mature tissue expressions similar to T1 expression data (data not shown).
□ T2 Mature tissue expression (if different expression pattern.)
Expression detected
T3 Seedling Expression Seedlings expressing / Seedlings screened
Event-01: N/A   Event-02: N/A
□ Scheduled
□ T3 Seedling tissue expressions similar to T2 seedling expression (data not shown).
□ T2 Mature tissue expression (if different expression pattern).
GFP Expression Detected
Promoter utility

| | |
|---|---|
| Trait Area: | Among other uses this promoter sequence is useful to improve: Water use efficiency; Nutrient |
| Sub-trait Area: | Plant size, growth rate, drought, water use efficiency, nitrogen utilization |
| Utility: | early establishment of Rhizobium infection by increasing expression of elicitors |
| Construct: | YP0068 |
| Promoter Candidate ID: | 11768798 |
| cDNA I.D: | 12678173 (Old ID: 1022896) |
| T1 lines expressing (T2 seed): | SR00598-01,-02 |

Sequence (SEQ ID NO: 38):

```
AAATTGGGGAGTGGGGAGATGTTTGGTTATATTCCCTTCTCATCGATGGT
CTAGATGTGCGAGGTGACTCTCATGGAGGTAAAGAACAATGGTGATTTTG
TGAAGAACCCAACGTAATGGTAATTCCTAAAAAGGTTTAGAAGTTTTTC
AGCTTGTTGTATTGCTAAAATGGGGTTGATGTACTCAACGACATCCAAGT
GTACTTGAGTGAGCTTTTTTGGGGTTGAGTACCTCGACCCATTATTCAAA
CTAATGTAAATGGTGAATGCAGCAGTGACTTTGTTGCCTTTTGCAAGAAC
TAAAGAAGACAGAAACAGGTTGTAAAAGAGAGCCAAGTGTGTGTTTATGG
TAGAAAGAGCAAAGTGAACGAAAGGTGTACCTTTTTGACTTGTTGTCACT
GGTTTTCTCCCACTTCATCCGTTTCATGCTGCATCAGAAAACAACATAAG
AAATGAATGACGTAACGCGAAGCATTAGGAGTTGCTTGTAAATTAATACA
TTGCCATTACTAACGTAATTCAGTAGATTCTAACTACAAATGAAGTCAAT
GTATCTATCTGTCTACTTTAGCCAATGTATGATAAGACCAAATAGTCTTC
TCTTTTTTCAGAAACTCTCTAGGATTAAAAAGTTTGTGGGTGAAAGAAAT
ATTATCGTGTGGATGATAAGAATAATTGATCTTGTGTTAGTAAATTAGGA
ATAGATATACAAGTAGGTTTCTCTCTAAATAAAAAATAAAAGAGTTTAAA
TTGCATGCGTATAAAAGAAAAAAGTAAGAAGAAAATATGTTCCGGTTAAT
GGTTGGGTGCATCCGAATCGAACCGGCGCAAACCAAAAAATCTAAAGGAG
ATTTGAGGTGATAAAAGGAAATCAGACATTGAACCAAAAAAACAAAAGCG
AGACGGTGGAAAGAAAAAACTGGAAAAGACAGTTTTAGCCCCTCCTAAAA
GCAAAGAAAAAAAAGATAATAAATAGCTTCGTCGTCGTGATCGACCTCTG
CCATTGCACTGGGATCCAACAATGTCCTCCGACTCGTCCAAGATCAAGAG
GAAGCGGAACCGCATCCCGTTAAACGAAGGC
```

Promoter Expression Report #39

Promoter Tested In: *Arabidopsis thaliana*, WS ecotype
Spatial expression summary:
Primary root  (H)root hairs
Observed expression pattern: High GFP expression specific to epidermal root hair at hypocotyls root transition zone. Screened under non-induced condition.
T1 mature: No expression detected.
T2 mature: No expression detected.
T3 seedling: Same expression as T2 seedlings. GFP specific to root hairs.
Expected expression pattern: Heat inducible.
Selection Criteria: Expression data (full chip) >30 fold induction at 42 C. at 1 h and 6
Gene: LMW heat shock protein -mitochondrial
GenBank: NM_118652 *Arabidopsis thaliana* mitochondrion-localized small heat shock protein (At4g25200) mRNA, complete cds
gi|30686795|ref|NM_118652.2|[30686795]

| | |
|---|---|
| Source Promoter Organism: | *Arabidopsis thaliana* WS |
| Vector: | pNewBin4-HAP1-GFP |
| Marker Type: | X GFP-ER |
| Generation Screened: | X T1 Mature X T2 Seedling X T2 Mature X T3 Seedling |

T1 Mature Plant Expression    Organs/Tissues screened
Events Screened: n = 3        Events Expressing: n = 0
No GFP Expression Detected

| | |
|---|---|
| □Flower | □pedicel □receptacle □nectary □sepal □petal □filament □anther □pollen □carpel □style □papillae □vascular □epidermis □stomata □trichome |
| □Silique | □stigma □style □carpel □septum □placentae □transmitting tissue □vascular □epidermis □stomata □abscission zone □ovule |

Promoter Expression Report #39

| | |
|---|---|
| ☐Ovule | Pre-fertilization: ☐inner integument ☐outer integument ☐embryo sac ☐funiculus ☐chalaza ☐micropyle ☐gametophyte<br>Post-fertilization: ☐zygote ☐inner integument ☐outer integument ☐seed coat ☐primordia ☐chalaza ☐micropyle ☐early endosperm ☐mature endosperm ☐embryo |
| ☐Embryo | ☐suspensor ☐preglobular ☐globular ☐heart ☐torpedo ☐late ☐mature ☐provascular ☐hypophysis ☐radicle ☐cotyledons ☐hypocotyl |
| ☐Stem | ☐epidermis ☐cortex ☐vascular ☐xylem ☐phloem ☐pith ☐stomata ☐trichome |
| ☐Leaf | ☐petiole ☐mesophyll ☐vascular ☐epidermis ☐trichome ☐primordia ☐stomata ☐stipule ☐margin |

T2 Seedling Expression  Organs/Tissues Screened
Events Screened: n = 2  Events Expressing: n = 2
Seedlings expressing/Seedlings screened
Event-01: No data
Event-02: No data
GFP Expression Detected

| | |
|---|---|
| ☐Hypocotyl | ☐epidermis ☐cortex ☐vascular ☐xylem ☐phloem ☐stomata |
| ☐Cotyledon | ☐mesophyll ☐vascular ☐epidermis ☐trichome ☐margin ☐stomata |
| ☐Rosette Leaf | ☐mesophyll ☐vascular ☐epidermis ☐trichome ☐petiole ☐primordia ☐stomata ☐stipule ☐margin |
| X Primary Root | ☐epidermis ☐trichoblast atrichoblast ☐cortex ☐endodermis ☐vascular ☐xylem ☐phloem ☐pericycle ☐quiescent ☐columella ☐cap H root hairs |
| ☐Lateral root | ☐epidermis ☐initials ☐flanking cells ☐vascular ☐cap |
| ☐Shoot apical meristem | ☐SAM ☐epidermis |

X in the Root hair (Rh) of the Root (Rt)

T2 Mature Plant Expression
Plants expressing/Plants screened
Event-01: 0/3 Event-02: 0/3
☐Scheduled
☐T2 Mature tissue expressions similar to T1 expression data (data not shown).
☐T2 Mature tissue expression (if different expression pattern).
No expression detected T3 Seedling Expression
Seedlings expressing/Seedlings screened
Event-01: No data Event-02: No data
☐Scheduled
X T3 Seedling tissue expressions similar to T2 seedling expression.
☐T2 Mature tissue expression (if different expression pattern).
GFP Expression Detected
X in the root hair Promoter utility
Trait Area: Among other uses this promoter sequence is useful to improve:
Water use efficiency; Nutrient
Sub-trait Area: Increase plant growth or seed yield under heat stress conditions, nitrogen utilization, low N tolerance
Utility: Useful for root nutrient uptake

| | |
|---|---|
| Construct: | YP0082 |
| Promoter Candidate I.D: | 13148250 (Old ID: 11768604) |
| cDNA I.D: | 13609100 (Old IDs: 12678209, 6462494) |
| T1 lines expressing (T2 seed): | SR00606-01,-02,-03 |

Sequence (SEQ ID NO: 39):

AAGGGATGCGGTTCCGCTTCCTCTTGATCTTGGACGAGTCGGAGGACATT

GTTGGATCCCAGTGCAATGGTTTGTAGAGAAACAGGAAGCTTTGTTGAGA

AAGTTTTAACAGTGAGTTTAGTATTTATCTGAGAACTGTGTGCGACGAAA

CTGGAGACAGGGGAGGACTATATACAGGAGTTAAGTGTTGAAGGTGGGAT

ATTGTCAGTGAGTGAATGTTCTGGAGAAGTGGGGAGATTGATATTTCTCT

GGATGTTTCTAGAGATCCGTGGCTCCCAAGCTAAGTGAAACAAATATAAA

TTGTCTTGTTTATTAACGGGCTACGGCCCATCGGTATTAGGCCTGTTTTA

GTAGATTTATGGTCAACAAGTCAAATGACCCTAGAACATGGTACATGAAT

GAAAAGGACCAAAATGTGGACAGAAATCAACCAAAGGCCGAGGCGGCCAC

CAACCACCGAACGTGGGAAGGTCTGGTTCGGGCAAACATTCGAAAAGACC

AAGAAGACTCGGATAAACAATTAAAAAAAATCAGATATTGGGGAAGGCAAA

TATATATTGGTGTTGAGGTCAAGACTTAGAGTTTTGACGTTATTTTAAAA

AAAATATTTTTGGGTAAAGACCAAAGAGTTTGACGCTATCTTGAGGTTTA

TTTATTCAACGTAGACTATATACTATGGGGCCGTTCTGAATTGGACCTTT

TAAGTTTTGATTTTATTAAAACGCCATGTTGTTTAGTCGAGAGATAAACA

AAAGACGTGTCTCTAGCTAAGCTGACCTTCATATATGCTTTGACATAATA

CATTAATTATAATCTCTCTTTTTGGTGTGTGTAAAAAATACACTCTATAT

TTTATTATGTAGACACACTACATGCAGAAGTGTTCTTACCTCTGCCTCTA

CGTGCTGTCAACTCCTACAGATCTTCAAGTACCCCAACCGTTATCTAACA

GATTAAATATAATATACCCCTAACTATATTTATATATCACAATTGTTCAAA

CCAGTGTATATAGACTAGACGATTCCTTGAACCATATAATTCCAGCTTTA

CTATAAGAGTCTTAAGGACA

Promoter Expression Report #40

Promoter Tested In: *Arabidopsis thaliana*, WS ecotype
Spatial expression summary:
Hypocotyl   (H)epidermis
Primary Root  (H)epidermis, (H)trichoblast, (H)root hairs
Observed expression pattern: High GFP expression throughout epidermal layer of hypocotyl and upper root including root hairs. Not detected in lower root. No expression observed in T1 mature plants. T2 mature: No expression observed. T3 seedling: Same expression as T2 seedlings.
Expected expression pattern: Root
Selection Criteria:   Genome annotation
Gene: ABI3-interacting protein 2 homolog; unknown protein
GenBank: NM_101286 *Arabidopsis thaliana* zinc finger (C3HC4-type RING finger) protein family (At1g14200) mRNA, complete cds gi|30683647|ref|NM_101286.2|[30683647]
Source Promoter Organism: *Arabidopsis thaliana* WS
Vector: pNewBin4-HAP1-GFP
Marker Type: X GFP-ER
Generation Screened: X T1 Mature X T2 Seedling X T2 Mature X T3 Seedling T1 Mature Plant Expression  Organs/Tissues screened
Events Screened: n = 5  Events Expressing: n = 0
No GFP Expression Detected

| | |
|---|---|
| ☐Flower | ☐pedicel ☐receptacle ☐nectary ☐sepal ☐petal ☐filament ☐anther ☐pollen ☐carpel ☐style ☐papillae ☐vascular ☐epidermis ☐stomata ☐trichome |
| ☐Silique | ☐stigma ☐style ☐carpel ☐septum ☐placentae ☐transmitting tissue ☐vascular ☐epidermis ☐stomata ☐abscission zone ☐ovule |
| ☐Ovule | Pre-fertilization: ☐inner integument ☐outer integument ☐embryo sac ☐funiculus ☐chalaza ☐micropyle ☐gametophyte<br>Post-fertilization: ☐zygote ☐inner integument ☐outer integument ☐seed coat ☐primordia ☐chalaza ☐micropyle ☐early endosperm ☐mature endosperm ☐embryo |

| Promoter Expression Report #40 | |
|---|---|
| ☐Embryo | ☐suspensor ☐preglobular ☐globular ☐heart ☐torpedo ☐late ☐mature ☐provascular ☐hypophysis ☐radicle ☐cotyledons ☐hypocotyl |
| ☐Stem | ☐epidermis ☐cortex ☐vascular ☐xylem ☐phloem ☐pith ☐stomata ☐trichome |
| ☐Leaf | ☐petiole ☐mesophyll ☐vascular ☐epidermis ☐trichome ☐primordia ☐stomata ☐stipule ☐margin |

T2 Seedling Expression   Organs/Tissues Screened
Events Screened: n = 2   Events Expressing: n = 2
Seedlings expressing/Seedlings screened
Event-01: No data.
Event-02: No data.
GFP Expression Detected

| X Hypocotyl | H epidermis ☐cortex ☐vascular ☐xylem ☐phloem ☐stomata |
|---|---|
| ☐Cotyledon | ☐mesophyll ☐vascular ☐epidermis ☐trichome ☐margin ☐stomata |
| ☐Rosette Leaf | ☐mesophyll ☐vascular ☐epidermis ☐trichome ☐petiole ☐primordia ☐stomata ☐stipule ☐margin |
| X Primary Root | H epidermis H trichoblast ☐atrichoblast ☐cortex ☐endodermis ☐vascular ☐xylem ☐phloem ☐pericycle ☐quiescent ☐columella ☐cap H root hairs |
| ☐Lateral root | ☐epidermis ☐initials ☐flanking cells ☐vascular ☐cap |
| ☐Shoot apical meristem | ☐SAM ☐epidermis |

X in the Epidermis (Ep) and Root hair (Rh) of the hypocotyl root transition zone T2 Mature Plant Expression
Plants expressing/Plants screened
Event-01: 0/2 Event-02: 0/1
☐Scheduled
X T2 Mature tissue expressions similar to T1 expression data (data not shown).
☐T2 Mature tissue expression (if different expression pattern).
Expression detected T3 Seedling Expression
Seedlings expressing/Seedlings screened
Event-01: 2/3 Event-02: Not screened
☐Scheduled
X T3 Seedling tissue expressions similar to T2 seedling expression (data not shown).
☐T2 Mature tissue expression (if different expression pattern).
GFP Expression Detected

| Promoter utility | |
|---|---|
| Trait Area: | Among other uses this promoter sequence is useful to improve: PG&D |
| Sub-trait Area: | Nitrogen utilization; plant size, growth rate |
| Utility: | Useful for nutrient uptake e.g., root hairs root epidermis |
| Construct: | YP0019 |
| Promoter Candidate I.D: | 11768613 |
| cDNA I.D: | 4909291 |
| T1 lines expressing (T2 seed): | SR00489-01, -02 |

Sequence (SEQ ID NO: 40):

TTACGCGGCGCTACACTCTTATCAAAGTTTGAAGATTTTTCAAGAGACAC

AACAGATTCAAGTTTTCTGGTGGCTAAACTTACAATGACAGTACATGGAG

GATCTCCGCGAATGGAYTTCTGCAATGTACTAGCGTAGAACAAACACTTT

TTGTTAAAGTCATCAACCAACATAGCATAGAGTTGTTTATCTGAACAGAA

CACTGAAAGTCTTGGTTTTGTTTGTGTTCCAGTAAACTGTGTCAAAATGA

AAGAAAATACTTATTAACAAGTTCGGCAAAAAAAATTCAAACTTTTGTGC

ATTATTATATGAAAGCACTTCTAGAAAGCTACCTTCTTCCTGCTCCTCCT

GTTCCTAGTTTTCGGACTCTCCACTCGAGTGTTCCCTCTCGCTTCAATCA

CAAACGGCTTTACTACAGACATAGCTGATAAAAGGGTCGAAAAATCATGA

ACCAAGTAAGCGAAACAGAGGATAATAAACATGGAAGAAGAACAGAGTAA

GACGAATTATACCACTCACTTGTTATTCGAATTGGAAACTGGGGATAAGG

TTTCAAACGAGTTCCGAGAATGTCAGAGACTCTAAACTGAACAGTAGAAA

GAGAAGTCAAAGCAGCCATGCCAAGTATCATTCGTAAAGCATCGAAAGTC

AGAACATTACCCTCAGCGGAATTTAATCAAACACCTTCTGTGCAGGAATA

ATCTCTGGGGGTTTTATCAACACTCAAAAAAAACTGGAACTTTGTAAATA

AAATTATAAATGTTCGTACCTTTATGCAAAATTTCTCACAGCGTAATTAT

CTATTTCCTTTTTGTCCTTTATGAAAGAGGATAAGGTTTTTAAATAATAA

ATACTAAATTGTTTTTAAAAGAAACTAAAAATAAATGGAAAGCCTTAAGC

GTCGTCAATGGTTCTAGAGTCTTCTGCAACTTTCTTTTCATGAAACTACT

GTAATCTTCTGCTAACATATATAATCTCAAACACTATCTTCTCCAATT

| Promoter Expression Report #41 | |
|---|---|

Promoter Tested In: *Arabidopsis thaliana*, WS ecotype
Spatial expression summary:
Cotyledon     (M)stomata
Rosette Leaf   (M)petiole, (M)stomata
Observed expression pattern: GFP expression specific to stomata of cotyledons and primary rosette leaves of seedlings. No expression detected in T1 mature plants.
T2 mature: Same as T1 mature. No expression detected.
T3 seedlings: Same expression pattern as T2 seedlings.
Expected expression pattern: constitutive in all tissues
Selection Criteria:          cDNA cluster
Gene: 40S ribosomal protein S2
GenBank: NM_115609 *Arabidopsis thaliana* 40S ribosomal protein S2 (RPS2D) (At3g57490) mRNA, complete cds
gi|30694654|ref|NM_115609.2|[30694654]

| Source Promoter Organism: | *Arabidopsis thaliana* WS |
|---|---|
| Vector: | pNewBin4-HAP1-GFP |
| Marker Type: | X GFP-ER |
| Generation Screened: | X T1 Mature X T2 Seedling X T2 Mature X T3 Seedling |

T1 Mature Plant Expression   Organs/Tissues screened
Events Screened: n = 3   Events Expressing: n = 2
X No GFP Expression Detected

| ☐Flower | ☐pedicel ☐receptacle ☐nectary ☐sepal ☐petal ☐filament ☐anther ☐pollen ☐carpel ☐style ☐papillae ☐vascular ☐epidermis ☐stomata ☐trichome |
|---|---|
| ☐Silique | ☐stigma ☐style ☐carpel ☐septum ☐placentae ☐transmitting tissue ☐vascular ☐epidermis ☐stomata ☐abscission zone ☐ovule |
| ☐Ovule | Pre-fertilization: ☐inner integument ☐outer integument ☐embryo sac ☐funiculus ☐chalaza ☐micropyle ☐gametophyte Post-fertilization: ☐zygote ☐inner integument ☐outer integument ☐seed coat ☐primordia ☐chalaza ☐micropyle ☐early endosperm ☐mature endosperm ☐embryo |
| ☐Embryo | ☐suspensor ☐preglobular ☐globular ☐heart ☐torpedo ☐late ☐mature ☐provascular ☐hypophysis ☐radicle ☐cotyledons ☐hypocotyl |
| ☐Stem | ☐epidermis ☐cortex ☐vascular ☐xylem ☐phloem ☐pith ☐stomata ☐trichome |
| ☐Leaf | ☐petiole ☐mesophyll ☐vascular ☐epidermis ☐trichome ☐primordia ☐stomata ☐stipule ☐margin |

| Promoter Expression Report #41 | |
|---|---|
| T2 Seedling Expression | Tissues Screened |
| Events Screened: n = 2 | Events Expressing: n = 2 |
| Seedlings expressing/Seedlings screened | |
| Event-01: 2/4 Event-02: 1/3 | |
| GFP Expression Detected | |
| ☐Hypocotyl | ☐epidermis ☐cortex ☐vascular ☐xylem ☐phloem ☐stomata |
| X Cotyledon | ☐mesophyll ☐vascular ☐epidermis ☐trichome ☐margin M stomata |
| X Rosette Leaf | ☐mesophyll ☐vascular ☐epidermis ☐trichome M petiole ☐primordia M stomata ☐stipule ☐margin |
| ☐Primary Root | ☐epidermis ☐trichoblast atrichoblast ☐cortex ☐endodermis ☐vascular ☐xylem ☐phloem ☐pericycle ☐quiescent ☐columella ☐cap ☐root hairs |
| ☐Lateral root | ☐epidermis ☐initials ☐flanking cells ☐vascular ☐cap |
| ☐Shoot apical meristem | ☐SAM ☐epidermis |
| X in the Guard cells (Gc) of the cotyledon, petiole and rosette leaf | |

T2 Mature Plant Expression
Plants expressing/Plants screened
Event-01: 0/2
Event-02: 0/1
☐Scheduled
☐T2 Mature tissue expressions similar to T1 expression data (data not shown).
☐T2 Mature tissue expression (if different expression pattern).
No expression detected T3 Seedling Expression
Seedlings expressing/Seedlings screened
Event-01: 0/1 Event-02: 1/2
☐Scheduled
X T3 Seedling tissue expressions similar to T2 seedling expression.
☐T2 Mature tissue expression (if different expression pattern).
GFP Expression Detected
X in the Guard cells (Gc) of the cotyledon

| Promoter utility | |
|---|---|
| Trait Area: | Among other uses this promoter sequence is useful to improve: PG&D Water use efficiency |
| Sub-trait Area: | Drought, Water used efficiency |
| Utility: | Useful for water use efficiency under drought condition |
| Construct: | YP0084 |
| Promoter Candidate I.D: | 12748730 |
| cDNA I.D: | 13621692 (Old IDs: 12395524, 5668493) |
| T1 lines expressing (T2 seed): | SR00581-02, -03 |

Sequence (SEQ ID NO: 41):

```
gaTATAAGTAGAATCATTTTTTGCCGCCGTTTCTCGCTAACACACCGAAA
ACTGAATCAAATCTCCTAGCTCTTTCTACGCAAAATCGAGTGCATCGACA
ATGGCGGAACGTGGTGTCGAACGTGGTGGAGATCGCGGCGATTTCGGACG
TGGATTCGGTGGTCGCGGCGGTGGAAGAGGTGGTCCGAGAGGTCGTGGTC
GCCGTGCAGGTCGTGCTCCAGAGGAGGAGAAATGGGTGCCAGTGACTAAG
CTTGGTCGTCTCGTAAAGGAAGGTAAGATCACAAAGATTTGAGCAGATCT
ACCTCCATTCTCTCCCAGTCAAGGAGTACCAGATCATAGATTTACTCGTC
GGTCCTTCATTGAAAGACGAAGTGATGAAAATCATGCCGGTTTCAAAAAC
AAACCAGAGCCGGTCAGAGAACGAGATTCAAGGCCTTCATCGTCGTCGGA
GATAGTAACGGTCACGTCGGATTAGGAGTCAAATGCTCCAAGGAAGTTTG
CGACGGCGATCAGAGGCGCGATCATTCTCGCGAAATTGTCTGTGGTTCCG
ATACGAAGAGGTTATTGGGGTAACAAGATTGGAAAACCACATACGGTTCC
GTGTAAGGTAACCGGGAAATGTGGATCTGTTACTGTACGTATGGTTCCAG
CTCCGAGAGGTTCTGGTATTGTGGCGGCTAGAGTTCCTAAGAAGGTTCTT
CAATTCGCTGGAATTGATGATGTCTTTACTTCTTCTAGAGGATCCACCAA
AACTCTTGGAAACTTCGTCAAGGTATGTACTTTCACAATGGCTGTTTTGG
TTTGATGAACTCTGAATTAGGCAGTgaaaaagTAATCATTACCAGTTAAG
TGAATTTATATTGAAGATTAGGATTTAGCTGATTGTATTGGTTTGAGCAT
GTGAGTTTGTGTTTAAGATTGCTTGAATTGAAATGCTTTAGGTTGTTTGA
TTACGCTAAATTCTGACTAATGTAATTcaaattgTTGTTgttttttttg
gtc
```

| Promoter Expression Report #42 | |
|---|---|

Promoter Tested In: *Arabidopsis thaliana*, WS ecotype
Spatial expression summary:
Flower          (L)receptacle, (L)vascular
Silique         (L)vascular
Stem            (L)vascular, (L)phloem
Primary root:   (H)phloem
Observed expression pattern: High GFP expression specific to the seedling root phloem tissue. T1 mature: No expression was observed. T2 mature: Low expression in flower and stem vascular tissues was not observed in T1 mature. T3 seedlings: Same vascular expression exists as T2 seedlings.
Expected expression pattern: Constitutive in all green tissues
Selection Criteria:         cDNA cluster
Gene: 40S ribosomal protein S5
GenBank: NM_129283 *Arabidopsis thaliana* 40S ribosomal protein S5 (RPS5A) (At2g37270) mRNA, complete cds
gi|30687090|ref|NM_129283.2|[30687090]
Source Promoter Organism: *Arabidopsis thaliana* WS
Vector:                    pNewBin4-HAP1-GFP
Marker Type:               X GFP-ER
Generation Screened:       X T1 Mature X T2 Seedling X T2 Mature X T3 Seedling

| T1 Mature Plant Expression | Organs/Tissues screened |
|---|---|
| Events Screened: n = 3 | Events Expressing: n = 0 |
| No GFP Expression Detected | |
| ☐Flower | ☐pedicel ☐receptacle ☐nectary ☐sepal ☐petal ☐filament ☐anther ☐pollen ☐carpel ☐style ☐papillae ☐vascular ☐epidermis ☐stomata ☐trichome |
| ☐Silique | ☐stigma ☐style ☐carpel ☐septum ☐placentae ☐transmitting tissue ☐vascular ☐epidermis ☐stomata ☐abscission zone ☐ovule |
| ☐Ovule | Pre-fertilization: ☐inner integument ☐outer integument ☐embryo sac ☐funiculus ☐chalaza ☐micropyle ☐gametophyte Post-fertilization: ☐zygote ☐inner integument ☐outer integument ☐seed coat ☐primordia ☐chalaza ☐micropyle ☐early endosperm ☐mature endosperm ☐embryo |
| ☐Embryo | ☐suspensor ☐preglobular ☐globular ☐heart ☐torpedo ☐late ☐mature ☐provascular ☐hypophysis ☐radicle ☐cotyledons ☐hypocotyl |
| ☐Stem | ☐epidermis ☐cortex ☐vascular ☐xylem ☐phloem ☐pith ☐stomata ☐trichome |
| ☐Leaf | ☐petiole ☐mesophyll ☐vascular ☐epidermis ☐trichome ☐primordia ☐stomata ☐stipule ☐margin |

| T2 Seedling Expression | Tissues Screened |
|---|---|
| Events Screened: n = 2 | Events Expressing: n = 2 |
| Seedlings expressing/Seedlings screened | |
| Event-01: 2/3 Event-02: 1/3 | |
| GFP Expression Detected | |
| ☐Hypocotyl | ☐epidermis ☐cortex ☐vascular ☐xylem ☐phloem ☐stomata |

Promoter Expression Report #42

| | |
|---|---|
| ☐Cotyledon | ☐mesophyll ☐vascular ☐epidermis ☐trichome ☐margin ☐stomata |
| ☐Rosette Leaf | ☐mesophyll ☐vascular ☐epidermis ☐trichome ☐petiole ☐primordia ☐stomata ☐stipule ☐margin |
| X Primary Root | ☐epidermis ☐trichoblast atrichoblast ☐cortex ☐endodermis ☐vascular ☐xylem H phloem ☐pericycle ☐quiescent ☐columella ☐cap ☐root hairs |
| ☐Lateral Root | ☐epidermis ☐initials ☐flanking cells ☐vascular ☐cap |
| ☐Shoot apical meristem | ☐SAM ☐epidermis |

X in the Phloem (Ph) of the hypocotyl root transition zone and the root differentiation zone T2 Mature Plant Expression
Plants expressing/Plants screened
Event-01: 1/1 Event-02: 1/1
☐Scheduled
☐T2 Mature tissue expressions are similar to T1 expression data (data not shown).
X T2 Mature tissue expression (if different expression pattern).
☐No expression was detected

| | |
|---|---|
| X Flower | ☐pedicel L receptacle ☐nectary ☐sepal ☐petal ☐filament ☐anther ☐pollen ☐carpel ☐style ☐papillae L vascular ☐epidermis ☐stomata ☐trichome |
| X Silique | ☐stigma ☐style ☐carpel ☐septum ☐placentae ☐transmitting tissue L vascular ☐epidermis ☐stomata ☐abscission zone ☐ovule |
| X Stem | ☐epidermis ☐cortex L vascular ☐xylem L phloem ☐pith ☐stomata ☐trichome |

X in the Recpetacle (Re), Silique (Si) and Vasculature (Vs) of the flower
X in the vascular bundle of the stem Seedling Expression
Seedlings expressing/Seedlings screened
Event-01: 2/3 Event-02: no germination
☐Scheduled
X T3 Seedling tissue expressions are similar to T2 seedling expression.
☐T2 Mature tissue expression (if different expression pattern).
GFP Expression was Detected
X in the root Promoter utility
| | |
|---|---|
| Trait Area: | Among other uses this promoter sequence is useful to improve: PG&D, Nutrient economy |
| Sub-trait Area: | Plant size, growth rate, low nitrogen tolerance, NUE |
| Utility: | Useful for root nutrient uptake, source/sink relationships, root growth |

| | |
|---|---|
| Construct: | YP0087 |
| Promoter Candidate I.D: | 12748731 |
| cDNA I.D: | 13580795 (Old IDs: 11006078, 12581302) |
| T1 lines expressing (T2 seed): | SR00583-01, -02 |

Sequence (SEQ ID NO: 42):

TGAATTGAGTAAAATGTGTTTTCAAACAGTTAGGTGGTAGAAGGTAAAGG

TAATAACATCATGATCTTACTAAAAGAATTGTTGCATACTAACTATCAAT

ATTCTCAACAACATAATATAATGTTTTTTTAGGTAATTTTCCATTTTAAT

TTTTTGTGATTAAACAATTAAACAACTCGAATGATGATGATAAAAAAAAA

AAATTAACAACTCGAATAAGTTAAAGTAGCAATACACATGTCGTTCAATT

CAACCAATAAAGTAAGACTTATATTTTTAAGAAGTTGACTAATAGCCTAA

TAAGTTGGAAAACTTGTGTAGTTTCTTAATTCCCACGTGCAGTAAGAAAT

AAAAATGAAAAAAATTATTATATCCTTCCCACTCTCGCGACTTTTCTTTTA

TTTTATCAAATATTAAAAAGATTCAAAAATAGATAAACTCATATCACAGT

TTACACATTGAAATCATAAACGATAATTATGTATTTTGTAATAAAAAGTT

AGTTCTGAAGCTCATACTTTGGATAGTCGCTAGTCGCTAATATGCTCCTT

GTAATAATTAAAGTCACTACGACGCACGTCAAAGCCGATATTTAGGGCTT

AATTGATGCGTGTTTTTCTTTTCATATAATAGTAATATAAATTAGTACTA

ATAAAGTATGATGGATGGTTGAGACAGAAAAGAAAAAAGATGACTGTATG

GTCATCATTACAAAGAAGAATGTATTCTTCATGTTCTTAAGAATAATAAA

ATGTCACTTGTAAATCAAGTTTGGTAAGCATTTTGAGAACTTTGTTCGAT

GCAACGTATGATGATTTATGTAGACAAAAGATAAAACCGTATCTTCAACT

ATTGCCAAGAAAAGATAAAACCTAATCTAGTCAGTCTCTCAACATAAATA

CAACCCAATAGCCAAAGTGTGTCCAATTCGGAGAGAAACTAAACTAAAAC

AAAACACAAAAGCCCAACATAAGCCCAATAAAACCCATTTTATAAACAGA

ACATTACTAACACTCA

Promoter Expression Report #43

Promoter Tested In: *Arabidopsis thaliana*, WS ecotype
Spatial expression summary: Screened under non-induced conditions

| | |
|---|---|
| Flower | (H)petal, (H)epidermis, (H)anther |
| Stem | (H)epidermis |
| Cotyledon | (H)epidermis |
| Hypocotyl | (L)epidermis, (L)stomata |
| Rosette Leaf | (L)petiole, (L)stomata |
| Primary Root | (H)phloem, (H)vascular |

Observed expression pattern: T1 mature: High GFP expression in petals of developing to mature flowers and in and pollen nutritive lipid rich ameboid tapetum cells in developing anthers. T2 seedling: High GFP expression in root phloem with weak expression in epidermal tissues of seedlings. T2 mature: Same as T1 mature with additional stem epidermal expression was not observed in T1 mature plants. T3 seedling: Same as T2 seedling, however, no expression was seen in epidermal cells of hypocotyls as in T2 seedlings.
Expected expression pattern:: Inducible promoter - was induced by different forms of stress (e.g., drought, heat, cold)
Selection Criteria        *Arabidopsis* microarray
Gene: Putative strictosidine synthase
GenBank: NM_147884 *Arabidopsis thaliana* strictosidine synthase family (At5g22020) mRNA, complete cds
gi|30688266|ref|NM_147884.2|[30688266]

| | |
|---|---|
| Source Promoter Organism: | *Arabidopsis thaliana* WS |
| Vector: | pNewBin4-HAP1-GFP |
| Marker Type: | X GFP-ER |
| Generation Screened: | XT1 Mature X T2 Seedling XT2 Mature X T3 Seedling |

T1 Mature Plant Expression     Organs/Tissues screened
Events Screened: n = 3         Events Expressing: n = 2
GFP Expression Detected

| | |
|---|---|
| X Flower | ☐pedicel ☐receptacle ☐nectary ☐sepal H petal ☐filament H anther ☐pollen ☐carpel ☐style ☐papillae ☐vascular H epidermis ☐stomata ☐trichome |
| ☐Silique | ☐stigma ☐style ☐carpel ☐septum ☐placentae ☐transmitting tissue ☐vascular ☐epidermis ☐stomata ☐abscission zone ☐ovule |
| ☐Ovule | Pre-fertilization: ☐inner integument ☐outer integument ☐embryo sac ☐funiculus ☐chalaza ☐micropyle ☐gametophyte |
| | Post-fertilization: ☐zygote ☐inner integument ☐outer integument ☐seed coat ☐primordia ☐chalaza ☐micropyle ☐early endosperm ☐mature endosperm ☐embryo |
| ☐Embryo | ☐suspensor ☐preglobular ☐globular ☐heart ☐torpedo ☐late ☐mature ☐provascular ☐hypophysis ☐radicle ☐cotyledons ☐hypocotyl |
| ☐Stem | ☐epidermis ☐cortex ☐vascular ☐xylem ☐phloem ☐pith ☐stomata ☐trichome |

Promoter Expression Report #43

☐Leaf ☐petiole ☐mesophyll ☐vascular ☐epidermis ☐trichome ☐primordia ☐stomata ☐stipule ☐margin
X in the Petal (Pe) in the developing flower
X in the Locules (Lo), Pollen (Po), Silique (Si) and Tapetum ameboid (Tp)

T2 Seedling Expression  Organs/Tissues Screened
Events Screened: n = 3  Events Expressing: n = 2
GFP Expression Detected
X Hypocotyl  L epidermis ☐cortex ☐vascular ☐xylem ☐phloem L stomata
☐Cotyledon  ☐mesophyll ☐vascular ☐epidermis ☐trichome ☐margin ☐stomata
X Rosette Leaf  ☐mesophyll ☐vascular ☐epidermis ☐trichome L petiole ☐primordia L stomata ☐stipule ☐margin
X Primary Root  ☐epidermis ☐trichoblast atrichoblast ☐cortex ☐endodermis H vascular ☐xylem H phloem ☐pericycle ☐quiescent ☐columella ☐cap ☐root hairs
☐Lateral root  ☐epidermis ☐initials ☐flanking cells ☐vascular ☐cap
☐Shoot apical meristem  ☐SAM ☐epidermis
X in the Epidermis (Ep) and Guard cells (Gc) of the hypocotyl
X in the Guard cells (Gc) of the petiole
X in the Phloem (Ph) in the root differentiation zone T2 Mature Plant Expression
Plants expressing/Plants screened
Event-01: 2/8 Event-02: 1/2
☐Scheduled
☐T2 Mature tissue expressions similar to T1 expression data (data not shown).
X T2 Mature tissue expression (if different expression pattern).
☐No expression detected
X Flower  ☐pedicel ☐receptacle ☐nectary ☐sepal ☐petal ☐filament ☐anther ☐pollen ☐carpel ☐style ☐papillae ☐vascular H epidermis ☐stomata ☐trichome ☐silique
X Stem  H epidermis ☐cortex ☐vascular ☐xylem ☐phloem ☐pith ☐stomata ☐trichome
X in the Epidermis (Ep) of the pedicle and stem T3 Seedling Expression
Seedlings expressing/Seedlings screened
Event-01: 2/3 Event-02: 2/3
☐Scheduled
☐T3 Seedling tissue expressions similar to T2 seedling expression (data not shown).
X T2 Mature tissue expression (if different expression pattern).
GFP Expression Detected
X Cotyledon  ☐mesophyll ☐vascular L epidermis ☐margin ☐stomata ☐hydathode
X in the Epidermis (Ep) of the cotyledon Promoter utility
Trait Area:  PD&G, Nutrient, seed, water use efficiency
Sub-trait Area:  Nutrient uptake, C/N partitioning, Source enhancement, source/sink
Utility:  Useful for nutrient uptake and transport in root, transport or mobilization of steroid reserves Construct:  YP0180
Promoter Candidate I.D:  11768712
cDNA I.D:  5787483 (Old IDs: 2918666, 12367001)
T1 lines expressing (T2 seed):  SR00902-01, -02, -03

Sequence (SEQ ID NO: 43):

CAATCTGATCTCTAGTGCCAGTCGATTGGTTATTGTTGAAACGGATGGTAT

CCAGATTCATAGAGTTATACGTTGTTGACCTCGTACAGGATGAATTCATTA

TCTTCTTCCTTTTGCAGCATGGCAGGTGATCGATGGGTATGACTTGTGA

TGATAGCCATGTCCACCAAATCAGCCAAGAAAAGATCAAGACCTCGGCTGC

TTACGTTCTGTTCTATAAACGCCTTTGTAGACTAAAGAAACTGAAGCGGAA

AAGACAAGAAAGAGGTATTTGCATTTTTGCCGGGTTTGGCTTATTTAAAAA

CATCATTGGCTTGATTCTAATTCACTACAAGATCAAGATGAAAGCAGCTCT

GCGTTGAGGCTAATTTACAGAAGAGAGAGAGAGTTGGGAAGAAGAGCAA

AAGACCGAGAGGACATGTTGCGGGGAATTTATTTTATTCTTACAAAAATTG

GTATCTGATTATTTTATTAACCATATTCAATTAGAGAATAGAAGAATAGAG

AAAAGCCCTTTTGTGGGATATGGTTCTAAATTGTTGTTTAGTTCTTGTGTG

TCAGTTTTGGCTCTCGTCGACCAAAGAAGATTAAAGAAACCTCTACCTTAT

TTTAACTCAATTCTTTTGTTTTTGCAATGTCCTTTGCTTTCCAAAATTGTT

AGTCTTACTTTTCACTACTTTGATAGACATTGCCTTTGCGTTTCCCTGATT

AATAAGCCAGAGTACTTAAATCAAAATTGACTGTTTTGTGCATCCTGCATC

ACGTTTCCAATCAGAACCATAGTGTTGTCGTTGTGTCATTATCCGAATTTA

AGTGGAGACATTGGTAAGTTATTTATAAACTAATTACAATCTATTTTTCTA

ATTATTTCAAATAACATATTTAAGCTCTGTAGCTTCCACTAGACGGTGAAG

ATTTGAAGTGAGAGCTCTCTTTGCATTGCTCACCCACCAATGGATCTACCT

ACCCTTCTTCTTCTTCTCCTCCTTTTAAACCCTAAAAGTTTCCCTTTCCGT

TCAACAACGCCACAATCCATTGCACTGGGATCCAACAATGTCCTCCGACTC

GTCCAAGATCAAGAGGAAGCG

Promoter Expression Report #44

Promoter Tested In: *Arabidopsis thaliana*, WS ecotype
Spatial expression summary:
Hypocotyl  (L)epidermis
Observed expression pattern: Low GFP expression in the epidermal cells of hypocotyl. Screened under non-induced conditions. No T1 mature expression was observed. T2 mature: No expression was observed T3 seedling: Same expression as the T2 seedling seen in one of two events. Guard cell expression was observed in second event.
Expected expression pattern: Induced by different forms of stress (e.g., drought, heat, cold).
Selection Criteria:  Arabidopsis microarray. Induced by different forms of stress (e.g., drought, heat, cold)
Gene: Berberine bridge enzyme
GenBank: NM_100078 *Arabidopsis thaliana* FAD-linked oxidoreductase family (At1g01980) mRNA, complete cds
cds gi|18378905|ref|NM_100078.1|[18378905]
Source Promoter Organism:  *Arabidopsis thaliana* WS
Vector:  pNewBin4-HAP1-GFP
Marker Type:  X GFP-ER
Generation Screened:  X T1 Mature X T2 Seedling X T2 Mature X T3 Seedling T1 Mature Plant Expression  Organs/Tissues screened
Events Screened: n = 3  Events Expressing: n = 0
No GFP Expression Detected
☐Flower  ☐pedicel ☐receptacle ☐nectary ☐sepal ☐petal ☐filament ☐anther ☐pollen ☐carpel ☐style ☐papillae ☐vascular ☐epidermis ☐stomata ☐trichome
☐Silique  ☐stigma ☐style ☐carpel ☐septum ☐placentae ☐transmitting tissue ☐vascular ☐epidermis ☐stomata ☐abscission zone ☐ovule
☐Ovule  Pre-fertilization: ☐inner integument ☐outer integument ☐embryo sac ☐funiculus ☐chalaza ☐micropyle ☐gametophyte
Post-fertilization: ☐zygote ☐inner integument ☐outer integument ☐seed coat ☐primordia ☐chalaza ☐micropyle ☐early endosperm ☐mature endosperm ☐embryo

| Promoter Expression Report #44 | |
|---|---|
| ☐Embryo | ☐suspensor ☐preglobular ☐globular ☐heart ☐torpedo ☐late ☐mature ☐provascular ☐hypophysis ☐radicle ☐cotyledons ☐hypocotyl |
| ☐Stem | ☐epidermis ☐cortex ☐vascular ☐xylem ☐phloem ☐pith ☐stomata ☐trichome |
| ☐Leaf | ☐petiole ☐mesophyll ☐vascular ☐epidermis ☐trichome ☐primordia ☐stomata ☐stipule ☐margin |

T2 Seedling Expression    Tissues Screened
Events Screened: n = 2        Events Expressing: n = 2
Seedlings expressing/Seedlings screened
Event-01: 1/2 Event-02: 2/2
GFP Expression Detected

| X Hypocotyl | L epidermis ☐cortex ☐vascular ☐xylem ☐phloem ☐stomata |
|---|---|
| ☐Cotyledon | ☐mesophyll ☐vascular ☐epidermis ☐trichome ☐margin ☐stomata |
| ☐Rosette Leaf | ☐mesophyll ☐vascular ☐epidermis ☐trichome ☐petiole ☐primordia ☐stomata ☐stipule ☐margin |
| ☐Primary Root | ☐epidermis ☐trichoblast ☐atrichoblast ☐cortex ☐endodermis ☐vascular ☐xylem ☐phloem ☐pericycle ☐quiescent ☐columella ☐cap ☐root hairs |
| ☐Lateral root | ☐epidermis ☐initials ☐flanking cells ☐vascular ☐cap |
| ☐Shoot apical meristem | ☐SAM ☐epidermis |

X in the Epidermis (Ep) of the hypocotyl

T2 Mature Plant Expression
Plants expressing/Plants screened
Event-01: 0/2 Event-02: 0/2
☐Scheduled
X T2 Mature tissue expressions similar to T1 expression data (data not shown).
☐T2 Mature tissue expression (if different expression pattern).
Expression detected T3 Seedling Expression
Seedlings expressing/Seedlings screened
Event-01: 1/3 Event-02: 2/3
☐Scheduled
X T3 Seedling tissue expressions similar to T2 seedling expression (data not shown).
☐T2 Mature tissue expression (if different expression pattern).
GFP Expression Detected Promoter utility
| Trait Area: | Among other uses this promoter sequence is useful to improve: Water use efficiency; PG&D |
|---|---|
| Sub-trait Area: | Heat |
| Utility: | Seedling establishment under sub-optimal or marginal conditions |

| Construct: | YP0186 |
|---|---|
| Promoter Candidate I.D: | 11768854 |
| cDNA I.D: | 13647840 (Old IDs: 12689527, 11437778) |
| T1 lines expressing (T2 seed): | SR00906-02, -03 |

Sequence (SEQ ID NO: 44):

```
TGGACAATTACTCTTGTGTGTATCCTTGGAGTTGCTGTTTCATATGTAAGT
GGACAATTACTCTTGTGTGTAGCCTTGGAGTTTTTTATTTACGTTATTTT
GGTCAGCCTTTAATTATTTTGCAAAAAATGTATCTGTTTTTGCCACATGCC
CACATAATACATTTCGCAAATTTGATACATTATGCTTTGGCCCTTGTATAT
TCGGTAAAAAAAAAAGCTCAGGCTACTCTCAAAACCGGCTCTGAGTATTCG
TAGGCCACAATCGAAGAAAAAAGTGCCGATTTACATATTTTTCATACAAA
AAATTAAAACTGTTATGTATTATTCAAAAGCTATTTACATATGTTTTACTA
ACACGTTTTCAATATTTTCTTAATCCTTTTCAAAATTTAACTAAGTATAAT
ACTTTTTTTGTGTGTTATTTCGTTGTTTTGGTTAAAGAAAAACGAAAAAAA
GAGAGAGTTATTCATCCTTGCAGATAAGGCTAGGGTTGGTTGAATAAAGAT
GTGCATATCTTATACCACTAGACCAAAGAAACAGTCACAAGTAAAAGGCCG
AATCCTTTTTATAAAATATAAACAGACGAAAGCTAATGCTTCATGGGCTTG
GCCCAAGTGCAGGCTCTCGCTAGTCGCTACGCTACAACTATCCCATATTTA
ATTAGTGAAGAGTATTTTATTATTTTGGTCAACGGGCTATCTTTGTTGACA
AAACTATCCCATTGGTAAAGAAATAGCAAAATAGGCGTTTCATTCTCTATA
TTTAAACTTGATTTTATGAAGAGTTGAATAGCTGAACCAGGAAGATATTTA
AGAAGCCCGTACTTCACGCTTTAACTGTCAATCGATAGATCATAATAAATG
ACTATCTATGGATAGGAACTATAACTGAATTCAGAAAGAATCTACTACTAC
TATAAATACTAAAAGAGTATTAATACAACGGAAAAAACAAAACAAAAAAAA
GGGGGAACAAGGGAGTTTCATGTTAAAAAG
```

| Promoter Expression Report #45 | |
|---|---|

Promoter Tested In: *Arabidopsis thaliana*, WS ecotype
Spatial expression summary:
Ovule    Pre-fertilization: (H)inner integument
             Post-fertilization: (H)inner integument, (H)outer integument
Observed expression pattern: High GFP expression specific to the inner integuments of developing pre-fertilized ovules and outer integuments at the mycropylar end of post fertilized ovules. GFP detected throughout inner integument of developing seed at mature embryo stage. T2 seedling: No expression observed. T2 Mature: Same expression as observed in T1 mature. T3 seedling: Not screened.
Expected expression pattern: Expressed in ovules and different parts of seeds
Selection Criteria:    Greater than 50x up in pi ovule microarray
Gene: pectin methylesterase [*Arabidopsis thaliana*].
GenBank: NM_124295 *Arabidopsis thaliana* pectinesterase family (At5g49180) mRNA, complete cds
gi|30695612|ref|NM_124295.2|[30695612]
Source Promoter Organism: *Arabidopsis thaliana* WS
| Vector: | pNewBin4-HAP1-GFP |
|---|---|
| Marker Type: | X GFP-ER |
| Generation Screened: | XT1 Mature X T2 Seedling X T2 Mature T3 Seedling |

T1 Mature Plant Expression    Organs/Tissues screened
Events Screened: n = 3        Events Expressing: n = 3
GFP Expression Detected

| ☐Flower | ☐pedicel ☐receptacle ☐nectary ☐sepal ☐petal ☐filament ☐anther ☐pollen ☐carpel ☐style ☐papillae ☐vascular ☐epidermis ☐stomata ☐trichome |
|---|---|
| ☐Silique | ☐stigma ☐style ☐carpel ☐septum ☐placentae ☐transmitting tissue ☐vascular ☐epidermis ☐stomata ☐abscission zone ☐ovule |
| X Ovule | Pre-fertilization: H inner integument ☐outer integument ☐embryo sac ☐funiculus ☐chalaza ☐micropyle ☐gametophyte
Post-fertilization: ☐zygote H inner integument H outer integument ☐seed coat ☐primordia ☐chalaza ☐micropyle ☐early endosperm ☐mature endosperm ☐embryo |
| ☐Embryo | ☐suspensor ☐preglobular ☐globular ☐heart ☐torpedo ☐late ☐mature ☐provascular ☐hypophysis ☐radicle ☐cotyledons ☐hypocotyl |
| ☐Stem | ☐epidermis ☐cortex ☐vascular ☐xylem ☐phloem ☐pith ☐stomata ☐trichome |
| ☐Leaf | ☐petiole ☐mesophyll ☐vascular ☐epidermis ☐trichome ☐primordia ☐stomata ☐stipule ☐margin |

X in the Inner integuments (Ii), Micropyle (Mp) and Outer integuments (Oi) of the pre-fertilized ovule

Promoter Expression Report #45

X in the Micropyle (Mp) and Outer integuments (Oi) of the post fertilized ovule
X in the ovule containing the early embryo and mature embryo T2 Seedling Expression    Organs/Tissues Screened
Events Screened: n = 2    Events Expressing: n = 0
No GFP Expression Detected
☐Hypocotyl         ☐epidermis ☐cortex ☐vascular ☐xylem ☐phloem
                   ☐stomata
☐Cotyledon         ☐mesophyll ☐vascular ☐epidermis ☐trichome
                   ☐margin ☐stomata
☐Rosette Leaf      ☐mesophyll ☐vascular ☐epidermis ☐trichome
                   ☐petiole ☐primordia ☐stomata ☐stipule ☐margin
☐Primary Root      ☐epidermis ☐trichoblast atrichoblast ☐cortex
                   ☐endodermis ☐vascular ☐xylem ☐phloem
                   ☐pericycle ☐quiescent ☐columella ☐cap
                   ☐root hairs
☐Lateral root      ☐epidermis ☐initials ☐flanking cells ☐vascular ☐cap
☐Shoot apical      ☐SAM ☐epidermis
meristem T2 Mature Plant Expression
Plants expressing/Plants screened
Event-01: 2/3 Event-02: 0/3
☐Scheduled
X T2 Mature tissue expressions similar to T1 expression data (data not shown).
☐T2 Mature tissue expression (if different expression pattern).
Expression detected T3 Seedling Expression
Seedlings expressing/Seedlings screened
Event-01: Not screened.    Event-02: Not screened
☐Scheduled
☐T3 Seedling tissue expressions similar to T2 seedling expression (data not shown).
☐T2 Mature tissue expression (if different expression pattern).
GFP Expression Detected Promoter utility
Trait Area:     Seed, Yield, Nutrient, cold, water use efficiency
Sub-trait Area: Ovule/seed abortion, seed enhancement, seed number,
                seed size, total yield, seed nitrogen, cold germination and
                vigor
Utility:        Useful for improvement for seed yield, composition,
                moisture stress at seed set, moisture stress during seed fill Construct:                  YP0121
Promoter Candidate I.D:     11768686
cDNA I.D:                   12646933 (Old IDs: 12370661, 7080188)
T1 lines expressing (T2 seed): SR00805-01, -02, -03

Sequence (SEQ ID NO: 45):

TTGGATTTTTTTTTGTTGAGTCAGCAGACCATCTAATCTCTCTTTTTCCA

CCACAGCCTGCTTTCTATGAAGCATTTGGGCTTACGGTTGTGGAATCAATG

ACTTGTGCACTCCCAACGTTTGCTACCTGTCATGGTGGACCCGCAGAGATT

ATCGAAAACGGAGTTTCTGGGTTCCACATTGACCCATATCATCCAGACCAG

GTTGCAGCTACCTTGGTCAGCTTCTTTGAGACCTGTAACACCAATCCAAAT

CATTGGGTTAAAATCTCTGAAGGAGGGCTCAAGCGAATCTATGAAAGGTTG

GCCCATTCTCCTTGACAGGCTTAACAATACAACTTGTATCGCTTCAACAAG

ATGATGGCTTAATAAGGATTTTTGCATGTATAGGTACACATGGAAGAAGTA

CTCAGAGAGACTGCTTACCCTGGCTGGAGTCTATGCATTCTGGAAACATGT

GTCTAAGCTCGAAAGGAGAGAAACACGACGTTACCTAGAGATGTTTTACTC

ATTGAAATTTCGTGATTTGGTTAGTGTAACCCACTGTTATTCTTTTGATGT

CTACATCTACTTTACTTACATTATTCTTTTCTTCGGTTTGCAGGCCAATTC

AATCCCGCTGGCAACAGATGAGAACTGATCATGACAGGGTAGGATTTTATT

TCCTGCACTTTCTTTAGATCTTTTGTTTGTGTTATCTTGAATAAAAATTGT

TGGGTTTTGTTTCCTTCAGTGGTTTGATTTTGGACTTATTTGTGTTAATGT

TGTTTTGGCTGTTCTCTTAATATCAATAACAAATAAATTTACTGGTTGGTA

TCTAAGATCTAACAATAGTTACTATTTTAGAGGTAAAGACACCAACCTTGT

TATATTGGTCAGAGAGCTAAAACCTTGACTTGTTGGGAAAACAAAACTCTA

ATGACAGAAAATCTGACATGATGCCTTATAATTCACAGCCTCATGTTCTAC

ATAAATCCTAACAATAGCACTTTGTTTCT

Promoter Expression Report #46

Promoter Tested In: *Arabidopsis thaliana*, WS ecotype
Spatial expression summary:
Silique    (H)ovule
Ovule      Pre-fertilization: (H)embryo sac, (H)gametophyte
           Post-fertilization: (H)zygote
Observed expression pattern: GFP expression is specific to female
gametophyte and surrounding sporophytic tissue, of pre-fertilized ovules
and zygote of fertilized ovule 0–5 hours after fertilization (HAF). Not
detected in developing embryos. T2 mature: Did not germinate. T3
seedlings: No seeds available.
Expected expression pattern: Expressed in ovules and different parts of
seeds
Selection Criteria:       Greater than 50x up in pi ovule microarray
Gene: hypothetical protein
GenBank: NM_123661 *Arabidopsis thaliana* expressed protein
(At5g42955) mRNA, complete cds
gi|18422274|ref|NM_123661.1|[18422274]
Source Promoter Organism: *Arabidopsis thaliana* WS
Vector:                   pNewBin4-HAP1-GFP
Marker Type:              X GFP-ER
Generation Screened:      XT1 Mature X T2 Seedling T2 Mature
                          T3 Seedling T1 Mature Plant Expression    Organs/Tissues screened
Events Screened: n = 3        Events Expressing: n = 3
GFP Expression Detected
☐Flower           ☐pedicel ☐receptacle ☐nectary ☐sepal ☐petal
                  ☐filament ☐anther ☐pollen ☐carpel ☐style ☐papillae
                  ☐vascular ☐epidermis ☐stomata ☐trichome
X Silique         ☐stigma ☐style ☐carpel ☐septum ☐placentae
                  ☐transmitting tissue ☐vascular ☐epidermis ☐stomata
                  ☐abscission zone H ovule
X Ovule           Pre-fertilization: ☐inner integument ☐outer
                  integument H embryo sac ☐funiculus ☐chalaza
                  ☐micropyle H gametophyte
                  Post-fertilization: H zygote ☐inner integument ☐outer
                  integument ☐seed coat ☐primordia ☐chalaza
                  ☐micropyle ☐early endosperm ☐mature endosperm
                  ☐embryo
☐Embryo           ☐suspensor ☐preglobular ☐globular ☐heart ☐torpedo
                  ☐late ☐mature ☐provascular ☐hypophysis ☐radicle
                  ☐cotyledons ☐hypocotyl
☐Stem             ☐epidermis ☐cortex ☐vascular ☐xylem ☐phloem
                  ☐pith ☐stomata ☐trichome
☐Leaf             ☐petiole ☐mesophyll ☐vascular ☐epidermis
                  ☐trichome ☐primordia ☐stomata ☐stipule ☐margin
X in the pre-fertilized ovule
X in the Egg cell (Ec) and Synergid cell (Sn) of the Female gametophyte (Fgm)
X in the Zygote (Zg) an Hour after fertilization (HAF)

T2 Seedling Expression    Tissues Screened
Events Screened: n = 2    Events Expressing: n = 0

Promoter Expression Report #46

Seedlings expressing/Seedlings screened
Event-01: No data. Event-02: No data.
No GFP Expression Detected
☐Hypocotyl ☐epidermis ☐cortex ☐vascular ☐xylem ☐phloem ☐stomata
☐Cotyledon ☐mesophyll ☐vascular ☐epidermis ☐trichome ☐margin ☐stomata
☐Rosette Leaf ☐mesophyll ☐vascular ☐epidermis ☐trichome ☐petiole ☐primordia ☐stomata ☐stipule ☐margin
☐Primary Root ☐epidermis ☐trichoblast atrichoblast ☐cortex ☐endodermis ☐vascular ☐xylem ☐phloem ☐pericycle ☐quiescent ☐columella ☐cap ☐root hairs
☐Lateral root ☐epidermis ☐initials ☐flanking cells ☐vascular ☐cap
☐Shoot apical meristem ☐SAM ☐epidermis T2 Mature Plant Expression
Plants expressing/Plants screened
Event-01: No germination.
Event-02: No germination.
☐Scheduled
☐T2 Mature tissue expressions similar to T1 expression data (data not shown).
☐T2 Mature tissue expression (if different expression pattern).
Expression detected T3 Seedling Expression
Seedlings expressing/Seedlings screened
Event-01: No seeds available.
Event-02: No seeds available.
☐Scheduled
☐T3 Seedling tissue expressions similar to T2 seedling expression (data not shown).
☐T2 Mature tissue expression (if different expression pattern).
GFP Expression Detected Promoter utility
Trait Area: Among other uses this promoter sequence is useful to improve: Seed, yield, quality
Sub-trait Area: Ovule/seed abortion, harvest index, test weight, seed size, total yield, amino acid, protein, total oil, total seed composition
Utility: This is promoter is useful for enhance of seed composition, seed size, seed number and yield, etc.

Construct: YP0096
Promoter Candidate I.D: 13148242 (Old ID: 11768682)
cDNA I.D: 4949423 (Old IDs: 12325608, 1007532)
T1 lines expressing (T2 seed): SR00775-01, -02

Sequence (SEQ ID NO: 46):

GAGGTCAGTGAGTCGATTGGTGCAAAATTGAAAAATTGAAGGGTGAAACAA

ATTTAAAGATAATATCTATTAAATCCTCTAATTTTAAAAATTTAGCAAAAA

TTGTATTTTCTTATGGATCTGTTAGTTCACACGTATCTTAATTAGTACCAA

ATCATATCTAATGATTAGTGATAAAACTAGTTAGATATCTATATGTGTCTT

TACCATTTAACTTGAATCCTTCTTCTTTTTTTACGTAAACAACTTGAATC

CTTCGTTAATACATAAATTTAAAGCATTTTTTCTTTAATTCTATTGATCGG

TATATATTTACTATAAGTTTTAGCTCATATGCAATTTCAAATGATATGCTT

TTAAATTTTGTCTAGGTGTGATAGTTGTATCTTTAACATAAATCTTATAGC

AAAATTATACTTGATATTCTAAATTTATCTATTTGCTCTTGTGAACCTCAT

ATTAGTCTAGAGAAACTTTGAAATCCTTTCAATTAGTTGTATGTCCAATAC

ATTTTTACTAACATTTATTAGTCTTTTTAATTAAGATTATTGTTAGAAAAA

AAAAGATTTTTTAAAAATAAATAATATGTTTTAGATACAATGTGAGTTAGG

CTTCTTATATTTTAAAAAATAAATTTATTTCATACTTAAAAATAGTTTGGA

ATTTCAATTTATTTGGCTGAATACCATAAAATATGTCAATTTGAACCTTAT

ACCCATTGACTATTTGGTGTTAGAAACCCTTTAACAAAAAAAAACTATTTG

GTGTTAGATATCAAAATAAAAAAAGTTTAACCATTGGTTTCTTATATTGAA

TTGGATATTGTTACATGTATTAAAGTTTTTTTGGTTTAATTTTGAAACGTT

GATAGAAACTATTAAGTTTAAGTTTGGTAGTATATTTATTTGTGGAAAATT

TAATTGCCATTAAATATAACGTCAACTTTTTTTGGTTTTTTTTGAGAAGTT

ACGTTGTGATTTTGATTTCCTATATAAAAGTTAGATTACGTCATTTTTTAA

Promoter Expression Report #47

Promoter Tested In: *Arabidopsis thaliana*, WS ecotype
Spatial expression summary:
Flower (H)pedicel, (H)stomata
Silique (M)stomata
Stem (M)stomata
Rosette Leaf (L)stomata
Primary Root (H)root hairs
Observed expression pattern: Guard cell expression throughout stem, pedicels, and siliques. High GFP preferential expression to root hairs of seedlings and medium to low expression in primary rosette leaves and petioles and stems. T2 mature: Same expression as T1 mature. T3 seedlings: Same expression as T2 seedlings.
Expected expression pattern: Expressed in ovules and different parts of seeds
Selection Criteria: Greater than 50x up in P1 ovule microarray
Gene: hypothetical protein
GenBank: NM_122878 *Arabidopsis thaliana* expressed protein (At5g34885) mRNA, complete cds
gi|30692647|ref|NM_122878.2|[30692647]
Source Promoter Organism: *Arabidopsis thaliana* WS
Vector: pNewBin4-HAP1-GFP
Marker Type: X GFP-ER
Generation Screened: X T1 Mature X T2 Seedling X T2 Mature X T3 Seedling T1 Mature Plant Expression Organs/Tissues screened
Events Screened: n = 3 Events Expressing: n = 2
GFP Expression Detected
☐Flower ☐pedicel ☐receptacle ☐nectary ☐sepal ☐petal ☐filament ☐anther ☐pollen ☐carpel ☐style ☐papillae ☐vascular ☐epidermis ☐stomata ☐trichome
☐Silique ☐stigma ☐style ☐carpel ☐septum ☐placentae ☐transmitting tissue ☐vascular ☐epidermis ☐stomata ☐abscission zone ☐ovule
☐Ovule Pre-fertilization: ☐inner integument ☐outer integument ☐embryo sac ☐funiculus ☐chalaza ☐micropyle ☐gametophyte
Post-fertilization: ☐zygote ☐inner integument ☐outer integument ☐seed coat ☐primordia ☐chalaza ☐micropyle ☐early endosperm ☐mature endosperm ☐embryo
☐Embryo ☐suspensor ☐preglobular ☐globular ☐heart ☐torpedo ☐late ☐mature ☐provascular ☐hypophysis ☐radicle ☐cotyledons ☐hypocotyl
X Stem ☐epidermis ☐cortex ☐vascular ☐xylem ☐phloem ☐pith M stomata ☐trichome
☐Leaf ☐petiole ☐mesophyll ☐vascular ☐epidermis ☐trichome ☐primordia ☐stomata ☐stipule ☐margin
X in the Guard cell (Gc) and Stomata (So) of the stem T2 Seedling Expression Tissues Screened
Events Screened: n = 2 Events Expressing: n = 2
Seedlings expressing/Seedlings screened
Event-01: No data. Event-02: No data
GFP Expression Detected

Promoter Expression Report #47

| | |
|---|---|
| ☐Hypocotyl | ☐epidermis ☐cortex ☐vascular ☐xylem ☐phloem ☐stomata |
| ☐Cotyledon | ☐mesophyll ☐vascular ☐epidermis ☐trichome ☐margin ☐stomata |
| X Rosette Leaf | ☐mesophyll ☐vascular ☐epidermis ☐trichome ☐petiole ☐primordia L stomata ☐stipule ☐margin |
| X Primary Root | ☐epidermis ☐trichoblast atrichoblast ☐cortex ☐endodermis ☐vascular ☐xylem ☐phloem ☐pericycle ☐quiescent ☐columella ☐cap H root hairs |
| ☐Lateral root | ☐epidermis ☐initials ☐flanking cells ☐vascular ☐cap |
| ☐Shoot apical meristem | ☐SAM ☐epidermis |

X in the root hairs of the root
X in the Guard cell (Gc) of the leaf and leaf petiole T2 Mature Plant Expression
Plants expressing/Plants screened
Event-01: ½   Event-02: 1/1
☐Scheduled
X T2 Mature tissue expressions similar to T1 expression data.
☐T2 Mature tissue expression (if different expression pattern).
Expression detected

| | |
|---|---|
| X Flower | H pedicel ☐receptacle ☐nectary ☐sepal ☐petal ☐filament ☐anther ☐pollen ☐carpel ☐style ☐papillae ☐vascular ☐epidermis ☐trichome |
| X Silique | ☐stigma ☐style ☐carpel ☐septum ☐placentae ☐transmitting tissue ☐vascular ☐epidermis M stomata ☐abscission zone ☐ovule |

X in the inflorescence meristem, pedicel and the pre-fertilized silique

T3 Seedling Expression
Seedlings expressing/Seedlings screened
Event-01: 2/3   Event-02: 2/3
☐Scheduled
X T3 Seedling tissue expressions similar to T2 seedling expression.
☐T2 Mature tissue expression (if different expression pattern).
GFP Expression Detected
X in the Epidermis (Ep)

Promoter utility
| | |
|---|---|
| Trait Area: | Among other uses this promoter sequence is useful to improve: Water use efficiency, PG&D, nutrient |
| Sub-trait Area: | Drought, heat, water use efficiency, plant size, low nitrogen utilization |
| Utility: | Useful for root nutrient uptake, plant growth under drought, heat |

| | |
|---|---|
| Construct: | YP0098 |
| Promoter Candidate I.D: | 12758479 |
| cDNA ID: | 4906343 (Old IDs: 12662283, 1024001) |
| T1 lines expressing (T2 seed): | SR00896-01, -02 |

Sequence (SEQ ID NO: 47):

TATTTTTATAAATTATCTTAGTAAAAGTATGTATTTTCTAATAGATCTGTT

AGTTCATACATATCTTAATTAGTGTTAAATTAGATCTAATGATTAGTGATA

AAGTTTTTAGATATCGATATAGGTGTCTTTACCATTTAACTTGAATCCTTT

GTTAATGTAAAATTTTAAAATATTTTGCTTTGATTCTACTTATTGGTATAT

AATTTTAACATATCAATCCAATGCCACTCTTAAATTATCATGTACTTTTCG

ATATATGTTATGACTCACTTGTTATGAAACAATGGATTTTCACCAATTTTG

GTTATTTATTAACTAGAAGTTTTAGCTCTTGTGCAATTTTAAATGATATGC

TTTTAAAATTGGTCTAGTTATAATAGTTGTATCTATAACATAAAACTTATA

ACAAAACTATACTTGATATTCAAAAATTATTGATTTGCTCTTGTGAACTTC

ATATTAGCCTAGAGAACTTTGAAAACCTTTCAATAAATTGTATGTCGAATA

AAGTTTTACAAACATTTATTAGCCATTTCGATTAAGACTATTGTGAGCAAA

AGTTTTTTTTATTATAAAATAAATAATATGTTTAAGATAAATTGTGAGTTA

GGCTTCTTATATTTTAAAAATTATATAAGTTTATACTGAAAAAGAGTTAAA

ATTTTCAAATTTTAAATTTATTTGGCTTAAGAACATAAATATGTCAATTTG

AACCTTATACCCACTAAATATTCCATGTTAGATAACGAAATAAAAGAAAAT

TAACTATTGGTTTCTTATATTGAATTGGATATTGTTACTTGTATTTATGTT

TTTTGTTTCATTTTTAAACGTTGATAAAATCATTAAACTAAAGTTTTGTAG

TATATTTATTTGTCGAAAATTTATTCCCATTAAATATAACGTTAAATTTAT

TTGTCTTTATTAAAAAAGTTACTTTGTGATTTTGATTTCCTATATAAATT

TAGATAACTTCAATTTTCAAATAAAAAAT

Promoter Expression Report #48

| | |
|---|---|
| Promoter Tested In: | Arabidopsis thaliana, WS ecotype |
| Spatial expression summary: | |
| Flower | (H)pedicel, (H)sepal, (H)vascular |
| Silique | (H)septum, (H)vascular |
| Stem | (H)vascular |
| Leaf | (H)petiole, (H)vascular, (H)phloem |
| Hypocotyl | (H)vascular |
| Primary Root | (H)vascular, (H)phloem |
| Observed expression pattern: | High GFP expression throughout mature and seedling vascular tissue. |
| T2 mature and T3 seedling: | Not screened. |
| Expected expression pattern: | Expressed in ovules and different parts of seeds |
| Selection Criteria: | Greater than 50× up in pi ovule micro-array |
| Gene: | unknown protein; expressed protein |
| GenBank: | NM_129068 Arabidopsis thaliana expressed protein (At2g35150) mRNA, complete cds gi\|30686319\|ref\| NM_129068.2[30686319] |
| Source Promoter Organism: | Arabidopsis thaliana WS |
| Vector: | pNewBin4-HAP1-GFP |
| Marker Type: | X GFP-ER |
| Generation Screened: | XT1 Mature X T2 Seedling T2 Mature T3 Seedling |

T1 Mature Plant Expression Organs/Tissues screened

Events Screened:  n = 2   Events Expressing:  n = 2
GFP Expression Detected

| | |
|---|---|
| X Flower | H pedicel ☐receptacle ☐nectary H sepal ☐petal ☐filament ☐anther ☐pollen ☐carpel ☐style ☐papillae H vascular ☐epidermis ☐stomata ☐trichome |
| X Silique | ☐stigma ☐style ☐carpel H septum ☐placentae ☐transmitting tissue H vascular ☐epidermis ☐stomata ☐abscission zone ☐ovule |
| ☐ Ovule | Pre-fertilization: ☐inner integument ☐outer integument ☐embryo sac ☐funiculus ☐chalaza ☐micropyle ☐gametophyte<br>Post-fertilization: ☐zygote ☐inner integument ☐outer integument ☐seed coat ☐primordia ☐chalaza ☐micropyle ☐early endosperm ☐mature endosperm ☐embryo |
| ☐ Embryo | ☐suspensor ☐preglobular ☐globular ☐heart ☐torpedo ☐late ☐mature ☐provascular ☐hypophysis ☐radicle ☐cotyledons ☐hypocotyl |
| X Stem | ☐epidermis ☐cortex H vascular ☐xylem ☐phloem ☐pith ☐stomata ☐trichome |

Promoter Expression Report #48

| | |
|---|---|
| X Leaf | H petiole ☐mesophyll H vascular ☐xylem H phloem ☐epidermis ☐trichome ☐primordia ☐stomata ☐stipule ☐margin |
| X in the Vascular (Vs) and Pedicel (Pd) of the inflorescence meristem | |
| X in the Vascular (Vs) of the sepal, leaf and stem | |
| X in the Sepal (Se) and Pedicel (Pd) of the flower bud | |
| X in the Septum (Sp) of the silique | |

T2 Seedling Expression Tissues Screened

Events Screened: n = 2  Events Expressing: n = 2
GFP Expression Detected

| | |
|---|---|
| X Hypocotyl | ☐epidermis ☐cortex H vascular ☐xylem ☐phloem ☐stomata |
| ☐ Cotyledon | ☐mesophyll ☐vascular ☐epidermis ☐trichome ☐margin ☐stomata |
| ☐ Rosette Leaf | ☐mesophyll ☐vascular ☐epidermis ☐trichome ☐petiole ☐primordia ☐stomata ☐stipule ☐margin |
| X Primary Root | ☐epidermis ☐trichoblast atrichoblast ☐cortex ☐endodermis H vascular ☐xylem H phloem ☐pericycle ☐quiescent ☐columella ☐cap ☐root hairs |
| ☐ Lateral root | ☐epidermis ☐initials ☐flanking cells ☐vascular ☐cap |
| ☐ Shoot apical meristem | ☐SAM ☐epidermis |
| X in the hypocotyl root transition zone | |
| X in the Phloem (Ph) of the Root (Rt) | |

T2 Mature Plant Expression Plants expressing/Plants screened

Event-01: Not screened.  Event-02: Not screened.
☐ Scheduled
☐ T2 Mature tissue expressions similar to T1 expression data (data not shown).
☐ T2 Mature tissue expression (if different expression pattern).
Expression detected
T3 Seedling Expression Seedlings expressing/Seedlings screened Event-01: Not screened.  Event-02: Not screened.
☐ Scheduled
☐ T3 Seedling tissue expressions similar to T2 seedling expression (data not shown).
☐ T2 Mature tissue expression (if different expression pattern).
GFP Expression Detected
Promoter utility

| | |
|---|---|
| Trait Area: | Among other uses this promoter sequence could is to improve: PG&D, nutrient, seed |
| Sub-trait Area: | Growth rate, plant size, low nitrogen use efficiency, nitrogen utilization, seed size and yield |
| Utility: | Useful for root nutrient uptake and transport, enhance plant growth rate under low nitrogen condition. Enhance plant to use water efficiently. |
| Construct: | YP0108 |
| Promoter Candidate I.D: | 11768683 |
| cDNA I.D: | 13601936 (Old IDs: 12339941 ,4768517) |
| T1 lines expressing (T2 seed): | SR00778-01,-02 |

Sequence (SEQ ID NO: 48):

TTAGCTGAACCAGGAAATTGATCTCTTATACCAGTTTCCGGGTTTAGATTG

GTTTGATGGCGATTTGATTAAACCCCCGAAATTTTATGTCGTAGTTGTGCA

TAGTATTATTATTCTTTGCGGACAATAGACGTATCGGGACCAAGTTCTGTA

GCAAAATTGTATAAGCTTAAGTTTGATGAAATTTAAAGGTAATCACTAAAA

CCCAAATGGGACAATAAACCGGTGAAGATTTAGAGTTTTTAATTTTGACTC

ATGAATCTGGAGAAAGAGCCCTCGTTAAAAGGAGTGAATCAATCCATAGGG

GAAAAAGTTTTGTCTTTTTAAAAACTAAAGAACCAAACCTTAATAGAAGCA

GCTCAATGTGTGACAACTTTCCACTGGCACTAAGATAAAGTGACTAGCGAT

GAGTGCAATTATTGAAATAGTAGATGGTAAATATTACATACAAGAGTAAAA

ATATCTTTATGTCAATGCTTAATTCAGTGTTTCTGGTTAACAAGAGAATCT

TCTCTAACTTTCGTAATTGGGTCTTATAAAATTTTATGCAATTATGATTTT

ACCCTTTTACTACTTTTCATTAGCTTTCACGAATCTATTTTGACAAGAGAA

ATCATTAGAGGTAAACATGCTTTTTGGTCAAGGGCCTTAACAGTTCCACCA

ATCAAGCTCAAAAGTTGTACTTAACCGACATCTTCTGTGAAAACATATAAT

TACATGTACAAATCAAAACTACCTTATGAAATAAATAGAAATATTGCAGTT

CATTTCTAATTTAACCTCTTCAACTTTTAAAACTATTTACATTTCTTTATG

TCATTTCTAGTCATTTTGATGCAAATTGTACCATTTATGGATTATCTTCAC

AAATTTTTAAGTTGGTGAAAACTTTTTGGTGGGTAGTTAAAACTTGAAATA

GAAATTTACTTTACCAAAATAAACTAATGAAAAGTAATCACTCCACTCCCT

ATAATAAGATTTCCAACGTTCCCACTAAGC

Promoter Expression Report #49

| | |
|---|---|
| Promoter Tested In: | Arabidopsis thaliana, WS ecotype |
| Spatial expression summary: | Screened under non-induced conditions. |
| Flower | (H)septum, (H)epidermis |
| Silique | (L)carpel, (H)septum, (H)epidermis, (M)vascular |
| Stem | (M)epidermis |
| Hypocotyl | (L)epidermis, (L)stomata |
| Cotyledon | (L)epidermis, (L)guard cell |
| Primary Root | (H)epidermis, (H)trichoblast, (H)atrichoblast, (H)root hairs |
| Observed expression pattern: | High preferential GFP expression in septum epidermal cells in siliques and root hair cells of seedlings. Low expression in cotyledon and hypocotyl epidermal cells. |
| T2 mature: | Stem epidermal and silique vascular expression observed in addition to expression observed in T1 mature. Expression in stem epidermal cells appears variable. |
| T3 seedling: | Same expression as T2 seedlings with additional guard cell expression in siliques. |
| Expected expression pattern: | Root |
| Selection Criteria: | Greater than 10× induced by Roundup. Induced in Arabidopsis microarray at 4 hours |
| Gene: | Hypothetical protein |
| GenBank: | NM_111930 Arabidopsis thaliana expressed protein (At3g10930) mRNA, complete cds gi\|30681550\|ref\| NM_111930.2\|[30681550] |
| Source Promoter Organism: | Arabidopsis thaliana WS |
| Vector: | pNewBin4-HAP1-GFP |
| Marker Type: | X GFP-ER |
| Generation Screened: | XT1 MatureX T2 Seedling X T2 Mature X T3 Seedling |

T1 Mature Plant Expression Organs/Tissues screened

Events Screened: n = 3  Events Expressing: n = 2
GFP Expression Detected

| | |
|---|---|
| X Flower | ☐pedicel ☐receptacle ☐nectary ☐sepal ☐petal ☐filament ☐anther ☐pollen ☐carpel ☐style H septum ☐papillae ☐vascular (H) epidermis ☐stomata ☐trichome |

Promoter Expression Report #49

| | |
|---|---|
| X Silique | ☐stigma ☐style L carpel H septum ☐placentae ☐transmitting tissue ☐vascular H epidermis ☐stomata ☐abscission zone ☐ovule |
| ☐ Ovule | Pre-fertilization: ☐inner integument ☐outer integument ☐embryo sac ☐funiculus ☐chalaza ☐micropyle ☐gametophyte<br>Post-fertilization: ☐zygote ☐inner integument ☐outer integument ☐seed coat ☐primordia ☐chalaza ☐micropyle ☐early endosperm ☐mature endosperm ☐embryo |
| ☐ Embryo | ☐suspensor ☐preglobular ☐globular ☐heart ☐torpedo ☐late ☐mature ☐provascular ☐hypophysis ☐radicle ☐cotyledons ☐hypocotyl |
| ☐ Stem | ☐epidermis ☐cortex ☐vascular ☐xylem ☐phloem ☐pith ☐stomata ☐trichome |
| ☐ Leaf | ☐petiole ☐mesophyll ☐vascular ☐epidermis ☐trichome ☐primordia ☐stomata ☐stipule ☐margin |

X in the Septum (Sp) and Epidermis (Ep) of the silique Carpel (Ca), Style (Sy).
T2 Seedling Expression Tissues Screened Events Screened: n = 2 Events Expressing: n = 2
Seedlings expressing/Seedlings screened Event-01: No data. Event-02: No data.
GFP Expression Detected

| | |
|---|---|
| X Hypocotyl | L epidermis ☐cortex ☐vascular ☐xylem ☐phloem L stomata |
| X Cotyledon | ☐mesophyll ☐vascular L epidermis ☐trichome ☐margin ☐stomata |
| ☐ Rosette Leaf | ☐mesophyll ☐vascular ☐epidermis ☐trichome ☐petiole ☐primordia ☐stomata ☐stipule ☐margin |
| X Primary Root | H epidermis H trichoblast H atrichoblast ☐cortex ☐endodermis ☐vascular ☐xylem ☐phloem ☐pericycle ☐quiescent ☐columella ☐cap H root hairs |
| ☐ Lateral root | ☐epidermis ☐initials ☐flanking cells ☐vascular ☐cap |
| ☐ Shoot apical meristem | ☐SAM ☐epidermis |

X in the Epidermis (Ep) and Root Hair (Rh) of the hypocotyl
X in the Epidermis (Ep) of the cotyledon
X in the Atrichoblast (At) and Trichoblast (Tr) of the root differentiation zone
T2 Mature Plant Expression Plants expressing/Plants screened Event-01: 2/2 Event-02: 2/2
☐ Scheduled
☐ T2 Mature tissue expressions similar to T1 expression data (data not shown).
☐ T2 Mature tissue expression (if different expression pattern).
Expression detected

| | |
|---|---|
| X Flower | ☐pedicel ☐receptacle ☐nectary ☐sepal ☐petal ☐filament ☐anther ☐pollen ☐carpel ☐style H septum ☐papillae ☐vascular (H) epidermis ☐stomata ☐trichome |
| X Silique | ☐stigma ☐style L carpel H septum ☐placentae ☐transmitting tissue M vascular H epidermis ☐stomata ☐abscission zone ☐ovule |
| X Stem | M epidermis ☐cortex ☐vascular ☐xylem ☐phloem ☐pith ☐stomata ☐trichome |

X in the Epidermis (Ep) and Vasculature (Vs) of the silique
X in the Epidermis (Ep) and Cortex (Cr) of the stem
T3 Seedling Expression Seedlings expressing/Seedlings screened Event-01: No germination. Event-02: 2/3
☐ Scheduled X T3 Seedling tissue expressions similar to T2 seedling expression.
☐ T2 Mature tissue expression (if different expression pattern).
GFP Expression Detected X in the root
Promoter utility

| | |
|---|---|
| Trait Area: | Among other uses this promoter sequence is useful to improve: Water use efficiency, PG&D, nutrient, yield |
| Sub-trait Area: | Drought, growth rate, plant size, low nitrogen use efficiency, nitrogen utilization; seed yield |
| Utility: | Useful for root nutrient uptake, enhance plant growth rate under low nitrogen condition. Enhance plant to use water efficiency, useful for pod shatter |
| Construct: | YP0134 |
| Promoter Candidate I.D: | 11768684 |
| cDNA I.D: | 13489977 (Old IDs: 12332605, 6403797) |
| T1 lines expressing T2 seed: | SR00780-02,-03 |

Sequence (SEQ ID NO: 49):

CCTACTTTAGGCTTAAACAAGAAGAAAATATGACTGCTAAGTCATATTTTT

CAACTCTCATGAGCAACCGTAAAGTTGCACCGCAATATCCAACAAATGACA

TTCGTGTTATCTACAATCTAATGTTGAAAATTTGGCTCATCTAATAAAGGA

GACAAAAGTTATATCTCTTTCACACACACGTTAATGGAAGTGTAAAGGCGG

TGAGAGTGTGGGAGAGACTTGGGGAACAAGAAGAAGGACGCGGTCAAAAAG

TGACGGTGGGCTACGGCTTTTCTTGGTAGCAGTTGGAAATTCCATTAATGA

CTTAAAAAGTGTAAATCTTATCTTCTTTTTATTTTCTGATTTGATATGCAC

ATTCATTTCATGAAAATATTTGTATAGTTTGATGATCATACGACAAACTTA

TAGGGTTCACAAAGTAGATGCAATAGTTGCATACCTCTGTTTAAATGTTCT

TGTTAATATTATAATTGATGACGGAACTCGTGAATGTTATTCAAAATGTCC

ATGTAATTCAAGATCATGCACTATAATAAGTAATCTATCATTTTCAGCACA

ACAATTTTGACAAAAAGTAAAAATAAAATAGAGTAAACTGATATCATATTT

CCGAATTATATATATAAACGTTTTCTGTTTCTCAATGGTCTCTTTCACTCT

TGTGTTTTCTAATATTTCATTTAAACCTATTTCTAAACTAAGCACATCTTT

GTTGATTGATTGCATTTCAACCAAAATCGATAACCGAATCATTGTTTTTTT

ATGTTTTATTTCAGCTTACCACACACGTTTAGAATTTTAAAAATAAAACAA

AAAAAAGTTAACTCGTTACAAATGAAAATGATATTTTTAATTGGACTCGAT

GGAAAGGACCAATTTATTCAACACTATTGTTTAGTCCGAACACTTGCCGCG

TAAGTTTTCCAACTCCCCCCATTGACCTTTCGCACTTTCACAAACTCCGTA

TATATATAATGGATACACTCTCTCTTTGATCT

Promoter Expressiong Report #50

| | |
|---|---|
| Promoter Tested In: | *Arabidopsis thaliana*, WS ecotype |
| Spatial expression summary: | Screened under non-induced conditions |
| Flower | (H)pedicel, (L)petal, (H)silique |
| Silique | (H)carpel, (H)cortex, (H)epidermis |

Promoter Expressiong Report #50

| | |
|---|---|
| Ovule | Post-fertilization: (L)outer integument |
| Embryo | (L)mature |
| Stem | (M)epidermis, (H)cortex, (H)endodermis |
| Leaf | (H)petiole, (H)mesophyll, (H)epidermis |
| Cotyledon | (H)mesophyll, (H)epidermis |
| Rosette Leaf | (H)mesophyll, (L)vascular, (H)epidermis |
| Primary Root | (H)cortex |
| Lateral root | (H)cortex, (H)flanking cells |
| Observed expression pattern: | High preferential GFP expression in photosynthetic, cortical and epidermal tissues in mature plants and seedlings. |
| T2 mature: | Weak outer integument expression in mature ovules and mature embryo in addition to expression observed in T1 mature plants. |
| T3 seedling: | Same expression observed as T2 seedlings (seen in one event). Weak epidermal and high lateral root flanking cell expression observed in second event. |
| Expected expression pattern: | Root hairs |
| Selection Criteria: | Ceres Microarray 2.5–5× down in rhi (root hair less) mutant |
| Gene: | probable auxin-induced protein |
| GenBank: | NM_119642 *Arabidopsis thaliana* auxin-induced (indole-3-acetic acid induced) protein family (At4g34760) mRNA, complete cds gi\|30690121\| ref\|NM_119642.2\|[30690121] |
| Source Promoter Organism: | *Arbidopsis thaliana* WS |
| Vector: | pNewBin4-HAP1-GFP |
| Marker Type: | X GFP-ER |
| Generation Screened: | XT1 Mature X T2 Seedling X T2 Mature X T3 Seedling |

T1 Mature Plant Expression Organs/Tissues screened

Events Screened: n = 3  Events Expressing: n = 2
GFP Expression Detected

| | |
|---|---|
| X Flower | H pedicel □receptacle □nectary □sepal L petal □filament □anther □pollen □carpel □style H silique □papillae □vascular □epidermis □stomata □trichome |
| X Silique | □stigma □style H carpel H Cortex □septum □placentae □transmitting tissue □vascular H epidermis □stomata □abscission zone □ovule |
| □ Ovule | Pre-fertilization: □inner integument □outer integument □embryo sac □funiculus □chalaza □micropyle □gametophyte Post-fertilization: □zygote □inner integument □outer integument □seed coat □primordia □chalaza □micropyle □early endosperm □mature endosperm □embryo |
| □ Embryo | □suspensor □preglobular □globular □heart □torpedo □late □mature □provascular □hypophysis □radicle □cotyledons □hypocotyl |
| X Stem | M epidermis H cortex H endodermis □vascular □xylem □phloem □pith □stomata □trichome |
| X Leaf | H petiole H mesophyll □vascular H epidermis □trichome □primordia □stomata □stipule □margin |

X in the inflorescence meristem
X in the Epidermis (Ep) of the petal and stem
X in the Epidermis (Ep), Mesophyll (Me) and Cortex (Cr) of the silique
X in the Epidermis (Ep) and Cortex (Cr) of the stem
X in the Epidermis (Ep) and Mesophyll (Me) of the leaf
T2 Seedling Expression Tissues Screened Events Screened: n = 2  Events Expressing: n = 2
Seedlings expressing/Seedlings screened Event-01: No data  Event-02: No data

Promoter Expressiong Report #50

GFP Expression Detected

| | |
|---|---|
| □ Hypocotyl | □epidermis □cortex □vascular □xylem □phloem □stomata |
| X Cotyledon | H mesophyll □vascular H epidermis □trichome □margin □stomata |
| X Rosette Leaf | H mesophyll L vascular H epidermis □trichome □petiole □primordia □stomata □stipule □margin |
| X Primary Root | □epidermis □trichoblast atrichoblast H cortex □endodermis □vascular □xylem □phloem □pericycle □quiescent □columella □cap □root hairs |
| X Lateral root | □epidermis □initials □flanking cells H cortex □vascular □cap |
| □ Shoot apical meristem | □SAM □epidermis |

X in the rosette leaf
X in the Epidermis (Ep) and Mesophyll (Me) of the cotyledon and rosette leaf
X in the Vasculature (Vs) of the rosette leaf
X in the Cortex (Cr) of the lateral root, the root elongation zone and the root tip
T2 Mature Plant Expression Plants expressing/Plants screened Event-01: 1/2  Event-02: 1/1
□ Scheduled
X T2 Mature tissue expressions similar to T1 expression data.
X T2 Mature tissue expression (if different expression pattern).
Expression detected

| | |
|---|---|
| X Ovule | Pre-fertilization: □inner integument □outer integument □embryo sac □funiculus □chalaza □micropyle □gametophyte Post-fertilization: □zygote □inner integument L outer integument □seed coat □primordia □chalaza □micropyle □early endosperm □mature endosperm □embryo |
| X Embryo | □suspensor □preglobular □globular □heart □torpedo □late L mature □provascular □hypophysis □radicle □cotyledons □hypocotyl |

X in the Epidermis (Ep) and Cortex (Cr) of the stem
X in the Micropyle (Mp) of the mature ovule
T3 Seedling Expression Seedlings expressing/Seedlings screened Event-01: 1/3  Same as T2 seedling. No images.
Event-02: 2/6  Weak epidermis, no root expression, high lateral root flanking cell expression.
□ Scheduled
X T3 Seedling tissue expressions similar to T2 seedling expression (data not shown).
X T2 Mature tissue expression (if different expression pattern).
GFP Expression Detected

| | |
|---|---|
| X Lateral root | □epidermis □initials H flanking cells □cortex □vascular □cap |

X in the flanking cells of the Lateral root (Lr) in the root transition zone
Promoter utility

| | |
|---|---|
| Trait Area: | Among other uses this promoter sequence is useful to improve: PG&D, Nutrient; C3–C4 optimization |
| Sub-trait Area: | Low nitrogen use efficiency, nitrogen utilization, low nitrogen tolerance plant size, growth rate, water use efficiency; manipulate expression of C3–C4 enzymes in leaves |
| Utility: | Useful for root nutrient uptake and transport, enhance plant growth rate, also for enhance of plant water use efficiency |
| Additional notes: | |

X in the Epidermis (Ep) and Mesophyll (Me) of the leaf

| | |
|---|---|
| Construct: | YP0138 |
| Promoter Candidate I.D: | 13148247 (Old ID: 11768685) |

Promoter Expressiong Report #50

| | |
|---|---|
| cDNA I.D: | 12333534 (Old ID: 7077536) |
| T1 lines expressing (T2 seed): | SR00781-01,-02,-03 |

Sequence (SEQ ID NO: 50):

TGTGTGTCCTAAATAGTTTCTTTTTAAAATTTGTAAATACCAAGACGCGTA

TTTAAGAGTATTTTGAAAAGATATTTGATTATAAAAAGAAAGAAAAAGAGA

AGGCTGAGGATTAACTGCAACGTCTACCGTTGGAAAAGAAAAACGATCAGA

AAACACAGAAATTAATAAAAAGAGAGAAAAAAAAATAGAGTATGAGAGATG

CACATGGGTGCCTGCAAAAAAAAGGTAGAAGAAATTTGTCTGAAAGTGTCA

CAGGCACACTCTCTCGAACCACATTTAACAACACTCCAAACACTCTTCTTC

TACTTTGTACCCTTCAGTACATTACTCTTTCCAAAGTCCGTGATTTACGCT

CTTCGATGACACCTCTCAACAGAGAGAGACTACATGTGTACATTTTCTTCT

ACCATTAAATTTTGAAGATTTTCGATGATTCAATTTAGTATATATATGGAA

GATAAAATTTTCATTGTCTTTCTACATGATAGTAACGGTTTTAGAAGGGTG

GTTATCACTTATAGTATTTGAGTTAAGAAATATAAAAATATACGTGACTGT

TTTTCCTTGTAAACTATTTTTAGGCCCTTATTTTTATTCAAGTAGTCACAT

ACGTGTTTGAAGTGTATTTAACTAAGAAAAAGAAAGTAGGAAATGAAAAGG

ATATAGTATTTATGGTGTAATCTTGGTAAGGACCAGGAGATCAGAAGGGGC

CACAATGTCACAAAGAGGACCAACAATGAAATTAAATCCACAGCTGGCCTT

TAACATTTTGGCTCCCACCATCTCCTTCCACACATATGCACATGTCTTCAT

GTCTCTCTCTCTATACGTTACCTACACAAATATGTACAGACAAATAGCC

CATTACAAAATCTTTATTTATAAATATATACTCCTCAACTCCCTCAATATC

CACCCATCTCCTTCTCCATAACTCTCTCTCTCTCCCTAAACACAACCAA

AAGACTTTTATCTCTCAGGAACCCCAAAAAC

Promoter Expression Report #51

| | |
|---|---|
| Promoter Tested In: | *Arabidopsis thaliana*, WS ecotype |
| Spatial expression summary: | Screened under non-induced condition |
| Flower | (L)epidermis, (L)pedicel, (L)receptacle, (L)stomata |
| Silique | (L)stomata |
| Stem | (L)epidermis, (L)stomata |
| Rosette Leaf | (L)stomata |
| Primary Root | (H)root hairs |
| Observed expression pattern: | GFP is preferentially expressed in epidermal root hairs of hypocotyl root transition zone. Low expression in stomatal cells of stem and siliques of mature T1 plants. |
| T2 mature: | No expression detected. |
| T3 seedling: | Same as T2 seedling expression detected in one of two events. |
| Expected expression pattern: | Induced by different forms of stress (e.g., drought, heat, cold) |
| Selection Criteria: | *Arabidopsis* microarray |
| Gene: | putative strictosidine synthase |
| GenBank: | NM_129692 *Arabidopsis thaliana* late embryogenesis abundant M10 protein (At2g41280) mRNA, complete cds gi\|30688595\|ref\|NM_129692.2\|[30688595] |

Promoter Expression Report #51

| | |
|---|---|
| Source Promoter Organism: | *Arabidopsis thaliana* WS |
| Vector: | pNewBin4-HAP1-GFP |
| Marker Type: | X GFP-ER |
| Generation Screened: | T1 Mature X T2 Seedling X T2 Mature X T3 Seedling |

T1 Mature Plant Expression Organs/Tissues screened

Events Screened:  n = 4   Events Expressing:  n = 4
GFP Expression Detected

| | |
|---|---|
| X Flower | L pedicel L receptacle ☐nectary ☐sepal ☐petal ☐filament ☐anther ☐pollen ☐carpel ☐style ☐papillae ☐vascular L epidermis L stomata ☐trichome |
| X Silique | ☐stigma ☐style ☐carpel ☐septum ☐placentae ☐transmitting tissue ☐vascular ☐epidermis L stomata ☐abscission zone ☐ovule |
| ☐ Ovule | Pre-fertilization: ☐inner integument ☐outer integument ☐embryo sac ☐funiculus ☐chalaza ☐micropyle ☐gametophyte Post-fertilization: ☐zygote ☐inner integument ☐outer integument ☐seed coat ☐primordia ☐chalaza ☐micropyle ☐early endosperm ☐mature endosperm ☐embryo |
| ☐ Embryo | ☐suspensor ☐preglobular ☐globular ☐heart ☐torpedo ☐late ☐mature ☐provascular ☐hypophysis ☐radicle ☐cotyledons ☐hypocotyl |
| X Stem | L epidermis ☐cortex ☐vascular ☐xylem ☐phloem ☐pith L stomata ☐trichome |
| ☐ Leaf | ☐petiole ☐mesophyll ☐vascular ☐epidermis ☐trichome ☐primordia ☐stomata ☐stipule ☐margin |

X in the Guard cells (Gc) of the flower pedicel, the siligue and the stem
T2 Seedling Expression Organs/Tissues Screened Events Screened:  n = 2   Events Expressing:  n = 2
Seedlings expressing/Seedlings screened Event-01:  1/3  Event-02:  1/3
GFP Expression Detected

| | |
|---|---|
| ☐ Hypocotyl | ☐epidermis ☐cortex ☐vascular ☐xylem ☐phloem ☐stomata |
| ☐ Cotyledon | ☐mesophyll ☐vascular ☐epidermis ☐trichome ☐margin ☐stomata |
| X Rosette Leaf | ☐mesophyll ☐vascular ☐epidermis ☐trichome ☐petiole ☐primordia L stomata ☐stipule ☐margin |
| X Primary Root | ☐epidermis ☐trichoblast atrichoblast ☐cortex ☐endodermis ☐vascular ☐xylem ☐phloem ☐pericycle ☐quiescent ☐columella ☐cap H root hairs |
| ☐ Lateral root | ☐epidermis ☐initials ☐flanking cells ☐vascular ☐cap |
| ☐ Shoot apical meristem | ☐SAM ☐epidermis |

X in the Guard cell (Gc) of the rosette leaf
X in the Root hair (Rh) of the hypocotyl root transition zone
T2 Mature Plant Expression Plants expressing/Plants screened Event-01:  0/3  Event-02:  0/2
☐ Scheduled
☐ T2 Mature tissue expressions similar to T1 expression data (data not shown).
☐ T2 Mature tissue expression (if different expression pattern).
No expression detected
T3 Seedling Expression Seedlings expressing/Seedlings screened Event-01:  2/3  Event-02:  0/3
☐ Scheduled
X T3 Seedling tissue expressions similar to T2 seedling expression data not shown
☐ T2 Mature tissue expression (if different expression pattern).

Promoter Expression Report #51

| | |
|---|---|
| GFP Expression Detected | |
| Promoter utility | |
| Trait Area: | Stress |
| Sub-trait Area: | |
| Utility: | Among other uses this promoter sequence is useful to improve: Tolerance to stress and to increase plant growth or seed yield under stress conditions |
| Construct: | YP0177 |
| Promoter Candidate I.D: | 11768710 |
| cDNA I.D: | 12735519 (Old ID: 2709268) |
| T1 lines expressing (T2 seed): | SR00900-01,-02,-03,-04 |

Sequence (SEQ ID NO: 51):

tgTGTGTCCTAAATAGTTTCTTTTTAAAATTTGTAAATACCAAGACGCGTA

TTTAAGAGTATTTTGAAAAGATATTTGATTATAAAAAGAAAgaaaaagagA

AGGCTGAGGATTAACTGCAACGTCTACCGTTGGAAAAGAAAAACGATCAGA

AAACACAGAAATTAATAAAAAGAGAGAAAAAAAAATAGAGTATGAGAGATG

CACATGGGTGCCTGCAAAAAAAAGGTAGAAGAAATTTGTCTGAAAGTGTCA

CAGGCACACTCTCTCGAACCACATTTAACAACACTCCAAACACTCTTCTTC

TACTTTGTACCCTTCAGTACATTACTCTTTCCAAAGTCCGTGATTTACGCT

CTTCGATGACACCTCTCAACAGAGAGAGACTACAtgtgtACATTTTCTTCT

ACCATTAAATTTTGAAGATTTTCGATGATTCAATTTAGTATATATATGGAA

GATAAATTTTCATTGTCTTTCTACATGATAGTAACGGTTTTAGAAGGGTG

GTTATCACTTATAGTATTTGAGTTAAGAAATATAAAAATATACGTGACTGT

TTTTCCTTGTAAACTATTTTTAGGCCCTTATTTTTATTCAAGTAGTCACAT

ACGTGTTTGAAGTGTATTTAACTAAGAAAAAGAAAGTAGGAAATGAAAAGG

ATATAGTATTTATGGTGTAATCTTGGTAAGGACCAGGAGATCAGAAGGGGC

CACAATGTCACAAAGAGGACCAACAATGAAATTAAATCCTCAGCTGGCCTT

TAACATTTTGGCTCCCACCATCTCCTTCCACACATATGCACATGTCTTCAT

GTCTCTCTCTCtctatACGTTACCTACACAAATATGTACAGACAAATAGCC

CATTACAAAATCTTTATTTATAAATATATACTCCTCAACTCCCTCAATATC

CACCCATCTCCTTCTCCATAACTCTCTCTCTCTCCCTAAACACAACCAA

AGACTTTTATCTCTCAGGAACCCCAAAAac

Promoter Expression Report #52

| | |
|---|---|
| Promoter Tested In: | *Arabidopsis thaliana*, WS ecotype |
| Spatial expression summary: | |
| Flower | (L)sepal, (L)vascular |
| Rosette Leaf | (L)vascular, (L)stomata |
| Observed expression pattern: | Weak GFP expression in sepal vasculature of developing flower buds. Weak expression in vasculature and guard cells of rosette leaves. Not detected in mature flowers. |
| T2 mature: | Same expression as T1 mature detected in one of two events. Vascular expression in pedicels of developing flowers. |
| T3 seedlings: | No expression detected. |
| Expected expression pattern: | Shoot apex including leaf primordia and parts of leaves |

Promoter Expression Report #52

| | |
|---|---|
| Selection Criteria: | Greater than 5× up in stm microarray |
| Gene: | unknown protein |
| GenBank: | NM_122151 *Arabidopsis thaliana* esterase/lipase/thioesterase family (At5g22460) mRNA, complete cds gi| 30688485|ref|NM_122151.2| [30688485] |
| Source Promoter Organism: | *Arabidopsis thaliana* WS |
| Vector: | pNewBin4-HAP1-GFP |
| Marker Type: | X GFP-ER |
| Generation Screened: | X T1 Mature X T2 Seedling X T2 Mature X T3 Seedling |

T1 Mature Plant Expression Organs/Tissues screened

Events Screened: n = 2   Events Expressing: n = 2
GFP Expression Detected

| | |
|---|---|
| X Flower | ☐pedicel ☐receptacle ☐nectary L sepal ☐petal ☐filament ☐anther ☐pollen ☐carpel ☐style ☐papillae L vascular ☐epidermis ☐stomata ☐trichome |
| ☐ Silique | ☐stigma ☐style ☐carpel ☐septum ☐placentae ☐transmitting tissue ☐vascular ☐epidermis ☐stomata ☐abscission zone ☐ovule |
| ☐ Ovule | Pre-fertilization: ☐inner integument ☐outer integument ☐embryo sac ☐funiculus ☐chalaza ☐micropyle ☐gametophyte Post-fertilization: ☐zygote ☐inner integument ☐outer integument ☐seed coat ☐primordia ☐chalaza ☐micropyle ☐early endosperm ☐mature endosperm ☐embryo |
| ☐ Embryo | ☐suspensor ☐preglobular ☐globular ☐heart ☐torpedo ☐late ☐mature ☐provascular ☐hypophysis ☐radicle ☐cotyledons ☐hypocotyl |
| ☐ Stem | ☐epidermis ☐cortex ☐vascular ☐xylem ☐phloem ☐pith ☐stomata ☐trichome |
| ☐ Leaf | ☐petiole ☐mesophyll ☐vascular ☐epidermis ☐trichome ☐primordia ☐stomata ☐stipule ☐margin |

X in the Vasculature (Vs) of the inflorescence meristem and the Sepal (Se)
T2 Seedling Expression Organs/Tissues Screened Events Screened: n = 2   Events Expressing: n = 2
Seedlings expressing/Seedlings screened Event-01: No data   Event-02: No data
GFP Expression Detected

| | |
|---|---|
| ☐ Hypocotyl | ☐epidermis ☐cortex ☐vascular ☐xylem ☐phloem ☐stomata |
| ☐ Cotyledon | ☐mesophyll ☐vascular ☐epidermis ☐trichome ☐margin ☐stomata |
| X Rosette Leaf | ☐mesophyll L vascular ☐epidermis ☐trichome ☐petiole ☐primordia L stomata ☐stipule ☐margin |
| ☐ Primary Root | ☐epidermis ☐trichoblast atrichoblast ☐cortex ☐endodermis ☐vascular ☐xylem ☐phloem ☐pericycle ☐quiescent ☐columella ☐cap ☐root hairs |
| ☐ Lateral root | ☐epidermis ☐initials ☐flanking cells ☐vascular ☐cap |
| ☐ Shoot apical meristem | ☐SAM ☐epidermis |

X in the Guard cell (Gc) and Vasculature (Vs) of the leaf
T2 Mature Plant Expression Plants expressing/Plants screened Event-01: 1/1   Event-02: 0/2
☐ Scheduled
X T2 Mature tissue expressions similar to T1 expression data.
☐ T2 Mature tissue expression (if different expression pattern).

Promoter Expression Report #52

Expression detected

X in the inflorescence meristem
T3 Seedling Expression Seedlings expressing/Seedlings screened Event-01: 0/3  Event-02: 0/2
☐ Scheduled
☐ T3 Seedling tissue expressions similar to T2 seedling expression (data not shown).
☐ T2 Mature tissue expression (if different expression pattern).
No GFP Expression Detected

| Promoter utility | |
|---|---|
| Trait Area: | Among other uses this promoter sequence could be useful to improve: Water use efficiency |
| Sub-trait Area: | Water use efficiency |
| Construct: | YP0192 |
| Promoter Candidate ID: | 11768715 |
| cDNA I.D: | 12688453 (Old IDs: 12384618, 3434328) |
| T1 lines expressing (T2 seed): | SR00908-01,-02 |
| Utility: | This is weak promoter expressed in guard cell and flower. Useful for water use efficiency |

Sequence (SEQ ID NO: 52):

TCCTCCTACTGTCTGCTACGTCAACAAGTGGATTGCAATCAGACGGTGATT

GTGTCTCTTTTCATTCTCTCTCTTTTACTAATTTCTCTGATAATTAAACTG

AGAATGTATATTAAGAAAAAAAAACAAAAACAAGAGAGGAATTTTCATACA

CACTAACTTAAGACTCTTTGTAAGTTTTCCCAAATATGGATTTTCTAGTAT

AAATATGAGTTCATTAGTTTCACCAAGCCTACAAGCATCTCTCCATCTCAA

ATCATATTCACCTAAAAATCAGGTCCCCTCTCTTTATATCTCTAACATTCT

TATATCAGATCATATTTTTTGGATTTCTTGTTAAGTAACACCAATCTTTTA

AAAGTGTTTTCAGGTTAATATAAAAGAATAATGATGTTTTCGGTGACGGTT

GCGATCCTTGTTTGTCTTATTGGCTACATTTACCGATCATTTAAGCCTCCA

CCACCGCGAATCTGCGGCCATCCTAACGGTCCTCCGGTTACTTCTCCGAGA

ATCAAGCTCAGTGATGGAAGATATCTTGCTTATAGAGAATCTGGGGTTGAT

AGAGACAATGCTAACTACAAGATCATTGTCGTTCATGGCCTCAACAGCTCC

AAAGACACTGAATTTTCCATCCCTAAGGTTCACTCTTATTCTCAATATTAA

CTCTCGTACATGTCACATGCCCATTTTCACCATTTTAGATATACAGTTTTG

ATACTTTACTTTGCATTTATTTTGCTATATGTAATTGAGGATATTGTTTTA

ATTTCTTTGGGTTTTTTTTTTCGGCTAAATGAGAATTCACTGTCTTTGGT

TCTTGAAAAAAAAGTATTTGTTAATGGTAAACGCTAAACGCTATTTGAGTT

TATGTTTTTTCAAGAACTGAAAACGTTTTATTGAAAATATACACTTTTTTT

GCTATTTATAGGAAAGCATATCACATCACATCTAGACGCAAACGCAAAATT

GAGTTTTAAAGCAACCACAATCTTAAATGCAATGAAA

Promoter Expression Report #53

| Promoter Tested In: | *Arabidopsis thaliana*, WS ecotype |
|---|---|
| Spatial expression summary: | |
| Flower | (H)pedicel, (H)vascular |
| Primary Root | (H)epidermnis, (H)trichoblast, (H)atrichoblast, (L)root hair |

Promoter Expression Report #53

| Observed expression pattern: | |
|---|---|
| T1 mature: | High GFP expression specific in floral pedicel vascular tissue of developing flowers. Not detected in pedicels and stems of mature plants. High GFP expression throughout epidermal layers of primary seedling root. |
| T2 mature: | No expression in 3 plants observed. |
| T3 seedling: | Same as T2 seedling expression. |
| Expected expression pattern: | Inducible promoter - induced by different forms of stress (e.g., drought, heat, cold). |
| Selection Criteria: | *Arabidopsis* microarray |
| Gene: | Reticuline oxidase; berberine bridge enzyme |
| GenBank: | NM_102806 *Arabidopsis thaliana* FAD-linked oxidoreductase family (At1g30700) mRNA, complete cds gi| 30692021|ref|NM_102806.2|[30692021] |
| Source Promoter Organism: | *Arabidopsis thaliana* WS |
| Vector: | pNewBin4-HAP1-GFP |
| Marker Type: | X GFP-ER |
| Generation Screened: | X T1 Mature X T2 Seedling X T2 Mature X T3 Seedling |

T1 Mature Plant Expression Organs/Tissues screened

Events Screened: n = 4  Events Expressing: n = 2
GFP Expression Detected

| X Flower | H pedicel ☐receptacle ☐nectary ☐sepal ☐petal ☐filament ☐anther ☐pollen ☐carpel ☐style ☐papillae H vascular ☐epidermis ☐stomata ☐trichome |
|---|---|
| ☐ Silique | ☐stigma ☐style ☐carpel ☐septum ☐placentae ☐transmitting tissue ☐vascular ☐epidermis ☐stomata ☐abscission zone ☐ovule |
| ☐ Ovule | Pre-fertilization: ☐inner integument ☐outer integument ☐embryo sac ☐funiculus ☐chalaza ☐micropyle ☐gametophyte Post-fertilization: ☐zygote ☐inner integument ☐outer integument ☐seed coat ☐primordia ☐chalaza ☐micropyle ☐early endosperm ☐mature endosperm ☐embryo |
| ☐ Embryo | ☐suspensor ☐preglobular ☐globular ☐heart ☐torpedo ☐late ☐mature ☐provascular ☐hypophysis ☐radicle ☐cotyledons ☐hypocotyl |
| ☐ Stem | ☐epidermis ☐cortex ☐vascular ☐xylem ☐phloem ☐pith ☐stomata ☐trichome |
| ☐ Leaf | ☐petiole ☐mesophyll ☐vascular ☐epidennis ☐trichome ☐primordia ☐stomata ☐stipule ☐margin |

X in the inflorescence meristem
T2 Seedling Expression Organs/Tissues Screened

Events Screened: n = 2  Events Expressing: n = 2
Seedlings expressing/Seedlings screened Event-01: No data.  Event-02: No data.
GFP Expression Detected

| ☐ Hypocotyl | ☐epidermis ☐cortex ☐vascular ☐xylem ☐phloem ☐stomata |
|---|---|
| ☐ Cotyledon | ☐mesophyll ☐vascular ☐epidermis ☐trichome ☐margin ☐stomata |
| ☐ Rosette Leaf | ☐mesophyll ☐vascular ☐epidermis ☐trichome ☐petiole ☐primordia ☐stomata ☐stipule ☐margin |
| X Primary Root | H epidermis H trichoblast H atrichoblast ☐cortex ☐endodermis ☐vascular ☐xylem ☐phloem ☐pericycle ☐quiescent ☐columella ☐cap L root hairs |

Promoter Expression Report #53

☐ Lateral root ☐epidermis ☐initials ☐flanking cells ☐vascular ☐cap
☐ Shoot apical meristem ☐SAM ☐epidermis
X in the seedling root
X in the Epidermis (Ep) and Root hair (Rh) of the hypocotyl root transition zone
X in the Epidermis (Ep) and Root hair (Rh) of the root differentiation zone
T2 Mature Plant Expression Plants expressing/Plants screened Event-01: 0/3 Event-02: 0/3
☐ Scheduled
☐ T2 Mature tissue expressions similar to T1 expression data (data not shown).
☐ T2 Mature tissue expression (if different expression pattern).
No expression detected
T3 Seedling Expression Seedlings expressing/Seedlings screened Event-01: 2/3 Event-02: 2/3
☐ Scheduled
X T3 Seedling tissue expressions similar to T2 seedling expression.
☐ T2 Mature tissue expression (if different expression pattern).
GFP Expression Detected X in the root
Inductions:

| Treatment: | Age: | Generation: | Time points: | Response: |
|---|---|---|---|---|
| ABA (100 um) | 14 d | T3 | 8Hr | No |
|  | 14 d. | T2 | 1Hr, 6Hr | Possible |

Observed expression (Arrows point to area of potential response):
ABA (100 um): No differences between experimental and control grown seedlings. High GFP expression throughout root epidermis identical to T2, T3 seedling expression in report 53.
ABA (100 um): GFP expression restricted to hypocotyl-root transition zone in control grown seedlings. ABA treated seedlings express GFP throughout hypocotyl decreasing toward apex.
ABA (100 um)
YP0204.02.02 8Hr CONTROL
YP0204.02.02 8Hr EXP.
YP0204.02.03 8Hr EXP.
ABA (100um)
YP0204.02.ABA 1Hr. CONTROL  YP0204.02.ABA 1Hr EXP.
ABA (100 um)
YP0204.02.ABA 1Hr. CONTROL  YP0204.02.ABA 1Hr EXP.
X in the root                X in the root
YP0204.02.H.6Hr.ABA.CTRL
X in the root
YP0204.02.H.6Hr.ABA
X in the hypocotyl and the root
YP0204.03.H.6Hr.ABA.CTRL    YP0204.03.H.6Hr.ABA
X in the hypocotyl           X in the hypocotyl
Report 53.YP0204 T3 seedling expression review. Root GFP expression restricted to root retion of seedling.
Inductions:          Lines Screened

| ID | Treatment | Time point | # Screened | # Expressing |
|---|---|---|---|---|
| YP0204-02 | ABA | 1Hr | 6 | 6 |
| YP0204-02 | ABA-Control | 1Hr | 6 | 4 |
| YP0204-02 | ABA | 6Hr | 6 | 4 |
| YP0204-02 | ABA-Control | 6Hr | 6 | 2 |
| YP0204-03 | ABA | 1Hr | 5 | 5 |
| YP0204-03 | ABA-Control | 1Hr | 6 | 5 |
| YP0204-03 | ABA | 6Hr | 6 | 6 |
| YP0204-03 | ABA-Control | 6Hr | 4 | 2 |
| YP0204-02-02 | ABA | 8H | 6 | 6 |
| YP0204-02-02 | ABA-CTRL | 8H | 6 | 6 |
| YP0204-03-02 | ABA | 8H | 6 | 5 |
| YP0204-03-02 | ABA-CTRL | 8H | 6 | 5 |

Promoter Expression Report #53

Promoter utility

| | |
|---|---|
| Trait Area: | PG&D, Nutrient. Seed development, yield |
| Sub-trait Area: | Plant size, growth rate, nitrogen use efficiency and utilization |
| Utility: | Very useful for root nutrient uptake, enhancement for plant growth under low nitrogen condition |
| Construct: | YP0204 |
| Promoter Candidate I.D: | 11768721 |
| cDNA I.D: | 12669615 (Old ID: 7089815) |
| T1 lines expressin T2 seed | YP0204 -02,-03,-04 |

Sequence (SEQ ID NO: 53):

AACTAATTAGGTCGTTAATTGTCCAAGGGTTTTTCATAGTTGATATAGTTC

TGTTCAAATATAGCCATCCTTAATCGATTCATGGGATCGTAAATTACTACT

TCGAGTGTTGTAAAAAAAAATGAAACTTCTACATTACAAACTCGAATTTAA

TGCATCTGGAGTGATACTATAAAAGTAGGGATGCTCTCAGGTCGCATTTGA

GAGACACAGAAATGATTTTAATGGAATTAATATATTTTCAGTTTTTCACAA

AAAAAAATTGTGTTTATAACAACTGCAGATTCAATGCTGATTTTATGAGTC

TCACCTATAGAATTTATATTTCTATATTCATAGAGGCAGTATAGGTGTTGA

CCCAACATCGAAAGAACACTTCGTAAAAAATTCTTTGGAACAAGGCTGAAA

ATTTACTCCCAAATTTAGCTATCCGATGAAGATAAATCATTTACCGTTTAT

TAAAGAATTATCGAGATTTTAGTCAAAACCAAAAGAGATTATGAGCCTAAG

ATTTTGAATTTGTATTGGTAAAGGAAATTGAACGAAAATTTCAGAAAAAAA

TATTAATAAATTGAACGATAGAGTTCACTTACTACATAGTCAACTAGTGCC

TAGCTATAATAGTTTCAAAAGACAAAAAAAACAAAATCGGTTAACTACTTC

CGTGACATAATTCTCATCTTGATTTTTGAATCCAGTCTAATTTGAAAAGTA

TATTCAAAATCTTTAAATCCATTAATGATAACTTTTATAATACGTTGACAC

ACGCAATTGTATATACAATATTCTTGAATTTTAAATGTAAATTCTAGAATA

TATTGCGATCACCACACTAATCAAAATCTTTGGGACAACTTGAACCCACAT

TTGACTTTTCTTGGTCAAATATTTTGGCATCATGCATGATCTTCTCTATAA

AAACCAAAAGGCCTCAACGACATTCATAAACTCAGTCATTATATTTATTTT

TGTTGTATTTCAACGTTCAATCTCTGAAAACCATTGCACTGGGATCCAACA

ATGTCCTCCGACTCGTCCAAGATCAAGAGGAAGCGGAACCGCATCCCGCTC

Promoter Expression Report #58

| | |
|---|---|
| Promoter Tested In: | *Arabidopsis thaliana*, WS ecotype |
| Spatial expression summary: | |
| Cotyledon | (H)vascular, (H)epidermis, (H)hydathode |
| Rosette Leaf | (H)hydathode |
| Lateral root | (H)initials |
| Flower | (H)carpel |
| Silique | (M)style, (M)carpel |
| Leaf | (L)vascular, (H)hydathode |

Promoter Expression Report #58

| | |
|---|---|
| Observed expression pattern: | |
| T2 seedlings: | High expression was seen in the epidermal and vascular tissues of cotyledons, lateral root initials and primordia. Expression was seen in the distal margin of the cotyledon and rosette leaves in the region of the hydathode which is a highly modified vascular and ground tissue that permits the release of water through a pore in the epidermis. |
| T2 mature: | High expression existed in the distal margin of cotyledons in mature embryos similar to that of T2 seedling expression. Low vascular expression can be seen in sepals and midvein leading to the hydathode region. High specific GFP expression was observed at the carpel differentiation zone early in silique development and continues through to maturity. An optical section of silique primordia shows arrows pointing to the boundary where carpel, style and placental tissues are rapidly differentiating. At maturity, expression decreases and is localized to tissues within the style. Endothelium expression was not observed as previously detected by UV-based standard fluorescent microscopy. Plants screened by confocal microscopy were 4 weeks old where inner integuments may not have differentiated into mature endothelium. |
| Expected expression pattern: | Aleurone in rice. An aleurone equivalent tissue in *Arabidopsis* is the endothelium of the ovule. The endothelium differentiates from the inner most layer of the inner integument of the developing ovule surrounding the embryo. Although not derived from endosperm, the endothelium is thought to provide a nutritive role for the embryo. |
| Selection Criteria: | Endosperm specificity in rice was demonstrated using GUS and GFP as reporters. |
| Gene: | GluB-1 gene; glutelin; storage protein. |
| GenBank: | X54314.1 GI:20209 |
| Source Promoter Organism: | *Oryza sativa* |
| Vector: | pCRS-HT2 |
| Marker Type: | GFP-ER |
| Generation Screened: | ☐ T1 Mature XT2 Seedling X T2 Mature ☐ T3 Seedling |

T1 Mature Plant Expression Organs/Tissues screened

Events Screened: n =    Events Expressing:    n =
GFP Expression Detected
T2 Seedling Expression Tissues Screened Events Screened: n = 2   Events Expressing:   n = 2
Seedlings expressing/Seedlings screened Event-01: No data.   Event-02: No data.
☐ Scheduled
GFP Expression Detected

| | |
|---|---|
| ☐ Hypocotyl | ☐epidermis ☐cortex ☐vascular ☐xylem ☐phloem ☐stomata |
| X Cotyledon | ☐mesophyll H vascular H epidermis ☐margin ☐stomata H hydathode |
| X Rosette Leaf | ☐mesophyll ☐vascular ☐epidermis ☐trichome ☐petiole ☐primordia ☐stomata ☐stipule ☐margin H hydathode |
| ☐ Primary Root | ☐epidermis ☐trichoblast ☐atrichoblast ☐cortex ☐endodermis ☐vascular ☐xylem ☐phloem ☐pericycle ☐quiescent ☐columella ☐root cap ☐root hairs |
| X Lateral root | ☐epidermis ☐trichoblast ☐atrichoblast ☐cortex ☐endodermis H initials ☐flanking cells ☐vascular ☐lateral root cap |
| ☐ Shoot apical meristem | ☐Shoot apical meristem |

X in the Epidermis (Ep) and Vasculature (Vs) of the cotyledon
X in the Epidermis (Ep) and Mesophyll (Me) of the primary leaf
X in the Lateral root (Lr), lateral root initial and lateral root primordia
T2 Mature Plant Expression Organs/Tissues screened Events Screened: n = 2   Events Expressing:   n = 2
Plants expressing/Plants screened Event-01: No data.   Event-02: No data.
☐ Scheduled
GFP Expression Detected

| | |
|---|---|
| X Flower | ☐pedicel ☐receptacle ☐nectary L sepal ☐petal ☐filament ☐anther ☐pollen H carpel ☐style ☐papillae ☐vascular ☐epidermis ☐stomata ☐trichome |
| X Silique | ☐stigma M style M carpel ☐septum ☐placentae ☐transmitting tissue ☐epidermis ☐cortex ☐vascular ☐stomata ☐abscission zone ☐ovule |
| ☐ Ovule | Pre-fertilization: ☐inner integument ☐outer integument ☐embryo sac ☐funiculus ☐chalaza ☐micropyle ☐gametophyte Post-fertilization: ☐zygote ☐inner integument ☐outer integument ☐seed coat ☐primordia ☐chalaza ☐micropyle ☐early endosperm ☐mature endosperm ☐embryo |
| ☐ Embryo | ☐suspensor ☐preglobular ☐globular ☐heart ☐torpedo ☐late ☐mature ☐provascular ☐hypophysis ☐radicle ☐cotyledons ☐hypocotyl |
| ☐ Stem | ☐epidermis ☐cortex ☐vascular ☐xylem ☐phloem ☐pith ☐stomata ☐trichome |
| X Leaf | ☐petiole ☐mesophyll L vascular ☐epidermis ☐trichome ☐primordia ☐stomata ☐stipule ☐margin H hydathode |

X in the silique primordia
X in the Cortex (Cr) and Stigma (Sg) of the developing and fertilized silique
X in the Vasculature (Vs) of the sepal, mature embryo and the leaf
GFP expression in mature embryo cotyledon and endothelium layer of the developing seed
Promoter utility

| | |
|---|---|
| Trait - Sub-trait Area: | Among other uses, this promoter sequence is useful to improve: Seed development-Endosperm production, seed abortion, seed composition, starch production, PGD-Root architecture, nutrient uptake and utilization |
| Construct: | pCRS-HT2-pGluB-1 |
| Promoter Candidate I.D: | No data |
| cDNA I.D: | No data |

Sequence (SEQ ID NO: 54):

```
gatctcgattttttgaggaatttttagaagttgaacagagtcaatcgaacaga cagttgaagagatatggattttctaagatcgggggaccgagtggaccggac gaggatgtggcctaggacgagtgcacaaggctagtggactcggtccccgcg
```

-continued

```
cggtatcccgagtggtccactgtctgcaaacacgattcacatagagcgggc
agacgcgggagccggtcctaggtgcaccggaagcaaatccgtcgcctgggt
ggatttgagtgacacggcccacgtgtagcctcacagctctccgtggtcaga
tgtgtaaaattatcataatatgtgtttttcaaatagttaaataatatatat
aggcaagttatatgggtcaataagcagtaaaaaggcttatgacatggtaaa
attacttacaccaatatgccttactgtctgatatattttacatgacaacaa
agttacaagtacgtcatttaaaaatacaagttacttatcaattgtagtgta
tcaagtaaatgacaacaaacctacaaatttgctattttgaaggaacactta
aaaaaatcaataggcaagttatatagtcaataaactgcaagaaggcttatg
acatggaaaattacatacaccaatatgctttattgtccggtatattttac
aagacaacaaagttataagtatgtcatttaaaaatacaagttacttatcaa
ttgtcaagtaaatgaaaacaaacctacaaatttgttattttgaaggaacac
ctaaattatcaaatatagcttgctacgcaaaatgacaacatgcttacaagt
tattatcatcttaaagttagactcatcttctcaagcataagagctttatgg
tgcaaaaacaaatataatgacaaggcaaagatacatacatattaagagtat
ggacagacatttctttaacaaactccatttgtattactccaaaagcaccag
aagtttgtcatggctgagtcatgaaatgtatagttcaatcttgcaaagttg
cctttccttttgtactgtgttttaacactacaagccatatattgtctgtac
gtgcaacaaactatatcaccatgtatcccaagatgctttttttattgctata
taaactagcttggtctgtctttgaactcacatcaattagcttaagtttcca
taagcaagtacaaatagct
```

| Promoter Expression Report #60 | |
|---|---|
| Promoter Tested In: | *Arabidopsis thaliana*, WS ecotype |
| Spatial expression summary: | |
| Ovule | Post-fertilization: (L)endothelium |
| Prima root □cortex | |
| Observed expression pattern: | |
| T1 mature: | Expression was seen in the endothelium (the inner cell layer of the inner integument). Beginning in late embryogenesis or onset of seed maturation, the endothelium differentiates from the inner most layer of the inner integument of the developing ovule surrounding the embryo. Although not derived from endosperm, the endothelium is thought to provide a nutritive role for the embryo. |
| T2 seedling: | Low expression was seen in the root cortex near the hypocotyl root transition zone of the seedling approximately 3 days after germination. Expression was observed in 3-day old seedling due to low and delayed germination. The seedling was normally screened at 7–10 days old when all structures have developed. |
| Expected expression pattern: | Seed, flower, root |
| Selection Criteria: | *Arabidopsis* public |
| Gene: | Strong similarity to EREBP-2 (Ethylene-inducible DNA binding proteins that interact with an ethylene-responsive element)/ product = "EREBP-2 protein" |

| Promoter Expression Report #60 | |
|---|---|
| GenBank: | NM_117855 *Arabidopsis thaliana* ethylene responsive element binding factor 1 (At4g17500) mRNA, complete cds, gi30684064|ref|NM_117855.2|[30684064] |
| Source Promoter Organism: | *Arabidopsis thaliana* WS |
| Vector: | pNewBin4-HAP1-GFP |
| Marker Type: | GEP-ER |
| Generation Screened: | X T1 Mature X T2 Seedling T2 Mature T3 Seedling |

T1 Mature Plant Expression Organs/Tissues screened

Events Screened: n = 2  Events Expressing: n = 2
GFP Expression Detected

| | |
|---|---|
| □ Flower | □ pedicel □ receptacle □nectary □sepal □petal □filament □anther □pollen □carpel □style □papillae □vascular □epidermis □stomata □trichome |
| □ Silique | □stigma □style □carpel □septum □placentae □transmitting tissue □vascular □epidermis □stomata □abscission zone □ovule |
| X Ovule | Pre-fertilization: □inner integument □outer integument □embryo sac □funiculus □chalaza □micropyle □gametophyte Post-fertilization: □zygote □inner integument L outer integument □seed coat L endothelium □primordia □chalaza □micropyle □early endosperm □mature endosperm □embryo |
| □ Embryo | □suspensor □preglobular □globular □heart □torpedo □late □mature □provascular □hypophysis □radicle □cotyledons □hypocotyl |
| □ Stem | □epidermis □cortex □vascular □xylem □phloem □pith □stomata □trichome |
| □ Leaf | □petiole □mesophyll □vascular □epidermis □trichome □primordia □stomata □stipule □margin |

X in the Endothelium (Ed) of the mature seed
T2 Seedling Expression Tissues Screened Events Screened: n = 2  Events Expressing: n = 2
GFP Expression Detected

| | |
|---|---|
| □ Hypocotyl | □epidermis □cortex □vascular □xylem □phloem □stomata |
| □Cotyledon | □mesophyll □vascular □epidermis □margin □stomata □hydathode |
| □ Rosette Leaf | □mesophyll □vascular □epidermis □trichome □petiole □primordia □stomata □stipule □margin |
| X Primary Root | □epidermis □trichoblast □atrichoblast L cortex □endodermis □vascular □xylem □phloem □pericycle □quiescent □columella □cap □root hairs |
| □ Lateral root | □epidermis □trichoblast □atrichoblast □cortex □endodermis □initials □flanking cells □vascular □cap |
| □ Shoot apical meristem | □SAM □epidermis |

X in the Cortex (Cr) of the seedling
T2 Mature Plant Expression Plants expressing/Plants screened Event-01: no data  Event-02: no data
□ Scheduled
□ T2 Mature tissue expressions similar to T1 expression data (data not shown).
□ T2 Mature tissue expression (if different expression pattern). Expression detected

Promoter Expression Report #60

T3 Seedling Expression Seedlings expressing/Seedlings screened

Event-01: no data  Event-02: no data
☐ Scheduled
☐ T3 Seedling tissue expressions similar to T2 seedling expression (data not shown).
☐ T2 Mature tissue expression (if different expression pattern).
GFP Expression Detected
Promoter utility

| | |
|---|---|
| Trait - Sub-trait Area: | Among other uses, this promoter sequence is useful to improve: Seed development- seed abortion, seed size, seed fill |
| Construct: | YP0008 |
| Promoter Candidate I.D: | 13148261 |
| cDNA I.D: | 12679464 |
| T1 lines expressing (T2 seed): | SR00409-10,-11 |

Sequence (SEQ ID NO: 55):

ctCGAGAGATGAAGTCTTAGTAATGTTTGAACAAACAATAATCACGTTTTC
CATCAAATTCGAGCATTTAAAGTTTATATTACTACATGCCCCAAGATGATA
CCGTCCATCTCATCCGAAAATATTTCTGAAATTGCGCTAAGACAACAATGT
TTGCTCAAATTCGATCATTTAAAGTTTACAAATCTCTCATcaatcTTACAA
ACTTCTCACACTAAACAGAGGTACATATTTTCTTATAAAGACAAAAGGTTC
GAACAGCTGGCTTCTCAACTCGAGTTGTTTGTCAGGGCCTCTCTTCACTAA
CTACAAGTTGGTACTTCAAATATTGGTGGCTAGCTTCACGTGATATTGTCT
ACAAATTAAACCCATGAAAAAGCTGCATTAATTGTTCCAAGTGAACCCTGA
GGAGTGTCAATAGTCTTTGCTTTAGTGTGATCATTAAACCAAATCTCTAAA
TTCCTAATTTGTACTAACATTTGGAACGTATTTCCTACTCTTCTCCCTGCT
CCAACTCCCAAAAATAAGATTAGTTAGATTTCTATAACTAATATACATGTA
TACTCCCAAAAACAGTAAAACCATATTAATAAAGCTAATTTTGCATAGATT
TATTTCGGTAAACCGGCGGTTCAAGTTGGGGAAAAAAAAGACAAACGGTCT
AAAGTCATCCAAAGACAAAAAACCAAAGACAAGTTGAGAGAGACGAGACCA
ATCACAACATTGcttcgtAGATTGCGTGACATCATCCTTGACGGCTACTTT
CATTTGTGTCTTATTTGGATAAAACGCACGTGTTTAATTCACGAACCTTCA
TAGCAATAAGAAATTTCCATTACTTTCATATTTTCAACTTTTTTTATTACC
cattaCATGCTTAAAATATTAATTCACAAGTCTTTGTCAAAATTCAATATT
TTCCAGGTTCATGAACCCTTTTTATCTCAATCTACTCTATAATATCTCCCT
ATAAATTACAAcaaaacctctttatttttca

Promoter Expression Report # 61

Promoter Tested In: *Arabidopsis thaliana*, WS ecotype
Spatial expression summary:

| | |
|---|---|
| Hypocotyl | (H)epidermis, (H)cortex |
| Primary Root | (L)epidermis, (M)vascular, (M)pericycle |
| Stem | (H)vascular |
| Leaf | (L)vascular, (M)epidermis, (M)stomata |

Observed expression pattern: T1 mature: Was not screened. T2 seedling: GFP is expressed throughout the cortical and vascular tissues of the seedling root. Highest expression was seen in the cortical and epidermal tissues at the hypocotyl root transition zone, decreasing toward the apex. T2 mature plant: Expression was seen in the leaf and stem vascular tissue. Low expression was seen in the leaf epidermal cells.

| | |
|---|---|
| Expected expression pattern: | Seed, flower, root |
| Selection Criteria: | *Arabidopsis* public |
| Gene: | ethylene responsive element binding factor 5 (ATERF5) |
| GenBank: | NM_124094 *Arabidopsis thaliana* ethylene responsive element binding factor 5 (AtERF5) (At5g47230) mRNA, complete cds gi\|30695137\|ref\|NM_124094.2\|[30695137] |
| Source Promoter Organism: | *Arabidopsis thaliana* WS |
| Vector: | pNewBin4-HAP1-GFP |
| Marker Type: | GFP-ER |
| Generation Screened: | ☐ T1 Mature  X T2 Seedling  X T2 Mature  ☐ T3 Seedling |
| T1 Mature Plant Expression | Organs/Tissues screened |
| Events Screened:  n = | Events Expressing:  n = |
| GFP Expression Detected | |
| T2 Seedling Expression | Tissues Screened |
| Events Screened: n = 5 | Events Expressing: n = 2 |
| GFP Expression Detected | |
| X Hypocotyl | H epidermis H cortex ☐ vascular ☐ xylem ☐ phloem ☐ stomata |
| ☐ Cotyledon | ☐ mesophyll ☐ vascular ☐ epidermis ☐ margin ☐ stomata ☐ hydathode |
| ☐ Rosette Leaf | ☐ mesophyll ☐ vascular ☐ epidermis ☐ trichome ☐ petiole ☐ primordia ☐ stomata ☐ stipule ☐ margin |
| X Primary Root | L epidermis ☐ trichoblast ☐ atrichoblast H cortex ☐ endodermis M vascular ☐ xylem ☐ phloem M pericycle ☐ quiescent ☐ columella ☐ cap ☐ root hairs |
| ☐ Lateral root | ☐ epidermis ☐ trichoblast ☐ atrichoblast ☐ cortex ☐ endodermis ☐ initials ☐ flanking cells ☐ vascular ☐ cap |

Promoter Expression Report # 61

☐ Shoot apical meristem   ☐ SAM ☐ epidermis
X in the Epidermis (Ep) and Cortex (Cr) of the hypocotyl root zone
X in the Epidermis (Ep), Cortex (Cr) Pericycle (Pr) and Vasculature (Vs) of the root
T2 Mature Plant Expression Events Screened: n = 3   Events Expressing: n = 2
☐ Scheduled
☐ T2 Mature tissue expressions similar to T1 expression data (data not shown).
☐ T2 Mature tissue expression (if different expression pattern).
☐ Flower    ☐ pedicel ☐ receptacle ☐ nectary ☐ sepal ☐ petal ☐ filament ☐ anther ☐ pollen
            ☐ carpel ☐ style ☐ papillae ☐ vascular ☐ epidermis ☐ stomata ☐ trichome
☐ Silique   ☐ stigma ☐ style ☐ carpel ☐ septum ☐ placentae ☐ transmitting tissue ☐ vascular
            ☐ epidermis ☐ stomata ☐ abscission zone ☐ ovule
☐ Ovule     Pre-fertilization: ☐ inner integument ☐ outer integument ☐ embryo sac ☐ funiculus
            ☐ chalaza ☐ micropyle ☐ gametophyte
            Post-fertilization: ☐ zygote ☐ inner integument ☐ outer integument ☐ seed coat
            ☐ primordia ☐ chalaza ☐ micropyle ☐ early endosperm ☐ mature endosperm
            ☐ embryo
☐ Embryo    ☐ suspensor ☐ preglobular ☐ globular ☐ heart ☐ torpedo ☐ late ☐ mature
            ☐ provascular ☐ hypophysis ☐ radicle ☐ cotyledons ☐ hypocotyl
X Stem      ☐ epidermis ☐ cortex H vascular ☐ xylem ☐ phloem ☐ pith ☐ stomata ☐ trichome
X Leaf      ☐ petiole ☐ mesophyll L vascular M epidermis ☐ trichome ☐ primordia M stomata
            ☐ stipule ☐ margin
X in the Guard cell (Gc), Epidermis (Ep) and Vasculature (Vs) of the leaf
X in the Vascular bundle (Vb) of the stem
T3 Seedling Expression X Scheduled
☐ T3 Seedling tissue expressions similar to T2 seedling expression (data not shown).
☐ T2 Mature tissue expression (if different expression pattern).
Promoter utility Trait - Sub-trait Area:   Among other uses, this promoter sequence is useful to improve:
                          Nutrients-Low N tolerance, enhanced uptake, translocation, NUE improved
                          PGD
Construct:                YP0009
Promoter Candidate I.D:   11768607
cDNA I.D:                 12719868 (Old ID: 4902397)
T1 lines expressing (T2 seed):   SR00410-02,-03

Sequence (SEQ ID NO: 56):

```
aattcGTTTTTTATACTCCCTCTGTTCCAAGATACTTGATATTTTGGGTTT

TTGCACAAGAATTAAGAAAAGTAACTTTTATATTTTTAATTATTCTTTTAG

TTAGTTTAATAATATTAATTTTACTTCTCTCATTTCATTATTGGTTACAAA

CAAAAATAATAATGATAGTTTTTCAAAACATCAATTTTGGTGGAACAAAta aaaaaactcAAAATATCAAATAACTTGAAACAGAGGGAGTAGTTAATtaaa aaaagATATTTCACACTTTGACTTGGCGAAGCCTCATAACAATGAAGTTAT

GTATGAACTATATATGAAGTTAGAAACAATGGAAAACAGCTTGTAAATATT

CATTGTTGTATATATGTTTTTTTGGGTCAATTTGGTGCATGAACAAAAATA

AAAACGTAGATGAAAACCGGATATTTTGGTGTTAACATTTGCATTTGAACT

TCGTGAAAGACGGATAAAAGCTCATTTTTGTTTTTTATTATATGGCTGCTA

TTAGTACACAGAGTTGAACTTTAGAATACTAAAAATCTCGACATCTTTTAT

TTTATTTTTGTCAAGCATCGACATCTTTTCTGTTCAAGAAAACGACCGCAA

TAGTCGAATAATATAACTCTTGGACTAGTTAATATATATTTGCGATAGATT

TTCGATCTCACTTATATCTTATAACCAAGAGACAAAAACAATATTGCAGTC

AAGTACAAAACGAAAACAATCACAATGTCGACTATAGATGAGTCGGTCATT

CGATCCAACGGCTCTGAGTCCACGAAACACGCAACCAAGTGGTGCTCTCTT

TTACACCAAATCATATTAtataaaacTTAAAAGAAAGAGAGGATGGTTCGT

TGGCTCCTTCTTGTTCCTTAATTAATTCAAATTATATTCATCACCTCCATT

GAATAAGTCCATTTCACGACAAAGTCACCAATGCTTCTTTTACATGTATAT

ATActtctttccactccctcttctctactca
```

| Promoter Expression Report # 62 |

Promoter Tested In: *Arabidopsis thaliana*, WS ecotype
Spatial expression summary:

Flower          (H)carpel, (L)style, (M)vascular, (M)stomata
Silique         (H)vascular, (L)cortex, (L)style, (H)septum
Leaf            (H)vascular, (H)hydathode
Primary Root   (H)vascular (H)phloem
Observed expression pattern: T1 mature: Target tissues were screened. No expression was observed. T2 seedling: High expression existed in the vasculature of the seedling root. T2 mature: Strong GFP expression was seen in the siliques and vasculature of mature leaves. Vasculature expression was seen throughout the leaf including the hydathode secretory gland which discharges water from the interior leaf. Hydathodes are thought to release water actively as true glands and passively under control of root pressure. Expression of GFP is seen in guard cells and vasculature of prefertilized siliques and cortical cells of style and septum in mature siliques. Expression appears as a gradient, strongest in septum and weakening toward style.
Expected expression pattern:    Seed, flower, root
Selection Criteria:             *Arabidopsis* public
Gene:                        Contains similarity to ethylene responsive element binding factor
GenBank:                NM_125553 *Arabidopsis thaliana* AP2 domain transcription factor, putative (At5g61600) mRNA, complete cds
                             gi|30697557|ref|NM_125553.2|[30697557]
Source Promoter Organism:   *Arabidopsis thaliana* WS
Vector:                     pNewBin4-HAP1-GFP
Marker Type:           GFP-ER
Generation Screened:      T1 Mature   X T2 Seedling   X T2 Mature   T3 Seedling
T1 Mature Plant Expression    Organs/Tissues screened
Events Screened:    Events Expressing:
GFP Expression Detected
T2 Seedling Expression    Tissues Screened
Events Screened: n = 2    Events Expressing: n = 2
Seedlings expressing / Seedlings screened
Event-01: No data.    Event-02: No data.
GFP Expression Detected
☐ Hypocotyl                 ☐ epidermis ☐ cortex ☐ vascular ☐ xylem ☐ phloem ☐ stomata
☐ Cotyledon                ☐ mesophyll ☐ vascular ☐ epidermis ☐ margin ☐ stomata ☐ hydathode
☐ Rosette Leaf            ☐ mesophyll ☐ vascular ☐ epidermis ☐ trichome ☐ petiole ☐ primordia
                                ☐ stomata ☐ stipule ☐ margin
X Primary Root            ☐ epidermis ☐ trichoblast ☐ atrichoblast ☐ cortex ☐ endodermis
                                H vascular ☐ xylem H phloem ☐ pericycle ☐ quiescent ☐ columella
                                ☐ cap ☐ root hairs
☐ Lateral root             ☐ epidermis ☐ trichoblast ☐ atrichoblast ☐ cortex ☐ endodermis
                                ☐ initials ☐ flanking cells ☐ vascular ☐ cap
☐ Shoot apical meristem    ☐ SAM ☐ epidermis
X in the Phloem Ph of the root
T2 Mature Plant Expression Events Screened: n = 6    Events Expressing: n = 2
☐ Scheduled
☐ T2 Mature tissue expressions similar to T1 expression data (data not shown).
☐ T2 Mature tissue expression (if different expression pattern).
X Flower         ☐ pedicel ☐ receptacle ☐ nectary ☐ sepal ☐ petal ☐ filament ☐ anther ☐ pollen
               H carpel L style ☐ papillae H vascular ☐ epidermis M stomata ☐ trichome
X Silique         ☐ stigma L style ☐ carpel L septum ☐ placentae ☐ transmitting tissue H vascular
               ☐ epidermis L cortex ☐ stomata ☐ abscission zone ☐ ovule
☐ Ovule         Pre-fertilization: ☐ inner integument ☐ outer integument ☐ embryo sac ☐ funiculus
               ☐ chalaza ☐ micropyle ☐ gametophyte
               Post-fertilization: ☐ zygote ☐ inner integument ☐ outer integument ☐ seed coat
               ☐ primordia ☐ chalaza ☐ micropyle ☐ early endosperm ☐ mature endosperm
               ☐ embryo
☐ Embryo       ☐ suspensor ☐ preglobular ☐ globular ☐ heart ☐ torpedo ☐ late ☐ mature
               ☐ provascular ☐ hypophysis ☐ radicle ☐ cotyledons ☐ hypocotyl
☐ Stem           ☐ epidermis ☐ cortex ☐ vascular ☐ xylem ☐ phloem ☐ pith ☐ stomata ☐ trichome
X Leaf           ☐ petiole ☐ mesophyll H vascular ☐ epidermis ☐ trichome ☐ primordia ☐ stomata
               ☐ stipule ☐ margin H hydathode
X in the Guard cell (Gc) of the Pedicel (Pd) and Sepal (Se) of the flower
X in the Guard cell (Gc) and Vasculature (Vs) of the silique and pre-fertilized silique
X in the Carpel (Ca), Stigma (Sg) and Style (Sy) of the mature silique
X in the Septum (Sp) of the silique
X in the Hydathode (Hd) of the leaf
X in the Mesophyll (Me) of the adaxial leaf
X in the Vasculature (Vs) and Hydathode (Hd) of the abaxial leaf
T3 Seedling Expression Seedlings expressing / Seedlings screened
Event-01: no data    Event-02: no data
☐ Scheduled
☐ T3 Seedling tissue expressions similar to T2 seedling expression (data not shown).

| Promoter Expression Report # 62 |
| --- |

☐ T2 Mature tissue expression (if different expression pattern).
GFP Expression Detected
Promoter utility Trait - Sub-trait Area:  Among other uses, this promoter sequence can be useful to improve:
                       Nutrients- Modify N transport, sugar transport
                       PGD
Construct:                   YP0010
Promoter Candidate I.D:      11768608
cDNA I.D:                    12370148 (Old ID: 4907378)
T1 lines expressing (T2 seed):   SR00411-02,-03

Sequence (SEQ ID NO: 57):

```
aattcGTCTTGCATTGGTAATCCAATATTCCATGTGATGCTTTTCTTTCTA

ACTGAAGGTATTCGTGAAAACGAATTCAAGATTGTGGGAGATAATTAGGGT

TTCGTCAAAAGCATGAATTAGGAAAATTtgggatTGATTTTTTGAATTTGG

GAAAAGTCCTAATTTTAATTCGATCAAAGCTTAAATGATGTCGTTTTGGGC

TGACTAACGAAGTCGTTAACAGGTGCCAACGAGTGTTAAAAATCTGTTATC

GCTTGATAActctttgGTTTTTTAGTCTAATCAACACATTCTCATGTTTCA

AACAGTTAATCAACATATTGTTCATGTTAAAAAATTAACACATGTGAAATT

GATAtataaaaatATCATATATTTTCAAAAGTTGGATCATTAAAtAAAAAT

TTTCCCTATTTTTGAAATAATTCTAAAACAGTATTAAAGATATTTCCTGAA

ATTGTTTGCATGTGATCGGTTTTGGACCGAAACTAAAAAACTTAGAAACTA

TATTAACTTTGAGTTGTCGAGATGAAGATGTGAAATAGAAATATAGGATCA

ATGGTTAGAATTTTGGCAAATGTATGAAGGTGTGTTTGATTGAATATTCCA

AGTCCTTTGCCTTTTGGAATAGGCATAACTACTACAACAAAGTTTTGATAG

GTTTTCCGAATTCTTTAAACTCCTTAAATTTTTAATACATCTCAATCAAAC

TCCACTTATACTAAAAATAATCCATATTGCATTTTTAAAAatcctAAAAGA

AGAATCACATGATAACTTGATAAGCACTTTTAAATGATAGATGTCCACGTA

GAGGAATAAGACAAAAAGACAAAATAAAGAAAAAGGACGAAATCTAAAGAG

AGAAAATAAGTAACAAGTCCAAGAAAAGGTAGTATGATCTTTCTCGGTCCG

ATCCTCGAAACTCCCTCGAAGGCTCGAACCCTCTCTTTGTTTTTTaccac tatataagaaagtccgattcctcgtcactct
```

| Promoter Expression Report # 64 |
| --- |

Promoter Tested In: *Arabidopsis thaliana*, WS ecotype
Spatial expression summary:

| | |
| --- | --- |
| Flower | (H)pollen |
| Silique | (H)ovule |
| Ovule | Pre-fertilization: (H)gametophyte |
| | Post-fertilization: (H)embryo |
| Embryo | (H)preglobular, (H)globular, (H)heart, (H)torpedo, (M)late, (L)mature, (L)cotyledons |
| Primary Root | (L)cortex |
| Lateral root | (H)primordia |

Observed expression pattern: T1 mature: Strong GFP expression was seen in the embryo sac early in ovule development through female gametophyte development. Expression seen before fertilization in the central cell, egg apparatus and in antipodal cells which degenerate before fertilization. GFP emissions rapidly degenerate within the egg sac post fertilization. High GFP expression is detected in cotyledons of heart stage embryos (approximately 60 hours after fertilization) and continues through embryo growth phase. No expression existed in mature embryos. High GFP is also seen in mature pollen. T2 seedling: High GFP expression was detected in mature root and lateral root primordia. Weak expression was detected in cortical cells at the root tip.

| | |
| --- | --- |
| Expected expression pattern: | Roots |
| Selection Criteria: | Ceres Microarray. 10x up in *Arabidopsis* root tips (enzymatic digestion), 2 of 2 reps 2.5 - 5x up in Yiwen's corn root tips (cut), 2 of 2 reps |
| Gene: | 60s 17a RIBOSOMAL Protein |
| GenBank: | NM_130329 *Arabidopsis thaliana* 60S ribosomal protein L7A (RPL7aA) (At2g47610) mRNA, complete cds gi\|30690728\|ref\|NM_130329.2\|[30690728] |

-continued

| Promoter Expression Report # 64 |
| --- |

Source Promoter Organism:  *Arabidopsis thaliana* WS
Vector:                    pNewBin4-HAP1-GFP
Marker Type:               GFP-ER
Generation Screened:       X T1 Mature   X T2 Seedling   ☐ T2 Mature   ☐ T3 Seedling
T1 Mature Plant Expression   Organs/Tissues screened
Events Screened:    n = 4    Events Expressing:    n = 3
GFP Expression Detected
X Flower        ☐ pedicel ☐ receptacle ☐ nectary ☐ sepal ☐ petal ☐ filament ☐ anther
                H pollen ☐ carpel ☐ style ☐ papillae ☐ vascular ☐ epidermis ☐ stomata
                ☐ trichome
X Silique       ☐ stigma ☐ style ☐ carpel ☐ septum ☐ placentae ☐ transmitting tissue
                ☐ vascular ☐ epidermis ☐ stomata ☐ abscission zone H ovule
X Ovule         Pre-fertilization: ☐ inner integument ☐ outer integument H embryo sac
                ☐ funiculus ☐ chalaza ☐ micropyle H gametophyte
                Post-fertilization: ☐ zygote ☐ inner integument ☐ outer integument ☐ seed
                coat ☐ primordia ☐ chalaza ☐ micropyle ☐ early endosperm ☐ mature
                endosperm H embryo
X Embryo        ☐ suspensor H preglobular H globular H heart H torpedo M late
                L mature ☐ provascular ☐ hypophysis ☐ radicle L cotyledons ☐ hypocotyl
☐ Stem          ☐ epidermis ☐ cortex ☐ vascular ☐ xylem ☐ phloem ☐ pith ☐ stomata
                ☐ trichome
☐ Leaf          ☐ petiole ☐ mesophyll ☐ vascular ☐ epidermis ☐ trichome ☐ primordia
                ☐ stomata ☐ stipule ☐ margin
X in the Antipodal cells (Ap), Central cell (Cc), Central cell vacuole (Cv) and Egg cell (Ec) of
   the pre-fertilized ovule
X in the globular stage, heart stage and torpedo stage embryo in the ovule
X in the Cotyledon (Co) of the ovule
X in the mature pollen
X in the fertilized ovule and embryo
T2 Seedling Expression    Tissues Screened
Events Screened: n = 2    Events Expressing: n = 2
Seedlings expressing / Seedlings screened
Event-01: No data.    Event-02: No data.
GFP Expression Detected
☐ Hypocotyl              ☐ epidermis ☐ cortex ☐ vascular ☐ xylem ☐ phloem ☐ stomata
☐ Cotyledon              ☐ mesophyll ☐ vascular ☐ epidermis ☐ margin ☐ stomata ☐ hydathode
☐ Rosette Leaf           ☐ mesophyll ☐ vascular ☐ epidermis ☐ trichome ☐ petiole ☐ primordia
                         ☐ stomata ☐ stipule ☐ margin
X Primary Root           ☐ epidermis ☐ trichoblast ☐ atrichoblast L cortex ☐ endodermis
                         ☐ vascular ☐ xylem ☐ phloem ☐ pericycle ☐ quiescent ☐ columella
                         ☐ cap ☐ root hairs
X Lateral root           ☐ epidermis ☐ trichoblast ☐ atrichoblast ☐ cortex ☐ endodermis
                         ☐ initials ☐ flanking cells H primordia ☐ vascular ☐ cap
☐ Shoot apical meristem  ☐ SAM ☐ epidermis
X in the lateral root primordial
X in the lateral root
X in the Cortex (Cr) of the root and the root tip
T2 Mature Plant Expression Plants expressing / Plants screened
Event-01: no data    Event-02: no data
☐ Scheduled
☐ T2 Mature tissue expressions similar to T1 expression data (data not shown).
☐ T2 Mature tissue expression (if different expression pattern).
expression detected
T3 Seedling Expression Seedlings expressing / Seedlings screened
Event-01: no data    Event-02: no data
☐ Scheduled
☐ T3 Seedling tissue expressions similar to T2 seedling expression (data not shown).
☐ T2 Mature tissue expression (if different expression pattern).
GFP Expression Detected
Promoter utility Trait - Sub-trait Area:   Among other uses, this promoter sequence can be useful to improve:
                          Seed development-seed abortion, seed fill, seed size, seed composition
                          Nutrients-nutrient uptake
                          PGD-root number, root size
Construct:                YP0039
Promoter Candidate I.D:   11768622
cDNA I.D:                 13603142
T1 lines expressing (T2 seed):   SR00536-02,-03

Sequence (SEQ ID NO: 58):

```
ccgttcgagtatttgaaaatttcgggtacacccgcctaaataggcggacccttatctagtatatatatacatttgaactatattgtttactTTTTagttgATT TAGGCTATgtcatGACATtgacATAAATCTACCTGTTATTTATCACGtgtaatTCGtgtaaagtgtaaactagaaagttcaaatacgtatttgttttgttc tgttataggattgtcatagttgtaaatctacaatttattacaacatgaataagtacacaagcaatgtaattggatttaattgctaaactctttacatggt caatctaaatttgataagaaatacgtcacatattactaagactgatagttttttgttgtcaccaattattttttgtaaattgacgaaaacaattccaaaaa ctcaaatgtacaaaatcatacagtctcacaaacatctcatagagaaagatataaatctcccatatgggaacgataacacgaggtcgaaatactattcgtaaa actaaaacgccttagttataaatcgttagttgtaaccgcggtcgagaatacatacagatccacgaaactactactacacatgctgctgaattggaatttgga aaagaccatcttctttaggaagagctcacccaatgagtgacaaaggtgtcggtggcttgttttctacccatatgtatacatcaaatggtagtttcattaacg tttggttttgagaaaagtaagacTTTGGCTAGTAGCTAGGTTCGTATATAATAAACTCTTTTGAGAAAGTTCATCACTGGTGGAAAATGTTAAACCGGTTTT TTCTCATTTTTTCCGCCATGTTAACCACCGGTTTAAAAAGACCGTAACACATTGAAAGATTAATAAGGGTATATTTGTAATTACGGTTTGCTGGCAATTTTT AATTATTATTTTAATTAGAGAAAATAGAGAAGCCCTATCAATGTACATGGTATATATATAAAAGGCAAAACCCTAGAAAACgatactattcgactcagccgt cctt
```

---

| Promoter Expression Report # 66 |
|---|

Promoter Tested In: *Arabidopsis thaliana*, WS ecotype
Spatial expression summary:

| | |
|---|---|
| Silique | (H)placentae, (L)ovule |
| Ovule | (L)chalaza |
| Hypocotyl | (L)epidermis |
| Primary Root | (L)root hairs |

Observed expression pattern: T1 mature: High specific expression was seen in the funiculus of placenta and the ovule attachment site to funiculus. T2 seedling: Low epidermal expression was seen in the hypocotyl near pedicles
of cotyledons and root hairs.

| | |
|---|---|
| Expected expression pattern: | Drought inducible |
| Selection Criteria: | Expression data, >10 fold induction under drought conditions |
| Gene: | Unknown protein |
| GenBank: | NM_101993 *Arabidopsis thaliana* F-box protein family (At1g21410) mRNA, complete cds gi\|30687347\|ref\|NM_101993.2\|[30687347] |
| Source Promoter Organism: | *Arabidopsis thaliana* WS |
| Vector: | pNewBin4-HAP1-GFP |
| Marker Type: | GFP-ER Histone-YFP |
| Generation Screened: | X T1 Mature   X T2 Seedling   ☐ T2 Mature   ☐ T3 Seedling |
| T1 Mature Plant Expression | Organs/Tissues screened |
| Events Screened:   n = 6 | Events Expressing:   n = 2 |

GFP Expression Detected
| | |
|---|---|
| ☐ Flower | ☐ pedicel ☐ receptacle ☐ nectary ☐ sepal ☐ petal ☐ filament ☐ anther ☐ pollen ☐ carpel ☐ style ☐ papillae ☐ vascular ☐ epidermis ☐ stomata ☐ trichome |
| X Silique | ☐ stigma ☐ style ☐ carpel ☐ septum H placentae ☐ transmitting tissue ☐ vascular ☐ epidermis ☐ stomata ☐ abscission zone L ovule |
| X Ovule | Pre-fertilization: ☐ inner integument ☐ outer integument ☐ embryo sac ☐ funiculus ☐ chalaza ☐ micropyle ☐ gametophyte
Post-fertilization: ☐ zygote ☐ inner integument ☐ outer integument ☐ seed coat ☐ primordia L chalaza ☐ micropyle ☐ early endosperm ☐ mature endosperm ☐ embryo |
| ☐ Embryo | ☐ suspensor ☐ preglobular ☐ globular ☐ heart ☐ torpedo ☐ late ☐ mature ☐ provascular ☐ hypophysis ☐ radicle ☐ cotyledons ☐ hypocotyl |
| ☐ Stem | ☐ epidermis ☐ cortex ☐ vascular ☐ xylem ☐ phloem ☐ pith ☐ stomata ☐ trichome |
| ☐ Leaf | ☐ petiole ☐ mesophyll ☐ vascular ☐ epidermis ☐ trichome ☐ primordia ☐ stomata ☐ stipule ☐ margin |

X in the Funiculus (Fn)
X in the Chalaza (Ch) of the mature ovule
T2 Seedling Expression     Tissues Screened
Events Screened: n = 2     Events Expressing: n = 2
Seedlings expressing / Seedlings screened
Event-01: 6/6     Event-02: 1/3
GFP Expression Detected

| | |
|---|---|
| X Hypocotyl | L epidermis ☐ cortex ☐ vascular ☐ xylem ☐ phloem ☐ stomata |
| ☐ Cotyledon | ☐ mesophyll ☐ vascular ☐ epidermis ☐ margin ☐ stomata ☐ hydathode |
| ☐ Rosette Leaf | ☐ mesophyll ☐ vascular ☐ epidermis ☐ trichome ☐ petiole ☐ primordia ☐ stomata ☐ stipule ☐ margin |

| Promoter Expression Report # 66 | |
|---|---|
| X Primary Root | ☐ epidermis ☐ trichoblast ☐ atrichoblast ☐ cortex ☐ endodermis<br>☐ vascular ☐ xylem ☐ phloem ☐ pericycle ☐ quiescent ☐ columella<br>☐ cap L root hairs |
| ☐ Lateral root | ☐ epidermis ☐ trichoblast ☐ atrichoblast ☐ cortex ☐ endodermis<br>☐ initials ☐ flanking cells ☐ vascular ☐ cap |
| ☐ Shoot apical meristem | ☐ SAM ☐ epidermis |
| X in the Epidermis (Ep) of the petiole | |
| X in the Hypocotyl (Hy) | |
| X in the Root hair (Rh) of the hypocotyl | |

T2 Mature Plant Expression

X Scheduled
☐ T2 Mature tissue expressions similar to T1 expression data (data not shown).
☐ T2 Mature tissue expression (if different expression pattern).

T3 Seedling Expression

X Scheduled
☐ T3 Seedling tissue expressions similar to T2 seedling expression (data not shown).
☐ T2 Mature tissue expression (if different expression pattern).

Promoter utility

| | |
|---|---|
| Trait - Sub-trait Area: | Among other uses, this promoter sequence could be useful to improve:<br>Seed development-seed abortion, seed size, seed fill<br>Nutrients-nutrient uptake |
| Construct: | YP0070 |
| Promoter Candidate I.D: | 13148246 |
| cDNA I.D: | 13612791 |
| T1 lines expressing (T2 seed): | SR00600-02,-10 |

Sequence (SEQ ID NO: 59):

```
ttggcgTTAATCGTTAAGAAAAAAACGTGCCTACCTAGCCAAATGACATCTTCCTCTTTTGTGTTTAGCAC

AAGTGAATGATCCAAATATCATCTACCTAATATGACCCATAAAATAGTATGTGATTGTCTTTGGATGTT

ATCCCATAACATAACTTAAATTTGGGATGCATGCATATATTATATACTTCATATAAAATGAGTGGACCT

CATAAGTTGCGGTTTCGATTTTTATCAAAAACAACAGTTGTCCACTTTTTGATTTTGACACacacccaCATT

CAAGCATCTCCTTTCTTCTATATTATTACTCAAAGAATAACACCCCCTAAGGATAACACCATTACACAA

ATCAATTCTCAGTTAATCATTTGTTTCAATATATGTTAGTACTTAAGAAATATTCGAATAGTTTTACGTA

TTCAAATTTTATAAATTCAGTGAATGTTTAATTACCAAGTCATTTTGGCTTGGAATCTATTCAATTATTC

AAAAAAATAAATAAATAATACTGCATTTTAACGTATCAGCCAGTCAATATATTACACGTGTCATAAAG

CATTACCCACACGTTTCTCCTGCCTCTTTCCCTTTCATTTTTTTTTTCATTTTTTTGTTTCTTCTCTTTGTT

GTTGTTATCTTCTTCTAGCTAGCTCTGTGAAACACTTCAAATGAACAAATATATCAAATAATAATAGTG

TAATTAAGTCGGAGGAAAACAACAAGAACCCAGAAAGAGGAACGAAGAAACTAATTCAAAGGTATGA

TcttttattcTTTGAGAGAATTATGTTTTCTTTGTAGCAAATCCTCTGGTCTTACGTTTAGTCACTGAATTTGTT

CCACTTCTGGAAAAATCTAGACACcaaaagCAATCTATGAACTTTAATTTCCAATCACTACCGTCTTTTGA

GGTTGTAAAATCGGTAAATGGCAGATTTTTCACTCTCATTCCTTTGTGGTGATAGGATCAAGTTCaccgctt cattttagtcattaaacaaaga
```

| Promoter Expression Report # 68 | |
|---|---|

Promoter Tested In: *Arabidopsis thaliana*, WS ecotype
Spatial expression summary:

| | |
|---|---|
| Flower | (H)pedicel, (H)receptacle, (H)nectary, (H)sepal, (H)filament, (L)anther,<br>(H)pollen, (H)carpel, (H)style, (H)epidermis |

Promoter Expression Report # 68

| | |
|---|---|
| Silique | (H)style, (H)carpel, (H)septum, (H)placentae, (H)epidermis, (H)abscission zone, (H)ovule |
| Ovule | Pre-fertilization: (H)inner integument, (H)outer integument, (H)funiculus, (H)chalaza, (H)micropyle |
| | Post-fertilization: (L)inner integument, (L)outer integument, (H)embryo |
| Embryo | (H)suspensor, (H)heart, (H)torpedo, (H)mature, (H)hypophysis, (H)radicle, (H)cotyledons |
| Stem | (H)epidermis, (H)cortex, (H)vascular, (H)pith |
| Leaf | (H)mesophyll, (H)vascular, (H)epidermis |
| Hypocotyl | (H)epidermis, (H)cortex, (H)vascular |
| Cotyledon | (H)vascular, (H)epidermis |
| Rosette Leaf | (H)mesophyll, (H)vascular, (H)epidermis |
| Primary Root | (H)epidermis, (H)cortex, (H)endodermis, (H)vascular, (H)pericycle, (H)cap, (H)root hairs |
| Lateral root | (H)epidermis, (H) cortex, (H)endodermis, (H)initials, (H)vascular, (H)cap |

Observed expression pattern: T1 mature: Expressed strongly throughout the inflorescence meristem, shoot apical meristem and all of the floral organs. High expression was seen throughout all tissues of the pre-fertilized silique including the ovary and ovule primordial. Not expressed in the endosperm. Expression decreases in the outer and inner integuments of fertilized ovule at heart stage embryo. High expression first observed in heart stage
embryo, suspensor and mycroplyar apparatus. High expression in embryo continues through to mature embryo with preferential expression at the root meristem. High expression was detected through all tissues of leaf and stem. T2 seedling: High expression was detected in the epidermal, vascular, and photosynthetic tissues of seedling. No expression was detected in the cortex cells of the hypocotyl.

| | |
|---|---|
| Expected expression pattern: | Constitutive |
| Selection Criteria: | *Arabidopsis* public |
| Gene: | 40S ribosomal protein S5 |
| GenBank: | NM_180233 *Arabidopsis thaliana* 40S ribosomal protein S5 (RPS5B) (At3g11940) mRNA, complete cds gi\|30681967\|ref\|NM_180233.1\|[30681967] |
| Source Promoter Organism: | *Arabidopsis thaliana* WS |
| Vector: | pNewBin4-HAP1-GFP |
| Marker Type: | GFP-ER |
| Generation Screened: | X T1 Mature   X T2 Seedling   T2 Mature   T3 Seedling |
| T1 Mature Plant Expression | Organs/Tissues screened |
| Events Screened:   n = 4 | Events Expressing:   n = 3 |
| GFP Expression Detected | |
| X Flower | H pedicel H receptacle H nectary H sepal ☐ petal H filament L anther H pollen H carpel H style ☐ papillae ☐ vascular H epidermis ☐ stomata ☐ trichome |
| X Silique | ☐ stigma H style H carpel H septum H placentae ☐ transmitting tissue ☐ vascular H epidermis ☐ stomata H abscission zone H ovule |
| X Ovule | Pre-fertilization: H inner integument H outer integument ☐ embryo sac H funiculus H chalaza H micropyle ☐ gametophyte Post-fertilization: ☐ zygote L inner integument L outer integument ☐ seed coat ☐ chalaza ☐ micropyle ☐ early endosperm ☐ mature endosperm H embryo |
| X Embryo | H suspensor ☐ preglobular ☐ globular H heart H torpedo ☐ late H mature ☐ provascular H hypophysis H radicle H cotyledons |
| X Stem | H epidermis H cortex H vascular ☐ xylem ☐ phloem H pith ☐ stomata ☐ trichome |
| X Leaf | ☐ petiole H mesophyll H vascular H epidermis ☐ trichome ☐ primordia ☐ stomata ☐ stipule ☐ margin |
| X Shoot apical meristem | H Shoot apical meristem |

X in the Shoot apical meristem (SAM), Silique (Si), Stamen (St) and Sepal (Se) of the inflorescence meristem
X in the Placenta Silique (Si), Stamen (St), Sepal (Se), Abscision zone (Az) and Nectary (Ne) of the Flower
X in the Carpel (Ca), Ovule (Ov) and Stigma (Sg) of the immature silique
X in the Carpel (Ca), Ovule (Ov) and Placenta (Pl), of the ovary
X in the Filament (Fi) of the Anther (An) in the stamen
X in the Cortex (Cr) of the silique
X in the Outer integument (Oi) and Funiculus (Fn) of the pre-fertilized and fertilized ovule
X in the Embryo (Em), Suspensor (Su) and Micropyle (Mp) of the ovule
X in the Pollen (Po)
X in the Hyphosis (Hp) and Suspensor (Su) of the embryo
X in the Cotyledon (Co) and Root (Rt) of the mature embryo
X in the Epidermis (Ep), Pith (Pi) and Vascular bundle (Vb) of the stem
X in the Epidermis (Ep), Mesophyll (Me) and Vascular bundle (Vs) of the leaf
T2 Seedling Expression   Tissues Screened
Events Screened: n = 2   Events Expressing: n = 2
Seedlings expressing / Seedlings screened
Event-01: 1/1   Event-02: 2/3

Promoter Expression Report # 68

GFP Expression Detected

| | |
|---|---|
| X Hypocotyl | H epidermis H cortex H vascular ☐ xylem ☐ phloem ☐ stomata |
| X Cotyledon | ☐ mesophyll H vascular H epidermis ☐ margin ☐ stomata ☐ hydathode |
| X Rosette Leaf | H mesophyll H vascular H epidermis ☐ trichome ☐ petiole ☐ primordia ☐ stomata ☐ stipule ☐ margin |
| X Primary Root | H epidermis ☐ trichoblast ☐ atrichoblast H cortex H endodermis H vascular ☐ xylem ☐ phloem H pericycle ☐ quiescent ☐ columella H cap H root hairs |
| X Lateral root | H epidermis ☐ trichoblast ☐ atrichoblast H cortex H endodermis H initials ☐ flanking cells H vascular H cap |
| ☐ Shoot apical meristem | ☐ SAM ☐ epidermis |

X in the Hypocotyl (Hy) and Rosette leaf (Rl) in the seedling
X in the of the cotyledon
X in the Epidermis (Ep), Mesophyll (Me) and Vasculature (Vs) of the rosette leaf
X in the Epidermis (Ep), Vasculature (Vs) and Root hair (Rh) in the hypocotyl root
X in the Vasculature bundle (Vb), Cortex (Cr) and Epidermis (Ep) of the root T2 Mature Plant Expression Plants expressing / Plants screened
Event-01: no data      Event-02: no data
☐ Scheduled
☐ T2 Mature tissue expressions similar to T1 expression data (data not shown).
☐ T2 Mature tissue expression (if different expression pattern).
Expression detected T3 Seedling Expression Seedlings expressing / Seedlings screened
Event-01: no data      Event-02: no data
☐ Scheduled
☐ T3 Seedling tissue expressions similar to T2 seedling expression (data not shown).
☐ T2 Mature tissue expression (if different expression pattern).
GFP Expression Detected Promoter utility

| | |
|---|---|
| Trait - Sub-trait Area: | Among other uses, this promoter sequence can be useful to improve: PGD-size, growth rate, source strength, nutrient economy, yield, stress tolerance |
| Construct: | YP0086 |
| Promoter Candidate I.D: | 13148255 |
| cDNA I.D: | 12420894 |
| T1 lines expressing (T2 seed): | SR00582-10,-11 |

Sequence (SEQ ID NO: 60):

```
cttatcctttaacaatgaacaggttttagaggtagcttgatgattcctgcacatgtgatcttggcttcaggcttaattttccaggtaaagcattatgaga tactcttatatctcttacatacttttgagataatgcacaagaacttcataactatatgctttagtttctgcatttgacactgccaaattcattaatctcta atatctttgttgttgatctttggtagacatgggtactagaaaaagcaaactacaccaaggtaaaatactttttgtacaaacataaactcgttatcacggaac atcaatggagtgtatatctaacggagtgtagaaacatttgattattgcaggaagctatctcaggatattatcggtttatatggaatctcttctacgcagag tatctgttattccccttcctctagctttcaatttcatggtgaggatatgcagttttctttgtatatcattcttcttcttctttgtagcttggagtcaaaat cggttccttcatgtacatacatcaaggatatgtccttctgaattttttatatcttgcaataaaaatgcttgtaccaattgaaacaccagcttttttgagttct atgatcactgacttggttctaaccaaaaaaaaaaaaatgtttaATTTACATATCTAAAAGTAGGTTTAGGGAAACCTAAACAGTAAAATATTTGTATATTA TTCGAATTTCACTCATCATAAAAACTTAAATTGCACCATAAAATTTTGTTTTACTATTAATGATGTAATTTGTGTAACTTAAGATAAAAATAATATTCCGT AAGTTAACCGGCTAAAACCACGTATAAACCAGGGAACCTGTTAAACCGGTTCTTTACTGGATAAAGAAATGAAAGCCCATGTAGACAGCTCCATTAGAGCC CAAACCCTAAATTTCTCATCTATATAAAAGGAGTGACATTAGGGTTTTTGTTCGTCCTCTTAAAGcttctcgttttctctgccgtctctc
```

Promoter Expression Report # 69

Promoter Tested In: *Arabidopsis thaliana*, WS ecotype
Spatial expression summary:

Ovule      Post-fertilization: (H)embryo

-continued

| Promoter Expression Report # 69 |  |
|---|---|
| Embryo | (H)suspensor, (H)heart, (H)torpedo, (H)late, (H)mature, (H)hypophysis, (H)radicle, (H)cotyledons |
| Rosette Leaf | (H)mesophyll, (H)epidermis |
| Primary Root | (L)epidermis, (H)cap |
| Lateral root | (H)epidermis, (H)initials, (H)cap |

Observed expression pattern: T1 mature: High expression was seen throughout heart stage through mature embryo with preferential expression in the embryonic root meristem. T2 seedling: High expression was detected in epidermal and mesophyll cells of the rosette leaf and not detected in the cotyledon. Low expression was seen throughout root epidermal cells with high preferential expression in the lateral and primary root tip.

| | |
|---|---|
| Expected expression pattern: | Constitutive |
| Selection Criteria: | *Arabidopsis* public |
| Gene: | ribosomal protein S2 |
| GenBank: | NM_104618 *Arabidopsis thaliana* 40S ribosomal protein S2 (RPS2A) (At1g58380) mRNA, complete cds gi\|30696258\|ref\|NM_104618.2\|[30696258] |
| Source Promoter Organism: | *Arabidopsis thaliana* WS |
| Vector: | pNewBin4-HAP1-GFP |
| Marker Type: | GFP-ER |
| Generation Screened: | X T1 Mature   X T2 Seedling   ☐ T2 Mature   ☐ T3 Seedling |

T1 Mature Plant Expression   Organs/Tissues screened
Events Screened:   n = 8   Events Expressing:   n = 2
GFP Expression Detected

| | |
|---|---|
| ☐ Flower | ☐ pedicel ☐ receptacle ☐ nectary ☐ sepal ☐ petal ☐ filament ☐ anther ☐ pollen ☐ carpel ☐ style ☐ papillae ☐ vascular ☐ epidermis ☐ stomata ☐ trichome |
| ☐ Silique | ☐ stigma ☐ style ☐ carpel ☐ septum ☐ placentae ☐ transmitting tissue ☐ vascular ☐ epidermis ☐ stomata ☐ abscission zone ☐ ovule |
| X Ovule | Pre-fertilization: ☐ inner integument ☐ outer integument ☐ embryo sac ☐ funiculus ☐ chalaza ☐ micropyle ☐ gametophyte |
| | Post-fertilization: ☐ zygote ☐ inner integument ☐ outer integument ☐ seed coat ☐ primordial ☐ chalaza ☐ micropyle ☐ early endosperm ☐ mature endosperm H embryo |
| X Embryo | H suspensor ☐ preglobular ☐ globular H heart H torpedo H late H mature ☐ provascular H hypophysis H radicle H cotyledons |
| ☐ Stem | ☐ epidermis ☐ cortex ☐ vascular ☐ xylem ☐ phloem ☐ pith ☐ stomata ☐ trichome |
| ☐ Leaf | ☐ petiole ☐ mesophyll ☐ vascular ☐ epidermis ☐ trichome ☐ primordia ☐ stomata ☐ stipule ☐ margin |

X in the Hypophysis (Hp) and Suspensor (Su) of the heart stage embryo
X in the torpedo stage embryo
X in the Root apical meristem (RAM) of the mature embryo
X in the mature embryo
T2 Seedling Expression   Tissues Screened
Events Screened: n = 3   Events Expressing: n = 3
Seedlings expressing / Seedlings screened
Event-01: 3/3   Event-02: 6/6   Event-03: 6/6
GFP Expression Detected

| | |
|---|---|
| ☐ Hypocotyl | ☐ epidermis ☐ cortex ☐ vascular ☐ xylem ☐ phloem ☐ stomata |
| ☐ Cotyledon | ☐ mesophyll ☐ vascular ☐ epidermis ☐ margin ☐ stomata ☐ hydathode |
| X Rosette Leaf | H mesophyll ☐ vascular H epidermis ☐ trichome ☐ petiole ☐ primordia ☐ stomata ☐ stipule ☐ margin |
| X Primary Root | L epidermis ☐ trichoblast ☐ atrichoblast ☐ cortex ☐ endodermis ☐ vascular ☐ xylem ☐ phloem ☐ pericycle ☐ quiescent ☐ columella H cap ☐ root hairs |
| X Lateral root | H epidermis ☐ trichoblast ☐ atrichoblast ☐ cortex ☐ endodermis H initials ☐ flanking cells ☐ vascular H cap |
| ☐ Shoot apical meristem | ☐ SAM ☐ epidermis |

X in the rosette leaf
X in the Lateral root (Lr).
X in the Epidermis (Ep) of the root
X in the Lateral root tip and the root timp
T2 Mature Plant Expression Plants expressing / Plants screened
Event-01: no data   Event-02: no data
☐ Scheduled
☐ T2 Mature tissue expression similar to T1 expresson data (data not shown).
☐ T2 Mature tissue expression (if different expression pattern).
Expression detected
T3 Seedling Expression Seedlings expressing / Seedlings screened
Event-01: no data   Event-02: no data
☐ Scheduled
☐ T3 Seedling tissue expressions similar to T2 seedling expression (data not shown).
☐ T2 Mature tissue expression (if different expression pattern).
GFP Expression Detected -continued Promoter Expression Report # 69

Promoter utility

| | |
|---|---|
| Trait - Sub-trait Area: | Among other uses, this promoter sequence can be useful to improve: Seed development-seed abortion, seed size, seed fill, seed composition Nutrients-root size, root number |
| Construct: | YP0088 |
| Promoter Candidate I.D: | 13148240 |
| cDNA I.D: | 13619634 |
| T1 lines expressing (T2 seed): | SR00584-10 |

Sequence (SEQ ID NO: 61):

```
tcgattgggattactacttcatctagtaaggttctgaaaacgtttgttgttgataaggaagattcgtctcaggttattactgttgatcttcaaggtttgtg attgtgacgcttatacatgtgctgaaactgtggtgtttatttattgaaaacaaaaaaaagtctctcttgtagtttcattgtactaaatagaaaacaagaa acgttttttctttaatcttctacattgataatattggatcaaaggattgtttctgcaagacacaacacaaacatacttatactagtttacttctactaag tactaactacatacccatacacacacttgcacctagactttacttctagacatcattaccctaaggtagaaccaagcttacaagcaagttttaccgacaac tcttacattacaactctagtctgtagtctttaacgtagacttactaactagtcattagtggtttaattttttaaattttcatccatatgtttttgttgtag atataaactaaagtcgGTCACATTTAATAATTGTCATTATGTCCGCGTAAAAGTCAATTCAGCTATTGGACATTTATGAAATGTAAGATTTTCTCTCTCAT CCCCGTGCGTGAAGACATGCATTGGTTTTTCTGTAATAATCAACAAATCCAAACCCCTTTTCGATCTTTATTTGGACattgttagagacaaaatttctcta tagTCTTTTTCCTAATTTGATACCATgtttttgtttcTGCACAAatttacTCACTggtttaactaacTATCCACTTatttatGATTTTACCattaggcgtc aGCTAGCCctagtCAAatttgtAAACAAGCCAAGCTATCTACAtaaatcgagatgtcATTAACGTTAATCGTCgttaatTCGAATTTgaaaacaTAGATAG ctttagcagtacaatgggcaatggtaagaagaatagcaaaagGCCCAAtatttgGTTTGCAgaaattaAAGCCTtaaaaaaaagcCCACAGATATTTGTCA AAgaaccctaAT
```

Promoter Expression Report # 70

Promoter Tested In: *Arabidopsis thaliana*, WS ecotype
Spatial expression summary:

| | |
|---|---|
| Silique | (L)ovule |
| Ovule | Pre-fertilization: (L)gametophyte |
| | Post-fertilization: (L)embryo sac |
| Leaf | (L)mesophyll |
| Hypocotyl | (H)epidermis, (H)cortex |
| Primary Root | (M)epidermis, (H)cortex, (H)cap, (L)root hairs |
| Lateral root | (H)epidermis |

Observed expression pattern: T1 mature: Low expression was observed in the region of the central cell of the developing female gametophyte of prefertilized ovules. GFP levels appear to be degrading entering maturity and are not detected in the mature gametophyte. T2 seedlings: High epidermal expression was detected in the root hypocotyl transition zone decreasing toward the root elongation zone, then increasing again at the root cap.

| | |
|---|---|
| Expected expression pattern: | Expressed in ovules and different parts of seeds |
| Selection Criteria: | Greater than 50x up in pi ovule microarray |
| Gene: | putative calmodulin |
| GenBank: | NM_106315 *Arabidopsis thaliana* calcium-binding EF-hand family protein (At1g76650) mRNA, complete cds gi|30699187|ref|NM_106315.2|[30699187] |
| Source Promoter Organism: | *Arabidopsis thaliana* WS |
| Vector: | pNewBin4-HAP1-GFP |
| Marker Type: | GFP-ER |
| Generation Screened: | X T1 Mature   X T2 Seedling   T2 Mature   T3 Seedling |
| T1 Mature Plant Expression | Organs/Tissues screened |
| Events Screened:   n = 8 | Events Expressing:   n = 2 |
| GFP Expression Detected | |
| ☐ Flower | ☐ pedicel ☐ receptacle ☐ nectary ☐ sepal ☐ petal ☐ filament ☐ anther ☐ pollen ☐ carpel ☐ style ☐ papillae ☐ vascular ☐ epidermis ☐ stomata ☐ trichome |
| X Silique | ☐ stigma ☐ style ☐ carpel ☐ septum ☐ placentae ☐ transmitting tissue ☐ vascular ☐ epidermis ☐ stomata ☐ abscission zone L ovule |
| X Ovule | Pre-fertilization: ☐ inner integument ☐ outer integument ☐ embryo sac ☐ funiculus ☐ chalaza ☐ micropyle L gametophyte |

Promoter Expression Report # 70

| | |
|---|---|
| | Post-fertilization: ☐ zygote L embryo sac ☐ inner integument ☐ outer integument ☐ seed coat ☐ primordia ☐ chalaza ☐ micropyle ☐ early endosperm ☐ mature endosperm ☐ embryo |
| ☐ Embryo | ☐ suspensor ☐ preglobular ☐ globular ☐ heart ☐ torpedo ☐ late ☐ mature ☐ provascular ☐ hypophysis ☐ radicle ☐ cotyledons ☐ hypocotyl |
| ☐ Stem | ☐ epidermis ☐ cortex ☐ vascular ☐ xylem ☐ phloem ☐ pith ☐ stomata ☐ trichome |
| X Leaf | ☐ petiole L mesophyll ☐ vascular ☐ epidermis ☐ trichome ☐ primordia ☐ stomata ☐ stipule ☐ margin |

X in the Chalaza (Ch), Female gametophyte (Fgm), Funiculus (Fn) and Micropyle (Mp) of the pre-fertilized ovule
X in the Embryo (Es)
X in the Mesophyll (Me) of the leaf
T2 Seedling Expression      Tissues Screened
Events Screened: n = 2      Events Expressing: n = 2
Seedlings expressing / Seedlings screened
Event-01: 6/6      Event-02: 3/3
☐ No GFP Expression Detected

| | |
|---|---|
| X Hypocotyl | H epidermis H cortex ☐ vascular ☐ xylem ☐ phloem ☐ stomata |
| ☐ Cotyledon | ☐ mesophyll ☐ vascular ☐ epidermis ☐ margin ☐ stomata ☐ hydathode |
| ☐ Rosette Leaf | ☐ mesophyll ☐ vascular ☐ epidermis ☐ trichome ☐ petiole ☐ primordia ☐ stomata ☐ stipule ☐ margin |
| X Primary Root | M epidermis ☐ trichoblast ☐ atrichoblast H cortex ☐ endodermis ☐ vascular ☐ xylem ☐ phloem ☐ pericycle ☐ quiescent ☐ columella H cap L root hairs |
| X Lateral root | H epidermis ☐ trichoblast ☐ atrichoblast ☐ cortex ☐ endodermis ☐ initials ☐ flanking cells ☐ vascular ☐ cap |
| ☐ Shoot apical meristem | ☐ SAM ☐ epidermis |

X in the Hypocotyl (Hy) root
X in the Hypocotyl (Hy) root zone
X in the Root hair (Rh)
X in the Cortex (Cr) and Epidermis (Ep) of the root
X in the Epidermis (Ep) and Root hair (Rh) of the lateral root
X in the Epidermis (Ep) of the root tip
T2 Mature Plant Expression Plants expressing / Plants screened
Event-01: no data      Event-02: no data
☐ Scheduled
☐ T2 Mature tissue expressions similar to T1 expression data (data not shown).
☐ T2 Mature tissue expression (if different expression pattern).
Expression detected
T3 Seedling Expression Seedlings expressing / Seedlings screened
Event-01: no data      Event-02: no data
☐ Scheduled
☐ T3 Seedling tissue expressions similar to T2 seedling expression (data not shown).
☐ T2 Mature tissue expression (if different expression pattern).
GFP Expression Detected
Promoter utility Trait - Sub-trait Area:    Among other uses, this promoter sequence can be useful to improve:
                         Seed development- endosperm production, seed abortion, seed size
Construct:                     YP0101
Promoter Candidate I.D:      11768659
cDNA I.D:                       13616623 (Old ID: 1378049)
T1 lines expressing (T2 seed):   SR00708-01,-10

Sequence (SEQ ID NO: 62):

```
Ttctcgttctctagaatattgctggaccggattaggtcaatattattgggccagattagatattgaattgtcgacgttgcttacgttacgttatatcttgt ttaagaattaaacctatcgacttagtcttaattaagaaaacattgccttaaattctctggtctgcgaccgttttttgaccgttaacccctaattaaagaa acaaataattatagaaagagcactgaaatgtgattattttaacagtactcttatgagaaaattcgtacttttagttttttttttgtacaaatctctaag aaaaacactactactaattaagaaacgtttcaaacaattttatttcgttggctcataatctttctttctcggtccgggactaaccgttggcaaaaaaaa aaaaagttgacaataattattaaagcgtaaatcatacctctcaaataaaaacttgaatttggaaacaaagacaactaaaaaactcgaatttaagagaatt cctaaaatcaagtgaagtatcatcacttggtaaaatttcataaccgttggcttctatttctatgtgtgccttggtttgcaggagataatatttcatttca
```

-continued

```
accaatgatattcgtacacatagtcaaacaaatgtttgtctttgttattatattgagaaagaacaagaaagagagagagagatagataagacgaaggaagt gaagcttccaagcgcccaccgttaaaaatctcgtgtgcaagtttcaaatacaagtggccggtggtctccataatttgatcgtcatccaattaaaaggaag aaaaagcgtgttttaTACAAGAAAACTCATTAAAAtagcaagtctagaaatatctcaacACTAATCTaccacgTCTATTACACACACACACACAcacttt gATCTTAATTTATTTTCAAGATTCAAGAAAATACCCATTCCattaccaCAACTtgaccacacgCCTATATAaaaacataaaagcccttcccc
```

| Promoter Expression Report # 71 |
|---|

Promoter Tested In: *Arabidopsis thaliana*, WS ecotype
Spatial expression summary:

| | |
|---|---|
| Silique | (H)ovule |
| Ovule | Pre-fertilization: (L)primordia, (L)inner integument, (L)outer integument, (L)funiculus |
| | Pre-fertilization: (H)outer integument, (H)seed coat |
| Hypocotyl | (M)epidermis |
| Cotyledon | (L)vascular |
| Primary Root | (H)root hairs |

Observed expression pattern: T1 mature: High expression was detected in the outer integuments of ovules. Expression can be detected in low levels in primordia to mature stage ovules and seed. T2 seedlings: Medium expression was detected in the epidermal cells of the hypocotyl and root. Root epidermal expression does not extend to the root cap. Low expression was seen in the vasculature of cotyledons.
Expected expression pattern: Integument
Selection Criteria:

| | |
|---|---|
| Gene: | "amine acid permease" (At5g09220) |
| GenBank: | NM_120958 *Arabidopsis thaliana* amino acid permease 2 (AAP2) (At5g09220) mRNA, complete cds |
| | gi\|30682579\|ref\|NM_120958.2\|[30682579] |
| Source Promoter Organism: | *Arabidopsis thaliana* WS |
| Vector: | pNewBin4-HAP1-GFP |
| Marker Type: | GFP-ER |
| Generation Screened: | X T1 Mature  X T2 Seedling  ☐ T2 Mature  ☐ T3 Seedling |

T1 Mature Plant Expression   Organs/Tissues screened
Events Screened:   n = 8   Events Expressing:   n = 3
GFP Expression Detected

| | |
|---|---|
| ☐ Flower | ☐ pedicel ☐ receptacle ☐ nectary ☐ sepal ☐ petal ☐ filament ☐ anther ☐ pollen ☐ carpel ☐ style ☐ papillae ☐ vascular ☐ epidermis ☐ stomata ☐ trichome |
| X Silique | ☐ stigma ☐ style ☐ carpel ☐ septum ☐ placentae ☐ transmitting tissue ☐ vascular ☐ epidermis ☐ stomata ☐ abscission zone H ovule |
| X Ovule | Pre-fertilization: L primordia L inner integument L outer integument ☐ embryo sac L funiculus ☐ chalaza ☐ micropyle ☐ gametophyte |
| | Post-fertilization: ☐ zygote ☐ inner integument H outer integument H seed coat ☐ chalaza ☐ micropyle ☐ early endosperm ☐ mature endosperm ☐ embryo |
| ☐ Embryo | ☐ suspensor ☐ preglobular ☐ globular ☐ heart ☐ torpedo ☐ late ☐ mature ☐ provascular ☐ hypophysis ☐ radicle ☐ cotyledons ☐ hypocotyl |
| ☐ Stem | ☐ epidermis ☐ cortex ☐ vascular ☐ xylem ☐ phloem ☐ pith ☐ stomata ☐ trichome |
| ☐ Leaf | ☐ petiole ☐ mesophyll ☐ vascular ☐ epidermis ☐ trichome ☐ primordia ☐ stomata ☐ stipule ☐ margin |

X in the Funiculus (Fn), Inner integument (Ii), Megaspore mother cell (Mmc) and Outer integument (Oi) of the ovule primordia
X in the Funiculus (Fn) and Outer integument (Oi) of the pre-fertilized ovule
X in the Seed coat (Sc) of the developing seed
T2 Seedling Expression   Tissues Screened
Events Screened:   n = 2   Events Expressing:   n = 2
Seedlings expressing / Seedlings screened
Event-01: 3/4   Event-02: 1/6
GFP Expression Detected

| | |
|---|---|
| X Hypocotyl | M epidermis ☐ cortex ☐ vascular ☐ xylem ☐ phloem ☐ stomata |
| X Cotyledon | ☐ mesophyll L vascular ☐ epidermis ☐ margin ☐ stomata ☐ hydathode |
| ☐ Rosette Leaf | ☐ mesophyll ☐ vascular ☐ epidermis ☐ trichome ☐ petiole ☐ primordia ☐ stomata ☐ stipule ☐ margin |
| X Primary Root | H epidermis ☐ trichoblast ☐ atrichoblast ☐ cortex ☐ endodermis ☐ vascular ☐ xylem ☐ phloem ☐ pericycle ☐ quiescent ☐ columella ☐ cap H root hairs |
| ☐ Lateral root | ☐ epidermis ☐ trichoblast ☐ atrichoblast ☐ cortex ☐ endodermis ☐ initials ☐ flanking cells ☐ vascular ☐ cap |
| ☐ Shoot apical meristem | ☐ SAM ☐ epidermis |

X in the Epidermis (Ep) of the hypocotyl, root and root tip
X in the Root hair (Rh) of the hypocotyl-root transition zone
X in the Vascular (Vs) of the cotyledon -continued Promoter Expression Report # 71

T2 Mature Plant Expression

Plants expressing / Plants screened
Event-01: no data    Event-02: no data
☐ Scheduled
☐ T2 Mature tissue expressions similar to T1 expression data (data not shown).
☐ T2 Mature tissue expression (if different expression pattern).
Expression detected
T3 Seedling Expression Seedlings expressing / Seedlings screened
Event-01: no data    Event-02: no data
☐ Scheduled
☐ T3 Seedling tissue expressions similar to T2 seedling expression (data not shown).
☐ T2 Mature tissue expression (if different expression pattern).
GFP Expression Detected
Promoter utility Trait - Sub-trait Area:   Among other uses this promoter sequence can be useful to improve:
                          Seed development-seed abortion, seed size, seed germination
Utility:                  Improve germination rate, seed longevity and nutrition quality
Construct:                YP0115
Promoter Candidate I.D:   13148237
cDNA I.D:                 12561466
T1 lines expressing (T2 seed):   SR00692-03,-11,-12

Sequence (SEQ ID NO: 63):

ATGATGAACATTCTACATATATAATTATTATGTTTAAGCACTTAGACAGCATAAATTCTTTCTAATTAT

ATAAATCTAACCTTGTTACATTGTACATCTATAAATTACTTGAAGAAATAACGAGTTCTATTTCTTTTA

AAAATTAAAAATACTATACCATATCTCAGTGATTAAGTTGAACCAAAAGGTACGGAGGAGAAACAAG

CATTTGATTCTTCCTTATTTTATTTTATTCATCTCTCACTAATGATGGTGGAGAAAAAAGAAAATACCT

AACAAACAAATATATATTGTCATACAAAAATATTTCTATATTTTTAGTTAATTAGTTTATATTCCTCACT

TTTCAGGGCTTATATAAGAAAGTGAGCAAACACAAATCAAAATGCAGCAGCAAATACTATCATCACCC

ATCTCCTTAGTTCTATTTTATAATTCCTCTTCTTTTTGTTCATAGCTTTGTAATTATAGTCTTATTTCTCTT

TAAGGCTCAATAAGAGGAGGTACTATTACTACACTTCTCTCTACTTTTACTTGTATTTTAGCATTAAAAT

CCTAAAATCCGTTTTAAATTCAAAAATAAACTTAGAGATGTTTAATCTCGATTCGGTTTTTCGGCTTTA

GGAGAATAATTATATGAAATTAGTATGGATATCTTTACTAGTTTCCATTCAAATGATTCTGATTTCAAT

CTAATACTCTCACTCTTTAATTAAACTATATGTAGTGTAATTTCACACTGTTAAATTTCTACCATGTCAT

GTATATTAGAGTTGCATAGAAAATTGTAAAACATCCATTTGAATTCGAATGAAACAAAATGTTTTAAA

ATAAAATTTTGGTTTTTAAAAGAAAAATCTAAAACTGAATTATATCGTTTAACCAAGTTGTAAAAGTCA

TAAAACGTAGTATCTTGTAAATCGCTCTTCCACGGTCCAAATAGACTTCTAGTAATAAACAAGTAAAAC

TAATTTTGGTTTCTTACTAATT

Promoter Expression Report # 72

Promoter Tested In: *Arabidopsis thaliana*, WS ecotype
Spatial expression summary:

Stem            (H)stomata
Hypocotyl       (L)epidermis
Cotyledon       (L)petiole
Rosette Leaf    (L)epidermis, (L)petiole
Primary Root    (M)epidermis, (L)root hairs
Observed expression pattern: T1 mature: High expression was seen in stem guard cells, but not -continued Promoter Expression Report # 72 observed in any other tissues. T2 seedling: High epidermal expression was detected in the hypocotyl at the petiole junction then decreasing in gradient fashion toward proximal organs. Low expression was seen throughout the root epidermis.

| | |
|---|---|
| Expected expression pattern: | COB RNA is upregulated in cells in the root elongation zone; expressed in siliques, stem, roots using northerns, less so in flowers |
| Selection Criteria: | Literature; COBRA encodes a putative GPI-anchored protein, which is polarly localized and necessary for oriented cell expansion in *Arabidopsis*. Genes Dev. 2001 May 1; 15(9): 1115-27. |
| Gene: | putative glycosylphosphatidylinositol (GPI) -anchored protein |
| GenBank: | NM_125485 *Arabidopsis thaliana* phytochelatin synthetase - like protein (At5g60920) mRNA, complete cds gi\|30697444\|ref\|NM_125485.2\|[30697444] |
| Source Promoter Organism: | *Arabidopsis thaliana* WS |
| Vector: | pNewBin4-HAP1-GFP |
| Marker Type: | GFP- |
| Generation Screened: | X T1 Mature   X T2 Seedling   ☐ T2 Mature   ☐ T3 Seedling |

T1 Mature Plant Expression     Organs/Tissues screened
Events Screened:     n = 7     Events Expressing:     n = 3
GFP Expression Detected ☐ Flower      ☐ pedicel ☐ receptacle ☐ nectary ☐ sepal ☐ petal ☐ filament ☐ anther ☐ pollen
              ☐ carpel ☐ style ☐ papillae ☐ vascular ☐ epidermis ☐ stomata ☐ trichome
☐ Silique     ☐ stigma ☐ style ☐ carpel ☐ septum ☐ placentae ☐ transmitting tissue ☐ vascular
              ☐ epidermis ☐ stomata ☐ abscission zone ☐ ovule
☐ Ovule       Pre-fertilization: ☐ inner integument ☐ outer integument ☐ embryo sac ☐ funiculus
              ☐ chalaza ☐ micropyle ☐ gametophyte
              Post-fertilization: ☐ zygote ☐ inner integument ☐ outer integument ☐ seed coat
              ☐ richoblas ☐ chalaza ☐ micropyle ☐ early endosperm ☐ mature endosperm
              ☐ embryo
☐ Embryo      ☐ suspensor ☐ preglobular ☐ globular ☐ heart ☐ torpedo ☐ late ☐ mature
              ☐ provascular ☐ hypophysis ☐ radicle ☐ cotyledons ☐ hypocotyl
X Stem        ☐ epidermis ☐ cortex ☐ vascular ☐ xylem ☐ phloem ☐ pith H stomata ☐ trichome
☐ Leaf        ☐ petiole ☐ mesophyll ☐ vascular ☐ epidermis ☐ trichome ☐ richoblas ☐ stomata
              ☐ stipule ☐ margin
X in the Guard cell (Gc)

T2 Seedling Expression     Tissues Screened
Events Screened: n = 2     Events Expressing: n = 2
Seedlings expressing / Seedlings screened
Event-01: 2/6     Event-02: 0/6
GFP Expression Detected X Hypocotyl              L epidermis ☐ cortex ☐ vascular ☐ xylem ☐ phloem ☐ stomata
X Cotyledon              ☐ mesophyll ☐ vascular epidermis ☐ margin ☐ stomata ☐ hydathode
                         L petiole
X Rosette Leaf           ☐ mesophyll ☐ vascular L epidermis ☐ trichome L petiole ☐
                         richoblas ☐ stomata ☐ stipule ☐ margin
X Primary Root           M epidermis ☐ richoblasts ☐ atrichoblast ☐ cortex ☐ endodermis
                         ☐ vascular ☐ xylem ☐ phloem ☐ pericycle ☐ quiescent ☐ columella
                         ☐ cap L root hairs
☐ Lateral root           ☐ epidermis ☐ trichoblast ☐ atrichoblast ☐ cortex ☐ endodermis
                         ☐ initials ☐ flanking cells ☐ vascular ☐ cap
☐ Shoot apical meristem  ☐ SAM ☐ epidermis X in the Epidermis (Ep) of the Rosette leaf (Rl) and Petiole (Pt) in the seedling
X in the Epidermis (Ep) and Root hair (Rh), of the root T2 Mature Plant Expression Plants expressing / Plants screened
Event-01: no data     Event-02: no data
☐ Scheduled
☐ T2 Mature tissue expressions similar to T1 expression data (data not shown).
☐ T2 Mature tissue expression (if different expression pattern).
Expression detected T3 Seedling Expression Seedlings expressing / Seedlings screened
Event-01: no data     Event-02: no data
☐ Scheduled
☐ T3 Seedling tissue expressions similar to T2 seedling expression (data not shown).
☐ T2 Mature tissue expression (if different expression pattern).
GFP Expression Detected
Promoter utility

| | |
|---|---|
| Trait - Sub-trait Area: | Among other uses this promoter sequence can be useful to improve: PG & D - stress tolerance, nutrient uptake |
| Construct: | YP0133 |
| Promoter Candidate I.D: | 11768667 |
| cDNA I.D: | 13601536 |
| T1 lines expressing (T2 seed): | SR00722-01,-11,-12 |

Sequence (SEQ ID NO: 64):

```
gtcgattggtaTTAGTCCAATAACTTTCACAGTTTTACTATAATATAATATTGAAAGTATGGTTAATTGACAAT

AGGGTATTTCCACTGATAATCAGTCACCAGTAATAATAATTTGTTGGGACTAGAATCAATCACTTGAGT

TTTAAATTGATATATGCCTAGATGGTTGTTAGGACCAATATTCCTAAACAATACCAAATTTTAATATAG

AAATGTAAAATAATTCGCCGACACATTATTTCGTTATTGACATTGAATATTTCAATGATATCAACTCTG

TTTATTTACATCTATTTAGTATAATTTCTTGAGCAACAAAAAAAGTAGTTTTAAAGTTATTTTCCCTAGA

TTTTTCTATTGTAAAAGCCTATATATCACAAcaaaaattaACCATTTTCTCTTTTGGCAAGTTTAAAATTTTTA

TAATGAATATACCattttaaaaaaaaaatTATCCAAACTAAATTAACCATTTTCTCTTTTGGCAACAAAAATTAAC

CatttaaaaaaaaaaaaaaaaaaaagTTTAAAATTTTTATAACAACAGAAAGTAATATTATCCAAACTATGAATAAT

TAAAAAATCTGTCCACATACGATCATATATTTCTCTCCACCGACAGCCGAAAACACTGTCAATGCCCA

CGTTCCTCTAAAAGCTGTCGTCTTCGGTAATATTTTCCGGTAATAAACTAACTTCCGATCACAATTACA

CAAAAGCCCCTTTCTCGTTTATAATCATAGGCTATGATTCATAGCAAACTTACAGAGTTGGTTATTAAG

AAGTCAAAAATACAGATTCCTTAAAATATTTTTTTCTGTTCATATATTTTTATCGAGAAACAATTActta aacATAAGAAGCAAGACAAGAATTAATGTTCTTATTAACATGATGCTAATATAATCGGAAAACAAAATC AAATCATGATAGAAGGGTAAAAtggt-
caaatcatcgttcccggctcaaattttactaaaacagccactagccagccagatcc
```

| Promoter Expression Report #73 | |
|---|---|
| Promoter Tested In: | *Arabidopsis thaliana*, WS ecotype |
| Spatial expression summary: | |
| Silique | (L)ovule |
| Ovule | (H)embryo sac, (H)gametophyte, (M)embryo sac |
| Primary Root | (H)epidermis, (H)endodermis, (H)root hairs |
| Lateral root | (H)epidennis |
| Observed expression pattern: | |
| T1 mature: | Images F–I show expression throughout the developing female gametophyte. Onset of expression is at approximately fertilization stage and decreases shortly after fertilization while expression continues in degenerated synergid cells. No expression was detected in embryo or endosperm beyond division of central cell and normal onset of endosperm cellularization. Expression in gametophyte cells of abnormal unfertilized mature ovules. Expression in penetrated synergid cells appears degenerated at mycropylar pole which indicate pollination has occurred, however, fertilization of egg cell and central cell did not occur resulting in lack of embryo and endosperm. |
| T2 seedling: | High expression in epidermal cells throughout root. |
| Expected expression pattern: | carpel walls |
| Selection Criteria: | *Arabidopsis* |
| Gene: | GDSL-motif lipase/hydrolase-like protein |
| GenBank: | NM_123959 *Arabidopsis thaliana* GDSL-motif lipase/hydrolase protein (At5g45910) mRNA, complete cds gi\|18422608\|ref\|NM_123959.1\| [18422608] |

| Promoter Expression Report #73 | |
|---|---|
| Source Promoter Organism: | *Arabidopsis thaliana* WS |
| Vector: | |
| Marker Type: | GFP-ER |
| Generation Screened: | X T1 Mature X T2 Seedling T2 Mature T3 Seedling |
| T1 Mature Plant Expression Organs/Tissues screened | |
| Events Screened: n = 3 Events Expressing: n = 2 | |
| GFP Expression Detected | |
| ☐ Flower | ☐ pedicel ☐ receptacle ☐ nectary ☐ sepal ☐ petal ☐ filament ☐ anther ☐pollen ☐ carpel ☐ style ☐ papillae ☐ vascular ☐ epidermis ☐ stomata ☐ trichome |
| X Silique | ☐ stigma ☐ style ☐ carpel ☐ septum ☐ placentae ☐ transmitting tissue ☐ vascular ☐ epidermis ☐ stomata ☐ abscission zone L ovule |
| X Ovule | Pre-fertilization: ☐ inner integument ☐ outer integument H embryo sac funiculus chalaza micropyle H gametophyte Post-fertilization: ☐ zygote M embryo sac ☐ inner integument ☐ outer integument ☐ seed coat ☐ richoblas ☐ chalaza ☐ micropyle ☐ early endosperm ☐ mature endosperm ☐ embryo |
| ☐ Embryo | ☐ suspensor ☐ preglobular ☐ globular ☐ heart ☐ torpedo late mature ☐ provascular ☐ hypophysis ☐ radicle E cotyledons ☐ hypocotyl epidermis cortex vascular ☐ xylem |
| ☐ Stem | ☐ phloem ☐ pith ☐ stomata ☐ trichome |

Promoter Expression Report #73

☐ Leaf petiole mesophyll ☐ vascular epidermis
☐ trichome ☐ richoblas ☐ stomata
☐ stipule ☐ margin X in the Egg apparatus (Ea) of the ovule and fertilized ovule
X in the Antipodal cells (Ap), Central cell (Cc), Synergid cell (Sn), Egg sac (Es), Egg apparatus (Ea) and Micropyle (Mp) of the ovule
X in the Antipodal cells (Ap), Central cell (Cc), Synergid cell (Sn) and Egg apparatus (Ea) of the fertilized ovule
Chalaza (Ch),), Egg cell (Ec), Funiculus (Fn),
X in the Antipodal cells (Ap), Central cell (Cc), Cv, Sc and Micropyle (Mp) in an abnormal ovule
Chalaza (Ch), Egg apparatus w/ synergid cells (Ea), Egg sac (Es), Funiculus (Fn)

T2 Seedling Expression Tissues Screened

Events Screened: n = 2   Events Expressing: n = 1
Seedlings expressing/Seedlings screened Event-01: 1/3   Event-02: 0/12
☐ Scheduled
GFP Expression Detected ☐ Hypocotyl ☐ epidermis ☐ cortex ☐ vascular
 ☐ xylem ☐ phloem ☐ stomata
☐ Cotyledon ☐ mesophyll ☐ vascular ☐ epidermis
 ☐ margin ☐ stomata ☐ hydathode
☐ Rosette Leaf ☐ mesophyll ☐ vascular ☐ epidermis
 ☐ trichome ☐ petiole ☐ richoblas
 ☐ stomata ☐ stipule ☐ margin
X Primary Root H epidermis ☐ richoblasts ☐ atrichoblast
 ☐ cortex H endodermis ☐ vascular
 ☐ xylem ☐ phloem ☐ pericycle
 ☐ quiescent ☐ columella ☐ cap H root hairs
X Lateral root H epidermis ☐ trichoblast ☐ atrichoblast
 ☐ cortex ☐ endodermis ☐ initials
 ☐ flanking cells ☐ vascular ☐ cap

Promoter Expression Report #73

☐ Shoot apical meristem ☐ SAM ☐ epidermis
X in the Root hair (Rh) of the root
X in the Epidermis (Ep) of the root and Lateral root (Lr)
X in the upper and lower portions of the root
X in the Endodermis (Ed) of the root T2 Mature Plant Expression Plants expressing/Plants screened Event-01: no data   Event-02: no data
☐ Scheduled
☐ T2 Mature tissue expressions similar to T1 expression data (data not shown).
☐ T2 Mature tissue expression (if different expression pattern). Expression detected T3 Seedling Expression Seedlings expressing/Seedlings screened Event-01: no data   Event-02: no data
☐ Scheduled
☐ T3 Seedling tissue expressions similar to T2 seedling expression (data not shown).
☐ T2 Mature tissue expression (if different expression pattern).
GFP Expression Detected
Promoter utility Trait - Sub-trait Area: Among other uses this promoter sequence can be useful to improve: Seed Development - endosperm production, seed size, seed abortion
Utility: Increase seed size and yield
Construct: YP0137
Promoter I.D: 11768695
cDNA I.D: 13603975
T1 lines expressing (T2 seed): SR00840-10, -11

Sequence (SEQ ID NO: 65):

```
gtgGCACATGCTGAAACCCCGAGCATCTCTCCGGAAGACACGCGTCGTTCGCTCCAAAGAAAACAGTCA
CAGCTGCCGGAGAATCTCCGCCGTCTTCTTCTGCCACCGGAAAAACTCTCTCCACCACTTTCAGTGCCC
ACCTCGTGTTATATCCACTGTATCCTCGTAGCACCATATCAGCCTAATAAAATTTTATGTATCAAATTTT
AAGACATAGCCGAAACTACACTATACTAGACAATAATAATATGATTTGTTTCCTGAAAAATTATGGTTT
CATGAGAAACATTAATCATCTATAAAACAAATTAGCTATGGCATCGAAGAGTTATCAATCAAAActgatG
AATCTTTACTTAATATATACAACATATCTTTACCTTGCGGCGGAGAAGATCGGCGAGAGAAGCACCCC
AGCCACCGTCACTAAAGGATTCTTCAGTGATGGAATCACCAAAGAGAAAAACCTTCCGTCTCATCATC
TTCCACACAATCTTCTTGAGAAAATCTGAGAGATAAGAAAGGTGTAGTGGTTTTGCTGAAGTGATCGT
GTTTGATTTAGTAAAGAAATGCTTTATTTATTGTTGGGGGAAACATAAATAAATAAAGTAAAAGTGGA
TGCACTAAATGCTTTCACCCACTAATCACCGACCTTTCATGGTTTATTGTGAAATACACTCATAGATAG
ACATACAATACCTTATGTACGTAAATAACATTTTATTTGTCGACACTTATGTAAGTAACGCATAGATTA
TTTTCTATGTGATTGCCACTCTCAGACTCTCAGTTTCAACCAATAATAACAATAACTACAACAACATTA
ATCATAAACATATGCTCTGGTTTACAATTAAAGCTtagatTAAGAAACTGTAACAACGTTACAGAAAAA
AATGTTATTTACGTTTTGTAAGATTAGTCTCTAGAATCATCACCGTTTTTTATATATTAATGATTCTTTCT
TATATataaaacctttctcgaaatacccatgaaa
```

| Promoter Expression Report #74 | |
|---|---|
| Promoter Tested In: | *Arabidopsis thaliana*, WS ecotype |
| Spatial expression summary: | |
| Flower | (H)pedicel, (H)sepal, (H)carpel, (H)style, (H)epidermis |
| Silique | (H)style, (H)carpel, (M)septum, (H)epidermis, (H)cortex |
| Stem | (H)epidermis, (H)cortex |
| Leaf | (H)mesophyll, (L)vascular, (H)epidermis |
| Hypocotyl | (H)peidermis, (H)cortex |
| Cotyledon | (H)mesophyll, (H)epidermis |
| Rosette Leaf | (H)epidermis |
| Observed expression pattern: | |
| T1 mature: | High expression throughout vegetative tissues. No expression observed in reproductive organs, ovules or embryos. Not expressed in guard cells. |
| T2 seedling: | High expression throughout vegetative tissues. No expression observed in root. |
| Expected expression pattern: | N induced, source tissue, cDNA AFLP, 24h N induced |
| Selection Criteria: | *Arabidopsis* AFLP-nitrogen |
| Gene: | ATH131206 *Arabidopsis thaliana* mRNA for microbody NAD-dependent malate dehydrogenase |
| GenBank: | NM_121003 *Arabidopsis thaliana* malate dehydrogenase, glyoxysomal (At5g09660) mRNA, complete cds gi|30682786|ref|NM_121003.2| [30682786] |
| Source Promoter Organism: | *Arabidopsis thaliana* WS |
| Vector: | pNewbin4-HAP1-GFP |
| Marker Type: | GFP-ER |
| Generation Screened: | X T1 Mature X T2 Seedling T2 Mature T3 Seedling |

T1 Mature Plant Expression Organs/Tissues screened

Events Screened: n = 3  Events Expressing: n = 3
GFP Expression Detected

| | |
|---|---|
| ☐Flower | H pedicel ☐ receptacle ☐ nectary H sepal ☐ petal ☐ filament ☐ anther ☐pollen (H)carpel (H)style ☐ papillae ☐ vascular H epidermis ☐ stomata ☐ trichome |
| XSilique | ☐ stigma H style H carpel M septum ☐ placentae ☐ transmitting tissue ☐ vascular H epidermis H cortex ☐ stomata ☐ abscission zone ☐ ovule |
| ☐ Ovule | Pre-fertilization: ☐ inner integument ☐ outer integument ☐ embryo sac ☐ funiculus ☐ chalaza ☐ micropyle ☐ gamtophyte Post-fertilization: ☐ zygote ☐ inner integument ☐ outer integument ☐ seed coat ☐ primordia ☐ chalaza ☐ micropyle ☐ early endosperm ☐ mature endosperm ☐ embryo |
| ☐ Embryo | ☐ suspensor ☐ preglobular ☐ globular ☐ heart ☐ torpedo ☐ late ☐ mature ☐ provascular ☐ hypophysis ☐ radicle ☐ cotyledons ☐ hypocotyl |
| Xstem | H peidermis H cortex ☐ vascular ☐ xylem ☐ phloem ☐ pith ☐ stomata ☐trichome |
| Xleaf | ☐ petiole H mesophyll L vascular H epidermis ☐ trichome ☐ primordia ☐ stomata ☐ stipule ☐ margin |

X in the flower
X in the Carpel (Ca), Stigma (Sg) and Style (Sy) of the Silique (Si)
X in the Cortex (Co) and Epidermis (Ep) of the carpel
X in the Guard cell (Gc) of the carpel
X in the Epidermis (Ep) and Mesophyll (Me) of the leaf
X in the Vasculature of the leaf
X in the Cortex (Cr) and Epidermis (Ep) of the stem -continued

| Promoter Expression Report #74 | |
|---|---|

T2 Seedling Expression Tissues Screened

Events Screened: n = 2  Events Expressing: n = 2
Seedlings expressing/Seedlings screened Event-01: 2/6  Event-02: 2/3
X Scheduled
GFP Expression Detected

| | |
|---|---|
| X Hypocotyl | (H)epidermis (H)cortex ☐ vascular ☐ xylem ☐ phloem ☐ stomata |
| X Cotyledon | (H)mesophyll ☐ vascular (H)epidermis ☐ margin ☐ stomata ☐ hydathode |
| X Rosette Leaf | mesophyll ☐ vascular (H)epidermis ☐ trichome ☐ petiole ☐ primordia ☐ stomata ☐ stipule ☐ margin |
| ☐ Primary Root | ☐ epidermis ☐ trichoblast ☐ atrichoblast ☐ cortex ☐ endodermis ☐ vascular ☐ xylem ☐ phloem ☐ pericycle ☐ quiescent ☐ columella ☐ cap ☐ root hairs |
| ☐ Lateral root | ☐ epidermis ☐ trichoblast ☐ atrichoblast ☐ cortex ☐ endodermis ☐ initials ☐ flanking cells ☐ vascular ☐ cap |
| ☐ Shoot apical meristem | ☐ SAM ☐ epidermis |

X in the Cotyledon (Co), Hypocotyl (Hy) and Rosette leaf (Rl) of the seedling
X in the Epidermis (Ep) of the seedling Cotyledon (Co), Hypocotyl (Hy) and Rosette leaf (Rl)

T2 Mature Plant Expression Plants expressing/Plants screened

Event-01: no data  Event-02: no data
☐ Scheduled
☐ T2 Mature tissue expressions similar to T1 expression data (data not shown).
☐ T2 Mature tissue expression (if different expression pattern).
Expression detected T3 Seedling Expression Seedlings expressing/Seedlings screened Event-01: no data  Event-02: no data
☐ Scheduled
☐ T3 Seedling tissue expressions similar to T2 seedling expression (data not shown).
☐ T2 Mature tissue expression (if different expression pattern).
GFP Expression Detected Promoter utility

| | |
|---|---|
| Trait - Sub-trait Area: | Among other uses, this promoter sequence can be useful to improve: PGD-Size, biomass, source strength, yield, stress tolerance |
| Construct: | YP0144 |
| Promoter Candidate I.D: | 13148149 |
| cDNA I.D: | 12705120 |
| T1 lines expressing (T2 seed): | SR00730-10, -11, -12 |

Sequence (SEQ ID NO: 66):

```
aaacGTTGCAAGATTATTGATTGTGAgaaagaGTGCTCAAGGTAGTACTGATTTCTGTAAAGCTCACGGTGG
TGGGAAACGATGTTCTTGGGGAGATGGGAAATGTGAgaaaatttgCTAGAGGAAAgaagcGGTTTATGCGCTG
CGCATAACACTATTATGTCTCGGGAGAACAAAGATGGAAGCAAGAGCGGTTTGATTGGACCGGGACTC
TTTAGTGGCCTTGTTTTTGGCTCTACTTCTGATCATTCTCAGTCTGGAGCTAGCGCTGTCTCTGATTGTA
CTGATTCTGTTAACGAATACAGTTTGAGAATAGGCAGAAGAACAAGAAGATGATGATACCGATGCAG
GTTCTAGTACCTTCATCAATGAAATCTCCAAGTAATTCACATGAAGGAGAAACAAACATCTATGACTTC
ATGGTTCCGGAGGAGAGAGTTCACGGCGGCGGTGGGCTAGTAATGTCTTTACTTGGTGGCTCCATTGATCGA
AACTGAAAGCCATTTATGGTAAAAGTGTCACATTCTCAGCAAAAACCTGTGTAAAGCTGTAAAATGTG
TGGGAATCTCCGAATCTGTTTGTAGCCGGTTACGTTATGCTGGATCAAAAACTCAAGATTTGTTGGATA
TTGTTATGCTGGATCGGTGGTGAAACCACTTCCCGGTTGCTAAATAAATAAACGTTTTTGTTTTATAAT
CTTTTTCACTAAACGGCAGTATGGGCCTTTAGTGGGCTTCCTTTAAGCGACCAATACAATCGTCGCACC
GGAATCTACTACCATTTATAGGTTTATTCATGTAAAACCTCGGAAAATTTGAGAGCCACAACGGTCAA
GAGACAAAAACAACTTGAAGATAAAGGGATAAGGAAGGCTTCCTACATGATGGACAACATTTCTTTCC
ACACAAATTCTCATAATAAAAATCTTATAATACAAATACTTACGTCATAATCATTCAATCTAGTCCCCA
TGTTTTAaggtcctgtttcttgtctgatacaaat
```

| Promoter Expression Report #75 | |
|---|---|
| Promoter Tested In: | *Arabidopsis thaliana*, WS ecotype |
| Spatial expression summary: | |
| Flower | (L)stomata |
| Silique | (L)ovule |
| Ovule | Post-fertilization: (M)embryo |
| Embryo | (M)torpedo, (M)late, (M)mature, (H)radicle, (M)cotyledons |
| Stem | (L)stomata |
| Observed expression pattern: | |
| T1 mature: | High preferential expression was detected in the radicle and root cap of developing embryos. GFP levels increased in cotyledons as the embryo reached maturity. Low guard cell expression was detected in flowers and stems. |
| T2 seedlings: | No expression was detected. |
| Expected expression pattern: | Induced during embryogenesis |
| Selection Criteria: | Literature; bZIP transcription factors in *Arabidopsis*. Trends Plant Sci. 2002 Mar; 7(3): 106–11. Review. |
| Gene: | AtBZIP67, bZIP protein, At3g44460 |
| GenBank: | NM_114314 *Arabidopsis thaliana* bZIP protein (At3g44460) mRNA, complete cds gi|30692145|ref|NM_114314.2| [30692145] |
| Source Promoter Organism: | *Arabidopsis thaliana* WS |
| Vector: | pNewbin4-HAP1-GFP |
| Marker Type: | GFP-ER |
| Generation Screened: | X T1 Mature X T2 Seedling T2 Mature T3 Seedling |
| T1 Mature Plant Expression Organs/Tissues screened | |
| Events Screened: n = 2 Events Expressing: n = 2 | |
| GFP Expression Detected | |
| X Flower | ☐ pedicel ☐ receptacle ☐ nectary ☐ sepal ☐ petal ☐ filament ☐ anther ☐ pollen ☐ carpel ☐ style ☐ papillae ☐ vascular ☐ epidermis L stomata ☐ trichome |

| Promoter Expression Report #75 | |
|---|---|
| X Silique | ☐ stigma ☐ style ☐ carpel ☐ septum ☐ placentae ☐ transmitting tissue ☐ vascular ☐ epidermis ☐ stomata ☐ abscission zone L ovule |
| X Ovule | Pre-fertilization: ☐ inner integument ☐ outer integument ☐ embryo sac ☐ funiculus ☐ chalaza ☐ micropyle ☐ gametophyte Post-fertilization: ☐ zygote ☐ inner integument ☐ outer integument ☐ seed coat ☐ richoblas ☐ chalaza ☐ micropyle ☐ early endosperm ☐ mature endosperm M embryo |
| X Embryo | ☐ suspensor ☐ preglobular ☐ globular ☐ heart M torpedo M late M mature ☐ provascular ☐ hypophysis H radicle M cotyledons |
| X Stem | ☐ epidermis ☐ cortex ☐ vascular ☐ xylem ☐ phloem ☐ pith L stomata ☐ trichome |
| ☐ Leaf | ☐ petiole ☐ mesophyll ☐ vascular ☐ epidermis ☐ trichome ☐ richoblas ☐ stomata ☐ stipule ☐ margin |

X in the flower Guard cells and Guard cells of the Sepal (Se)
X in the stem Guard cells
X in the Cotyledon (Co) and Radicle (Rd) of the ovule
X in the Radicle (Rd) of the torpedo stage embryo
X in the Cotyledon (Co) and Radicle (Rd) of the embryo
X in the Root cap (Rc) of the mature embryo
X in the Cotyledon (Co)

T2 Seedling Expression Tissues Screened

Events Screened: n = 2 Events Expressing: n = 0
Seedlings expressing/Seedlings screened Event-01: 0/6 Event-02: 0/3
☐ Scheduled
No GFP Expression Detected

| ☐ Hypocotyl | ☐ epidermis ☐ cortex ☐ vascular ☐ xylem ☐ phloem ☐ stomata |
|---|---|

Promoter Expression Report #75

| | |
|---|---|
| ☐ Cotyledon | ☐ mesophyll ☐ vascular ☐ epidermis ☐ margin ☐ stomata ☐ hydathode |
| ☐ Rosette Leaf | ☐ mesophyll ☐ vascular ☐ epidermis ☐ trichome ☐ petiole ☐ richoblas ☐ stomata ☐ stipule ☐ margin |
| ☐ Primary Root | ☐ epidermis ☐ richoblasts ☐ atrichoblast ☐ cortex ☐ endodermis ☐ vascular ☐ xylem ☐ phloem ☐ pericycle ☐ quiescent ☐ columella ☐ cap ☐ root hairs |
| ☐ Lateral root | ☐ epidermis ☐ trichoblast ☐ atrichoblast ☐ cortex ☐ endodermis ☐ initials ☐ flanking cells ☐ vascular ☐ cap |
| ☐ Shoot apical meristem | ☐ SAM ☐ epidermis |

T2 Mature Plant Expression Plants expressing/Plants screened

Event-01: no data  Event-02: no data
☐ Scheduled
☐ T2 Mature tissue expressions similar to T1 expression data (data not shown).
☐ T2 Mature tissue expression (if different expression pattern).
Expression detected
T3 Seedling Expression Seedlings expressing/Seedlings screened Event-01: no data  Event-02: no data
☐ Scheduled
☐ T3 Seedling tissue expressions similar to T2 seedling expression (data not shown).
☐ T2 Mature tissue expression (if different expression pattern).
GFP Expression Detected
Promoter utility

| | |
|---|---|
| Trait - Sub-trait Area: | Among other uses, this promoter sequence can be useful to improve: Seed development-seed size, seed composition, root development |
| Construct: | YP0143 |
| Promoter Candidate I.D: | 11768669 |
| cDNA I.D: | 13607229 |
| T1 lines expressing (T2 seed): | SR00729-10, -11 |

Promoter Expression Report #76

| | |
|---|---|
| Promoter Tested In: | *Arabidopsis thaliana*, WS ecotype |
| Spatial expression summary: | |
| Ovule | Post-fertilization: (H)embryo |
| Embryo | (L)radicle, (H)cotyledons |
| Primary Root | (H)epidermis, (H) richoblasts, (H)atrichoblast, (H)root hairs |
| Observed expression pattern: | |
| T1 mature: | High preferential expression in cotyledons of developing embryo with low expression in radicle of mature embryos. |
| T2 seedling: | High expression in epidermal cells near root transition zone decreasing toward root tip observed in one of two events screened (I. YP0156-10 T2 seedling expression). The second event showed expression in lateral and primary root meristematic cells but not epidermal (YP0156-13 T2 seedling expression). Additional events screened showed epidermal expression patterns similar to line -10, however lateral and primary root expression in these lines remains inconclusive. |
| Expected expression pattern: | Induced during embryogenesis |
| Selection Criteria: | Literature |
| Gene: | AtBZIP12 |
| GenBank: | NM_180010 *Arabidopsis thaliana* bZIP family transcription factor (At2g41070) mRNA, complete cds gi\|30688516\|ref\|NM_180010.1\| [30688516] |
| Source Promoter Organism: | *Arabidopsis thaliana* WS |
| Vector: | Newbin4-HAP1-GFP |
| Marker Type: | GFP-ER |
| Generation Screened: | X T1 Mature X T2 Seedling ☐ T2 Mature ☐ T3 Seedling |

T1 Mature Plant Expression Organs/Tissues screened

Events Screened:  n = 3  Events Expressing:  n = 2

Sequence (SEQ ID NO: 67):

atACAACAGATGGCAGATATCGAGTTAAAtacgtGAATCAGCCGTTACGATATTTTAAAACTAGAAAATTA

TTTAAAAATATTGCAAAATACCATTTAATTTCATTGTTCATAAAAAAAAGAAattcaaaaacTTAAAAACTG

ATTCAAAAATTTGGATTAattctcattaACAGTCTTCAACACTACAACAACATGTTTCTAATTTATTTTATATT

TTAATAATTAAACAATATATACGTCTGCACATTGTTGCTCCGACATAATCTAGTATAAAAATAGTTGCA

GCATATGTGAAAAGCAAGCAGCATTTatcacTCAATActtttaATTTTatctgTTGTATGTATTAAGGTTTTGTAG

CTTTAAGAAAACGCTTATAATATAAAATAACTTCtaaaagATATTTCATGCGTATACAATAAATATTTGTG

AAAAAACATTTCGAAAACGTGTAcaatatATAAACTATTGTGTTATCTTTTGACATTCAAACAAATGTTGA

CAATGTAATTTTATCCATGATATGATTGGCCAATTAGCTGCGAGGTAAAAATCCGTATACGAGTAAAA

GTAAGATAAAATTTCGCAAGAAGATTTTTAGCAGGAAATCTAAGACAAGTGTCATGAACGTGTCAATC

AACAAACGAAAGGAGAATTATAGAATCCAGATTCGACGTACCACATTAATAAATATCAAACATTTT

ATGTTATTTTATTTTTGGTCTGGCAGTTACACTCTTTTTCATTGCTCCAATAAAAAAatcacTCGCATGCAT

GCATATATATACACCATAGTAAACTCCGCCTCTTCTTCATTTTAAAAGTATCAGTTTACACTGACACAA

TCCTTAACTATTTTCCTTTGTTCTTCTTCATCTTTATTACACATTTTTTTCAAGGTAACAAATAATCTTTT

TAAGTCACTTTTATACTCTTTAAATCTTAGATTGATATATGAATGCATGTTAATATTtcaagatttataggtctaccaa ac -continued Promoter Expression Report #76

GFP Expression Detected

| | |
|---|---|
| ☐ Flower | ☐ pedicel ☐ receptacle ☐ nectary ☐ sepal ☐ petal ☐ filament ☐ anther ☐ pollen ☐ carpel ☐ style ☐ papillae ☐ vascular ☐ epidermis ☐ stomata ☐ trichome |
| ☐ Silique | ☐ stigma ☐ style ☐ carpel ☐ septum ☐ placentae ☐ transmitting tissue ☐ vascular ☐ epidermis ☐ stomata ☐ abscission zone ☐ ovule |
| X Ovule | Pre-fertilization: ☐ inner integument ☐ outer integument ☐ embryo sac ☐ funiculus ☐ chalaza ☐ micropyle ☐ gametophyte Post-fertilization: ☐ zygote ☐ inner integument ☐ outer integument ☐ seed coat ☐ richoblas ☐ chalaza ☐ micropyle ☐ early endosperm ☐ mature endosperm H embryo |
| X Embryo | ☐ suspensor ☐ preglobular ☐ globular ☐ heart ☐ torpedo ☐ late ☐ mature ☐ provascular ☐ hypophysis L radicle H cotyledons |
| ☐ Stem | ☐ epidermis ☐ cortex ☐ vascular ☐ xylem ☐ phloem ☐ pith ☐ stomata ☐ trichome |
| ☐ Leaf | ☐ petiole ☐ mesophyll ☐ vascular ☐ epidermis ☐ trichome ☐ richoblas ☐ stomata ☐ stipule ☐ margin |

X in the Cotyledon (Co) and Radicle (Rd) of the mature embryo
T2 Seedling Expression Tissues Screened Events Screened: n = 4  Events Expressing: n = 4
Seedlings expressing/Seedlings screened Event-01: Line -10   3/3   Event-02: Line -13   3/3
*shows different expression pattern.
Event-03: Line -11   6/6   Event-04: Line -12   6/6
☐ Scheduled
GFP Expression Detected

| | |
|---|---|
| ☐ Hypocotyl | ☐ epidermis ☐ cortex ☐ vascular ☐ xylem ☐ phloem ☐ stomata |
| ☐ Cotyledon | ☐ mesophyll ☐ vascular ☐ epidermis ☐ margin ☐ stomata ☐ hydathode |
| ☐ Rosette Leaf | ☐ mesophyll ☐ vascular ☐ epidermis ☐ trichome ☐ petiole ☐ richoblas ☐ stomata ☐ stipule ☐ margin |

-continued

Promoter Expression Report #76

| | |
|---|---|
| X Primary Root | H epidermis H trichoblast H atrichoblast ☐ cortex ☐ endodermis ☐ vascular ☐ xylem ☐ phloem ☐ pericycle ☐ quiescent ☐ columella ☐ cap H root hairs |
| ☐ Lateral root | ☐ epidermis ☐ trichoblast ☐ atrichoblast ☐ cortex ☐ endodermis ☐ initials ☐ flanking cells ☐ vascular ☐ cap |
| ☐ Shoot apical meristem | ☐ SAM ☐ epidermis |

I. YP0156-10 T2 seedling expression.

X in the root
X in the Epidermis (Ep) and Root hair (Rh) of the root
Addition events screened shown to have similar expression pattern as line -10.
II. YP0156-13 T2 seedling expression.

X in the lateral root primordial and lateral root tip
X in the root tip
Line -13 shows different pattern.
T2 Mature Plant Expression Plants expressing/Plants screened Event-01:  no data   Event-02:  no data
☐ Scheduled
☐ T2 Mature tissue expressions similar to T1 expression data (data not shown).
☐ T2 Mature tissue expression (if different expression pattern).
Expression detected
T3 Seedling Expression Seedlings expressing/Seedlings screened Event-01:  no data   Event-02:  no data
☐ Scheduled
☐ T3 Seedling tissue expressions similar to T2 seedling expression (data not shown).
☐ T2 Mature tissue expression (if different expression pattern).
GFP Expression Detected
Promoter utility

| | |
|---|---|
| Trait - Sub-trait Area: | Among other use, this promoter sequence can be useful to improve: PGD-C/N partitioning, amino acid transport |
| Construct: | YP0156 |
| Promoter Candidate I.D: | 11768688 |
| cDNA I.D: | 12323871 |
| T1 lines expressing (T2 seed): | SR00810-10, -11, -12, -13 |

Sequence (SEQ ID NO: 68):

```
ttggtttgCATTGTGAAGATTTGTATTAACTATAGAACATTGAATTGATGGTGTTAAGTTCTTACACAAGCGT
GCTTCTCGGTTTGAACTGTTTCTTTTGTATGTTGAATCAGAGCTTAGTTTATAGGAACCAGAGTATCTAC
TTAGTCATTCTctgatGCTAAGTGCTAAGGTTCTACCTAGTTGCCCTCTAGGCCCTTATGTTATTGATAACT
TATGAAGCTATTTGAACACTTGATTCTTAGGAGACCTAAGTTGGTACAGCCAGATAGAGTGTATGTTCT
TGTTCTCTATGTGACAGGATCAAGCTGCCACACATAGTTCAAGGGTATGCTCTGTGTGGGTTTGCTCAG
ATTGAGGACAAATCTATACAAGGAAGTAGAGTCTTTGACATTTTGATGTTGTATGATAAGAAGAAGAA
AGGAGAGTAATAAAGAAAGAGAAAAGGGAAACAGAAACACGTGGGAGAACATCCCAAAGAGGAAGC
ACACGCGGATCTTCATGCAAAGCTCCCGATTCTCCCATGTGGTCCCTTTCTCCCTTTGTCCCCCTCCTC
TTTCTTCTTTTCTCATTTTACTCCTTTTTTTACCATTATACAACGAATCTTTTTTATCATAATTTTTTGGTT
TTGGTTTATTTTCCAATAACACTTTCTTGGTTACTTCCCATTCTCACTTTTTCATATAAGAAACTCACTTT
GGGAAACTTATGTTTGAGAATGACAAGTCTTTTTAGAGAAAGTGATGTAACAAATCTAAAGTGATTAT
ATAATAACCTTGCACAATGTTTTTGATTTTTTGTAAGATTCGAATATTAGGTTTATTATTCGTAGGGAAT
```

-continued

```
AAACTTACTTTCAAAAGCGTTCATAAGTTAATACTTTCATATATGATCATAAGTACGGACACTATTGTT

TTTTGTTTGTTTGTGTTTATTCTAAAAGAAAGTAGCTTTTAATTGAAATGTCCtcggaGGCACAGTTTAAA

GTTCGAGTgtaacagtttctaaggca
```

Promoter Expression Report #77

| | |
|---|---|
| Promoter Tested In: | *Arabidopsis thaliana*, WS ecotype |
| Spatial expression summary: | |
| Flower | (H)pedicel, (H)receptacle, (H)sepal, (H)petal, (L)filament, (H)vascular (H)epidermis |
| Stem | (H)epidermis, (H)cortex |
| Hypocotyl | (H)epidennis, (H)cortex, (H)vascular |
| Cotyledon | (H)vascular, (H)epidermis, (H)hydathode |
| Rosette Leaf | (H)vascular, (H)epidermis, (H)petiole, (H)primordia |
| Primary Root | (H)epidermis, (H)vascular |
| Observed expression pattern: | |
| T1 mature: | High expression in epidermal and vascular tissues in floral organs and inflorescence meristem. Expressed in stem epidermis and cortex. Not detected in mesophyll cells. |
| T2 seedling: | Very high expression levels epidermal and vascular tissues of seedling. Medium expression in cortical tissues in lower hypocotyl decreasing toward apex. In root, preferentially expressed in epidermal non-root hair producing atrichoblast cells and vascular tissues. Not detected in mesophyll cells or shoot apical meristem and rosette leaf richoblas. |
| Expected expression pattern: | Roots |
| Selection Criteria: | Ceres Microarray 5–10× up. Unique Arab. Clones + Yiwen's corn root tips only (2.5× and up) |
| Gene: | protein kinase homolog |
| GenBank: | NM_124535 *Arabidopsis thaliana* leucine-rich repeat transmembrane protein kinase, putative (At5g51560) mRNA, complete cds gi\|30696067\|ref\| NM_124535.2\|[30696067] |
| Source Promoter Organism: | *Arabidopsis thaliana* WS |
| Vector: | Newbin4-HAP1-GFP |
| Marker Type: | GFP-ER |
| Generation Screened: | X T1 Mature X T2 Seedling ☐ T2 Mature ☐ T3 Seedling |

T1 Mature Plant Expression Organs/Tissues screened

Events Screened: n = 4  Events Expressing: n = 2
GFP Expression Detected

| | |
|---|---|
| X Flower | H pedicel H receptacle ☐ nectary H sepal H petal L filament ☐ anther ☐ pollen ☐ carpel ☐ style ☐ papillae H vascular H epidermis ☐ stomata ☐ trichome |
| ☐ Silique | ☐ stigma ☐ style ☐ carpel ☐ septum ☐ placentae ☐ transmitting tissue ☐ vascular ☐ epidermis ☐ stomata ☐ abscission zone ☐ ovule |
| ☐ Ovule | Pre-fertilization: ☐ inner integument ☐ outer integument ☐ embryo sac ☐ funiculus ☐ chalaza ☐ micropyle ☐ gametophyte Post-fertilization: ☐ zygote ☐ inner integument ☐ outer integument ☐ seed coat ☐ richoblas ☐ chalaza ☐ micropyle ☐ early endosperm ☐ mature endosperm ☐ embryo |
| ☐ Embryo | ☐ suspensor ☐ preglobular ☐ globular ☐ heart ☐ torpedo ☐ late ☐ mature ☐ provascular ☐ hypophysis ☐ radicle ☐ cotyledons ☐ hypocotyl |
| X Stem | H epidermis H cortex ☐ vascular ☐ xylem ☐ phloem ☐ pith ☐ stomata ☐ trichome |
| ☐ Leaf | ☐ petiole ☐ mesophyll ☐ vascular ☐ epidermis ☐ trichome ☐ richoblas ☐ stomata ☐ stipule ☐ margin |

X in the Epidermis (Ep) and Vasculature (Vs) of the flower/pedicel
X in the Vasculature (Vs) of the flower petal
X in the Epidermis (Ep) and Cortex (Cr) of the stem
T2 Seedling Expression Tissues Screened Events Screened: n = 2  Events Expressing: n = 2
Seedlings expressing/Seedlings screened Event-01: 1/3  Event-02: 1/6
☐ Scheduled
GFP Expression Detected

| | |
|---|---|
| X Hypocotyl | H epidermis H cortex H vascular ☐ xylem ☐ phloem ☐ stomata |
| X Cotyledon | ☐ mesophyll H vascular H epidermis ☐ margin ☐ stomata H hydathode |
| X Rosette Leaf | ☐ mesophyll H vascular H epidermis ☐ trichome H petiole H primordia ☐ stomata ☐ stipule ☐ margin |
| X Primary Root | H epidermis ☐ richoblasts ☐ atrichoblast ☐ cortex ☐ endodermis H vascular ☐ xylem ☐ phloem ☐ pericycle ☐ quiescent ☐ columella ☐ cap ☐ root hairs |
| ☐ Lateral root | ☐ epidermis ☐ trichoblast ☐ atrichoblast ☐ cortex ☐ endodermis ☐ initials ☐ flanking cells ☐ vascular ☐ cap |
| ☐ Shoot apical meristem | ☐ SAM ☐ epidermis |

X in the Shoot apical menstem (SAM) of the mflorescence menstem
X in the Epidermis (Ep) and Vasculature (Vs) of the rosette leaf and root
X in the Hydothode (Hd), Epidermis (Ep) and Vasculature (Vs) of the cotyledon
X in the seedling
X in the Epidermis (Ep) and Vasculature (Vs) of the hypocotyl
X in the Epidermis (Ep) and Root hair (Rh) of the hypocotyl/root
T2 Mature Plant Expression Plants expressing/Plants screened Event-01: no data  Event-02: no data
☐ Scheduled
☐ T2 Mature tissue expressions similar to T1 expression data (data not shown).
☐ T2 Mature tissue expression (if different expression pattern).
Expression detected
T3 Seedling Expression Seedlings expressing/Seedlings screened Event-01: no data  Event-02: no data
☐ Scheduled
☐ T3 Seedling tissue expressions similar to T2 seedling expression (data not shown).
☐ T2 Mature tissue expression (if different expression pattern).
GFP Expression Detected
Promoter utility

| | |
|---|---|
| Trait - Sub-trait Area: | Among other uses, this promoter sequence can be useful to improve: PGD-size, growth rate, yield, stress tolerance |

Promoter Expression Report #77

| | |
|---|---|
| Construct: | YP0158 |
| Promoter Candidate I.D: | 11768620 |
| cDNA I.D: | 13602983 |
| T1 lines expressing (T2 seed): | SR00842-12, -13 |

Sequence (SEQ ID NO: 69):

ttattagattaatagattgcatTGCATTGCTTGTGCTTTCAATTTACAAATTGTCTCCCAACTCCATCGACACATCTCTT

TTTGTGTATATAAGATTCAGACTTGTTATATTTTTTTATAAATATGTTATTAGCATCTTAAGTTAAATT

GATTTTTTATATCTGCATTAAGGATTACACGACTATATTTGCGATTGTGTGTTGGTTAAAATATAATTTA

GGATTGTCTTTAACTACATTTAGGATTATATGACTATATTTGGTTAAATATAAAATCTagctgTGATTATT

AGTATTcaaaaatAAGTAGCCTAACCAATTAAAACAACGGCTATTGGGGCAAATTAGAACATTTTAGTGTG

TCCAAAATATAATGGTCATTAGGTCATATTCCTCCTAGCTTCATCGCAGCATAATTGAATGATTGCCTT

ATTTAGAAGAGCTTTTCCACTTTCCCAAAATCTAGGTGGGATCTTTTTGTTTTGACCTTCATTTTTCTTGT

TTACCATTTTTAGCTAAATTATTTACGATTACAAAAGATATCAAAAGTTGGATCATAATACAATTTATA

GACTTACTGTAGAAAATTCGTATGTACAAGTACAACAAATTCTTCATAATAAATTTTGAAAATTCTATT

ACAAATGTTGTAAGAAATAGAATTTGAAATATATATAAACTAAGGAGAAAAAAAAAGAGAACATGCA

TTGCTCTAGTCAGAGTGGACCAACATCAACGAGATAAGATAACATAAAAACCAACTCACCATAACTAA

AAACATCCCAAGAGATCCAACGATTCATATCAAACACAAAAACATCGAACGATCAGATTTAAACCATC

TCTGGTATCTCCAAAACACAAACActtttttttttctTTTGTCTGAATGGAACAAAAGCATGCGACATCTCTGTGT

CTTTATCTTCTCTCCTCTTCTTGAAAAACTGAACCTTTAATTCTTTCTTCACAtctcctttagctttctgaagctgcta

PromoterExpression Report #79 integuments of pre- and post-fertilized ovules. GFP expression observed from globular to mature embryo development with preferential expression in root

PromoterExpression Report #79

| | |
|---|---|
| Promoter Tested In: | *Arabidopsis thaliana*, WS ecotype |
| Spatial expression summary: | |
| Flower | (M)pedicel, (L)receptacle, (L)nectary, (H)sepal, (H)filament, (M)carpel, (M)epidermis |
| Silique | (H)carpel, (H)placentae, (H)epidermis, (M)ovule |
| Ovule | Pre-fertilization: (L)inner integument, (H)funiculus<br>Post-fertilization: (H)inner integument, (H)embryo |
| Embryo | (H)globular, (H)heart, (H)torpedo, (H)late, (H)mature, (H)hypophysis, (H)radicle, (H)cotyledons |
| Stem | (L)cortex, (H)vascular |
| Hypocotyl | (H)epidermis, (H)cortex, (L)vascular |
| Cotyledon | (L)epidermis, (L)petiole |
| Primary Root | (H)vascular, (H)pericycle, (H)cap |
| Lateral root | (H)initials, (L)vascular, (H)cap |
| Observed expression pattern: | |
| T1 mature: | Expression was detected throughout the epidermal and cortical cells in the inflorescence meristem with preferential expression in vascular tissues. Low expression existed in the shoot apical meristem with highest expression in developing floral and sepal richoblas. High expression was seen throughout the reproductive tissues in the ovary of developing prefertilized flowers with high specific expression in the inner |
| T2 seedling: | meristemic tissues also observed in T2 seedlings root. High expression throughout stem tissue. High expression was seen in the epidermal and cortical tissues of hypocotyl. Expression was observed throughout the vasculature and root, and lateral root tips. |
| Expected expression pattern: Selection Criteria: | N induced, source tissue |
| Gene: | "putative serine/threonine protein kinase" |
| GenBank: | NM_119436 *Arabidopsis thaliana* protein kinase, gi|30689505|ref| NM_119436.2|[30689505] |
| Source Promoter Organism: | *Arabidopsis thaliana* WS |
| Vector: | Newbin4-HAP1-GFP |
| Marker Type: | GFP-ER |
| Generation Screened: | X T1 Mature X T2 Seedling<br>☐ T2 Mature ☐ T3 Seedling |

T1 Mature Plant Expression Organs/Tissues screened

Events Screened: n = 6   Events Expressing: n = 4
GFP Expression Detected

X Flower    M pedicel L receptacle L nectary
           H sepal ☐ petal H filament ☐ anther
           ☐ pollen M carpel ☐ style
           ☐ papillae ☐ vascular M epidermis
           ☐ stomata ☐ trichome -continued PromoterExpression Report #79

| | |
|---|---|
| X Silique | ☐ stigma ☐ style H carpel ☐ septum H placentae ☐ transmitting tissue ☐ vascular H epidermis ☐ stomata ☐ abscission zone M ovule |
| X Ovule | Pre-fertilization: L inner integument ☐ outer integument ☐ embryo sac H funiculus ☐ chalaza ☐ micropyle ☐ gametophyte Post-fertilization: ☐ zygote H inner integument ☐ outer integument ☐ seed coat ☐ richoblas ☐ chalaza ☐ micropyle ☐ early endosperm ☐ mature endosperm H embryo |
| X Embryo | ☐ suspensor ☐ preglobular H globular H heart H torpedo H late H mature ☐ provascular H hypophysis H radicle H cotyledons |
| X Stem | ☐ epidermis L cortex H vascular ☐ xylem ☐ phloem ☐ pith ☐ stomata ☐ trichome |
| Leaf | ☐ petiole ☐ mesophyll ☐ vascular ☐ epidermis ☐ trichome ☐ richoblas ☐ stomata ☐ stipule ☐ margin |

X in the Epidermis (Ep) and Vasculature (Vs) of the inflorescence
X in the Sepals (Se) and Shoot apical meristem (SAM)
X in the Vasculature (Vs) of the stamen filament
X in the Nectary (Ne) and Ovule (Ov) of the flower
X in the Epidermis (Ep) and Cortex (Cr) of the silique
X in the Placenta (Pl), Ovule (Ov) and Funiculus (Fn) of the ovary.
X in the Outer integument (Oi) of the ovule
X in the Embryo (Em) of the ovule at the globular stage
X in the Embryo (Em) and the Root apical meristem (RAM) of the embryo at the heart stage
X in the Embryo (Em) at the torpedo stage
X in the Root apical meristem (RAM) of the mature embryo
X in the root tip
X in the Pith (Pi), Cortex (Cr) and Vascular bundle (Vb) of the stem
T2 Seedling Expression Tissues Screened Events Screened: n = 2  Events Expressing: n = 2
Seedlings expressing/Seedlings screened Event-01: 1/3  Event-02: 1/3
☐ Scheduled
GFP Expression Detected

| | |
|---|---|
| X Hypocotyl | H epidermis H cortex L vascular ☐ xylem ☐ phloem ☐ stomata |
| X Cotyledon | ☐ mesophyll ☐ vascular L epidermis ☐ margin ☐ stomata ☐ hydathode L petiole |

-continued

PromoterExpression Report #79

| | |
|---|---|
| ☐ Rosette Leaf | ☐ mesophyll ☐ vascular ☐ epidermis ☐ trichome ☐ petiole ☐ richoblas ☐ stomata ☐ stipule ☐ margin |
| X Primary Root | ☐ epidermis ☐ richoblasts ☐ atrichoblast ☐ cortex ☐ endodermis H vascular ☐ xylem ☐ phloem H pericycle ☐ quiescent ☐ columella H cap ☐ root hairs |
| X Lateral root | ☐ epidermis ☐ trichoblast ☐ atrichoblast ☐ cortex ☐ endodermis H initials ☐ flanking cells L vascular H cap |
| ☐ Shoot apical meristem | ☐ SAM ☐ epidermis |

X in the Epidermis (Ep), of the hypocotyl
X in the Lateral root (Lr) and Vasculature (Vs) of the root
X in the lateral root tip
X in the Pericycle (Pr) and Vasculature (Vs) of the lateral root initial
X in the lateral root primordial
X in the Root apical meristem (RAM) of the root tip
T2 Mature Plant Expression Plants expressing/Plants screened Event-01: no data  Event-02: no data
☐ Scheduled
☐ T2 Mature tissue expressions similar to T1 expression data (data not shown).
☐ T2 Mature tissue expression (if different expression pattern).
Expression detected
T3 Seedling Expression Seedlings expressing/Seedlings screened Event-01: no data  Event-02: no data
☐ Scheduled
☐ T3 Seedling tissue expressions similar to T2 seedling expression (data not shown).
☐ T2 Mature tissue expression (if different expression pattern).
GFP Expression Detected
Promoter utility

| | |
|---|---|
| Trait - Sub-trait Area: | Among other uses, this promoter sequence can be useful to improve: PGD-shoot development and architecture, branch number, flower number, seed number and yield, source strength, growth rate, size, root development and architecture |
| Construct: | YP0164 |
| Promoter Candidate ID: | |
| cDNA I.D: | 12385295 |
| T1 lines expressing (TZ seed): | SR00813-10, -11, -13, -15 |

Sequence (SEQ ID NO: 70):

```
gtcgattggcaTTACTAGAGTTTTAGATTTCACAGAATTCTTTTGTTTGGTCTGTTCGTCCTCTACTGTGT

TTTTCTTTTGTTTTGGCTATTTTGCCGTCTGTTAAAAAATTGGGGTTTTCCGATAATGTATtgtatATGCCTG

AATTATGGAAATATCACTAAAAACACTTTTTTGCACTTTTGTATATATTGCAATTAAGATTTAATTTTTC

TATTTTGAAGACTTTTTGTTAAAAGAGAGATTTGCTAACTCAAAATTACCGGAGTTAATAAGTTCGTTC

TCATCAGATTAGCAAAACATTCATCTTTAAAGAAATCTGTTTATCTCACGTAAAATTCTACTAATTGGC

AGCAgcacaCTACTTTAATGGGCCTATTACTATTTCAATATGCACTGAAAACTTCATTGGACTGTCCAATA

ACATTATAACATTATTAAAACTAAACTACATTGTATTTGGGTTACAATTTTATAAAGAGTAAGACTCA

AGATACTAATTGGGCTGCAGACAACTTTAAAAGCCTTACTACAAAAATCAAAACCATTCTTAATTAACT

AACAACCAGGTAAAAATCTCAGTACAATATTTACACTAAAAATAGGTGCCACCCACTATGCAAAAGTT

TAGGGCCACGAACAAAAAAACCTGTAAATTGTTATGTCTTCACAATATGTGTTTTAATACACATGAATT
```

-continued

```
TTAGCTGcgGTTAATGTAAATTTTGTAGTTAAATTAAGGCTAAACAATCTCAAATATAAATTGGTCAGG

TCCACAGACAACAGCCTGGCAAGTGGCAAGCACTAAAAATTCGACCGTTATTTTTTGCCCCTTTTTTA

ATATTTCGAAATTGTATCTTTTAGTTTTATTTTAAAGCTTTTTAGCCCGCtcctcCTCCGCTCCACCTTTAAT

TTTTTCACCAATTGGATTTGGATCTGTCAAAAATATTGGCCTCTTTCTCTCTTTCTCTCTTGCTCTCTTTC

TTTGTTGGGTTga
```

| Promoter Expression Report #80 | |
|---|---|
| Promoter Tested In: | *Arabidopsis thaliana*, WS ecotype |
| Spatial expression summary: | |
| Silique | (H)ovule |
| Ovule | Post-fertilization: (H)inner integument, (H)outer integument, (H)seed coat |
| Observed expression pattern: | |
| T1 mature: | Ovules from within the same silique show variable expression levels in the outer and inner integuments of ovules. Series of optical sections of ovule show high expression in the inner integument and no or low expression in the outer integument. Optical sections of ovules also show opposite expression pattern. Series stacked sections of ovules show an equal level of expression. Expression levels off as ovules mature. Expression in late endosperm is detected. Detailed observation of endosperm required. |
| T2 seedling: | No expression was detected. |
| Expected expression pattern: | Expressed in ovules and different parts of seeds |
| Selection Criteria: | Greater than 50× up in pi ovule microarray |
| Gene: | AGAMOUS-LIKE MADS BOX PROTEIN |
| GenBank: | NM_115740 *Arabidopsis thaliana* MAD S-box protein (At3g58780) mRNA, complete cds. gi|30694874|ref| NM_115740.2|[30694874] |
| Source Promoter Organism: | *Arabidopsis thaliana* WS |
| Vector: | Newbin4-HAP1-GFP |
| Marker Type: | GFP-ER |
| Generation Screened: | X T1 Mature X T2 Seedling ☐ T2 Mature ☐ T3 Seedling |

T1 Mature Plant Expression Organs/Tissues screened

Events Screened: n = 3  Events Expressing: n = 2
GFP Expression Detected

| | |
|---|---|
| ☐ Flower | ☐ pedicel ☐ receptacle ☐ nectary ☐ sepal ☐ petal ☐ filament ☐ anther ☐ pollen ☐ carpel ☐ style ☐ papillae ☐ vascular ☐ epidermis ☐ stomata ☐ trichome |
| X Silique | ☐ stigma ☐ style ☐ carpel ☐ septum ☐ placentae ☐ transmitting tissue ☐ vascular ☐ epidermis ☐ stomata ☐ abscission zone H ovule |
| X Ovule | Pre-fertilization: ☐ inner integument ☐ outer integument ☐ embryo sac ☐ funiculus ☐ chalaza ☐ micropyle ☐ gametophyte Post-fertilization: ☐ zygote H inner integument H outer integument H seed coat ☐ primordia ☐ chalaza ☐ micropyle ☐ early endosperm ☐ mature endosperm ☐ embryo |
| ☐ Embryo | ☐ suspensor ☐ preglobular ☐ globular ☐ heart ☐ torpedo ☐ late ☐ mature ☐ provascular ☐ hypophysis ☐ radicle ☐ cotyledons ☐ hypocotyl |
| ☐ Stem | ☐ epidermis ☐ cortex ☐ vascular ☐ xylem ☐ phloem ☐ pith ☐ stomata ☐ trichome |
| ☐ Leaf | ☐ petiole ☐ mesophyll ☐ vascular ☐ epidermis ☐ trichome ☐ primordia ☐ stomata ☐ stipule ☐ margin |

X in the silique
X in the Inner integument (Ii) of the ovule
X in the Endosperm (En) and Inner integument (Ii) of the ovule ath the torpedo stage
X in the Outer integument (Oi) of the ovule at the zygote stage
X in the Inner integument (Ii) and Outer integument (Oi) of the ovule
X in the Seed coat (Sc) of the seed T2 Seedling Expression Tissues Screened Events Screened: n = 2  Events Expressing: n = 0
Seedlings expressing/Seedlings screened Event-01: 0/6  Event-02: 0/6
☐ Scheduled
No GFP Expression Detected

| | |
|---|---|
| ☐ Hypocotyl | ☐ epidermis ☐ cortex ☐ vascular ☐ xylem ☐ phloem ☐ stomata |
| ☐ Cotyledon | ☐ mesophyll ☐ vascular ☐ epidermis ☐ margin ☐ stomata ☐ hydathode |
| ☐ Rosette Leaf | ☐ mesophyll ☐ vascular ☐ epidermis ☐ trichome ☐ petiole ☐ primordia ☐ stomata ☐ stipule ☐ margin |
| ☐ Primary Root | ☐ epidermis ☐ trichoblast ☐ atrichoblast ☐ cortex ☐ endodermis ☐ vascular ☐ xylem ☐ phloem ☐ pericycle ☐ quiescent ☐ columella ☐ cap ☐ root hairs |
| ☐ Lateral root | ☐ epidermis ☐ trichoblast ☐ atrichoblast ☐ cortex ☐ endodermis ☐ initials ☐ flanking cells ☐ vascular ☐ cap |
| ☐ Shoot apical meristem | ☐ SAM ☐ epidermis |

T2 Mature Plant Expression Plants expressing/Plants screened

Event-01: no data  Event-02: no data
☐ Scheduled
☐ T2 Mature tissue expressions similar to T1 expression data (data not shown).
☐ T2 Mature tissue expression (if different expression pattern). Expression detected T3 Seedling Expression Seedlings expressing/Seedlings screened Event-01: no data  Event-02: no data
☐ Scheduled
☐ T3 Seedling tissue expressions similar to T2 seedling expression (data not shown).
☐ T2 Mature tissue expression (if different expression pattern). GFP Expression Detected

Promoter Expression Report #80

Promoter utility

| | |
|---|---|
| Trait - Sub-trait Area: | Among other uses, this promoter sequence can be useful to improve: Seed development-seed size, seed abortion, endosperm production, seed composition |
| Construct: | YP0119 |
| Promoter Candidate I.D: | 13148175 |
| cDNA I.D: | 13607852 |
| T1 lines expressing (T2 seed): | SR00712-01, -11, -15 |

Sequence (SEQ ID NO: 71):

taCCAAAAATAAGGAGTTtccaaaagATGGTTCTGATGAGAAACAGAGCCCATCCCTCTCCTTTTCCCCTTCC
CATGAAAGAAATCGGATGGTCCTCCTTCAATGTCCTCCACCTACTCTTCTCTTCTTTCTTTTTTTCTTTCT
TATTATTAACCATTTAATTAATTTCCCCTTCAATTTCAGTTTCTAGTTCTGTAAAAAGAAAATACACATC
TCACTTATAGATATCCATATCTATTTATATGCATGTATAGAGAATAAAAAAGTGTGAGTTTCTAGGTAT
GTTGAGTATGTGCTGTTTGGACAATTGTTAGATGATCTGTCCATTTTTTCTTTTTTCTTCTGTGTATAAA
TATATTTGAGCACAAAGAAAAACTAATAACCTTCTGTTTTCAGCAAGTAGGGTCTTATAACCTTCAAAG
AAATATTCCTTCAATTGAAAACCCATAAACCAAAATAGATATTACAAAAGGAAAGAGAGATATTTTCA
AGAACAACATAATTTAGAAAAGCAGAAGCAGCAGTTAAGTGGTACTGAGATAAATGATATAGTTTCTCT
TCAAGAACAGTTTCTCATTACCCACCTTCTCCTTTTGCTGATCTATCGTAATCTTGAGAACTCAGGTAA
GGTTGTGAATATTATGCACCATTCATTAACCCTAAAAATAAGAGATTTAAAATAAATGTTTCTTCTTTC
TCTGATTCTTGTGTAACCAATTCATGGGTTTGATATGTTTCTTGGTTATTGCTTATCAACAAAGAGATTT
GATCATTATAAAGTAGATTAATAACTCTTAAACACACAAAGTTTCTTTATTTTTAGTTACATCCCTAAT
TCTAGACCAGAACATGGATTTGATCTATTTCTTGGTTATGTATTCTTGATCAGGAAAAGGGATTTGATC
ATCAAGATTAGCCTTCTCTCTCTCTCTAGATATCTTTCTTGAATTTAGAAATCTTTATTTAATTATTTG
GTGATGTCATatataggatcaa

Promoter Expression Report #82

| | |
|---|---|
| GenBank: | NM_106319 *Arabidopsis thaliana* 12-oxophytodienoate reductase (OPR2) (At1g76690) mRNA, complete cds gi\|3069919\|ref\|NM_106319.2\|[30699191] |
| Source Promoter Organism: | *Arabidopsis thaliana* WS |
| Vector: | Newbin4-HAP1-GFP |
| Marker Type: | GFP-ER |
| Generation Screened: | X T1 Mature X T2 Seedling |
| | ☐ T2 Mature ☐ T3 Seedling |

Promoter Expression Report #82

| | |
|---|---|
| Promoter Tested In: | *Arabidopsis thaliana*, WS ecotype |
| Spatial expression summary: | |
| Silique | (H)style, (H)septum, (H)epidermis, (H)cortex |
| Primary Root | (L)epidermis, (H)endodermis, (L)pericycle, (L)vascular |
| Observed expression pattern: | |
| T1 mature: | High expression was seen in the style of silique which extends down to the carpel - septum connective region. |
| T2 seedling: | High expression was detected throughout the endodermis and pericycle cells of root. Low epidernnal and vascular expression was detected. |
| Expected expression pattern: | 2–3× induced in senescing leaves versus non-senescing leaves |
| Selection Criteria: | Literature |
| Gene: | 12-OXO-PHYTODIENOIC ACID-10, 11-REDUCTASE |

T1 Mature Plant Expression Organs/Tissues screened

Events Screened: n = 5    Events Expressing: n = 2
GFP Expression Detected

| | |
|---|---|
| ☐ Flower | ☐ pedicel ☐ receptacle ☐ nectary |
| | ☐ sepal ☐ petal ☐ filament ☐ anther |
| | ☐ pollen ☐ carpel ☐ style |
| | ☐ papillae ☐ vascular ☐ epidermis |
| | ☐ stomata ☐ trichome |
| X Silique | ☐ stigma H style ☐ carpel H septum |
| | ☐ placentae ☐ transmitting tissue |
| | ☐ vascular H epidermis H cortex |
| | ☐ stomata ☐ abscission zone |
| | ☐ ovule |
| ☐ Ovule | Pre-fertilization: ☐ inner integument |
| | ☐ outer integument ☐ embryo sac |
| | ☐ funiculus ☐ chalaza |
| | ☐ micropyle ☐ gametophyte |
| | Post-fertilization: ☐ zygote ☐ inner integument ☐ outer integument |
| | ☐ seed coat ☐ richoblas ☐ chalaza |

Promoter Expression Report #82

☐ Embryo
☐ micropyle ☐ early endosperm
☐ mature endosperm ☐ embryo
☐ suspensor ☐ preglobular
☐ globular ☐ heart ☐ torpedo ☐ late
☐ mature ☐ provascular
☐ hypophysis ☐ radicle
☐ cotyledons ☐ hypocotyl ☐ Stem
☐ epidermis ☐ cortex ☐ vascular
☐ xylem ☐ phloem ☐ pith
☐ stomata ☐ trichome ☐ Leaf
☐ petiole ☐ mesophyll ☐ vascular
☐ epidermis ☐ trichome
☐ richoblas ☐ stomata
☐ stipule ☐ margin X in the Stigma (Sg) and Style (Sy) of the distal silique
X in the Carpel (Ca) of the proximal silique
T2 Seedling Expression Tissues Screened Events Screened: n = 2  Events Expressing: n = 2
Seedlings expressing/Seedlings screened Event-01: 2/3  Event-02: 2/3
☐ Scheduled
GFP Expression Detected ☐ Hypocotyl
☐ epidermis ☐ cortex ☐ vascular
☐ xylem ☐ phloem ☐ stomata ☐ Cotyledon
☐ mesophyll ☐ vascular
☐ epidermis ☐ margin ☐ stomata
☐ hydathode ☐ Rosette Leaf
☐ mesophyll ☐ vascular
☐ epidermis ☐ trichome ☐ petiole
☐ richoblas ☐ stomata ☐ stipule
☐ margin X Primary Root
L epidermis ☐ richoblasts
☐ atrichoblast ☐ cortex ☐ Lateral root
H endodermis L vascular ☐ xylem
☐ pliloem L pericycle ☐ quiescent
☐ columella ☐ root cap ☐ root hairs
☐ epidermis ☐ trichoblast
☐ atrichoblast ☐ cortex
☐ endodermis ☐ initials
☐ flanking cells ☐ vascular
☐ lateral root cap ☐ Shoot apical meristem      ☐ SAM ☐ epidermis X in the Vasculature (Vs), Pericycle (Pr), Endothelium (Ed) and Epidermis (Ep) of the root
T2 Mature Plant Expression Plants expressing/Plants screened Event-01: no data   Event-02: no data
☐ Scheduled
☐ T2 Mature tissue expressions similar to T1 expression data (data not shown).
☐ T2 Mature tissue expression (if different expression pattern).
Expression detected
T3 Seedling Expression Seedlings expressing/Seedlings screened Event-01: no data   Event-02: no data
☐ Scheduled
☐ T3 Seedling tissue expressions similar to T2 seedling expression (data not shown).
☐ T2 Mature tissue expression (if different expression pattern).
GFP Expression Detected
Promoter utility Trait - Sub-trait Area: Among other uses, this promoter sequence can be useful to improve: PGD-root development and architecture Nutrients-nutrient uptake
Construct: YP0171
Promoter Candidate ID: 3148156
cDNA I.D: 13619728 (Old ID: 4954325)
T1 lines expressing (T2 seed): SR00846-01, -02

Sequence (SEQ ID NO: 72):

```
aatGAAAACAATGGGAGAAGTACATGCTTGTCCTCACACACTAATGCCGATGAGGAAAgccttttaAGGGGAC

TTTTATCTCCGCAGGAGGTTTCACGAGGGAAGATGGGAATGAGGCTGTGTCAAAGGGAAGAACTGATT

TGGTGGCTTATGGTCGATGGTTTCTAGCCAACCCGGACCTGCCAAAGAGGTTCCAAGTGGATGCACCG

CTGAATAAGTACGATAGACCAACGTTTTACACTTCTGATCCAGTCGTCGGTTACACCGATTACCCTTTC

CTCGAATCAACAGCTTAAAATTgttatcAATAATGTAATGTAGTGTGTTTCCCTTATATAAGATGTAATAAG

TTTCTGGCTTTTCATTTATACTTTTTAAGTTTAAGTCATAAAACCTTCACAAAAATTTCCACGGACACAT

TATCACAAAAGCGCTTTCTAGAGACCAACATAACTTAACTTGATTGTTGATTTCTGTTTGATGTGATCA

TGCCGCAATCCAGTGTGTTCTCATGATGCTATCTTCCCTCCTTTCACATGCTGCACAGAACAAAACAGA

GCATTTTCCTCCCAACTATACCTAATTTTTTTGGTCGGTGGTCAAAGTTATACATCGGAAGAATCTGTT

GAAATCATATTGAGGCCCCTCATTTGTTATGTTATGTAATCTCCAATGGATCAAAAGTAGAATCCCAAC

TGTAGAAGATGATACTATCATGCTAGGTAGAAGACAGCATGGAATATGGGGTAAGTTCAAAGTGGTTA

CACTCTAATGTCGTCTCAACGAATACGTCTTTATGAAGAAATAAAAAAATCTAAGTGGTTGGATGCGTC

ATCAATGACGACCACGTCGTTAAAGACAGAAAGAAACACTTGCGTTCCTGATTCTCTGATCAATCAAT

GTGTATAAATATGTTCGGATATGTCCATTATCTTACGCAATCTTGAAAAGTGTTTTTGAGAGAAATATA

GGTTTTACAAAATCCACCgttgtgaattca
```

Promoter Expression Report #84

| | |
|---|---|
| Promoter Tested In: | *Arabidopsis thaliana*, WS ecotype |

Spatial expression summary:

| | |
|---|---|
| Flower | (L)stomata |
| Silique | (H)placentae, (H)vascular, (H)ovule, (H)funiculus |
| Ovule | Pre-fertilization: (H)funiculus<br>Post-fertilization: (H)funiculus, (H)chalaza, (H)micropyle, (H)embryo |
| Embryo | (H)suspensor, (H)preglobular, (H)globular, (H)heart, (H)torpedo, (H)hypophysis (H)radicle |
| Stem | (L)cortex, (H)vascular |
| Leaf | (H)mesophyll, (H)vascular, (H)epidermis |
| Hypocotyl | (H)epidermis, (H)vascular |
| Cotyledon | (H)mesophyll, (H)vascular, (H)epidermis, (H)hydathode, (H)petiole |
| Rosette Leaf | (H)mesophyll, (H)vascular, (H)epidermis, (H)petiole |
| Primary Root | (H)vascular, (H)pericycle |
| Lateral root | (H)initials |

Observed expression pattern:

| | |
|---|---|
| T1 mature: | High expression was seen in reproductive tissues throughout the developing embryo. Expression was detected early in suspensor and hyphsis of the early globular embryo and later in throughout the maturing embryo. Mature embryos beyond the torpedo stage were not screened. Ovule expression was restricted to the outer and inner integuments at the chalaza and micropyle region. High expression was observed throughout all tissues in the leaf and vasculature of the stem. Low guard cell expression was seen in the flowers and stem. |
| T2 seedling: | High epidermal, vascular, and mesophyll expression existed in all anal seedling tissues. High expression extends throughout the stele of the seedling root. Expression was observed only in the lateral root initials and primordial. |
| Expected expression pattern: | High in siliques |
| Selection Criteria: | *Arabidopsis* microarray |
| Gene: | Fe-superoxide dismutase |
| GenBank: | NM_179110 *Arabidopsis thaliana* iron superoxide dismutase (FSD1) (At4g25100) mRNA, complete cds gi30686767refNM_179110.1 [30686767] |
| Source Promoter Organism: | *Arabidopsis thaliana* WS |
| Vector: | Newbin4-HAP1-GFP |
| Marker Type: | GFP-ER |
| Generation Screened: | X T1 Mature X T2 Seedling ☐ T2 Mature ☐ T3 Seedling |

T1 Mature Plant Expression Organs/Tissues screened

Events Screened: n = 3  Events Expressing: n = 3
GFP Expression Detected

| | |
|---|---|
| X Flower | ☐ pedicel ☐ receptacle ☐ nectary<br>☐ sepal ☐ petal ☐ filament ☐ anther<br>☐ pollen ☐ carpel ☐ style ☐ papillae<br>☐ vascular ☐ epidermis L stomata<br>☐ trichome |
| X Silique | ☐ stigma ☐ style ☐ carpel ☐ septum<br>H placentae ☐ transmitting tissue<br>H vascular ☐ epidermis ☐ stomata<br>☐ abscission zone H ovule H funiculus |
| X Ovule | Pre-fertilization: ☐ inner integument<br>☐ outer integument ☐ embryo sac<br>H funiculus ☐ chalaza ☐ micropyle<br>☐ gametophyte<br>Post-fertilization: ☐ zygote ☐ inner integument ☐ outer integument ☐ seed coat ☐ richoblas H chalaza H funiculus |
| | H micropyle ☐ early endosperm ☐ mature endosperm H embryo |
| X Embryo | H suspensor H preglobular H globular H heart H torpedo ☐ late ☐ mature ☐ provascular H hypophysis H radicle ☐ cotyledons |
| X Stem | ☐ epidermis L cortex H vascular ☐ xylem ☐ phloem ☐ pith ☐ stomata ☐ trichome |
| X Leaf | ☐ petiole H mesophyll H vascular H epidermis ☐ trichome ☐ primordia ☐ stomata ☐ stipule ☐ margin |

X in the Guard cell (Gc), of the Pedicel (Pd) and Sepal (Se)
X in the Placenta (Pl) and Funiculus (Fn)
X in the Suspensor (Su) of the early globular embryo
X in the Suspensor (Su), Embryo (Em), Hypocotyl (Hy) and Outer integument (Oi) of the late globular embryo
X in the Suspensor (Su) and Embryo (Em) of the early heart stage embryo
X in the mid-heart, late heart and torpedo stage embryo
X in the leaf Epidermis (Ep), Mesophyll (Me) and Vasculature (Vs)
X in the Cortex (Cr), Epidermis (Ep) and Guard cell (Gc) of the stem T2 Seedling Expression Tissues Screened Events Screened: n = 2  Events Expressing: n = 2
Seedlings expressing/Seedlings screened Event-01: 1/3  Event-02: 2/3
☐ Scheduled
GFP Expression Detected

| | |
|---|---|
| X Hypocotyl | H epidermis ☐ cortex H vascular ☐ xylem ☐ phloem ☐ stomata |
| X Cotyledon | H mesophyll H vascular H epidermis ☐ margin ☐ stomata H hydathode H petiole |
| X Rosette Leaf | H mesophyll H vascular H epidermis ☐ trichome H petiole ☐ primordia ☐ stomata ☐ stipule ☐ margin |
| X Primary Root | ☐ epidermis ☐ trichoblast ☐ atrichoblast ☐ cortex ☐ endodermis H vascular ☐ xylem ☐ phloem H pericycle ☐ quiescent ☐ columella ☐ root cap ☐ root hairs |
| X Lateral root | ☐ epidermis ☐ trichoblast ☐ atrichoblast ☐ cortex ☐ endodermis H initials ☐ flanking cells ☐ vascular ☐ lateral root cap |
| ☐ Shoot apical meristem | ☐ SAM ☐ epidermis |

X in the Vasculature (Vs), Epidermis (Ep) and Root hair (Rh) of the hypocotyl-root transition Zone
X in the Vasculature (Vs), Hydathode (Hd), Epidermis (Ep) and Mesophyll (Me) of the Cotyledon (Co)
X in the Epidermis (Ep) and Mesophyll (Me) of the rosette leaf
X in the Vasculature (Vs) and Epidermis (Ep) of the root
X in the Pericycle (Pr) of the Lateral root (Lr)
X in the lateral root primordial T2 Mature Plant Expression Plants expressing/Plants screened Event-01: no data  Event-02: no data
☐ Scheduled
☐ T2 Mature tissue expressions similar to T1 expression data data not shown.
☐ T2 Mature tissue expression (if different expression pattern).
Expression detected T3 Seedling Expression Seedlings expressing/Seedlings screened Event-01: no data  Event-02: no data
☐ Scheduled
☐ T3 Seedling tissue expressions similar to T2 seedling expression (data not shown).
☐ T2 Mature tissue expression (if different expression pattern).
GFP Expression Detected

Promoter Expression Report #84

Promoter utility

| | |
|---|---|
| Trait-Sub-trait Area: | Among other uses, this promoter sequence can be useful to improve: Seed development-seed abortion, seed size, seed composition |
| Coastruct: | YP0188 |
| Promoter Candidate I.D: | 13148244 |
| cDNA I.D: | 13504706 |
| T1 lines expressin (T2 seed): | SR00851-01, -02, -03 |

Sequence (SEQ ID NO: 73):

gattggtaTGAAATTTCGGAGACCAACAAAAAAAACTTTATTTGAGCTTGGAGTGAAGCTATATATATGGGG

CAAGATCATAATATGTTTATATCGGCCTTTtcgttaACTGAAAATAATAGTTTTGAGAAATATATCAAATG

GTAAACAGACATCATCTTTGAAAAATACCATCAATGAAGTTAATATTGTTATTGGCATATGGTTTACCC

ATCTTAATTTTAATGCAACCAAACAAACAAGAAACAAAAACTGTATAAGATACAAGGTGTTTTACGAT

TTTCCGTCTTAAAACCGAAATATTTTTGTTCCTACGACTTTAAACGGACTTTGCTTAAGTTGTGTGCATG

TAAGCTCGTCGtccctcgattgtcaTCAACATTCACCAATATCAGCCTCTATCACACGAGtgaaggtggtgattcgGCTTA ATGAAAACagagaaatatttcaatatgattcctattaaattttaaatctttttctcaatctctagattttcattaaaagcatcatgattttttccactat gttcatatatctctatcacagttttaggtacattgtagaaattggataagatacgtcatacgtctaacatgaatttggtctagcaaggaaggtttgagata ataagtgaaagaaaacacaagataataaattataatttataaatgctttatagtattgaaaaataagatgattttttttttttttaataccggatTGGCT GATCCACTTATGATGACTCAAATGTTATTAAGTTTCAAGACAATTTATGATGacacaaatcacaATGAGTCAATAGTAgccacgAAGCCAGAAAAAAAAA TGTACTACAAAAAGATAATGATAGTACAAAATGATACGTCGTACTGCCACATGTACGACACAACTCGATTACCAAAAAGCAGAGCCATCCAACCATAAAAC TCAAAACACACAGATTCCACTGGCGTGTGCTCTCctcacTTCACTCGTCCTTGAAACTtgaggtactga

Promoter Expression Report #85

| | |
|---|---|
| Promoter Tested In: | *Arabidopsis thaliana*, WS ecotype |
| Spatial expression summary: | |
| Flower | (L)receptacle, (L)sepal, (L)petal, (L)vascular, (L)epidermis |
| Primary Root | (L)epidermis, (L)root hairs |
| Observed expression pattern: | |
| T1 mature: | Low expression was seen in the vasculature of developing floral buds of inflorescence meristem. Expression was not detected in mature flowers. |
| T2 seedling: | Low expression was seen throughout root epidermal cells. |
| Expected expression pattern: | cotyledon/Leaf/sepal/petal richoblas, not in SAM |
| Selection Criteria: | |
| Gene: | "expressed protein with a DUF607 Pfam domain" |
| GenBank: | NM_126063 *Arabidopsis thaliana* expressed protein (At5g66650) mRNA, complete cds gi\|30698243\|refl NM_126063.2\|[30698243] |
| Source Promoter Organism: | *Arabidopsis thaliana* WS |
| Vector: | pNewBin4-HAP1-GFP |
| Marker Type: | GFP-ER |
| Generation Screened: | X T1 Mature  X T2 Seedling  T2 Mature  T3 Seedling |

Promoter Expression Report #85

T1 Mature Plant Expression Organs/Tissues screened

Events Screened:  n = 3   Events Expressing:   n = 2
GFP Expression Detected

| | |
|---|---|
| X Flower | ☐ pedicel L receptacle ☐ nectary L sepal L petal ☐ filament ☐ anther ☐ pollen ☐ carpel ☐ style ☐ papillae L vascular L epidermis ☐ stomata ☐ trichome |
| ☐ Silique | ☐ stigma ☐ style ☐ carpel ☐ septum ☐ placentae ☐ transmitting tissue ☐ vascular ☐ epidermis ☐ stomata |
| ☐ Ovule | ☐ abscission zone ☐ ovule Pre-fertilization: ☐ inner integument ☐ outer integument ☐ embryo sac ☐ funiculus ☐ chalaza ☐ micropyle ☐ gametophyte Post-fertilization: ☐ zygote ☐ inner integument ☐ outer integument ☐ seed coat ☐ richoblas ☐ chalaza ☐ micropyle ☐ early endosperm ☐ mature endosperm ☐ embryo |
| ☐ Embryo | ☐ suspensor ☐ preglobular ☐ globular ☐ heart ☐ torpedo ☐ late ☐ mature ☐ provascular ☐ hypophysis ☐ radicle ☐ cotyledons ☐ hypocotyl |
| ☐ Stem | ☐ epidermis ☐ cortex ☐ vascular ☐ xylem ☐ pliloem ☐ pith ☐ stomata ☐ trichome |
| ☐ Leaf | ☐ petiole ☐ mesophyll ☐ vascular ☐ epidermis ☐ trichome ☐ richoblas ☐ stomata ☐ stipule ☐ margin |

X in the Epidermis (Ep), Guard cell (Gc) and Vasculature (Vs) of the Sepal (Se) in developing floral buds
T2 Seedling Expression Tissues Screened Events Screened:  n = 2   Events Expressing:  n = 2
Seedlings expressing/Seedlings screened Event-01:  6/6   Event-02:  6/6

| Promoter Expression Report #85 | |
|---|---|
| GFP Expression Detected | |
| ☐ Hypocotyl | ☐ epidermis ☐ cortex ☐ vascular ☐ xylem ☐ phloem ☐ stomata |
| ☐ Cotyledon | ☐ mesophyll ☐ vascular ☐ epidermis ☐ margin ☐ stomata ☐ hydathode |
| ☐ Rosette Leaf | ☐ mesophyll ☐ vascular ☐ epidermis ☐ trichome ☐ petiole ☐ richoblas ☐ stomata ☐ stipule ☐ margin |
| X Primary Root | L epidermis ☐ richoblasts ☐ atrichoblast ☐ cortex ☐ endodermis ☐ vascular ☐ xylem ☐ phloem ☐ pericycle ☐ quiescent ☐ columella ☐ cap L root hairs |
| ☐ Lateral root | ☐ epidermis ☐ trichoblast ☐ atrichoblast ☐ cortex ☐ endodermis ☐ initials ☐ flanking cells ☐ vascular ☐ cap |
| ☐ Shoot apical meristem | ☐ SAM ☐ epidermis |

X in the Epidermis (Ep), Hypocotyl (Hy) and Root hair (Rh) of the hypocotyl root transition zone
X in the Epidermis (Ep) of the root
T2 Mature Plant Expression Plants expressing/Plants screened Event-01: no data   Event-02:   no data
☐ Scheduled
☐ T2 Mature tissue expressions similar to T1 expression data (data not shown).

☐ T2 Mature tissue expression (if different expression pattern). Expression detected
T3 Seedling Expression Seedlings expressing/Seedlings screened Event-01: no data   Event-02:   no data
☐ Scheduled
☐ T3 Seedling tissue expressions similar to T2 seedling expression (data not shown).
☐ T2 Mature tissue expression (if different expression pattern).
GFP Expression Detected
Promoter utility

| | |
|---|---|
| Trait-Sub-trait Area: | Among other uses, this promoter sequence can be useful to improve: PGD-nutrient uptake and transport, seedling establishment, stress tolerance, drought tolerance |
| Utility: | Express insecticidal proteins, increase transport and uptake of nitrogen compounds |
| Construct: | YP0258 |
| Promoter Candidate I.D: | 11768747 |
| cDNA I.D: | 12688873 |
| T1 lines expressing (T2 seed): | SR01015-02, -03 |

Sequence (SEQ ID NO: 74):

```
taAATAACTTACTTAAATTTATATTAAAACCGTTTACATCTGATATAATTTAAAAGGTTTTAGACGAATT

AGTATTAGTGAACCATTATCAAGATGTATTTATTACAAAATCTATAATAATAAAAACAAAACTGGGAA

AGCAATGGGAAGAAGATCTGATTGGCTTtggaagACTTCGCGTGTTAATAAGATTTTTCTCAAAAAAGAA

AGATCGGACGGCAATGCGTGGCAAGTCGCTTATGACGTCGGAAGCTTAGCTTGCCACGTGTACGGTCA

TCACCATTTAGGTGACCGATATAATGTATTTCCCGTGACTTGACAATCTAATCTCCCAATTTATCGTGCT

CCAGTGTCTCAAGAGAGAACTTACTCTATTGGTTACCCAAAACTCACATAAAACGTGGATTTTATATTT

TTTTTTTATCAAATAATTTGATGTGCAATATAAACATATATGTATTATTATCTTGCATGTTTAAAAAATGC

TAACTTAAATTTTTCTTCAATGATTGAGATTTTTCATACACATCCATCGAGTTCACACTTATGATTAAAC

AAAGTGTATTGTTACACTAATAACGGTTCTAAGTTGTTTCAATACGTTTATGATAACGGTTCTATACTA

ATACTAGTATTCATACGTTTATGAAACTCGTTAATTATATATTTAACTTTGTTTAGCTGTATCATAACAA

GCGTTTTAAGAAATAATTTAATAAAAAATGAgaaaacgaTAAGCGACGCCTTATCGCCTATGTGTAATTAT

CGTGTCAAAATATCGTGATAAGGAAGCTGTTTCAGAGGAGCCTTCTCGTTTGTTGCGTCGTTGCTCTGA

GCCAACAACGCTAATATAAAAGGAAGCTCAAGTCTCTCTGTTTTAATCTCGGACCAATATACAAAACC

GTGTGTTCTTCTCTGTATCTTATTAAATCAAAACCAATTTTGTTCTTCTTCTTTGATTCTTTTTTCCTTCAT

TTTTtaacgtatcttgagagatcgac
```

Promoter Expression Report #86

| | |
|---|---|
| Promoter Tested In: | *Arabidopsis thaliana*, WS ecotype |

Spatial expression summary:

| | |
|---|---|
| Flower | (L)sepal, (M)petal, (L)filament, (H)carpel, (H)vascular, (H)epidermis |
| Silique | (H)carpel, (H)cortex, (H)placentae, (H)vascular, (H)epidermis, (H)stomata, (H)ovule |
| Ovule | Pre-fertilization: (H)outer integument, (H)funiculus<br>Post-fertilization: (H)outer integument, (H)seed coat, (H)embryo |
| Embryo | (H)globular, (H)heart, (H)hypophysis |
| Stem | (L)vascular |
| Leaf | (L)mesophyll |
| Cotyledon | (L)epidermis |
| Rosette Leaf | (H)mesophyll, (H)epidermis, (H)trichome, (H)richoblas |
| Primary Root | (H)epidermis, (H)cap, (H)root hairs |

Observed expression pattern:

| | |
|---|---|
| T1 mature: | High expression was restricted to the sepals of developing floral buds in inflorescence meristem and throughout all organs in mature flowers. High expression was observed in vascular tissues of reproductive tissues and floral organs. High vascular expression in placenta extended through to developing pre-fertilized ovules. Expression in ovules was restricted to outer integument, seed coat, and embryonic root meristem cell. Expression in leaf was specific to abaxial spongy mesophyll cells. |
| T2 seedling: | High expression was seen in root meristem and epidermal cells of primary root and mesophyll cells of rosette leaf. (Expression in seedling rosette leaf also appears to be abaxial specific). Low expression was seen in epidermal cells at margin cotyledons. |
| Expected expression pattern: | SAM leaf richoblas, 1 mm leaf margin |
| Selection Criteria: | CSHL gene trap GT1040 |
| Gene: | T28119.100; expressed protein |
| GenBank: | NM_119943 *Arabidopsis thaliana* expressed protein (At4g37820) mRNA, complete cds gi\|30691596\|ref\| NM_119943.2\|[30691596] |
| Source Promoter Organism: | *Arabidopsis thaliana* WS |
| Vector: | pNewBin4-HAP1-GFP |
| Marker Type: | GEP-ER |
| Generation Screened: | X T1 Mature X T2 Seedling ☐ T2 Mature ☐ T3 Seedling |

T1 Mature Plant Expression Organs/Tissues screened

Events Screened: n = 3  Events Expressing: n = 3
GFP Expression Detected

| | |
|---|---|
| X Flower | ☐ pedicel ☐ receptacle ☐ nectary<br>L sepal M petal L filament ☐ anther<br>☐ pollen H carpel ☐ style ☐ papillae<br>H vascular H epidermis ☐ stomata<br>☐ trichome |
| X Silique | ☐ stigma ☐ style H carpel ☐ septum<br>H cortex H placentae ☐ transmitting tissue<br>H vascular H epidermis H stomata<br>☐ abscission zone H ovule |
| X Ovule | Pre-fertilization: ☐ inner integument<br>H outer integument ☐ embryo sac<br>H funiculus ☐ chalaza ☐ micropyle<br>☐ gametophyte<br>Post-fertilization: ☐ zygote ☐ inner integument H outer integument H seed coat ☐ richoblas ☐ chalaza |
| X Embryo | ☐ micropyle ☐ early endosperm<br>☐ mature endosperm H embryo<br>☐ suspensor ☐ preglobular H globular<br>H heart ☐ torpedo ☐ late ☐ mature<br>☐ provascular H hypophysis ☐ radicle<br>☐ cotyledons ☐ hypocotyl |
| X Stem | ☐ epidermis ☐ cortex L vascular<br>☐ xylem ☐ phloem ☐ pith<br>☐ stomata ☐ trichome |
| X Leaf | ☐ petiole L mesophyll ☐ vascular<br>☐ epidermis ☐ trichome ☐ richoblas<br>☐ stomata ☐ stipule ☐ margin |

X in the inflorescence meristem
X in the Epidermis (Ep) and Vasculature (Vs) in the Sepal (Se) of the inflorescence
X in the Epidermis (Ep) and Vasculature (Vs) in the Petal (Pe)
X in the Vasculature (Vs) in the Filament (Fi) of the stamen
X in the Guard cell (Gc) and Vasculature (Vs) in the silique
X in the Guard cell (Gc) in the. Style (Sy) of the silique
X in the Cortex (Cr), of the Carpel (Ca) in the silique
X in the Guard cell (Gc), Septum (Sp) and Vasculature (Vs) of the proximal silique
X in the Placenta (Pl)
X in the Funiculus (Fn)
X in the Placenta (Pl) of the ovary
X in the Outer integument (Oi), Funiculus (Fn), Placenta (Pl) and Vasculature (Vs) of the pre-fertilized ovule
X in the Embryo (Em) of the fertilized ovule
X in the ilypocotyl (Hy) of the heart stage embryo
X in the Outer integument (Oi) of the fertilized ovule
X in the adaxial and abaxial leaf
X in the Epidermis (Ep) and Vasculature (Vs) of the stem T2 Seedling Expression Tissues Screened Events Screened: n = 2  Events Expressing: n = 2
Seedlings expressing/Seedlings screened Event-01: 2/3  Event-02: 1/3
GFP Expression Detected

| | |
|---|---|
| ☐ Hypocotyl | ☐ epidermis ☐ cortex ☐ vascular<br>☐ xylem ☐ phloem ☐ stomata |
| X Cotyledon | ☐ mesophyll ☐ vascular L epidermis<br>☐ margin ☐ stomata ☐ hydathode |
| X Rosette Leaf | H mesophyll ☐ vascular H epidermis<br>H trichome ☐ petiole H primordia<br>☐ stomata ☐ stipule ☐ margin |
| X Primary Root | H epidermis ☐ richoblasts ☐ atrichoblast<br>☐ cortex ☐ endodermis ☐ vascular<br>☐ xylem ☐ phloem ☐ pericycle<br>☐ quiescent ☐ columella H cap H root hairs |
| ☐ Lateral root | ☐ epidermis ☐ trichoblast ☐ atrichoblast<br>☐ cortex ☐ endodermis ☐ initials<br>☐ flanking cells ☐ vascular ☐ cap |
| ☐ Shoot apical meristem | ☐ SAM ☐ epidermis |

X in the Root hair (Rh) of the hypocotyl root transition zone
X in the Epidermis (Ep) of the cotyledon
X in the Epidermis (Ep) and Trichome (Tc) of the rosette leaf
X in the Epidermis (Ep) and Root hair (Rh) of the root
X in the root tip T2 Mature Plant Expression Plants expressing/Plants screened Event-01: no data  Event-02: no data
☐ Scheduled
☐ T2 Mature tissue expressions similar to T1 expression data (data not shown).
☐ T2 Mature tissue expression (if different expression pattern).
Expression detected T3 Seedling Expression Seedlings expressing/Seedlings screened Event-01: no data  Event-02: no data
☐ Scheduled
☐ T3 Seedling tissue expressions similar to T2 seedling expression (data not shown).
☐ T2 Mature tissue expression (if different expression pattern).
GFP Expression Detected

Promoter Expression Report #86

| | |
|---|---|
| Promoter utility | |
| Trait-Sub-trait Area: | Among other uses, this promoter sequence can be useful to improve: PGD-stress tolerance, seedling development and establishment, nutrient transport Seed development-embryo-development and composition, seed composition |
| Construct: | YP0265 |
| Promoter Candidate I.D: | 11768754 |
| cDNA I.D: | 13604752 |
| T1 lines expressing (T2 seed): | SR01022-04, -05, -06 |

Sequence (SEQ ID NO: 75):

```
taAATAACTTACTTAAATTTATATTAAAACCGTTTACATCTGATATAATTTAAAAGGTTTTAGACGAATT
AGTATTAGTGAACCATTATCAAGATGTATTTATTACAAAATCTATAATAATAAAAACAAAACTGGGAA
AGCAATGGGAAGAAGATCTGATTGGCTTtggaagACTTCGCGTGTTAATAAGATTTTTCTCAAAAAAGAA
AGATCGGACGGCAATGCGTGGCAAGTCGCTTATGACGTCGGAAGCTTAGCTTGCCACGTGTACGGTCA
TCACCATTTAGGTGACCGATATAATGTATTTCCCGTGACTTGACAATCTAATCTCCCAATTTATCGTGCT
CCAGTGTCTCAAGAGAGAACTTACTCTATTGGTTACCCAAAACTCACATAAAACGTGGATTTTATATTT
TTTTTTATCAAATAATTTGATGTGCAATATAAACATATATGTATTATTATCTTGCATGTTTAAAAAATGC
TAACTTAAATTTTTCTTCAATGATTGAGATTTTTCATACACATCCATCGAGTTCACACTTATGATTAAAC
AAAGTGTATTGTTACACTAATAACGGTTCTAAGTTGTTTCAATACGTTTATGATAACGGTTCTATACTA
ATACTAGTATTCATACGTTTATGAAACTCGTTAATTATATATTTAACTTTGTTTAGCTGTATCATAACAA
GCGTTTTAAGAAATAATTTAATAAAAAATGAgaaaacgaTAAGCGACGCCTTATCGCCTATGTGTAATTAT
CGTGTCAAAATATCGTGATAAGGAAGCTGTTTCAGAGGAGCCTTCTCGTTTGTTGCGTCGTTGCTCTGA
GCCAACAACGCTAATATAAAAGGAAGCTCAAGTCTCTCTGTTTTAATCTCGGACCAATATACAAAACC
GTGTGTTCTTCTCTGTATCTTATTAAATCAAAACCAATTTTGTTCTTCTTCTTTGATTCTTTTTTCCTTCAT
TTTTtaacgtatcttgagagatcgac
```

Promoter Expression Report #99

| | |
|---|---|
| T2 seedling: | Strong expression observed throughout vasculature of root and hypocotyl. Expression in a few epidermal and cortex cells of hypocotyl at cotyledon junction. Weak epidermis and mesophyll expression in developing leaves. |
| Expected expression pattern: | Stem cell population in center of shoot apical, inflorescence and floral meristem. |
| Selection Criteria: | *Arabidopsis* public. Clark S E, Williams R W, Meyerowitz E M. The CLAVATA1 gene encodes a putative receptor kinase that controls shoot and floral meristem size in Arabidopsis. Cell. May 16, 1997; 89(4): 575–85. |
| Gene: | CLAVATA1 receptor kinase (CLV1) |
| GenBank: | NM_106232 *Arabidopsis thaliana* CLAVATA1 receptor kinase (CLV1) (At1g75820) mRNA, complete cds gi\|30699119\|ref\| NM_106232.2\|[30699119] |
| Source Promoter Organism: | *Arabidopsis thaliana* WS |
| Vector: | pNewbin4-HAP1-GFP |
| Marker Type: | GFP-ER |
| Generation Screened: | X T1 Mature X T2 Seedling ☐ T2 Mature ☐ T3 Seedling |

T1 Mature Plant Expression Organs/Tissues screened

Events Screened: n = 2  Events Expressing: n = 2
GFP Expression Detected

| | |
|---|---|
| X Flower | L pedicel L receptacle ☐ nectary L sepal L petal L filament ☐ anther ☐ pollen ☐ carpel ☐ style ☐ papillae |

Promoter Expression Report #99

| | |
|---|---|
| Promoter Tested In: | *Arabidopsis thaliana*, WS ecotype |
| Spatial expression summary: | |
| Flower | L pedicel, L receptacle, L sepal, L petal, L filament, L epidermis |
| Stem | L vascular |
| Leaf | M vascular, L rib |
| Hypocotyl | L epidermis, L cortex, H vascular |
| Cotyledon | L mesophyll, L epidermis |
| Rosette Leaf | L mesophyll, L vascular, L epidermis, H petiole |
| Primary Root | H vascular |
| Observed expression pattern: | |
| T1 mature: | Weak vascular expression throughout inflorescence meristem and flowers. Variable levels of expression in cells at receptacle of flowers. Expressed in both vascular and supporting ground tissue in leaves. |

Promoter Expression Report #99

| | |
|---|---|
| ☐ Silique | ☐ vascular L epidermis ☐ stomata<br>☐ trichome ☐ silique<br>☐ stigma ☐ style ☐ carpel ☐ septum<br>☐ placentae ☐ transmitting tissue<br>☐ vascular ☐ epidermis<br>☐ stomata ☐ abscission zone<br>☐ ovule |
| ☐ Ovule | Pre-fertilization: ☐ inner integument<br>☐ outer integument ☐ embryo sack<br>☐ funiculus ☐ chalaza<br>☐ micropyle ☐ gametophyte<br>Post-fertilization: ☐ zygote<br>☐ embryo sack ☐ inner<br>integument ☐ outer integument<br>☐ endothelium ☐ seed coat<br>☐ primordia ☐ chalaza<br>☐ micropyle ☐ early endosperm<br>☐ mature endosperm ☐ embryo |
| ☐ Embryo | ☐ suspensor ☐ preglobular ☐ globular<br>☐ heart ☐ torpedo ☐ late<br>☐ mature ☐ provascular<br>☐ hypophysis ☐ radicle<br>☐ cotyledons ☐ hypocotyl |
| X Stem | ☐ epidermis ☐ cortex L vascular<br>☐ xylem ☐ phloem ☐ pith<br>☐ stomata ☐ trichome |
| X Leaf | ☐ petiole ☐ mesophyll M vascular<br>☐ epidermis ☐ trichome ☐ primordia<br>☐ stomata ☐ stipule ☐ margin L rib |
| ☐ Shoot apical meristem | ☐ Shoot apical meristem ☐ Flower primordium |

X in the flower bud and inflorescence meristem
X in the Cortex (Cr) of the Receptacle (Re) and the Vasculature (Vs) of the Sepal (Se) of the flower
X in the Vasculature (Vs) of the leaf and mid-vein rib T2 Seedling Expression Tissues Screened Events Screened:  n = 2   Events Expressing:   n = 2
Seedlings expressing/Seedlings screened Event-01:  2/2
Event-02:  2/2
☐ Scheduled
GFP Expression Detected

| | |
|---|---|
| X Hypocotyl | L epidermis L cortex H vascular ☐ xylem<br>☐ phloem ☐ stomata |
| X Cotyledon | L mesophyll ☐ vascular L epidermis<br>☐ margin ☐ stomata ☐ hydathode |
| X Rosette Leaf | L mesophyll L vascular L epidermis<br>☐ trichome H petiole ☐ primordia<br>☐ stomata ☐ stipule ☐ margin<br>☐ hydathode |
| X Primary Root | ☐ epidermis ☐ trichoblast ☐ atrichoblast<br>☐ cortex ☐ endodermis H vascular<br>☐ xylem ☐ phloem ☐ pericycle<br>☐ quiescent ☐ columella ☐ root<br>cap ☐ root hairs |
| ☐ Lateral root | ☐ epidermis ☐ trichoblast ☐ atrichoblast<br>☐ cortex ☐ endodermis ☐ initials<br>☐ flanking cells ☐ vascular ☐ lateral<br>root cap |
| ☐ Shoot apical meristem | ☐ Shoot apical meristem |

X in the Vasculature (Vs) and Cortex (Cr) of the hypocotyl
X in the Vasculature (Vs) and Guard cells (Gc) of the leaf
X in the Epidermis (Ep) and Mesophyll (Me) of the rosette leaf
X in the Vasculature (Vs) of the petiole
X in the Vasculature (Vs) of the root transition zone Promoter utility

| | |
|---|---|
| Trait Area: | |
| Sub-trait Area: | |
| Utility: | Translocation, seed fill. Improved loading of phloem, increased source capacity. Increased seed yield. Cotyledon angle, improved seedling survival. |
| Notes: | Extensive studies on plant signaling molecules over the past decade indicate that plant cell-to-cell communication, as is the case with animal systems, makes use of small peptide signals and specific receptors. To date, four peptide-ligand-receptor pairs have been identified and shown to be involved in a variety of processes. CLV1 is one of them. Matsubayashi. Ligand-receptor pairs in plant peptide signaling. J Cell Sci. Oct. 1, 2003; 116(Pt 19): 3863–70. |
| Construct: | YP0071 |
| Promoter candidate I.D: | 11768674 |
| cDNA I.D: | 12721583 (OCKHAM3-C) |
| Lines expressing: | YP0071-01, YP0071-02 |

Sequence (SEQ ID NO: 76):

```
ataggccctacttctaattaaagcccatttacttctctccttgtcttcttattcctcttttctccccatcacgtgacgacgatgctataaacgccgtcgga ttatataactggtgccgttgacaagacggcgacagaagaaagaaagaagaaaccacaggctctagggaacgtaacgttatgtcctgtctatagcatttata acggtcagatcaacgccgtttagataaagatctgtcaatgttaaagaagagatgcatctctacaccgttaaatttaaaacgccgtgaacctcttatctatt gattttgtttgatgaagccaaaacaaatcgtgtcagaagacttatcagagaagaagaaaacgacgacgttccgtttctccatgtctaataagtgtagtag tggcggctactaaaaactctaaagtttgactccagtaaaactgcctttctagtgtaattccagtgattttagagtttgaatagtgtgtgaccaaatttgaa agtacaatctagcaatattattgatcactcgttataaaagaatcgaatgtaaaaatagccaatgagagactgagacgtatgtgtttgaccataagtcgtat agtttgtatctatctacctgcaagatcagcagatggttctctgatcaattgtaccttaattatcttttattttcgtaaaatttctctattcacaaatgata aatctacttaagacagtaaccataacaagatttacaagataatttgaaaaatgaacacataaaagtattttggcgcattattttttaataataacatattt atgtaaagtcacataaaagtatatattcgctcacaaagtcttacggtatttagaacagtagtaccacatcgattctcttcatcttcttccttcataatatgc cattgttcatgtctctgtgtcctatcgcataacactcacgctatcttattattttctctcgctctttctcactga
```

Promoter Expression Report#100

| | |
|---|---|
| Promoter Tested In: | *Arabidopsis thaliana*, WS ecotype |
| Spatial expression summary: | |
| Flower | (H)pedicel, (H)receptacle, (H)nectary, (H)sepal, (H)petal, (H)filament, (H)anther, (H)carpel, (H)style, (H)stigma, (H)epidermis, (H)silique |
| Silique | (H)abscission zone |
| Hypocotyl | (H)epidermis, (L)vascular |
| Cotyledon | (L)epidermis, (L)petiole, (L)vascular |
| Rosette Leaf | (H)mesophyll, (L)vascular (H)epidermis, (L)primordia |
| Primary Root | (H)epidermis, (H)trichoblast, (H)atrichoblast, (H)cortex, (H)endodermis (L)vascular, (H)pericycle, (H)quiescent, (H)columella, (H)root cap, (H)root hair |
| Observed expression pattern: | |
| T1 mature: | Strong expression throughout inflorescence meristem, sepals of floral primordial and all tissues of developing flowers. Not expressed in placenta, ovules and shoot apical meristem. |
| T2 seedling: | High expression throughout root tissues. High root vascular expression weakens through hypocotyl petioles and leaves. High epidermal and mesophyll expression in leaves. Not expressed in lateral roots. |
| Expected expression pattern: | Shoot apex including leaf primordia and parts of leaves |
| Selection Criteria: | Greater than 5× up in stm microarray |
| Gene: | Chalcone synthase |
| GenBank: | NM_121396 *Arabidopsis thaliana* chalcone synthase (naringenin-chalcone synthase) (At5g13930) mRNA, complete cds gi|30684674|ref| NM_121396.2|[30684674] |
| Source Promoter Organism: | *Arabidopsis thaliana* WS |
| Vector: | Newbin4-HAP1-GFP |
| Marker Type: | GFP-ER |
| Generation Screened: | X T1 Mature X T2 Seedling ☐ T2 Mature ☐ T3 Seedling |

T1 Mature Plant Expression Organs/Tissues screened

Events Screened: n = 3 Events Expressing: n = 3
☐ No GFP Expression Detected

| | |
|---|---|
| X Flower | H pedicel H receptacle H nectary ☐ sepal H petal H filament H anther ☐ pollen ☐ carpel H style H stigma ☐ vascular H epidermis ☐ stomata ☐ trichome H silique |
| X Silique | H stigma H style H carpel H septum ☐ placentae ☐ transmitting tissue ☐ vascular H epidermis ☐ stomata H abscission zone ☐ ovule |
| ☐ Ovule | Pre-fertilization: ☐ inner integument ☐ outer integument ☐ embryo sac ☐ funiculus ☐ chalaza ☐ micropyle ☐ gametophyte Post-fertilization: ☐ zygote ☐ inner integument ☐ outer integument ☐ endothelium ☐ seed coat ☐ primordia ☐ chalaza ☐ micropyle ☐ early endosperm ☐ mature endosperm ☐ embryo |
| ☐ Embryo | ☐ suspensor ☐ preglobular ☐ globular ☐ heart ☐ torpedo ☐ late ☐ mature ☐ provascular ☐ hypophysis ☐ radicle ☐ cotyledons ☐ hypocotyl |
| ☐ Stem | ☐ epidermis ☐ cortex ☐ vascular ☐ xylem ☐ phloem ☐ pith ☐ stomata ☐ trichome |
| ☐ Leaf | ☐ petiole ☐ mesophyll ☐ vascular ☐ epidermis ☐ trichome ☐ primordia ☐ stomata ☐ stipule ☐ margin |

X in the Anther (An), Petal (Pe) and Sepal (Se) of the inflorescence meristem
X in the Anther (An), Silique (Si), Ovule (Ov), Placenta (Pl), Petal (Pe) and Sepal (Se) of the flower
X (weak) in the leaf
X in sepals of floral primordial T2 Seedling Expression Tissues Screened Events Screened: n = 2 Events Expressing: n = 2
Seedlings expressing/Seedlings screened Event-01: 2/3 Event-02: 1/3
☐ Scheduled
GFP Expression Detected

| | |
|---|---|
| X Hypocotyl | H epidermis ☐ cortex L vascular ☐ xylem ☐ phloem ☐ stomata |
| X Cotyledon | ☐ mesophyll ☐ vascular L epidermis ☐ margin ☐ stomata ☐ hydathode L petiole L vascular |
| X Rosette Leaf | H mesophyll L vascular H epidermis ☐ trichome ☐ petiole L primordia ☐ stomata ☐ stipule ☐ margin |
| X Primary Root | H epidermis H trichoblast H atrichoblast H cortex H endodermis L vascular ☐ xylem ☐ phloem H pericycle H quiescent H columella H root cap H root hairs |
| ☐ Lateral root | ☐ epidermis ☐ trichoblast ☐ atrichoblast ☐ cortex ☐ endodermis ☐ initials ☐ flanking cells ☐ vascular ☐ lateral root cap |
| ☐ Shoot apical meristem | ☐ SAM ☐ epidermis ☐ ☐ |

X in the Root hair (Rh) and Vasculature (Vs) of the hypocotyl-root transition zone
X in the Epidermis (Ep) of the hypocotyl
X in the Epidermis (Ep) and Vasculature (Vs) of the root
X in the Epidermis (Ep) and Vasculature (Vs) of the cotyledon petiole
X in the Epidermis (Ep), Mesophyll (Me) and Vasculature (Vs) of the rosette leaf
X in the Epidermis (Ep), Vasculature (Vs) of the Cortex (Cr), Endothelium (Ed), Pericycle (Pr) and Root hair (Rh) of the root
X in the primary root cap T2 Mature Plant Expression Plants expressing/Plants screened Event-01: no data Event-02: no data
☐ Scheduled
☐ T2 Mature tissue expressions similar to T1 expression data (data not shown).
☐ T2 Mature tissue expression (if different expression pattern).
Expression detected T3 Seedling Expression Seedlings expressing/Seedlings screened Event-01: no data Event-02: no data
☐ Scheduled
☐ T3 Seedling tissue expressions similar to T2 seedling expression (data not shown).
☐ T2 Mature tissue expression (if different expression pattern).
GFP Expression Detected Promoter utility

| | |
|---|---|
| Trait-Sub-trait Area: | Among other uses, this promoter sequence can be useful to improve: PGD-shoot development and architecture, branched inflorescence number, flower number, seed yield, stress tolerance |
| Construct: | YP0214 |
| Promoter Candidate I.D: | 11768733 |
| cDNA I.D: | 12705056 (Old IDs: 12371852, 7080526) |
| T1 lines expressing (T2 seed): | SR00546-01, -02, -03 |

Sequence (SEQ ID NO: 77):

```
ccagtcgattggcgcctcgcatgCCTATCATATTTAACCGTCAATAATGGATTTGGCGGTTTTGGTAGGCCGGGTCA

ACCGGATTAAAAGAAAACGGTTTGGAGTCCTTCCTTGCAATTGAATTTTCACACATTCGGGTTTTGTGA

TTTCTCTGTCATAATGGGCCCGGCACATATGGTTCATAACCCATGTGGGCCTATGGTATAATTTTTCCA

ATTAAAACTATTGTTAGGTCGATAAAACAAAAAACAATAAAAACGAGTGGAATACACATACCAAAAA

GAATGTGATGAACATTAGTAATTTTATTTTGATGGTTAATGAAAAACAAAATAAATGCATCTTGGCATC

TTCCGTTGGAAAGCGCAAATAGGGCAGATTTTCAGACAGATATCACTATGATGGGGGtgagaGAAAGA

AAACGAGGCGTACCTAATGTAACACTACTTAATTAGTCGTTAGTTATAGGACTTTTTTTTGTTTGGGC

CTAGTTATAGGATCATAAGGTAAAAATGAAGAATGAATATTAGATTAGTAGGAGCTAATGATGGAGTT

AAGTATGCACGTGTAAGAACTGGGAAGTGAAACCTCCTGTATGGTGAAGAAACTATACAACAAAGCCC

TTTGTTGGTGTATACGTATTAATTTTTATTCTTTTATCACAAGCGATACgtatcttaAGACATAATAAATATA

TATCTTACTCATAATAAATATCTTAAGATATATATACAGTATACACCTGTATATATATAATAAATAGGC

ATATAGTAGAAATTAATATGAGTTGTTGTTGTTGCAAATATATAAATCAATCAAAAGATTTAAAACCC

ACCATTCAATCTTGGTAAGTAACGAAAAAAAAGGGAAGCAAGAAGAACCACAGAAAAGGGGGCTAAC

AACTAGACACGTAGATCTTCATCTGCCCGTCCATCTAACCTACCACACTCTCATCTTCTTTTTCCCGTGT

CAGTTTGTTATATAAGCTCTCACTCTCCGtatatttccccattgcactgga
```

| Promoter Expression Report #101 | |
|---|---|
| Promoter Tested In: | *Arabidopsis thaliana*, WS ecotype |
| Spatial expression summary: | |
| Flower | H pedicel, H receptacle |
| Silique | H placentae |
| Stem | H epidermis H cortex H vascular, L pith |
| Hypocotyl | H epidermis, H vascular |
| Cotyledon | H mesophyll, H vascular, H epidermis, H hydathode |
| Rosette Leaf | H mesophyll, H vascular, H epidermis, H primordia |
| Primary Root | H epidermis, H cortex, H vascular |
| Lateral root | H epidermis, H cortex |
| Observed expression pattern: | |
| T1 mature: | High expression in epidermis and cortical cells of stem and pedicles near inflorescence shoot apex. Weakens near floral organs except in the placenta where GFP is also highly expressed. Not expressed in ovules or embryos. High GFP expression in vasculature of stem. |
| T2 seedling: | High expression throughout leaves and epidermis of hypocotyl. No expression observed in ground tissues of hypocotyl. High epidermal, cortex and vascular expression in root. |
| Expected expression pattern: | Enzyme located in chloroplasts, >4 fold high in seedlings |
| Selection Criteria: | Ceres *Arabidopsis* microarray |
| Gene: | product = "DEF (CLA1) protein" CLA1 (for "cloroplastos alterados", or "altered chloroplasts") CLA1 encodes 1-deoxy-d-xylulose 5-phosphate synthase, which catalyses the first step of the non-mevalonate isoprenoid biosynthetic pathway. |
| GenBank: | NM 117647 *Arabidopsis thaliana* DEF (CLA1) protein (At4g15560) mRNA, complete cds gi\|30683316\|ref\| NM_117647.2[30683316] |
| Source Promoter Organism: | *Arabidopsis thaliana* WS |
| Vector: | pNewbin4-HAP1-GFP |
| Marker Type: | GFP-ER |
| Generation Screened: | X T1 Mature X T2 Seedling ☐ T2 Mature ☐ T3 Seedling |
| T1 Mature Plant Expression Organs/Tissues screened | |
| Events Screened: n = 4 | Events Expressing: n = 4 |
| GFP Expression Detected | |
| X Flower | H pedicel H receptacle ☐ nectary ☐ sepal ☐ petal ☐ filament ☐ anther ☐ pollen ☐ carpel ☐ style ☐ papillae ☐ vascular ☐ epidermis ☐ stomata ☐ trichome ☐ silique |
| X Silique | ☐ stigma ☐ style ☐ carpel ☐ septum H placentae ☐ transmitting tissue ☐ vascular ☐ epidermis ☐ stomata ☐ abscission zone ☐ ovule |
| ☐ Ovule | Pre-fertilization: ☐ inner integument ☐ outer integument ☐ embryo sack ☐ funiculus ☐ chalaza ☐ micropyle ☐ gametophyte Post-fertilization: ☐ zygote ☐ embryo sack ☐ inner integument ☐ outer integument ☐ endothelium ☐ seed coat ☐ primordia ☐ chalaza ☐ micropyle ☐ early endosperm ☐ mature endosperm ☐ embryo |

Promoter Expression Report #101

| | |
|---|---|
| ☐ Embryo | ☐ suspensor ☐ preglobular ☐ globular ☐ heart ☐ torpedo ☐ late ☐ mature ☐ provascular ☐ hypophysis ☐ radicle ☐ cotyledons ☐ hypocotyl |
| X Stem | H epidermis H cortex H vascular ☐ xylem ☐ phloem L pith ☐ stomata ☐ trichome |
| ☐ Leaf | ☐ petiole ☐ mesophyll ☐ vascular ☐ epidermis ☐ trichome ☐ primordia ☐ stomata ☐ stipule ☐ margin |
| ☐ Shoot apical ineristem | ☐ Shoot apical meristem ☐ Flower primordium |

X in the Epidermis (Ep) of the inflorescence meristem
X in the Embryo (Em) and Placenta (Pl) of the ovule
X in the Vascular bundle Vb of the stem T2 Seedling Expression Tissues Screened Events Screened: n = 2  Events Expressing: n = 2
Seedlings expressing/Seedlings screened Event-01: 2/2
Event-02: 2/2
☐ Scheduled
GFP Expression Detected

| | |
|---|---|
| X Hypocotyl | H epidermis ☐ cortex H vascular ☐xylem ☐ phloem ☐ stomata |
| X Cotyledon | H mesophyll H vascular H epidermis ☐ margin ☐ stomata H hydathode |
| X Rosette Leaf | H mesophyll H vascular H epidermis ☐ trichome ☐ petiole H primordia ☐ stomata ☐ stipule ☐ margin ☐ hydathode |
| X Primary Root | H epidermis ☐ trichoblast ☐ atrichoblast H cortex ☐ endodermis H vascular ☐ xylem ☐ phloem ☐ pericycle ☐ quiescent ☐ columella ☐ root cap ☐ root hairs |
| X Lateral root | H epidermis ☐ trichoblast ☐ atrichoblast H cortex ☐ endodermis ☐ initials ☐ flanking cells ☐ vascular ☐ lateral root cap |
| ☐ Shoot apical meristem | ☐ Shoot apical meristem |

X in the Epidermis (Ep), Mesophyll (Me), Hydathode (Hd) and Vasculature (Vs) of the cotyledon
X in the Epidermis (Ep), Mesophyll (Me) and Vasculature (Vs) of the rosette leaf (Cr), Lateral root (Lr), Rosette leaf (Rl), Promoter utility

| | |
|---|---|
| Utility: | Increased photosynthetic capacity and source capacity. Larger plants. Altered plant morphology. Altered plant metabolism. Increased seed Loading and seed yield. |
| Notes: | CLA1 encodes 1-deoxy-d-xylulose 5-phosphate synthase, which catalyses the first step of the non-mevalonate isoprenoid biosynthetic pathway. Crowell D N, Packard C E, Pierson C A, Giner J L, Downes B P, Chary S N. Identification of an allele of CLA1 associated with variegation in *Arabidopsis thaliana*. Physiol Plant. May 2003; 118(1): 29–37. |
| Construct: | YP0216 |
| Promoter candidate I.D: | 13148171 |
| cDNA I.D: | 12575820 |
| Lines expressing: | YP0216-01, -02, -03, -04 |

Sequence (SEQ ID NO: 78):

```
ttttgtttctaatagtttgatgtttatatcaacattattatttactttcatttgttaccgatagaaagaggagaaaattgttgacaaaaacaaagataaaa gtaaaattaatattattaaattaataaaaataacaaactgtaaaagctattttttaaaaattttgtgtaaaacatctaaaaattattcttttagaaacag aagaatatcattgaagataatagtgtgaaattatatatatatatagaaatatataaagtaggattttttctgtatacaaatatacgtttccaattttatc aaaaactgtaaagatttttttctttgtcagtacctgctaaacttgttaattttttattaaaaaaaaatcaaattacaattcttctataatcattttaaat tccatttctttataccacaaaagattatattgcctttatcgtctttggnatgtatgcgtgaatatatttatttattttctttctttcattttcttttaa agaactttataaatgaaataaggaacaaacaatatacatatgtactaacgtatataaataatatcatcaatatctatccaaaacttggatttcatggttga cgtggcccaaccaaaatctcaagttctctgcggatgacgaaccatctcaccatctcttttttctctctcttttttttttttaatatcatcagcacggttac ataaaattcgtgatccatgaagttggctttcttgtcgttttacttcatcacccatttttttaaaagtctccatctttatacttcttcaactctccaccacc accattgtcaccaccacatttaaacacacactttcacttgtagtgggattagaaagtgcgttttattcatttgttttactgttttgataacctcaaaatt tgcctaaattttattctctataaatccttatatgttttacttacattcctaaagttttcaactttcctgagcttcaaaaag
```

| Promoter Expression Report #102 | |
|---|---|
| Promoter Tested In: | *Arabidopsis thaliana*, WS ecotype |
| Spatial expression summary: | |
| Ovule | Pre-fertilization: L primordia L inner integument L outer integument Post-fertilization: H suspensor |
| Observed expression pattern: | |
| T1 mature: | Weak expression observed throughout ovule primordia including mother megaspore cell. Post-fertilization expression specific to suspensor cells of embryol Degeneration of expression in suspensor at torpedo stage. |
| T2 Seedling: | No expression. |
| Expected expression pattern: | Nucellus and megaspore mother cell |
| Selection Criteria: | Literature. Yang W C, Ye D, Xu I, Sundaresan V. The SPOROCYTELESS gene of *Arabidopsis* is required for initiation of sporogenesis and encodes a novel nuclear protein. Genes Dev. Aug. 15, 1999; 13(16): 2108–17. |
| Gene: | Nozzle Sporocyteles |
| GenBank: | NM_118867 *Arabidopsis thaliana* NOZZLE SPOROCYTELESS (At4g27330) RNA, complete sgi\|18416968\|ref\|NM_118867.1\|[18416968] |
| Source Promoter Organism: | *Arabidopsis thaliana* WS |
| Vector: | pNewbin4-HAP1-GFP |
| Marker Type: | GFP-ER |
| Generation Screened: | XT1 Mature XT2 Seedling ☐ T2 Mature ☐ T3 Seedling |

T1 Mature Plant Expression Organs/Tissues screened

Events Screened:  n = 3  Events Expressing:  n = 2
GFP Expression Detected

| | |
|---|---|
| L Flower | ☐ pedicel ☐ receptacle ☐ nectary ☐ sepal ☐ petal ☐ filament ☐ anther ☐ pollen ☐ carpel ☐ style ☐ papillae ☐ vascular ☐ epidermis ☐ stomata ☐ trichome ☐ silique |
| ☐ Silique | ☐ stigma ☐ style ☐ carpel ☐ septum ☐ placentae ☐ transmitting tissue ☐ vascular ☐ epidermis ☐ stomata ☐ abscission zone ☐ ovule |
| X Ovule | Pre-fertilization: L primordia L inner integument L outer integument ☐ embryo sack ☐ funiculus ☐ chalaza ☐ micropyle ☐ gametophyte Post-fertilization: ☐ zygote H suspensor ☐ embryo sack ☐ inner integument ☐ outer integument ☐ endothelium ☐ seed coat ☐ primordia ☐ chalaza ☐ micropyle ☐ early endosperm ☐ mature endosperm ☐ embryo |
| ☐ Embryo | ☐ suspensor ☐ preglobular ☐ globular ☐ heart ☐ torpedo ☐ late ☐ mature ☐ provascular ☐ hypophysis ☐ radicle ☐ cotyledons ☐ hypocotyl |
| ☐ Stem | ☐ epidermis ☐ cortex ☐ vascular ☐ xylem ☐ phloem ☐ pith ☐ stomata ☐ trichome |
| ☐ Leaf | ☐ petiole ☐ mesophyll ☐ vascular ☐ epidermis ☐ trichome ☐ primordia ☐ stomata ☐ stipule ☐ margin |
| ☐ Shoot apical meristem | ☐ Shoot apical meristem ☐ Flower primordium |

X in the Megaspore mother cell (Mmc), Outer integument (Oi) and Funiculus (Fn) of the ovule primordia
X in the Suspensor cells (Su) of the globular embryo stage in the ovule
X in the Suspensor apparatus. After first asymmetrical cell division of zygote, the larger basal cell differentiates into 9 cells See Willemsen, V., et. al. Development. Feb. 1998; 125(3): 521–31.
X in the Suspensor cells (Sn) of the heart stage embryo
X in the Micopyle (Mp)

-continued

| Promoter Expression Report #102 | |
|---|---|

T2 Seedling Expression Tissues Screened

Events Screened:  n = 2  Events Expressing:  n = 0
Seedlings expressing/Seedlings screened Event-01:  0/6
Event-02:  0/6
☐ Scheduled
No GFP Expression Detected

| | |
|---|---|
| ☐ Hypocotyl | ☐ epidermis ☐ cortex ☐ vascular ☐ xylem ☐ phloem ☐ stomata |
| ☐ Cotyledon | ☐ mesophyll ☐ vascular ☐ epidermis ☐ margin ☐ stomata ☐ hydathode |
| ☐ Rosette Leaf | ☐ mesophyll ☐ vascular ☐ epidermis ☐ trichome ☐ petiole ☐ primordia ☐ stomata ☐ stipule ☐ margin ☐ hydathode |
| ☐ Primary Root | ☐ epidermis ☐ trichoblast ☐ atrichoblast ☐ cortex ☐ endodermis ☐ vascular ☐ xylem ☐ phloem ☐ pericycle ☐ quiescent ☐ columella ☐ root cap ☐ root hairs |
| ☐ Lateral root | ☐ epidermis ☐ trichoblast ☐ atrichoblast ☐ cortex ☐ endodermis ☐ initials ☐ flanking cells ☐ vascular ☐ lateral root cap |
| ☐ Shoot apical meristem | ☐ Shoot apical meristem |

Promoter utility

| | |
|---|---|
| Trait Area: | SSR |
| Sub-trait Area: | Sink strength, apomixis, seed size, embryo size, genetic containment |
| Utility: | Better embryo fill, larger embryo and seed. Altered seed composition. Increased seed weight and yield. Better performing seedlings. Seedlings Tolerant to stress. Altered source-sink balance. Control of seed coat development. Increase endosperm production and increase seed fill. |
| Notes: | Balasubramanian S, Schneitz K. NOZZLE links proximal-distal and adaxial-abaxial pattern formation during ovule development in *Arabidopsis thaliana*. Development. Sep. 2002; 129(18): 4291– |
| Construct: | YP0271 |
| Promoter candidate I.D: | 11768757 |
| cDNA I.D: | 12658070 |
| Lines expressing: | YP0271-01, -02 |

Sequence (SEQ ID NO: 79):

```
atctctgatttttttatcaggaacaagttaaataaatagctttgagttttttgttttttttctacattcttcgcccaaaagatgtaagaaaataaggatt
tgaaaccttgttctgttgttactcctttaaattcttagaaactataaatcattatatctttgatctgtttcacaaactaatcatattcgttgcaaagtgag
aattcgtcccactttactctttacaccgatactagtattatagatgtacagcatagtattccatatctagttatttagtcaaaactctatatattaagagg
taggttaattaattaaggagtaattgaagattatagaagaataaaaaataccatttaatggacagaaccaaagataactaactatcatactataatgttg
aatttcttccacgatccaatgcatggataacaacatcaatcaaatcatacattcatgctatataacatagttttcagttacaaactctctttttttatttat
ttcagttgttccttttcatgaccatattaacatcaaataatgcattttttcaacgtctcttgacttacacccactaatattgacaaattgaacatctata
cgactatacgcacataagttaaaaatgcatgcaagtgctaagggaatttataacatctaaggttaataagactaagaaagtataaaataagaatacgtatt
atgaatttatgatatactttactaatcttttgaaaaatactttaatttaatctactataggggtaaaaagtaaaaaagaaataaagatacgtttatccg
catatagtacctggaaataacagaaataaaaacacaggtaagtactttgcctgagctagtatatgaacactaaagagatacacacacacaaaaagagagc
agaaacaaaacacacacttaaagctttcgtctttacctcttcccttctctctctatctaaaaagagttccga
```

| Promoter Expression Report #103 | |
|---|---|
| Promoter Tested In: | *Arabidopsis thaliana*, WS ecotype |
| Spatial expression summary: | |
| Silique | L ovule |
| Ovule | Post-fertilization: M zygote L embryo sack L embryo |
| Embryo | M suspensor L torpedo L radicle |
| Rosette Leaf | M mesophyll H epidermis H stomata |
| Primary Root | H pericycle |
| Lateral root | H initials H flanking cells H primordia |
| Observed expression pattern: | |
| T1 mature: | High expression throughout mature female gametophyte at fertilization and in embryo from zygote to torpedo stage embryo. Expression in embryo restricted to radicle. Not observed in leaf, however this may coincide with severe yellowing of leaves in plants screened during this time. May have not been detected due to intense auto-florescence of necrotic tissue. |
| T2 seedling: | High GFP expression in mesophyll and epidermal cells of rosette leaves. Expression in root is specific to pericycle cells and lateral root primordia. |
| Expected expression pattern: | Leaf |
| Selection Criteria: | Literature. Leaf-Specific Upregulation of Chloroplast Translocon Genes by a CCT Motif Containing Protein, CIA 2. Sun C W, Chen U, Lin L C, Li H M. Plant Cell. Sep. 2001; 13(9): 2053–2062. PMCID: 139451 |
| Gene: | CIA2 |
| GenBank: | NM_125100 *Arabidopsis thaliana* CIA2 (CIA2) (At5g57180) mRNA, complete cds gi\|30696839\|ref\| NM_125100.2\|[30696839] |
| Source Promoter Organism: | *Arabidopsis thaliana* WS |
| Vector: | pNewbin4-HAP1-GFP |
| Marker Type: | GFP-ER |
| Generation Screened: | XT1 Mature XT2 Seedling ☐ T2 Mature ☐ T3 Seedling |

T1 Mature Plant Expression Organs/Tissues screened

Events Screened:  n = 3   Events Expressing:  n = 3
GFP Expression Detected

| | |
|---|---|
| ☐ Flower | ☐ pedicel ☐ receptacle ☐ nectary ☐ sepal ☐ petal ☐ filament ☐ anther ☐ pollen ☐ carpel ☐ style ☐ papillae ☐ vascular ☐ epidermis ☐ stomata ☐ trichome ☐ silique |
| X Silique | ☐ stigma ☐ style ☐ carpel ☐ septum ☐ placentae ☐ transmitting tissue ☐ vascular ☐ epidermis ☐ stomata ☐ abscission zone L ovule |
| W Ovule | Pre-fertilization: ☐ inner integument ☐ outer integument ☐ embryo sack ☐ funiculus ☐ chalaza ☐ micropyle ☐ gametophyte Post-fertilization: M zygote L embryo sack ☐ inner integument ☐ outer integument ☐ endothelium ☐ seed coat ☐ primordia ☐ chalaza ☐ micropyle ☐ early endosperm ☐ mature endosperm L embryo |
| X Embryo | M suspensor ☐ preglobular ☐ globular ☐ heart L torpedo ☐ late ☐ mature ☐ provascular ? hypophysis L radicle ☐ cotyledons ☐ hypocotyl |
| ☐ Stem | ☐ epidermis ☐ cortex ☐ vascular ☐ xylem ☐ phloem ☐ pith ☐ stomata ☐ trichome |
| ☐ Leaf | ☐ petiole ☐ mesophyll ☐ vascular ☐ epidermis ☐ trichome ? primordia ☐ stomata ☐ stipule ☐ margin |
| ☐ Shoot apical meristem | ☐ Shoot apical meristem ☐ Flower primordium |

X in the Embryo (Em), Embryo sack (Es) and Micropyle (Mp) of the fertilized ovule
X in the Embryo proper (Ep) and Suspensor (Su) of the zygote
X in the Micropyle (Mp) pole of the ovule
X in the fertilized ovule
X in the Radicle (Rd) and Root apical meristem (Ram) of the torpedo stage embryo T2 Seedling Expression Tissues Screened Events Screened:  n = 2   Events Expressing:  n = 2
Seedlings expressing/Seedlings screened Event-01: 2/3
Event-02: 1/3
☐ Scheduled
GFP Expression Detected

| | |
|---|---|
| ☐ Hypocotyl | ☐ epidermis ☐ cortex ☐ vascular ☐ xylem ☐ phloem ☐ stomata |
| ☐ Cotyledon | ☐ mesophyll ☐ vascular ☐ epidermis ☐ margin ☐ stomata ☐ hydathode |
| X Rosette Leaf | M mesophyll ☐ vascular H epidermis ☐ trichome ☐ petiole ☐ primordia |

Promoter Expression Report #103

| | |
|---|---|
| | H stomata ☐ stipule ☐ margin ☐ hydathode |
| X Primary Root | ☐ epidermis ☐ trichoblast ☐ atrichoblast ☐ cortex ☐ endodermis ☐ vascular ☐ xylem ☐ phloem H pericycle ☐ quiescent ☐ columella ☐ root cap ☐ root hairs |
| X Lateral root | ☐ epidermis ☐ trichoblast ☐ atrichoblast ☐ cortex ☐ endodermis H initials H flanking cells H primordia ☐ vascular ☐ lateral root cap |
| ☐ Shoot apical meristem | ☐ Shoot apical meristem |

X in the Epidermis (Ep), Guard cells (Gc) and Mesophyll (Me) of the rosette leaf
X in the root and root transition zone
X in the Pericycle (Pr) of the lateral root initials
X in the lateral root primordia Promoter utility

| | |
|---|---|
| Trait Area: | SSR |
| Sub-trait Area: | Embryo size, sink strength, seed size. |
| Utility: | Nutrition. Imprint modulation through female, heavier seed, lighter seed, seedless fruits. Increased lateral root growth. More lateral roots, larger lateral roots. Improved drought tolerance. Improved performance in low-nitrogen soil, improved source capacity. |
| Construct: | YP0279 |
| Promoter candidate I.D: | 11768839 |
| cDNA I.D: | 12600234 (OCKHAM3-C) |
| Lines expressing: | YP00279-01, -02, -03 |

Sequence (SEQ ID NO: 80):

```
cgctttattataggtttaacaattgattttcattattttgttttcaatctccaaatcatttctcaataactctcaaacattgtttaaagcttttttctt
aattaacattataacaaaaaatataatagagaaatttactttgattcaaacaccagtcattgtagattagccaagagttttcagtaacaaaatttaccta
taaacttttgaatggctatttctgaaatggaatagaatctttagtcgtggaagtatctctatccataagaaaactcgttttacaaagtaattttaaatca
atacaaaaagtgaaaaatccactggtggaccccattcattccagaattgccgattacgagctatcttgtcccttcttccaccattcgctcactctctc
tctctctcgtcttcttcttcccaccactctctctgtttctccacaacttctcttctcaaagttaaaattaccctaaaccaaaaaaaaaaaaacgctctt
cactatttatttactaaactctcctttgtttgttactaagctctcactaaaaccctaatctttctcctcttatatatctcgtgactcttcttctcctcca
atctctctcccctcttcacaaaccaattagcttctttctgtaaaacctcactcgttggccaattcttttggttttcatacacataaatctcagattccaa
atgggttttcttagctctttctttcaaatgatgaactttgttagcagaatcttcctcattccctaaagttttgatcttttttccccttcaatttgtat
tttctcaccaaataaaaaaggtttcttcagtgggttttaagggtttattattatcttaaaattaaacacaattctttaatcaaaaggcaaaaatcttaat
ttcatcactctcttctcactcacaaaagttcttacaatcttcaaagttttggtcttgtttcttttcc
```

Promoter Expression Report #119

Promoter Tested In: *Arabidopsis thaliana*, WS ecotype
Spatial expression summary:
Silique H ovule
Ovule Pre-fertilization: H outer integument
Post-fertilization: H outer integument, H seed coat
Observed expression pattern:
T1 Mature: GFP expressed in outer integument early in ovule development through seed coat of mature seeds.
T2 Seedling: No expression observed.
Expected expression pattern: Expressed in ovules and different parts of seeds

Promoter Expression Report #119

Selection Criteria: Greater than 50x up in pi ovule microarray
Gene: "hypothetical protein/product = "expressed protein"
GenBank: NM 117365 *Arabidopsis thaliana* expressed protein (At4g12960) mRNA, complete cds gi|30682287|ref| NM_117365.2|[30682287]
Source Promoter Organism: *Arabidopsis thaliana* WS
Vector: pNewbin4-HAP1-GFP
Marker Type: GFP-ER
Generation Screened: X T1 Mature X T2 Seedling ☐T2 Mature ☐T3 Seedling
T1 Mature Plant Expression   Organs/Tissues screened
Events Screened: n = 4   Events Expressing: n = 3
GFP Expression Detected

| | |
|---|---|
| ☐ Flower | ☐pedicel ☐receptacle ☐nectary ☐sepal ☐petal ☐filament ☐anther ☐pollen ☐carpel ☐style ☐papillae ☐vascular ☐epidermis ☐stomata ☐trichome ☐silique |
| X Silique | ☐stigma ☐style ☐carpel ☐septum ☐placentae ☐transmitting tissue ☐vascular ☐epidermis ☐stomata ☐abscission zone L ovule |
| X Ovule | Pre-fertilization: ☐inner integument ☐outer integument M embryo sack ☐funiculus ☐chalaza ☐micropyle ☐gametophyte Post-fertilization: ☐zygote ☐embryo sack ☐inner integument ☐outer integument ☐endothelium ☐seed coat ☐primordia ☐chalaza ☐micropyle ☐early endosperm ☐mature endosperm ☐embryo |
| ☐ Embryo | ☐suspensor ☐preglobular ☐globular ☐heart ☐torpedo ☐late ☐mature ☐provascular ☐hypophysis ☐radicle ☐cotyledons ☐hypocotyl |
| ☐ Stem | ☐epidermis ☐cortex ☐vascular ☐xylem ☐phloem ☐pith ☐stomata ☐trichome |
| X Leaf | ☐petiole ☐mesophyll L vascular ☐epidermis ☐trichome ☐primordia ☐stomata ☐stipule ☐margin |
| ☐ Shoot apical meristem | ☐Shoot apical meristem ☐Flower primordium |

X in the Vasculature (Vs) of the leaf
X in the Embryo sack (Es) of the pre-fertilized and fertilized ovule
T2 Seedling Expression   Tissues Screened
Events Screened: n = 2 Events Expressing: n = 2
Seedlings expressing/Seedlings screened
Event-01: 5/6
Event-02: 3/5
☐ Scheduled
GFP Expression Detected

| | |
|---|---|
| X Hypocotyl | ☐epidermis ☐cortex L vascular ☐xylem ☐phloem ☐stomata |

| Promoter Expression Report #119 | |
|---|---|
| X Cotyledon | ☐mesophyll L vascular ☐epidermis ☐margin ☐stomata M hydathode |
| ☐ Rosette Leaf | ☐mesophyll ☐vascular ☐epidermis ☐trichome ☐petiole ☐primordia ☐stomata ☐stipule ☐margin ☐hydathode |
| X Primary Root | L epidermis ☐trichoblast ☐atrichoblast ☐cortex ☐endodermis M vascular ☐xylem ☐phloem M pericycle ☐quiescent ☐columella ☐root cap ☐root hairs |
| ☐ Lateral root | ☐epidermis ☐trichoblast ☐atrichoblast ☐cortex ☐endodermis ☐initials ☐flanking cells ☐vascular ☐lateral root cap |
| ☐ Shoot apical meristem | ☐Shoot apical meristem |

X in the Vasculature (Vs) of the hypocotyl
X in the Vasculature (Vs) and Epidermis (Ep) of the root transition zone
X in the Hydathode (Hd) and Vasculature (Vs) of the cotyledon
X in the Pericycle (Pr), Vasculature (Vs) and Epidermis (Ep) of the root
Promoter utility
Trait Area: SSR
Sub-trait Area: Methylation control, endosperm production, sink strength
Utility: Imprint modulation through female, larger (heavier) seeds, smaller (lighter) seeds, seedless fruits. Altered endosperm and seed composition, improved drought tolerance. Improved performance in low-nitrogen soil.
Construct: YP0285
Promoter candidate I.D.: 11768588
cDNA I.D.: 13609092
Lines expressing: YP0285-01, -02, -04

Sequence (SEQ ID NO: 81):

```
gggattatatatgatagacgattgtatttgcgggacattgagatgtttccgaaaatagtcatcaaatatcaaaccagaatttgatgtgaaaacactaatta
aaacatataattgacaactagactatatcatttgttaagttgagcgttgaaagaaaatgaaagagtgtagactgtagtacgtatgagtttcccaaaagatg
gtgcttgaatattattgggaagagactttggttggttcggttgaatgaagattttttacctgccatgttgatagagaaaggcaaataaatgtagggtcgat
gtctaacgtaaagactggatcaaccaagagtcctcctcctcgtcttcaccaaaaaaaagagtcctcctcgtggaaacttatttcttctccagccaagatc
tcatctcatctcttcactctatgaaatataaaggaatcttatggttttctaaaactatagtacgtctatataccaaaggaaacaatataaaatcagtta
atctgataaattttgagtaaataataaagttaactttgtacttacctatatcaaactaattcacaaaataaagtaataataacaaagaattttagtagat
ccacaatatacacacactatgagaaatcataatagagaattttaatgattttgtctaactcatagcaacaagtcgctttggccgagtggttaaggcgtg
tgcctgctaagtacatgggctctgcccgcgagagttcgaatctctcaggcgacgtttcttttgtttcggccataaaggaaaaagcccaattaacacgtct
cgcttataagcccataaagcaaacaatgggctgtctctgtctcactcacacacgcgttttcctacttttttgactattttataaccggcgggtctgactta
attagggttttctttaataatcagacactctctcactcgtttcgtcaacattgaacacagacaaaaccgcgt
```

| Promoter Expression Report #106 | |
|---|---|

Expected expression pattern: Shoot apical meristem
Selection Criteria: Greater than 5× down in stm microarray
Gene: Leucine-rich repeat transmembrane protein kinase
GenBank: NM_118146 *Arabidopsis thaliana* leucine-rich repeat transmembrane protein kinase, putative (At4g20270) mRNA, complete cds gi|30685044|ref|NM_118146.2|[30685044]
Source Promoter Organism: *Arabidopsis thaliana* WS
Vector: pNewbin4-HAP1-GFP
Marker Type: GFP-ER
Generation Screened: X T1 Mature X T2 Seedling ☐T2 Mature ☐T3 Seedling
T1 Mature Plant Expression   Organs/Tissues screened
Events Screened: n = 3 Events Expressing: n = 3
GFP Expression Detected

| X Flower | ☐pedicel ☐receptacle ☐nectary ☐sepal ☐petal ☐filament ☐anther ☐pollen ☐carpel ☐style ☐papillae H vascular ☐epidermis ☐stomata ☐trichome ☐silique |
|---|---|
| X Silique | ☐stigma ☐style ☐carpel ☐septum ☐placentae ☐transmitting tissue H vascular ☐epidermis ☐stomata ☐abscission zone ☐ovule |
| ☐ Ovule | Pre-fertilization: ☐inner integument ☐outer integument ☐embryo sack ☐funiculus ☐chalaza ☐micropyle ☐gametophyte Post-fertilization: ☐zygote ☐embryo sack ☐inner integument ☐outer integument ☐endothelium ☐seed coat ☐primordia ☐chalaza ☐micropyle ☐early endosperm ☐mature endosperm ☐embryo |

| Promoter Expression Report #106 | |
|---|---|

Promoter Tested In: *Arabidopsis thaliana*, WS ecotype
Spatial expression summary

| Flower | H vascular |
|---|---|
| Silique | H vascular |
| Stem | H vascular |
| Leaf | H vascular |
| Hypocotyl | H vascular |
| Cotyledon | H vascular |
| Rosette Leaf | H vascular |
| Primary Root | H vascular, H pericycle |
| Lateral root | H pericycle H vascular |

Observed expression pattern:
T1 mature: Very high expression in vasculature of flowers, stems, and leaves. Not detected in reproductive tissues in silique.
T2 seedling: Very high expression throughout seedling vasculature. Expression in root extending into pericycle cells.

| Promoter Expression Report #106 | |
|---|---|
| ☐ Embryo | ☐suspensor ☐preglobular ☐globular ☐heart ☐torpedo ☐late ☐mature ☐provascular ☐hypophysis ☐radicle ☐cotyledons ☐hypocotyl |
| X Stem | ☐epidermis ☐cortex H vascular ☐xylem ☐phloem ☐pith ☐stomata ☐trichome |
| X Leaf | ☐petiole ☐mesophyll H vascular ☐epidermis ☐trichome ☐primordia ☐stomata ☐stipule ☐margin |
| ☐ Shoot apical meristem | ☐Shoot apical meristem ☐Flower primordium |

X in the vasculature of the inflorescence meristem
X in the Petal (Pe) and Silique (Si) of the flower
X in the Medial vasculature (Mv) in the silique
X in the Vascular bundle (Vb) of the leaf and stem
T2 Seedling Expression   Tissues Screened
Events Screened: n = 2 Events Expressing: n = 2

Promoter Expression Report #106

Seedlings expressing/Seedlings screened
Event-01: 2/2
Event-02: 2/4
☐ Scheduled
GFP Expression Detected
X Hypocotyl ☐epidermis ☐cortex H vascular ☐xylem ☐phloem ☐stomata
X Cotyledon ☐mesophyll H vascular ☐epidermis ☐margin ☐stomata ☐hydathode
X Rosette Leaf ☐mesophyll H vascular ☐epidermis ☐trichome ☐petiole ☐primordia ☐stomata ☐stipule ☐margin ☐hydathode
X Primary Root ☐epidermis ☐trichoblast ☐atrichoblast ☐cortex ☐endodermis H pericycle ☐initials ☐flanking cells H vascular ☐lateral root cap
☐ Shoot apical meristem ☐Shoot apical meristem
X in the Rosette leaf (Rl)
X in the Vascular (Vs) of the hypocotyly, leaf and root
X in the Pericycle (Pr) of the root and lateral root
Promoter utility
Trait Area: Nutrition
Sub-trait Area: Nitrogen use efficiency
Utility: Improved translocation, improved source capacity and seed fill. Heavier seeds. More seeds. Larger siliques. Improved seed yield. Moderate nitrate and/or amino acid transport. Increased transport to floorsink.
Notes: LRR kinases play key roles in cell-cell interactions and interactions Between plant and microbial cells. Specific leucine repeats bind Low molecular weight ligands.
Construct: YP0080
Promoter candidate I.D.: 11768676
cDNA I.D.: 12603755 (OCKHAM3-C)
Lines expressing: YP0080 -01, -02, -03

Promoter Expression Report #107

Selection Criteria: *Arabidopsis* public: The BELL1 gene encodes a homeodomain protein involved in pattern formation in the *Arabidopsis* ovule primordium.
Gene: = "homeodomain protein, BELL1 (BEL1)"
GenBank: NM 123506 *Arabidopsis thaliana* homeodomain protein, BELL1 (BEL1) (At5g41410) mRNA, complete cds gi|30693794|ref| NM_123506.2|[30693794]
Source Promoter Organism: *Arabidopsis thaliana* WS
Vector: pNewbin4-HAP1-GFP
Marker Type: GFP-ER
Generation Screened: X T1 Mature X T2 Seedling ☐T2 Mature ☐T3 Seedling
T1 Mature Plant Expression   Organs/Tissue screened
Events Screened: n = 3 Events Expressing: n = 0
No GFP Expression Detected
☐ Flower ☐pedicel ☐receptacle ☐nectary ☐sepal ☐petal ☐filament ☐anther ☐pollen ☐carpel ☐style ☐papillae ☐vascular ☐epidermis ☐stomata ☐trichome ☐silique
☐ Silique ☐stigma ☐style ☐carpel ☐septum ☐placentae ☐transmitting tissue ☐vascular ☐epidermis ☐stomata ☐abscission zone ☐ovule
☐ Ovule Pre-fertilization: ☐inner integument ☐outer integument ☐embryo sack ☐funiculus ☐chalaza ☐micropyle ☐gametophyte
Post-fertilization: ☐zygote ☐embryo sack ☐inner integument ☐outer integument ☐endothelium ☐seed coat ☐primordia ☐chalaza ☐micropyle ☐early endosperm ☐mature endosperm ☐embryo
☐ Embryo ☐suspensor ☐preglobular ☐globular ☐heart ☐torpedo ☐late ☐mature ☐provascular ☐hypophysis ☐radicle ☐cotyledons ☐hypocotyl
☐ Stem ☐epidermis ☐cortex ☐vascular ☐xylem ☐phloem ☐pith ☐stomata ☐trichome
☐ Leaf ☐petiole ☐mesophyll ☐vascular ☐epidermis ☐trichome ☐primordia ☐stomata ☐stipule ☐margin Sequence (SEQ ID NO: 82):

```
aagcggcaatttagtaagaagtattcaatgtatcatttaccaaaagtatatggttttgggaagagttgttagggatgtattctttctaaacagatgatatg
acgatgttcttgaaaactaatgttaaagacgggatctctcgcatcttcactcgggagatatattaaaccgttgattgtagttagccatgtacttagcttag
tgcacaaataatctgctgcaagaaatcttttctattataatatctctcatttaaacattagaacatattgtttaacttgttcttctagaaataaaactgc
taatttcttatggtaaactattttcctttagattgcacaatcgaactcgaaaatctagtggagactatgtgactatgtttatatatatgaaacctaaatca
aattatcccaataattgggagacacaaaagaaaaaagaaaacaggaaatcaaatcaaaagataaagagaaggtaaaacaaaaggcaagaagcactaatgt
ttaatatttatagttttctccattaaagaaaaagcgatgatgtgtgtgttctcatcttttgtgaaagtatatatattgcttttgctcttcaaaagcaaa
agactcatccaacaacaacaaaaaaaacctaaagctcaatccaaaagacgaagaatgcattggatactacaacttcttttcacttttctttcgaat
ttacaattatgattttcacaatacagtgtattcaaaatatataaaaaaaacgaggcatgaaaataatgattatcctcttcacttattaagccactcactat
aagcagagcaactccagaacatagtgagccccaaaacattaaagcatgatgatgtctaatgatgatgatcttcttcgttccatttctctaaatttttggg
atttctgcgaagaccttcttctctttctcttctctgaacttcaagattcgtgtcggacaaattttgttttt
```

Promoter Expression Report #107

Promoter Tested In: *Arabidopsis thaliana*, WS ecotype
Spatial expression summary:
Rosette Leaf   L vascular M epidermis
Primary Root   H epidermis M root hairs
Observed expression pattern: T1 mature: No expression observed. Predicted expression in ovule primordium. Possibly missed low expression. T2 seedling: High expression throughout root epidermal cells. Low epidermal and vasculature expression at leaf margins.
Expected expression pattern: Integument.

Promoter Expression Report #107

☐ Shoot apical meristem ☐Shoot apical meristem ☐Flower primordium
T2 Seedling Expression   Tissues Screened
Events Screened: n = 3 Events Expressing: n = 2
Seedlings expressing/Seedlings screened
Event-01: 3/6
Event-02: 3/5
☐ Scheduled

Promoter Expression Report #107

GFP Expression Detected
- ☐ Hypocotyl ☐epidermis ☐cortex ☐vascular ☐xylem ☐phloem ☐stomata
- ☐ Cotyledon ☐mesophyll ☐vascular ☐epidermis ☐margin ☐stomata ☐hydathode
- X Rosette Leaf ☐mesophyll L vascular M epidermis ☐trichome ☐petiole ☐primordia ☐stomata ☐stipule ☐margin ☐hydathode
- X Primary Root H epidermis ☐trichoblast ☐atrichoblast ☐cortex ☐endodermis ☐vascular ☐xylem ☐phloem ☐pericycle ☐quiescent ☐columella ☐root cap M root hairs
- ☐ Lateral root ☐epidermis ☐trichoblast ☐atrichoblast ☐cortex ☐endodermis ☐initials ☐flanking cells ☐vascular ☐lateral root cap
- ☐ Shoot apical meristem ☐Shoot apical meristem
- X in the Epidermis (Ep) of the root transition zone, the root and the cotyledon
- X in the Vasculature (Vs) of the cotyledon Promoter utility
Trait Area: Nutrition
Sub-trait Area: Low nitrogen use efficiency.
Utility: Improve ion uptake in roots
Notes: Homeodomain proteins are transcription factors. Homeoproteins cooperate to control cell fate specification.
Construct: YP0122
Promoter candidate I.D.: 11768849
cDNA I.D.: 13593439 (OCKHAM3-C)
Lines expressing: YP0122-01, -02

Sequence (SEQ ID NO: 83):

```
agtttaattatttgttatctatccaatcaattttttttctaaactgtttggaccaatgtacgtacgtaccatccttttgatttttttgtaaactaaat
tttcggattagcaggttcttaataattgaacgaagaaaataaagaatagaggtagacacctgtagtattttcttggtcagaccaataatttataattcaac
gtcaaagaagaagaaaaatataaaccattatttcattatgacttacgtataccaaaatacacaaattaaatgtataattgtgaggcattttatatgcggga
aaaataaaataaaaagaatattaatatttcttttgaaaattgtaaagcattttgacccacttgtgatatatatatatagatatatatagagagagagatt
aaaacattgatggctagctatagagtctatggcagggtcatgatcacctatcttctgatctctgaagagataccaatctgatttttttctcttcctaggttt
aatttttattttaccatttttataattctttattttgcctgtagtacaatttacagacccatactaaaagaaaaattaaatttgtcaaagtacaaaacaaa
gagagaggtgaagccacacaatctcttttcttctctctctctgttatatctcttctgtttaattcttttattcttcttcgtctatcttctcctataatc
tcttctctctccctcttcacctaaagaataagaagaaaataattcacatctttatgcaaactactttcttgtagggttttaggagctatctctattgtct
tggttctgatacaaagttttgtaattttcatggtatgagaaratttgcctttctattttgtttattggttcttttaacttttcttggagatgggttctt
gtagatcttaatgaaacttctgttttgtcccaaaaagagttttcttttttcttctcttcttttttggttttcaattc
```

Promoter Expression Report #108.02 hypocotyl, and petioles.
Expected expression pattern: Expressed in mid torpedo stage of embryos and root.
Selection Criteria: Literature Bodenlos, (same as IAA12 Hamann et al. (1999). Develop. Vol. 126: 1387–1395
Gene: Indoleacetic acid-induced protein 12
GenBank: NM 100334 Arabidopsis thaliana auxin-responsive protein IAA12 (Indoleacetic acid-induced protein 12) (At1g04550) mRNA, complete cds gi|30678909|ref|NM_100334.2
Source Promoter Organism: Arabidopsis thaliana, Ws ecotype
Vector: pNewbin4-HAP1-GFP
Marker Type: GFP-ER
Generation Screened: X T1 Mature X T2 Seedling ☐T2 Mature ☐T3 Seedling
T1 Mature Plant Expression    Organs/Tissues screened
Events Screened: n = 5 Events Expressing: n = 2
GFP Expression Detected
- X Flower ☐pedicel ☐receptacle ☐nectary ☐sepal ☐petal ☐filament ☐anther ☐pollen ☐carpel ☐style ☐papillae L vascular ☐epidermis ☐stomata ☐trichome ☐silique
- X Silique ☐stigma ☐style ☐carpel ☐septum M placenta ☐transmitting tissue M vascular ☐epidermis ☐stomata ☐abscission zone ☐ovule
- ☐ Ovule Pre-fertilization: ☐inner integument ☐outer integument ☐embryo sac ☐funiculus ☐chalaza ☐micropyle ☐gametophyte
  Post-fertilization: ☐zygote ☐embryo sack ☐inner integument ☐outer integument ☐endothelium ☐seed coat ☐primordia ☐chalaza ☐micropyle ☐early endosperm ☐mature endosperm ☐embryo
- ☐ Embryo ☐suspensor ☐preglobular ☐globular ☐heart ☐torpedo ☐late ☐mature ☐provascular ☐hypophysis ☐radicle ☐cotyledons ☐hypocotyl
- ☐ Stem ☐epidermis ☐cortex ☐vascular ☐xylem ☐phloem

Promoter Expression Report #108.02

Promoter Tested In: Arabidopsis thaliana, WS ecotype
Spatial expression summary:
Flower       M vascular
Silique      M placenta, M vascular
Hypocotyl    H vascular
Cotyledon    H vascular, H petiole
Primary Root H vascular
Observed expression pattern:
T1 mature: GFP expressed in vasculature of silique and pedicles of flowers.
T2 seedling: High GFP expression throughout vasculature of root, ☐pith ☐stomata ☐trichome
- ☐ Leaf ☐petiole ☐mesophyll ☐vascular ☐epidermis ☐trichome ☐primordia ☐stomata ☐stipule ☐margin
- ☐ Shoot apical meristem ☐shoot apical meristem ☐flower primordium
- X in the Vasculature (Vs) of the flower and the Silique (Si)

T2 Seedling Expression    Tissues Screened
Events Screened: n = 2 Events Expressing: n = 2
Seedlings expressing/Seedlings screened
Event-01: 5/6

Promoter Expression Report #108.02

Event-02: 4/6
☐ Scheduled
GFP Expression Detected

| | |
|---|---|
| X Hypocotyl | ☐epidermis ☐cortex H vascular ☐xylem ☐phloem ☐stomata |
| X Cotyledon | ☐mesophyll H vascular ☐epidermis H Petiole ☐margin ☐stomata ☐hydathode |
| ☐ Rosette Leaf | ☐mesophyll ☐vascular ☐epidermis ☐trichome ☐petiole ☐primordia ☐stomata ☐stipule ☐margin ☐hydathode |
| X Primary Root | ☐epidermis ☐trichoblast ☐atrichoblast ☐cortex ☐endodermis H vascular ☐xylem ☐phloem ☐pericycle ☐quiescent ☐columella ☐rootcap ☐root hairs |
| ☐ Lateral root | ☐epidermis ☐trichoblast ☐atrichoblast ☐cortex ☐endodermis ☐initials ☐flanking cells ☐vascular ☐lateral root cap |
| ☐ Shoot apical meristem | ☐Shoot apical meristem |

X in the Vasculature (Vs) of the hypocotyl and root
Promoter utility
Trait Area: Nutrients, PG&D
Sub-trait Area: Plant size, root architecture,
Utility: Modulation of nutrient uptake, loading and transport. Modulation of root growth and development.
Construct: YP0226
Promoter candidate I.D.: 13148249
cDNA I.D.: 12327003
Lines expressing: YP0226 -02, -05

Sequence (SEQ ID NO: 84):

ctccttgataatgattttgatcaaaagtgtaatttccacaaaccaattgcgcctgcaaaagttttcaaaggatcatcaaacataatgatgaatatctcatc accacgatttttataataatgcatcttttcccaccattttttttccctcactttcttttataatcttgttcgacaacaatcatggtctaaggaaaagttga aaatatatattatcttagttattagaaaagaaagataatcaaatggtcgatatgcaaatggcatatgaccataaacgagtttgctagtataaagaatgatg gccaacctgttaaagagagactaaaattaggtctaaaatctaggagcaatgtaaccaatacatagtatatgaaatataaaagttaatttagattttttgat tagcccaaattaaagaaaaatggtatttaaaacagagactcttcatcctaaaggctaaagcaatacaattttggttaagaaaagaaaaaaaccacaagcg gaaaagaaaacaaaaaaactatattatgatgcaacagcaacacaaagcaacaccttgcacacacacatacaactgtaaacaagtttcttgggactctcta ttttctcttgctgcttgaaccaaacaacaacgatatcccaacgagagcacaacaggtttgattatgtcggaagacaagttttgagagaaaacaaacaat attttataacaaaggagaagacttttggttaggaaaaattggtatggccattacaagacatatgggtcccaattctcatcactctctccaccaccaaaatc ctcctctctctctctcttttactctgttttcatcatctctttctctcgtctctctcaaacccttaaatacactctttctcttcttgttgtctccattctc tctgtgtcatcaagcttcttttttgtgtgggttatttgaaagacactttctctgctggtatcattggagtctagggttttgttattgaca

Promoter Expression Report #110.02

Promoter Tested In: *Arabidopsis thaliana*, WS ecotype
Spatial expression summary:
Flower H Pollen
Observed expression pattern:
T1 mature: Pollen specific expression in mature plants. Expression appears to be prior to gametogenesis.
T2 seedling: No GFP expression observed.
Expected expression pattern: Gametophyte
Selection Criteria: *Arabidopsis* knockout line, gametophytic lethal
Gene: Ca2 + -ATPase 7
GenBank: NM 127860 *Arabidopsis thaliana* potential calcium-transporting ATPase 7, plasma membrane-type (Ca2 + -ATPase, isoform 7) (At2g22950) mRNA, complete cds

Promoter Expression Report #110.02 gi|18400128|ref|NM_127860.1|[18400128]
Source Promoter Organism: *Arabidopsis thaliana*, WS ecotype
Vector: pNewbin4-HAP1-GFP
Marker Type: GFP-ER
Generation Screened: X T1 Mature X T2 Seedling ☐T2 Mature ☐T3 Seedling
T1 Mature Plant Expression    Organs/Tissues screened
Events Screened: n = 6 Events Expressing: n = 3
GFP Expressin Detected

| | |
|---|---|
| X Flower | ☐pedicel ☐receptacle ☐nectary ☐sepal ☐petal ☐filament ☐anther H pollen ☐carpel ☐style ☐papillae ☐vascular ☐epidermis ☐stomata ☐trichome ☐silique |
| ☐ Silique | ☐stigma ☐style ☐carpel ☐septum ☐placentae ☐transmitting tissue ☐vascular ☐epidermis ☐stomata ☐abscission zone ☐ovule |
| ☐ Ovule | Pre-fertilization: ☐inner integument ☐outer integument ☐embryo sac ☐funiculus ☐chalaza ☐micropyle ☐gametophyte Post-fertilization: ☐zygote ☐embryo sack ☐inner integument ☐outer integument ☐endothelium ☐seed coat ☐primordia ☐chalaza ☐micropyle ☐early endosperm ☐mature endosperm ☐embryo |
| ☐ Embryo | ☐suspensor ☐preglobular ☐globular ☐heart ☐torpedo ☐late ☐mature ☐provascular ☐hypophysis ☐radicle ☐cotyledons ☐hypocotyl |
| ☐ Stem | ☐epidermis ☐cortex ☐vascular ☐xylem ☐phloem ☐pith ☐stomata ☐trichome |
| ☐ Leaf | ☐petiole ☐mesophyll ☐vascular ☐epidermis ☐trichome ☐primordia ☐stomata ☐stipule ☐margin |
| ☐ Shoot apical meristem | ☐shoot apical meristem ☐flower primordium |

Promoter Expression Report #110.02

X in the pollen
T2 Seedling Expression    Tissues Screened
Events Screened: n = 3 Events Expressing: n = 0
Seedlings expressing/Seedlings screened
Event-01: 0/6 Event-02: 0/6
Event-03: 0/6
☐ Scheduled
No GFP Expression Detected
Promoter utility
Trait Area:    Reproductive biology
Sub-trait Area:    Yield
Utility:    Modulation of pollen tube growth, gametophytic incompatiblity.

Promoter Expression Report #110.02

Notes: Modulation of breedling biology for example to generate male steriles.
Construct: YP0244
Promoter candidate I.D.: 11768821
cDNA I.D.: 12736016 (OCKHAM3-C)
Lines expressing: YP0244 -01, -02, -10

Sequence (SEQ ID NO: 85):

```
ttgatttgatgtatagttactatttaaagtcttatttgtgaaattttacaaatgttggaaaaaagcattttatggtgctatatttgtcagtttcccttgat
tatatatccttttgaaaagtaatgttttttttatgtgtgtgtattcatgaaccttggaaaaactacaaatcagatcatggtctgttttaggtgaaaattt
agaacacagttacgcaagaaagatatcggtaaattttttgtttctttgaatcgaaattaatcaaaaagtattttccattatataacaacaactaatctctgt
ttttttttttttttttaacaactaatctcttatcaaatgacactacagaatcacgattgtaaatcttcaaaagggcagtctgaaaaaatattcatgagg
atgagattttattcattcatggttgtaagtaatcattatgtaaagtttaggataaggacgttcaaaatcatataaaaaaactctacgaataaagtttatag
tctatcatattgattcatatttcatagaaagttactggaaaacattacacaagtattctcgattttacgagtttgtttagtagtcgcaaaattttatttt
acttttgagtatacgaacccataagctgattttctttccaagttccaataatgatatcatagtgtactcttcatgaatgtttcaagcatataattataacg
ttcataagtaacattctactgcatgtttgttattataaattaactaataatcgaacgtatgagttttggttgagattgttgtgctcacgaaatgaaggact
cggtcaattctaaagcttaaaataagaagctcagatcttaaaactcgctttcgtcttcgtcctccatttaagtttgcgattcttttgctcttctttctctc
tcacattttgtcccaaaacaataaaaagaaacaataatagaaagtgttacagaaaaagaaagaaaactatcattgaagttgggaaggagaaa
```

Promoter Expression Report #111

| | |
|---|---|
| ☐ Silique | ☐stigma ☐style ☐carpel ☐septum ☐placentae ☐transmitting tissue ☐vascular ☐epidermis ☐stomata ☐abscission zone ☐ovule |
| ☐ Ovule | Pre-fertilization: ☐inner integument ☐outer integument ☐embryo sac ☐funiculus ☐chalaza ☐micropyle ☐gametophyte<br>Post-fertilization: ☐zygote ☐embryo sack ☐inner integument ☐outer integument ☐endothelium ☐seed coat ☐primordia |

Promoter Expression Report #111

Promoter Tested In: *Arabidopsis thaliana*, Wassilewskija (WS) ecotype
Spatial expression summary:
Flower L pedicel L epidermis
Stem L epidermis
Hypocotyl H epidermis
Cotyledon H mesophyll H vascular H epidermis H petiole
Rosette Leaf H epidermis H petiole
Primary Root H epidermis
Lateral root H lateral root cap
Observed expression pattern: T1 mature: Low epidermal expression in stem and pedicles near inflorescence apical meristem. T2 seedling: High epidermal expression in cotyledons, petioles of emerging rosette leaves, hypocotyl, and root. Expression observed in vascular and mesophyll cells of cotyledons.
Expected expression pattern: Drought inducible
Selection Criteria: Ceres expression data
Gene: Hypothetical protein
GenBank: NM_102758 *Arabidopsis thaliana* hypothetical protein (At1g30190) mRNA, complete cds
gi|18397396|ref|NM_102758.1|[18397396]
Source Promoter Organism: *Arabidopsis thaliana*, WS ecotype
Vector: pNewbin4-HAP1-GFP
Marker Type: GFP-ER
Generation Screened: X T1 Mature X T2 Seedling ☐T2 Mature ☐T3 Seedling

| Treatment: | Age: | Gen: | Time points: | Events Screened Response: | Response: |
|---|---|---|---|---|---|
| 1. Drought | 7 days | T2 | 3 Hrs Air dry | 2/0 | No |
| 2. Drought | 4 weeks | T2 | 10–12 day No H2O | 2/2 | Yes |

T1 Mature Plant Expression  Organs/Tissues screened
Events Screened: n = 6 Events Expressing: n = 2
GFP Expression Detected
X Flower L pedicel ☐receptacle ☐nectary ☐sepal ☐petal ☐filament ☐anther ☐pollen ☐carpel ☐style ☐papillae ☐vascular L epidermis ☐stomata ☐trichome ☐silique

Promoter Expression Report #111

| | |
|---|---|
| | ☐chalaza ☐micropyle ☐early endosperm ☐mature endosperm ☐embryo |
| ☐ Embryo | ☐suspensor ☐preglobular ☐globular ☐heart ☐torpedo ☐late ☐mature ☐provascular ☐hypophysis ☐radicle ☐cotyledons ☐hypocotyl |
| X Stem | L epidermis ☐cortex ☐vascular ☐xylem ☐phloem ☐pith ☐stomata ☐trichome |
| ☐ Leaf | ☐petiole ☐mesophyll ☐vascular ☐epidermis ☐trichome ☐primordia ☐stomata ☐stipule ☐margin |
| ☐ Shoot apical meristem | ☐shoot apical meristem ☐flower primordium |

X in the Pedicel (Pd) of the inflorescence meristem and the flower
X in the stem
T2 Seedling Expression    Tissues Screened
Events Screened: n = 2 Events Expressing: n = 2
Seedlings expressing/Seedlings screened
Event-04: 6/6
Event-06: 4/6
☐ Scheduled
GFP Expression Detected

| | |
|---|---|
| X Hypocotyl | H epidermis ☐cortex ☐vascular ☐xylem ☐phloem ☐stomata |
| X Cotyledon | H mesophyll H vascular H epidermis ☐margin H petiole ☐stomata ☐hydathode |
| X Rosette Leaf | ☐mesophyll ☐vascular H epidermis ☐trichome H petiole ☐primordia ☐stomata ☐stipule ☐margin ☐hydathode |
| X Primary Root | H epidermis ☐trichoblast ☐atrichoblast ☐cortex ☐endodermis ☐vascular ☐xylem ☐phloem ☐pericycle ☐quiescent ☐columella ☐root cap ☐root hairs |
| X Lateral root | ☐epidermis ☐trichoblast ☐atrichoblast ☐cortex ☐endodermis ☐initials ☐flanking cells ☐vascular H lateral root cap |
| ☐ Shoot apical | ☐Shoot apical meristem |

Promoter Expression Report #111 meristem
X in the Epidermis (Ep) of the Hypocotyl (Hy), Rosette leaf (Rl), Cotyledon (Co), root transition zone, root and lateral root
X in the Mesophyll (Me) and Vasculature (Vs) of the cotyledon
Promoter utility
Trait Area: Water use efficiency
Sub-trait Area: Drought
Utility: Among other uses this promoter sequence can be useful to improve: Modulation growth and development. Modulation of nutrient uptake and loading. Expression of nitrate transports and water pumps. Modulation of drought responses, including modulation of water uptake and transport under drought conditions.
Notes: Endogenous promoter induced under drought.
Construct: YP0286
Promoter candidate I.D.: 11768589
cDNA I.D.: 12669548 (OCKHAM3-C)
Lines expressing: YP0286 -04, -06;

Sequence (SEQ ID NO: 86):

gaaaacaatcataggttacgctattatcatcgaaaggtatgtgatgcatattcccattgaaccagatttccatatattttatttgtaaagtgataatgaat cacaagatgattcaatattaaaaatgggtaactcactttgacgtgtagtacgtggaagaatagttagctatcacgcatacatatatctatgaataagtgtg tatgacataagaaactaaatatttacctaaagtccagttactcatactgatttcatgcatatatgtattatttatttatttttaataaagaagcgattgg tgttttcatagaaatcatgatagattgataggtatttcagttccacaaatctagatctgtgtgctatacatgcatgtattaattttttccccttaaatcat ttcagttgataatattgctctttgttccaactttagaaaaggtatgaaccaacctgacgattaacaagtaaacattaattaatctttatatgagataaaac cgaggatatatatgattgtgttgctgtctattgatgatgtgtcgatattatgcttgttgtaccaatgctcgagccgagcgtgatcgatgccttgacaaact atatatgtttcccgaattaattaagttttgtatcttaattagaataacattttttatacaatgtaatttctcaagcagacaagatatgtatcctatattaat tactatatatgaattgccgggcacctaccaggatgtttcaaatacgagagcccattagtttccacgtaaatcacaatgacgcgacaaaatctagaatcgtg tcaaaactctatcaatacaataatatatatttcaagggcaatttcgacttctcctcaactcaatgattcaacgccatgaatctctatataaaggctacaac accacaaaggatcatcagtcatcacaaccacattaactcttcaccactatctctcaatctctcgtttcatttcttgacgcgtgaaaa

Promoter Expression Report #112

Promoter Tested In: *Arabidopsis thaliana*, Wassilewskija (WS) ecotype
Spatial expression summary:
Flower L anther
Ovule Post-fertilization: L endothelium
Cotyledon H epidermis
Rosette Leaf H trichome
Primary Root H epidermis H root hairs
Observed expression pattern
T1 mature: Low GFP expression in endothelium cells of mature ovules and stomium region of developing and dehiscencing anthers. Endothelium expression is very weak and may not have been detected by standard screen. Only tissue with visible GFP expression is analyzed by confocal microscopy. This may account for the expressing/screened ratio. Not expressed in pollen. T2 seedling: High GFP expression specific to epidermal tissues of cotyledons, root and trichomes of rosette leaves.
Expected expression pattern: Drought-inducible
Selection Criteria: Ceres expression data
Gene: phi-1-related protein
GenBank: NM 125822 *Arabidopsis thaliana* phi-1-related protein (At5g64260) mRNA, complete cds gi|30697983|ref|
NM_125822.2|[30697983] "phosphate-responsive 1 family protein"
Source Promoter Organism: *Arabidopsis thaliana*, WS ecotype
Vector: pNewbin4-HAP1-GFP
Marker Type: GFP-ER Generation Screened: X T1 Mature X T2 Seedling □T2 Mature □T3 Seedling

| Treatment: | Age: | Gen: | Time points: | Events Screened/Response: | Response: |
|---|---|---|---|---|---|
| 1. Drought | 7 days | T2 | 3 Hrs | 2/0 | No |
| 2. Drought | 4 weeks | T2 | 10–12 days no H20 | 2/0 | No |

T1 Mature Plant Expression   Organs/Tissues screened
Events Screened: n = 9 Events Expressing: n = 3
GFP Expression Detected
X Flower □pedicel □receptacle □nectary □sepal □petal □filament L anther □pollen □carpel □style □papillae □vascular □epidermis □stomata □trichome □silique
□ Silique □stigma □style □carpel □septum □placentae □transmitting tissue □vascular □epidermis □stomata □abscission zone □ovule
X Ovule Pre-fertilization: □inner integument □outer integument □embryo sac □funiculus □chalaza □micropyle □gametophyte
Post-fertilization: □zygote □embryo sack □inner integument □outer integument L endothelium □seed coat □primordia □chalaza □micropyle □early endosperm □mature endosperm □embryo
□ Embryo □suspensor □preglobular □globular □heart □torpedo □late □mature □provascular □hypophysis □radicle □cotyledons □hypocotyl
□ Stem □epidermis □cortex □vascular □xylem □phloem □pith □stomata □trichome
□ Leaf □petiole □mesophyll □vascular □epidermis □trichome □primordia □stomata □stipule □margin
□ Shoot □shoot apical meristem □flower primordium
apical meristem
X in the Endothelium (Ed), Stomium region (StR), Pollen (Po) of the developing, mature and dehiscing anther
T2 Seedling Expression    Tissues Screened
Events Screened: n = 9 Events Expressing: n = 3
Seedlings expressing/Seedlings screened
Event-01: 5/6 Event-02: 3/6 Event-03: Not tested
□ Scheduled
GFP Expression Detected
□ Hypocotyl □epidermis □cortex □vascular □xylem □phloem □stomata
X Cotyledon □mesophyll □vascular H epidermis □margin H petiole □stomata □hydathode

Promoter Expression Report #112

| | |
|---|---|
| X Rosette Leaf | ☐mesophyll ☐vascular ☐epidermis H trichome ☐petiole ☐primordia ☐stomata ☐stipule ☐margin ☐hydathode |
| X Primary Root | H epidermis ☐trichoblast ☐atrichoblast ☐cortex ☐endodermis ☐vascular ☐xylem ☐phloem ☐pericycle ☐quiescent ☐columella ☐root cap H root hairs |
| ☐ Lateral root | ☐epidermis ☐trichoblast ☐atrichoblast ☐cortex ☐endodermis ☐initials ☐flanking cells ☐vascular ☐lateral root cap |
| ☐ Shoot apical meristem | ☐shoot apical meristem |

X in the Epidermis (Ep) of the Cotyledon (Co), cotyledon petiole and root
X in the Guard Cells (Gc) of the cotyledon
X in the Hypocotyl (Hy)-root transition zone
X in the Root hair (Rh)
X in the Trichomes (Tc) of the Rosette leaf (Rl)
Induction Screens
1. Drought - No differences observed.
2. Drought - No differences observed.
Promoter utility

| | |
|---|---|
| Trait Area: | PG&D |
| Sub-trait Area: | Yield, Germination and mobilization of nutrient reserves |
| Utility: | Among other uses this promoter sequence can be useful to improve: Modulation seed size and seed shape. Modulation of pollen development and dehiscence and engineering of male sterility. Engineering of plant responses to insects and production and loading of volatiles into trichomes and other epidermal cells. Alteration in loading and transport of metabolites from the soil and environment. Protection against insects and microbes. Modulation of root signaling. Drive CDS that can play a role in shade avoidance. |
| Notes: | Endogenous promoter is up-regulated in far red light. |

Construct: YP0289
Promoter candidate I.D.: 11768596
cDNA I.D.: 12326995
Lines expressing: YP0289 -03; 6/4/03, -10, -13

Seqeunce (SEQ ID NO: 87):

```
atggacttttcttctattatatggtcaaacaattactgctcaatgtatttgcgtatagagcatgtccaataccatgcctcatgatgtgagattgcgaggcg gagtcagagaacgagttaaagtgacgacgttttttgtttttttgggcatagtgtaaagtgatattaaaatttcatggttggcaggtgactgaaaataaa aatgtgtataggatgtgtttatatgctagacggaaaaatagttactcaactaatacagatctttataaagagtatataagtctatggttaatcatgaatgg caatatataagagtagatgagatttatgtttatattgaaacaagggaaagatatgtgtaattgaaacaatggcaaaatatatagtcaaatcaaactggttt ctgataatatatgtgttgaatcaatgtatatcttggtattcaaaaccaaaacaactacaaccaatttctttaaaaaaccagttgatctaataactacattt taatactagtagctattagctgtatttcataatcaatttcttgcattaaaatttgaagtgggttttgcatttaaacttactcggtttgtattaatagactt tcaagattaaaagaaaactactgcattcagagaataaagctatcttactaaacactacttttaaagtttctttttttcacttattaatcttcttatacaaat ggatctgtctctctgcatggcaaaatacttacactaattttattttcttttgtttgataacaaatttatcggctaagcatcacttaaatttaatacacgtta tgaagactaaaaccacgtcacactataagaaccttacaggctgtcaaacacccttccctacccactcacatctctccacgtggcaatctttgatattgaca ccttagccactacagctgtcacactcctctctcggtttcaaaacaacatctctggtataaatacctctgtatatctttataaacccca
```

Promoter Expression Report #116

Promoter Tested In: *Arabidopsis thaliana*, WS ecotype
Spatial expression summary:
Flower L pedicel, L sepal, H carpel, H epidermis, L stomata, H silique
Silique H carpel, H epidermis, L stomata, L abscission zone
Leaf H mesophyll, L vascular, H epidermis
Observed expression pattern:
T1 mature: GFP expression at the base of sepals at abscission zone of developing and mature flowers. High expression specific to carpels of developing and mature siliques. T2 seedling: Weak root hair expression at hypocotyl transition zone observed in 1 in 6 seedlings and in only 1 of 2 events screened.
Expected expression pattern: Flowers, seed, roots.
Selection Criteria: *Arabidopsis* public; containing AP2 DNA binding domain.
Gene: EREBP-2
GenBank: NM 124093 *Arabidopsis thaliana* ethylene responsive element binding factor 2 (EREBP-2) (At5g47220) mRNA, complete cds gi|30695135|ref|NM_124093.2|[30695135]
Source Promoter Organism: *Arabidopsis thaliana* WS
Vector: pNewbin4-HAP1-GFP
Marker Type: GFP-ER
Generation Screened: X T1 Mature X T2 Seedling ☐T2 Mature ☐T3 Seedling
T1 Mature Plant Expression    Organs/Tissues screened
Events Screened: n = 4 Events Expressing: n = 3
GFP Expression Detected

| | |
|---|---|
| X Flower | L pedicel ☐receptacle ☐nectary L sepal ☐petal ☐filament ☐anther ☐pollen H carpel ☐style ☐papillae ☐vascular H epidermis L stomata ☐trichome H silique |
| X Silique | ☐stigma ☐style H carpel ☐septum ☐placentae ☐transmitting tissue ☐vascular H epidermis L stomata L abscission zone ☐ovule |
| ☐ Ovule | Pre-fertilization: ☐inner integument ☐outer integument ☐embryo sack ☐funiculus ☐chalaza ☐micropyle ☐gametophyte |
| | Post-fertilization: ☐zygote ☐embryo sack ☐inner integument ☐outer integument ☐endothelium ☐seed coat ☐primordia ☐chalaza ☐micropyle ☐early endosperm ☐mature endosperm ☐embryo |
| ☐ Embryo | ☐suspensor ☐preglobular ☐globular ☐heart ☐torpedo ☐late ☐mature ☐provascular ☐hypophysis ☐radicle ☐cotyledons ☐hypocotyl |
| ☐ Stem | ☐epidermis ☐cortex ☐vascular ☐xylem ☐phloem ☐pith ☐stomata ☐trichome |
| X Leaf | ☐petiole H mesophyll L vascular H epidermis ☐trichome ☐primordia ☐stomata ☐stipule ☐margin |
| ☐ Shoot apical meristem | ☐Shoot apical meristem ☐Flower primordium |

Promoter Expression Report #116

X in the Abscission zone (Ab), Cortex (Cr), Epidermis (Ep) and Guard cells (Gc) of the flower
X in the Guard cells (Gc) of the pedicle, and pre-fertilized silique
X in the Abscission zone (Ab) and Carpel (Ca) of the mature silique
X in the Cortex (Cr) and Epidermis (Ep) of the carple
X in the Mesophyll (Me), Vasculature (Vs) and Epidermis (Ep) of the leaf
T2 Seedling Expression   Tissues Screened
Events Screened: n = 2 Events Expressing: n = 1
Seedlings expressing/Seedlings screened
Event-01: 0/6
Event-02: 1/6
☐ Scheduled
GFP Expression Detected
☐ Hypocotyl      ☐epidermis ☐cortex ☐vascular ☐xylem ☐phloem ☐stomata
☐ Cotyledon     ☐mesophyll ☐vascular ☐epidermis ☐margin ☐stomata ☐hydathode
☐ Rosette Leaf  ☐mesophyll ☐vascular ☐epidermis ☐trichome ☐petiole ☐primordia ☐stomata ☐stipule ☐margin ☐hydathode
X Primary Root  ☐epidermis ☐trichoblast ☐atrichoblast ☐cortex ☐endodermis ☐vascular ☐xylem ☐phloem ☐pericycle ☐quiescent ☐columella ☐root cap L root hairs
☐ Lateral root  ☐epidermis ☐trichoblast ☐atrichoblast ☐cortex ☐endodermis ☐initials ☐flanking cells ☐vascular ☐lateral root cap
☐ Shoot apical meristem      ☐Shoot apical meristem X in the Root hair (Rh) and Root transition (Rt) of the Hypocotyl (Hy)
Promoter utility
Utility: Increased leaf size and volume, increased source capacity. Tolerance to drought. Improved performance in low nitrogen conditions. Larger siliques, increased seed number. Increased seed yield. Altered dehiscence and seed scatter.
Construct: YP0015
Promoter candidate I.D.: 11768611
cDNA I.D.: 13612380
Lines expressing: YP0015 -03, -04

Sequence (SEQ ID NO: 88):

Promoter Expression Report #118

Silique M ovule
Ovule Pre-fertilization: H outer integument H embryo sack H gametophyte
Post-fertilization: M outer integument H seed coat H embryo
Embryo H suspensor H heart H late H mature L radicle L cotyledons
Stem H epidermis H stomata H trichome
Leaf H stomata
Hypocotyl H epidermis L cortex H stomata
Cotyledon H mesophyll H vascular H epidermis H stomata
Rosette Leaf H stomata
Primary Root H cortex
Observed expression pattern:
T1 mature: Expressed in pollen cells throughout development. Expression visible during pollination when dehisced pollen attaches to stigma resulting in extension of the cell wall to establish an attachment site or "foot". Once attached, pollen is hydrated and germination of pollen tubes follows through the stigma at the attachment site. These processes are likely targets in regulation of self-incompatibility and species-specific pollen recognition. No expression is observed after hydration.
Expressed in egg sack of pre-fertilized ovules, inner integument, endosperm, heart stage embryo and suspensor cells of developing ovules. High specific expression in and epidermal cell files flanking trichomes of stem and guard cells throughout mature plant. T2 seedling: High expression in epidermal and guard cells throughout seedling. High expression epidermal, vascular, and mesophyll cells of cotyledons. Not observed in leaf primordia. High expression specific to cortical cells of root.
Expected expression pattern: Induced prior to cell division and usually associated with dividing cells.
Selection Criteria: Ceres BLAST search homology; CDC2-like protein
Gene: putative protein kinase /note="similar to cyclin-dependent kinase cdc2MsE [Medicago sativa]
GenBank: NM 125756 Arabidopsis thaliana protein kinase, putative (At5g63610) mRNA, complete cds gi|30697871|ref| NM_125756.2|[30697871]
Source Promoter Organism: Arabidopsis thaliana WS
Vector: pNewbin4-HAP1-GFP
Marker Type: GFP-ER
Generation Screened: X T1 Mature X T2 Seedling ☐T2 Mature ☐T3 Seedling
T1 Mature Plant Expression    Organs/Tissues screened
Events Screened: n = 5 Events Expressing: n = 2
☐ No GFP Expression Detected

Promoter Expression Report #118

Promoter Tested In: *Arabidopsis thaliana*, WS ecotype
Spatial expression summary:
Flower H anther H pollen L vascular H stomata X Flower   ☐pedicel ☐receptacle ☐nectary ☐sepal ☐petal ☐filament
H anther H pollen ☐carpel ☐style ☐papillae L vascular ☐epidermis H stomata ☐trichome ☐silique

```
ttgagccttattgttgttattgacttttagccaatagaaagagatggaaattcaataattatccacaaaattccaaatcattggtgtacaaaaagatctaa ggctgttatatttccaaaaagaaagaaaagaaatgcaacaaatatggattaaactgtggtttgtaaattgagctttgcatgaaaactttatcactatgat ttcactactccatatttattgactaaagtggcactaatgaatttcttaatcatgaaatcttgtatcaaaaagtactaaaataaacatgacattggcaatta ggaaaattctaaattagaaattagtaaaaatgaaaggtgaaagggaaagatgatgatatgaattggttggtgaccaggagaaatgtatcccgattttgca gacactttcagtgtccccattcatataattatggcccacctcgttaagattttcattcaccaccataacaagatctaagcttagatttcatgtaattaaa catataatatacttgccaatactatctaataaagtatacttaagcaaaaattattactctagtgtaaggcgatgaaatataagtttagttgaaaatttatg tcgatataacaaagtataatgaattaagaccttggttttcgattaacaaactaattaaacactagttttgcctaataaaaccgggaatcgtattcaaaacc gaacgacaaaacaagggacaagttgagagacaaaaccaaatcagcatctttcttccagaaatgtcatgaccacatgacgtcatcttgaccttcttcattg tgatatctgtggataaagcgcacgtgtttaattcacgaaccttcgtagtaacgaaaaatccacaactttcatatttttaattacccactaaactaaaaca aatttggaaaaacatgaaaaacttttcttttttccaggttcgtgaacctcgtaccctctatataaacctctta
```

Promoter Expression Report #118

| | |
|---|---|
| X Silique | ☐stigma ☐style ☐carpel ☐septum ☐placentae ☐transmitting tissue ☐vascular ☐epidermis ☐stomata ☐abscission zone M ovule |
| X Ovule | Pre-fertilization: ☐inner integument H outer integument H embryo sack ☐funiculus ☐chalaza ☐micropyle H gametophyte<br>Post-fertilization: ☐zygote ☐embryo sack ☐inner integument M outer integument ☐endothelium H seed coat ☐primordia ☐chalaza ☐micropyle ☐early endosperm ☐mature endosperm H embryo |
| X Embryo | H suspensor ☐preglobular ☐globular H heart ☐torpedo H late H mature ☐provascular ☐hypophysis L radicle L cotyledons |
| X Stem | H epidermis ☐cortex ☐vascular ☐xylem ☐phloem ☐pith H stomata H trichome |
| X Leaf | ☐petiole ☐mesophyll ☐vascular ☐epidermis ☐trichome ☐primordia H stomata ☐stipule ☐margin |
| ☐ Shoot apical meristem | ☐Shoot apical meristem ☐Flower primordium |

X in the Vascular (Vs) of the Petal (Pe) in immature and mature flowers
X in the Guard cells (Gc) of immature flowers
X in the anther and pollen mother cells
X in the Pollen (Po) during attachment ("foot"), adhesion and hydration
X in the Seed coat (Sc) of theovule
X in the mature Embryo (Em)
X in the heart stage Embryo (Em) of the ovule
X in the Embryo sack (Es) of the pre-fertilized ovule
X in the Guard cells (Gc), Trichomes (Tc) and Epidermis (Ep) of the stem
X in the Guard cells (Gc) of the leaf
T2 Seedling Expression    Tissues Screened
Events Screened: n = 2 Events Expressing: n = 2
Seedlings expressing/Seedlings screened
Event-01: 5/5
Event-02: 1/5
☐ Scheduled
GFP Expression Detected

| | |
|---|---|
| X Hypocotyl | H epidermis L cortex ☐vascular ☐xylem ☐phloem H stomata |
| X Cotyledon | H mesophyll H vascular H epidermis ☐margin H stomata ☐hydathode |
| ☐ Rosette Leaf | ☐mesophyll ☐vascular ☐epidermis ☐trichome ☐petiole ☐primordia H stomata ☐stipule ☐margin ☐hydathode |
| X Primary Root | ☐epidermis ☐trichoblast ☐atrichoblast H cortex ☐endodermis ☐vascular ☐xylem ☐phloem ☐pericycle ☐quiescent ☐columella ☐root cap ☐root hairs |
| ☐ Lateral root | ☐epidermis ☐trichoblast ☐atrichoblast ☐cortex ☐endodermis ☐initials ☐flanking cells ☐vascular ☐lateral root cap |
| ☐ Shoot apical meristem | ☐Shoot apical meristem |

X in the Epidermis (Ep) and Guard Cells (Gc) of the hypocotyl apex
X in the Guard cells (Gc), Vascular (Vs) and Mesophyll (Me) of the cotyledon
X in the Epidermis (Ep) and Cortex (Cr) of the root transition zone
X in the Cortex (Cr) and Nucleus (Nu) of the root Promoter utility
Trait Area:      SSR
Sub-trait Area:  Sink strength, embryo size
Utility:         Imprint modulation through male, larger (heavier) seeds, smaller (lighter) seeds. Male sterility and altered breeding barriers. Altered pollen composition. Altered fertility. Resistance to drought.
Construct: YP0230
Promoter candidate I.D.: 13148201
cDNA I.D.: 12676237
Lines expressing: YP0230 -02, -03 (9/08/03)

Sequence (SEQ ID NO: 89):

```
aatcattaaatctttgatgagaaatatccaatctactaatgtatatcgatgatttaaatgaaattacttatttgaacacaaaaataaatgaatttactaat aaataaatagcgtagttgcgagcaagtggctaaaaaaattacaaatctagtttccattctcagcggcggggtgcttggaacgtcaccgttttttggaaaac gcaatcttcctcccttccgggacgtctcaccggaattttctcgcttttgtctactcctccatctccgaggttctccaagctcagctcctcttcccatca ttcatccgaccgccttatccggtcagatcctttacgtatttctattttcctgatcgtcgattttgagaaatgtaaaacagatcgtataaggcctcgaag tttttaatttgaaagtggtatcgaaattttttggtctttgattaggttagggcaccgtagctctgggtattgaatttgtagggttttcctctggttattgg tctttggagcttggtaatttctgctgaattgattgatcccttttccatcttttgaagtaaagtctcgagctttcgtgtctcgatgtagatgaattctattt tgaatatgagatttgataagacgtcaattgctgataatttggagtctttgtgtctgaatttgttcatatgaagttttctgagggatgtgaatttattgtc tgctaattttgaaacgttccttttggaatttggtttgtgaggagtcctagatcttttctgttaagtttcttgcttgtaagttttctggatcacttgattg agtctagaatctagatagattacatgttcggtttgattcctttggctgattttccaaagtttttgttcaaatttcaggagaactacaaagagggaaaccaaga tggttttgttttgttagactctaccccttttccgattcacatggtaaggacattgaggtag
```

| Promoter Expression Report #119 | |
|---|---|
| Promoter Tested In: | *Arabidopsis thaliana*, WS ecotype |
| Spatial expression summary: | |
| Silique | H ovule |
| Ovule | Pre-fertilization: H outer integument<br>Post-fertilization: H outer integument, H seed coat |
| Observed expression pattern: | |
| T1 Mature: | GFP expressed in outer integument early in ovule development through seed coat of mature seeds. |
| T2 Seedling: | No expression observed. |
| Expected expression pattern: | Expressed in ovules and different parts of seeds |
| Selection Criteria: | Greater than 50× up in pi ovule micro-array |
| Gene: | "hypothetical protein/product = "expressed protein" |
| GenBank: | NM_117365 *Arabidopsis thaliana* expressed protein (At4g12960) mRNA, complete cds gi\|30682287\|ref\| NM_117365.2[30682287] |
| Source Promoter Organism: | *Arabidopsis thaliana* WS |
| Vector: | pNewbin4-HAP1-GFP |
| Marker Type: | GFP-ER |
| Generation Screened: | XT1 Mature XT2 Seedling □T2 Mature □T3 Seedling |
| T1 Mature Plant Expression Organs/Tissues screened | |
| Events Screened: n = 2 Events Expressing: n = 2 | |
| GFP Expression Detected | |
| □Flower | □pedicel □receptacle □nectary □sepal □petal □filament □anther □pollen □carpel □style □papillae □vascular □epidermis □stomata □trichome □silique |
| X Silique | □stigma □style □carpel □septum □placentae □transmitting tissue □vascular □epidermis □stomata □abscission zone H ovule |
| X Ovule | Pre-fertilization: □inner integument H outer integument □embryo sack □funiculus □chalaza □micropyle □gametophyte<br>Post-fertilization: □zygote □embryo sack □inner integument H outer integument □endothelium H seed coat □primordia □chalaza □micropyle □early endosperm □mature endosperm □embryo |
| □Embryo | □suspensor □preglobular □globular □heart □torpedo □late □mature □provascular □hypophysis □radicle □cotyledons □hypocotyl |
| □Stem | □epidermis □cortex □vascular □xylem □phloem □pith □stomata □trichome |
| □Leaf | □petiole □mesophyll □vascular □epidermis □trichome □primordia □stomata □stipule □margin |
| □Shoot apical meristem | □Shoot apical meristem □Flower primordium |

X in the ovules of the pre-fertilized and fertilized silique
X in the Outer integument (Oi) of the fertilized ovule
X in the maturing seed
X in the Seed coat (Sc) of the mature seed T2 Seedling Expression Tissues Screened Events Screened: n = 2 Events Expressing: n = 0
Seedlings expressing/Seedlings screened Event-01: 0/6
Event-02: 0/6
□Scheduled
No GFP Expression Detected

| | |
|---|---|
| □Hypocotyl | □epidermis □cortex □vascular □xylem □phloem □stomata |
| □Cotyledon | □mesophyll □vascular □epidermis □margin □stomata □hydathode |
| □Rosette Leaf | □mesophyll □vascular □epidermis □trichome □petiole □primordia □stomata □stipule □margin □hydathode |
| □Primary Root | □epidermis □trichoblast □atrichoblast □cortex □endodermis □vascular □xylem □phloem □pericycle □quiescent □columella □root cap □root hairs |
| □Lateral root | □epidermis □trichoblast □atrichoblast □cortex □endodermis □initials □flanking cells □vascular □lateral root cap |
| □Shoot apical meristem | □Shoot apical meristem |

Promoter utility

| | |
|---|---|
| Trait Area: | Nutrition/Composition, SSR |
| Sub-trait Area: | Nitrogen use efficiency, seed size |
| Utility: | Seed size determination. Increased seed size. Altered seed composition. Tolerance of seeds to desiccation. Resistance of seeds to abortion. Increase sink strength by expression of A.A. transporters. |
| Construct: | YP0120 |
| Promoter candidate I.D: | 11768656 |
| cDNA I.D: | 12370095 |
| Lines expressing: | YP0120-01, -02 |

Sequence (SEQ ID NO: 90):

```
tagttttgatttaatctacgttttcttaatcataaatgggtaattattagttttgcaaaatcaaaatccaaaaattgttctaaacactgcaaccattt aaggcctatatcactcagaaaatttctggtgggagaactaatcgtttgtcctttctaaatctcacatattagaatttagaattagtgtgctacataagaat attagttcagctcggaacaactatttttggtaaaacagagaacttaaacaaatgcattatttatcaacatgcatttgaattgaatataaaatttcata attgtaaagacataaattacataaaattttacatgaaaaatagatatagaaagaaatgaaactaactgatgatatgctctctaaatttttaatctcat aacaagaattcaaattaattagttcatattttggttaatataacatttacctgtctaagttggaactttcattttttctgttttgtttagtcagtattc ttaatgtgaaacggaaagttgaatttattcaaacttaaattcaatagcattaattaaaggcgaaagctattatctctacatgtggttcaaactagacatcc aatttaattagcttattgacgttgaaatgttttccaaaactactatagtttggcaatttgaaagatgcatcagaactactcagacaggtaaaagtagaacc tctagctgtgtgaattgtatgttagtccataaagaacatcttgtaaacttcatacttaagatatatattacaatatatacttgaatggtagataaaaacga
```

-continued ttagtctgattgctagcatactcacaactatttggaaatgagtaagatattggcattctagagttactactatggagacaaaagtcgaataaaagagacct cacgtgaaaatgttacgagctagtaaaaaaagcatttacactaacggtaaaaaaagtatctataaatgtttacacaaggtagtagtcatt

| Promoter Expression Report #120 | |
|---|---|
| Promoter Tested In: | *Arabidopsis thaliana*, WS ecotype |
| Spatial expression summary: | |
| Flower | H sepal |
| Rosette Leaf | H epidermis H stomata |
| Observed expression pattern: | |
| T1 Mature: | High epidermal expression in petals of developing and mature flowers. Not detected in other organs. |
| T2 Seedlings: | High expression in epidermal cells of initial leaf primordia. |
| Expected expression pattern: | Emerging true leaves. |
| Selection Criteria: | Literature; Cho H T, Cosgrove D J Altered expression of expansin modulates leaf growth and pedicel abscission in *Arabidopsis thaliana*. Proc Natl Acad Sci USA. Aug. 15, 2000; 97 (17): 9783–8. |
| Gene: | product = "expansin, putative (EXP10)" |
| GenBank: | NM_102440 *Arabidopsis thaliana* expansin, putative (EXP10) (At1g26770) mRNA, complete cds gi\|30689629\|ref\| NM_102440.2\|[30689629] |
| Source Promoter Organism: | *Arabidopsis thaliana* WS |
| Vector: | pNewbin4-HAP1-GFP |
| Marker Type: | GFP-ER |
| Generation Screened: | XT1 Mature XT2 Seedling ☐T2 Mature ☐T3 Seedling |

T1 Mature Plant Expression Organs/Tissues screened

Events Screened: n = 2   Events Expressing: n = 2
GFP Expression Detected

| X Flower | ☐pedicel ☐receptacle ☐nectary H sepal ☐petal ☐filament ☐anther ☐pollen ☐carpel ☐style ☐papillae ☐vascular ☐epidermis ☐stomata ☐trichome ☐silique |
|---|---|
| ☐Silique | ☐stigma ☐style ☐carpel ☐septum ☐placentae ☐transmitting tissue ☐vascular ☐epidermis ☐stomata ☐abscission zone ☐ovule |
| ☐Ovule | Pre-fertilization: ☐inner integument ☐outer integument ☐embryo sack ☐funiculus ☐chalaza ☐micropyle ☐gametophyte Post-fertilization: ☐zygote ☐embryo sack ☐inner integument ☐outer integument ☐endothelium ☐seed coat ☐primordia ☐chalaza ☐micropyle ☐early endosperm ☐mature endosperm ☐embryo |
| ☐Embryo | ☐suspensor ☐preglobular ☐globular ☐heart ☐torpedo ☐late ☐mature ☐provascular ☐hypophysis ☐radicle ☐cotyledons ☐hypocotyl |
| ☐Stem | ☐epidermis ☐cortex ☐vascular ☐xylem ☐phloem ☐pith ☐stomata ☐trichome |
| ☐Leaf | ☐petiole ☐mesophyll ☐vascular ☐epidermis ☐trichome ☐primordia ☐stomata ☐stipule ☐margin |
| ☐Shoot apical meristem | ☐Shoot apical meristem ☐Flower primordium |

X in the Epidermis (☐p) and Vasculature (Vs) of the Petal (Pe)

| Promoter Expression Report #120 | |
|---|---|
| T2 Seedling Expression Tissues Screened | |
| Events Screened: n = 2   Events Expressing: n = 2 | |
| Seedlings expressing/Seedlings screened | |
| Event-01: | 6/6 |
| Event-02: | 3/6 |
| ☐Scheduled | |
| GFP Expression Detected | |
| ☐Hypocotyl | ☐epidermis ☐cortex ☐vascular ☐xylem ☐phloem ☐stomata |
| ☐Cotyledon | ☐mesophyll ☐vascular ☐epidermis ☐margin ☐stomata ☐hydathode |
| X Rosette Leaf | ☐mesophyll ☐vascular H epidermis ☐trichome ☐petiole ☐primordia H stomata ☐stipule ☐margin ☐hydathode |
| ☐Primary Root | ☐epidermis ☐trichoblast ☐atrichoblast ☐cortex ☐endodermis ☐vascular ☐xylem ☐phloem ☐pericycle ☐quiescent ☐columella ☐root cap ☐root hairs |
| ☐Lateral root | ☐epidermis ☐trichoblast ☐atrichoblast ☐cortex ☐endodermis ☐initials ☐flanking cells ☐vascular ☐lateral root cap |
| ☐Shoot apical meristem | ☐Shoot apical meristem |

X in the Epidermis (Ep) and Guard cells (Gc) of the rosette leaf primordia
Promoter utility

| Trait Area: | PG&D, SSR |
|---|---|
| Sub-trait Area: | Organ size, cell number, shape, source strength |
| Utility: | Leaf size and photosynthetic capacity. Increased source strength. Increased sucrose loading. Increased leaf expansion, resulting in improved seedling stress tolerance. Modulate size of organs, young leaf specific exp. |
| Notes: | Expansions are thought to hydrolyte non-covalent bonds with cell wall structural polysaccharides, allowing turgor-driven slippage and increase in cell volume. |
| Construct: | YP0261 |
| Promoter candidate I.D: | 11768750 |
| cDNA I.D: | 12385291 |
| Lines expressing: | YP0261 -01, -03 |

Sequence (SEQ ID NO: 91):

ttgtaaattagtttatcgtagaagtaccaaatcaagtgattcaatggttaaattaaggtattaagttacatttgatatttaaaagtatccagaccttcatt atagctcataagggttaaaattttgtcgttcttttgtatattcatggcaagctctaattcatgactaagtcacatttttcaaatatgttttagttttac ttatgttggtaattagtggatttatagttaagttaaaaagttggcgagttctagctttgaaactcatttagaaatatatatatatatatatatattcaatt ttagtaaattgttaatctattctaatggtgtaactgtaacaaatgagaatgaaaaaaatatactattgtaataaaacccacacaacacattactataat aagttaaacttcttttttataggcgcctggaaaaaaagaaaagcaacaagagggstgtgaggacgcatcaccnggtttcgtagcacacatgtgcatttg tctctttgcttttcggttttttcttgccaatcaatttattttgttcctcagaaaaagaaatctaaaccaaaatatatattataacctcatttaata aacaacaaaatgtttgttgaaaaaaaaaagttttatttatcttgaccttatttctttgaagaaaataaagcttggttattaaagaagtccaagttagt tgccaccatcagtggcataacggtaaattaaagccaacttcctctaactaaagttttctataaattcaaccactcacctcccactctaaacccaacaaca taatttcacatatctctctttctttctcttgaaggaaagacgaagatctccaagtcccaagtacgtaactactttctccatctacattcaattgtttctcc ttaatttctctagtacatatttacttgtgctataagtaattgattttatatcacccatgtgcaggttgttaacacaaga

| Promoter Expression Report #121 | |
|---|---|
| Promoter Tested In: | *Arabidopsis thaliana*, WS ecotype |
| Spatial expression summary: | |
| Flower | H pedicel H receptacle H filament |
|  | H anther H carpel H vascular H silique |
| Silique | H vascular |
| Stem | H vascular |
| Leaf | H vascular |
| Hypocotyl | L epidermis H vascular |
| Cotyledon | H vascular L epidermis |
| Rosette Leaf | H epidermis |
| Primary Root | H cortex H root cap |
| Observed expression pattern: | |
| T1 Mature: | High GFP expression in vasculature of stem and leaves, also pedicles, siliques and stamen of flowers. Not detected in sepals and petals. Expression in silique specific to medial vasculature. |
| T2 Seedling: | High GFP expression in hypocotyl and cotyledon vasculature and cortex of root. Not observed in root vasculature. |
| Expected expression pattern: | Stem and root elongation zones. |
| Selection Criteria: | Hanzawa Y, Takahashi T, Michael A J, Burtin D, Lone D, Pineiro M, Coupland G, Komeda Y. ACAULIS5, an *Arabidopsis* gene required for stem elongation, encodes a spermine synthase. EMBO J. Aug. 15, 2000; 19 (16): 4248–56. |
| Gene: | *Arabidopsis* ACAULIS5 (ACL5) |
| GenBank: | NM_121958 *Arabidopsis thaliana* spermine synthase (ACL5) (At5g19530) mRNA, complete cds gi|30687363|ref| NM_121958.2|[30687363] |
| Source Promoter Organism: | *Arabidopsis thaliana* WS |
| Vector: | pNewbin4-HAP1-GFP |
| Marker Type: | GFP-ER |
| Generation Screened: | XT1 Mature XT2 Seedling ☐T2 Mature ☐T3 Seedling |
| T1 Mature Plant Expression Organs/Tissues screened | |
| Events Screened: n = 3  Events Expressing: n = 1 | |

-continued

| Promoter Expression Report #121 | |
|---|---|
| GFP Expression Detected | |
| X Flower | H pedicel H receptacle ☐nectary ☐sepal ☐petal H filament H anther ☐pollen H carpel ☐style ☐papillae H vascular ☐epidermis ☐stomata ☐trichome H silique |
| X Silique | ☐stigma ☐style ☐carpel ☐septum ☐placentae ☐transmitting tissue H vascular ☐epidermis ☐stomata ☐abscission zone ☐ovule |
| ☐Ovule | Pre-fertilization: ☐inner integument ☐outer integument ☐embryo sack ☐funiculus ☐chalaza ☐micropyle ☐gametophyte Post-fertilization: ☐zygote ☐embryo sack ☐inner integument ☐outer integument ☐endothelium ☐seed coat ☐primordia ☐chalaza ☐micropyle ☐early endosperm ☐mature endosperm ☐embryo |
| ☐Embryo | ☐suspensor ☐preglobular ☐globular ☐heart ☐torpedo ☐late ☐mature ☐provascular ☐hypophysis ? radicle ☐cotyledons ☐hypocotyl |
| X Stem | ☐epidermis ☐cortex H vascular ☐xylem ☐phloem ☐pith ☐stomata ☐trichome |
| X Leaf | ☐petiole ☐mesophyll H vascular ☐epidermis ☐trichome ☐primordia ☐stomata ☐stipule ☐margin |
| ☐Shoot apical meristem | ☐Shoot apical meristem ☐Flower primordium |
| X in the Vasculature (Vs) of the inflorescence meristem and the Pedicel (Pd) and Receptacle (Rc) of the flower | |
| X in the Medial vasculature (Mv) of the leaf | |
| X in the stem | |
| X in the Medial vasculature (Mv) of the immature and mature silique | |
| X in the Vasculature (Vs) of the Anther (An) | |
| Abscission zone (Az), Filament (Fi), Carpel (Ca), Filament (Fi), Funiculus (Fn), Ovule (Ov), Placenta (Pl), Root cap (Rc), Sepal (Se), Silique (Si), | |
| T2 Seedling Expression Tissues Screened | |
| Events Screened: n = 3  Events Expressing: n = 3 | |

Promoter Expression Report #121

Seedlings expressing/Seedlings screened

Event-01: 4/6
Event-02: 1/6
Event-03: 2/6
☐Scheduled
GFP Expression Detected

| | |
|---|---|
| X Hypocotyl | L epidermis ☐cortex H vascular ☐xylem ☐phloem ☐stomata |
| X Cotyledon | ☐mesophyll H vascular L epidermis ☐margin ☐stomata ☐hydathode |
| X Rosette Leaf | ☐mesophyll ☐vascular H epidermis ☐trichome ☐petiole ☐primordia ☐stomata ☐stipule ☐margin ☐hydathode |
| X Primary Root | ☐epidermis ☐trichoblast ☐atrichoblast H cortex ☐endodermis ☐vascular ☐xylem ☐phloem ☐pericycle ☐quiescent ☐columella H root cap ☐root hairs |
| ☐Lateral root | ☐epidermis ☐trichoblast ☐atrichoblast ☐cortex ☐endodermis ☐initials ☐flanking cells ☐vascular ☐lateral root cap |
| ☐Shoot apical meristem | ☐Shoot apical meristem |

X in the Epidermis (Ep) of the Rosette leaf (Rl) of the seeding
X in the Cortex (Cr) of the root
X in the vasculature of the seedling and cotyledon
X in the root tip
Promoter utility

| | |
|---|---|
| Trait Area: | Nutrition |
| Sub-trait Area: | Low nitrogen tolerance |
| Utility: | Translocation to the flower, seed fill. Sucrose loading and transport. Improved source capacity, lending to larger plant organs, larger plants, Increased biomass, increased yield. Improved root growth and soil penetration. Resistance to drought, improved uptake of nitrogen and phosphate. Modify nitrate uptake and translocation to Xylem |
| Notes: | Spermine is an alkaloid. |
| Construct: | YP0263 |
| Promoter candidate I.D: | 11768752 |
| cDNA I.D: | 12640578 |
| Lines expressing: | YP0263 -10, -11, -12 |

Promoter Expression Report #123

| | |
|---|---|
| Promoter Tested In: | *Arabidopsis thaliana*, WS ecotype |

Spatial expression summary:

| | |
|---|---|
| Flower | M stomata |
| Silique | M stomata |
| Ovule | Post-fertilization: L embryo |
| Embryo | L provascular, L cotyledons |
| Primary Root | L epidermis, L xylem |

Observed expression pattern:

| | |
|---|---|
| T1 mature: | Strong expression in embryonic vascular tissue of cotyledons. Weak guard cell expression in flower pedicle and silique. |
| T2 seedling: | Weak degrading root epidermis expression near transition zone. Weak root vascular expression in elongation zone. Expression in very thin cell layer appears to be xylem. |
| Expected expression pattern: | root, flowers, ovules, young silique |
| Selection Criteria: | *Arabidopsis* Two component line CS9135. |
| Gene: | Hypothetical protein containing helix-loop-helix DNA binding domain. |
| GenBank: | NM_116493 *Arabidopsis thaliana* bHLH protein (At4g02590) mRNA, complete cds gi\|30679204\|ref\| NM_116493.2\|[30679204] |
| Source Promoter Organism: | *Arabidopsis thaliana* WS |
| Vector: | pNewbin4-HAP1-GFP |
| Marker Type: | GFP-ER |
| Generation Screened: | XT1 Mature XT2 Seedling ☐T2 Mature ☐T3 Seedling |

T1 Mature Plant Expression Organs/Tissues screened

Events Screened:  n = 3   Events Expressing:   n = 2
GFP Expression Detected

| | |
|---|---|
| X Flower | ☐pedicel ☐receptacle ☐nectary ☐sepal ☐petal ☐filament ☐anther ☐pollen ☐carpel ☐style ☐papillac ☐vascular ☐epidermis M stomata ☐trichome ☐silique |
| X Silique | ☐stigma ☐style ☐carpel ☐septum ☐placentae ☐transmitting tissue ☐vascular ☐epidermis M stomata ☐abscission zone ☐ovule |

Sequence (SEQ ID NO: 92):

```
atctagctgtggattccaccaaaattctggcagggccatgatctaaaaactgagactgcgcgtgttgttttgcagtgatttgtatttcatatttgcaccat cctacacagtccacttggtatcgtaaccaaacataaggagaacctaattacattattgttttaatttcgtcaaactggttttttaccttttagttacatagt tgattcttcatttgttttagtagttatggagcacaataatgtgcaacaaagaaagatcatagtggattaatatgttgagaggtcagaaattcttggttaac aaaaaaagttacaaggactgagattttgggtgggagaaagccatagcttttaaaacatgattgaacttaaaagtgatgttatggtttgaggggaaaaagg ttgatgtcaactaagatagttgaagtaatgtcttaaactaaagtaaaccaccggtccaaccgtggtccggaagcatctctggtatgatttatcctaaaaat caaaatagtagaaacatactttaaatatatacattgatcggacgaaaattgtaaactagtatagtttcaaaaactagttgaacaggttatgtaccttaaac atttatttcaaacttaaacactaaagaacatatatgaatagaagtttatataaattactatatatctaccataaatctcttataattatgatgtcacgatg aggaagtgttgaaacgttaaaatgccaaaatataagcatgcgacggaattttggcagaagattgtagagttgtaatctgtcgcaatcattactcgtgctag catttttcattttccttcatttgtggataacgcacgatataacattctacacaccaacaagattctataaaaacgcaaaggttgtctccatagaatatcg tc
```

-continued

Promoter Expression Report #123

| | |
|---|---|
| X Ovule | Pre-fertilization: ☐inner integument ☐outer integument ☐embryo sack ☐funiculus ☐chalaza ☐micropyle ☐gametophyte<br>Post-fertilization: ☐zygote ☐embryo sack ☐inner integument ☐outer integument ☐endothelium ☐seed coat ☐primordia ☐chalaza ☐micropyle ☐early endosperm ☐mature endosperm L embryo |
| X Embryo | ☐suspensor ☐preglobular ☐globular ☐heart ☐torpedo ☐late ☐mature L provascular ☐hypophysis ☐radicle L cotyledons |
| L Stem | ☐epidermis ☐cortex ☐vascular ☐xylem ☐phloem ☐pith ☐stomata ☐trichome |
| ☐Leaf | ☐petiole ☐mesophyll ☐vascular ☐epidermis ☐trichome ☐primordia ☐stomata ☐stipule ☐margin |
| ☐Shoot apical meristem | ☐Shoot apical meristem ☐Flower primordium |

X in the Guard cells (Gc) of the flower, pedicel and silique
X in the Vasculature (Vs) of the mature embryo and the cotyledons T2 Seedling Expression Tissues Screened Events Screened:  n = 2   Events Expressing:   n = 2
Seedlings expressing/Seedlings screened Event-01:  2/4
Event-02:  1/4
☐Scheduled
GFP Expression Detected

| | |
|---|---|
| ☐Hypocotyl | ☐epidermis ☐cortex ☐vascular ☐xylem ☐phloem ☐stomata |
| ☐Cotyledon | ☐mesophyll ☐vascular ☐epidermis ☐margin ☐stomata ☐hydathode |
| ☐Rosette Leaf | ☐mesophyll ☐vascular ☐epidermis ☐trichome ☐petiole ☐primordia ☐stomata ☐stipule ☐margin ☐hydathode |
| X Primary Root | L epidermis ☐trichoblast ☐atrichoblast ☐cortex ☐endodermis ☐vascular L xylem ☐phloem ☐pericycle ☐quiescent ☐columella ☐root cap ☐root hairs |
| ☐Lateral root | ☐epidennis ☐trichoblast ☐atrichoblast ☐cortex ☐endodermis ☐initials ☐flanking cells ☐vascular ☐lateral root cap |
| ☐Shoot apical meristem | ☐Shoot apical meristem |

X in the Root hair (Rh) of the Hypocotyl (Hy) and the root transition zone
X in the Epidermis (Ep) of the upper and lower Root (Rt)
X in the Vascular (Vs) of the lower root Promoter utility

| | |
|---|---|
| Trait Area: | SSR |
| Sub-trait Area: | Sink strength enhancement and size. |
| Utility: | Translocation to cotyledons, seed fill. Increased embryo and seed weight. Altered embryo and seed composition. Improved seedling vigor, seedling resistance to drought, cold, cold/wet conditions. |
| Construct: | YP0003 |
| Promoter candidate ID: | 13148213 |
| cDNA I.D: | 12649228 |
| Lines expressing: | YP0003 -04, -06 |

Sequence (SEQ ID NO: 93):

```
tggatctgctagatatatgagaacgaaagaaccagaagctattagaggcgggaggagatatgtggggatgatttcagtgcaattccacgacgcaccattt ccactttcgtaacacctaaacgaccgcttcggccgtataaaatcgcaaatgtttggtctcagtgtattttccaatttccaaatacatcaattcaaatta tataatatctagtggcaattataagtatatcatatattttcaaaattaattaaaaagattactaaattatgtttgactacaactattataatagttaaaa acataaacaaaaacaaagaaactattttaataaaaaaatcaagtaaacattaaaacataagcaaaaaataatgttaaagaaattattaattattaattta ctaataattaatacctctataaattaattgttagaggtttaacgtaatttataaggaaaactaaagaagactttaacccataaagaaaaaacaaagact gaattgaaggcccatatttagaagaagagaaagaagacccaaatatgatataaaatccagcccatttatatattttattttgtttctggaaggaaaata agaaaatggcaaaaacgaaataatctgaaaaagtaaggtcttttaccaaaaaggatattttttttataaacagagcataaagttttcacttttcttctgc tcctttctcgtctctgtcttcttcgtcctcattcgttttaaagcatcaaaatttcatcaacccaaaatagattaaaaaaatctgtagctttcgcatgtaa atctctctttgaaggttcctaactcgttaatcgtaactcacagtgactcgttcgagtcaaagt
```

| Promoter Expression Report #125 | |
|---|---|
| Promoter Tested In: | *Arabidopsis thaliana*, Wassilewskija (WS) ecotype |
| Spatial expression summary: | |
| Flower | H pedicel H petal H epidermis |
| Silique | H stigma L style L carpel L septum L epidermis |
| Ovule | Post-fertilization: H outer integument |
| Stem | H epidermis H stomata |
| Hypocotyl | H epidermis |
| Cotyledon | H epidermis |
| Rosette Leaf | H epidermis H trichome |
| Observed expression pattern: | |
| T1 mature: | GFP expression specific to epidermal cell types. High GFP expression in epidermis of stem decreasing toward pedicles and inflorescence apex. In the flower, high expression observed in epidermal cells of petals and stigma, and lower expression in carpels. High expression in outer integuments of maturing ovules. High expression throughout epidermal cells of mature lower stem. |
| T2 seedling: | GFP expression specific to epidermal cell types. High expression in epidermis of hypocotyl, cotyledon, and trichomes of rosette leaves. Not detected in root. |
| Expected expression pattern: | Drought inducible |
| Selection Criteria: | Public reference; Mol Gen Genet. Apr. 1993; 238 (1–2): 17–25. |
| Gene: | Dehydration-induced protein RD22 |
| GenBank: | NM_122472 *Arabidopsis thaliana* dehydration-induced protein RD22 (At5g25610) mRNA, complete cds gi\|30689960\|ref\|NM_122472.2\| [30689960] |
| Source Promoter Organism: | *Arabidopsis thaliana*, WS ecotype |
| Vector: | Newbin4-HAP1-GFP |
| Marker Type: | GFP-ER |
| Generation Screened: | XT1 Mature XT2 Seedling □T2 Mature □T3 Seedling |

Inductions completed:

| Treatment: | Age: | Gen: | Time points: | Events Screened/Response | Response: |
|---|---|---|---|---|---|
| 1. Drought | 7 days | T2 | 3 Hr air dry | 2/2 | Yes |
| 2. ABA 100 uM | 10 days | T2 | 2 Hr 6 Hr | 2/0 | No |
| 3. Drought | 4 weeks | T2 | 10–12 days no H20 | 2/2 | Yes |

Inducible expression summary:

| Treatment: | Time point induced: | Organs induced: | Tissues induced: |
|---|---|---|---|
| 1. Drought | 3 Hr air dry | Rosette leaf | Epidermal, Vascular |
| 3. Drought | 10–12 days no H20 | Siligue, Leaf, Stem | Epidermal |

T1 Mature Plant Expression Organs/Tissues screened
Events Screened: n = 2  Events Expressing: n = 2
GFP Expression Detected

| X Flower | H pedicel □receptacle □nectary □sepal H petal □filament □anther □pollen □carpel □style □papillae □vascular H epidermis □stomata □trichome □silique |
|---|---|
| X Silique | H stigma L style L carpel L septum □placentae □transmitting tissue □vascular L epidermis □stomata □abscission zone □ovule |
| X Ovule | Pre-fertilization: □inner integument □outer integument □embryo sac □funiculus □chalaza □micropyle □gametophyte Post-fertilization: □zygote □embryo sack □inner integument H outer integument □endothelium □seed coat □primordia □chalaza □micropyle □early endosperm □mature endosperm □embryo |
| □Embryo | □suspensor □preglobular □globular □heart □torpedo □late □mature □provascular □hypophysis □radicle □cotyledons □hypocotyl |
| X Stem | H epidermis □cortex □vascular □xylem □phloem □pith H stomata □trichome |
| □Leaf | □petiole □mesophyll □vascular □epidermis □trichome □primordia □stomata □stipule □margin |
| □Shoot apical meristem | □shoot apical meristem □flower primordium |

X in the Pedicel (Pd) of the inflorescence meristem and the flower
X in the item below the inflorescence meristem
X in the Stigma (Sg) of the flower
X in the Petal (Pe) of the flower
X in the Style (Sy) and Carpel (Ca) of the silique
X in the Outer integument (Oi) of the ovule
X in the Epidermis (Ep) of the stem T2 Seedling Expression Tissues Screened Events Screened: n = 2  Events Expressing: n = 2
Seedlings expressing/Seedlings screened Event-01: 1/6
Event-04: 4/6
□Scheduled
GFP Expression Detected

| X Hypocotyl | H epidermis □cortex □vascular □xylem □phloem □stomata |
|---|---|
| X Cotyledon | □mesophyll □vascular H epidermis □margin □stomata □hydathode |
| X Rosette Leaf | □mesophyll □vascular H epidermis H trichome □petiole □primordia □stomata □stipule □margin □hydathode |
| □Primary Root | □epidermis □trichoblast □atrichoblast □cortex □endodermis □vascular □xylem □phloem □pericycle □quiescent □columella □root cap □root hairs |
| □Lateral root | □epidermis □trichoblast □atrichoblast □cortex □endodermis □initials □flanking cells □vascular □lateral root cap |
| □Shoot apical meristem | □shoot apical meristem |

X in the Epidermis (Ep) of the hypocotyl, the root transition zone, the cotyledon and the rosette leaf
X in the Trichomes (Tc) of the rosette leave and trichome base cells Promoter utility

| Trait Area: | PG&D, Stress, Nutrients |
|---|---|
| Sub-trait Area: | Drought, heat and cold |
| Utility: | Among other uses this promoter sequence can be useful to improve: Modulation of compatibility/incompatibility. Modulation seed size and seed shape. Modulation of stem size and shape. Protection against insects and microbes. Modulation of ROS signaling. Uptake of nutrients. Modulation of drought responses including leaf and flower wilting, ovule abortion, infertility and seed abortion. Alteration of seed development and shape, attention of seed dormancy and germination. |

Promoter Expression Report #125

| | |
|---|---|
| Notes: | Goh C H, Nam H G, Park Y S. Stress memory in plants: a negative regulation of stomatal response and transient induction of rd22 gene to light in abscisic acid-entrained *Arabidopsis* plants. Plant J. Oct. 2003; 36 (2): 240–55.<br>Iwasaki T, Yamacuchi-Shinozaki K, Shinozaki K. Identification of a cis-regulatory region of a gene in *Arabidopsis thaliana* whose induction by dehydration is mediated by abscisic acid and requires protein synthesis. Mol Gen Genet. May 20, 1995; 247 (4): 391–8.<br>Yamaguchi-Shinozaki K, Shinozaki K. The plant hormone abscisic acid mediates the drought-induced expression but not the seed-specific expression of rd22, a gene responsive to dehydration stress in *Arabidopsis thaliana*. Mol Gen Genet. Apr. 1993; 238 (1–2): 17–25.<br>Endogenous promoter is down-regulated in roots and only mildly and inconsistently up-regulated in drought. |
| Construct: | YP0356 |
| Promoter candidate I.D: | 11768602 |
| cDNA I.D: | 12394809 |
| Lines expressing: | YP0356 -01, -04 |

Promoter Expression Report #126

| | |
|---|---|
| T2 seedling: | Medium to low expression in root vascular bundles weakening toward hypocotyl. Weak expression in epidermal cells at root transition zone. |
| Expected expression pattern: | Drought inducible |
| Selection Criteria: | Ceres, Inc. Expression data |
| Gene: | Putative cytochrome P450 |
| GenBank: | NM_112814 *Arabidopsis thaliana* cytochrome P450, putative (At3g19270) mRNA, complete cds gi\|18402178\|ref\| NM_112814.1\|[18402178] |
| Source Promoter Organism: | *Arabidopsis thaliana*, Columbia ecotype |
| Vector: | pNewbin4-HAP1-GFP |
| Marker Type: | GFP-ER |
| Generation Screened: | ☒T1 Mature ☒T2 Seedling ☐T2 Mature ☐T3 Seedling |

Inductions completed: Drought, Heat

| Treatment: | Age: | Gen: | Time points: | Events Screened/ Response | Response: |
|---|---|---|---|---|---|
| 1. Drought | 4 wks | T2 | 10–12 d. No H20 | 2/0 | No |
| 2. Drought | 7 days | T2 | 3 hrs Air Dry | 2/0 | No |
| 3. Heat 42 C. | 7 days | T2 | 1 Hr | 2/0 | No |
| | | | 4 Hr | 2/0 | No |
| | | | 24 Hr post-treatment | 2/1 | Yes |

Sequence (SEQ ID NO: 94):

```
ttagttcattgaaacgtcaacttttttacttgcaaccactttgtaggaccattaactgcaaaataagaattctctaagcttcacaaggggttcgtttggtgc
tataaaacattgttttaagaactggtttactggttctataaatctataaatccaaatatgaagtatggcaataataataacatgttagcacaaaaaatac
tcattaaattcctacccaaaaaaaatctttatatgaaactaaaacttatatacacaataatagtgatacaaagtaggtcttgatattcaactattcgggat
tttctggtttcgagtaattcgtataaaaggtttaagatctattatgttcactgaaatcttaactttgttttgtttccagttttaactagtagaaattgaaa
ttttttaaaaattgttacttacaataaaatttgaatcaatatccttaatcaaaggatcttaagactagcacaattaaaacatataacgtagaatatctgaaa
taactcgaaaatatctgaactaagttagtagttttaaaatataatcccggtttggaccgggcagtatgtacttcaatacttgtgggttttgacgattttgg
atcggattgggcgggccagccagattgatctattacaaatttcacctgtcaacgctaactccgaacttaatcaaagattttgagctaaggaaaactaatca
gtgatcacccaaagaaaacattcgtgaataattgtttgctttccatggcagcaaaacaaataggacccaaataggaatgtcaaaaaaagaaagacacgaa
acgaagtagtataacgtaacacacaaaaataaactagagatattaaaaacacatgtccacacatggatacaagagcatttaaggagcagaaggcacgtagt
ggttagaaggtatgtgatataattaatcggcccaaatagattggtaagtagtagccgtctatatcatccatactcatcataacttcaacct
```

Promoter Expression Report #126

| | |
|---|---|
| Promoter Tested In: | *Arabidopsis thaliana*, Wassilewskija (WS) ecotype |

Spatial expression summary:

| | |
|---|---|
| Ovule Pre-fertilization: | H outer integument |
| Post-fertilization: | L outer integument L chalaza |
| Hypocotyl | L vascular |
| Primary Root | L epidermis M vascular M pericycle |

Observed expression pattern:

| | |
|---|---|
| T1 mature: | GFP expressed in outer integument of developing ovule primordium. Higher integument expression at chalazal pole observed through maturity. |

Inducible expression summary:

| Treatment: | Time point induced: | Organs induced: | Tissues induced: |
|---|---|---|---|
| 3. Heat | 24 Hr post-treatment | Rosette leaf | Epidermis Vascular |

T1 Mature Plant Expression Organs/Tissues screened
Events Screened: n = 2 Events Expressing: n = 2
GFP Expression Detected

| | |
|---|---|
| ☐Flower | ☐pedicel ☐receptacle ☐nectary ☐sepal ☐petal ☐filament ☐anther ☐pollen ☐carpel ☐style ☐papillae ☐vascular ☐epidermis ☐stomata ☐trichome ☐silique |

Promoter Expression Report #126

| | |
|---|---|
| ☐Silique | ☐stigma ☐style ☐carpel ☐septum ☐placentae ☐transmitting tissue ☐vascular ☐epidermis ☐stomata ☐abscission zone ☐ovule |
| X Ovule | Pre-fertilization: ☐inner integument H outer integument ☐embryo sac ☐funiculus ☐chalaza ☐micropyle ☐gametophyte Post-fertilization: ☐zygote ☐embryo sack ☐inner integument L outer integument ☐endothelium ☐seed coat ☐primordia L chalaza ☐micropyle ☐early endosperm ☐mature endosperm ☐embryo |
| ☐Embryo | ☐suspensor ☐preglobular ☐globular ☐heart ☐torpedo ☐late ☐mature ☐provascular ☐hypophysis ☐radicle ☐cotyledons ☐hypocotyl |
| ☐Stem | ☐epidermis ☐cortex ☐vascular ☐xylem ☐phloem ☐pith ☐stomata ☐trichome |
| ☐Leaf | ☐petiole ☐mesophyll ☐vascular ☐epidermis ☐trichome ☐primordia ☐stomata ☐stipule ☐margin |
| ☐Shoot apical meristem | ☐shoot apical meristem ☐flower primordium |

X in the Chalaza (Ch), Funiculus (Fn) and Outer integument (Oi) of the ovule primordial
X in the Chalaza (Ch) in the pre-fertilized ovule
X in the Chalaza (Ch) and Micropyle (Mp) of the fertilized ovule and developing seed
X in the Chalaza (Ch) of the mature seed T2 Seedling Expression Tissues Screened Events Screened: n = 2  Events Expressing: n = 2
Seedlings expressing/Seedlings screened Event-01: 3/5
Event-02: 1/6
☐Scheduled
GFP Expression Detected

| | |
|---|---|
| X Hypocotyl | ☐epidermis ☐cortex L vascular ☐xylem ☐phloem ☐stomata |
| ☐Cotyledon | ☐mesophyll ☐vascular ☐epidermis ☐margin ☐stomata ☐hydathode |
| ☐Rosette Leaf | ☐mesophyll ☐vascular ☐epidermis ☐trichome ☐petiole ☐primordia ☐stomata ☐stipule ☐margin ☐hydathode |
| X Primary Root | L epidermis ☐trichoblast ☐atrichoblast ☐cortex ☐endodermis M vascular ☐xylem ☐phloem M pericycle ☐quiescent ☐columella ☐root cap ☐root hairs |
| ☐Lateral root | ☐epidermis ☐trichoblast ☐atrichoblast ☐cortex ☐endodermis ☐initials ☐flanking cells ☐vascular ☐lateral root cap |
| ☐Shoot apical meristem | ☐shoot apical meristem |

X in the Epidermis (Ep) of the seedling root
X in the Vascular (Vs) of the Hypocotyl (Hy) and root transition zone
X in the Vascular (Vs) and Pericycle (Pr) of the root Promoter utility

| | |
|---|---|
| Trait Area: | Seed Biology, Stress |
| Sub-trait Area: | Seed fill, seed size, stress during seed fill, stress protection, endosperm production |
| Utility: | Among other uses this promoter sequence can be useful to improve: Protection against ovule and seed abortion. Modulation seed size, seed shape. Modulation of endosperm growth and development. Modulation of heat responses and protection against heat stress. Modulation of water and mineral ion uptake and transport. Loading and transport of metabolites into seeds. Modulation of breeding system. |
| Notes: | Heat stress is a major determinant of seed and fruit yield in many crops, and protection against transient heat stress is a primary goal of modern agriculture. This promoter 11768817 induces in leaves at approximately 24 hour after heat stress. The leaf induction can protect against water loss from the leaf, offering a possibility of protection against heat and drought conditions, which often coincide. Promoter is mildly induced by drought and drought-like conditions. |
| Construct: | YP0374 |
| Promoter candidate I.D: | 11768817 |
| cDNA I.D: | 12370888 |
| Lines expressing: | YP0374-01, -02 |

Sequence (SEQ ID NO: 95):

```
aagacacccgtaaatgttgtcatgtagaagaaactagaaacgttaaacgcatcaaatcaagaaattaaattgaaggtaattttaacgccgcctttcaaat attcttcctaggagaggctacaagacgcgtatttctttcgaattctccaaaccattaccattttgatatataataccgacatgccgttgataaagtttgta tgcaaatcgttcattgggtatgagcaaatgccatccattggttcttgtaattaaatggtccaaaaatagtttgttcccactactagttactaatttgtatc actctgcaaaataatcatgatatataaacgtatgtgctatttctaattaaaactcaaaagtaatcaatgtacaatgcagagatgaccataaaagaacattaaa acactacttccactaaatctatggggtgccttggcaaggcaattgaataaggagaatgcatcaagatgatatagaaaatgctattcagtttataacattaa tgttttggcggaaaattttctatatattagacctttctgtaaaaaaaaaaaatgatgtagaaaatgctattatgtttcaaaaatttcgcactagtataat acggaacattgtagtttacactgctcattaccatgaaaaccaaggcagtatataccaacattaataaactaaatcgcgatttctagcaccccattaatta attttactattatacattctctttgcttctcgaaataataaacttctctatatcattctacataataaataagaaagaaatcgacaagatctaaatttaga tctattcagcttttttcgcctgagaagccaaaattgtgaatagaagaaagcagtcgtcatcttcccacgtttggacgaaataaaacataacaataataaaat aataaatcaaatatataaatccctaatttgtctttattactccacaattttctatgtgtatatatatacccacctctctcttgtgtatttg
```

Promoter Expression Report #127

| | |
|---|---|
| Promoter Tested In: | *Arabidopsis thaliana*, Wassilewskija (WS) ecotype |
| Spatial expression summary: | |
| Flower | M sepal M petal M epidermis |
| Hypocotyl | L epidermis L vascular H stomata |
| Cotyledon | M vascular L epidermis |
| Primary Root | M epidermis M vascular M root hairs |
| Observed expression pattern: | |
| T1 mature: | Expressed in epidermal cells of sepals and petals in developing flowers. |
| T2 seedling: | Medium to low expression in epidermal and vascular cells of hypocotyls and cotyledons. Epidermal and vascular expression at root transition zone decreasing toward root tip. |
| Expected expression pattern: | PEG or Osmotic stress-inducible |
| Selection Criteria: | Ceres expression data |
| Gene: | product = "glycine-rich protein", note: unknown protein |
| GenBank: | NM_100587 *Arabidopsis thaliana* glycine-rich protein (At1g07135) mRNA, complete cds gi|22329385|ref| NM_100587.2|[22329385] |
| Source Promoter Organism: | *Arabidopsis thaliana*, WS ecotype |
| Vector: | pNewbin4-HAP1-GFP |
| Marker Type: | GFP-ER |
| Generation Screened: | XT1 Mature XT2 Seedling ☐T2 Mature ☐T3 Seedling |

Inductions completed:

| Treatment: | Age: | Gen: | Time points: | Events Screened/ Response | Response: |
|---|---|---|---|---|---|
| 1. Drought | 7 days | T2 | 3 Hrs airy dry | 2/2 | Yes |
| 2. Drought | 4 weeks | T2 | 10–12 days no H2O | 2/2 | Decrease |

Inducible expression summary:

| Treatment: | Time point induced: | Organs induced: | Tissues induced: |
|---|---|---|---|
| 1. Drought | 3 Hrs airy dry | Cotyledons | Epidermis |

Impeded expression summary:

| Treatment: | Time point impeded: | Organs impeded: | Tissues impeded: |
|---|---|---|---|
| 2. Drought | 10–12 days no H2O | Inflorescence meristem | Sepals |
| | | Sepals | Epidermis, Cortex, Vascular |
| | | Stem | Epidermis, Cortex |
| | | Silique | Epidermis, Cortex |

Notes: Decreased levels of GFP were observed in the primary inflorescence shoot meritem. Stems and siliques were taken from top third of mature plants. No expression observed in stems and siliques from bottom half of secondary inflorescence of mature plants. No differences observed between primary and secondary inflorescence meritems.

T1 Mature Plant Expression Organs/Tissues screened
Events Screened: n = 2 Events Expressing: n = 2
GFP Expression Detected

| | |
|---|---|
| X Flower | ☐pedicel ☐receptacle ☐nectary M sepal M petal ☐filament ☐anther ☐pollen ☐carpel ☐style ☐papillae ☐vascular M epidermis ☐stomata ☐trichome ☐silique |
| ☐Silique | ☐stigma ☐style ☐carpel ☐septum ☐placentae ☐transmitting tissue ☐vascular ☐epidermis ☐stomata ☐abscission zone ☐funiculus ☐ovule |
| ☐Ovule | Pre-fertilization: ☐inner integument ☐outer integument ☐embryo sac ☐funiculus ☐chalaza ☐micropyle ☐gametophyte Post-fertilization: ☐zygote ☐embryo sack ☐inner integument ☐outer integument ☐funiculus ☐endothelium ☐seed coat ☐primordia ☐chalaza ☐micropyle ☐early endosperm ☐mature endosperm ☐embryo |
| ☐Embryo | ☐suspensor ☐preglobular ☐globular ☐heart ☐torpedo ☐late ☐mature ☐provascular ☐hypophysis ☐radicle ☐cotyledons ☐hypocotyl |
| ☐Stem | ☐epidermis ☐cortex ☐vascular ☐xylem ☐phloem ☐pith ☐stomata ☐trichome |
| ☐Leaf | ☐petiole ☐mesophyll ☐vascular ☐epidermis ☐trichome ☐primordia ☐stomata ☐stipule ☐margin |
| ☐Shoot apical meristem | ☐shoot apical meristem ☐flower primordium |

X in the Petal (Pe), and Sepal (Se) of the flower
X in the flower bud

T2 Seedling Expression Tissues Screened

Events Screened: n = 2 Events Expressing: n = 2
Seedlings expressing/Seedlings screened Event-02: 4/6
Event-06: 5/6
☐Scheduled
GFP Expression Detected

| | |
|---|---|
| X Hypocotyl | L epidermis ☐cortex L vascular ☐xylem ☐phloem H stomata |
| X Cotyledon | ☐mesophyll M vascular L epidermis ☐margin ☐stomata ☐hydathode |
| ☐Rosette Leaf | ☐mesophyll ☐vascular ☐epidermis ☐trichome ☐petiole ☐primordia ☐stomata ☐stipule ☐margin ☐hydathode |
| X Primary Root | M epidermis ☐trichoblast ☐atrichoblast ☐cortex ☐endodermis M vascular ☐xylem ☐phloem ☐pericycle ☐quiescent ☐columella ☐root cap M root hairs |
| ☐Lateral root | ☐epidermis ☐trichoblast ☐atrichoblast ☐cortex ☐endodermis ☐initials ☐flanking cells ☐vascular ☐lateral root cap |
| ☐Shoot apical meristem | ☐shoot apical meristem |

X in the Epidermis (Ep), Vasculature (Vs) and Guard cells (Gc) of the seedling apex
X in the Vasculature (Vs) of the Cotyledon (Co) petiole, Hypocotyl (Hy) and root
X in the Epidermis (Ep) of the root and Cotyledon (Co) petiole Promoter utility

| | |
|---|---|
| Trait Area: | Nutrients, Stress |
| Sub-trait Area: | Drought, Nitrogen uptake |
| Utility: | Among other uses this promoter sequence can be useful to improve: Modulation of water and nutrient uptake and seedling establishment. Modulation of plant-microbe interactions. Changes to flower development and structure. Modulation of responses to drought, especially in the flower and inflorescence and in the stigma. Changes in pollination biology and incompatibility upon drought. |
| Notes: | Endogenous promoter is up-regulated under PEG treatment but not with ABA and drought. |

Promoter Expression Report #127

| | |
|---|---|
| Construct: | YP0377 |
| Promoter candidate I.D: | 11768593 |
| cDNA I.D: | 13613778 |
| Lines expressing: | YP0377 -02, -06 |

Sequence (SEQ ID NO: 96):

TATAAACCATTCCTATAACACCATATTTAAACATAACAATGAATTGCTTGGATTTCAAACTTTATTAAATTTGGATTTTAAA

TTTTAATTTGATTGAATTATACCCCCTTAATTGGATAAATTCAAATATGTCAACTTTTTTTTGTAAGATTTTTTTATGGAA

AAAAAAATTGATTATTCACTAAAAAGATGACAGGTTACTTATAATTTAATATATGTAAACCCTAAAAAGAAGAAAATAGTTT

CTGTTTTCACTTTAGGTCTTATTATCTAAACTTCTTTAAGAAAATCGCAATAAATTGGTTTGAGTTCTAACTTTAAACACAT

TAATATTTGTGTGCTATTTAAAAAATAATTTACAAAAAAAAAAACAAATTGACAGAAAATATCAGGTTTTGTAATAAGATAT

TTCCTGATAAATATTTAGGGAATATAACATATCAAAAGATTCAAATTCTGAAAATCAAGAATGGTAGACATGTGAAAGTTGT

CATCAATATGGTCCACTTTTCTTTGCTCTATAACCCAAAATTGACCCTGACAGTCAACTTGTACACGCGGCCAAACCTTTTT

ATAATCATGCTATTTATTTCCTTCATTTTTATTCTATTTGCTATCTAACTGATTTTTCATTAACATGATACCAGAAATGAAT

TTAGATGGATTAATTCTTTTCCATCCACGACATCTGGAAACACTTATCTCCTAATTAACCTTACTTTTTTTTAGTTTGTGT

GCTCCTTCATAAAATCTATATTGTTTAAAACAAAGGTCAATAAATATAAATATGGATAAGTATAATAAATCTTTATTGGATA

TTTCTTTTTTAAAAAAGAAATAAATCTTTTTGGATATTTTCGTGGCAGCATCATAATGAGAGACTACGTCGAAACCGCTG

GCAACCACTTTTGCCGCGTTTAATTTCTTTCTGAGGCTTATATAAATAGATCAAAGGGGAAAGTGAGATATAATACAGACAA

AACAAGAGAAAAGA

Promoter Expression Report #128

| | |
|---|---|
| GenBank: | NM_128898 *Arabidopsis thaliana* RD20 protein (At2g33380) mRNA, complete cds gi30685670refl NM_128898.2[30685670] |
| Source Promoter Organism: | *Arabidopsis thaliana*, WS ecotype |

Promoter Expression Report #128

| | |
|---|---|
| Promoter Tested In: | *Arabidopsis thaliana*, Wassilewskija (WS) ecotype |

Spatial expression summary:

| | |
|---|---|
| Flower | H pedicel H receptacle H sepal H petal H filament H anther H carpel H style H stigma H epidermis H stomata H silique |
| Silique | H stigma H style H carpel H septum H placentae H epidermis |
| Stem | L epidermis L cortex H stomata |
| Leaf | H mesophyll H epidermis H trichome H stomata |
| Hypocotyl | H epidermis H stomata |
| Cotyledon | H mesophyll H epidermis |
| Rosette Leaf | H mesophyll H epidermis |
| Primary Root | H epidermis |

Observed expression pattern:

| | |
|---|---|
| T1 mature: | Vegetative expression. Not expressed in shoot apical meristem, early flower primordia, pollen and ovules. High expression throughout floral organs. High expression in stem guard cells and cortex cells surrounding stomal chamber. Expression throughout placenta and funiculus but not in any ovule tissue. |
| T2 seedling: | Expressed in all tissues near seedling apex increasing toward root. High root epidermis expression. Not expressed in cotyledon and rosette leaf guard cells. |
| Expected expression pattern: | Drought inducible |
| Selection Criteria: | Ceres, Inc. microarray |
| Gene: | Responsive to Dehydration 20 |

| | |
|---|---|
| Vector: | pNewbin4-HAP1-GFP |
| Marker Type: | GFP-ER |
| Generation Screened: | XT1 Mature XT2 Seedling ☐T2 Mature ☐T3 Seedling |

Inductions completed:

| Treatment: | Age: | Gen: | Time points: | Events Screened/ Response | Response: |
|---|---|---|---|---|---|
| 1. Drought | 7 days | T2 | 3 hours air dry | 2/2 | Yes |
| 2. Drought | 7 days | T2 | At Wilt | 2/2 | Yes |
| 3. ABA 100 uM | 7 days | T2 | 6 Hrs | 2/2 | Yes |
| 4. Drought | 4 weeks | T2 | 10–12 days no H2O | 2/2 | Yes |

Inducible expression summary:

| Treatment: | Time point induced: | Organs induced: | Tissues induced: |
|---|---|---|---|
| 1. Drought | 3 hours air dry | Cotyledons Hypocotyl | Epidermis Guard cells |
| 2. Drought | At Wilt | Cotyledons Root | Epidermis Epidermis |
| 3. ABA 100 uM | 6 Hrs | Cotyledons, Rosette leaf | Epidermis, Guard cells Mesophyll, Vasculature |
| 4. Drought | 10–12 days no H2O | Roots Flower | Epidermis Silique, Abscission zone |
| | | Silique Leaf | Epidermis Epidermis, |

Promoter Expression Report #128

|  | Stem | mesophyll Cortex, Epidermis |
|---|---|---|

T1 Mature Plant Expression Organs/Tissues screened
Events Screened: n = 3  Events Expressing: n = 3
GFP Expression Detected

| X Flower | H pedicel H receptacle □nectary H sepal H petal H filament H anther □pollen H carpel H style H stigma □vascular H epidermis H stomata □trichome H silique |
|---|---|
| X Silique | H stigma H style H carpel H septum H placentae □funiculus □transmitting tissue □vascular H epidermis □stomata □abscission zone □ovule |
| □Ovule | Pre-fertilization: □inner integument □outer integument □embryo sac □funiculus □chalaza □micropyle □gametophyte Post-fertilization: □zygote □embryo sack □inner integument □outer integument □funiculus □endothelium □seed coat □primordia □chalaza □micropyle □early endosperm □mature endosperm □embryo |
| □Embryo | □suspensor □preglobular □globular □heart □torpedo □late □mature □provascular □hypophysis □radicle □cotyledons □hypocotyl |
| X Stem | L epidermis L cortex □vascular □xylem □phloem □pith H stomata □trichome |
| X Leaf | □petiole H mesophyll □vascular H epidermis H trichome □primordia H stomata □stipule □margin |
| □Shoot apical meristem | □shoot apical meristem □flower primordium |

X in the Flower (Fl), of the inflorescence meristem
X in the Silique (Si), Stamen (St), Petal (Pe), and Sepal (Se) of the immature flower
X in the Silique (Si), Sepal (Se) and Receptacle (Re) of the mature flower
X in the Anther (An)
X in the Valve margin (Vin) of the silique
X in the Funiculus (Fn) of the placenta and mature ovule
X in the ovule primordial and developing ovule
X in the Trichome (Tc), Epidermis (Ep), Nucleus (Nu) and Guard cells (Gc)
X in the Epidermis (Ep), Mesophyll (Me) and Guard cells (Gc) of the abaxial leaf
X in the Mesophyll (Me) of the adaxial leaf
X in the Cortex (Cr), Epidermis (Ep) and Guard cells (Gc) of the stem
T2 Seedling Expression Tissues Screened Events Screened: n = 2  Events Expressing: n = 2
Seedlings expressing/Seedlings screened Event-01:  4/6
Event-04:  5/6
□Scheduled
GFP Expression Detected

| X Hypocotyl | H epidermis □cortex □vascular □xylem □phloem H stomata |
|---|---|
| X Cotyledon | H mesophyll □vascular H epidermis □margin □stomata □hydathode |
| X Rosette Leaf | H mesophyll □vascular H epidermis □trichome □petiole □primordia □stomata □stipule □margin □hydathode |
| X Primary Root | H epidermis □trichoblast □atrichoblast □cortex □endodermis □vascular □xylem □phloem □pericycle □quiescent □columella □root cap □root hairs |
| □Lateral root | □epidermis □trichoblast □atrichoblast □cortex □endodermis □initials □flanking cells □vascular □lateral root cap |
| □Shoot apical meristem | □shoot apical meristem |

X in the seedling, seedling apex, hypocotyl, cotyledon and root
X in the Rosette leaf (Rl)
X in the Root (Rt),
X in the Mesophyll (Me), Epidermis (Ep) and Guard cells (Gc) of the leaf
Promoter utility

| Trait Area: | Water stress, Seed Biology, PG&D |
|---|---|
| Sub-trait Area: | Drought, Seed fill |
| Utility: | Among other uses this promoter sequence can be useful to improve: Valuable as drought-inducible promoter for yield protection in drought or heat stress conditions. Modulation of plant growth rate and architecture. Modulation of growth and development in absence of effects on reproductive cells. Enhancement of source strength and seed filling. Engineering of male sterility. |
| Notes: | Takahashi S, Katagiri T, Yamaguchi-Shinozaki K, Shinozaki K. An *Arabidopsis* gene encoding a Ca2+-binding protein is induced by abscisic acid during dehydration. Plant Cell Physiol. Jul. 2000; 41 (7): 898–903. Yamaguchi-Shinozaki K, Shinozaki K. The plant hormone abscisic acid mediates the drought-induced expression but not the seed-specific expression of rd22, a gene responsive to dehydration stress in *Arabidopsis thaliana*. Mol Gen Genet. Apr. 1993; 238 (1–2): 17–25. Endogenous gene is up-regulated under drought and ABA. |
| Construct: | YP0380 |
| Promoter candidate I.D: | 11768580 |
| cDNA I.D: | 12462179 (OCKHAM3-CD) |
| Lines expressing: | YP0380-01, -04, -02 |

Sequence (SEQ ID NO: 97):

```
acaagtaccattcactttttactttcaatgtatacaatcatcatgtgataaaaaaaaaatgtaaccaatcaacacactgagatacggccaaaaaatgg taatacataaatgtttgtaggttttgtaatttaaatactttagttaagttatgattttattattttgcttatcacttatacgaaatcatcaatctattgg tatctcttaatcccgcttttttaatttccaccgcacacgcaaatcagcaaatggttccagccacgtgcatgtgaccacatattgtggtcacagtactcgtcc ttttttttctttgtaatcaataaatttcaatcctaaaacttcacacattgagcacgtcggcaacgttagctcctaaatcataacgagcaaaaaagttca
```

```
aattagggtatatgatcaattgatcatcactacatgtctacataattaatatgtattcaaccggtcggtttgttgatactcatagttaagtatatatgtgc taattagaattaggatgaatcagttcttgcaaacaactacggtttcatataatatgggagtgttatgtacaaaatgaaagaggatggatcattctgagatg ttatgggctcccagtcaatcatgttttgctcgcatatgctatcttttgagtctcttcctaaactcatagaataagcacgttggttttttccaccgtcctcc tcgtgaacaaaagtacaattacattttagcaaattgaaaataaccacgtggatggaccatattatatgtgatcatattgcttgtcgtcttcgttttctttt aaatgtttacaccactacttcctgacacgtgtccctattcacatcatccttgttatatcgttttacttataaaggatcacgaacaccaaaacatcaatgtg tacgtcttttgcataagaagaaacagagagcattatcaattattaacaattacacaagacagcgagattgtaaaagagtaagagagagag
```

Promoter Expression Report #129

| | |
|---|---|
| Promoter Tested In: | *Arabidopsis thaliana*, Wassilewskija (WS) ecotype |
| Spatial expression summary: | |
| Flower | L pedicel H nectary L epidermis |
| Hypocotyl | L vascular |
| Primary Root | H vascular |
| Observed expression pattern: | |
| T1 mature: | High expression in nectary glands of flowers. Low expression in epidermis of pedicels of developing flowers |
| T2 seedling: | GFP expressed in root and hypocotyl vasculature. |
| Expected expression pattern: | Drought inducible |
| Selection Criteria: | Ceres, Inc. microarray data |
| Gene: | Unknown expressed protein |
| GenBank: | NM_113878 *Arabidopsis thaliana* expressed protein (At3g29575) mRNA, complete cds gi\|30689672\|ref\| NM_113878.3\|[30689672] |
| Source Promoter Organism: | *Arabidopsis thaliana*, Ws ecotype |
| Vector: | pNewbin4-HAP1-GFP |
| Marker Type: | GFP-ER |
| Generation Screened: | XT1 Mature XT2 Seedling ☐T2 Mature ☐T3 Seedling |

Inductions completed:

| Treatment: | Age: | Gen: | Time points: | Events Screened/ Response | Response: |
|---|---|---|---|---|---|
| 1. Drought | 7 days | T2 | 3 hours air dry | 2/0 | No |
| 2. ABA 100 uM | 7 days | T2 | 6 Hrs | 2/1 | Yes |
| 3. Drought | 4 weeks | T2 | 10–12 days no H20 | 2/2 | Yes |

Inducible expression summary:

| Treatment: | Time point induced: | Organs induced: | Tissues induced: |
|---|---|---|---|
| 2. ABA 100 uM* | 6 Hrs | Root | Vasculature |
| 3. Drought | 10–12 days no H20 | Flower | Sepals, Petals, Silques, Pedicles, Nectaries, Abscission zone |
| | | Silique | Carpels, Epidermis, Vascular |
| | | Leaf | Epidermis, Mesophyll, Vascular |
| | | Stem | Vascular, Pith |

Promoter Expression Report #129

T1 Mature Plant Expression Organs/Tissues screened
Events Screened: n = 2  Events Expressing: n = 2
GFP Expression Detected

| | |
|---|---|
| X Flower | L pedicel ☐receptacle H nectary ☐sepal ☐petal ☐filament ☐anther ☐pollen ☐carpel ☐style ☐papillae ☐vascular L epidermis ☐stomata ☐trichome ☐silique |
| ☐Silique | ☐stigma ☐style ☐carpel ☐septum ☐placentae ☐transmitting tissue ☐vascular ☐epidermis ☐stomata ☐abscission zone ☐ovule |
| ☐Ovule | Pre-fertilization: ☐inner integument ☐outer integument ☐embryo sac ☐funiculus ☐chalaza ☐micropyle ☐gametophyte Post-fertilization: ☐zygote ☐embryo sack ☐inner integument ☐outer integument ☐endothelium ☐seed coat ☐primordia ☐chalaza ☐micropyle ☐early endosperm ☐mature endosperm ☐embryo |
| ☐Embryo | ☐suspensor ☐preglobular ☐globular ☐heart ☐torpedo ☐late ☐mature ☐provascular ☐hypophysis ☐radicle ☐cotyledons ☐hypocotyl |
| ☐Stem | ☐epidermis ☐cortex ☐vascular ☐xylem ☐pliloem ☐pith ☐stomata ☐trichome |
| ☐Leaf | ☐petiole ☐mesophyll ☐vascular ☐epidermis ☐trichome ☐primordia ☐stomata ☐stipule ☐margin |
| ☐Shoot apical meristem | ☐shoot apical meristem ☐flower primordium |

X in the Pedicel (Pd) of the inflorescence meristem
X in the lateral and medial Nectary (Ne) in the flower
X in the modified stomata opening in the lateral nectary
T2 Seedling Expression Tissues Screened Events Screened: n = 2  Events Expressing: n = 2
Seedlings expressing/Seedlings screened Event-05: 1/6
Event-06: 6/6
☐Scheduled
GFP Expression Detected

| | |
|---|---|
| X Hypocotyl | ☐epidermis ☐cortex L vascular ☐xylem ☐phloem ☐stomata |
| ☐Cotyledon | ☐mesophyll ☐vascular ☐epidermis ☐margin ☐stomata ☐hydathode |
| ☐Rosette Leaf | ☐mesophyll ☐vascular ☐epidermis ☐trichome ☐petiole ☐primordia ☐stomata ☐stipule ☐margin ☐hydathode |

| Promoter Expression Report #129 | |
|---|---|
| X Primary Root | ☐epidermis ☐trichoblast ☐atrichoblast ☐cortex ☐endodermis H vascular ☐xylem ☐phloem ☐pericycle ☐quiescent ☐columella ☐root cap ☐root hairs |
| ☐Lateral root | ☐epidermis ☐trichoblast ☐atrichoblast ☐cortex ☐endodermis ☐initials ☐flanking cells ☐vascular ☐lateral root cap |
| ☐Shoot apical meristem | ☐Shoot apical meristem |
| X in the Vasculature (Vs) of the Hypocotyl (Hy) and root | |
| Promoter utility | |
| Trait Area: | PG&D |
| Sub-trait Area: | Breeding biology |
| Utility: | Among other uses this promoter sequence can be useful to improve: Modulation of plant secondary products including volatiles or fragrances. Could be useful to drive genes important in insect attraction for stimulation of outbreeding and hybridization. Useful for making flowerless plants. Modulation of drought stress tolerance. Modulation of heat stress tolerance. |
| Notes: | Baum S F, Eshed Y. Bowman J L. The *Arabidopsis* nectary is an ABC-independent floral structure. Development. Nov. 2001; 128 (22): 4657–67. Endogenous promoter is up-regulated in drought, ABA and far red light. |
| Construct: | YP0381 |
| Promoter candidate I.D: | 11768582 |
| cDNA I.D: | 12736859 (OCKHAM3-CD) |
| Lines expressing: | YP0381-05, -06 |

Sequence (SEQ ID NO: 98):

cacggtcaaagtattgctaacatggtcattacattgaaaaagaaaattaattgtctttactcatgtttattctatacaaataaaaatattaaccaaccatcg cactaacaaaatagaaatcttattctaatcacttaattgttgacaattaaatcattgaaaaatacacttaaatgtcaaatattcgttttgcatacttttcaat ttaaatacatttaaagttcgacaagttgcgtttactatcatagaaaactaaatctcctaccaaagcgaaatgaaactactaaagcgacaggcaggttacataa cctaacaaatctccacgtgtcaattaccaagagaaaaaagagaagataagcggaacacgtggtagcacaaaaagataatgtgatttaaattaaaaaacaaa aacaaagacacgtgacgacctgacgctgcaacatcccaccttacaacgtaataaccactgaacataagacacgtgtacgatcttgtctttgttttctcgatga aaaccacgtgggtgctcaaagtccttgggtcagagtcttccatgattccacgtgtcgttaatgcaccaaacaagggtactttcggtattttggcttccgcaaa ttagacaaaacagcttttgtttgattgatttttctcttctcttttccatctaaattctctttgggctcttaatttcttttgagtgttcgttcgagattt gtcggagatttttcggtaaatgttgaaattttgtgggatttttttttatttctttattaaactttttttattgaatttataaaaagggaaggtcgtcatt aatcgaagaaatggaatcttccaaaatttgatattttgctgttttcttgggatttgaattgctctttatcatcaagaatctgttaaaatttctaatctaaaat ctaagttgagaaaaagagagatctctaatttaaccggaattaatattctccgaccgaagttattatgttgcaggct

| Promoter Expression Report #130 | |
|---|---|
| Promoter Tested In: | *Arabidopsis thaliana*, Wassilewskija (WS) ecotype |
| Spatial expression summary: | |
| Flower | H nectary M sepal M vascular |
| Hypocotyl | L vascular |
| Cotyledon | L vascular |
| Rosette Leaf | L vascular |
| Primary Root | H epidermis H root cap L root hairs |
| Observed expression pattern: | |
| | T1 mature: Expressed in nectary glands of flowers and vasculature of sepals. T2 seedling: High GFP expression in root epidermal cells through to root cap. Low GFP expression in vasculature aerial organs. |
| Expected expression pattern: | PEG or Osmotic stress-inducible |
| Selection Criteria: | Ceres, Inc. Expression data |
| Gene: | product = "expressed protein" |
| GenBank: | NM_129727 *Arabidopsis thaliana* expressed protein (At2g41640) mRNA, complete cds gi\|30688728\|ref\|NM_129727.2\|[30688728] |
| Source Promoter Organism: | *Arabidopsis thaliana*, Ws ecotype |
| Vector: | pNewbin4-HAP1-GFP |
| Marker Type: | GFP-ER |
| Generation Screened: | X T1 Mature X T2 Seedling ☐T2 Mature ☐T3 Seedling |

-continued

Promoter Expression Report #130

Inductions completed.

| Treatment: | Age: | Gen: | Time points: | Events Screened/ Response | Response: |
|---|---|---|---|---|---|
| 1. Drought | 7 days | T2 | 3 Hr air dry | 2/0 | No |
| 2. Drought | 4 weeks | T2 | 10–12 days no H20 | 2/0 | No |

Inducible expression summary:
| Treatment: | Time point induced: | Organs induced: | Tissues induced: |
|---|---|---|---|
| 1. Drought | No differences observed. | | |
| 2. Drought | No differences observed. | | |

T1 Mature Plant Expression Organs/Tissues screened
Events Screened: n = 2    Events Expressing: n = 2
GFP Expression Detected

| X Flower | ☐pedicel ☐receptacle H nectary M sepal ☐petal ☐filament ☐anther ☐pollen ☐carpel ☐style ☐papillae M vascular ☐epidermis ☐stomata ☐trichome ☐silique |
|---|---|
| ☐ Silique | ☐stigma ☐style ☐carpel ☐septum ☐placentae ☐transmitting tissue ☐vascular ☐epidermis ☐stomata ☐abscission zone ☐ovule |
| ☐ Ovule | Pre-fertilization: ☐inner integument ☐outer integument ☐embryo sac ☐funiculus ☐chalaza ☐micropyle ☐gametophyte<br>Post-fertilization: ☐zygote ☐embryo sack ☐inner integument ☐outer integument ☐endothelium ☐seed coat ☐primordia ☐chalaza ☐micropyle |
| ☐ Embryo | ☐early endosperm ☐mature endosperm ☐embryo ☐suspensor ☐preglobular ☐globular ☐heart ☐torpedo ☐late ☐mature ☐provascular ☐hypophysis ☐radicle ☐cotyledons ☐hypocotyl |
| ☐ Stem | ☐epidermis ☐cortex ☐vascular ☐xylem ☐phloem ☐pith ☐stomata ☐trichome |
| ☐ Leaf | ☐petiole ☐mesophyll ☐vascular ☐epidermis ☐trichome ☐primordia ☐stomata ☐stipule ☐margin |
| ☐ Shoot apical meristem | ☐shoot apical meristem ☐flower primordium |

X in the Nectary (Ne) of the flower
X in the Vasculature (Vs) of the Sepal (Se)
T2 Seedling Expression    Tissues Screened
Events Screened: n = 2    Events Expressing: n = 2
Seedlings expressing/Seedlings screened
Event-04: 5/6
Event-05: 4/6
☐ Scheduled
GFP Expression Detected

| X Hypocotyl | ☐epidermis ☐cortex L vascular ☐xylem ☐phloem ☐stomata |
|---|---|
| X Cotyledon | ☐mesophyll L vascular ☐epidermis ☐margin ☐stomata ☐hydathode |
| X Rosette Leaf | ☐mesophyll L vascular ☐epidermis ☐trichome ☐petiole ☐primordia ☐stomata ☐stipule ☐margin ☐hydathode |
| X Primary Root | H epidermis ☐trichoblast ☐atrichoblast ☐cortex ☐endodermis ☐vascular ☐xylem ☐phloem ☐pericycle ☐quiescent ☐columella H root cap L root hairs |
| ☐ Lateral root | ☐epidermis ☐trichoblast ☐atrichoblast ☐cortex ☐endodermis ☐initials ☐flanking cells ☐vascular ☐lateral root cap |
| ☐ Shoot apical meristem | ☐shoot apical meristem |

X in the Vasculature (Vs) of the cotyledon and Rosette leaf (Rs)
X in the Epidermis (Ep) and Root hair (Rh), of the root
X in the seedling root and root cap
Induction Screens 1. Drought    No differences observed.
2. Drought    No differences observed.
Promoter utility Trait Area:    PGD, Stress
Sub-trait Area: Drought, Root Architecture, Nutrient Uptake
Utility:    Among other uses this promoter sequence can be useful to improve: Modification of growth and development, especially of flower development. Improvements to nectary tissue and nectar production, and improvements in insect and pollination (outcrossing) biology. Modulation of water and nutrient uptake, loading and transport.

Note: Nectaries are secretory structures that produce nectar, a solution composed mainly of sugars. Carpels, stamen, sepals, and nectary vasculature are derived from vascular bundles of the receptacle.
    Endogenous promoter is down-regulated in shoots, siliques and flowers.

| Promoter Expression Report #130 | |
|---|---|
| Construct: | YP0382 |
| Promoter candidate I.D: | 11768592 |
| cDNA I.D: | 12735575 (OCKHAM3-CD) |
| Lines expressing: | -04, -05 |

Sequence (SEQ ID NO: 99):

gcaaacaataatttatcgtaagagttttttaaaattcgttggaacttggaagggattttaaatattattttgttttccttcattttataggttaataat tgtcaaagatacaactcgatggaccaaaataaaataataaaattcgtcgaatttggtaaagcaaaacggtcgaggatagctaatatttatgcgaaacccgt tgtcaaagcagatgttcagcgtcacgcacatgccgcaaaaagaatatacatcaacctcttttgaacttcacgccgttttttaggcccacaataatgctacg tcgtcttctgggttcaccctcgttttttttttaaacttctaaccgataaaataaatggtccactatttcttttcttctctgtgtattgtcgtcagagatgg tttaaaagttgaaccgaactataacgattctcttaaaatctgaaaaccaaactgaccgattttcttaactgaaaaaaaaaaaaaaaactgaatttaggc caacttgttgtaatatcacaaagaaaattctacaatttaattcatttaaaaataaagaaaaatttaggtaacaatttaactaagtggtctatctaaatctt gcaaattctttgactttgaccaaacacaacttaagttgacagccgtctcctctctgttgtttccgtgttattaccgaaatatcagaggaaagtccactaaa ccccaaatattaaaaatagaaacattactttctttacaaaaggaatctaaattgatccctttcattcgtttcactcgtttcatatagttgtatgtatatat gcgtatgcatcaaaaagtctctttatatcctcagagtcacccaatcttatctctctctccttcgtcctcaagaaaagtaattctctgtttgtgtagttttc tttaccggtgaattttctcttcgttttgtgcttcaaacgtcacccaaatcaccaagatcgatcaaaatcgaaacttaacgtttcagaaga

| Promoter Expression Report #131 | |
|---|---|
| Promoter Tested In: | *Arabidopsis thaliana*, Wassilewskija (WS) ecotype |

Spatial expression summary:

| | |
|---|---|
| Flower | H filament H anther H stomata |
| Silique | H ovule |
| Ovule | Post-fertilization: H outer integument H seed coat H chalaza |
| Leaf | L vascular H stomata |
| Primary Root | H epidermis |

Observed expression pattern:

T1 mature: Very high GFP expression levels in stamens of developing flowers. Low expression in vasculature of leaves and guard cells throughout plant. High expression in outer integument of ovules and in seed coats. High incidence of aborted ovules. T2 seedling: Low expression in root epidermal cells.

| | |
|---|---|
| Expected expression pattern: | Drought inducible |
| Selection Criteria: | Ceres, Inc. Expression data |
| Gene: | product = "protein phosphatase 2C (PP2C), putative" |
| GenBank: | NM_125312 *Arabidopsis thaliana* protein phosphatase 2C (PP2C), putative (At5g59220) mRNA, complete cds gi\|30697191\|ref\|NM_125312.2\|[3O697191] |
| Source Promoter Organism: | *Arabidopsis thaliana*, Ws |
| Vector: | pNewbin4-HAP1-GFP |
| Marker Type: | GFP-ER |
| Generation Screened: | XT1 Mature   XT2 Seedling   ☐T2 Mature   ☐T3 Seedling |

Inductions completed:

| Treatment: | Age: | Gen: | Time points: | Events Screened/ Response | Response: |
|---|---|---|---|---|---|
| 1. ABA 100 uM | 7 days | T2 | 6 Hr | 2/1 | Yes |
| | | | 16 Hr post-treatment | 2/2 | Yes |
| 2. Drought | 7 days | T2 | 3 Hr air dry | 2/0 | No |
| 3. Drought | 4 weeks | T2 | 10–12 days no H20 | 2/2 | Yes |

Inducible expression summary:

| Treatment: | Time point induced: | Organs induced: | Tissues induced: |
|---|---|---|---|
| 1. ABA 100 uM | 6 Hr | Leaf | Vasculature |
| | 16 Hr post-treatment | Cotyledons | Vasculature, Guard cells |
| | | Hypocotyl | Epidermis, Vasculature |
| | | Leaf | Epidermis, Vasculature, Guard cells |
| 3. Drought | 10–12 days no H20 | Flowers | Sepals, Epidermis, Guard cells |
| | | Leaf | Epidermis, Mesophyll |
| | | Stem | Epidermis |

-continued

Promoter Expression Report #131

T1 Mature Plant Expression Organs/Tissues screened
Events Screened: n = 4     Events Expressing: n = 2
GFP Expression Detected

| | |
|---|---|
| X Flower | ☐pedicel ☐receptacle ☐nectary ☐sepal ☐petal H filament H anther ☐pollen ☐carpel ☐style ☐papillae ☐vascular ☐epidermis H stomata ☐trichome ☐silique |
| X Silique | ☐stigma ☐style ☐carpel ☐septum ☐placentae ☐transmitting tissue ☐vascular ☐epidermis ☐stomata ☐abscission zone H ovule |
| X Ovule | Pre-fertilization: ☐inner integument ☐outer integument ☐embryo sac ☐funiculus ☐chalaza ☐micropyle ☐gametophyte |
| | Post-fertilization: ☐zygote ☐embryo sack ☐funiculus ☐inner integument H outer integument ☐endothelium H seed coat ☐primordia H chalaza ☐micropyle ☐early endosperm ☐mature endosperm ☐embryo |
| ☐ Embryo | ☐suspensor ☐preglobular ☐globular ☐heart ☐torpedo ☐late ☐mature ☐provascular ☐hypophysis ☐radicle ☐cotyledons ☐hypocotyl |
| ☐ Stem | ☐epidermis ☐cortex ☐vascular ☐xylem ☐phloem ☐pith ☐stomata ☐trichome |
| X Leaf | ☐petiole ☐mesophyll L vascular ☐epidermis ☐trichome ☐primordia H stomata ☐stipule ☐margin |
| ☐ Shoot apical meristem | ☐shoot apical meristem ☐flower primordium |

X in the Guard cells (Gc) and Seed coat (Sc) of the inflorescence meristem
X in the Stamen (St) of the flower
X in the Seed coat (Sc) of the developing seed
X in the Chalaza (Ch) and Outer integument (Oi) of aborted ovules
X in the Guard cells (Gc) and Vasculature (Vs) of the leaf
T2 Seedling Expression     Tissues Screened
Events Screened: n = 2     Events Expressing: n = 2
Seedlings expressing/Seedlings screened
Event-01: 4/6
Event-02: 4/5
☐ Scheduled
GFP Expression Detected

| | |
|---|---|
| ☐ Hypocotyl | ☐epidermis ☐cortex ☐vascular ☐xylem ☐phloem ☐stomata |
| ☐ Cotyledon | ☐mesophyll ☐vascular ☐epidermis ☐margin ☐stomata ☐hydathode |
| ☐ Rosette Leaf | ☐mesophyll ☐vascular ☐epidermis ☐trichome ☐petiole ☐primordia ☐stomata ☐stipule ☐margin ☐hydathode |
| X Primary Root | H epidermis ☐trichoblast ☐atrichoblast ☐cortex ☐endodermis ☐vascular ☐xylem ☐phloem ☐pericycle ☐quiescent ☐columella ☐root cap ☐root hairs |
| ☐ Lateral root | ☐epidermis ☐trichoblast ☐atrichoblast ☐cortex ☐endodermis ☐initials ☐flanking cells ☐vascular ☐lateral root cap |
| ☐ Shoot apical meristem | ☐shoot apical meristem |

X in the Epidermis (Ep) of the seedling root
Promoter utility

| | |
|---|---|
| Trait Area: | PG&D, Nutrients, Seed Biology |
| Sub-trait Area: | Seed size, heat tolerance, drought |
| Utility: | Among other uses this promoter sequence can be useful to improve: Modulation of seed size and seed shape by transgene-induced alteration of endosperm loading and/or integument growth. Modulation of flower structure and development especially stamen and anther development. Modulation of root growth and improved water and nutrient loading and transport. Engineering of male sterility and manipulation of stamen and anther development. Improved drought and heat stress tolerance. Improved seedling performance in drought and heat stress conditions. Making longer filaments to improve fertility. |

Notes: Sulpice R, Tsukaya H, Nonaka H, Mustardy L, Chen TH, Murata N.
Enhanced formation of flowers in salt-stressed *Arabidopsis* after genetic engineering of the synthesis of glycine betaine. Plant J. 2003 Oct; 36(2): 165–76.
Saez A, Apostolova N, Gonzalez-Guzman M, Gonzalez-Garcia MP, Nicolas C, Lorenzo O, Rodriguez PL.
Gain-of-function and loss-of-function phenotypes of the protein phosphatase 2C HAB1 reveal its role as a negative regulator of abscisic acid signalling. Plant J. 2004 Feb; 37(3):354–369.
Tahtiharju S, Palva T. Antisense inhibition of protein phosphatase 2C accelerates cold acclimation in *Arabidopsis thaliana*. Plant J. 2001 May; 26(4): 461–70.
Endogenous promoter is induced in drought and drought-like conditions.

| | |
|---|---|
| Construct: | YP0388 |
| Promoter candidate I.D: | 11768590 |
| cDNA I.D: | 13593066 (OCKHAM3-CD) |
| Lines expressing: | YP0388 -01, -05 |

Sequence (SEQ ID NO: 100):

```
agaagtattcacgcaccaaggttatatttgtagtgacatattctacaattatcacattttctcttatgtttcgtagtcgcagatggtcaatttttctat
aataatttgtccttgaacacaccaaactttagaaacgatgatatataccgtattgtcacgctcacaatgaaacaaacgcgatgaatcgtcatcaccagcta
aaagcctaaaacaccatcttagttttcactcagataaaaagattatttgtttccaacctttctattgaattgattagcagtgatgacgtaattagtgatag
tttatagtaaaacaaatggaagtggtaataaatttacacaacaaaatatggtaagaatctataaaataagaggttaagagatctcatgttatattaaatga
ttgaaagaaaaacaaactattggttgatttccatatgtaatagtaagttgtgatgaaagtgatgacgtaattagttgtatttatagtaaaacaaattaaaa
tggtaaggtaaatttccacaacaaaacttggtaaaaatcttaaaaaaaaaaaagaggtttagagatcgcatgcgtgtcatcaaaggttcttttcactt
aggtctgagtagtgttagactttgattggtgcacgtaagtgtttcgtatcgcgatttaggagaagtacgttttacacgtggacacaatcaacggtcaagat
ttcgtcgtccagatagaggagcgatacgtcacgccattcaacaatctcctcttcttcattccttcattttgattttgagttttgatctgcccgttcaaaag
tctcggtcatctgcccgtaaatataaagatgattatatttatttatatcttctggtgaaagaagctaatataaagcttccatggctaatcttgtttaagct
tctcttcttcttctctctcctgtgtctcgttcactagttttttttcgggggagagtgatggagtgtgtttgttgaatagttttgacgatca
```

| Promoter Expression Report #133 |
|---|

Promoter Tested In: *Arabidopsis thaliana*, Wassilewskija (WS) ecotype
Spatial expression summary:

| | |
|---|---|
| Flower | H sepal H petal H anther H style |
| Silique | H style H ovule |
| Ovule | Prefertilization: H outer integument |
| | Postfertilization: H outer integument L seed coat |
| Leaf | H vascular |
| Primary Root | H epidermis |

Observed expression pattern: T1 mature: High GFP expression in the style, sepals, petals, and anthers in flowers. Expressed in outer integuments of ovule primordia through developing seed stages and in remnants of aborted ovules. High vasculature expression in leaf. T2 seedling: Medium to low root epidermal expression at root transition zone decreasing toward root tip. Specific to epidermal cells flanking lateral roots.

| | |
|---|---|
| Expected expression pattern: | Drought-inducible |
| Selection Criteria: | Ceres expression data |
| Gene: | PAR-related protein |
| GenBank: | NM_124618 *Arabidopsis thaliana* photoassimilate-responsive protein PAR-related protein (At5g52390) mRNA, complete cds gi\|30696178\|ref\|NM_124618.2\|[30696178] |
| Source Promoter Organism: | *Arabidopsis thaliana*, Ws ecotype |
| Vector: | pNewbin4-HAP1-GFP |
| Marker Type: | GFP-ER |
| Generation Screened: | XT1 Mature   XT2 Seedling   ☐T2 Mature   ☐T3 Seedling |
| Inductions completed: | |

| Treatment: | Age: | Gen: | Time points: | Events Screened/ Response | Response: |
|---|---|---|---|---|---|
| 1. Drought | 7 days | T2 | 3 Hrs air dry | 2/0 | No |
| 2. Drought | 4 weeks | T2 | 10–12 days no H20 | 2/2 | Yes |

Inducible expression summary:

| Treatment: | Time point induced: | Organs induced: | Tissues induced: |
|---|---|---|---|
| 2. Drought | 10–12 days no H20 | Flowers | Sepals, Petals, Anthers, Silique |
| | | Silique | Carpels, Epidermis, Cortex |
| | | Leaf | Epidermis, Mesophyll |

T1 Mature Plant Expression Organs/Tissues screened
Events Screened: n = 4     Events Expressing: n = 3
GFP Expression Detected

| | |
|---|---|
| X Flower | ☐pedicel ☐receptacle ☐nectary H sepal H petal ☐filament H anther ☐pollen ☐carpel H style ☐papillae ☐vascular ☐epidermis ☐stomata ☐trichome ☐silique |
| X Silique | ☐stigma H style ☐carpel ☐septum ☐placentae ☐funiculus ☐transmitting tissue ☐vascular ☐epidermis ☐stomata ☐abscission zone H ovule |
| X Ovule | Pre-fertilization: ☐inner integument H outer integument ☐embryo sac ☐funiculus ☐chalaza ☐micropyle ☐gametophyte |
| | Post-fertilization: ☐zygote ☐embryo sack ☐inner integument H outer integument ☐funiculus ☐endothelium L seed coat ☐primordia ☐chalaza ☐micropyle ☐early endosperm ☐mature endosperm ☐embryo |
| ☐ Embryo | ☐suspensor ☐preglobular ☐globular ☐heart ☐torpedo ☐late ☐mature ☐provascular ☐hypophysis ☐radicle ☐cotyledons ☐hypocotyl |

-continued

Promoter Expression Report #133

☐ Stem ☐epidermis ☐cortex ☐vascular ☐xylem ☐phloem ☐pith ☐stomata ☐trichome
X Leaf ☐petiole ☐mesophyll H vascular ☐epidermis ☐trichome ☐primordia
☐stomata ☐stipule ☐margin
☐ Shoot apical meristem ☐shoot apical meristem ☐flower primordium
X in the Style (Sy) of the Silique (Si)
X in the Anther (An), Petal (Pe) and Sepal (Se) of the flower
X in the anther locules
X in the Outer integument (Oi) of the normal Ovule (Ov) and aborted ovule
X in the H dathode (Hd) and Vasculature (Vs) of the leaf
T2 Seedling Expression    Tissues Screened
Events Screened: n = 2    Events Expressing: n = 2
Seedlings expressing/Seedlings screened
Event-01: 2/4
Event-02: 5/5
☐ Scheduled
GFP Expression Detected ☐ Hypocotyl ☐epidermis ☐cortex ☐vascular ☐xylem ☐phloem ☐stomata
☐ Cotyledon ☐mesophyll ☐vascular ☐epidermis ☐margin ☐stomata
☐hydathode
☐ Rosette Leaf ☐mesophyll ☐vascular ☐epidermis ☐trichome ☐petiole
☐primordia ☐stomata ☐stipule ☐margin ☐hydathode
X Primary Root H epidermis ☐trichoblast ☐atrichoblast ☐cortex ☐endodermis
☐vascular ☐xylem ☐phloem ☐pericycle ☐quiescent
☐columella ☐root cap ☐root hairs
☐ Lateral root ☐epidermis ☐trichoblast ☐atrichoblast ☐cortex ☐endodermis
☐initials ☐flanking cells ☐vascular ☐lateral root cap
☐ Shoot apical meristem ☐shoot apical meristem
X in the Epidermis (Ep) of the root
Promoter utility Trait Area:       Abiotic stresses, PG&D
Sub-trait Area:   Drought, Root architecture
Utility:          Among other uses this promoter sequence can be useful to
                  improve: Modulation self-incompatability including gametophytic
                  incompatibility. Modulation of flower development and structure. Modulation
                  of seed size and shape. Altered seed uptake of water and mineral ions and an
                  altered seed dormancy and germination. Modulation of drought responses
                  including leaf and flower wilting, ovule abortion, infertility and seed abortion.
Notes: Fujita K, Okada M, Lei K, Ito J, Ohkura K, Adu-Gyamfi JJ, Mohapatra PK.
Effect of P-deficiency on photoassimilate partitioning and rhythmic changes in fruit and stem diameter of tomato
(*Lycopersicon esculentum*) during fruit growth.
J Exp Bot. 2003 Nov; 54(392): 2519–28.
Murillo I, Roca R, Bortolotti C, Segundo BS.
Engineering photoassimilate partitioning in tobacco plants improves growth and productivity and provides
pathogen resistance.
Plant J. 2003 Nov; 36(3):330–41.
The endogenous gene is consistently induced under drought conditions but not surrogate drought
treatments.
Construct:             YP0396
Promoter candidate I.D: 11768788
cDNA I.D:              12646726
Lines expressing:      YP0396 -02, -03

Sequence (SEQ ID NO: 101):

catagtaaaagtgaatttaatcatactaagtaaaataagataaaacatgttatttgaatttgaatatcgtgggatgcgtatttcggtatttgattaaaggt ctggaaaccggagctcctataacccgaataaaaatgcataacatgttcttccccaacgaggcgagcgggtcagggcactagggtcattgcaggcagctcat aaagtcatgatcatctaggagatcaaattgtatgtcggccttctcaaaattacctctaagaatctcaaacccaatcatagaacctctaaaaagacaaagtc gtcgctttagaatgggttcggttttggaaccatatttcacgtcaatttaatgtttagtataatttctgaacaacagaattttggatttatttgcacgtat acaaatatctaattaataaggacgactcgtgactatccttacattaagtttcactgtcgaaataacatagtacaatacttgtcgttaatttccacgtctca agtctataccgtcatttacggagaaagaacatctctgtttttcatccaaactactattctcactttgtctatatatttaaaattaagtaaaaagactcaa tagtccaataaaatgatgaccaaatgagaagatggttttgtgccagattttaggaaaagtgagtcaaggtttcacatctcaaatttgactgcataatcttc gccattaacaacggcattatatatgtcaagccaattttccatgttgcgtacttttctattgaggtgaaaatatgggtttgttgattaatcaaagagtttgc -continued
ctaactaatataactacgacttttcagtgaccattccatgtaaactctgcttagtgtttcatttgtcaacaatattgtcgttactcattaaatcaaggaa aaatatacaattgtataattttcttatattttaaaattaattttgatgtattacccctttataaataggctatcgctacaacaccaataac

---

Promoter Expression Report #135.02

Promoter Tested In: *Arabidopsis thaliana*, WS ecotype
Spatial expression summary:

Flower L anther
Observed expression pattern:

T1 mature: Low expression in anther walls early in stamen development through pre-dehiscence stage. Not in pollen. T2 seedling: No expression observed.

| | |
|---|---|
| Expected expression pattern: | Root hairs |
| Selection Criteria: | Mature root exp in endodermis |
| Gene: | CYCD1 |
| GenBank: | NM_105689 *Arabidopsis thaliana* cyclin delta-1 (CYCD1) (At1g70210) mRNA, complete cds gi30698007\|refNM_105689.2\|[30698007]. Go function: cyclin-dependent protein kinase regulator |
| Source Promoter Organism: | *Arabidopsis thaliana*, Columbia ecotype |
| Vector: | pNewbin4-HAP1-GFP |
| Marker Type: | GEP-ER |
| Generation Screened: | XT1 Mature   XT2 Seedling   ☐T2 Mature   ☐T3 Seedling |

T1 Mature Plant Expression Organs/Tissues screened
Events Screened: n = 6   Events Expressing: n = 2
GFP Expression Detected

| | |
|---|---|
| X Flower | ☐pedicel ☐receptacle ☐nectary ☐sepal ☐petal ☐filament ☐anther ☐pollen ☐carpel ☐style ☐papillae ☐vascular ☐epidermis ☐stomata ☐trichome ☐silique |
| ☐ Silique | ☐stigma ☐style ☐carpel ☐septum ☐placentae ☐transmitting tissue ☐vascular ☐epidermis ☐stomata ☐abscission zone ☐ovule |
| ☐ Ovule | Pre-fertilization: ☐primordia ☐inner integument ☐outer integument ☐embryo sac ☐funiculus ☐chalaza ☐micropyle ☐gametophyte Post-fertilization: ☐zygote ☐suspensor ☐embryo sack ☐inner integument ☐outer integument ☐endothelium ☐seed coat ☐primordia ☐chalaza ☐micropyle ☐early endosperm ☐mature endosperm ☐embryo |
| ☐ Embryo | ☐suspensor ☐preglobular ☐globular ☐heart ☐torpedo ☐late ☐mature ☐provascular ☐hypophysis ☐radicle ☐cotyledons ☐hypocotyl |
| ☐ Stem | ☐epidermis ☐cortex ☐vascular ☐xylem ☐phloem ☐pith ☐stomata ☐trichome |
| ☐ Leaf | ☐petiole ☐mesophyll ☐vascular ☐epidermis ☐trichome ☐primordia ☐stomata ☐stipule ☐margin |
| ☐Shoot apical meristem X in the Filament (Fi) | ☐shoot apical meristem ☐flower primordium |

T2 Seedling Expression   Tissues Screened
Events Screened: n = 2   Events Expressing: n = 0
Seedlings expressing/Seedlings screened
Event-01: 0/6
Event-02: 0/6
☐Scheduled
No GFP Expression Detected Promoter utility

| | |
|---|---|
| Trait Area: | PG&D |
| Sub-trait Area: | Yield - for hybrid systems |
| Utility: | Modulation of anther dehiscense and breeding system. Engineering of male sterility. |
| Construct: | PT0506 |
| Promoter candidate I.D: | 11768709 |
| cDNA I.D: | 13497447 |
| Lines expressing: | PT0506 -03, -05 |

Sequence (SEQ ID NO: 102):

aggacttccactactctttcccacacgctccagaccactgtttgctttcctctgattaaccaatctcaattaaactactaatttataattcaagataatta gataaccaatcttaaaatttggaatcttcttccctcacttgatattacaaaaaaaaactgatttatcatacggttaattcaagaaaacagcaaaaaatt gcactataatgcaaaacatcaattaattacattcgattaaaaaatcatcattgaatctaaaatggcctcaaatctattgagcatttgtcatgtgcctaaaa -continued

```
tggttcaggagttttacatctaatcacataaaaagcaaacaataaccaaaaaaattgcattttagcaaatcaaatacttatatatatacgtatgattaagc gtcatgactttaaaacctctgtaaaattttgatttattttttcgatgcttttattttttaaccaatagtaataaagtccaaatcttaaatacgaaaaatgt ttctttctaagcgaccaacaaaatggtccaaatcacagaaaatgttccataatccaggcccattaagctaatcaccaagtaatacattacacgtcaccaat taatacattacacgtacggccttctctcttcacgagtaatatgcaaacaaacgtacattagctgtaatgtactcactcatgcaacgtcttaacctgccacg tattacgtaattacaccactccttgttcctaacctacgcatttcactttagcgcatgttagtcaaaaaacacaaacataaactacaaataaaaaaactcaa aacaaaacccaatgaacgaacggaccagccccgtctcgattgatggaacagtgacaacagtcccgttttctcgggcataacggaaacggtaaccgtctctc tgtttcatttgcaacaacaccatttttataaataaaaacacatttaaataaaaaattattaaaacctcaaaaaatctctgtttcttgttta
```

---

Promoter Expression Report #136.02

---

Promoter Tested In: *Arabidopsis thaliana*, WS ecotype
Spatial expression summary:

| | |
|---|---|
| Flower | H filament H anther L vascular |
| Cotyledon | L vascular L petiole |
| Primary Root | L epidermis |

Observed expression pattern:
T1 mature: High expression at vascular connective tissue between locules of anther.
T2 seedling: Low expression in root epidermal cells and vasculature of petioles.

| | |
|---|---|
| Expected expression pattern: | Shoot apex including leaf primordia and parts of leaves |
| Selection Criteria: | Ceres expression data. Greater than 5x up in stm microarray |
| Gene: | Major intrinsic protein (MIP) |
| GenBank: | NM_106724 *Arabidopsis thaliana* major intrinsic protein (MIP) family (At1g80760) mRNA, complete cds gi\|30699534\|ref\|NM_106724.2\|[30699534]. |
| Source Promoter Organism: | *Arabidopsis thaliana*, Columbia ecotype |
| Vector: | pNewbin4-HAP1-GFP |
| Marker Type: | GFP-ER |
| Generation Screened: | XT1 Mature   X T2 Seedling   ☐T2 Mature   ☐T3 Seedling |

T1 Mature Plant Expression Organs/Tissues screened
Events Screened: n = 2    Events Expressing: n = 2
GFP Expression Detected

| | |
|---|---|
| X Flower | ☐pedicel ☐receptacle ☐nectary ☐sepal ☐petal H filament H anther ☐pollen ☐carpel ☐style ☐papillae L vascular ☐epidermis ☐stomata ☐trichome ☐silique |
| ☐ Silique | ☐stigma ☐style ☐carpel ☐septum ☐placentae ☐transmitting tissue ☐vascular ☐epidermis ☐stomata ☐abscission zone ☐ovule |
| ☐ Ovule | Pre-fertilization: ☐primordia ☐inner integument ☐outer integument ☐embryo sac ☐funiculus ☐chalaza ☐micropyle ☐gametophyte Post-fertilization: ☐zygote ☐suspensor ☐embryo sack ☐inner integument ☐outer integument ☐endothelium ☐seed coat ☐primordia ☐chalaza ☐micropyle ☐early endosperm ☐mature endosperm ☐embryo |
| ☐ Embryo | ☐suspensor ☐preglobular ☐globular ☐heart ☐torpedo ☐late ☐mature ☐provascular ☐hypophysis ☐radicle ☐cotyledons ☐hypocotyl |
| ☐ Stem | ☐epidermis ☐cortex ☐vascular ☐xylem ☐phloem ☐pith ☐stomata ☐trichome |
| ☐ Leaf | ☐petiole ☐mesophyll ☐vascular ☐epidermis ☐trichome ☐primordia ☐stomata ☐stipule ☐margin |
| ☐ Shoot apical meristem | ☐shoot apical meristem ☐flower primordium |

X in the Anther (An) and Vascular (Vs) of the anther
T2 Seedling Expression   Tissues Screened
Events Screened: n = 2    Events Expressing: n = 2
Seedlings expressing/Seedlings screened
Event-01: 1/6
Event-02: 3/6
☐ Scheduled
GFP Expression Detected

| | |
|---|---|
| ☐ Hypocotyl | ☐epidermis ☐cortex, ☐vascular ☐xylem ☐phloem ☐stomata |
| X Cotyledon | ☐mesophyll L vascular ☐epidermis ☐margin ☐stomata ☐hydathode L petiole |
| ☐ Rosette Leaf | ☐mesophyll ☐vascular ☐epidermis ☐trichome ☐petiole ☐primordia ☐stomata ☐stipole ☐margin ☐hydathode |
| X Primary Root | ☐epidermis ☐trichoblast ☐atrichoblast ☐cortex ☐endodermis ☐vascular ☐xylem ☐phloem ☐pericycle ☐quiescent ☐columella ☐root cap ☐root hairs |
| ☐ Lateral root | ☐epidermis ☐trichoblast ☐atrichoblast ☐cortex ☐endodermis ☐initials ☐flanking cells ☐vascular ☐lateral root cap |
| ☐ Shoot apical meristem | ☐shoot apical meristem |

X in the root and Vascular (Vs) of the Pedicle (Pd)

Promoter Expression Report #136.02

Promoter utility

Trait Area: PG&D, Nutrients
Sub-trait Area: Drought, Low nitrogen
Utility: Modulation of water and nutrient uptake. Modification of seedling vitality and establishment. Modulation of dehiscence properties.
Notes: cd00333 MIP: Major intrinsic protein (MIP) superfamily. Members of the MIP superfamily function as membrane channels that selectively transport water, small neutral molecules, and ions out of and between cells. The channel proteins share a common fold: the N-terminal cytosolic portion followed by six transmembrane helices, which might have arisen through gene duplication. On the basis of sequence similarity and functional characteristics, the superfamily can be subdivided into two major groups: water-selective channels called aquaporins (AQPs) and glycerol uptake facilitators (GlpFs). AQPs are found in all three kingdoms of life, while GlpFs have been characterized only within microorganisms. [cd00333|24161]
Construct: PT0511
Promoter candidate I.D: 11768782
cDNA I.D: 12711931 (OCKHAM3-CD)
Lines expressing: PT0511 -04, -05

Sequence (SEQ ID NO: 103):

```
tttaattttgattctaaagagttgtgacgggtcatcacagattcttcgttt
ttttatagatagaaaaggaataacgttaaaagtatacaaattatatgcaag
agtcattcgaaagaattaaataaagagatgaactcaaaagtgattttaaat
tttaatgataagaatatacatctcacagaaatcttttatttgacatgtaaa
atcttgttttcacctatcttttgttagtaaacaagaatatttaatttgagc
ctcacttggaacgtgataataatatacatcttatcataattgcatattttg
cggatagttttttgcatggggagattaaaggcttaataaagccttgaatttc
cgaggggaggaatcatgttttatacttgcaaactatacaaccatctgcatc
gataattggtgttaatacatgcaaggattatacactaaaacaaatcattta
tttccttacaaaaagagagtcgactgtgagtcacattctgtgacaaggaaa
ggtcaagaaccatcgcttttatcatcattctctttgctaacaacttacaac
cacacaaacgcaagagttccattctcatggagaagaacatattatgcaaaa
taatgtatgtcgatcgatagagaaaaggatccacaattattgctccatctc
aaaagcttctttagtacacgatacatgtatcatgtaaatagaaatatgaaa
gatacaatacacgacccattctcataaagatagcaacatttcatgttatgt
aaagagtcttccttaggacacatgcattaaaactaaggattaccaacccac
atactcctcactccaaccaaatatcaatcatctattttgggtccttcactc
ttaagtcaactctcatgccttcctctataaataccgtaccctacgcatccc
ttagttctacatcacataaaaacaatcatagcaaaaacatatatcctcaaa
ttaattagatctcatctatctctaccctcga
```

Promoter Expression Report #141

Promoter Tested In: *Arabidopsis thaliana*, WS ecotype
Spatial expression summary:

Flower          H stomata
Primary Root    H pericycle
Lateral root    H initials
Observed expression pattern:

T1 mature: Guard cell expression in flowers.
T2 seedling: Highly specific GFP expression in pericycle cells at positions of lateral root initiation.
Expected expression pattern: Leaf Vasculature high expression
Selection Criteria: Mutant lines- CSHL gene trap GT31
Gene: Expressed protein of unknown function (DUF810).
GenBank: NM_120779 *Arabidopsis thaliana* expressed protein (At5g06970) mRNA, complete cds gi|22326640|ref|NM_120779.2|[22326640]
Source Promoter Organism: *Arabidopsis thaliana* WS
Vector: pNewbin4-HAP1-GFP
Marker Type: GFP-ER -continued Promoter Expression Report #141

| | |
|---|---|
| Generation Screened: | XT1 Mature  XT2 Seedling  ☐T2 Mature  ☐T3 Seedling |
| T1 Mature Plant Expression | Organs/Tissues screened |
| Events Screened: n = 6 | Events Expressing: n = 2 |
| GFP Expression Detected | |
| X Flower | ☐pedicel ☐receptacle ☐nectary ☐sepal ☐petal ☐filament ☐anther ☐pollen ☐carpel ☐style ☐papillae ☐vascular ☐epidermis H stomata ☐trichome ☐silique |
| ☐ Silique | ☐stigma ☐style ☐carpel ☐septum ☐placentae ☐transmitting tissue ☐vascular ☐epidermis ☐stomata ☐abscission zone ☐ovule |
| ☐ Ovule | Pre-fertilization: ☐primordia ☐inner integument ☐outer integument ☐embryo sac ☐funiculus ☐chalaza ☐micropyle ☐gametophyte  Post-fertilization: ☐zygote ☐suspensor ☐embryo sack ☐inner integument ☐outer integument ☐endothelium ☐seed coat ☐primordia ☐chalaza ☐micropyle ☐early endosperm ☐mature endosperm ☐embryo |
| ☐ Embryo | ☐suspensor ☐preglobular ☐globular ☐heart ☐torpedo ☐late ☐mature ☐provascular ☐hypophysis ☐radicle ☐cotyledons ☐hypocotyl |
| ☐ Stem | ☐epidermis ☐cortex ☐vascular ☐xylem ☐phloem ☐pith ☐stomata ☐trichome |
| ☐ Leaf | ☐petiole ☐mesophyll ☐vascular ☐epidermis ☐trichome ☐primordia ☐stomata ☐stipule ☐margin |
| ☐ Shoot apical meristem | ☐Shoot apical meristem ☐Flower primordium |
| X Guard Cells (GC) that define the stomate | |
| T2 Seedling Expression | Tissues Screened |
| Events Screened: n = 2 | Events Expressing: n = 2 |
| Seedlings expressing/Seedlings screened | |
| Event-01: 1/6 | |
| Event-02: 2/6 | |
| ☐Scheduled | |
| GFP Expression Detected | |
| ☐ Hypocotyl | ☐epidermis ☐cortex ☐vascular ☐xylem ☐phloem ☐stomata |
| ☐ Cotyledon | ☐mesophyll ☐vascular ☐epidermis ☐margin ☐stomata ☐hydathode |
| ☐ Rosette Leaf | ☐mesophyll ☐vascular ☐epidermis ☐trichome ☐petiole ☐primordia ☐stomata ☐stipule ☐margin ☐hydathode |
| X Primary Root | ☐epidermis ☐trichoblast ☐atrichoblast ☐cortex ☐endodermis ☐vascular ☐xylem ☐phloem H pericycle ☐quiescent ☐columella ☐root cap ☐root hairs |
| X Lateral root | ☐epidermis ☐trichoblast ☐atrichoblast ☐cortex ☐endodermis H initials ☐flanking cells ☐vascular ☐lateral root cap |
| ☐Shoot apical meristem | ☐Shoot apical meristem |
| X Lateral root (Lr), Pericycle (Pr) | |
| Promoter utility | |
| Trait Area: | Water use efficiency, nutrients, seed yield |
| Sub-trait Area: | Low nitrogen tolerance, nitrogen use efficiency (20–22), nitrogen utilization, ovule/seed abortion, seed enhancement, seed number, harvest index |
| Utility: | Root initiation regulate number and growth rate of lateral roots to improve lodging tolerance and nutrient acquisition, such as improved nitrate uptake. |
| Construct: | YP0262 |
| Promoter candidate I.D: | 11768751 |
| cDNA I.D: | 12653589 (OCKHAM3-CD) |
| Lines expressing: | YP0262 -21, -22 |

Sequence (SEQ ID NO: 104):

```
tacttcgtaaggttaatatatgatatagtgggcctgacaaaaaatcatatg
ggcttgacaaaatctatgtttatatccagttcggtccaaaattcgaaaca
taaacaatgtggaaagatgtgttggctaatctgataccatgtcaaaaaac
atagaagttcttgtgaggtttcttgtttattcatgtggaggcaattgccct
tgtatacaaggcttgtgaaagaagtaaagaagataagtttaggaagaaggt
ggcccatgagggcccaatattcatatcattagtgaaaagcataggaatttc
aacttgtaatattaaaatcagtgataattgaataacattaatctttttaag
atttccaaattaattcaaatcttcattaagaaataagatttaggaatacta
aaaagctaaataattatctaattacttaaaatcagtaatgaaaattaatat
tatactcccatagtatattttcttcactatgaatgaagttgagacttcaat
tttgacaaattcggtgttctggaataacaaaagaagtcaaagaaagaaaat
tagggagatagagtaaattaaagttgagacaaatcagcttcattttgtttt
tcccaaataataatatacagatagatctttcggccccggcgcattctctag
atttgctcatcaccacctcgaaatttctgctcgaagttctccaaaacagtt
```

-continued

```
cattcatctacatttaccagatcatattcgtattcagtcgtctctaaattc tcactaaatcaatccttcctttggataattccggtgtttgcgaggaatctg ttgaaatgattggttagttcagttaaactctacttctaaaactaaatctgc
```

-continued

```
attcaaatgtagtctctagttctcgtacttgaagtagacttgattcgattt gatttactgattcgtggcttttgatttcacaggtcaattggaaatctgaga atccgtgtgactattattgcagctggatcg
```

Promoter Expression Report #142.02

Promoter Tested In: *Arabidopsis thaliana*, WS ecotype
Spatial expression summary:

Primary Root     H epidermis H trichoblast H atrichoblast L root cap H root hairs
Observed expression pattern:

T1 mature: No expression.
T2 seedling: High expression in root epidermal at transition zone decreasing toward root tip.
Expected expression pattern:    Leaf
Selection Criteria:    CSHL gene trap GT318
Gene:    Glycosyl hydrolase family.
GenBank:    NM_115876 *Arabidopsis thaliana*, glycosyl hydrolase family 1 (At3g60130) mRNA, complete cds gi|30695130|ref|NM_115876.2|[30695130]
Source Promoter Organism:    *Arabidopsis thaliana*, WS ecotype
Vector:    pNewbin4-HAP1-GFP
Marker Type:    GFP-ER
Generation Screened:    XT1 Mature    XT2 Seedling    ☐T2 Mature    ☐T3 Seedling
T1 Mature Plant Expression Organs/Tissues screened
Events Screened: n = 3    Events Expressing: n = 0
No GFP Expression Detected T2 Seedling Expression    Tissues Screened
Events Screened: n = 2    Events Expressing: n = 2
Seedlings expressing/Seedlings screened
Event-01: 4/6
Event-02: 3/6
☐ Scheduled
GFP Expression Detected

| | |
|---|---|
| ☐ Hypocotyl | ☐epidermis ☐cortex ☐vascular ☐xylem ☐phloem ☐stomata |
| ☐ Cotyledon | ☐mesophyll ☐vascular ☐epidermis ☐margin ☐stomata ☐hydathode |
| ☐ Rosette Leaf | ☐mesophyll ☐vascular ☐epidermis ☐trichome ☐petiole ☐primordia ☐stomata ☐stipule ☐margin ☐hydathode |
| X Primary Root | H epidermis H trichoblast H atrichoblast ☐cortex ☐endodermis ☐vascular ☐xylem ☐phloem ☐pericycle ☐quiescent ☐columella L root cap H root hairs |
| ☐ Lateral root | ☐epidermis ☐trichoblast ☐atrichoblast ☐cortex ☐endodermis ☐initials ☐flanking cells ☐vascular ☐lateral root cap |
| ☐ Shoot apical meristem | ☐shoot apical meristem |

X in the seedling root, Epidermis (Ep), Root cap (Rc) and Root hair (Rh) of the root
Promoter utility Trait Area:    PG&D, Nutrients
Sub-trait Area:    Drought, Nutrient uptake
Utility:    Modulation of root growth rate, size and shape. Modulation of water and nutrient uptake. Modulation of plant-microbe including plant rhizobium interactions. Useful for making insecticidal proteins for protection against root worm.
Construct:    YP0275
Promoter candidate I.D:    11768836
cDNA I.D:    12668112 (OCKHAM3-CD)
Lines expressing:    YP0275 -21, -22

Sequence (SEQ ID NO: 105):

```
aaacattaatatgtagtaactatgggcgtatgctttacttttaaaatggg
cctatgctataattgaatgacaaggattaaacaactaataaaattgtagat
gggttaagatgacttattttttacttaccaatttataatgggcttcgatg
tactgaaatatatcgcgcctattaacgaggccattcaacgaatgttttaag
ggccctatttcgacattttaaagaacacctaggtcatcattccagaaatgg
atattataggatttagataatttcccacgtttggtttatttatctatttt
tgacgttgaccaacataatcgtgcccaaccgtttcacgcaacgaatttata
tacgaaatatatatatttttcaaattaagataccacaatcaaaacagctgt
tgattaacaaagagatttttttttttggttttgagttacaataacgttag
aggataaggtttcttgcaacgattaggaaatcgtataaaataaaatatgtt
ataattaagtgttttattttataatgagtattaatataaataaaacctgca
aaaggatagggatattgaataataaagagaaacgaaagagcaattttactt
ctttataattgaaattatgtgaatgttatgtttacaatgaatgattcatcg
ttctatatattgaagtaaagaatgagtttattgtgcttgcataatgacgtt
aacttcacatatacacttattacataacatttatcacatgtgcgtctttt
ttttttttactttgtaaaatttcctcacttttaagacttttaatacaatta
ctagtaaaataaagttgcttggggctacacccttctccctccaacaactc
tatttatagataacattatatcaaaatcaaaacatagtccctttcttctat
aaaggttttttcacaaccaaatttccattataaatcaaaaaataaaaactt
aattagtttttacagaagaaaagaaaaca
```

| Promoter Expression Report #143 | |
|---|---|
| Promoter Tested In: | *Arabidopsis thaliana*, Wassilewskija (WS) ecotype |
| Spatial expression summary: | |
| Primary Root | L epidermis L trichoblast L atrichoblast L root hair |
| Observed expression pattern: | |
| T1 mature: No expression. T2 seedling: Low expression in root epidermal cells at transition zone decreasing to expression in single cells at mid root. | |
| Expected expression pattern: | Drought inducible. |
| Selection Criteria: | Ceres, Inc. Expression data |
| Gene: | Unknown protein. |
| GenBank: | NM_101546 *Arabidopsis thaliana* expressed protein (At1g16850) mRNA, complete cds gi\|18394408\|ref\|NM_101546.1\|[18394408] |
| Source Promoter Organism: | *Arabidopsis thaliana*, WS ecotype |
| Vector: | pNewbin4-HAP1-GFP |
| Marker Type: | GFP-ER |
| Generation Screened: | XT1 Mature  XT2 Seedling  ☐T2 Mature  ☐T3 Seedling |
| Inductions completed: | |

| Treatment: | Age: | Gen. | Time points: | Events Screened/Response | Response: |
|---|---|---|---|---|---|
| 1. Drought | 4 wks | T2 | 10–12 d. No H20 | 3/3 | Yes |
| 2. Drought | 7 days | T2 | 3 Hr. Air Dry | 2/0 | No |
| 3. Cold 4C | 7 days | T2 | 2 Hr | 0/3 | No |
| | | | 6 Hr. | 0/3 | No |
| | | | 24 Hr post-treatment | 3/2 | Yes |
| 4. ABA 100 um | 7 days | T2 | 6 Hr. | 2/2 | Yes |

Inducible expression summary:

| Treatment: | Time point induced: | Organs induced: | Tissues induced: |
|---|---|---|---|
| 1. Drought | 10–12 d. No H20: | Flowers | Sepals Petals Guard cells |
| 3. Cold 4C | 24 Hr post-treatment: | Cotyledons | Epidermis Vascular |
| | | Root | Epidermis Vascular |
| 4. ABA 100 um | 6 Hr | Cotyledons | Vascular |

T1 Mature Plant Expression Organs/Tissues screened
Events Screened: n = 3   Events Expressing: n = 0
No GFP Expression Detected T2 Seedling Expression   Tissues Screened
Events Screened: n = 3   Events Expressing: n = 3
Seedlings expressing/Seedlings screened
Event-01: 3/6
Event-02: 3/6
Event-03: 2/6
☐ Scheduled

Promoter Expression Report #143

GFP Expression Detected

| | |
|---|---|
| ☐ Hypocotyl | ☐epidermis ☐cortex ☐vascular ☐xylem ☐phloem ☐stomata |
| ☐ Cotyledon | ☐mesophyll ☐vascular ☐epidermis ☐margin ☐stomata ☐hydathode |
| ☐ Rosette Leaf | ☐mesophyll ☐vascular ☐epidermis ☐trichome ☐petiole ☐primordia ☐stomata ☐stipule ☐margin ☐hydathode |
| X Primary Root | L epidermis L trichoblast L atrichoblast ☐cortex ☐endodermis ☐vascular ☐xylem ☐phloem ☐pericycle ☐quiescent ☐columella ☐root cap L root hairs |
| ☐ Lateral root | ☐epidermis ☐trichoblast ☐atrichoblast ☐cortex ☐endodermis ☐initials ☐flanking cells ☐vascular ☐lateral root cap |
| ☐ Shoot apical meristem | ☐shoot apical meristem |

X in the Epidermis (Ep) and Root hair (Rh) of the seedling root

Promoter utility

| | |
|---|---|
| Trait Area: | PG&D, Nutrients |
| Sub-trait Area: | Drought, Nutrient uptake |
| Utility: | Among other uses this promoter sequence can be useful to improve: Modulation of root growth rate, size and shape. Modulation of leaf growth, size and shape. Modulation of water and nutrient uptake. Modulation of plant-microbe including plant rhizobium interactions. Useful for making insecticidal proteins for protection against root worm. Modulation of drought responses and protection against drought and desiccation. Modulation of cold stress responses and protection against cold stress. |
| Notes: | This promoter may have multiple utilities, both in plant growth and development and in protection against plant stress. In stress, the promoter 11768598 is useful for protecting against drought and cold which are something associated (at high latitude and/or high altitude) and sometimes not associated (in temperate regions), suggesting potentially very versatile utility or protection against abiotic stress. The cold-induction can be very valuable since roots are very sensitive to cold stress. The drought induction in the leaf can protect against water loss through the leaf. Endogenous promoter induced in heat and drought as well as surrogate drought treatments. |
| Construct: | YP0337 |
| Promoter candidate I.D: | 11768598 |
| cDNA I.D: | 12326510 |
| Lines expressing: | YP0337 -01,-02,-03 |

Sequence (SEQ ID NO: 106):

```
taatttttttattttttggaactaacacttattagtttaggtttccatcacc
tatttaattcgtaattcttatacatgcatataatagagatacatatataca
aatttatgatcattttgcacaacatgtgatctcattcattagtatgcatt
atgcgaaaacctcgacgcgcaaaagacacgtaatagctaataatgttactc
atttataatgattgaagcaagacgaaaacaacaacatatatatcaaattgt
aaactagatatttcttaaaagtgaaaaaaacaaagaaatataaaggacaa
ttttgagtcagtctcttaatattaaaacatatatacataaataagcacaaa
cgtggttacctgtcttcatgcaatgtggactttagtttatctaatcaaaat
caaaataaaaggtgtaatagttctcgtcattttttcaaattttaaaaatcag
aaccaagtgattttttgtttgagtattgatccattgtttaaacaatttaaca
cagtatatacgtctcttgagatgttgacatgatgataaaatacgagatcgt
ctcttggttttcgaattttgaactttaatagttttcttttttagggaaact
ttaatagttgtttatcataagattagtcacctaatggttacgttgcagtac
cgaaccaattttttacccttttttctaaatgtggtcgtggcataatttcca
aaagagatccaaaacccggtttgctcaactgataagccggtcggttctggt
ttgaaaaacaagaaataatctgaaagtgtgaaacagcaacgtgtctcggtg
tttcatgagccacctgccacctcattcacgtcggtcattttgtcgtttcac
ggttcacgctctagacacgtgctctgtcccaccatgactttcgctgccga
ctcgcttcgctttgcaaactcaaacatgtgtgtatatgtaagtttcatcct
aataagcatctcttaccacattaattaaaaa
```

Promoter Expression Report #144

Promoter Tested In: *Arabidopsis thaliana*, Wassilewskija (WS) ecotype
Spatial expression summary:
Primary Root      H epidermis H trichoblast H atrichoblast
Observed expression pattern:

T1 mature: No expression.
T2 seedling: Root specific GFP expression. High expression throughout root epidermal cells.

| | |
|---|---|
| Expected expression pattern: | Drought inducible |
| Selection Criteria: | Ceres expression data |
| Gene: | Heat shock transcription factor family |
| GenBank: | NM_113182 *Arabidopsis thaliana* heat shock transcription factor family (At3g22830) |
| Source Promoter Organism: | *Arabidopsis thaliana*, WS ecotype |
| Vector: | pNewbin4-HAP1-GFP |
| Marker Type: | GFP-ER |
| Generation Screened: | XT1 Mature    XT2 Seedling    ☐T2 Mature    ☐T3 Seedling |

Inductions completed:

| Treatment: | Age: | Gen: | Time points: Response | Events Screened/Response: | |
|---|---|---|---|---|---|
| 1. Drought | 7 days | T2 | 3 Hrs air dry | 2/0 | No |
| 2. Drought | 4 weeks | T2 | 10–12 days no H20 | 2/2 | Yes |

Inducible expression summary:

| Treatment: | Time point induced: | Organs induced: | Tissues induced: |
|---|---|---|---|
| 1. Drought | 3 Hrs air dry | None detected. | |
| 2. Drought | 10–12 days no H20 | Leaf | Epidermis, Vascular |

T1 Mature Plant Expression    Organs/Tissues screened
Events Screened: n = 3     Events Expressing: n = 0
No GFP Expression Detected T2 Seedling Expression    Tissues Screened
Events Screened: n = 2     Events Expressing: n = 2
Seedlings expressing/Seedlings screened
Event-01: 4/6
Event-02: 3/4
☐ Scheduled
GFP Expression Detected

| | |
|---|---|
| ☐ Hypocotyl | ☐epidermis ☐cortex ☐vascular ☐xylem ☐phloem ☐stomata |
| ☐ Cotyledon | ☐mesophyll ☐vascular ☐epidermis ☐margin ☐stomata ☐hydathode |
| ☐ Rosette Leaf | ☐mesophyll ☐vascular ☐epidermis ☐trichome ☐petiole ☐primordia ☐stomata ☐stipule ☐margin ☐hydathode |
| X Primary Root | H epidermis H trichoblast H atrichoblast ☐cortex ☐endodermis ☐vascular ☐xylem ☐phloem ☐pericycle ☐quiescent ☐columella ☐root cap ☐root hairs |
| ☐ Lateral root | ☐epidermis ☐trichoblast ☐atrichoblast ☐cortex ☐endodermis ☐initials ☐flanking cells ☐vascular ☐lateral root cap |

☐ Shoot apical meristem    ☐shoot apical meristem
X in the seedling Root (Rt)
X in the Epidermis (Ep) of the root
Promoter utility

| | |
|---|---|
| Trait Area: | PG&D, Nutrients, Stress, Pest Protection |
| Sub-trait Area: | Drought, Nutrient uptake |
| Utility: | Among other uses this promoter sequence can be useful to improve: Modulation of root growth rate, size and shape. Modulation of water and nutrient uptake. Modulation of plant-microbe including plant rhizobium interactions. Useful for making insecticidal proteins for protection against root worm. Protection against drought stress conditions. Protection against heat stress conditions. |
| Notes: | Endogenous promoter up-regulated under drought, heat and PEG. |
| Construct: | YP0384 |
| Promoter candidate ID: | 11768599 |
| cDNA I.D: | 12730108 (OCKHAM3-CD) |
| Lines expressing: | YP0384 -01, -02 |

Sequence (SEQ ID NO: 107):

tttaaaaaattggataaaacaccgataaaaattcacatttgcaaattttaa ttcagtcggaatatatatttgaaacaagttttgaaatccattggacgatta aaattcattgttgagaggataaatatggatttgttcatctgaaccatgtcg ttgattagtgattgactaccatgaaaaatatgttatgaaaagtataacaac -continued ttttgataaatcacatttattaacaataaatcaagacaaaatatgtcaaca ataatagtagtagaagatattaattcaaattcatccgtaacaacaaaaaat cataccacaattaagtgtacagaaaaacctttttggatatatttattgtcgc ttttcaatgattttcgtgaaaaggatatatttgtgtaaaataagaaggatc ttgacgggtgtaaaaacatgcacaattcttaatttagaccaatcagaagac aacacgaacacttctttattataagctattaaacaaaatcttgcctattt gcttagaataatatgaagagtgactcatcagggagtggaaaatatctcagg atttgcttttagctctaacatgtcaaactatctagatgccaacaacacaaa -continued gtgcaaattcttttaatatgaaaacaacaataatatttctaatagaaaatt aaaaagggaaataaaatattttttaaaatatacaaaagaagaaggaatcc atcatcaaagttttataaaattgtaatataatacaaacttgtttgcttcct tgtctctccctctgtctctctcatctctcctatcttctccatatatacttc atcttcacacccaaaactccacacaaaatatctctccctctatctgcaaat tttccaaagttgcatcctttcaatttccactcctctctaatataattcaca ttttcccactattgctgattcatttttttttgtgaatttatttcaaacccac ataaaaaaatctttgtttaaatttaaaacca

| | |
|---|---|
| Promoter Expression Report #145.02 | |
| Promoter Tested In: | *Arabidopsis thaliana*, Ws ecotype |
| Spatial expression summary: | |
| | |
| Flower | H pedicel H receptacle L sepal L epidermis |
| Stem | L epidermis L cortex H stomata |
| Primary Root | L epidermis |
| Observed expression pattern: | |
| T1 mature: High GFP expression in the cortex cells of stems and pedicels of maturing flowers at the inflorescence apex decreasing toward base or mature stem. Low levels of GFP expression in epidermal cells of stem. High magnification of the stem reveals GFP expression within chloroplast containing cells of the cortex. Comparison to previously characterized GFP expression within stem can be seen. GFP-ER marker accumulations within ER membranes near cell walls which reveals cellular morphology while chloroplast cells remain fluorescent red. In this report, the chloroplasts within the cortical cells accumulate GFP. | |
| T2 seedling: Low GFP expression in epidermal cells of root near transition zone. | |
| Expected expression pattern: | Cell growth and differentiation, including the differentiation of root hairs and trichomes. |
| Selection Criteria: | Public reference. |
| Gene: | Ribosomal protein S5 family |
| GenBank: | NM_128939 *Arabidopsis thaliana* ribosomal protein S5 family (At2g33800) mRNA, complete cds gi\|30685842\|ref\|NM_128939.2\|[28269302] |
| Source Promoter Organism: | *Arabidopsis thaliana*, Columbia |
| Vector: | pNewbin4-HAP1-GFP |
| Marker Type: | GFP-ER |
| Generation Screened: | XT1 Mature   XT2 Seedling   ☐T2 Mature   ☐T3 Seedling |
| T1 Mature Plant Expression Organs/Tissues screened | |
| Events Screened: n = 4 | Events Expressing: n = 2 |
| GFP Expression Detected | |
| | |
| X Flower | H pedicel H receptacle ☐nectary L sepal ☐petal ☐filament ☐anther ☐pollen ☐carpel ☐style ☐papillae ☐vascular L epidermis ☐stomata ☐trichome ☐silique |
| ☐ Silique | ☐stigma ☐style ☐carpel ☐septum ☐placentae ☐transmitting tissue ☐vascular ☐epidermis ☐stomata ☐abscission zone ☐ovule |
| ☐ Ovule | Pre-fertilization: ☐primordia ☐inner integument ☐outer integument ☐embryo sac ☐funiculus ☐chalaza ☐micropyle ☐gametophyte Post-fertilization: ☐zygote ☐suspensor ☐embryo sac ☐inner integument ☐outer integument ☐endothelium ☐seed coat ☐primordia ☐chalaza ☐micropyle ☐early endosperm ☐mature endosperm ☐embryo |
| ☐ Embryo | ☐suspensor ☐preglobular ☐globular ☐heart ☐torpedo ☐late ☐mature ☐provascular ☐hypophysis ☐radicle ☐cotyledons ☐hypocotyl |
| X Stem | L epidermis L cortex ☐vascular ☐xylem ☐phloem ☐pith H stomata ☐trichome |
| ☐ Leaf | ☐petiole ☐mesophyll ☐vascular ☐epidermis ☐trichome ☐primordia ☐stomata ☐stipule ☐margin |
| ☐Shoot apical meristem | ☐Shoot apical meristem ☐Flower primordium |
| X in the Stem (Sm) of the inflorescence meristem | |
| X in the Pedicel (Pd) | |
| X in the Cortex (Cr) of the Pedicel (Pd) | |

-continued

Promoter Expression Report #145.02

X in the Epidermis (Ep) and Guard cell (Gc) of the stem
T2 Seedling Expression    Tissues Screened
Events Screened: n = 2    Events Expressing: n = 2
Seedlings expressing/Seedlings screened
Event-01: 3/5
Event-02: 3/3
GFP Expression Detected ☐ Hypocotyl          ☐epidermis ☐cortex ☐vascular ☐xylem ☐phloem ☐stomata
☐ Cotyledon          ☐mesophyll ☐vascular ☐epidermis ☐margin ☐stomata
                     ☐hydathode
☐ Rosette Leaf       ☐mesophyll ☐vascular ☐epidermis ☐trichome ☐petiole
                     ☐primordia ☐stomata ☐stipule ☐margin ☐hydathode
X Primary Root       L epidermis ☐trichoblast ☐atrichoblast ☐cortex ☐endodermis
                     ☐vascular ☐xylem ☐phloem ☐pericycle ☐quiescent
                     ☐columella ☐root cap ☐root hairs
☐ Lateral root       ☐epidermis ☐trichoblast ☐atrichoblast ☐cortex ☐endodermis
                     ☐initials ☐flanking cells ☐vascular ☐lateral root cap
☐Shoot apical meristem    ☐Shoot apical meristem
X in the root transition zone of the Hypocotyle (Hy)
X in the Epidermis (Ep) of the lower root
Promoter utility Trait Area:    Water use efficiency, nutrients
Sub-trait Area: Heat, drought, water potential, moisture stress at seed set, moisture
               stress during seed fill, low nitrogen tolerance, nitrogen use efficiency
Notes: Weijers D, Franke-van Dijk M, Vencken RJ, Quint A, Hooykaas P, Offringa R.
An *Arabidopsis* Minute-like phenotype caused by a semi-dominant mutation in a RIBOSOMAL
PROTEIN S5 gene. Development. 2001 Nov; 128(21): 4289–99.
Construct:              PT0535
Promoter candidate I.D:  11768627
cDNA I.D:               13609001
Lines expressing:       PT0535 -03, -05

Sequence (SEQ ID NO: 108):

tatcattattgtactgcctgtcaatttttgattgtatcttttattcagca gcatcacattctccttcagtgtccttctcttcttttcttttcttttcttt ttctttcctcattaaacccatacaattctacggtaaatattatggatttgc atacaaactctctaattgtttgtttgggtactataatatggggtccctata atatgtgtagcttaactttaagatagaactaagtcaacaagatccggagac accatgtcaaagttctatgttcttatgattagatgaacaaagttatgattt attcaagattatcacgattcgaactagttctaaacttgtaaacgtaaaata ataaataacgtttgcaactacaacactgaacataaattaatgaagtttgct tgatgtgttggttaaaatttggaatgggacaataaaaagaagaagagaact gagagaagtggtgggggaagtgggaaccttaacttccccacgtgacactaa cgagcaacgttaattgaatagtagtaggcccttttttgtagtacactctttt atatatggtcaccttttaattagtttgcaaatcacatacttttaaaatcat aaaagcaattaacgttgctcgttggtgtcatatgcgattgtagttagtata atcgatcttaattaaaacaaagtccatattaaaaatgaccaaagtatgtaa aaataaaatgttgaattagcatatggtcactgatcttttctattttaagat ttagtaaacctaagatgtatccgcaagcctatagggtttgatgtggattac tactagttacttttgtatgggcttgaagaaacttcattgggccacaaagag ggaggagtgagcgaagagcccaaattcaaacaaaaggatatgagggttcaa atgttattataaaaTATAttgtggccaatttgtaaagaaacttgataatta ctttaaaagccccaacacaattatatttaca Promoter Expression Report #146

Promoter Tested In: *Arabidopsis thaliana*, Wassilewskija (WS) ecotype
Spatial expression summary:
Flower          L receptacle
Silique         L abscission zone
Primary Root    H epidermis
Observed expression pattern:
T1 mature: Weak GFP expression specific to abscission zone of mature flowers.
T2 seedling: Weak expression in root epidermal cells. Expression rapidly decreases from root transition zone to mid root.
Expected expression pattern:    Drought inducible
Selection Criteria:             Ceres expression data
Gene:                           Neoxanthin cleavage enzyme
GenBank: NM_112304 *Arabidopsis thaliana* 9-cis-epoxycarotenoid
dioxygenase [neoxanthin cleavage enzyme] (NC1)(NCED1), putative
(At3g14440) mRNA, complete cds
Source Promoter Organism:       *Arabidopsis thaliana*, WS ecotype
Vector:                         pNewbin4-HAP1-GFP
Marker Type:                    GFP-ER
Generation Screened:            XT1 Mature XT2 Seedling ☐T2 Mature
                                ☐T3 Seedling Inductions completed:

| Treatment: | Age: | Gen: | Time points: | Events Screened/ Response | Response: |
|---|---|---|---|---|---|
| 1. Drought | 7 days | T2 | 3 Hr air dry | 2/2 | Yes |
| 2. ABA 100 uM | 7 days | T2 | 6 Hr | 4/1 | Yes |
| 3. Drought | 4 weeks | T2 | 10–12 days no H20 | 2/0 | No |

-continued

Promoter Expression Report #146

Inducible expression summary:
Time point
Treatment:   induced:     Organs induced:              Tissues induced:

1. Drought   3 Hr air dry  Hypocotyl, Cotyledon,        Epidermis,
                           Rosette Leaf, Primary Root   vascular
2. ABA       6 Hr          Cotyledon                    Epidermis
100 uM
3. Drought   10–12 days    No differences observed.
             no H20

| T1 Mature Expression | Organs/Tissues screened |
|---|---|
| Events Screened: n = 6 | Events Expressing: n = 3 |
| GFP Expression Detected | |
| X Flower | □pedicel L receptacle □nectary □sepal □petal □filament □anther □pollen □carpel □style □papillae □vascular □epidermis □stomata □trichome □silique |
| X Silique | □stigma □style □carpel □septum □placentae □transmitting tissue □vascular □epidermis □stomata L abscission zone □ovule |
| □Ovule | Pre-fertilization: □inner integument □outer integument □embryo sac □funiculus □chalaza □micropyle □gametophyte Post-fertilization: □zygote □embryo sack □inner integument □outer integument □endothelium □seed coat □primordia □chalaza □micropyle □early endosperm □mature endosperm □embryo |
| □Embryo | □suspensor □preglobular □globular □heart □torpedo □late □mature □provascular □hypophysis □radicle □cotyledons □hypocotyl |
| □Stem | □epidermis □cortex □vascular □xylem □phloem □pith □stomata □trichome |
| □Leaf | □petiole □mesophyll □vascular □epidermis □trichome □primordia □stomata □stipule □margin |
| □Shoot apical meristem | □shoot apical meristem □flower primordium |

X in the Abscission zone (Az) between the Pedicel (Pd) and Sepal (Se)
X in the Abscission zone (Az) in the flower

| Table 2. T2 Seedling Expression | Tissues Screened |
|---|---|
| Events Screened: n = 4 | Events Expressing: n = 3 |
| Seedlings expressing/Seedlings screened | |
| Event-01: 5/6 | |
| Event-02: 5/6 | |
| □Scheduled | |
| GFP Expression Detected | |
| □Hypocotyl | □epidermis □cortex □vascular □xylem □phloem □stomata |
| □Cotyledon | □mesophyll □vascular □epidermis □margin □stomata □hydathode |
| □Rosette Leaf | □mesophyll □vascular □epidermis □trichome □petiole □primordia □stomata □stipule □margin □hydathode |
| X Primary Root | H epidermis □trichoblast □atrichoblast □cortex □endodermis □vascular □xylem □phloem □pericycle □quiescent □columella □root cap □root hairs |
| □Lateral root | □epidermis □trichoblast □atrichoblast □cortex □endodermis □initials □flanking cells □vascular □lateral root cap |
| □Shoot apical meristem | ∈shoot apical meristem |

X in the Epidermis (Ep) of the seedling root

Promoter utility
Trait Area:      PG&D, Stress
Sub-trait Area:  Flower abscission, Drought
Utility:         Among other uses this promoter sequence can be
                 useful to improve: Delaying or accelerating flower
                 abscission in canola. Delaying or accelerating fruit
                 drop. Making flowerless plants. Modulation of water
                 and mineral nutrient uptake. Useful to drive genes
                 important in corn root worm resistance and other
                 interactions involving roots and pests or microbes.
                 Enhanced tolerance of drought conditions. Enhanced
                 tolerance of heat conditions.

-continued

Promoter Expression Report #146

Notes: Milborrow BV. The pathway of biosynthesis of abscisic acid in vascular plants: a review of the present state of knowledge of ABA biosynthesis. J Exp Bot. 2001 Jun; 52(359):1145–64. Review. Qin X, Zeevaart JA. The 9-cis-epoxycarotenoid cleavage reaction is the key regulatory step of abscisic acid biosynthesis in water-stressed bean. Proc Natl Acad Sci USA. 1999 Dec 21;96(26):15354-
Endogenous promoter generally up-regulated under drought.

Construct:              YP0385
Promoter candidate I.D: 11768579
cDNA I.D:               12658348 (OCKHAM3-C)
Lines expressing:       YP0385 -02, -03, -06

Sequence (SEQ ID NO: 109):

actcaacaataggacaagccaaaaaaattccaattattgtgttactctatt cttctaaatttgaacactaatagactatgacatatgagtatataatgtgaa gtcttaagatattttcatgtgggagatgaataggccaagttggagtctgca aacaagaagctcttgagccacgacataagccaagttgatgaccgtaattaa tgaaactaaatgtgtgtggttatatattagggacccatggccatatacaca attttttgtttctgtcgatagcatgcgtttatatatatttctaaaaaaacta acatatttactggatttgagttcgaatattgacactaatataaactacgta ccaaactacatatgtttatctatatttgattgatcgaagaattctgaactg ttttagaaaatttcaatacacttaacttcatcttcaacggtaaaagaaat caccactagacaaacaatgcctcataatgtctcgaaccctcaaactcaaga gtatacattttactagattagagaatttgatatcctcaagttgccaaagaa ttggaagcttttgttaccaaacttagaaacagaagaagccacaaaaaaga caaagggagttaaagattgaagtgatgcatttgtctaagtgtgaaaggtct caagtctcaactttgaaccataataacattactcacactccttttttttt ctttttttttcccaaagtaccctttttaattccctctataacccactcact ccattccctctttctgtcactgattcaacacgtggccacactgatgggatc cacctttcctcttacccacctcccggtttatataaacccttcacaacactt catcgctctcaaaccaactctctcttctctcttctctcctctcttctacaa gaagaaaaaaaacagagcctttacacatctcaaaatcgaacttactttaac caccaaatactgattgaacacacttgaaa Promoter Expression Report #147

Promoter Tested In: Arabidopsis thaliana, WS ecotype
Spatial expression summary:
Flower                M pedicel M stomata
Primary Root          L epidermis
Observed expression pattern:
T1 mature: Weak guard cell expression in pedicles. T2 seedling: Weak root epidermal expression.
Expected expression pattern:   Drought-Inducible
Selection Criteria:            Ceres expression data
Gene: Unknown protein. Contains putative conserved domains [ATPase family associated with various cellular activities (AAA). AAA family proteins often perform chaperone-like functions that assist in the assembly,

Promoter Expression Report #147 operation, or disassembly of protein complexes]
GenBank: NM_179511 *Arabidopsis thaliana* AAA-type ATPase family protein (At1g64110) mRNA, complete cds
gi|30696967|ref|NM_179511.1|[30696967]
Source Promoter Organism: *Arabidopsis thaliana*, Columbia ecotype
Vector: pNewbin4-HAP1-GFP
Marker Type: GFP-ER
Generation Screened: XT1 Mature XT2 Seedling □T2 Mature □T3 Seedling Inductions completed: ABA, Drought

| Treatment: | Age: | Gen: | Time points: | Events Screened/Response | Response: |
|---|---|---|---|---|---|
| 1. ABA 100 um | 7 days | T2 | 6 Hr | 2/0 | No |
| | | | 16 Hr-post treatment | 2/0 | |
| 2. Drought | 7 days | T2 | 3 Hr Air dry | 2/0 | No |
| 3. Drought | 4 wks | T2 | 10–12 d. no H20 | 2/0 | No |

Inducible expression summary: Increase in GFP expression relative to control in two events.

| Treatment: | Time point induced: | Organs induced: | Tissues induced: |
|---|---|---|---|
| 1. ABA 100 um | | No differences observed. | |
| 2. Drought | | No differences observed. | |
| 3. Drought | | No differences observed. | |

T1 Mature Plant Expression Organs/Tissues screened
Events Screened: n = 6    Events Expressing: n = 2
GFP Expression Detected

| | |
|---|---|
| X Flower | M pedicel □receptacle □nectary □sepal □petal □filament □anther □pollen □carpel □style □papillae □vascular □epidermis M stomata □trichome □silique |
| □Silique | □stigma □style □carpel □septum □placentae □transmitting tissue □vascular □epidermis □stomata □abscission zone □ovule |
| □Ovule | Pre-fertilization: □inner integument □outer integument □embryo sac □funiculus □chalaza □micropyle □gametophyte<br>Post-fertilization: □zygote □embryo sack □inner integument □outer integument □endothelium □seed coat □primordia □chalaza □micropyle □early endosperm □mature endosperm □embryo |
| □Embryo | □suspensor □preglobular □globular □heart □torpedo □late □mature □provascular □hypophysis □radicle □cotyledons □hypocotyl |
| □Stem | □epidermis □cortex □vascular □xylem □phloem □pith □stomata □trichome |
| □Leaf | □petiole □mesophyll □vascular □epidermis □trichome □primordia □stomata □stipule □margin |
| □Shoot apical meristem | □shoot apical meristem □flower primordium |

X in the Guard cell (GC) of the flower

T2 Seedling Expression    Tissues Screened
Events Screened: n = 2    Events Expressing: n = 2
Seedlings expressing/Seedlings screened
Event-01: 3/6
Event-02: 2/5
□Scheduled
GFP Expression Detected

| | |
|---|---|
| □Hypocotyl | □epidermis □cortex □vascular □xylem □phloem □stomata |
| □Cotyledon | □mesophyll □vascular □epidermis □margin □stomata □hydathode |
| □Rosette Leaf | □mesophyll □vascular □epidermis □trichome □petiole □primordia □stomata □stipule □margin □hydathode |
| X Primary Root | L epidermis □trichoblast □atrichoblast □cortex □endodermis □vascular □xylem □phloem □pericycle □quiescent □columella □root cap □root hairs |
| □Lateral root | □epidermis □trichoblast □atrichoblast □cortex □endodermis □initials □flanking cells □vascular □lateral root cap |
| □Shoot apical meristem | □shoot apical meristem |

X in the Epidermis (Ep) and Root hairs (Rh) of the seedling root
Promoter utility
Trait Area: Nutrients
Sub-trait Area: Nutrient uptake, Microbe interactions
Utility: Modulate water and nutrient uptake. Modulate seedling establishment.
Modulate plant-microbe including plant-Rhizobium interactions.

Construct: YP0371
Promoter candidate I.D: 11768813
cDNA I.D: 12657397 (OCKHAM3-CD)
Lines expressing: YP0371 -03, -05

Sequence (SEQ ID NO: 110):

gatatatttgtttaataatgcctacgattctgcgaagacaggagaagccat acctttcaatctaagccgtcaacttgttcccttacgtgggatcctattata caatccaacggttctaaatgagccacgccttccagatctaacacagtcatg ccttctacagtctgcaccccttttttttttagtgttttatctacatttttt cctttgtgtttaattttgtgccaacatctataacttaccctataaaaata ttcaattatcacagaatacccacaatcgaaaacaaaatttaccggaataat ttaattaaagctggactataatgacaattccgaaactatcaaggaataaat taaagaaactaaaaaactaaagggcattagagtaaagaagcggcaacatca gaattaaaaaactgccgaaaaaccaacctagtagccgtttatatgacaaca cgtacgcaaagtctcggtaatgactcatcagttttcatgtgcaaacatatt accccatgaaataaaaaagcagagaagcgatcaaaaaaatcttcattaaa agaaccctaaatctctcatatccgccgccgtctttgcctcattttcaacac cggtgatgacgtgtaaatagatctggttttcacggttctcactactctctg tgattttcagactattgaatcgttaggaccaaaacaagtacaaagaaact gcagaagaaaagatttgagagagatatcttacgaaacaaggtatatatttc tcttgttaaatctttgaaaatactttcaaagtttcggttggattctcgaat aagttaggttaaatagtcaatatagaattatagataaatcgatacctttg tttgttatcattcaattttattgttgttacgattagtaacaacgttttag atcttgatctatatattaataatactaatactttgttttttttgttttttt ttttaatacatattttgcttttggaagatca

Promoter Expression Report #148.02

Promoter Tested In: *Arabidopsis thaliana*, WS ecotype
Spatial expression summary:

| | |
|---|---|
| Flower | L pedicel L receptacle L sepal L carpel L style L stigma L epidermis L stomata L Silique |
| Silique | L stigma L style L carpel L epidermis L abscission zone |
| Stem | L vascular |
| Leaf | L epidermis |

| Promoter Expression Report #148.02 | |
|---|---|
| Hypocotyl | L epidermis H vascular |
| Cotyledon | L vascular L epidermis |
| Rosette Leaf | L epidermis |
| Primary Root | H epidermis H cortex H endodermis H vascular H root hairs |
| Lateral root | H epidermis H cortex H endodermis H vascular |

Observed expression pattern:
T1 mature: Variable expression throughout epidermal cells of mature flowers and leaves. GFP expression specific to remains of abscised floral organs. Low expression in vasculature of stem.
T2 seedling: High GFP expression throughout all root cells decreasing toward root transition zone. High GFP expression in vasculature of root extends to petioles of cotyledons. Low GFP expression throughout seedling epidermis.

| | |
|---|---|
| Expected expression pattern: | Flowers and buds |
| Selection Criteria: | Ceres expression data |
| Gene: | Expressed protein, Unknown function |
| GenBank: | NM_105657 *Arabidopsis thaliana* expressed protein (At1g69890) mRNA, complete cds gi\|30697942\|ref\|NM_105657.2\|[30697942] |
| Source Promoter Organism: | *Arabidopsis thaliana*, Columbia |
| Vector: | pNewbin4-HAP1-GFP |
| Marker Type: | GFP-ER |
| Generation Screened: | XT1 Mature XT2 Seedling □T2 Mature □T3 Seedling |

T1 Mature Plant Expression Organs/Tissues screened
Events Screened: n = 5    Events Expressing: n = 2
GFP Expression Detected

| | |
|---|---|
| X Flower | L pedicel L receptacle □nectary L sepal □petal □filament □anther □pollen L carpel L style L stigma □vascular L epidermis L stomata □trichome L silique |
| X Silique | L stigma L style L carpel □septum □placentae □transmitting tissue □vascular L epidermis □stomata L abscission zone □ovule |
| □Ovule | Pre-fertilization: □primordia □inner integument □outer integument □embryo sac □funiculus □chalaza □micropyle □gametophyte Post-fertilization: □zygote □suspensor □embryo sac □inner integument □outer integument □endothelium □seed coat □primordia □chalaza □micropyle □early endosperm □mature endosperm □embryo |
| □Embryo | □suspensor □preglobular □globular □heart □torpedo □late □mature □provascular □hypophysis □radicle □cotyledons □hypocotyl |
| X Stem | □epidermis □cortex L vascular □xylem □phloem □pith □stomata □trichome |
| X Leaf | □petiole □mesophyll □vascular L epidermis □trichome □primordia □stomata □stipule □margin |
| □Shoot apical meristem | □shoot apical meristem □flower primordium |

X Epidermis (Ep) and Guard cells (Gc) in the flower
X Abscission zone (AZ) in the silique
X Epidermis (Ep), Guard cells (Gc), and Stigma (Sg) in the pre-fertilized silique
X Epidermis (Ep), Guard cells (Gc), and Stigma (Sg) in the fertilized silique
X Epidermis (Ep) and Guard cells (Gc) in the leaf
X Vasculature (Vs) in the stem T2 Seedling Expression    Tissues Screened
Events Screened: n = 2    Events Expressing: n = 2
Seedlings expressing/Seedlings screened
Event-01:
Event-02:
□Scheduled
GFP Expression Detected

| | |
|---|---|
| X Hypocotyl | L epidermis □cortex H vascular □xylem □phloem □stomata |
| X Cotyledon | □mesophyll L vascular L epidermis □margin □stomata □hydathode |
| X Rosette Leaf | □mesophyll □vascular L epidermis □trichome □petiole □primordia □stomata □stipule □margin □hydathode |
| X Primary Root | H epidermis □trichoblast □atrichoblast H cortex H endodermis H vascular □xylem □phloem □pericycle □quiescent □columella □root cap H root hairs |
| X Lateral root | H epidermis □trichoblast □atrichoblast H cortex H endodermis □initials □flanking cells H vascular □lateral root cap |
| □Shoot apical meristem | □Shoot apical meristem |

| Promoter utility | |
|---|---|
| Trait Area: | Water use efficiency, nutrients, source |
| Sub-trait Area: | Heat, drought, water potential, moisture stress at seed set, moisture stress during seed fill, low nitrogen tolerance, nitrogen use efficiency |
| Construct: | PT0610 |
| Promoter candidate I.D: | 13148293 |
| cDNA I.D: | 13617251 |
| Lines expressing: | PT0610 -01, -05 |

Sequence (SEQ ID NO: 111):

ttagtgaaattatgacattaagtaaggttttcttagttagctaatgtatgg
ctattcaattgttatgttaggctattttagttagtatatgaatttaggcag
tctatgcaaatgatttcgttttcattttttcatatgtaaacatcaagatca
agtaacgccattcgagttgatatttttttttttaaattagtgtgtgtaaatt
ttggaccgcttatttgagtttgctaatgaagttgcatatatattacgttaa
accataggcaaactaatttgaaacatccgattcgatttcctgtaattttc
ttggttaattgaccaaaatcaagatcttcagaaataaaataaaagacgaaa
gaaagctgtcgcaaagcagattgtgttaaaaaaagtggattgggctcaaa
cgcaacttgtccagcccgtgacaattaccctatacgcaagtaagagtaacg
tatcactggcaaaagttggtattagttacgatatctttgtcatgggggcat
gcatgggcatggcttaagagttaagccttaagaagagtcccacactcgtga
ctctcatgatcacttgttgtttcttacgggcaaatacatttaactttattc
ttcatttattcacctatattcttttggataataacttttctctatataaaa
taacaaacatcgtacgtttcatttatttacaacaagcgatgagaattaaaa
ggagaccttaattgatgatactcttcttttctctcggttacaacgggatta
ttacagataatgataatctatatggatgctgacgtggaaaaacaaaatttg
gtgaaacacgtcaattaagcacgacttttccatggctagtggctaagatcg
tttcatcacatggctatatcatataatacttggatgaattcaaaataaacg
actgagaaaatgtccacgtcacggcgcaccgctttggacttaagtctccta
taataaatacaacaccaaacattgcattcca

| Promoter Expression Report #152 - | |
|---|---|

Promoter Tested In: *Arabidopsis thaliana*, Wassilewskija (WS) ecotype
Spatial expression summary:

| | |
|---|---|
| Flower | H stomata |
| Silique | H stomata |
| Rosette Leaf | H stomata H stipule |

Promoter Expression Report #152 -

| | |
|---|---|
| Primary Root | L epidermis L trichoblast H cortex L root hairs |

Observed expression pattern:
T1 mature: Guard cell expression throughout inflorescence apex and carpels in early flower buds.
T2 seedling: GFP expression specific within cortex cells overlaying lateral root primordia and root hair producing epidermal cells.

| | |
|---|---|
| Expected expression pattern: | Petiole |
| Selection Criteria: | Mutant lines |
| Gene: | product = "tetratricopeptide repeat (TPR)-containing |
| note = "contains Pfam profile PF00515 TPR Domain; go function: protein binding [goid 0005515]" | |
| GenBank: NM_129819 tetratricopeptide repeat (TPR)-containing protein (At2g42580) mRNA | |
| Source Promoter Organism: | *Arabidopsis thaliana*, Columbia (Col) ecotype |
| Vector: | pNewbin4-HAP1-GFP |
| Marker Type: | GFP-ER |
| Generation Screened: | X T1 Mature X T2 Seedling ☐T2 Mature ☐T3 Seedling |

| Treatment: | Age: | Gen: | Time points: | Events Screened/ Response | Response: |
|---|---|---|---|---|---|
| 1. Drought | 4 wks | T2 | 8 days no water | 2/0 | No |
| 2. Far red | 7 days | T2 | 1 Hr | 2/0 | No |
| Far Red$_{730}$ = | | | 4 Hr | 2/0 | No |
| 525 µW/cm$^2$ | | | 24 Hr | 2/0 | No |

T1 Mature Plant Expression Organs/Tissues screened
Events Screened: n = 6    Events Expressing: n = 2
GFP Expression Detected

| | |
|---|---|
| X Flower | ☐pedicel ☐receptacle ☐nectary ☐sepal ☐petal ☐filament ☐anther ☐pollen ☐carpel ☐style ☐papillae ☐vascular ☐epidermis H stomata ☐trichome ☐silique |
| X Silique | ☐stigma ☐style ☐carpel ☐septum ☐placentae ☐transmitting tissue ☐vascular ☐epidermis H stomata ☐abscission zone ☐ovule |
| Ovule | Pre-fertilization: ☐primordia ☐inner integument ☐outer integument ☐embryo sac ☐funiculus ☐chalaza ☐micropyle ☐gametophyte Post-fertilization: ☐zygote ☐suspensor ☐embryo sack ☐inner integument ☐outer integument ☐endothelium ☐seed coat ☐primordia ☐chalaza ☐micropyle ☐early endosperm ☐mature endosperm ☐embryo |
| Embryo | ☐suspensor ☐preglobular ☐globular ☐heart ☐torpedo ☐late ☐mature ☐provascular ☐hypophysis ☐radicle ☐cotyledons ☐hypocotyl |
| ☐Stem | ☐epidermis ☐cortex ☐vascular ☐xylem ☐phloem ☐pith ☐stomata ☐trichome |
| ☐Leaf | ☐petiole ☐mesophyll ☐vascular ☐epidermis ☐trichome ☐primordia ☐stomata ☐stipule ☐margin |
| ☐Shoot apical meristem | ☐shoot apical meristem ☐flower primordium |

X Guard cells (Gc) that define the stomata in the flower bud, pedicel and silique T2 Seedling Expression   Tissues Screened
Events Screened: n = 2   Events Expressing: n = 2
Seedlings expressing/Seedlings screened
Event-01: 5/6
Event-02: 4/6
☐Scheduled
GFP Expression Detected

| | |
|---|---|
| ☐Hypocotyl | ☐epidermis ☐cortex ☐vascular ☐xylem ☐phloem ☐stomata |
| ☐Cotyledon | ☐mesophyll ☐vascular ☐epidermis ☐margin ☐stomata ☐hydathode |
| X Rosette Leaf | ☐mesophyll ☐vascular ☐epidermis ☐trichome ☐petiole ☐primordia H stomata H stipule ☐margin ☐hydathode |
| X Primary Root | L epidermis L trichoblast ☐atrichoblast H cortex ☐endodermis ☐vascular ☐xylem ☐phloem ☐pericycle ☐quiescent ☐columella ☐root cap L root hairs |
| ☐Lateral root | ☐epidermis ☐trichoblast ☐atrichoblast ☐cortex ☐endodermis ☐initials ☐flanking cells ☐vascular ☐lateral root cap |
| ☐Shoot apical meristem | ☐Shoot apical meristem |

X Guard cell (Gc) that define the stomata and Stipules (Ss) in the seedling
X Cortex (Cr), in the root transition zone
X Guard cell (Gc) that define the stomata in the rosette leaf
X Epidermis (Ep), Cortex (Cr) and Lateral root (Lr) in the lateral root
X Epidermis (Ep), Cortex (Cr) and Root hair (Rh) in the root
X Cortex (Cr) and Lateral root (Lr) in lateral root initiation

| | |
|---|---|
| Promoter utility | |
| Trait Area: | Water use efficiency, nutrients |
| Sub-trait Area: | Heat, drought, water potential, moisture stress at seed set, moisture stress during seed fill, low nitrogen tolerance, nitrogen use efficiency |
| Utility: | Among other uses this promoter sequence could be useful to improve: Drought tolerance through regulation of stomatal closure |

| | |
|---|---|
| Construct: | PT0590 |
| Promoter candidate I.D: | 11768848 |
| cDNA I.D: | 12639140 (OCKHAM3-CD) |
| Lines expressing | PT0590 -03, -04 |

Sequence (SEQ ID NO: 112):

```
attattcaatttaataaaaattgagtcggccaatttaatgcgagacttctg tacaacgaccctaaaagtgggtttgataaatgaaacatattgcaacaaaaa aatactagtaataatgataaaatagtaacatgtcatggcgcattgaatatc ctacgaaggttagtgtttacttttaaaaaatcctaatatgatactagtac atatagctagcttgccttgcttatgctattgcatagtctgtattaataaat gatgttatacatttcgatagagtaacattttgggaacatgagtgaacgtgc ttgaatcttcgtgcccttgacgtcagaagctagtaattttaaatactaatt aacattcatacaaattaacagatacaatgtactatatcataattcgtttcc gtaacacaacgcaacaatttgaaagtagatgtactttagtacttagttagt gtgcaccaaaaaaaaagatgtagttagttagtaagggttaaatgttta atttattaagaaaacttaaattcattaaatgttagaaaagtctaattagt ttatattcgaacactgtgctcaaaattaaaaagtcaactattttagactat agagtttattaattaataataaattcgataaatcaccgtattattttcttc aacgacaagtagccgtgaagacacgggagcgaagagagataaacagaagat gaagaagaagatcaatgtcataatcttcaggggagataaatccgtaactttt attaatcaaggttaatcctttttttttttcttcatcttaattctttgcgtct tccttttctatttatcacgagatctgtctttcttttttcctcttctttctct ctcttctctctgaagacagtacttgtttctgtccggcgttaaaagcttcgg tggtggtctcttgacttctctgagaagaagaaaaggaagctgagtctcatt ttagattcagctcacgaggaagtgacgacga
```

| Promoter Expression Report #154.02 | |
|---|---|
| Promoter Tested In: | *Arabidopsis thaliana*, WS ecotype |
| Spatial expression summary: | |
| Flower | L pedicel L stomata |
| Ovule | Post-fertilization: H suspensor |
| Embryo | M suspensor |
| Stem | L stomata |
| Leaf | L stomata |
| Hypocotyl | L stomata |
| Cotyledon | L vascular L stomata |
| Primary Root | L epidermis H vascular L root cap |
| Observed expression pattern: | |
| T1 mature: GFP expression in embryo suspensor cells and root meristem cells in early embryos and in guard cells throughout stems and leaves. T2 seedling: Low GFP expression throughout vasculature tissue of seedlings and in epidermal tissues at root transition zone and root tip, including root cap cells. | |
| Expected expression pattern: | High in Siliques |
| Selection Criteria: | Diversity parameters |
| Gene: | Expressed protein |
| GenBank: NM_115605 *Arabidopsis thaliana* expressed protein (At3g57450) mRNA, complete cds gi\|42566002\|ref\|NM_115605.2\|[42566002] | |
| Source Promoter Organism: | *Arabidopsis thaliana*, Columbia |
| Vector: | pNewbin4-HAP1-GFP |
| Marker Type: | GFP-ER |
| Generated Screened: | X T1 Mature X T2 Seedling ☐T2 Mature ☐T3 Seedling |

| T1 Mature Plant Expression Organs/Tissues screened | |
|---|---|
| Events Screened: n = 2    Events Expressing: n = 2 | |
| GFP Expression Detected | |
| X Flower | L pedicel ☐receptacle ☐nectary ☐sepal ☐petal ☐filament ☐anther ☐pollen ☐carpel ☐style ☐papillae ☐vascular ☐epidermis L stomata ☐trichome ☐silique |
| ☐Silique | ☐stigma ☐style ☐carpel ☐septum ☐placentae ☐transmitting tissue ☐vascular ☐epidermis ☐stomata ☐abscission zone ☐ovule |
| X Ovule | Pre-fertilization: ☐primordia ☐inner integument ☐outer integument ☐embryo sac ☐funiculus ☐chalaza ☐micropyle ☐gametophyte Post-fertilization: ☐zygote H suspensor ☐embryo sack ☐inner integument ☐outer integument ☐endothelium ☐seed coat ☐primordia ☐chalaza ☐micropyle ☐early endosperm ☐mature endosperm ☐embryo |
| X Embryo | M suspensor ☐preglobular ☐globular ☐heart ☐torpedo ☐late ☐mature ☐provascular ☐hypophysis ☐radicle ☐cotyledons ☐hypocotyl |
| X Stem | ☐epidermis ☐cortex ☐vascular ☐xylem ☐phloem ☐pith L stomata ☐trichome |
| X Leaf | ☐petiole ☐mesophyll ☐vascular ☐epidermis ☐trichome ☐primordia L stomata ☐stipule ☐margin |
| ☐Shoot apical meristem | ☐shoot apical meristem ☐flower primordium |
| X in the Guard cells (Gc) of the pedicel and leaf, | |
| X in the Root apical meristem (RAM) and Suspensor (Su) of the late torpedo stage in the ovule | |
| X in the Suspensor (Su) of the ovule | |

| T2 Seedling Expression Tissues Screened | |
|---|---|
| Events Screened: n = 2    Events Expressing: n = 2 | |
| Seedlings expressing/Seedlings screened | |
| Event-01: 4/6 | |
| Event-02: 4/6 | |
| ☐Scheduled | |
| GFP Expression Detected | |
| X Hypocotyl | ☐epidermis ☐cortex ☐vascular ☐xylem ☐phloem L stomata |
| X Cotyledon | ☐mesophyll L vascular ☐epidermis ☐margin L stomata ☐hydathode |
| ☐Rosette Leaf | ☐mesophyll ☐vascular ☐epidermis ☐trichome ☐petiole ☐primordia ☐stomata ☐stipule ☐margin ☐hydathode |
| X Primary Root | L epidermis ☐trichoblast ☐atrichoblast ☐cortex ☐endodermis H vascular ☐xylem ☐phloem ☐pericycle ☐quiescent ☐columella L root cap ☐root hairs |

| Promoter Expression Report #154.02 | |
|---|---|
| ☐Lateral root | ☐epidermis ☐trichoblast ☐atrichoblast ☐cortex ☐endodermis ☐initials ☐flanking cells ☐vascular ☐lateral root cap |
| ☐Shoot apical meristem | ☐Shoot apical meristem |
| X in the Guard cells (Gc) and Vasculature (Vs) of the seedling | |
| X in the Vasculature (Vs) of the cotyledon and root | |
| X in the root transition zone | |
| X in the Root Cap (Rc) of the root tip | |
| Promoter utility | |
| Trait Area: | Water use efficiency, nutrients |
| Sub-trait Area: | Heat, drought, water potential, moisture stress at seed set, moisture stress during seed fill, low nitrogen tolerance, nitrogen use efficiency, seed yield, endosperm cell number/size, endosperm granule number, seed enhancement, seed number, harvest index |
| Construct: | PT0629 |
| Promoter candidate ID: | 13148325 |
| cDNA I.D: | 12688401 |
| Lines expressing: | PT0629 |

Sequence (SEQ ID NO: 113):

TTTAAGCATATCAAATGTGAAAATTGGTCTTAGGTTATGATGTATATCCTT

ATATAGTAAAAGTATATTAGTCTAAAAATTTAGATTTAAAAAGTGAACTAA

AATTTAAAAGCAAGCTGAATTACATAAATCAAGTGACAATTGTAATTTGTT

GTGACATTTGTAAGTTCATAATGGTACGTGTCACGCTATGTTAATTAAGTT

TGAAATATGAGATGTAAGAAAAAAGTGATCAAAAATTAAGTTCTTTTGGAG

CGTTAAGTCCAAAGGTCAATTAGAGCGCAATATCAGTCCAGAAAAGTGGAT

GAAAAATGTCCATCCATCCATCGAGAAATATGCTTAAAGTAAACGCTTACT

TTTCAAGCGACCTTCACGGTATTGCCGCAGTCAAAAATACGCGGCGACTGT

TTGGTTGGTATAGTGACGACCCACTCTCACGCGGATTCATTAATTTCCTAT

CACAAATAAGAAAAAAGAAACGTGAAATTAATTTGTTAAGTAACAAAAACA

AAAGAAAAAGGAAACTGACAAGAAACGCTAAAGTGGTTCCTTCCTTGTACT

CAAAAAAACGTTAATTTACAGCTCAGAATAAGTTTTTCTGTTTACCGTAAT

TCGACCCAATATTTTTACGAATAACAATTTAGTCCAAAACCTCTTTGATAT

ATTGCAATTTAATACCCTAATTAAGTCTTCTTATCTAGTAATTTGGTTTTA

TTTCCATGACCTACAATATAAGATAATAGTCATTAGTGCTAGATATAAAGA

CTGAATTAGGGTATATAAGATATATGGAATGCTAAGATTACAAAGAGATAG

AGAATCAAAAAAAGGAAAGAATTAAGGGGCAAATATGAAATAATTAAAAAC

AAGGGAGCCAAAGGAACAATGTAAGAAAAGCAATAAAATTAAAAACAAAAC

CCTCAAAAAGAAGAAAGCGGAGACTCGTTAGCTTTTTCCTGCCTCCTATAA

ATTGAACGCGACTTGCAGAACCTTTCCTCA

| Promoter Expression Report #160.02 | |
|---|---|
| Promoter Tested In: *Arabidopsis thaliana*, WS ecotype | |
| Spatial expression summary: | |
| Silique | L ovule |

Promoter Expression Report #160.02

| | |
|---|---|
| Ovule | Post-fertilization: M early endosperm M mature endosperm |
| Hypocotyl | L epidermis L stomata |
| Cotyledon | L epidermis L stomata |
| Rosette Leaf | L epidermis L stomata |
| Primary Root | L epidermis |

Observed expression pattern:
T1 mature: Modest GFP expression observed in endosperm from torpedo through to mature embryo-stage ovules.
T2 seedling: Low GFP expression throughout seedling epidermal tissues.
Expected expression pattern: Embryo-seed
Selection Criteria: Public: Rossak, Maren; Smith, Mark; Kunst, Ljerka. Expression of the FAE1 gene and FAE1 promoter activity in developing seeds of *Arabidopsis thaliana*. Plant Molecular Biology. August, 2001. 46(6):717–725.
Gene: Beta-ketoacyl-CoA synthase; FAE1 Like
GenBank: NM_123743 *Arabidopsis thaliana* beta-ketoacyl-CoA synthase, putative (At5g43760) mRNA, complete cds
gi|42568302|ref|NM_123743.3|[42568302]

| | |
|---|---|
| Source Promoter Organism: | *Arabidopsis thaliana*, Columbia |
| Vector: | pNewbin4-HAP1-GFP |
| Marker Type: | GFP-ER |
| Generation Screened: | XT1 Mature XT2 Seedling ☐T2 Mature ☐T3 Seedling |

| T1 Mature Plant Expression | Organs/Tissues screened |
|---|---|
| Events Screened: n = 3 | Events Expressing: n = 2 |

GFP Expression Detected

| | |
|---|---|
| ☐Flower | ☐pedicel ☐receptacle ☐nectary ☐sepal ☐petal ☐filament ☐anther ☐pollen ☐carpel ☐style ☐papillae ☐vascular ☐epidermis ☐stomata ☐trichome ☐silique |
| X Silique | ☐stigma ☐style ☐carpel ☐septum ☐placentae ☐transmitting tissue ☐vascular ☐epidermis ☐stomata ☐abscission zone L ovule |
| L Ovule | Pre-fertilization: ☐primordia ☐inner integument ☐outer integument ☐embryo sac ☐funiculus ☐chalaza ☐micropyle ☐gametophyte
Post-fertilization: ☐zygote ☐suspensor ☐embryo sac ☐inner integument ☐outer integument ☐endothelium ☐seed coat ☐primordia ☐chalaza ☐micropyle M early endosperm M mature endosperm ☐embryo |
| ☐Embryo | ☐suspensor ☐preglobular ☐globular ☐heart ☐torpedo ☐late ☐mature ☐provascular ☐hypophysis ☐radicle ☐cotyledons ☐hypocotyl |
| ☐Stem | ☐epidermis ☐cortex ☐vascular ☐xylem ☐phloem ☐pith ☐stomata ☐trichome |
| ☐Leaf | ☐petiole ☐mesophyll ☐vascular ☐epidermis ☐trichome ☐primordia ☐stomata ☐stipule ☐margin |
| ☐Shoot apical meristem | ☐shoot apical meristem ☐flower primordium |

X in the Endosperm (En) of the ovules at torpedo stage of the embryo and in mature ovules

| T2 Seedling Expression | Tissues Screened |
|---|---|
| Events Screened: n = 2 | Events Expressing: n = 2 |

Seedlings expressing/Seedlings screened
Event-01: 5/6
Event-02: 4/5
☐Scheduled
GFP Expression Detected

| | |
|---|---|
| X Hypocotyl | L epidermis ☐cortex ☐vascular ☐xylem ☐phloem L stomata |
| X Cotyledon | ☐mesophyll ☐vascular ☐epidermis ☐margin L stomata ☐hydathode |
| X Rosette Leaf | ☐mesophyll ☐vascular L epidermis ☐trichome ☐petiole ☐primordia L stomata ☐stipule ☐margin ☐hydathode |
| X Primary Root | L epidermis ☐trichoblast ☐atrichoblast ☐cortex ☐endodermis ☐vascular ☐xylem ☐phloem ☐pericycle ☐quiescent ☐columella ☐root cap ☐root hairs |
| ☐Lateral root | ☐epidermis ☐trichoblast ☐atrichoblast ☐cortex ☐endodermis ☐initials ☐flanking cells ☐vascular ☐lateral root cap |
| ☐Shoot apical meristem | ☐shoot apical meristem |

X in the Epidermis (Ep) of the seedling, hypocotyl, cotyledon and Root (Rt)

| | |
|---|---|
| Promoter utility | |
| Trait Area: | Nutrients: sink |
| Sub-trait Area: | Heat, drought, water potential, moisture stress at seed set, moisture stress during seed fill, low nitrogen tolerance, nitrogen use efficiency, seed yield, endosperm cell number/size, endosperm granule number, seed enhancement, seed number, harvest index, nitrogen use efficiency |
| Utility: | Increase seed sink strength to improve seed quality, protein content and oil content. |

| | |
|---|---|
| Construct: | PT0642 |
| Promoter candidate I.D: | 11768742 |
| cDNA I.D: | 13612923 |
| Lines expressing: | PT0642 -03, -05 |

Sequence (SEQ ID NO: 114):

ttgaacatccttaatttgaaccataaaaaatatgacattaactatctgatt aattttcacttaagggatggttagttaagttacattggattaaaaatggta ttagtagaccaattagaacatgtatgccattttttgtttacaaaaacctttt ttaagtggtatttataagacttgctcaatttcattcaaaagaacatgaaat ggatggactagttttaatggcaataacccacacaattactcatatttgtt caacaaacttctatttcggttcacttattaattttccatctatatatgaat catataatatgattaatttacacaagttcacacggccacgtaaaatgtaac tgtcttcaagttgtgcacataaagagggtagtttcgaagataacgggtcaa cgaaagggtaaaagagtaaattgcatagaacgcggccaaattaaaagcccc caattgggataaaagtcatcgccgtctcttaggtgtcaaatctcaactgtc taaaaacattaaaagcttcgttggggtagttgcatcttccctctctaatac aaaacttattttatccagttttagtttcgattttcatttgttaacatgtt ttcattttcttttaatgttaatagccttttttatttggaaaatgaaaacaa tttcacaatttaattctaaattaccatttctaaaaaatagaaataatataa ataataatattgaataatacatggactaaaaaattatagtactgtcctaaa caaaattgcttgactagattgaacagaaaatgttttttgatgtcttactagt ttgaacaatttatttgctaacattattctctttgtatatttcttaaaaacc catatttttccttaaatatttcccatttcccctaactacattcaatagct aagtctctctctccctctctctttctctctcactcaaaaatttcccattaa aattctcaaattttctccaacttttttaggcca

Promoter Expression Report #161

Promoter Tested In: *Arabidopsis thaliana*, Wassilewskija (WS) ecotype
Spatial expression summary:

| | |
|---|---|
| Flower | H pedicel H sepal H petal H filament H anther H carpel H style H epidermis H stomata H silique |

Promoter Expression Report #161

| | |
|---|---|
| Silique | H style H carpel H transmitting tissue H epidermis H ovule |
| Ovule | Pre-fertilization: L funiculus L outer integument Post-fertilization: H funiculus H outer integument H seed coat |
| Stem | L vascular L phloem |
| Leaf | L vascular |
| Hypocotyl | H epidermis L vascular |
| Cotyledon | L epidermis |
| Rosette Leaf | L vascular L epidermis |
| Primary Root | H epidermis H cortex H endodermis H vascular H quiescent H root cap H root hairs |

Observed expression pattern:
T1 mature: GFP expression in sepals, petals, stamens and siliques of developing floral buds through to mature flowers. GFP expression throughout all tissues of stamen excluding pollen. GFP expression throughout all tissues of silique excluding stigma. Within ovules, highest GFP expression is at funiculus, outer integument and mature seed coat. GFP expression in vascular tissues of flowers, stems and leaves. In stem, expression in phloem cells within vascular bundle. Expression in guard cells throughout plant.
T2 seedling: High GFP expression throughout epidermal tissues of seedlings. High GFP expression throughout all root cell types decreasing toward elongation zone. GFP is expressed in root cap and meristem cells.

| | |
|---|---|
| Expected expression pattern: | High in siliques |
| Selection Criteria: | Microarray data |
| Gene: | Chlorophyll A-B binding family protein/early light-induced protein |
| GenBank: | NM_113183 *Arabidopsis thaliana* chlorophyll A-B binding family protein/early light-induced protein (ELIP)(At3g22840) mRNA, complete cds gi\|30686801\| |
| Source Promoter Organism: | *Arabidopsis thaliana*, Columbia (Col) ecotype |
| Vector | pNewbin4-HAP1-GFP |
| Marker Type: | GFP-ER |
| Generation Screened: | X T1 Mature X T2 Seedling □T2 Mature □T3 Seedling |

Inductions completed.

| Treatment: | Age: | Gen: | Time points: | Events Screened/Response: | Response: |
|---|---|---|---|---|---|
| 1. Drought | 4 wks | T2 | 8 days no water | 2/0 | No |
| 2. Heat | 7 days | T2 | 2 Hr 42C | 3/0 | No |
| | | | 6 Hr 42C | 3/0 | No |
| | | | 16 Hrs-Post 42C | 3/0 | No |

T1 Mature Plant Expression   Organs/Tissues screened
Events Screened: n = 6   Events Expressing: n = 3
GFP Expression Detected

| | |
|---|---|
| X Flower | H pedicel □receptacle □nectary H sepal H petal H filament H anther □pollen H carpel H style □papillae □vascular H epidermis H stomata □trichome H silique |
| X Silique | □stigma H carpel □septum □placentae H transmitting tissue □vascular H epidermis □stomata □abscission zone H ovule |
| X Ovule | Pre-fertilization: □primordia □inner integument L outer integument □embryo sac L funiculus □chalaza □micropyle □gametophyte Post-fertilization: □zygote □suspensor □embryo sac H funiculus □inner integument H outer integument □endothelium H seed coat □primordia □chalaza □micropyle □early endosperm □mature endosperm □embryo |
| □Embryo | □suspensor □preglobular □globular □heart □torpedo □late □mature □provascular □hypophysis □radicle □cotyledons □hypocotyl |
| X Stem | □epidermis □cortex L vascular □xylem L phloem □pith □stomata □trichome |
| X Leaf | □petiole □mesophyll L vascular □epidermis □trichome □primordia □stomata □stipule □margin |
| □Shoot apical meristem | □shoot apical meristem □flower primordium |

X Pedicel (Pd) and Stem (Sm) in the inflorescence meristem
X Pedicel (Pd) and flower bud in the inflorescence meristem
X Sepal (Se) in the flower
X Pollen (Po), Petal (Pe) and Stamen (St) in the stamen
X Pollen (Po), Ovule (Ov) and Stigma (Sg) in the pre-fertilized silique
X Stigma (Sg) and Pollen transmitting tract (Tt) in the unfertilized stigma
X Funiculus (Fn) in the pre-fertilized ovule
X Funiculus (Fn) and Chalaza (Ch) in the fertilized ovule
X Funiculus (Fn), Placenta (Pl) and Outer Integument (Oi) in the developing seed
X and Outer Integument (Oi) in the developing seed
X Seed coat (Sc) in the early mature seed
X in the Seed coat (Sc)
X Columella (Cm), Radial wall (Rw) and Starch granule (Sg) in the seed coat
X in the embryo
X Guard cell (Gc), Vasculature (Vs) and Hydathode (Hd) in the Leaf
X in the stem T2 Seedling Expression   Tissues Screened
Events Screened: n = 3   Events Expressing: n = 3
Seedlings expressing/Seedlings screened
Event-01: 3/4
Event-05: 3/6
Event-06: 4/6
□Scheduled
GFP Expression Detected

| | |
|---|---|
| X Hypocotyl | H epidermis □cortex L vascular □xylem □phloem □stomata |
| X Cotyledon | □mesophyll □vascular L epidermis □margin □stomata □hydathode |
| X Rosette Leaf | □mesophyll L vascular L epidermis □trichome □petiole □primordia □stomata □stipule □margin □hydathode |
| X Primary Root | H epidermis □trichoblast □atrichoblast H cortex H endodermis H vascular □xylem □phloem □pericycle H quiescent □columella H root cap H root hairs |
| □Lateral root | □epidermis □trichoblast □atrichoblast □cortex □endodermis □initials □flanking cells □vascular □lateral root cap |
| □Shoot apical meristem | □shoot apical meristem |

X in the leaf
X Epidermis (Ep) and Vasculature (Vs) in the leaf
X Epidermis (Ep), Hypocotyl (Hy), Root (Rt) and Vasculature (Vs) in the seedling
X Root apical meristem (RAM) in the root tip Promoter utility
| | |
|---|---|
| Trait Area: | Nutrients, seed yield, water use efficiency |
| Sub-trait Area: | Nitrogen use efficiency, ovule/seed abortion, endosperm cell number/size, endosperm granule number/size, seed enhancement, seed number, harvest index, heat, water potential, drought, moisture stress at seed set |
| Utility: | Among other uses this promoter sequence could be useful to improve: |

Notes: This promoter is strongly differentially regulated under drought conditions and in a number of tissues.

| | |
|---|---|
| Construct: | PT0623 |
| Promoter candidate I.D: | 11768718 |
| cDNA I.D: | 23644072 |
| Lines expressing: | PT0623 -01, -05, -06 |

Sequence (SEQ ID NO: 115):

aaagttattgacattttgaaaggaccgtaaatattaccaaaaaactgacgg agttaggatcggccacgtagaaagggacaaagagagaacagtcacggactc ggccagactaagtatgggcctgtctgaatccaaactcagctaagttccaaa agcataaagagagatgtgtaatgaaatgaacgtattctagaaacgaaagca -continued

```
atgttatgctttgttttgagccacatgttttgggagatggagagaatct
ttttacgttttaacctaacccacttggcacttggccaaaaaagtgagaag
aaactgtggcgaatgagtaggccacgccatggactttgttccttgtcctc
aaaagttaaatttatgttatgcgtggggacaatctaagcaacgtggttcct
ttaaatatcgcagcttcctcttttacacttttggagcctacgtgttttgtt
ttggaccggccaaatacacgagtcagtcagtttagaaataatttggatgtc
caaaaatcttggagatccaaataaaataattagcatgttttagttcataag
aatatgaaatgtagataaactgtctatattaatttttccatagaattggct
ttttatcgaggtgatgtacttaatgactttgttgattactactcgtataac
aataaagaatatgatactatgtgagacttataatgaatttggtgtgtgtta
attaatccagttgaaacagtttaataacaaatcagaataaaaattgtagta
agaaaatttgaacgctgatccttcaacctagatagtgaaccttcaaatac
tatatgattcacgtgtaatgttttgaccgttggttatttttgtgtgaact
atattaacttatcaatatcgaaaggctaaataagtaaataactaaaagaaa
gttcaggaaacaactcgacctaatgacctatcatttctgatcacccgtcct
ataaatacatacgtaagatcattcgttact
```

| Promoter Expression Report #163 | |
|---|---|
| Promoter Tested In: *Arabidopsis thaliana*, Wassilewskija (WS) ecotype | |
| Spatial expression summary: | |
| Flower | H pollen |
| Silique | M ovule |
| Ovule | Post-fertilization: M inner integument M endothelium M embryo |
| Embryo | M mature embryo H root tip L radicle |
| Stem | L vascular |
| Primary Root | H epidermis H cortex L root cap H root hairs |
| Observed expression pattern: | |
| T1 mature: High GFP expression in endothelium cell layer of ovules and root cap of embryos. GFP expressed in pollen. Low GFP expression in stem vascular tissue. | |
| T2 seedling: High GFP expression specific to epidermal cells and root cap. GFP expression in epidermal cells decreases toward root elongation zone where no expression is observed. | |
| Expected expression pattern: | Flowers and buds |
| Selection Criteria: | Microarray data |
| Gene: product = "expressed protein"/note = "similar to myo-inositol oxygenase | |
| GenBank: NM_127538 *Arabidopsis thaliana* expressed protein (At2g19800) mRNA, complete | |
| Source Promoter Organism: *Arabidopsis thaliana*, Columbia (Col) ecotype | |
| Vector: | pNewbin4-HAP1-GFP |
| Marker Type: | GFP-ER |
| Generation Screened: | XT1 Mature XT2 Seedling □T2 Mature □T3 Seedling |

Inductions completed.

| Treatment: | Age: | Gen: | Time points: | Events Screened/ Response: | Response: |
|---|---|---|---|---|---|
| 1. Drought | 4 wks | T2 | 8 days no water | 5/0 | No |
| 2. ABA 100 uM | 7 days | T2 | 2 Hr | 4/0 | No |
| | | | 6 Hr | 4/0 | No |

T1 Mature Plant Expression  Organs/Tissues screened
Events Screened: n = 4  Events Expressing: n = 2
GFP Expression Detected

| Promoter Expression Report #163 | |
|---|---|
| X Flower | □pedicel □receptacle □nectary □sepal □petal □filament □anther H pollen □carpel □style □papillae □vascular □epidermis □stomata □trichome □silique |
| X Silique | □stigma □style □carpel □septum □placentae □transmitting tissue □vascular □epidermis □stomata □abscission zone M ovule |
| X Ovule | Pre-fertilization: □primordia □inner integument □outer integument □embryo sac □funiculus □chalaza □micropyle □gametophyte Post-fertilization: □zygote □suspensor □embryo sac M inner integument □outer integument M endothelium □seed coat □primordia □chalaza □micropyle □early endosperm □mature endosperm M embryo |
| X Embryo | □suspensor □preglobular □globular □heart □torpedo □late M mature □provascular □hypophysis H root tip L radicle □cotyledons □hypocotyl |
| X Stem | □epidermis □cortex L vascular □xylem □phloem □pith □stomata □trichome |
| □Leaf | □petiole □mesophyll □vascular □epidermis □trichome □primordia □stomata □stipule □margin |
| □Shoot apical meristem | □shoot apical meristem □flower primordium |

X Pollen (Po) and Stigma (Sg) in the silique
X Pollen (Po) in the pollen
X Endothelium (Ed) and Radicle (Rd) in the embryo
X Root (Rt) and Radicle (Rd) in the embryo
X Vasculature (Vs) in the stem T2 Seedling Expression  Tissues Screened
Events Screened: n = 2  Events Expressing: n = 2
Seedlings expressing/Seedlings screened
Event-01: 5/6
Event-02: 4/6
□Scheduled
GFP Expression Detected

| □Hypocotyl | □epidermis □cortex □vascular □xylem □phloem □stomata |
|---|---|
| □Cotyledon | □mesophyll □vascular □epidermis □margin □stomata □hydathode |
| □Rosette Leaf | □mesophyll □vascular □epidermis □trichome □petiole □primordia □stomata □stipule □margin □hydathode |
| X Primary Root | H epidermis □trichoblast □atrichoblast H cortex □endodermis □vascular □xylem □phloem □pericycle □quiescent □columella L root cap H root hairs |
| □Lateral root | □epidermis □trichoblast □atrichoblast □cortex □endodermis □initials □flanking cells □vascular □lateral root cap |
| □Shoot apical meristem | □shoot apical meristem |

X Epidermis (Ep), Root hair (Rh), Cortex (Cr) and Hypocotyl (Hy) in the root
X Epidermis (Ep) and Root cap (Rc) in the root tip

| Promoter utility | |
|---|---|
| Trait Area: | Seed, yield, nutrients |
| Sub-trait Area: | Seed enhancement, harvest index, nitrogen use efficiency |
| Nominated By: | Diversity parameters |
| Investigators: | Medrano, L., Theiss, N. |
| Utility: | Among other uses this promoter sequence could be useful to improve: Seed enhancement, nutrient uptake and thus yield. |

Notes: Lorence A, Chevone BI, Mendes P, Nessler CL. myo-inositol oxygenase offers a possible entry point into plant ascorbate biosynthesis. Plant Physiol. 2004 Mar; 134(3):1200–5. Epub 2004 Feb 19.

| Construct: | PT0613 |
|---|---|
| Promoter candidate I.D: | 13148297 |
| cDNA I.D: | 23555688 |
| Lines expressing: | PT0613 -01, -04 |

Sequence (SEQ ID NO: 116):

ttaatactaacattgtagaaagccacaaaaaagaaattgaaatgtgagtag atgctgagtcagaggtttggtcaatacacaacagctaattgagataatatt atacacgtcacgatgacttgttttttctcctcccaacttgttaatttcttt attcttaaaattaaaccatcgcaaaaacagaagaacacagctgtttttctc gactcccaatttctattttgctgctaaggacatttcatttcattatttccc aattcaggactccttagattttcctaaatttgttttcctaacttgctctct ctcattctaacattttctcattttttagattatcttgtacttttagtag attattttatcaggttttacaaacatacattgacattctaaaaagggcttc taaaaattcagtgtggaatgctgatatactaaaaaaggtcatgcaaaatt atctacgatttatctaaaattagataatttgccatatataactattaacta ataatcgatcctttgattttttgtttagataaaacgaaacagctatatctt ttttttttgttatcggattttaatcgaataaaagctgaaaaataacagtta tatcttcttcttttttaactaatgaaacagttatatcttaaacaaacaaca gaaacagtaaaatattaatgcaaatccgcgtcaagagataaattttaacaa actaataacaattgagataagattagcgcaaaagaaactctaattttagag cgtgtaaacacaaacgtcttgaaagtaaacgtgaattacacgcttctaa aacgagcgtgagttttggttataacgaagatacggtgaagtgtgacaccctt tctacgttaatttcagtttgaggacacaactcaagttatgtttgatatcta aggacttgcactgtctccaaatctgcaggaaggactttttgattggatcaa atataaataccatctccattctcgtctccttc

| Promoter Expression Report #261 |  |
|---|---|
| Report Date: | Mar. 24, 2005 |
| Promoter Tested In: | *Arabidopsis thaliana*, Wassilewskija (WS) ecotype |

Spatial expression summary:
Tables 1.1, 2.1.
Flower         L pedicel L receptacle L vascular
Silique        L placenta L vascular
Ovule          Post-fertilization: L chalaza
Hypocotyl      L vascular
Cotyledon      L vascular
Rosette Leaf   L vascular
Primary Root   H vascular H pericycle
Observed expression patterns: T1 mature: GFP expressed in vasculature of the receptacle, placenta, and ovules of flowers. T2 Seedling: GFP highly expressed throughout vasculature of root decreasing toward shoot and root apex. Weak GFP expression in vasculature of cotyledons and rosette leaves.
Expected expression pattern: Phloem of the stem; xylem-to-phloem transfer tissues and in the veins of supplying seeds. Vascular strands of siliques and in funiculi. Also expressed in the vascular system of the cotyledons in developing seedlings.
Selection Criteria: *Arabidopsis* public PNAS 92, 12036–12040 (1995)
Gene:          AAP2 (X95623)
GenBank: NM_120958 *Arabidopsis thaliana* amino acid permease 2 (AAP2) (At5g09220)
Source Promoter Organism: *Arabidopsis thaliana*, Wassilewskija (WS) ecotype
Vector:        pNewbin4-HAP1-GFP
Marker Type:   X GFP-ER
Generation Screened:   X T1 Mature X T2 Seedling ☐T3 Mature ☐T3 Seedling Mature Plant Expression     Organs/Tissues screened
Events Screened: n = 3      Events Expressing: n = 2

Promoter Expression Report #261

GFP Expression Detected
X Flower        L pedicel L receptacle ☐nectary ☐sepal ☐petal ☐filament ☐anther ☐pollen ☐carpel ☐style ☐papillae L vascular ☐epidermis ☐stomata ☐trichome ☐silique
X Silique       ☐stigma ☐style ☐carpel ☐septum L placenta ☐funiculus ☐transmitting tissue L vascular ☐epidermis ☐stomata ☐abscission zone ☐ovule
X Ovule         Pre-fertilization: ☐primordia ☐inner integument ☐outer integument ☐embryo sac ☐funiculus ☐chalaza ☐micropyle ☐gametophyte
                Post-fertilization: ☐zygote ☐suspensor ☐embryo sack ☐funiculus ☐inner integument ☐outer integument ☐endothelium ☐seed coat ☐primordia L chalaza ☐micropyle ☐early endosperm ☐mature endosperm ☐embryo
Embryo          ☐suspensor ☐preglobular ☐globular ☐heart ☐torpedo ☐late mature ☐provascular ☐hypophysis ☐radicle ☐cotyledons ☐root meristem ☐shoot meristem
☐Stem           ☐epidermis ☐cortex ☐interfascicular region ☐vascular ☐xylem ☐phloem ☐pith ☐stomata ☐trichome
☐Leaf           ☐petiole ☐mesophyll ☐vascular ☐epidermis ☐trichome ☐primordia ☐stomata ☐stipule ☐margin
☐Shoot apical meristem   ☐Shoot apical meristem ☐Flower primordium
X in the vasculature (Vs) of the flower
X in the Placenta (Pl) and Funiculus (Fn) adjacent to the ovule attachment site
X in the Chalaza (Ch) of the ovule T2 Seedling Expression     Tissues Screened
Events Screened: n = 3      Events Expressing: n = 3
Seedlings expressing/Seedlings screened
Event-01: 6/6
Event-02: 6/6
Event-03: 4/6
GFP Expression Detected
X Hypocotyl     ☐epidermis ☐cortex L vascular ☐xylem ☐phloem ☐stomata
X Cotyledon     ☐mesophyll L vascular ☐epidermis ☐margin ☐petiole ☐stomata ☐hydathode
X Rosette Leaf  ☐mesophyll L vascular ☐epidermis ☐trichome ☐petiole ☐primordia ☐stomata ☐stipule ☐margin ☐hydathode
X Primary Root  ☐epidermis ☐trichoblast ☐atrichoblast ☐cortex ☐endodermis H vascular ☐xylem ☐phloem H pericycle ☐quiescent ☐columella ☐root cap ☐root hairs
☐Lateral root   ☐epidermis ☐trichoblast ☐atrichoblast ☐cortex ☐endodermis ☐initials ☐primordia ☐flanking cells ☐vascular ☐lateral root cap
☐Shoot apical meristem   ☐Shoot apical meristem
X in the Vascular (Vs) of the seedling between the Cotyledons (Co) and Hypocotyl (Hy)
X in the Root Hair (Rh) of the seedling
X in the Vascular bundle (Vb) of the root Promoter utility
Trait Area:      Nutrient
Sub-trait Area:  Storage in roots, uptake of minerals
Utility:         Among other uses this promoter sequence could be useful to improve:
                 Seed - Seed enhancement
                 Source - transport amino acids
                 Yield - harvest index, test weight, seed size,
                 Quality - amino acids, carbohydrate, protein, total seed composition Construct:                  YP0093
Promoter Candidate I.D:     13148232
cDNA ID:                    23617640
Lines expressing:           YP0093 -01, -02, -03

Sequence (SEQ ID NO: 117):

```
atgatgaacattctacatatataattattatgtttaagcacttagacagca
taaattctttctaattatataaatctaaccttgttacattgtacatctata
aattacttgaagaaataacgagttctatttctttttaaaaattaaaaatac
tataccatatctcagtgattaagttgaaccaaaaggtacggaggagaaaca
agcatttgattcttccttattttattttattcatctctcactaatgatggt
ggagaaaaaagaaaatacctaacaaacaaatatatattgtcatacaaaaa
tatttctatatttttagttaattagtttatattcctcacttttcagggctt
atataagaaagtgagcaaacacaaatcaaatgcagcagcaaatactatca
tcacccatctccttagttctattttataattcctcttcttttttgttcatag
ctttgtaattatagtcttatttctctttaaggctcaataagaggaggtact
attactacacttctctctacttttacttgtattttagcattaaaatcctaa
aatccgttttaaattcaaaaataaacttagagatgtttaatctcgattcgg
tttttcggctttaggagaataattatatgaaattagtatggatatctttac
tagtttccattcaaatgattctgatttcaatctaatactctcactctttaa
ttaaactatatgtagtgtaatttcacactgttaaatttctaccatgtcatg
tatattagagttgcatagaaaattgtaaaacatccatttgaattcgaatga
aacaaaatgttttaaaatAaaattttggtttttaaaagaaaaatctaaaac
tgaattatatcgtttaaccaagttgtaaaagtcataaaacgtagtatcttg
taaatcgctcttccacggtccaaatagacttctagtaataaacaagtaaaa
ctaattttggtttcttactaattttcacaga
```

TABLE 2

| Construct Name | Fl | Si | Lf | St | Em | Ov | Hy | Co | Rt |
|---|---|---|---|---|---|---|---|---|---|
| YP0226 | Y | Y |  |  |  |  | Y | Y | Y |
| YP0244 | Y |  |  |  |  |  |  |  |  |
| YP0286 | Y |  |  | Y |  |  | Y | Y | Y |
| YP0289 | Y |  |  |  |  | Y |  | Y | Y |
| YP0356 | Y | Y |  | Y |  | Y | Y | Y |  |
| YP0374 |  |  |  |  |  | Y | Y |  | Y |
| YP0377 | Y |  |  |  |  |  | Y | Y | Y |
| YP0380 | Y | Y | Y | Y |  |  | Y | Y | Y |
| YP0381 | Y |  |  |  |  |  | Y |  | Y |
| YP0382 | Y |  |  |  |  |  |  |  | Y |
| YP0388 | Y | Y | Y |  |  | Y |  |  | Y |
| YP0396 | Y | Y | Y |  |  | Y |  |  | Y |
| PT0506 | Y |  |  |  |  |  |  |  |  |
| PT0511 | Y |  |  |  |  |  |  | Y | Y |
| YP0275 |  |  |  |  |  |  |  |  | Y |
| YP0337 |  |  |  |  |  |  |  |  | Y |
| YP0384 |  |  |  |  |  |  |  |  | Y |
| YP0385 | Y | Y |  |  |  |  |  |  | Y |
| YP0371 | Y |  |  |  |  |  |  |  | Y |

Legend for Table 2
Fl   Flower
Si   Silique
Lf   Leaf
St   Stem
Em   Embryo
Ov   Ovule
Hy   Hypocotyl
Co   Cotyledon
Rt   Rosette Leaf The invention being thus described, it will be apparent to one of ordinary skill in the art that various modifications of the materials and methods for practicing the invention can be made. Such modifications are to be considered within the scope of the invention as defined by the following claims.

Each of the references from the patent and periodical literature cited herein is hereby expressly incorporated in its entirety by such citation.

SEQUENCE LISTING

```
<160> NUMBER OF SEQ ID NOS: 117

<210> SEQ ID NO 1
<211> LENGTH: 2039
<212> TYPE: DNA
<213> ORGANISM: Arabidopsis thaliana
<220> FEATURE:
<221> NAME/KEY: misc_feature
<222> LOCATION: (1)..(2039)
<223> OTHER INFORMATION: Ceres Promoter construct YP0001 as found in
      Promoter Report #1
<220> FEATURE:
<221> NAME/KEY: misc_feature
<222> LOCATION:
<223> OTHER INFORMATION: T1 Mature Plant Expression:  GFP expression
      observed in Sepal (Se), Receptacle (Re), Pedicel (Pd) in the upper
      part of the receptacle of the flower
<220> FEATURE:
<221> NAME/KEY: misc_feature
<222> LOCATION:
<223> OTHER INFORMATION: T2 Mature Plant Expression:  GFP expression
      observed in Pedicel (Pd) and Stem (Sm) in the inflorescence
      meristem, Epidermis (Ep), Pedicel (Pd) and Stem (Sm) in the
      pedicel junction of the stem, the flower
<220> FEATURE:
```

```
<221> NAME/KEY: misc_feature
<222> LOCATION:
<223> OTHER INFORMATION: T3 Seedling Expression:  GFP expression
      observed in the junction of the Cotyledons (Co), the Cotyledons
      and the Hypocotyl (Hy), the vasculature of the root, the Epidermis
      of the root tip
<220> FEATURE:
<221> NAME/KEY: misc_feature
<222> LOCATION: (2023)..(2023)
<223> OTHER INFORMATION: n is a, c, t, g, unknown, or other

<400> SEQUENCE: 1
ctgcattcac acatattttg ggctctcacg tgtttgtgaa tttaatatat ttgactacac     60
gatctttcaa cgtatgaaaa agtttatac tactattttc gtttgagtgg gaaataaaca    120
aatgatagct acagttatct atatggtata attttacact tttataacta ataatgatga   180
gtgatgacaa tcgagtgtcg gatataacag gccaacaagt ggaatggact tatgtaactt   240
tttaatcacg ggattaaatc acgtaaccca atgtcctaat tggtatttaa ttttgattat   300
ctcgatgcta catattgtca taggactcat atctttgatc acgtgccgct accaatccag   360 acatttagt atacaaaaaa aagaagata caaacttaag atatggaata tatatcagaa    420
ctatcagttt tagactttaa taattcgaat tgaataacta cgatcaatat ataaattggc   480
aaatagattg gtcaattgta gtgcaagaaa tttgtgaact ttattacagt acgaagagag   540
taagagaagc aagatccggt ttttaggcaa caagtaacat ttttgagttc agagagtttg   600
cttcttactt taagttacgt cactacaaaa gccaagttcc tacttcttag gtctaaagtc   660
aattttcgaa tattcagaaa aattgtactc tactagatcg aatagttttc accggtgaaa   720
cgatatataa atgaagacta caatattttt taattttttt aagcgtatga gttctagacc   780
tttggcacgt aaatttctcc ggtacctggg accaatcgtt gataatatca cgtttaagat   840
ttaatcatcc atcccaagta gagttgaact agtaaccttg agcacttttt ctcgagacaa   900 ctaaccatc atccacttag tgcaataaag cgtcattctt ttttttcttt tcaaaaattc    960
gtatttaatt ttaatttatt aaaaatattt cttttgtttt aaattgggac agaattatca  1020
tttaacatat ttaaaattta tattttttaat taaaaatagg gtaaaatata tttttcaaac  1080
aaaaattcaa aaatagggca attttcaaaa tcatccattc ttaaatctaa agtcggctac  1140
agtcttttcg ttgttttgtt gctaatttca atttatatac atgcaaatta caaaatataa  1200 tagttttttgg gggataatta tcttcttgcg ccttttttatt aaattaatat gctcatatag  1260
cagttcttac aattaatata actagggttt taaatttcaa tatcgagttg acaaaatgaa  1320
ttgtttacaa gtttttttct tttcaatatg cattgttcat cacgtattcg tagtgatgca  1380
aaaacaaact ataaattata attgcactag tgagattagc aagaagtgtt ataaattaga  1440
ataaacggaa ctatcaaact gtgttatgta caccatttat ttttgttaaa gaatatgtgt  1500
agtagttaga aaactgatca aattaaactg aaaattcaca ttacggagat caagttacat  1560
tgtctattga tgaaaaaaac aaaataaatc caaatggcac taaaagttgt agaaattgaa  1620
agaagaaaat agattttgt ctaggaataa aagtcaaat gggaaagaca aaaaaaagag    1680
aggcaaataa gcagtgatgg agctaaagca acgctttact cttttaatta tgaattattt  1740
gatttgacct ccactcgcct ggcttttttt ggttgttctt tatagaaaag taaataaca   1800 caattagcac ataacatgag ttatcgagaa accaattctc tttgtggtgt tttagttaat  1860
ttctataact tatgaaacca ttttctcagt ttatcatgat aattgatcct ctatttaaaa  1920
ccctaaagtt tatattttgt ttgttcaaac acagtcgcca ttgcactggg atccaacaat  1980
```

-continued gtcctccgac tcgtccaaga tcaagaggaa gcggaaccgc atnccttttaa cgaaggcga    2039

<210> SEQ ID NO 2
<211> LENGTH: 1129
<212> TYPE: DNA
<213> ORGANISM: Arabidopsis thaliana
<220> FEATURE:
<221> NAME/KEY: misc_feature
<222> LOCATION: (1)..(1129)
<223> OTHER INFORMATION: Ceres Promoter construct YP0007 as found in
      Promoter Report #2
<220> FEATURE:
<221> NAME/KEY: misc_feature
<222> LOCATION:
<223> OTHER INFORMATION: T1 Mature Plant Expression: GFP expression
      observed in the Endosperm (En) and Inner integument (Ii) of the
      fertilized Ovule (Ov), T2 Mature Plant Expression, T2 Mature
      tissue expressions similar to T1 expression data, the Inner
      Integument (Ii) of developing ovules at approximately late heart
      stage embryo, the Endothelium (Ed) which is derived from the inner
      integuments during the seed maturation stage
<220> FEATURE:
<221> NAME/KEY: misc_feature
<222> LOCATION:
<223> OTHER INFORMATION: T2 Seedling Expression: GFP expression
      observed in the root transition zone of the Root (Rt),
      Atrichoblast (At) within the root differentiation zone of the
      root, T3 Seedling Expression, cotyledons

<400> SEQUENCE: 2
agcagaacaa ctatatttat tgtgtcacat aaatctgaga tcatttataa ccaccaaaga    60
acctatacac agtaaatgac aaatgtatct ccctctatct ctattgccca tatgtagatg    120
ctaaagtaag atttctcttt tttttaatgt acttttttt gtataaagta tattccataa    180
gaaaaaggaa aagcttgttt atggatcaat tgaccccaaa aaaagttttt agatcaaagc    240
ccaatataaa aaaaaaacac agtagtgaca caaaggaact taaataaacc atgaattgat    300
ctataaacag tagagatcga taaggcgaac attttccatg tgaagtgtct tctttcatct    360
ataatatttt tgacatccaa taatttcctc tataatatca ttcacataat tgatagaaac    420
attatgttag aattgtccac atcatttgag ctgtaatata ttctgtttta acaaattata    480
tggtagttgc ttaatcttat gtccatcttc ttctatgcat cgttttcgcg cctagttgtc    540
cagtccattt caactaccta cctctaattc ttatcttaaa acaacatttt ttaatttaag    600
tattatgctc aaagactaac tagatagaaa accgttatta aacattaaac gaattaaaag    660
tcttacatgg aaaatgtagg tttataaacc acgagttatg attgacaata aaaaaaatgc    720
aaatcatcaa tcaaaagaga cttgagtgcg actctatatc aaccattgca attaaaatta    780
tctatcacaa aaattttaga cagattaagt taatttagtc taaattcact aatttatttt    840
ctataattag taattaacta tatttattta tttacacatt ttctgataat ttagaaattt    900
gcatgaataa caaatataag atttggaaa ttagtagcaa atttaattaa taattatttt    960
tgcctaaatg aaccaaacta taaaacctcc acatacacca gtcatcaaat ttacagagac    1020
aacaaactaa agttggtggt gatagagtga gagagaaaca ccattgcact gggatccaac    1080
aatgtcctcc gactcgtcca agatcaagag gaagcggaac cgcatcccg    1129

<210> SEQ ID NO 3
<211> LENGTH: 1035
<212> TYPE: DNA
<213> ORGANISM: Arabidopsis thaliana
<220> FEATURE:
<221> NAME/KEY: misc_feature
<222> LOCATION: (1)..(1035)
<223> OTHER INFORMATION: Ceres Promoter construct G0013 as found in

```
        Promoter Report #3
<220> FEATURE:
<221> NAME/KEY: misc_feature
<222> LOCATION:
<223> OTHER INFORMATION: T1 Mature Plant Expression: GFP expression
        observed in the Vascular (Vs) of the leaf
<220> FEATURE:
<221> NAME/KEY: misc_feature
<222> LOCATION:
<223> OTHER INFORMATION: T3 Seedling Expression: GFP expression
        observed in the Epidermis of the Hypocotyl (Hy), the Vasculature
        (Vs) of the root, the root tip and lateral root tip

<400> SEQUENCE: 3
atcttgtgat acacaattta ttactatttg gtacattttg aagtatttgt ttttgcatga      60
tatatgacgt taatttgaac tgatattagt caatttatgg gtacaaaagt tgaaagttta    120
gagcactatg ttggatttat taaaaatgat atcatacaat ggttcaatat atatatattt    180
ttttccacgt ttttaataac attttttgtaa acaagtcttc tactattgtc tttattgtta   240
atgagtttct agtacctaat taggaatttt gaggatatac gatacattaa tgagttacat    300
tatcccgaaa acaaaatctt gaaaacgaac aaagataatt tggacattac tcgttatgta   360
tacgtatgga attggataga gccgttgaac catcaagtgg gtcttcaagt caacgaactg    420
aatttgattt tacactcatg tacatcggcc acaattttat tcacacacta ctaacacctc    480
tggtgtccac ttttttcttt ctctagattg atgtgttaag attttttgttg caattcattt   540 attcaggtat ttttatatat atatatatat aaattagaat aaactaattt aaagaaagat    600
atagcaatta tgtttcacat tttaacattc tcaatcattt ataaaactaa tgtggtgatg    660
aatggtatat atatatatat atatatatat atatacatat atatattttg ttgtgaacta    720
atggtaaata tttaaaataa gacatacgta cataaatcca cgggctctta aagtcatgat    780
gcggttaata aatgttcaca taacggtaac caagtggctc aaaatcatga aacaacgtca    840
cataatttat cttataatgt ggataattag taccgcatta tttgtaagaa aattaaatta   900
attatagatt cacagctaag aaaatacgaa aagacagctc aacactttc cacttctatt    960 ccccactgtc tatataactc tgataaaata tctctgatct ctccaccatt gcactggtcc    1020
aggagataaa caaga                                                      1035

<210> SEQ ID NO 4
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct YP0097 as found in
        Promoter Report #4
<220> FEATURE:
<221> NAME/KEY: misc_feature
<222> LOCATION:
<223> OTHER INFORMATION: T1 Mature Plant Expression: GFP expression
        observed in the Embryo (Em) and Suspensor (Su) of the four day
        embryo, the globular Embryo (Em), the heart stage embryo and the
        torpedo stage embryo, the Embryo (Em) and Outer Integument (Oi) of
        the ovule, the Funiculus (Fn) and Placenta (Pl) of the ovary
<220> FEATURE:
<221> NAME/KEY: misc_feature
<222> LOCATION:
<223> OTHER INFORMATION: T2 Seedling Expression: GFP expression
        observed in the Epidermis (Ep) of the hypocotylin the Cotyledon
        (Co), the Stipules (Ss), the lateral root initial, the lateral
        root cap

<400> SEQUENCE: 4
```

```
ttcatcttta tatttaagag tttaaaaact gcaacttttg tttttctttc actaagtctt        60
atggccacag ttaattaaaa gcagatgaaa ggtggtccaa tggaaaagga gaatgtgatt       120
gggctagttg ggagagttct gatgtctagt gttgggtaca cgtgtccgtc agttacacat       180
agcattaaat cagacggcat gtcattattc aaatctagtt cacatagtac gactaatagc       240
tgataaatta atgattatac agcatatgaa ttatgaattc aaaaaaaaaa aaaaattgaa       300
aatgttaagg agatgctata ttttacaaaa ttcatcgcaa tgctttctac taatttgcta       360
agtggtcttc tccagttagt cttgtcgatt ccaagcgata ttattaaatc ttgaagcatc       420
gctcaaagca ttatagctta agataaccaa attgttatta aaacaccta gtgaaatttt        480 taaattaaaa caattttgat atctttgtaa tatctaatac tactctttct gtgtctaaaa       540
ggattaattt tcaaaattt cacacatatt aaaaaaaaaa aaaaattact agctaaacaa        600
ttttcaataa tcataaaaca atagtaactt ataattttt ttttattttc aaaatagtcc        660
ttcaagttta caattcattt tagtattata atcaacaaaa tttgtattaa aaagttggaa       720
aattaatctt tgtggaacaa aaaaatctag aaatcatttt ttagaattag agagaggttt       780
gataaaaaaa aataaaaaaa aatagagaga ggtagtacat actaaacgat gtgatactac       840
tattgacaaa atcttaattc tcagtttagt agaataaact agaaggaatg aatgaagtaa       900
atgcgaatcc aactactaac aaaccctact tagtcatcat attttcccat atgaaatccc       960
tatataaacc catcatcatc tcccacttt ttcatatcca                             1000
```

<210> SEQ ID NO 5
<211> LENGTH: 1068
<212> TYPE: DNA
<213> ORGANISM: Arabidopsis thaliana
<220> FEATURE:
<221> NAME/KEY: misc_feature
<222> LOCATION: (1)..(1068)
<223> OTHER INFORMATION: Ceres Promoter construct YP0111 as found in
      Promoter Report #5
<220> FEATURE:
<221> NAME/KEY: misc_feature
<222> LOCATION:
<223> OTHER INFORMATION: T1 Mature Plant Expression: GFP expression
      observed in the Endosperm (En) and Seed Coat (Sc) of ovules
<220> FEATURE:
<221> NAME/KEY: misc_feature
<222> LOCATION:
<223> OTHER INFORMATION: T2 Seedling Expression: GFP expression
      observed in the Endodermis (Ed), Epidermis (Ep), Lateral root
      primordium (Lr) of the root, the Pericycle (EP, PE) of the Stele
      (St)
<220> FEATURE:
<221> NAME/KEY: misc_feature
<222> LOCATION:
<223> OTHER INFORMATION: T2 Mature Plant Expression: GFP expression
      observed in T2 Mature tissue expressions similar to T1 expression
      data , the Inner Integument (Ii) of developing seed, the maturing
      seed

<400> SEQUENCE: 5

```
cgattggatt tagtctatac attatagggc gcaagtttgt ggatttaaga attatataaa        60
aacttgaaat atatagtttt tatgcattct cctcttgtgt aatacataaa ccaaatatga       120
gataggttaa tctgtatttc agataatatt aaattccaaa caatattttt acttgttata       180
agaaggcaat taatatctct ctgttaatgg caagtggtac caagtagtat taaactatta       240
atgcaatgga agagtactgt tggaaattat aatcctctat cacacattca aacagatctc       300
ctgaaatctt ctcttccaaa cttgtacttc tctgatccaa atgtaggctc caaaatatag       360
acatttacca tttactaagt ccacaactcc tttcttgtct ccttcaaaaa tgactcttgt       420
```

-continued

```
gtaaccacca tatgactccg acagttcggc attgccatga tgagagctta aaaattcacc      480
ttcctgagca tttcaagtct tcactccctt agcttgacct gaaccaagat aaaatgcctt      540
tgtcgtcccg taatatccat cctgctttgg acggcatcat agttacattc gatccatcct      600
atttacaatg ttattttagt attaaaaaca tgacaataaa tttgttgtta aacatattca      660
aatacaatat gattggattt ataagtaatt gtaatatgaa atgtccttag taatatgtta      720
aaaaatacat agatacacac acgtactaaa agaggcaacg cgggagatgt cattagagga      780
agaactagga agcagagcgt tcatgcaaaa tgctaccaaa aacgttaatg caatatctca      840
actaatcagc acagtccatt tcatactgag aatgtaaaaa ccaatcagca tcgtccattt      900
tttcatctaa ttatttgtta actcttaatt ggccacaact tccaaccaca tgacgctctt      960
tctattccct ttatatattc ccatctcaaa tgttcttgga gacacaaaat atcataaaca     1020
tataaacata aacgccaatc gcagcttttg tactttggc ggtttaca                   1068
```

<210> SEQ ID NO 6
<211> LENGTH: 1002
<212> TYPE: DNA
<213> ORGANISM: Arabidopsis thaliana
<220> FEATURE:
<221> NAME/KEY: misc_feature
<222> LOCATION: (1)..(1002)
<223> OTHER INFORMATION: Ceres Promoter construct YP0104 as found in
      Promoter Report #6
<220> FEATURE:
<221> NAME/KEY: misc_feature
<222> LOCATION:
<223> OTHER INFORMATION: T1 Mature Plant Expression: GFP expression
      observed in the Pedicel (Pd) of the inflorescence meristem, the
      stem
<220> FEATURE:
<221> NAME/KEY: misc_feature
<222> LOCATION:
<223> OTHER INFORMATION: T2 Seedling Expression: GFP expression
      observed in the Epidermis (Ep) of the hypocotyl, the Epidermis
      (Ep) of the cotyledon petiole, the Epidermis (Ep) and Cortex (Cr)
      of the hypocotyl

<400> SEQUENCE: 6

```
tttattttat tttttgaatg aaaatgtctt ctttattcgt aattttaaac tcactggtgg       60
tggatatatt gttatgtccc caattcgtct ggcaactctc gtatattagt gagaaaaatt      120
tgtccattat ttactgcact attaccctgt gttaattttt tgtattgaaa ttgttttttt      180
agtaattcac gtcatatagc gaatgattct ttaattttaa aaattcagtc ttaagtttac      240
aaattaaata acgctactgt aaccaactct gtacgaccaa catgttcgag tttttgtata      300
tacggccata tatgtacata ttttactata aagcgaaaaa atccataaat tatttaatta      360
atatataaag gtgccattct atttccaatg tgcttaggaa aatgcagaac ctcgtgctat      420
atctctgtcg ccacgtgcaa atataacaat atgaaataga actagcaaat cttgaaatct      480
aactcttaag actaattcaa gcacatacgt agagaaagtt gaccaacggt tatcagcatt      540
ttaacatgga ccttatcaac attttaacaa agtccacaaa caaccagtct tacaatcgca      600
ttggtacaag ataatcgaat tcatcttcca tataacaaaa cctaaacctt ggtgtgaaaa      660
ggagaagata tgtatgttaa aggccgccta tgcctctggt ttggggtata tgattctaag      720
attagggttt gaatattttc gttagcctgc catgagatat atttatgtga taatttagag      780
cctcttatgc attaatgcat aaccgactag atccatgtgg tattcagcta atcagtacac      840
acaagacaaa gtagtaaatg agtttgatga agactgtggt ctgataattc ctatcaacgt      900
```

-continued

```
taaatctgtc ggggccaggc agccagcaac attttgccta ccaacgctct gaattcaatt      960
gaacctaggc tatataatag caggctaact taactaagag tt                        1002
```

<210> SEQ ID NO 7
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct YP0075 as found in
      Promoter Report #7
<220> FEATURE:
<221> NAME/KEY: misc_feature
<222> LOCATION:
<223> OTHER INFORMATION: T1 Mature Plant Expression:  GFP expression
      observed in the Guard cell (Gc) and Vasculature (Vs) of the petal
      and sepal in the flower, the Lateral vasculature (Lv) and Medial
      vasculature (Mv), of the silique, the Guard cell (Gc) of the
      pedicel
<220> FEATURE:
<221> NAME/KEY: misc_feature
<222> LOCATION:
<223> OTHER INFORMATION: T2 Seedling Expression:  GFP expression
      observed in the Guard cell (Gc), that define the Stomata (So) of
      the cotyledon
<220> FEATURE:
<221> NAME/KEY: misc_feature
<222> LOCATION:
<223> OTHER INFORMATION: T2 Mature Plant Expression:  GFP expression
      observed in previous generation., T2 Mature tissue expression (if
      different expression pattern)., the Epidermis (Ep), Guard Cells
      (Gc) and  Vasculature (Vs) of the proximal, mid and distal
      siliques, the Epidermis (Ep) and Guard cells (Gc) of the mid
      region of the siliques and the stem
<220> FEATURE:
<221> NAME/KEY: misc_feature
<222> LOCATION:
<223> OTHER INFORMATION: T3 Seedling Expression:  GFP expression
      observed in T2 Mature tissue expression (if different expression
      pattern).

<400> SEQUENCE: 7

```
tggattacaa atcattaagc taatatcttc gatgaattaa gaagataagt ggataacaag       60
tacctaaccg caatagtcca taaattaaaa cattaatgta tttgtcgttg aaaatttggc      120 cgactttttat ttgttattct agtttccaca tcaaaaatgt ttgtacttcg tagcaatcca    180
tccacctaaa ccccaaatct taatttatat ttgttgcgtt taaatttggg tgagatttga     240
ttctaagtag ttgagataaa ttgatattct attcattagt aaaatgatag agaaattggt     300
ttataataat tttaccctag aacatgacat gatattggta accattaatc aaagaaagag     360
caaagcattt aatttaccct actctccaac cactccagcc tttattagtt gcagttggga     420
atcatttctt tatgattctt atgtcattgt ctcctaaatc aatgaagtgc cttgaccttg     480
ttactaattc gaacatagca aagccaacta catagatcct ttacaaagtt ctaaaaacag     540
gttgtttagg cgtctagaca aacaaaacca ttttgtacga ttcaacaaat tggtccatag     600
aatgttattg atctttcttg tttaggcatt cgataaatcg gctaatacat tatttttttg     660
ttttgctttt tccttattaa aaatatgcaa agtattatga tgtttaacct gaactgaatt     720
ttacatttaa ctggatatag gaaaatattg ggttgaattt aataattaag caattgtcac     780
gtaaatcaaa ttgggcttaa tatatattgt tgatttcagc aaagacaaag ttgggccgtt     840
tcaatagtct tcacgcgatg taagcgttca ctaaccaact agagaagaca atcaaatgaa     900
tacgttccac gtgacgctta cgaacttgtc agtcactttg gtaatatgac agacagtaac     960
cagtaaacta ctaatctctt tcgctaacga acacacaaaa                         1000
```

-continued

<210> SEQ ID NO 8
<211> LENGTH: 998
<212> TYPE: DNA
<213> ORGANISM: Arabidopsis thaliana
<220> FEATURE:
<221> NAME/KEY: misc_feature
<222> LOCATION: (1)..(998)
<223> OTHER INFORMATION: Ceres Promoter construct YP0016 as found in
      Promoter Report #8
<220> FEATURE:
<221> NAME/KEY: misc_feature
<222> LOCATION:
<223> OTHER INFORMATION: T1 Mature Plant Expression: GFP expression
      observed in the Receptacle (Re) and Vasculature (Vs) of the
      flower, the Phloem (Ph) of the leaf
<220> FEATURE:
<221> NAME/KEY: misc_feature
<222> LOCATION:
<223> OTHER INFORMATION: T2 Seedling Expression: GFP expression
      observed in the Phloem (Ph) of the root differentiation zone
<220> FEATURE:
<221> NAME/KEY: misc_feature
<222> LOCATION:
<223> OTHER INFORMATION: T2 Mature Plant Expression: GFP expression
      observed in similiar tissues to T1 mature expression data plus the
      hydathode region of mature leaves. Hydathode is a highly modified
      region of vascular and ground tissue that permits release of water
      through a pore in the epidermis.
<220> FEATURE:
<221> NAME/KEY: misc_feature
<222> LOCATION:
<223> OTHER INFORMATION: T3 Seedling Expression: GFP expression
      observed in T3 Seedling tissue expressions similar to T2 seedling
      expression plus, the Epidermis (Ep) of the root transition zone of
      the hypocotyl, the Vasculature (Vs) of the root, the Hydathode
      (Hd) and Vasculature (Vs) of the root

<400> SEQUENCE: 8
aaacatgttt tatgtaacta ctttgcttat gtgattgcct gaggatacta ttattctctg     60
tctttattct cttcacacca catttaaata gtttaagagc atataaatta attatcttca    120 aaaggtgat  tatatgcatg caaaatagca caccatttat gtttatattt tcgaattatt    180
taatacattt caatatttca taagtgtgat ttttttttt  tttgtcaatt tcataagtgt    240
gatttgtcat ttgtattaaa caattgtatc gcgcagtaca aataaacagt gggagaggtg    300
aaaatgcagt tataaaactg tccaataatt tactaacaca tttaaatatc taaaaagagt    360
gtttcaaaaa aaattctttt gaaataagaa aagtgataga tatttttacg ctttcgtctg    420
aaaataaaac aataatagtt tattagaaaa atgttatcac cgaaaattat tctagtgcca    480
ctcgctcgga tcgaaattcg aaagttatat tctttctctt tacctaatat aaaaatcaca    540
agaaaaatca atccgaatat atctatcaac atagtatatg cccttacata ttgtttctga    600
cttttctcta tccgaatttc tcgcttcatg gttttttttt aacatattct catttaattt    660
tcattactat tatataacta aaagatggaa ataaaataaa gtgtctttga gaatcgaacg    720
tccatatcag taagatagtt tgtgtgaagg taaaatctaa aagatttaag ttccaaaaac    780
agaaaataat atattcgct  aaaaagaag  aaaataatta aatacaaaac agaaaaaaat    840
aatatacgac agacacgtgt cacgaagata ccctacgcta tagacacagc tctgttttct    900
cttttctatg cctcaaggct ctcttaactt cactgtctcc tcttcggata atcctatcct    960
tctcttccta taaatacctc tccactcttc ctcttcct                            998

<210> SEQ ID NO 9
<211> LENGTH: 1000
<212> TYPE: DNA

```
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct YP0094 as found in
      Promoter Report #9
<220> FEATURE:
<221> NAME/KEY: misc_feature
<222> LOCATION:
<223> OTHER INFORMATION: T1 Mature Plant Expression:  GFP expression
      observed in Chalaza (Ch), developing floral buds (numbered),
      Embryo (Em), Inflorescence meristem (Im), Micropyle (Mp), and
      Phloem (Ph)
<220> FEATURE:
<221> NAME/KEY: misc_feature
<222> LOCATION:
<223> OTHER INFORMATION: T2 Seedling Expression:  GFP expression
      observed in Cortex (Cr), Cotyledon (Co), Epidermis (Ep), Hypocotyl
      (Hy), Lateral root (Lr), Pericycle (Pr), Rosette leaf (Rl), Phloem
      (Ph), Vascular bundle (Vb).
<220> FEATURE:
<221> NAME/KEY: misc_feature
<222> LOCATION:
<223> OTHER INFORMATION: T3 Seedling Expression:  GFP expression
      observed in Root vasculature

<400> SEQUENCE: 9
taaagatcag aagaggaagg tttcgccgcg gcggttgcat cttcaccgtc gatttcatcg      60
ttacagcgac gccggtaatt cctaggttgc ttagttccca ttctctctct aaaattaggg    120
ctcgaaatga attgttgaac aagatagaga tcttttctg atccccgtcg aacatttatt    180
caaggccaaa aaaagcacac gggaatttag agtaccaata catatcaaaa cctaatgggc    240
tttgaatggt tgcatgtgtg tgtttatttc tgatatgcaa agcgatcgat agtcttttcc    300
atacaagtgt aaactgtaaa caacgtaatt aagcataaca atacaactct ttcttctctt    360 ttttttgta aacacaaaat aaaattacat caattcatgc ttttcctagt tcatctgaca    420
ttttccaaaa ttcatgttcc attgagtccc taatacttgt tcatattcat attagggtac    480
atgaataaaa gttatcattc ttgaaactac taaatttca tagtttattt ttcttctttt    540
cgtttcactt tcgaacaaaa cactacgcgt ggcatttgca atgaattcca cattatatgg    600
aataacacca tgatgaacat tctacatata taattattat gtttaagcac ttagacagca    660
taaattcttt ctaattatat aaatctaacc ttgttacatt gtacatctat aaattacttg    720
aagaaataac gagttctatt tcttttaaa aattaaaaat actataccat atctcagtga    780
ttaagttgaa ccaaaaggta cggaggagaa acaagcattt gattcttcct tattttattt    840
tattcatctc tcactaatga tggtggagaa aaaagaaaa tacctaacaa acaaatatat    900
attgtcatac aaaaatattt ctatattttt agttaattag tttatattcc tcacttttca    960
gggcttatat aagaaagtga gcaaacacaa atcaaaatgc                          1000

<210> SEQ ID NO 10
<211> LENGTH: 691
<212> TYPE: DNA
<213> ORGANISM: Arabidopsis thaliana
<220> FEATURE:
<221> NAME/KEY: misc_feature
<222> LOCATION: (1)..(691)
<223> OTHER INFORMATION: Ceres Promoter construct YP0033 as found in
      Promoter Report #10
<220> FEATURE:
<221> NAME/KEY: misc_feature
<222> LOCATION:
<223> OTHER INFORMATION: T2 Mature Plant Expression:  GFP expression
      observed in the Vasculature (Vs) of the sepal of the flower, the
      Guard cell (Gc) of the pedicel, the Guard cell (Gc) of the silique
<220> FEATURE:
```

```
<221> NAME/KEY: misc_feature
<222> LOCATION:
<223> OTHER INFORMATION: T3 Seedling Expression:  GFP expression
      observed in the Guard cells (Gc) of the leaf, the Root hair (Rh)
      and Epidermis (Ep) of the root transition zone between hypocotyl
      and root, the Atrichoblast (At) and Trichoblast (Tr) of the root
      differentiation zone

<400> SEQUENCE: 10
gtcgattgga acttccaatt tctaaacgga tgcaataaga acttacatat tctctttcat        60
tagtcattta ttggccagat ttattaaaaa aagtttttact caatgaccaa ggattagagt      120
taaagataat atagattatt acatatatta ttcgaaaaaa tatacccatg tccgactttt      180
taaacctcaa aaatatcaaa accagaaaag atgatacaac acaaaaaaac aataaaataa      240
taagtggaag agatatcatc ggacaacagt acaagtacag caccagctct gccaaaagcc      300
aaaaccattt gtcaattaca gaaagatact aatgtttgaa attactaaat taccctcgg       360 actttacaaa agcatctcta acttatccac gtgtcagtca tctattgatt gtttcaatac      420
caccttgtat taacgcccca cgattcgtgg ttgggtacac ctgatagtcc gaggatattt      480
aaatctcacg cgctcgtgtc tataattcga ctgtactcgc ttttcttgtc gtgattttag      540
caatttacga agtcaaatgt ttgactcaat cagacttgcg cataggagag cgagtataaa      600
tgtttactat actcacgcaa gtggggcttt attgaaacta ctcttttgta ataaaaccag      660
cagtggtttt gttctgaatc cgctctcttg c                                    691

<210> SEQ ID NO 11
<211> LENGTH: 992
<212> TYPE: DNA
<213> ORGANISM: Arabidopsis thaliana
<220> FEATURE:
<221> NAME/KEY: misc_feature
<222> LOCATION: (1)..(992)
<223> OTHER INFORMATION: Ceres Promoter construct YP0049 as found in
      Promoter Report #11
<220> FEATURE:
<221> NAME/KEY: misc_feature
<222> LOCATION:
<223> OTHER INFORMATION: T1 Mature Plant Expression:  GFP expression
      observed in the Sepal (Se) and Pedicel (Pd) of the flower, the
      Epidermis (Ep) and Phloem (Ph) of the sepal, the Epidermis (Ep)
      and Phloem (Ph) of the petal
<220> FEATURE:
<221> NAME/KEY: misc_feature
<222> LOCATION:
<223> OTHER INFORMATION: T3 Seedling Expression:  GFP expression
      observed in the Phloem (Ph) and Epidermis (Ep) of the hypocotyl,
      the Phloem (Ph) of the root transition zone of the hypocotyl, the
      Guard cells (Gc) of the primary leaf, the Phloem (Ph) and
      Epidermis (Ep) of the Cotyledon (Co), the Phloem (Ph) of the root
      elongation zone and root differentiation zone
<220> FEATURE:
<221> NAME/KEY: misc_feature
<222> LOCATION:
<223> OTHER INFORMATION: T2 Mature Plant Expression:  GFP expression
      observed in T2 Mature tissue expressions similar to T1 expression
      data , the Vasculature (Vs) of the stem

<400> SEQUENCE: 11
ttccaaattc ttatggttct ctagtgtcat gattttgaga atcactcaac tccaaaaata       60
taatccacga tcccgtgtta attattgaag aatcaatcgt ttttaatttc tcaccaatag      120
atgttgctct tattacttaa aacaaattgt tcggacaaat gtagcaagtg tgatactttg      180
tgggatctta aagacgattt ctcctataac agaggacaaa acaggtcggt caattacaat      240
gtcatccctc tttgccctgt ctttttttttt cttcttaaaa cctaaccatt tgattgtttc      300
```

-continued

```
taaaggtatt tcaagaatat atgatcaatc tagatgaata ctataccgac gatgactaca    360
cacacaagga aatatatata tcagctttct tttcacctaa aagtggtccc ggtttagaat    420
ctaattcctt tatctctcat tttcttctgc ttcacattcc cgctagtcaa atgttaataa    480
gtgcacacaa cgttttctcg aagcattaga atgtcctcct cttaattaat ctccttctga    540
ttagattctc aatagagttt aaatttgtta atggagagat atattgggac cctcaaggct    600
tctaattata ccacgtttgg cataattctc tatcgtttgg ggccacatct ttcacacttc    660
attaccttat caccaaaaca taaaatcaat caactttttt ttgccttatt gattgtgttg    720
gatccctcca aaattaaaac ttgtgttccc cacaaaagct tacccaattt cacttcaatc    780
ttaacaaata ggaccaccac taccacgtac ggtttgcatc atacaaacca caaactcctt    840
cttcattaca attattatat catctactaa aacctctttc tccctctctc tttcttgttc    900
ttagtgctaa attttctttg ttcaggagaa atatccattg cactgggatc caacaatgtc    960
atccgactcg tccaagatca agaggaaagc gg                                  992
```

<210> SEQ ID NO 12
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct YP0060 as found in Promoter Report #12
<220> FEATURE:
<221> NAME/KEY: misc_feature
<222> LOCATION:
<223> OTHER INFORMATION: T2 Mature Plant Expression: GFP expression observed in the Guard Cells (Gc) and Vasculature (Vs) of the sepals of the flower, the Vasculature (Vs) of the Pedicel (Pd), the Vasculature (Vs) of the petiole
<220> FEATURE:
<221> NAME/KEY: misc_feature
<222> LOCATION:
<223> OTHER INFORMATION: T3 Seedling Expression: GFP expression observed in the Guard Cells (Gc) and Vascular (Vs) tissue of the Cotyledon (Co), the Phloem (Ph) of the petiole, the Vascular (Vs) tissue of the primary leaf, the Root hair (Rh) of the root transition zone

<400> SEQUENCE: 12

```
tggagcttta ttgaaatgca agaaagtaaa caaaggaaga tctttagatt gtcaccaaga     60
gtggtctgaa actctcataa cactcaatcc tcctcctcct catcaccacc actacaaaat    120
attatattct ctatctctca atctatgagg agatgtattc tatcaagcat ttgaaatgat    180
aagaaactgg cgatcatcct ctacgtcacc atcactccaa aattatcctc tttctaggtt    240
taagttttgt aatgatcgcc tttatttgtt gagatctcta acttctcgca tttccaaaat    300
gttaagtcca ataactgcat tggttaagtt ggggcgttac tagtcggctt aaatccaaat    360
atggatttga ttccatatgt atgtgacagt ttcttaacgt tcatattaca atgaatgatg    420
gatccttgac tagacaaaga gaaatggat tgtcacttcg taggaaaaat agaaattctc     480
cacgaaggct ggtctccttt atttaacgac aaattcactc atagtctcat tcacaatttg    540
aacttgtcta acacaatgtg ttatatactc gcgaaaagaa gcataatagg ctcttaaggg    600
taatccacga aaccaaaaca catataaaac attaatattt ttctctaaat ttattcatat    660
caataataaa gtttacaaaa aatataaaac aataatccat acttagccca tagcttcgtg    720
tggaagaaga cttgattttt gactagtcaa cgaaaatgag taaatgacgt attcagctat    780
agtaaaaggg atcataagcg gaaattacaa agaagctttg agggtaaact agtcaaaaag    840
```

-continued

```
cataatcaga aataacttag gcccaaagca aaaaggaaag ggctctggat ccagccgcaa       900
atcagaatct ggtaagttcg aacgccacgt catcacctaa atatctgaaa tatctaatta       960
agacttgtct atatataaag gcttctcctt tcacaatccc                            1000
```

<210> SEQ ID NO 13
<211> LENGTH: 1069
<212> TYPE: DNA
<213> ORGANISM: Arabidopsis thaliana
<220> FEATURE:
<221> NAME/KEY: misc_feature
<222> LOCATION: (1)..(1069)
<223> OTHER INFORMATION: Ceres Promoter construct YP0092 as found in
      Promoter Report #13
<220> FEATURE:
<221> NAME/KEY: misc_feature
<222> LOCATION:
<223> OTHER INFORMATION: T2 Mature Plant Expression:  GFP expression
      observed in the endothelium layer surrounding the embryo of mature
      ovules. Inner integument cell layers can, the Inner integument
      (Ii)
<220> FEATURE:
<221> NAME/KEY: misc_feature
<222> LOCATION:
<223> OTHER INFORMATION: T3 Seedling Expression:  GFP expression
      observed in

<400> SEQUENCE: 13

```
aaagattgag ttgagagaga tggtggagac gcagaacaga caaagggagt ttaccatata        60
gtgctctaaa gggcaatgag attgcagtga tgtggctatc cggggaatca tcgcaggtta       120
ttccttccca tgagcaacaa tcaatggatg ggttccaatt cagaggagaa acagaagaag       180
aaacgtttcc agagaaccac agtagggatt ctcgatcttg cgagttgcag agagcctctg       240
aaactgcaat agaaaggaca ctgatgaaaa gaacacactg aaggagtatg ccaatcatgt       300
gaaaactcag agcttgtatt ggtcttgtgg ttgatgaagt tctcacaaaa cctttggctt       360
tgaatctccc ctcattagtc atggtgagaa caagaacaag acgagaaaca gacaaagaag       420
atgaaaaaac ttgttggcca gtgttgacta agggggaata gccccagaca taacaaaatt       480
agacttgtcg tacatcttta atatttttt atctgtttct ttgtcctgac gctttcatta        540
ttcctgtgat caattttctc ataccattgg tccatcgtta atcctttctt aatttcattt       600
tctacgtaac atgagaggag accaagtcct atgagaacag ttgacgtaac agtggttgtt       660
aagttaagtt aaaagagga agctagtgag agtgaccgtt aggtagagaa gtgagatctt       720
taaccactct tctttctctc tctctctgct tttttcgtcg tctttcacat ctactgttcg       780
caaactctct tatgcttcca ataatggtga taccaattga gacttgcagg agaatctcct       840
cttctccaca ctctatcaac tggtcagcca tggaatggtc gtttcagttt caatattcct       900
ggattctttt taaggattcc tgtttctctt ctgttcctgg tatattctta acgacgaaat       960
tagtatcgga tcctggtaat acattttgaa gcttttaagt accattgcac tgggatccaa      1020
caatgtcctc cgactcgtcc aagatcaaga ggaagcggaa ccgcatccc                  1069
```

<210> SEQ ID NO 14
<211> LENGTH: 1687
<212> TYPE: DNA
<213> ORGANISM: Arabidopsis thaliana
<220> FEATURE:
<221> NAME/KEY: misc_feature
<222> LOCATION: (1)..(1687)
<223> OTHER INFORMATION: Ceres Promoter construct YP0113 as found in
      Promoter Report #14
<220> FEATURE:

<221> NAME/KEY: misc_feature
<222> LOCATION:
<223> OTHER INFORMATION: T1 Mature Plant Expression: GFP expression
      observed in the Lateral vasculature (Lv) and Medial vasculature
      (Mv) of the silique
<220> FEATURE:
<221> NAME/KEY: misc_feature
<222> LOCATION:
<223> OTHER INFORMATION: T2 Mature Plant Expression: GFP expression
      observed in T2 Mature tissue expressions similar to T1 expression
      data plus, the Medial vasculature (Mv) of the silique

<400> SEQUENCE: 14

```
tatgaagaaa ttataataga ctctcataaa aatagtgtta caacttacat tctcttatat      60
agaaattagg ataaacagaa atgtaaataa tatatttcga ataatgttaa aatttcctaa     120
attctaatat taatatttat aaatggtcat ttaactttt cgtaccggtt cgatgggaca     180
tgtgttatat tcagttaagg ttaccaccat gcgccaactt ggcctctacc aagtcaacat    240
ggatatggac cttatggtta catgccgcct ccgcctccac cgctaccggg atatggatac    300
agaggtccgc cacctcagca accgacgagg aatgaaacaa ggcaataata tattgatgct    360
attgtggatt tagttactga taattagtgc cttagtgaca gttcaaaaat gttgttcatc    420
aataatctac aatttaaggt ttgtgttgtg gaatgtttca tgatttttatg aagtcttgct    480
tatcaaaaag tatgatgatt aagaatttga cttcatggca tattcatttg agttagcaaa    540
acttttttgt gttgcacctt caaatttata aatttatgat ttttaaccat cgaaattata    600
tatttgaaaa gactatctct acaagccaaa cccactgggc caccaatatg ggtttatctg    660
cgaaatctgt gaaccttaga aaatcaaagc ccatatccac tttgctggaa cttgtctgga    720
atgtaggtta gacaaaacct taagacgcag ctacaagtct cttatgtggc agatgtcaaa    780
attaatgagc acgtataatt tacccaagag gagcaaaata agattagcag cttaaattaa    840
ttgtgttgga ttaaatgaaa cttgcactat gaatggcaaa aaagaggtta caatctagca    900
accacctcat aaaccctcat taatgagata ctgactcgtg aaccaatcaa atctcaagtt    960
tcgtagttta aataagtagt aaacaccctcc tgatcaaagc atcaccacca ccaaatatca   1020
aacgcaaaaa cctattatca aaagaactag ggaggaaatg actaatcccc atgatcatgg   1080
ttatgctgtt gttgtttctt gtgatgtcga ctagagcaga cgaagagctg attaagacag   1140
agtgtaatca cacagaatac caaaacgtat gcctcttctg tcttgaagcc gatcccaatc   1200
tccttcaata tcggaccgtg ctggacttgt caaccatcat taatacactg tctcgggatc   1260
tcaacttgat gttcttatca agtaagtttc accatgtaca ccattaatca ttattgtaca   1320
aataataata tttttaatgt gttttcacaa aattaatatt acctctttt tgtaaactaa   1380
tatgctacga aaattaacat actacgaaaa atgtgaatta atattacttt gcctgtaaat   1440
ttttacctcc ataataatat tagcatacca cgaaaaaatg taacgtattt cttttggtgt   1500
aatgtgaatt ttgctacggt aaacttactt tacaagaaa gaagagcgtt ttccaagtgg    1560
aaaataatac attttgcggt ttatatatta taggaacgac tattgatttg ttttttttggt   1620
tgtaccattg cactgggatc caacaatgtc ctccgactcg tccaagatca agaggaagcg   1680
gaaccgc                                                              1687
```

<210> SEQ ID NO 15
<211> LENGTH: 999
<212> TYPE: DNA
<213> ORGANISM: Oryza sativa
<220> FEATURE:
<221> NAME/KEY: misc_feature

```
<222> LOCATION: (1)..(999)
<223> OTHER INFORMATION: Ceres Promoter construct YP0095 as found in
      Promoter Report #15
<220> FEATURE:
<221> NAME/KEY: misc_feature
<222> LOCATION:
<223> OTHER INFORMATION: T2 Mature Plant Expression:  GFP expression
      observed in the Guard cell (Gc), Lateral vasculature (Lv) and
      Medial vasculature (Mv) of the silique

<400> SEQUENCE: 15
ttcctcgacc atgccgttgc cggaaccggc tagcgcggcc ggccggcggc ggcggggagg      60
ccgcagtggg acgacgggtg aaggatcctc cagctgcgga aggaggtggt cctcgaggcc    120 gaagggaga ggctacggag atggagggaa gccgaagaga agggaggctg ctgctgctgc     180
tgcatttggg agacgagaac tcgactcgag ccatggcggc agattggtgt ttcacggcgg    240
aatgctaact agatccagca tctccatagc aaaggtagaa tggtagattg aggtgagttt    300
tttttcccct cttctgcagt tttgatgtat tattactgcc ctcatctgat ctgggtaaca    360
tatttctgag ctcagtagaa ctgttaaaaa aaggcagaaa tgcacaaact cttctcacaa    420
aacaacatac aaatgcttat attttggagc ggaggcaata catggtatat tttttaaagt    480
gaaaaaaaca atcagacaca tggtattgag tgatagcaaa gctgggtgac cacagaaaat    540
acctcctgct ttaaatactt tatacctggg ctgtcaatcc tcggagttcc tcccaatgta    600
atgtctgagg aagaagtatt gcagctaaat tttaagggtt tcttgtacga aacagggaca    660
atcagagatt aagaaactct atgtggaaaa ggccatgcgc atttttgttat gtgattcaac    720 aaataagatg aggaggcaaa gtcatggttc tgttctaatt aacaaatcta ctatgggggc    780
cgttgctccc tattgtccac gctccttttc ttcatttctc tcctgcagga tatcttgtct    840
tttgattctt cattttaggt cttataaata tcacgtggtt caggcctcca atgtcaaatt    900
atcattacgt ggaactctct tagatgcttg agaaaagtta gctcttacct gtccatagaa    960
gctccaagga agcgagaata gtagatactt tggttggcc                          999

<210> SEQ ID NO 16
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct YP0102 as found in
      Promoter Report #16
<220> FEATURE:
<221> NAME/KEY: misc_feature
<222> LOCATION:
<223> OTHER INFORMATION: T2 Mature Plant Expression:  GFP expression
      observed in the Female gametophyte (Fgm) of early pre-fertilized
      ovules, the Embryo sac (Es) of pre-fertilized ovules
<220> FEATURE:
<221> NAME/KEY: misc_feature
<222> LOCATION:
<223> OTHER INFORMATION: T3 Seedling Expression:  GFP expression
      observed in the Epidermis (Ep), Lateral root initial (Lri) and
      Root hair (Rh) of the hypocotyl-root, the Epidermis (Ep), Lateral
      root initial (Lri) and Pericycle (Pr) of the lateral root initial,
      the root epidermis, the Pericycle (Pr) of the lateral root
      primordial, the Pericycle (Pr) of the lateral root

<400> SEQUENCE: 16
atttggttga taacgttttc actcgactaa ttatatactt cagaaggata gtaatagaat      60
accaaaataa ttaaatgatt ggttagtgcc ttagtgagaa cttttttaacc gattctaata   120 gactaatgat gtagctaagc atttatttgg gatcatcact gtttgaaaac gtgaaatgtg    180
```

```
ataaaagtta tgaaacgatt aaaatataaa ataaccgtac aaaacattat gtaccgtttt        240
tttctctgtt cttttggcga tttggtttag ttcgttacac tctaaatgtt attgcagata        300
tatatataat gatgcatttg catctgagga acatataatt ccggttaaca cttccaaatc        360
ttatatccgt ctaggtaggg attttataaa tcatttgtgt catcatgcgt tatgcttgtc        420
ggctttgacc ataacgcaga gatatagaac tagcttttac ttaactttta gatttattat        480
ttgatctaga gttaagtgga gatatatagt gttttгtta gattattggt ggatgtgaga        540
gtttgtcttt agtttcaagt tgagaatata aggcaagagg agactctgag gcaatcagag        600
gttttgattg gcaaaatatc caaaaggccc aaaccaagtc gaagcccatc tcgtacaaaa        660
aaagaaagag atctgtaaga aaaaatattc tttgatattc ttacaaaaat aagtgtaaaa        720
cttttattag tcaaaatctt caatctttaa aaactctcat cactcctacg aaagcgcgtg        780
agagttatga gacattcctt aatagcatta ctcacaagtc acaagttcaa aacgtctgac        840
tgaaacagaa acaagccttt gttgaagtct tgaagaagag acattagtac tcgtcgtata        900
gccataaaag gtaatatacg aaatttcttc gctaatctct tcaccttcct ctacgcgttt        960
cactttcact ttataaatcc aaatctccct tcgaaaacat                            1000
```

<210> SEQ ID NO 17
<211> LENGTH: 1004
<212> TYPE: DNA
<213> ORGANISM: Arabidopsis thaliana
<220> FEATURE:
<221> NAME/KEY: misc_feature
<222> LOCATION: (1)..(1004)
<223> OTHER INFORMATION: Ceres Promoter construct YP0103 as found in
      Promoter Report #17
<220> FEATURE:
<221> NAME/KEY: misc_feature
<222> LOCATION:
<223> OTHER INFORMATION: T1 Mature Plant Expression: GFP expression
      observed in the Female gametophyte (Fgm), Inner integument (Ii),
      and the Micropyle (Mp) in the pre-fertilized ovule, the Inner
      integument (Ii) of the fertilized ovule
<220> FEATURE:
<221> NAME/KEY: misc_feature
<222> LOCATION:
<223> OTHER INFORMATION: T2 Mature Plant Expression: GFP expression
      observed in T2 Mature tissue expression (if different expression
      pattern)., the outer integument(Oi) of the developing ovules, the
      seed coat (Sc) of the developing seed
<220> FEATURE:
<221> NAME/KEY: misc_feature
<222> LOCATION:
<223> OTHER INFORMATION: T3 Seedling Expression: GFP expression
      observed in root hairs.

<400> SEQUENCE: 17

```
gttttgaaga acaatctgga tcgaaatcta acataaggtc atcgtattca agttacgcag         60
tcaaggactt gacatcatcc tactctggtc tgaggttacc acttccaaag atgggatttt        120
tcgactcggt atgcttccta agaaattcgt tttattgaac ctagcaaata tcttgtaatg        180
taagattcct gagatgatga agaaaaaaca aacttttgtt acagcaggag aacggagaga        240
aagaaaacag agaaccaaat gctcttgaag caaacagaag aagaagacac aaatccaaac        300
ttgagacttc ttctacacca gaaaccgca gcattctggg acaacgcaaa acacgaaagt        360
gaaacgggca atgatatata tgtcttgggt gcgttacaag gcatcgtttg caactgttga        420
gttggataag tcaactgtct tcttttcctt tggttgtagt agctgccttt tttttccttt        480
gttgctttaa gaaatagccc gaaaaaaaga atgttctaca tttcggagca gaaaactaac        540
```

-continued

```
cgaatgagtt tttggtcgga tcatcggatc gatcagatat attttgagtt acgaactgtt      600
ataaaaaaag ccataatttt gtgttgagtt tgcaaaatac cttataactt gttatttgag      660
attgcacctc catatatatt aattcgtaag agtatttatt aagtaagctt tagtataaat      720
ccttttttcc tttaaagtaa gttaatgttc tactaaataa tagtaaagtt gaagaaccgc      780
tccgttttta caccatgcac gtgttatcta acaaagaaaa tatggtacac ctaatggcta      840
atgcaaagga caacacaatg aaactaactt gactctgtgt tatagaaacc catagacatc      900
tgcatacatc ctagtatttg tataaattgg actcaaattc ctgaggacaa tcatagcaaa      960
caatcacatc atcgcaatat acataaacaa aagaggaaga aaaa                      1004
```

<210> SEQ ID NO 18
<211> LENGTH: 1003
<212> TYPE: DNA
<213> ORGANISM: Arabidopsis thaliana
<220> FEATURE:
<221> NAME/KEY: misc_feature
<222> LOCATION: (1)..(1003)
<223> OTHER INFORMATION: Ceres Promoter construct YP0107 as found in
      Promoter Report #18
<220> FEATURE:
<221> NAME/KEY: misc_feature
<222> LOCATION:
<223> OTHER INFORMATION: T1 Mature Plant Expression: GFP expression
      observed in the mature embryo, the Endosperm (En), the Endothelium
      (Ed)
<220> FEATURE:
<221> NAME/KEY: misc_feature
<222> LOCATION:
<223> OTHER INFORMATION: T2 Mature Plant Expression: GFP expression
      observed in T2 Mature tissue expressions similar to T1 expression
      data., late torpedo stage of embryo

<400> SEQUENCE: 18

```
taacaatcct tgggaacatt gcatccatag atatccggtt aagatcgatc tttgaactca       60
taaaaactag tagattggtt ggttggtttc catgtaccag aaggcttacc ctattagttg      120
aaagttgaaa ctttgttccc tactcaattc ctagttgtgt aaatgtatgt atatgtaatg      180
tgtataaaac gtagtactta aatgactagg agtggttctt gagaccgatg agagatggga      240
gcagaactaa agatgatgac ataattaaga acgaatttga aaggctctta ggtttgaatc      300
ctattcgaga atgttttttgt caaagatagt ggcgattttg aaccaaagaa acatttaaa      360 aaatcagtat ccggttacgt tcatgcaaat agaaagtggt ctaggatctg attgtaattt      420
tagacttaaa gagtctctta agattcaatc ctggctgtgt acaaaactac aaataatcta      480
ttttagacta tttgggcctt aactaaactt ccactccatt atttactgag gttagagaat      540
agacttgcga ataaacacat tccccgagaa atactcatga tcccataatt agtcggaggg      600
tatgccaatc agatctaaga acacacattc cctcaaattt taatgcacat gtaatcatag      660
tttagcacaa ttcaaaaata atgtagtatt aagacagaa atttgtagac ttttttttgg      720
cgttaaaaga agactaagtt tatacgtaca ttttatttta agtggaaaac cgaaattttc      780
catcgaaata tatgaattta gtatatatat ttctgcaatg tactattttg ctattttggc      840
aactttcagt ggactactac tttattacaa tgtgtatgga tgcatgagtt tgagtataca      900
catgtctaaa tgcatgcttt gtaaaacgta acggaccaca aaagaggatc catacaaata      960
catctcatag cttcctccat tattttccga cacaacaga gca                        1003
```

<210> SEQ ID NO 19
<211> LENGTH: 1071
<212> TYPE: DNA

<213> ORGANISM: Arabidopsis thaliana
<220> FEATURE:
<221> NAME/KEY: misc_feature
<222> LOCATION: (1)..(1071)
<223> OTHER INFORMATION: Ceres Promoter construct YP0110 as found in
      Promoter Report #19
<220> FEATURE:
<221> NAME/KEY: misc_feature
<222> LOCATION:
<223> OTHER INFORMATION: T2 Mature Plant Expression: GFP expression
      observed in the Embryo sac (Es) of the pre-fertilized ovule, the
      Degenerated synergid cell (dSn) of the fertilized ovule

<400> SEQUENCE: 19

```
gggatgcggt tccgcttcct cttgatcttg dacgagtcgg aggacattgt tggatcccag    60
tgcaatggta atataaaaca agaaaacaag agattttata ggacaatcac taaatgacat   120
ttaattgatt aaacatttat tcattaataa ttgtatgtta ctaacttcaa catttaataa   180
ttttgtttaa gatacgttta catcagagac tattaatatt tttacaggtt gtaacttttaa  240 actttgtctt gaatcgaaca tgactataga ttttgggcaa acttaaagat aacaacattt   300 ccgtttttt tcaaattatt acaaatcaaa ctgatatatt agacacaaca cgattacacg    360
taatgaaaaa agaaaaagat aaaaagataa agaagggat cgattctgtt tggtctggtt    420
tagtgagatt caaagttaag ctcttccttt caagacatgc cttcttaaac cgggaatgtg   480
aacgtttgta atgtagtccg tccagttaat gcttccaaca tcaaatccaa attctctctt   540
ctcgtcctct gacatattct ccattaatct ctggggtatt gctgttatca aatctgtaaa   600
agaaaccaaa aaaaaagat gaaaactttg cgggtaccgg ttttgtctgc tctaagaatt    660
agaatgttaa tgagttctgt cttaccttcc accatagaaa gtgtatggct cataaatagt   720
agcaaggtgt ttggcttgtt caacagattt cttgcatata aactttagct tctgcatcat   780
cttactatcc actgaactca taccactcat caacccactc cgttcttgag catctctcca   840
caaatgatcc gagaaatcat caacggaatt gaaaagtttc atcaaacgca ccataatagg   900 atcacctta gagtccatgc atggagatgt tttgtagtgg ttataaagaa gctccgctaa    960
gtcttcgaaa accagcgggt ttatcgccga agaagcgatc tgatacacgt ttatttcagg  1020
ttccggatct gacattgcca ttccatgctt tgctatagca gctaacgttc c            1071
```

<210> SEQ ID NO 20
<211> LENGTH: 1453
<212> TYPE: DNA
<213> ORGANISM: Arabidopsis thaliana
<220> FEATURE:
<221> NAME/KEY: misc_feature
<222> LOCATION: (1)..(1453)
<223> OTHER INFORMATION: Ceres Promoter construct YP0112 as found in
      Promoter Report #20
<220> FEATURE:
<221> NAME/KEY: misc_feature
<222> LOCATION:
<223> OTHER INFORMATION: T2 Mature Plant Expression: GFP expression
      observed in the Medial vasculature (Mv), Lateral vasculature (Lv)
      and Guard cell (Gc) of the stigma, the Medial Guard cell (Gc) of
      the carpel

<400> SEQUENCE: 20

```
ttatgtgccc tgatgtccta tgcagatggt gcaactactg cttttggtga gaagcttcgc    60
gaacaagttg aggaaaggct agaatttat gacaaaggtg ttgccccacg caagaacgtg    120
gatgtaatga aggaggtgat agagaatcta aagcaaggta tttcttgtag ctgtttttt    180 ttggttgtaa tcagagtcct ctttatgatg gcaaactcag tgttttttta tctgttcctc   240
```

| | |
|---|---|
| ctttagaaga ggaagggaag gagccagttg atgcctcggt gaagaaaagc aagaagaaga | 300 |
| aggcaaaggg tgaagaagaa gaagaggtgg tggcaatgga ggaggacaag tcagagaaaa | 360 |
| agaagaagaa agagaagagg aagatggaga ctgcagagga gaacgagaaa tcagagaaga | 420 |
| agaagacaaa gaagagtaaa gctggaggag aagaggagac tgatgatggt cacagcacca | 480 |
| agaagaagaa gaagaagtct aagagcgctg aatagaaagg gatgcaacat taacaaaccc | 540 |
| tgtattgtat tttttttttg agctaaatta atgtcgtctg tttttcgtag tgaacatcgg | 600 |
| agaattttg ttttggtctg gaaacgattc aaggtttggc aatatcttaa gtttgtttag | 660 |
| gttttcacta ttttgacgtt tgcaaccgtg aaggaggctc ctccatttta taaaatacaa | 720 |
| ttaccaattc cagtgctttg caaatgtttc aataatagct aaactaacta ccaaattgga | 780 |
| aaactagctt aacaagtttg tgaaaatgaa tttggagcca tatgatttat tattttaccc | 840 |
| aaatggagta atagaagaag agcagctcgc gtttgaatgg tcagttaaca ttaacaaaag | 900 |
| gtaaaattga atagatgtta aaacttgtgt aagtaaacaa tagagctacc tccttttgag | 960 |
| aaggatagat aaactcgtga ccaaccacat tcccagtccc atattcttag tacaaataag | 1020 |
| aaattcacac ccctcaaaag aaatataaca taatcaatca taggaaatat acttcgcata | 1080 |
| atgacgataa tgatcaagtt tctcctgtta gctctgctcg tgatctctcc gatttgcgcc | 1140 |
| gagaaggacc tgatgaaaga ggaatgccat aatgcacaag ttccgaccat ttgcatgcaa | 1200 |
| tgtcttgaat ccgacccaac ctccgttcat gcagaccgtg ttggcatcgc cgagatcatc | 1260 |
| atacactgtc tcgactctcg tctcgatatc atcaccaagc aagttttccc ttctaataac | 1320 |
| catacatata tattaactta gatatatgac aatattctct aactaatata tcaatctttt | 1380 |
| tattgttcta ccattgcact gggatccaac aatgtcctcc gactcgtcca agatcaagag | 1440 |
| gaagcggaac cgc | 1453 |

<210> SEQ ID NO 21
<211> LENGTH: 1085
<212> TYPE: DNA
<213> ORGANISM: Arabidopsis thaliana
<220> FEATURE:
<221> NAME/KEY: misc_feature
<222> LOCATION: (1)..(1085)
<223> OTHER INFORMATION: Ceres Promoter construct YP0116 as found in
      Promoter Report #21
<220> FEATURE:
<221> NAME/KEY: misc_feature
<222> LOCATION:
<223> OTHER INFORMATION: T2 Mature Plant Expression: GFP expression
      observed in the transmitting tract of the stigma, the Epidermis
      (Ep)
<220> FEATURE:
<221> NAME/KEY: misc_feature
<222> LOCATION: (1065)..(1065)
<223> OTHER INFORMATION: n is a, c, t, g, unknown, or other
<220> FEATURE:
<221> NAME/KEY: misc_feature
<222> LOCATION: (1082)..(1082)
<223> OTHER INFORMATION: n is a, c, t, g, unknown, or other

<400> SEQUENCE: 21

| | |
|---|---|
| aaacgcctct tcggtccacg ctgtcgtttt attgaaggaa ttatatttta ttttaattgg | 60 |
| gcctgcaggc taaactataa gtccgtctga tatgggtcgg gttgggctta tgagttatgg | 120 |
| gtctggtagg ggtcaattag cttaatttcg atatgtgccc tactctcgac ctaacgtttt | 180 |
| gaacacgtaa gagagagttt ctaatattga gttgtctaat taactcgata ggcttataca | 240 |
| aagtgtttcc gcatttttacc ttcttaataa ctcatcattc actaactaag aaaagtttta | 300 |

-continued

```
ctcagaccat atcttccgct tcttgattat tgtcaatttg ttgtcactca atttatctct   360
tgcaaaattt agttgaaatc atttggtttc atctttggct cttgaatagt tgcatgtgtg   420
tatttagtaa gttctttca attaagaagg aagaataaaa caaattgtgg ccagaaacaa    480
ttatgttgag ttttatctca tacgttggct cactcatccc catctctctg cttttgaatc   540
attctactcc tcccattttt tgatcgtcct tttttctgct tctgaacatg gatcattgtg   600
catgttcgga tgttcctcga tcgtgctgaa actcaaagtc tgaatcgatt accatagact   660
ctcaacccat ctttgatata taaaaagag ccttaaccca tctcttctac tctccctctc    720
tagaaacaaa cacatcacgt gatgatctgt ttcccccat acttacggga tgatcagaat    780
gtggcatgag gaaaaagcca agaaataagt tgataaattt aaggtttaat ttaacaaaaa   840
tgagagatta atcttttcat tttagggtcg cacgcggtgt tttgtgcaac cgcagaaact   900
tcctataaat accgatacaa tgtgcatgct ttctacaact caactcactc aaaccaaaaa   960
aagaaacatc aaaccccaaa acacacataa caatcacaaa ccattgcact gggatccaac  1020
aatgtcctcc gactcgtcca agatcaagag gaagcggaac cgcancccgt ttggaaatca  1080 gnccg                                                              1085
```

<210> SEQ ID NO 22
<211> LENGTH: 1100
<212> TYPE: DNA
<213> ORGANISM: Arabidopsis thaliana
<220> FEATURE:
<221> NAME/KEY: misc_feature
<222> LOCATION: (1)..(1100)
<223> OTHER INFORMATION: Ceres Promoter construct YP0117 as found in
      Promoter Report #22
<220> FEATURE:
<221> NAME/KEY: misc_feature
<222> LOCATION:
<223> OTHER INFORMATION: T2 Mature Plant Expression: GFP expression
      observed in the stem pedicel branch, the secondary Inflorescence
      meristem (Im), the Lateral vasculature (Lv) and Medial vasculature
      (Mv) of the silique, the ovary, the Inner integument (Ii) and
      Micropyle (Mp) of the ovule
<220> FEATURE:
<221> NAME/KEY: misc_feature
<222> LOCATION:
<223> OTHER INFORMATION: T2 Seedling Expression: GFP expression
      observed in the Cortex (Cr) of the hypocotyl, the Epidermis (Ep)
      and Cortex (Cr) of the lateral root, the Epidermis (Ep) and Cortex
      (Cr) of the root differentiation zone
<220> FEATURE:
<221> NAME/KEY: misc_feature
<222> LOCATION:
<223> OTHER INFORMATION: T3 Seedling Expression: GFP expression
      observed in the Lateral root (Lr) of the hypocotyl root transition
      zone, the lateral root primordia, the Epidermis (Ep) and
      Vasculature (Vs) of the root

<400> SEQUENCE: 22

```
gtcagtgagt cgattggatc acagtccttt atgataaaac aaactcataa ttattccacc    60
gacaacatgc gttttaaatt attttttctt aaattatatt atattatatt gatatcaacc   120
tagctaaaat aattcggatg gcgaaatcgg acaattttta atagaaaaaa tgggtatgaa   180
gatagtctat gattccgttc ttagcgacta gagggacctg ctcaaatctc ccgggtgata   240
cgcgatgtca agctcaatag aaccccacaa ccgacgagac cgagaaatcc ttgatttggg   300
ctagaagatt ttgaaataaa tttaatatat tctaagtaac ttgcttaaat ttttttttcaa  360 actctaaaga cataactaac ataaagtaaa aaaaaaaaag ttaatacatg ggaagaaaaa   420
aattaaacta atgattagct ctctaacgtg tttaatctcg tatcaagttt tttttttaaaa  480
```

```
attatattgc tattaaaaca ttgtactatt gtttctattt tgtttagcta ttattcttgt    540
gaaatgaaaa gttgtgttta ttcaattact aaatggcaat atttatcttg gaaaactata    600
cctctaattg gattaggccc tagacatcct ctttagctta ttgacgttaa aattattccc    660
aaaactatta agtttagta gtttgaaaga tgcatcaaga cctactcaga taggtaaaag     720
tagaaaacta cagttagtgt gattatattt taaaatatat aaaacaatct tattaaacta    780
aatattcaag atatatactc aaatggaaga taaaaacatt tagtctgtta ccactaccag    840
cctagctagt cactaatagt cactttggaa ctgagtagat atttgcatct tgagttacca    900
tggactcaaa agtccaaaaa gagaccccga gtgaaaatgc taccaactta ataacaaaga   960
agcatttaca gcggtcaaaa agtatctata aatgtttaca caacagtagt cataagcacc   1020
attgcactgg gatccaacaa tgtcctccga ctcgtccaag atcaagagga agcggaaccg   1080
catcccgtta aacgaaggcg                                               1100
```

```
<210> SEQ ID NO 23
<211> LENGTH: 1001
<212> TYPE: DNA
<213> ORGANISM: Arabidopsis thaliana
<220> FEATURE:
<221> NAME/KEY: misc_feature
<222> LOCATION: (1)..(1001)
<223> OTHER INFORMATION: Ceres Promoter construct YP0118 as found in
      Promoter Report #23
<220> FEATURE:
<221> NAME/KEY: misc_feature
<222> LOCATION:
<223> OTHER INFORMATION: T1 Mature Plant Expression: GFP expression
      observed in the Lateral vasculature (Lv) and Medial vasculature
      (Mv) of the carpels of the silique

<400> SEQUENCE: 23
```

```
aattgagaaa ggtgcctcaa tttcagtaga acctgacgca aaatttcgcg atcatgcatg    60
actcaaattg gtttattcac ttaaataaaa aagttgtttc cctatctagt tgaagttctc    120
aattcaaacg caacttctta cttttcttt ttatttatac tggaatgaat ttttcgtcaa    180
tgctagacct caatatttgg tgattaagtc caaaaaatta tagcaatatt cattagttaa    240
atcataataa tatttgttat ttctgctaaa tatattagtt ttaaattggt aaatatatca    300
gtcatcatac tttatatatg tgcacaagaa aaagaggaaa aaaaactaac ttttaataaa    360
ttgaacgcta tcctctatat ctcgtcctgg tccaaatgta aacttcaata tccttttgat    420
tttattgctg attgctttaa aaaatttcac aaacactttt atcattcttt tattccacca    480
aaatctacag acataatact ttgtaatttt atgtaaaaat cttcaaaatt tgggaaaaga    540
aaaatcattt aaaatcaatt tgcattaact ggatttattt ccaaaggtgt ggtgttgtgt    600
ttatatatgt ggagttgttg gctagtaata taataaggaa aagagtgaaa catatgtagt    660
ataacgtatt tctagttttt tttctctgta ttaatgaatc actaattaag tagtatgcat    720
taattgaatt atcagaagct ggtcacaaaa gtctaccaaa aaaacaaaa aaattggtcg     780 gaagaaaatg aaaataatga gaataaaaaa gggaaaaaaa ataagaagct agcaaacaaa    840
gcaattaaca tttcaaggca gttaattcat catgcaaggt gcttatgtgt gacaacgtca    900
tgcgttactt tttgcgtcta cactcatctc tctaacgcaa tccactaatt ctggtaatgg    960
attctgctat ttagaccaac cagtttcttc gtctctcaat c                       1001
```

```
<210> SEQ ID NO 24
<211> LENGTH: 1076
<212> TYPE: DNA
```

<213> ORGANISM: Arabidopsis thaliana
<220> FEATURE:
<221> NAME/KEY: misc_feature
<222> LOCATION: (1)..(1076)
<223> OTHER INFORMATION: Ceres Promoter construct YP0126 as found in
      Promoter Report #24
<220> FEATURE:
<221> NAME/KEY: misc_feature
<222> LOCATION:
<223> OTHER INFORMATION: T1 Mature Plant Expression: GFP expression
      observed in the Petal (Pe), Sepal (Se) and Silique (Si) of the
      flower, the Epidermis (Ep) and Vasculature (Vs) of the sepal, the
      Epidermis (Ep) of the petal, the Mesophyll (Me), Epidermis (Ep)
      and Vasculature (Vs) of the leaf
<220> FEATURE:
<221> NAME/KEY: misc_feature
<222> LOCATION:
<223> OTHER INFORMATION: T2 Seedling Expression: GFP expression
      observed in the Epidermis (Ep) of the hypocotyl, the Epidermis
      (Ep), Mesophyll (Me), Cytoskeletal (Cy), Epidermal bodies (Eb),
      Guard

<400> SEQUENCE: 24
cattgtatct gagatgtgac tgtgaagaac aaagattcat gacatggtat tgttaagccg      60
cccatgtgga tgatcataac caaactctgt cctcagattt actcaacagt gtgtgtgaaa    120
caaaggctgg tttaagtatg aaaccggcac cacatatctc ttcttcttct gatcattctc    180
tcctacatag accgccatga atcctcttgg tgtcgacgat gattcccttc gaataatttg    240
cttagcaccc aagaaactcc tcaaaaaagc catattttcc cttatgtttt cctgaagctt    300
aaatgtttct tagtcttgga gaaagctttg agattttaaa attggatctt ctttagtttg    360
tgaatctaaa ggggtttagt tacttggtat ataaacgaac gtatgaaaga aatgattaag    420 gattttttgag gttttttcttt ttaattacag agcacatggc tttgggttgt agatactaaa    480
ccaagaacaa atcaataaat ggtgtctgag aagttagtgt ctaatgatgt cctacatgat    540
aacttcattg gggcttattt gtctcaaaga catcacatgc ccaaatctct ctatagatta    600
tgtagggaca tgaagttgtg tacctaatga accacaagtc tctatcactg attaagtcat    660
accttcttct caatgatatt caaaagacag gaccacatga tttgattata tactgacaaa    720
gtcacaaaag ccttcaaaaa aattctgtgg caagaaagga aaatttgact agttatagtg    780
tctatctaac aaacaagtgg tcatattgat ttctatcttc acatcagaaa tcatgaagat    840
tgatcactat agggccctta cttatcatgc cgtggtccgg caaagccatg tgcttgcttg    900
ttggtgtaaa aatttatgag ctgaaacttt tgaaaccaat aaagggttat ctacaagtaa    960
tgttcttatc tatatatact catcactgac tcctttctgc tctgccattg cactgggatc   1020
caacaatgtc ctccgactcg tccaagatca agaggaagcg gaaccgcatc ccgctc       1076

<210> SEQ ID NO 25
<211> LENGTH: 1017
<212> TYPE: DNA
<213> ORGANISM: Arabidopsis thaliana
<220> FEATURE:
<221> NAME/KEY: misc_feature
<222> LOCATION: (1)..(1017)
<223> OTHER INFORMATION: Ceres Promoter construct YP0127 as found in
      Promoter Report #25
<220> FEATURE:
<221> NAME/KEY: misc_feature
<222> LOCATION:
<223> OTHER INFORMATION: T1 Mature Plant Expression: GFP expression
      observed in the inflorescence meristem, the Vasculature (Vs) of
      the sepal, the stamen, the Micropyle (Mp), Funiculus (Fn), Inner
      integuement and Chalaza (Ch) of the ovule
<220> FEATURE:
<221> NAME/KEY: misc_feature

```
<222> LOCATION:
<223> OTHER INFORMATION: T2 Seedling Expression: GFP expression
      observed in the Phloem (Ph) of the hypocotyl root(Rt) and Lateral
      root (Lr), the Phloem (Ph) of the root, the Phloem (Ph) of the
      lateral root, the Phloem (Ph) and Pericycle (Pr) of the lateral
      root initial
<220> FEATURE:
<221> NAME/KEY: misc_feature
<222> LOCATION:
<223> OTHER INFORMATION: T1 Mature plus: GFP expression observed in the
      Vasculature (Vs) of the silique
<220> FEATURE:
<221> NAME/KEY: misc_feature
<222> LOCATION:
<223> OTHER INFORMATION: T3 Seedling Expression: GFP expression
      observed in T2 Mature tissue expression (if different expression
      pattern)., the Epidermis (Ep) of the cotyledon, the Hydathode (Hy)
      of the rosette leaf

<400> SEQUENCE: 25
tcagtgagtc gattggaacg tttaaagttg agacataacg cagtgatttc aaatttgtat      60
tagggtggtc ttattgtgtg tctagctact agctagagaa tactagaaga agaatacgta     120
gcaagatacg cataacattt ggtcctctct ttttttttact ttcttttaac acattgtcct    180
cttatgattt gcttattgat ttcagtatct ttttgtatca ataattccct ccaaatgatt     240
aaaccctaaa aaaatgtgat tcattcacca cccgaagatt agcatcatca agtaacacac     300
aataactacc aataacctag ttttcatttt tctatactaa aatcctaaac atcccataaa     360
aatacaaaca actctgaacc aataatttcc tctaatccac gtgcacccca tcgtctcctg     420
acgtaagatt tgtctataac ttatcaaatc ccaaattcag ctttgttttc attatatagt     480
acgtactctt ataaaaaaga gaagagtaca catctttaat actttaactt aaaagaagaa     540
agtaatacta atataagagg agtctgagtc agcgacaagt gttcgcggag aaacggaaac     600
gctctctttc tctctcttcc cccaacgcca ataccttgg aatccctccc taactctgtc      660
ctgtcctttc gtcctcactt tctctctttt tacatttcct acacaccaat aaaattgaaa     720
ccagcaactt ataaatcaac tcaagtttga attaatgatc gaaaaactag tttatttgtg     780
tcaatatgac ccattcttta ttcacataag tattttaact tttcaaaatg ttatctcaat     840
ctcctttgag tttctgtctt ccccataata aatttcaaat aattaataca catggttttt     900
taattagaaa taatgaaaa gaaggacaa aggaataaaa aagaaacaca agttggcaca       960
ctctctttat tattcactcc cctctataaa tctcatacta tcttctctca tcttctt      1017

<210> SEQ ID NO 26
<211> LENGTH: 1004
<212> TYPE: DNA
<213> ORGANISM: Arabidopsis thaliana
<220> FEATURE:
<221> NAME/KEY: misc_feature
<222> LOCATION: (1)..(1004)
<223> OTHER INFORMATION: Ceres Promoter construct YP0128 as found in
      Promoter Report #26
<220> FEATURE:
<221> NAME/KEY: misc_feature
<222> LOCATION:
<223> OTHER INFORMATION: T1 Mature Plant Expression: GFP expression
      observed in the vasculature (Lv) and Medial vasculature (Mv) of
      the silique
<220> FEATURE:
<221> NAME/KEY: misc_feature
<222> LOCATION:
<223> OTHER INFORMATION: T2 Seedling Expression: GFP expression
      observed in the Epidermis (Ep) of the root transition zone of the
      hypocotyl, the Epidermis (Ep) of the root specialization zone, the
      stipules, the Epidermis (Ep), Atrichoblast (At) and Trichoblast
      (Tr) of the root differentiation zone
```

<220> FEATURE:
<221> NAME/KEY: misc_feature
<222> LOCATION:
<223> OTHER INFORMATION: T3 Seedling Expression: GFP expression
observed in T2 Mature tissue expression (if different expression
pattern)., the Epidermis (Ep) of the cotyledon, the Epidermis (Ep)
and Hydathode (Hy)

<400> SEQUENCE: 26

```
gataaactga taatggaaaa gaacaaagaa accagttttt aactatttgc atatgtaatt      60
tatttgttgc aaattatatt tagttaaaat gtttcctcta tttatatata tatatatcag     120
tcaagcacta tgtataagaa atgtcaattt ataaattttt acatgtcctt taacagaaag     180
aaaatgaatt tttacatgtc attcatagag agtcactcgt ttatttctta tatagagaat     240
aacacactca catgcatatg catgcaatat gatacatttt atgacaaaga taatcaacgg     300
aaacggtcaa gacataattt gataaacaac ttgcacgatg cacagatctg atcaaatata     360 taactctttta acatatccaa aatattcaaa aagaaaaact cgatccaaac tagcaacatc     420
acgctcacgc ggtaggctaa aaatttatta atctccaaaa gtctttctta tgaacactgc     480
aaacacaaca acttgaaaag tcatataggt ttagatgatg acgcgtattg gctatcgctt     540
accggagtgg ctcataaata caataaacaa tacgtaaaag tcaaagtcaa atatatttag     600
tcaactataa ccattaatcg ggcaaaacct ttagctgtca aaacaacgtg aaaacgatat     660
ttgtatatat catcaagaat cagtagataa gagaatgatt taatcccctg actattacaa     720
ttttggtgta ataaacagtc tctattggtt tttattcttt gttttaattt ctcatgacct     780
atagagagaa ttaggtagtt tcgaaaattg gctaatcaac ttttgaaaac tactgtctac     840
tttgcttaaa ttctctacac ttagtttcgg ataagataat tgtcggacta atagttaatc     900
ccttgacaat ctttgatatt ataaaaggtt tagttaatct cttctctata taaatattca     960
tacaccagct ttcaaaaata tataatccaa acaccaaaaa caaa                    1004
```

<210> SEQ ID NO 27
<211> LENGTH: 1081
<212> TYPE: DNA
<213> ORGANISM: Arabidopsis thaliana
<220> FEATURE:
<221> NAME/KEY: misc_feature
<222> LOCATION: (1)..(1081)
<223> OTHER INFORMATION: Ceres Promoter construct YP0020 as found in
Promoter Report #27
<220> FEATURE:
<221> NAME/KEY: misc_feature
<222> LOCATION:
<223> OTHER INFORMATION: T1 and T2 Mature, T2 and T3 Seedling
Expression: GFP expression observed in the Root Hair (Rh) of the
hypocotyl, the Hydathode (Hd) of the cotyledon adaxial surface,
the Epidermis (Ep), Mesophyll (Me) and Vascular (Vs) of the
cotyledon, the Hydathode and Guard cells of the rosette leaf
<220> FEATURE:
<221> NAME/KEY: misc_feature
<222> LOCATION:
<223> OTHER INFORMATION: T3 Seedling Expression: GFP expression
observed in the Guard cell (Gc) of the flower, silique and
pedicle, in the Guard cell (Gc) and Vasculature (Vs) of the leaf

<400> SEQUENCE: 27

```
cagagcagtg catatttttt tttttttttt tttggtgtta gtgcatatct atatatatag      60
tactattata atatatttca atatatatat tttaagaaaa tatctgattc ttaagtttgg     120
acttatttgt caacaatagc cagtaaaaaa caaaagcgaa gttcactaa cttaaaaaat      180 aaccacattt gtatatttcg aatacatact ataaattaat aaatttatca aaacaactat     240
```

```
agaaactgtt atttccaatc aatttcttta tcaagattat atctgaaata tatttattaa    300
aattaatagt tatttacaag aactattttt atgaaagtgt aagaactctc tgaaaacttg    360
ataagtcaat attttttcta acatcgtaaa cataaactag attcaaattc gaatctagtt    420
attcaaaaac ttataaaaac ataaaaatga aatactgtta cttcaacaaa aaacattat    480 tattattttg tttaaatatc taatttattc atcaacagca aaatatttaa aagagtggga    540
aacaaataaa aattaaactc tgttttggta tgataaaatt atttactaaa ctaaactcaa    600
tatattttta gtatcacggt tataactata acaataatcg aactttgtta ttttcttggt    660
actggtttta gtagtataga tagatatttt agtcataact cataagatac atgtacaaat    720
atttgctata tatgatcagt gataactgaa tttcgtgctg aaaattgcca tagtttgctt    780
attttactct tgaaacaata acgatatggt cgttacttaa aacaacattt taaaaacgaa    840
gaaaattaaa cagagtttgt taaaataaat taaataccat aaatttctct ttgactcttc    900
ctatatagta aaatctctca tcccttctc tctctctctc atagcatgtt ggtctttagg    960
ttcctatata aacaacgcca cacacaccca tttagtccca ccattgcact gggatccaac   1020
aatgtcctcc gactcgtcca agatcaagag gaagcggaac cgcatcccgt taaacgaagg   1080
c                                                                  1081
```

<210> SEQ ID NO 28
<211> LENGTH: 1091
<212> TYPE: DNA
<213> ORGANISM: Arabidopsis thaliana
<220> FEATURE:
<221> NAME/KEY: misc_feature
<222> LOCATION: (1)..(1091)
<223> OTHER INFORMATION: Ceres Promoter construct YP0022 as found in
      Promoter Report #28
<220> FEATURE:
<221> NAME/KEY: misc_feature
<222> LOCATION:
<223> OTHER INFORMATION: T1 Mature Plant Expression: GFP expression
      observed in the Vasculature (Vs) of the pre-fertilized and
      fertilized silique
<220> FEATURE:
<221> NAME/KEY: misc_feature
<222> LOCATION:
<223> OTHER INFORMATION: T3 Seedling Expression: GFP expression
      observed in the Epidermis (Ep), Phloem (Ph) and Root hair (Rh) of
      the hypocotyl root zone, the Epidermis (Ep) and Vasculature (Vs)
      of the petiole leaf, the Epidermis (Ep), Phloem (Ph) and Vascular
      bundle (Vb) of the Cotyledon (Co), the Phloem (Ph) of the Lateral
      (Lr) and lateral root initial, the Phloem (Ph) and Vascular bundle
      (Vb) of the Root (Rt)
<220> FEATURE:
<221> NAME/KEY: misc_feature
<222> LOCATION:
<223> OTHER INFORMATION: T2 Mature Plant Expression: GFP expression
      observed in the Vasculature (Vs) of the inflorescence meristem and
      silique, the Guard cell (Gc) of the pedicle, the Septum (Sp) of
      the silique

<400> SEQUENCE: 28

```
tagttccatt acaatttcca aatgatttgt tacaaagcta caagattatt cgaaatagga     60
tttcatccat aagagagaat ggtgtggtcg acgctacaat gttgatttat tggttgtggt    120
ttgcatcttg gggatgtcaa atcctaagtt tcaagttctt gtaaaaacgt tttcaggttt    180
ctttaatata ttttaatatt aatgtaaaaa gaaagatat agcttttgta caaaaaaatt    240
tgtttaatca ctatgtagga ggatgcgatc aaattcatgg aatgatgtat tattagcttt    300
tctatcctca ctctaaaaac aatactatag tgagttaaat aatttgatca tttcaatgta    360
gattaaaatt ttattaaaag aagaaaaatt taaaagccta taacaaaata aaaaggagg    420
```

```
ctcgaggtat gatgggtgta gcagaagagc tggcaacagc tatcgactga gtgattacga    480
actcagtact cagtgttctc agctcacaca ctctttttt gttctctttc ttttggacag    540 cttcatttt ctcttttctt ttttctattt tgtttcaaaa ttccatccat attaaaataa    600
gcctgatcat gagaataaag gaaatactaa tgatgagttt ctcaataatg caataagatg    660
caattattat gagctattta ctattgaaaa tgagcaaata aatgtcaaaa cacaatctgg    720
ttaagttaga gcaactccat tgtataggat tcatgtagtt tctaagaaaa caaaatgtat    780
taatatttta cttttacatc caaaaaacca aaaaccaac ttatatgagt aatagaaacg    840
atcctcatat taggaatttt agagattttc tctcatctgt ttcttaactt ttcaatatt    900 ttatttttt aaattgtatg agtttctact aagaaactac tgctggagtt ggtcttagct    960
tcccaatgct tctccaccta tatatatgca tatctccttc ttaaaactcc attgcactgg   1020
gatccaacaa tgtcctccga ctcgtccaag atcaagagga agcggaaccg catcccttat   1080
actaaaggcg g                                                        1091
```

<210> SEQ ID NO 29
<211> LENGTH: 1082
<212> TYPE: DNA
<213> ORGANISM: Arabidopsis thaliana
<220> FEATURE:
<221> NAME/KEY: misc_feature
<222> LOCATION: (1)..(1082)
<223> OTHER INFORMATION: Ceres Promoter construct YP0024 as found in
      Promoter Report #29
<220> FEATURE:
<221> NAME/KEY: misc_feature
<222> LOCATION:
<223> OTHER INFORMATION: T3 Seedling Expression: GFP expression
      observed in the Root hair (Rh) of the hypoctyl root zone and the
      root, the Guard cells (Gc) of the leaf
<220> FEATURE:
<221> NAME/KEY: misc_feature
<222> LOCATION:
<223> OTHER INFORMATION: T2 Mature Plant Expression: GFP expression
      observed in the flower and silique
<220> FEATURE:
<221> NAME/KEY: misc_feature
<222> LOCATION: (1069)..(1069)
<223> OTHER INFORMATION: n is a, c, t, g, unknown, or other

<400> SEQUENCE: 29

```
tgttaaggga aggtttgcac ctaagaattt tgaaggaatt ttgcggcgat atatcagtaa     60
gtaactttct tcttagtctc aaaatttaag ttgccataaa agtatatcag tttggagttg    120
ttaacctctt gttttattat ttctcagctg actacgtcat ttgccttggt tgcaagagcc    180
cagacaccat tctctccaag gagaaccgtc tcttctttct gagatgtgaa aaggtataag    240
ttaatctaat tagtcctgat cttgatatgc attcctttgt ttctgttta cagtttact    300 ttctgcgcaa caaagtaata aagtattttg tgtgtttgaa tttgctaatg tgattaacga    360
gtgggctaca tggttttgc agtgtggatc tcaacgatct gtggctccga tcaaaacagg    420
gtttgttgct cgtgttagtc gcaggaagac ttgagaaatt agaaggtgaa gtgaccttgg    480
tatggagttt ggagctattc tactgcttct gtatgagttt atgagttgaa gaaatacttg    540
tcttgttttt tttattttgt tttggaatat gattatgact tgacttttaa aatgggatag    600
gatcaaaacc ttttactctg tcaggttcat gtggtcacct tgaaggttga tttagtaaat    660
ccatggactt cttttttgtg ttaagattat tcttagttca aaattaatag actaatgata    720
ttaacgtcca caggcattgc gttcaacatc tcaaattaaa gcgtggaagg ctcagaaagt    780
```

-continued

```
ccaatataca ctatgtttat ctacagttac aatcatacta caaaaaacaa ataatgtata      840
cggtttggtc taatatagcc gcatacgatt tagtatttac caacaaaaaa ttggtctcaa      900
accaaaccga acaattggta attaacaatt gttcttttgg tcttgaaccg aaccaaaccg      960
aactgaacta tattaaccga ccgacttcgt cctttcctcc ccattgcact gggatccaac     1020
aatgtcctcc gactcgtcca agatcaagag gaagcggaac cgcatcccnt taaacgaagg     1080
cg                                                                    1082
```

<210> SEQ ID NO 30
<211> LENGTH: 1031
<212> TYPE: DNA
<213> ORGANISM: Arabidopsis thaliana
<220> FEATURE:
<221> NAME/KEY: misc_feature
<222> LOCATION: (1)..(1031)
<223> OTHER INFORMATION: Ceres Promoter construct YP0028 as found in
      Promoter Report #30
<220> FEATURE:
<221> NAME/KEY: misc_feature
<222> LOCATION:
<223> OTHER INFORMATION: T3 Seedling Expression:  GFP expression
      observed in the Root hair (Rh) of the hypocotyl root zone, the
      Vasculature (Vs) and Vascular bundle (Vb) of the leaf, the
      Pericycle (Pr) of the root and lateral root
<220> FEATURE:
<221> NAME/KEY: misc_feature
<222> LOCATION:
<223> OTHER INFORMATION: T2 Mature Plant Expression:  GFP expression
      observed in T2 Mature tissue expression (if different expression
      pattern)., the Ovule (Ov) of the ovary and silique, the Funiculus
      (Fn) of the ovule primordia, the pre-fertilized and fertilized
      ovule

<400> SEQUENCE: 30

```
gtcagtgaag tcgattggta gtacttgaaa cacttggttg gtttcatgta tttggcctat       60
atataaacaa acatcgtaat tatatacgga ttttttttcgg aattttacgc catatctgta     120
agtatatata acatgcatgt cgttttcaaa ttcatatgat gaacgatcca cgtaagtgct     180
actactccta caatattgca tgagagagat atgtatttat aaattttatt ttgaagaaga     240
aataagaggg aaggttactt gggtggatcg atgtgaaaac aaaagaagaa aaagcgaaac     300
ccactaagcc attacatgat atcgaccttc ttatcttttt cctctttatt ttattttct     360 catcttcttt tgtcaggac ttttttctac ttaatgaaac ctccaaacta tctaactaat     420
acactcccat gtagaataaa gaaaattata taagatattg ttgatatttt gtaactagaa     480
aatatatttg ctctgtaatt tttcgtaagt taaatcaaca ttttaaagta gaaacaaata     540
ttactgcaaa aagtaggatc attattttttg tccaaaatct cagttagcta tagggttgta     600
gtaaaaacaa aacacattct tgatttgccc caaaaaataa agagagagaa gaatattgtt     660
caaaagtggt ctcttctctc tctaattatg ttttcactaa acccaattag attcaaacag     720
tctacaaagt ccaaaagata aacatgggac aacaattcga tgcaaaaaat cctcttttca     780
tgctcttttt ttattctcta gtcttttaaa ttactaataa aaactcacaa atccaccaaa     840
cccattctct acaactcacc ttcatctaga tttaccccact cccaccgaga aacacaagaa     900
aaaaaatata catatataaa tatacaagac aacacatgat gctgatgcaa tatacacaac     960
aaagtattaa atcttagata ttgtgggtct ccctttcttc tattcatttt cttattcatt    1020
aaaaaaaaaa a                                                          1031
```

<210> SEQ ID NO 31
<211> LENGTH: 1075

```
<212> TYPE: DNA
<213> ORGANISM: Arabidopsis thaliana
<220> FEATURE:
<221> NAME/KEY: misc_feature
<222> LOCATION: (1)..(1075)
<223> OTHER INFORMATION: Ceres Promoter construct YP0030 as found in
      Promoter Report #31
<220> FEATURE:
<221> NAME/KEY: misc_feature
<222> LOCATION:
<223> OTHER INFORMATION: T3 Seedling Expression: GFP expression
      observed in the Epidermis (Ep) and Root hair (Rh) of the hypocotyl
      root and root
<220> FEATURE:
<221> NAME/KEY: misc_feature
<222> LOCATION:
<223> OTHER INFORMATION: T2 Mature Plant Expression: GFP expression
      observed in the Guard cells of the flower

<400> SEQUENCE: 31
aggtcagtga agtcgattgg tacttgcctc atgtgtttgg atacgagatt actgaacgtt      60
gtggtgtatt ttatagtcat gggtttgtta attgttatca tgcttgccta cttaactagc     120
gtaattatgt tttttttgtac tacctcggaa gtagctattt tgtcgcttat tgacaacgag    180
atactttaag atgttccaca tccacgtcgt aatcggttga tcgaatggtg cctaatagat     240
caaagttatc ctcaacaaat atcgatgtgt agtatatacg tgaatatata gtagtctctt     300
gcatgcatat catatacaac ttaaatactc tttttgtttc aaaataaata atgttttagg     360
aaaaagatta ttgtgtcaaa ttaagtgttg gtctattcat ccaaacaaga aagaaaaaaa     420
atacgaattt gtttatatata tcattgacga acaatgttta gctaataata aataattatt    480
tatttataaa aattaaaagt tagatagttt cttaatttag gtgcatataa gttctttaac    540
aaaaaaaaca tttaggtgca taagtcttaa atatcaaata ttttggaaca gtaattttat    600
gtataacttt tttcgtacct atcttcacac cgcataaatt gccaaagtca acctttttgat   660 atttcattcc tcacaaaacc atattaattt atacacctca atattgttta atagtattat    720
catgttggct ttcgctgaat ttatcaaagt gcaacatgtt ttatcttaca aaaaaataaa    780
aagaaattca cgttgtgtga tcttgagagt tgacttttaa atatatcaca acttatataa    840
atacgcagca acattccaat ctctcaagaa aatctacagt tcctccaaat aataatacc    900 tccctctaag gttaaaaact atacctcatt aacacattaa gaagctagtc attacttcat    960
ttctatattt taaataatgt ttattgataa caattgcagg caactaattt tcagcaatca    1020
ccattgcact gggatccaac aatgtcctcc gactcgtcca agatcaagag gaagc        1075

<210> SEQ ID NO 32
<211> LENGTH: 1106
<212> TYPE: DNA
<213> ORGANISM: Arabidopsis thaliana
<220> FEATURE:
<221> NAME/KEY: misc_feature
<222> LOCATION: (1)..(1106)
<223> OTHER INFORMATION: Ceres Promoter construct YP0054 as found in
      Promoter Report #32
<220> FEATURE:
<221> NAME/KEY: misc_feature
<222> LOCATION:
<223> OTHER INFORMATION: T3 Seedling Expression: GFP expression
      observed in the Epidermis (Ep) of the hypocotyl root zone and
      cotyledon, the Epidermis (Ep) and Vascular bundle (Vb) of the root
      differentiation zone
<220> FEATURE:
<221> NAME/KEY: misc_feature
<222> LOCATION:
<223> OTHER INFORMATION: T3 Seedling Expression: GFP expression
      observed in the seedling root and root tip
```

```
<220> FEATURE:
<221> NAME/KEY: misc_feature
<222> LOCATION: (1094)..(1094)
<223> OTHER INFORMATION: n is a, c, t, g, unknown, or other

<400> SEQUENCE: 32
ctgatctcta gtccagtcga ttggagctta ttttgttcta ttctatcgta tttgattctt      60
ctttcgtttt ttttttgttt gacttaagaa accgattgtt tatagtagta aacatttgtt     120
tttaatgttg ctcgattcca gtgcacatgt ccaggctaga cacttgtcgt tataaaggtt     180
gctttggttc aatattgatc cactagagat gttacaacta ttgttgacat ctgagattgt     240
gtgataagaa aatatgaaac tggatttagt gaaagttaca atatataatc atacatcata     300
gataggaaat aaggaaatgt cagatatact tgaagaatac atcaaataga caaggtcctt     360
tttcttattg tcgactatta tagagccgta cagaaccttt tcacgtcttt agtaattagt     420
acattctcca tttcggctct ctcttatttt ttttccatct cttttttactt ctccaaataa    480
taacaataaa agcttcgatt ttgtgtgtgt ttgtatttac atcttgacat cgatattctt     540
ttcatcaatt ttttaccaaa aatgtaataa aaacaaaaaa aaaccaacgc tgaacacaga     600
catggttttct ccatccgttt atattcatcg tttgtatgtt tacttaacaa cttatttcaa    660
aatagtacat atcatggttg tgttttttaaa aaaagtatac agaacagaaa agcacatggt    720
agacaaaata atgaagccaa aattaataca agaagaagt tcaacttgta tttattaaca     780
cattttcttt ccttgtcaaa gacatgcaaa ttggttttgt tttcttattc ccatttttt     840
tttataataa aagaagaag agtaaaacaa aaaaactatc atttcttctt atcgcaaaac     900
tcttatctaa gcaagaaacc gacaaaacct atatctacat atattctcat caacatctct     960
tgagacatat tcattttggt taaagcaaaa gattttaaga gagaagggg gagaagtgag     1020
agagaccatt gcactgggat ccaacaatgt cctccgactc gtccaagatc aagaggaagc    1080
ggaaccgcat cccnttaacg aaggcg                                          1106

<210> SEQ ID NO 33
<211> LENGTH: 1017
<212> TYPE: DNA
<213> ORGANISM: Arabidopsis thaliana
<220> FEATURE:
<221> NAME/KEY: misc_feature
<222> LOCATION: (1)..(1017)
<223> OTHER INFORMATION: Ceres Promoter construct YP0025 as found in
      Promoter Report #33
<220> FEATURE:
<221> NAME/KEY: misc_feature
<222> LOCATION:
<223> OTHER INFORMATION: T3 Seedling Expression: GFP expression
      observed in the Guard cell (Gc) in the leaf
<220> FEATURE:
<221> NAME/KEY: misc_feature
<222> LOCATION:
<223> OTHER INFORMATION: T2 Mature Plant Expression: GFP expression
      observed in T2 Mature tissue expression (if different expression
      pattern)., the Guard cell (Gc) of the leaf and stem

<400> SEQUENCE: 33
gtcagtgaag tcgattgggt ctcaccatga gccaatgaaa agaaatagta atccaggtga      60
ttgtttctct ttgatgtctc actttctaat agctagtctc taaaagaacc tttgttttag     120
tgaattctaa tatagtaggg gttttgcagc gcaatttct tcagcaccga agaaaagtag      180
attgaagatc ggagagtcct ctgctttctt tacatatgtc aaatctactg tccttagaac     240
taacggtcag gatcctcctc ttgtcgatgg aaatggctca cttcatcttc atcggggttt     300
```

| | |
|---|---|
| ggcggagaag tttcaagtgg tggctagtga agggatcaac aacaccaaac aagcacgcag | 360 |
| agcaacacca aaatctactg tccttagaac taacggtcag gatcctcctc ttgtcaatgg | 420 |
| aaatggctca catcatcttc atcggggtgc ggcggaaaag tttcaagtgg tggctagtga | 480 |
| agggatcaac aacaccaaac aagcacacag aagtagaggg accgagcaat accattctca | 540 |
| aggagagacc ttgcagaatg gcgccagcta tccacattcc cttgagcggt cacgcacgct | 600 |
| tcccacatca atggaatctc atggtaggaa ctaccaagag ggcaatatga atattcccca | 660 |
| agttgctatg aacagaagta aagattcgtc tcaagttgat ggatcgggtt tctctgcacc | 720 |
| aaatgcctat ccttactata tgcatgggt catgaaccaa gttatgatgc aatcagcagc | 780 |
| catgatgcct caatatggtc atcaaattcc tcattgccaa ccaaatcatc cgaatggaat | 840 |
| gacgggatat ccttactacc accacccaat gaacacatct ttgcagcata gtcagatgtc | 900 |
| tttacagaat ggtcagatgt ctatggttca tcattcttgg tcaccggcag gaaatccgcc | 960 |
| ttctaatgag gtgagggtaa ataaacttga cagaagagag gaagctctgc tgaaatt | 1017 |

<210> SEQ ID NO 34
<211> LENGTH: 1026
<212> TYPE: DNA
<213> ORGANISM: Arabidopsis thaliana
<220> FEATURE:
<221> NAME/KEY: misc_feature
<222> LOCATION: (1)..(1026)
<223> OTHER INFORMATION: Ceres Promoter construct YP0050 as found in
      Promoter Report #34
<220> FEATURE:
<221> NAME/KEY: misc_feature
<222> LOCATION:
<223> OTHER INFORMATION: T1 Mature Plant Expression:  GFP expression
      observed in the Sepal (Se), the Carpel (Ca) and Style (Sy) in the
      silique, the Epidermis (Ep) and Mesophyll (Me) of the leaf
<220> FEATURE:
<221> NAME/KEY: misc_feature
<222> LOCATION:
<223> OTHER INFORMATION: T2 Seedling Expression:  GFP expression
      observed in the Epidermis (Ep), Root hair (Rh), Root (Rt) and
      Vasculature (Vs) of the hypocotyl root zone, the Epidermis (Ep)
      and Vasculature (Vs) of the hypocotyl, the Epidermis (Ep) and
      Mesophyll (Me) in the cotyledon, the Guard cell (Gc), Epidermis
      (Ep) and Mesophyll (Me) in the primary leaf, the Epidermis (Ep),
      Cortex (Cr) and Phloem (Ph) in the lateral root, the lateral root
      tip, the primary Root cap (Rc),
<220> FEATURE:
<221> NAME/KEY: misc_feature
<222> LOCATION:
<223> OTHER INFORMATION: T2 Mature Plant Expression:  GFP expression
      observed in T2 Mature tissue expressions similar to T1 expression
      plus, the immature flower, the sepal and the silique pedicle, the
      Cortex (Cr), Endodermis (Ed) and Epidermis (Ep) in the stem
<220> FEATURE:
<221> NAME/KEY: misc_feature
<222> LOCATION:
<223> OTHER INFORMATION: T3 Seedling Expression:  GFP expression
      observed in T3 Seedling tissue expressions similar to T2 seedling
      expression, the root, the Epidermis (Ep) of the cotyledon, the
      rosette leaf, the root cap

<400> SEQUENCE: 34

| | |
|---|---|
| aatctgatct ctagtccagt cgattggtac ttgagggaaa catcatattt ttaaaccttg | 60 |
| tctcagtaag ctaacacaca cccttgtga ttacttatcc atgtttatcc acaagaatgc | 120 |
| agttggattg agatattttc ttctttgttg aaatcaggcc tcaaggtgtt catgtggtct | 180 |
| gcaaaaaaat tcccaaaaat aaagatagtg acatctgaaa tcgataatgg attagacgaa | 240 |
| gagtttcgtg ttattccttg gtatgggcgg gtttggggac agatattttg gcacagacga | 300 |
| ggactaggcc actgtggtcc tgcagcatta ggtgtccctt ccatgtcctg cattacattt | 360 |

```
tattgatgga ttcatcaccc tatctactac aacggctaca caaactatga agagttttgt      420
ttactaataa atgcccaagt gaggggtcga tcgaacccgg gacacgtttt tcagtttacc      480
atatagaatt atccttggaa cccttgatac tccatagaac atcaccacct ctgttgtcat      540
ctcaggaatc caggttcaaa cctagtctct ctctccctag tgggaggtat atggccactg      600
ggccaatgat gacaaaatgc aaaaaaaata aaatacattt gggttcatta tctaaaatat      660
ctcttgtgtt tgtaagtttt ggttgcacac tcgtgtggtt gaagtgtgtg tgagaggtac      720
tatacaatac actctgcttt tgttttgtac ctatctcttt ctcttctcca catatccaag      780
actttgggga taaagctgag atcattggtt gccatttggt tgtgtagaag caatcaccca      840
tttgctttat ccgaggttga taaatttcct cgggttctcc ttctgacacg tatgacaaat      900
tctaatagta tattcctcgt agatattacc tatatattct caatagttgc aggtacttaa      960
ggctttgtct tggcatcctc gtcctcttca gcaaaactcg tctctcttgc actccaaaaa     1020
gcaacc                                                                1026
```

<210> SEQ ID NO 35
<211> LENGTH: 1087
<212> TYPE: DNA
<213> ORGANISM: Arabidopsis thaliana
<220> FEATURE:
<221> NAME/KEY: misc_feature
<222> LOCATION: (1)..(1087)
<223> OTHER INFORMATION: Ceres Promoter construct YP0040 as found in
      Promoter Report #35
<220> FEATURE:
<221> NAME/KEY: misc_feature
<222> LOCATION:
<223> OTHER INFORMATION: T3 Seedling Expression: GFP expression
      observed in the Phloem (Ph) and Epidermis (Ep) of the hypocotyl,
      the Phloem (Ph) of the hypocotyl root zone, the Phloem (Ph) of the
      petiole, cotyledon and root, the Pericycle (Pr) of the root
<220> FEATURE:
<221> NAME/KEY: misc_feature
<222> LOCATION:
<223> OTHER INFORMATION: T2 Mature Plant Expression: GFP expression
      observed in T2 Mature tissue expression (if different expression
      pattern)., the Epidermis (Ep) and Vasculature(Vs) of the
      inflorescence meristem, the Pollen (Po), the Epidermis (Ep), Guard
      cell (Gc) and Cortex (Cr) of the stem
<220> FEATURE:
<221> NAME/KEY: misc_feature
<222> LOCATION: (1077)..(1077)
<223> OTHER INFORMATION: n is a, c, t, g, unknown, or other

<400> SEQUENCE: 35

```
cccatcacat gtaacatcat tgggctatcc aaaagtctaa ccaataatgt caatctataa       60
accacattaa gtagttcatt tttttgtag tcgtgtttag cttgttaaac ctcataaaat      120
atgttttcac ttacgttaac aaaacaaata tcttcacgaa aaaaaataaa ataaaatatc      180
tttttgatac cgaaaaaata aaataaaata aaataatttt cccttcgat cataaaatgc      240 gtagataaga gaaactgtgt ttgaggctcc atttcatgtt cacctaccag tctaccacgt      300
catttctcaa agacgcaaat tttctaatta gggatgtgct cttttacat atagatcaat      360 atcctaaaaa aatttaagat attcatattt tcgtacatat atatcgagtt tcccgaaaaa      420
tccataaaaa gggtataatg atagtccttt ttctccttta ataataattt ctgaacaaaa      480
ttatatcata ataaacttgt gattttatac aaaatttatt tgtatatata atttactaa      540 acaacgtgaa cgataaaaat aatattctca taaaatgttg attaaaaatt acttaaaata      600
aataattatt taggattatg tattagtagt actcgaacca tttttttagt tatctgcatg      660
```

-continued

```
aagaccctaa ttttttcacat atatcgaaac taaaactttg gatatacact gtaatttgaa    720
aacgcttgga acggataatg tagttacctc acaagatttt gtacatccct gacattttat    780
attcattaaa gtgtgttttt ttcttcagaa aagaaaacac ttttttcttttt tgtgcttttta  840 gtttaaatta acaaaaaaat ggacaccatg agattccact aactcatgtg tatataacat    900
tagggaagca gtcaattcat ttcagcatcc acacacactt tgaatgctca atcaaagctt    960
cttcatagtt aaacttcctc acaacgtcaa aactcgagaa aagaccatt gcactgggat    1020 ccaacaatgt cctccgactc gtccaagatc aagaggaagc ggaaccgcat cccttttnaac   1080 gaaggcg                                                              1087
```

<210> SEQ ID NO 36
<211> LENGTH: 1071
<212> TYPE: DNA
<213> ORGANISM: Arabidopsis thaliana
<220> FEATURE:
<221> NAME/KEY: misc_feature
<222> LOCATION: (1)..(1071)
<223> OTHER INFORMATION: Ceres Promoter construct YP0041 as found in
      Promoter Report #36
<220> FEATURE:
<221> NAME/KEY: misc_feature
<222> LOCATION:
<223> OTHER INFORMATION: T1 Mature Plant Expression: GFP expression
      observed in the vasculature (Vs) and Guard Cells (Gc) of the stem
      and flower
<220> FEATURE:
<221> NAME/KEY: misc_feature
<222> LOCATION:
<223> OTHER INFORMATION: T2 Seedling Expression: GFP expression
      observed in the Guard cell (Gc) of the petiole, cotyledon and leaf
<220> FEATURE:
<221> NAME/KEY: misc_feature
<222> LOCATION:
<223> OTHER INFORMATION: T2 Mature Plant Expression: GFP expression
      observed in the developing flower and pedicle
<220> FEATURE:
<221> NAME/KEY: misc_feature
<222> LOCATION:
<223> OTHER INFORMATION: T3 Seedling Expression: GFP expression
      observed in T3 Seedling tissue expressions similar to T2 seedling
      expression

<400> SEQUENCE: 36

```
gggatgcggt tccgcttcct cttgatcttg gacgagtcgg aggacattgt tggatcccag    60
tgcaatggtg caacatcgaa tccaaattct cttaacatca taacacagac taaaatttca    120
ggctttcgtg ttaaaagaga gaatatcatt gaactttttc tcttaccttc atgattcctg    180
caagaacagc acctccgagg tataccatgt gtttccttct cggtggatct tcgatccgca    240
atctgagttt ctgattgata agaaaaacga agatataatgt taaaagctga gctaatgact    300
gacagtgatc atggcattat cagaattatc ttttttacct tcaagccatc tttgtttcct    360
tttagaactg tgtcgagata ccgatcctgt atttctttct caagactaga aacaaacaga    420
gaataaaaga cattgaaaca taaacaatg gaacttcttg ctgggtttat gataaacaaa    480
aaatatacga accggctagg taatcctggg tacatggtgc tacctccgct taaaactatg    540
tgttggtaga gctgtgaaaa aagagcaaag ggtttaagac agatacatga ttagttttgt    600
tggatctgtc ttttgaaata ccaagcaagc gtaagagtca cacgtaccat catgcggtta    660
tcaatatcca tttcttgaat acatcggaaa accatgtctg ccattccatc accttcaaca    720
tcaatgagtt cctgaaaaaa tatttggttg tgatcagcct cgagattctt ggagggttga    780
aactattcca aaagagaaat tagcagagga cgcgatgaag gttaccggaa gtaaaaagcg    840
```

-continued

```
cttcaggtgc ttggaatctt tcagtgccta ctttgataac cctcccatct ggaagctgat      900
cacagttcaa aaacacaacg ggttagtact ctggaaaaaa aataatttgg tgataatatc      960
agctttagag gctgcaactg gcacaagtat gaaactttat cgactatcgg atgaaaaatc     1020
ccaaacacag cgcccaagaa cagagaaacg atgtcatgaa agaaaagat g               1071
```

<210> SEQ ID NO 37
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter construct YP0056 as found in
      Promoter Report #37
<220> FEATURE:
<221> NAME/KEY: misc_feature
<222> LOCATION:
<223> OTHER INFORMATION: T2 Mature Plant Expression: GFP expression
      observed in the Guard cell (Gc) of the stem and pedicel, the
      Vascular (Vs) of the leaf
<220> FEATURE:
<221> NAME/KEY: misc_feature
<222> LOCATION:
<223> OTHER INFORMATION: T3 Seedling Expression: GFP expression
      observed in the Root hair (Rh) of the hypocotyl, the Epidermis
      (Ep) and Mesophyll (Me) of the cotyledon, the Vasculature (Vs) of
      the cotyledon
<220> FEATURE:
<221> NAME/KEY: misc_feature
<222> LOCATION:
<223> OTHER INFORMATION: T2 Mature Plant Expression: GFP expression
      observed in the inflorescence meristem
<220> FEATURE:
<221> NAME/KEY: misc_feature
<222> LOCATION:
<223> OTHER INFORMATION: T3 Seedling Expression: GFP expression
      observed in the Cotyledon (Co) and Root hair (Rh)

<400> SEQUENCE: 37

```
ataggaatct gcttcggtag aagattcgag agaggagagg aagcatcggt ggttttggag       60
ttccttattc ttctcttctt tccaaagttt tgtcattcgc caagattcct taaaaacttg      120
ttcacacatc ataattatgc accaataggt tataaatcat aatccaacaa gttagtcatt      180
ggctttaatt ttaaaaaatc ccataagagt aaaatctttt agaaagttaa tcaacccaca      240
catgggctag aaaaccaaaa accccacgaa cattgagatt acaagaaaca tttttaagtc      300
ctaaatgagc ccaagagcat tgcttaatga agaagaactg atattaatta actaatatta      360
ggacacataa aaaaatacga aaacaccaat cttcatgcca caaaatcaaa caaaaacgaa      420
aaaatcaatt ttcatgaaat ggataaagag agagcgtaat tatcaggaat ttgattgagt      480
acggttgtta tgatgatcat tcacaattat ctttgatctt gagatttagc aatagttaat      540
tttcggatgt tttttttgtta cttgctgctc acttcttgta tgcagattaa tttataagag      600
agaccagtta caactctttc ttatttgaat aagatttat aagatgtagt gtggccatgt       660
gggtttattg catgcagctc tctgcgttgg tcccaagtcc acgacaatag agagtttctg      720
cacttcacgg tatcgtcgtc gtcacaagtt ctttaccttta tcattggcac aagttagcca      780
ccgtctttgc gcaagttagc atgttgtgct acatacgtgt catgaactga ttggtcaaat      840
ttggatatat tttattcccg tcggttatgt ttggataaaa atataaaacg gaaatttctg      900
tttcagcctt ccttggtccc aaagaaaaat acgcacacct actcccttca ttctctatcc      960
tctccactca taatatatac atctaaatgc aatctctcc                            999
```

```
<210> SEQ ID NO 38
<211> LENGTH: 1080
<212> TYPE: DNA
<213> ORGANISM: Arabidopsis thaliana
<220> FEATURE:
<221> NAME/KEY: misc_feature
<222> LOCATION: (1)..(1080)
<223> OTHER INFORMATION: Ceres Promoter construct YP0068 as found in
      Promoter Report #38
<220> FEATURE:
<221> NAME/KEY: misc_feature
<222> LOCATION:
<223> OTHER INFORMATION: T2 Seedling Expression:  GFP expression
      observed in the collet root hairs only of the hypocotyl root zone

<400> SEQUENCE: 38
aaattgggga gtggggagat gtttggttat attcccttct catcgatggt ctagatgtgc      60
gaggtgactc tcatggaggt aaagaacaat ggtgattttg tgaagaaccc aacgtaatgg     120
taattcctaa aaaggttaga agttttttca gcttgttgta ttgctaaaat ggggttgatg     180
tactcaacga catccaagtg tacttgagtg agcttttttg gggttgagta cctcgaccca     240
ttattcaaac taatgtaaat ggtgaatgca gcagtgactt tgttgccttt tgcaagaact     300
aaagaagaca gaaacaggtt gtaaaagaga gccaagtgtg tgtttatggt agaaagagca     360
aagtgaacga aagtgtacc ttttttgactt gttgtcactg gttttctccc acttcatccg     420
tttcatgctg catcagaaaa caacataaga atgaatgac gtaacgcgaa gcattaggag      480
ttgcttgtaa attaatacat tgccattact aacgtaattc agtagattct aactacaaat     540
gaagtcaatg tatctatctg tctactttag ccaatgtatg ataagaccaa atagtcttct     600
cttttttcag aaactctcta ggattaaaaa gtttgtgggt gaaagaaata ttatcgtgtg     660
gatgataaga ataattgatc ttgtgttagt aaattaggaa tagatataca agtaggtttc     720
tctctaaata aaaataaaa gagtttaaat tgcatgcgta taaagaaaaa aagtaagaag      780
aaaatatgtt ccggttaatg gttgggtgca tccgaatcga accggcgcaa accaaaaaat    840
ctaaaggaga tttgaggtga taaaaggaaa tcagacattg aaccaaaaaa acaaaagcga     900
gacggtggaa agaaaaaact ggaaaagaca gttttagccc ctcctaaaag caaagaaaaa     960
aaagataata aatagcttcg tcgtcgtgat cgacctctgc cattgcactg ggatccaaca    1020
atgtcctccg actcgtccaa gatcaagagg aagcggaacc gcatcccgtt aaacgaaggc    1080
1080

<210> SEQ ID NO 39
<211> LENGTH: 1070
<212> TYPE: DNA
<213> ORGANISM: Arabidopsis thaliana
<220> FEATURE:
<221> NAME/KEY: misc_feature
<222> LOCATION: (1)..(1070)
<223> OTHER INFORMATION: Ceres Promoter construct YP0082 as found in
      Promoter Report #39
<220> FEATURE:
<221> NAME/KEY: misc_feature
<222> LOCATION:
<223> OTHER INFORMATION: T3 Seedling Expression:  GFP expression
      observed in the Root hair (Rh) of the Root (Rt)

<400> SEQUENCE: 39
aagggatgcg gttccgcttc ctcttgatct tggacgagtc ggaggacatt gttggatccc      60
agtgcaatgg tttgtagaga aacaggaagc tttgttgaga aagttttaac agtgagttta    120
gtatttatct gagaactgtg tgcgacgaaa ctggagacag gggaggacta tatacaggag    180
```

```
ttaagtgttg aaggtgggat attgtcagtg agtgaatgtt ctggagaagt ggggagattg      240
atatttctct ggatgtttct agagatccgt ggctcccaag ctaagtgaaa caaatataaa      300
ttgtcttgtt tattaacggg ctacggccca tcggtattag gcctgtttta gtagatttat      360
ggtcaacaag tcaaatgacc ctagaacatg gtacatgaat gaaaaggacc aaaatgtgga      420
cagaaatcaa ccaaaggccg aggcggccac caaccaccga acgtgggaag gtctggttcg      480
ggcaaacatt cgaaagacc aagaagactc ggataaacaa ttaaaaaaat cagatattgg       540
ggaaggcaaa tatatattgg tgttgaggtc aagacttaga gttttgacgt tattttaaaa      600
aaaatatttt tgggtaaaga ccaaagagtt tgacgctatc ttgaggttta tttattcaac      660
gtagactata tactatgggg ccgttctgaa ttggaccttt taagttttga ttttattaaa      720
acgccatgtt gtttagtcga gagataaaca aaagacgtgt ctctagctaa gctgaccttc      780
atatatgctt tgacataata cattaattat aatctctctt tttggtgtgt gtaaaaaata      840
cactctatat tttattatgt agacacacta catgcagaag tgttcttacc tctgcctcta      900
cgtgctgtca actcctacag atcttcaagt accccaaccg ttatctaaca gattaaatat      960 aatataccc taactatatt atatatcaca attgttcaaa ccagtgtata tagactagac      1020
gattccttga accatataat tccagcttta ctataagagt cttaaggaca              1070
```

```
<210> SEQ ID NO 40
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter construct YP0019 as found in
      Promoter Report #40
<220> FEATURE:
<221> NAME/KEY: misc_feature
<222> LOCATION:
<223> OTHER INFORMATION: T2 Seedling Expression: GFP expression
      observed in the Epidermis (Ep) and Root hair (Rh) of the hypocotyl
      root transition zone

<400> SEQUENCE: 40
```

```
ttacgcggcg ctacactctt atcaaagttt gaagattttt caagagacac aacagattca      60
agattttctg gtggctaaac ttacaatgac agtacatgga ggatctccgc gaatggaytt      120
ctgcaatgta ctagcgtaga acaaacactt tttgttaaag tcatcaacca acatagcata      180
gagttgttta tctgaacaga acactgaaag tcttggtttt gtttgtgttc cagtaaactg      240
tgtcaaaatg aaagaaaata cttattaaca agttcggcaa aaaaaattca aacttttgtg      300
cattattata tgaaagcact tctagaaagc taccttcttc ctgctcctcc tgttcctagt      360
tttcggactc tccactcgag tgttccctct cgcttcaatc acaaacggct ttactacaga      420
catagctgat aaaagggtcg aaaaatcatg aaccaagtaa gcgaaacaga ggataataaa      480 catgaagaa gaacagagta agacgaatta taccactcac ttgttattcg aattggaaac       540
tggggataag gtttcaaacg agttccgaga atgtcagaga ctctaaactg aacagtagaa      600
agagaagtca aagcagccat gccaagtatc attcgtaaag catcgaaagt cagaacatta      660
ccctcagcgg aatttaatca aacaccttct gtgcaggaat aatctctggg ggttttatca      720
acactcaaaa aaaactggaa ctttgtaaat aaaattataa atgttcgtac ctttatgcaa      780
aatttctcac agcgtaatta tctatttcct ttttgtcctt tatgaaagag ataaggtttt      840
ttaaataata aatactaaat tgttttttaaa agaaactaaa aataaatgga aagccttaag     900
```

```
cgtcgtcaat ggttctagag tcttctgcaa cttttctttc atgaaactac tgtaatcttc    960
tgctaacata tataatctca aacactatct tctccaatt                           999
```

<210> SEQ ID NO 41
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter construct YP0084 as found in
      Promoter Report #41
<220> FEATURE:
<221> NAME/KEY: misc_feature
<222> LOCATION:
<223> OTHER INFORMATION: T2 Seedling Expression:  GFP expression
      observed in the Guard cells (Gc) of the cotyledon, petiole and
      rosette leaf
<220> FEATURE:
<221> NAME/KEY: misc_feature
<222> LOCATION:
<223> OTHER INFORMATION: T3 Seedling Expression:  GFP expression
      observed in T3 Seedling tissue expressions similar to T2 seedling
      expression., the Guard cells (Gc) of the cotyledon

<400> SEQUENCE: 41

```
gatataagta gaatcatttt ttgccgccgt ttctcgctaa cacaccgaaa actgaatcaa    60
atctcctagc tcttctacgc aaaatcgagt gcatcgacaa tggcggaacg tggtgtcgaa   120
cgtggtggag atcgcggcga tttcggacgt ggattcggtg gtcgcggcgg tggaagaggt   180
ggtccgagag gtcgtggtcg ccgtgcaggt cgtgctccag aggaggagaa atgggtgcca   240
gtgactaagc ttggtcgtct cgtaaaggaa ggtaagatca caaagattga gcagatctac   300
ctccattctc tcccagtcaa ggagtaccag atcatagatt tactcgtcgg tccttcattg   360
aaagacgaag tgatgaaaat catgccggtt caaaaacaaa ccagagccgg tcagagaacg   420
agattcaagg ccttcatcgt cgtcggagat agtaacggtc acgtcggatt aggagtcaaa   480
tgctccaagg aagttgcgac ggcgatcaga ggcgcgatca ttctcgcgaa attgtctgtg   540
gttccgatac gaagaggtta ttggggtaac aagattggaa aaccacatac ggttccgtgt   600
aaggtaaccg ggaaatgtgg atctgttact gtacgtatgg ttccagctcc gagaggttct   660
ggtattgtgg cggctagagt tcctaagaag gttcttcaat tcgctggaat tgatgatgtc   720
tttacttctt ctagaggatc caccaaaact cttggaaact tcgtcaaggt atgtactttc   780
acaatggctg ttttggtttg atgaactctg aattaggcag tgaaaaagta atcattacca   840
gttaagtgaa tttatattga agattaggat ttagctgatt gtattggttt gagcatgtga   900
gtttgtgttt aagattgctt gaattgaaat gctttaggtt gtttgattac gctaaattct   960
gactaatgta attcaaattg ttgttgtttt tttttggtc                          999
```

<210> SEQ ID NO 42
<211> LENGTH: 1015
<212> TYPE: DNA
<213> ORGANISM: Arabidopsis thaliana
<220> FEATURE:
<221> NAME/KEY: misc_feature
<222> LOCATION: (1)..(1015)
<223> OTHER INFORMATION: Ceres Promoter construct YP0087 as found in
      Promoter Report #42
<220> FEATURE:
<221> NAME/KEY: misc_feature
<222> LOCATION:
<223> OTHER INFORMATION: T2 Seedling Expression:  GFP expression
      observed in the Pholem (Ph) of the hypocotyl root transition zone
      and the root differentiation zone

```
<220> FEATURE:
<221> NAME/KEY: misc_feature
<222> LOCATION:
<223> OTHER INFORMATION: T2 Mature Plant Expression:  GFP expression
      observed in T2 Mature tissue expression (if different expression
      pattern)., the Recpetacle (Re), Silique (Si) and Vasculature (Vs)
      of the flower, the vascular bundle of the stem, T3 Seedling tissue
      expressions are similar to T2 seedling expression.

<400> SEQUENCE: 42
tgaattgagt aaaatgtgtt ttcaaacagt taggtggtag aaggtaaagg taataacatc     60
atgatcttac taaaagaatt gttgcatact aactatcaat attctcaaca acataatata    120
atgttttttt aggtaatttt ccattttaat tttttgtgat taaacaatta acaactcga     180 atgatgatga taaaaaaaaa aaattaacaa ctcgaataag ttaaagtagc aatacacatg    240
tcgttcaatt caaccaataa agtaagactt atattttaa gaagttgact aatagcttaa     300
taagttggaa aacttgtgta gtttcttaat tcccacgtgc agtaagaaat aaaaatgaaa    360
aaaattatta tatccttccc actctgcgac ttttcttta ttttatcaaa tattaaaaag     420
attcaaaaat agataaactc atatcacagt ttacacattg aaatcataaa cgataattat    480
gtattttgta ataaaaagtt agttctgaag ctcatacttt ggatagtcgc tagtcgctaa    540
tatgctcctt gtaataatta aagtcactac gacgcacgtc aaagccgata tttagggctt    600
aattgatgcg tgttttctt ttcatataat agtaatataa attagtacta ataaagtatg     660
atggatggtt gagacagaaa agaaaaaaga tgactgtatg gtcatcatta caaagaagaa    720
tgtattcttc atgttcttaa gaataataaa atgtcacttg taaatcaagt tggtaagcat    780
tttgagaact tgttcgatg caacgtatga tgatttatgt agacaaaaga taaaaccgta     840
tcttcaacta ttgccaagaa aagataaaac ctaatctagt cagtctctca acataaatac    900
aacccaatag ccaaactgtg tccaattcgg agagaaacta aactaaaaca aaacacaaaa    960
gcccaacata agcccaataa aacccatttt ataaacagaa cattactaac actca        1015

<210> SEQ ID NO 43
<211> LENGTH: 1091
<212> TYPE: DNA
<213> ORGANISM: Arabidopsis thaliana
<220> FEATURE:
<221> NAME/KEY: misc_feature
<222> LOCATION: (1)..(1091)
<223> OTHER INFORMATION: Ceres Promoter construct YP0180 as found in
      Promoter Report #43
<220> FEATURE:
<221> NAME/KEY: misc_feature
<222> LOCATION:
<223> OTHER INFORMATION: T1 Mature Plant Expression:  GFP expression
      observed in the Petal (Pe) in the developing flower, the Locules
      (Lo), Pollen (Po), Silique (Si) and Tapetum ameboid (Tp)
<220> FEATURE:
<221> NAME/KEY: misc_feature
<222> LOCATION:
<223> OTHER INFORMATION: T2 Seedling Expression:  GFP expression
      observed in the Epidermis (Ep) and Guard cells (Gc) of the
      hypocotyl, the Guard cells (Gc) of the petiole, the Phloem (Ph) in
      the root differentiation zone
<220> FEATURE:
<221> NAME/KEY: misc_feature
<222> LOCATION:
<223> OTHER INFORMATION: T2 Mature Plant Expression:  GFP expression
      observed in the Epidermis (Ep) of the pedicle and stem
<220> FEATURE:
<221> NAME/KEY: misc_feature
<222> LOCATION:
<223> OTHER INFORMATION: T3 Seedling Expression:  GFP expression
      observed in T2 Mature tissue expression (if different expression
      pattern)., the Epidermis (Ep) of the cotyledon
```

```
<400> SEQUENCE: 43
caatctgatc tctagtgcca gtcgattggt tattgttgaa acggatggta tccagattca        60
tagagttata cgttgttgac ctcgtacagg atgaattcat tatcttcttc ttcttttgca       120
gcatggcagg tgatcgatgg gtatgacttg tgatgatagc catgtccacc aaatcagcca       180
agaaaagatc aagacctcgg ctgcttacgt tctgttctat aaacgccttg tagactaaag       240
aaactgaagc ggaaaagaca agaaagaggt atttgcattt ttgccgggtt tggcttattt       300
aaaaacatca ttggcttgat tctaattcac tacaagatca agatgaaagc agctctgcgt       360
tgaggctaat ttacagaaga gagagagaga gttgggaaga agagcaaaag accgagagga       420
catgttgcgg ggaatttatt ttattcttac aaaaattggt atctgattat tttattaacc       480
atattcaatt agagaataga agaatagaga aaagcccttt tgtgggatat ggttctaaat       540
tgttgtttag ttcttgtgtg tcagttttgg ctctcgtcga ccaaagaaga ttaaagaaac       600
ctctacctta ttttaactca attctttgt ttttgcaatg tcctttgctt tccaaaattg       660
ttagtcttac ttttcactac tttgatagac attgcctttg cgtttccctg attaataagc       720
cagagtactt aaatcaaaat tgactgtttt gtgcatcctg catcacgttt ccaatcagaa       780
ccatagtgtt gtcgttgtgt cattatccga atttaagtgg agacattggt aagttattta       840
taaactaatt acaatctatt tttctaatta tttcaaataa catatttaag ctctgtagct       900
tccactagac ggtgaagatt tgaagtgaga gctctctttg cattgctcac ccaccaatgg       960
atctacctac ccttcttctt cttctcctcc ttttaaaccc taaaagtttc cctttccgtt      1020
caacaacgcc acaatccatt gcactgggat ccaacaatgt cctccgactc gtccaagatc      1080
aagaggaagc g                                                           1091

<210> SEQ ID NO 44
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter construct YP0186 as found in
      Promoter Report #44
<220> FEATURE:
<221> NAME/KEY: misc_feature
<222> LOCATION:
<223> OTHER INFORMATION: T3 Seedling Expression:  GFP expression
      observed in the Epidermis (Ep) of the hypocotyl

<400> SEQUENCE: 44
tggacaatta ctcttgtgtg tatccttgga gttgctgttt catatgtaag tggacaatta        60
ctcttgtgtg tagccttgga gttttttttat ttacgttatt ttggtcagcc tttaattatt      120
ttgcaaaaaa tgtatctgtt tttgccacat gcccacataa tacatttcgc aaatttgata      180
cattatgctt tggcccttgt atattcggta aaaaaaaaag ctcaggctac tctcaaaacc      240
ggctctgagt attcgtaggc cacaatcgaa gaaaaaagt gccgatttac atatttttca      300
tacaaaaaat taaaactgtt atgtattatt caaaagctat ttacatatgt tttactaaca      360
cgttttcaat attttcttaa tcctttcaa aatttaacta agtataatac tttttttgtg      420
tgttatttcg ttgttttggt taagaaaaa cgaaaaaag agagagttat tcatccttgc      480
agataaggct agggttggtt gaataaagat gtgcatatct tataccacta gaccaaagaa      540
acagtcacaa gtaaaaggcc gaatccttttt tataaaatat aaacagacga aagctaatgc      600
```

```
ttcatgggct tggcccaagt gcaggctctc gctagtcgct acgctacaac tatcccatat    660
ttaattagtg aagagtattt tattattttg gtcaacgggc tatctttgtt gacaaaacta    720
tcccattggt aaagaaatag caaaataggc gtttcattct ctatatttaa acttgatttt    780
atgaagagtt gaatagctga accaggaaga tatttaagaa gcccgtactt cacgctttaa    840
ctgtcaatcg atagatcata ataaatgact atctatggat aggaactata actgaattca    900
gaaagaatct actactacta taaatactaa aagagtatta atacaacgga aaaaacaaaa    960
caaaaaaaag ggggaacaag ggagtttcat gttaaaaag                          999
```

<210> SEQ ID NO 45
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter construct YP0121 as found in
      Promoter Report #45
<220> FEATURE:
<221> NAME/KEY: misc_feature
<222> LOCATION:
<223> OTHER INFORMATION: T2 Mature Plant Expression: GFP expression
      observed in the Inner integuments (Ii), Micropyle (Mp) and Outer
      integuments (Oi) of the pre-, the Micropyle (Mp) and Outer
      integuments (Oi) of the post fertilized ovule, the ovule
      containing the early embryo and mature embryo

<400> SEQUENCE: 45

```
ttggattttt ttttgttga gtcagcagac catctaatct ctcttttcc accacagcct     60 gctttctatg aagcatttgg gcttacggtt gtggaatcaa tgacttgtgc actcccaacg    120
tttgctacct gtcatggtgg acccgcagag attatcgaaa acggagtttc tgggttccac    180
attgacccat atcatccaga ccaggttgca gctaccttgg tcagcttctt tgagacctgt    240
aacaccaatc caaatcattg ggttaaaatc tctgaaggag ggctcaagcg aatctatgaa    300
aggttggccc attctccttg acaggcttaa caatacaact tgtatcgctt caacaagatg    360
atggcttaat aaggattttt gcatgtatag gtacacatgg aagaagtact cagagagact    420
gcttaccctg gctggagtct atgcattctg gaaacatgtg tctaagctcg aaaggagaga    480
aacacgacgt tacctagaga tgttttactc attgaaattt cgtgatttgg ttagtgtaac    540
ccactgttat tcttttgatg tctacatcta ctttacttac attattcttt tcttcggttt    600
gcaggccaat tcaatcccgc tggcaacaga tgagaactga tcatgacagg gtaggatttt    660
atttcctgca ctttctttag atcttttgtt tgtgttatct tgaataaaaa ttgttgggtt    720
ttgtttcctt cagtggtttg attttggact tatttgtgtt aatgttgttt tggctgttct    780
cttaatatca ataacaaata aatttactgg ttggtatcta agatcaaaca atagttacta    840
tttttagagg taaagacacc aaccttgtta tattggtcag agagctaaaa ccttgacttg    900
ttgggaaaac aaaactctaa tgacagaaaa tctgacatga tgccttataa ttcacagcct    960
catgttctac ataaatccta acaatagcac tttgtttct                          999
```

<210> SEQ ID NO 46
<211> LENGTH: 1020
<212> TYPE: DNA
<213> ORGANISM: Arabidopsis thaliana
<220> FEATURE:
<221> NAME/KEY: misc_feature
<222> LOCATION: (1)..(1020)
<223> OTHER INFORMATION: Ceres Promoter construct YP0096 as found in
      Promoter Report #46

```
<220> FEATURE:
<221> NAME/KEY: misc_feature
<222> LOCATION:
<223> OTHER INFORMATION: T1 Mature Plant Expression: GFP expression
      observed in the pre-fertilized ovule, the Egg cell (Ec) and
      Synergid cell (Sn) of the Female gametophyte (Fgm), the Zygote
      (Zg) an Hour after fertilization (HAF)

<400> SEQUENCE: 46
gaggtcagtg agtcgattgg tgcaaaattg aaaaattgaa gggtgaaaca aatttaaaga    60
taatatctat taaatcctct aattttaaaa atttagcaaa aattgtattt tcttatggat   120
ctgttagttc acacgtatct taattagtac caaatcatat ctaatgatta gtgataaaac   180
tagttagata tctatatgtg tctttaccat ttaacttgaa tccttcttct ttttttacg    240 taaacaactt gaatccttcg ttaatacata aatttaaagc attttttctt taattctatt   300
gatcggtata tatttactat aagttttagc tcatatgcaa tttcaaatga tatgctttta   360
aattttgtct aggtgtgata gttgtatctt taacataaat cttatagcaa aattatactt   420
gatattctaa atttatctat ttgctcttgt gaacctcata ttagtctaga gaaactttga   480
aatcctttca attagttgta tgtccaatac attttttacta acattattta gtcttttttaa   540 ttaagattat tgttagaaaa aaaaagattt tttaaaaata aataatatgt tttagataca   600
atgtgagtta ggcttcttat attttaaaaa ataaatttat ttcatactta aaaatagttt   660
ggaatttcaa tttatttggc tgaataccat aaaatatgtc aatttgaacc ttatacccat   720
tgactatttg gtgttagaaa ccctttaaca aaaaaaaact atttggtgtt agatatcaaa   780
ataaaaaaag tttaaccatt ggtttcttat attgaattgg atattgttac atgtattaaa   840 gttttttttgg tttaattttg aaacgttgat agaaactatt aagtttaagt ttggtagtat   900
atttatttgt ggaaaattta attgccatta aatataacgt caacttttt tggttttttt    960 tgagaagtta cgttgtgatt ttgatttcct atataaaagt tagattacgt catttttaa   1020
1020

<210> SEQ ID NO 47
<211> LENGTH: 998
<212> TYPE: DNA
<213> ORGANISM: Arabidopsis thaliana
<220> FEATURE:
<221> NAME/KEY: misc_feature
<222> LOCATION: (1)..(998)
<223> OTHER INFORMATION: Ceres Promoter construct YP0098 as found in
      Promoter Report #47
<220> FEATURE:
<221> NAME/KEY: misc_feature
<222> LOCATION:
<223> OTHER INFORMATION: T2 Mature Plant Expression: GFP expression
      observed in the Guard cell (Gc) and Stomata (So) of the stem
<220> FEATURE:
<221> NAME/KEY: misc_feature
<222> LOCATION:
<223> OTHER INFORMATION: T2 Seedling Expression: GFP expression
      observed in the root hairs of the root, the Guard cell (Gc) of the
      leaf and leaf petiole
<220> FEATURE:
<221> NAME/KEY: misc_feature
<222> LOCATION:
<223> OTHER INFORMATION: T2 Mature Plant Expression: GFP expression
      observed in the inflorescence meristem, pedicel and the
      pre-fertilized silique
<220> FEATURE:
<221> NAME/KEY: misc_feature
<222> LOCATION:
<223> OTHER INFORMATION: T3 Seedling Expression: GFP expression
      observed in the Epidermis (Ep)
```

```
<400> SEQUENCE: 47
tatttttata aattatctta gtaaaagtat gtattttcta atagatctgt tagttcatac      60
atatcttaat tagtgttaaa ttagatctaa tgattagtga taaagttttt agatatcgat     120
ataggtgtct ttaccattta acttgaatcc tttgttaatg taaaatttta aaatattttg     180
ctttgattct acttattggt atataatttt aacatatcaa tccaatgcca ctcttaaatt     240
atcatgtact tttcgatata tgttatgact cacttgttat gaaacaatgg attttcacca     300
attttggtta tttattaact agaagtttta gctcttgtgc aattttaaat gatatgcttt     360
taaaattggt ctagttataa tagttgtatc tataacataa aacttataac aaaactatac     420
ttgatattca aaattattg atttgctctt gtgaacttca tattagccta gagaactttg      480
aaaacctttc aataaattgt atgtcgaata agttttaca acatttatt agccatttcg       540 attaagacta ttgtgagcaa agttttttt tattataaaa taaataatat gtttaagata      600
aattgtgagt taggcttctt atattttaaa aattatataa gttatactg aaaaagagtt      660 aaaattttca aattttaaat ttatttggct taagaacata aatatgtcaa tttgaacctt    720
atacccacta aatattccat gttagataac gaaataaaag aaaattaact attggtttct    780
tatattgaat tggatattgt tacttgtatt tatgtttttt gtttcatttt taaacgttga    840
taaaatcatt aaactaaagt tttgtagtat atttatttgt cgaaaattta ttcccattaa    900 ataacgtt aaatttattt gtctttatta aaaagttac tttgtgattt tgatttccta      960
tataaaattt agataacttc aattttcaaa taaaaaat                            998

<210> SEQ ID NO 48
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter construct YP0108 as found in
      Promoter Report #48
<220> FEATURE:
<221> NAME/KEY: misc_feature
<222> LOCATION:
<223> OTHER INFORMATION: T1 Mature Plant Expression: GFP expression
      observed in the Vascular (Vs) and Pedicel (Pd) of the
      inflorescence meristem, the Vascular (Vs) of the sepal, leaf and
      stem, the Sepal (Se) and Pedicel (Pd) of the flower bud, the
      Septum (Sp) of the silique
<220> FEATURE:
<221> NAME/KEY: misc_feature
<222> LOCATION:
<223> OTHER INFORMATION: T2 Seedling Expression: GFP expression
      observed in the hypocotyl root transition zone, the Phloem (Ph) of
      the Root (Rt)

<400> SEQUENCE: 48
ttagctgaac caggaaattg atctcttata ccagtttccg ggtttagatt ggtttgatgg      60
cgatttgatt aaaccccga aatttatgt cgtagttgtg catagtatta ttattctttg      120
cggacaatag acgtatcggg accaagttct gtagcaaaat tgtataagct taagtttgat    180
gaaatttaaa ggtaatcact aaaacccaaa tgggacaata aaccggtgaa gatttagagt    240
ttttaatttt gactcatgaa tctggagaaa gagccctcgt taaaaggagt gaatcaatcc    300
ataggggaaa aagttttgtc ttttttaaaaa ctaaagaacc aaaccttaat agaagcagct   360
caatgtgtga caactttcca ctggcactaa gataaagtga ctagcgatga gtgcaattat   420
tgaaatagta gatggtaaat attacataca agagtaaaaa tatctttatg tcaatgctta   480
```

-continued

```
attcagtgtt tctggttaac aagagaatct tctctaactt tcgtaattgg gtcttataaa      540
attttatgca attatgattt tacccttta ctacttttca ttagctttca cgaatctatt      600
ttgacaagag aaatcattag aggtaaacat gcttttgt caagggcctt aacagttcca       660
ccaatcaagc tcaaaagttg tacttaaccg acatcttctg tgaaaacata taattacatg     720
tacaaatcaa aactaccta tgaaataaat agaaatattg cagttcattt ctaatttaac      780
ctcttcaact tttaaaacta tttacatttc tttatgtcat ttctagtcat tttgatgcaa     840
attgtaccat ttatggatta tcttcacaaa tttttaagtt ggtgaaaact ttttggtggg     900
tagttaaaac ttgaaataga aatttacttt accaaaataa actaatgaaa agtaatcact     960
ccactcccta taataagatt tccaacgttc ccactaagc                            999
```

<210> SEQ ID NO 49
<211> LENGTH: 1001
<212> TYPE: DNA
<213> ORGANISM: Arabidopsis thaliana
<220> FEATURE:
<221> NAME/KEY: misc_feature
<222> LOCATION: (1)..(1001)
<223> OTHER INFORMATION: Ceres Promoter construct YP0134 as found in
      Promoter Report #49
<220> FEATURE:
<221> NAME/KEY: misc_feature
<222> LOCATION:
<223> OTHER INFORMATION: T1 Mature Plant Expression: GFP expression
      observed in the Septum (Sp) and Epidermis (Ep) of the silique
      Carpel (Ca), Style (Sy).
<220> FEATURE:
<221> NAME/KEY: misc_feature
<222> LOCATION:
<223> OTHER INFORMATION: T2 Seedling Expression: GFP expression
      observed in the Epidermis (Ep) and Root Hair (Rh) of the
      hypocotyl, the Epidermis (Ep) of the cotyledon, the Atrichoblast
      (At) and Trichoblast (Tr) of the root differentiation zone
<220> FEATURE:
<221> NAME/KEY: misc_feature
<222> LOCATION:
<223> OTHER INFORMATION: T2 Mature Plant Expression: GFP expression
      observed in the Epidermis (Ep) and Vasculature (Vs) of the
      silique, the Epidermis (Ep) and Cortex (Cr) of the stem
<220> FEATURE:
<221> NAME/KEY: misc_feature
<222> LOCATION:
<223> OTHER INFORMATION: T3 Seedling Expression: GFP expression
      observed in T3 Seedling tissue expressions similar to T2 seedling
      expression., the root

<400> SEQUENCE: 49

```
cctactttag gcttaaacaa gaagaaaata tgactgctaa gtcatatttt tcaactctca      60
tgagcaaccg taaagttgca ccgcaatatc caacaaatga cattcgtgtt atctacaatc     120
taatgttgaa aatttggctc atctaataaa ggagacaaaa gttatatctc tttcacacac     180
acgttaatgg aagtgtaaag gcggtgagag tgtgggagag acttggggaa caagaagaag     240
gacgcggtca aaaagtgacg gtgggctacg gcttttcttg gtagcagttg gaaattccat     300
taatgactta aaaagtgtaa atcttatctt ctttttattt tgtgatttga tatgcacatt     360
catttcatga aaatatttgt atagtttgat gatcatacga caaacttata gggttcacaa     420
agtagatgca atagttgcat acctctgttt aaatgttctt gttaatatta taattgatga     480
cggaactcgt gaatgttatt caaaatgtcc atgtaattca agatcatgca ctataataag     540
taatctatca ttttcagcac aacaattttg acaaaaagta aaaataaaat agagtaaact     600
gatatcatat ttccgaatta tatatataaa cgttttctgt ttctcaatgg tctcttcac      660 tcttgtgttt tctaatatt catttaaacc tatttctaaa ctaagcacat ctttgttgat      720
```

-continued

```
tgattgcatt tcaaccaaaa tcgataaccg aatcattgtt tttttatgtt ttatttcagc      780
ttaccacaca cgtttagaat tttaaaaata aaacaaaaaa aagttaactc gttacaaatg      840
aaaatgatat ttttaattgg actcgatgga aaggaccaat ttattcaaca ctattgttta      900
gtccgaacac ttgccgcgta agttttccaa ctcccccat tgacctttcg cactttcaca      960
aactccgtat atataatg gatacactct ctctttgatc t                          1001
```

<210> SEQ ID NO 50
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter construct YP0138 as found in Promoter Report #50
<220> FEATURE:
<221> NAME/KEY: misc_feature
<222> LOCATION:
<223> OTHER INFORMATION: T2 Mature Plant Expression: GFP expression observed in the inflorescence meristem, the Epidermis (Ep) of the petal and stem, the Epidermis (Ep), Mesophyll (Me) and Cortex (Cr) of the silique, the Epidermis (Ep) and Cortex (Cr) of the stem, the Epidermis (Ep) and Mesophyll (Me) of the leaf
<220> FEATURE:
<221> NAME/KEY: misc_feature
<222> LOCATION:
<223> OTHER INFORMATION: T2 Seedling Expression: GFP expression observed in the rosette leaf, the Epidermis (Ep) and Mesophyll (Me) of the cotyledon and rosette leaf, the Vasculature (Vs) of the rosette leaf, the Cortex (Cr) of the lateral root, the root elongation zone and the root tip
<220> FEATURE:
<221> NAME/KEY: misc_feature
<222> LOCATION:
<223> OTHER INFORMATION: T2 Mature Plant Expression: GFP expression observed in the Epidermis (Ep) and Cortex (Cr) of the stem, the Micropyle (Mp) of the mature ovule
<220> FEATURE:
<221> NAME/KEY: misc_feature
<222> LOCATION:
<223> OTHER INFORMATION: T3 Seedling Expression: GFP expression observed in T3 Seedling tissue expressions similar to T2 seedling expression, T2 Mature tissue expression (if different expression pattern), the flanking cells of the Lateral root (Lr) in the root transition zone, the Epidermis (Ep) and Mesophyll (Me) of the leaf

<400> SEQUENCE: 50

```
tgtgtgtcct aaatagtttc tttttaaaat ttgtaaatac caagacgcgt atttaagagt       60
attttgaaaa gatatttgat tataaaaaga aagaaaaaga gaaggctgag gattaactgc      120
aacgtctacc gttggaaaag aaaaacgatc agaaaacaca gaaattaata aaagagaga      180 aaaaaaaata gagtatgaga gatgcacatg ggtgcctgca aaaaaaggt agaagaaatt      240 tgtctgaaag tgtcacaggc acactctctc gaaccacatt taacaacact ccaaacactc      300
ttcttctact ttgtaccctt cagtacatta ctctttccaa agtccgtgat ttacgctctt      360
cgatgacacc tctcaacaga gagagactac atgtgtacat tttcttctac cattaaattt      420
tgaagatttt cgatgattca atttagtata tatatggaag ataaaatttt cattgtcttt      480
ctacatgata gtaacggttt tagaagggtg gttatcactt atagtatttg agttaagaaa      540
tataaaaata tacgtgactg ttttttcctg taaactattt ttaggcccct atttttattc      600
aagtagtcac atacgtgttt gaagtgtatt taactaagaa aaagaaagta ggaaatgaaa      660
aggatatagt atttatggtg taatcttggt aaggaccagg agatcagaag gggccacaat      720
gtcacaaaga ggaccaacaa tgaaattaaa tcctcagctg gcctttaaca ttttggctcc      780
```

```
caccatctcc ttccacacat atgcacatgt cttcatgtct ctctctctct atacgttacc     840
tacacaaata tgtacagaca aatagcccat tacaaaatct ttatttataa atatatactc     900
ctcaactccc tcaatatcca cccatctcct tctccataac tctctctctc tctccctaaa     960
cacaaccaaa gactttatc tctcaggaac cccaaaaac                             999
```

```
<210> SEQ ID NO 51
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter construct YP0177 as found in
      Promoter Report #51
<220> FEATURE:
<221> NAME/KEY: misc_feature
<222> LOCATION:
<223> OTHER INFORMATION: T1 Mature Plant Expression:  GFP expression
      observed in the Guard cells (Gc) of the flower pedicel, the
      silique and the stem
<220> FEATURE:
<221> NAME/KEY: misc_feature
<222> LOCATION:
<223> OTHER INFORMATION: T3 Seedling Expression:  GFP expression
      observed in the Guard cell (Gc) of the rosette leaf, the Root hair
      (Rh) of the hypocotyl root transition zone

<400> SEQUENCE: 51
```

```
tgtgtgtcct aaatagtttc tttttaaaat ttgtaaatac caagacgcgt atttaagagt      60
attttgaaaa gatatttgat tataaaaaga aagaaaaaga gaaggctgag gattaactgc     120
aacgtctacc gttggaaaag aaaaacgatc agaaaacaca gaaattaata aaagagaga     180 aaaaaaaata gagtatgaga gatgcacatg ggtgcctgca aaaaaaggt agaagaaatt     240 tgtctgaaag tgtcacaggc acactctctc gaaccacatt taacaacact ccaaacactc     300
ttcttctact ttgtacccttt cagtacatta ctctttccaa agtccgtgat ttacgctctt    360
cgatgacacc tctcaacaga gagagactac atgtgtacat tttcttctac cattaaattt    420
tgaagatttt cgatgattca atttagtata tatatggaag ataaaattt cattgtcttt     480 ctacatgata gtaacggttt tagaagggtg gttatcactt atagtattg agttaagaaa     540 tataaaaata tacgtgactg ttttccttg taaactattt ttaggccctt attttttattc    600 aagtagtcac atacgtgttt gaagtgtatt taactaagaa aaagaaagta ggaaatgaaa    660
aggatatagt atttatggtg taatcttggt aaggaccagg agatcagaag gggccacaat    720
gtcacaaaga ggaccaacaa tgaaattaaa tcctcagctg gcctttaaca ttttggctcc    780
caccatctcc ttccacacat atgcacatgt cttcatgtct ctctctctct atacgttacc    840
tacacaaata tgtacagaca aatagcccat tacaaaatct ttatttataa atatatactc    900
ctcaactccc tcaatatcca cccatctcct tctccataac tctctctctc tctccctaaa    960
cacaaccaaa gactttatc tctcaggaac cccaaaaac                             999
```

```
<210> SEQ ID NO 52
<211> LENGTH: 1006
<212> TYPE: DNA
<213> ORGANISM: Arabidopsis thaliana
<220> FEATURE:
<221> NAME/KEY: misc_feature
<222> LOCATION: (1)..(1006)
<223> OTHER INFORMATION: Ceres Promoter construct YP0192 as found in
      Promoter Report #52
<220> FEATURE:
```

```
<221> NAME/KEY: misc_feature
<222> LOCATION:
<223> OTHER INFORMATION: T2 Mature Plant Expression: GFP expression
      observed in the Vasculature (Vs) of the inflorescence meristem and
      the Sepal (Se)
<220> FEATURE:
<221> NAME/KEY: misc_feature
<222> LOCATION:
<223> OTHER INFORMATION: T2 Seedling Expression: GFP expression
      observed in the Guard cell (Gc) and Vasculature (Vs) of the leaf

<400> SEQUENCE: 52
tcctcctact gtctgctacg tcaacaagtg gattgcaatc agacggtgat tgtgtctctt      60
ttcattctct ctcttttact aatttctctg ataattaaac tgagaatgta tattaagaaa     120
aaaaaacaaa aacaagagag gaattttcat acacactaac ttaagactct ttgtaagttt     180
tcccaaatat ggatttttcta gtataaatat gagttcatta gtttcaccaa gcctacaagc    240
atctctccat ctcaaatcat attcacctaa aaatcaggtc ccctctcttt atatctctaa     300
cattcttata tcagatcata ttttttggat ttcttgttaa gtaacaccaa tcttttaaaa     360
gtgttttcag gttaatataa aagaataatg atgttttcgg tgacggttgc gatccttgtt     420
tgtcttattg gctacattta ccgatcattt aagcctccac caccgcgaat ctgcggccat     480
cctaacggtc ctccggttac ttctccgaga atcaagctca gtgatggaag atatcttgct     540
tatagagaat ctggggttga tagagacaat gctaactaca agatcattgt cgttcatggc     600
ctcaacagct ccaaagacac tgaattttcc atccctaagg ttcactctta ttctcaatat     660
taactctcgt acatgtcaca tgcccatttt caccattta gatatacagt tttgatactt     720
tactttgcat ttatttttgct atatgtaatt gaggatattg ttttaatttc tttgggtttt    780
tttttttcgg ctaaatgaga attcactgtc tttggttctt gaaaaaaaag tatttgttaa     840
tggtaaacgc taaacgctat ttgagtttat gttttttcaa gaactgaaaa cgttttattg     900
aaaatataca cttttttttgc tatttatagg aaagcatatc acatcacatc tagacgcaaa    960
cgcaaaattg agttttaaag caaccacaat cttaaatgca atgaaa                  1006

<210> SEQ ID NO 53
<211> LENGTH: 1071
<212> TYPE: DNA
<213> ORGANISM: Arabidopsis thaliana
<220> FEATURE:
<221> NAME/KEY: misc_feature
<222> LOCATION: (1)..(1071)
<223> OTHER INFORMATION: Ceres Promoter construct YP0204 as found in
      Promoter Report #53
<220> FEATURE:
<221> NAME/KEY: misc_feature
<222> LOCATION:
<223> OTHER INFORMATION: T1 Mature Plant Expression: GFP expression
      observed in the inflorescence meristem
<220> FEATURE:
<221> NAME/KEY: misc_feature
<222> LOCATION:
<223> OTHER INFORMATION: T3 Seedling Expression: GFP expression
      observed in the seedling root, the Epidermis (Ep) and Root hair
      (Rh) of the hypocotyl root transition zone, the Epidermis (Ep) and
      Root hair (Rh) of the root differentiation zone

<400> SEQUENCE: 53
aactaattag gtcgttaatt gtccaagggt ttttcatagt tgatatagtt ctgttcaaat      60
atagccatcc ttaatcgatt catgggatcg taaattacta cttcgagtgt tgtaaaaaaa    120
aatgaaactt ctacattaca aactcgaatt taatgcatct ggagtgatac tataaaagta    180
gggatgctct caggtcgcat ttgagagaca cagaaatgat tttaatggaa ttaatatatt    240
```

```
ttcagttttt cacaaaaaaa aattgtgttt ataacaactg cagattcaat gctgatttta      300
tgagtctcac ctatagaatt tatatttcta tattcataga ggcagtatag gtgttgaccc      360
aacatcgaaa gaacacttcg taaaaaattc tttggaacaa ggctgaaaat ttactcccaa      420
atttagctat ccgatgaaga taaatcattt accgtttatt aaagaattat cgagatttta      480
gtcaaaacca aaagagatta tgagcctaag atttttgaatt tgtattggta aaggaaattg     540
aacgaaaatt tcagaaaaaa atattaataa attgaacgat agagttcact tactacatag     600
tcaactagtg cctagctata atagtttcaa aagacaaaaa aaacaaaatc ggttaactac     660
ttccgtgaca taattctcat cttgattttt gaatccagtc taatttgaaa agtatattca    720
aaatctttaa atccattaat gataactttt ataatacgtt gacacacgca attgtatata    780
caatattctt gaattttaaa tgtaaattct agaatatatt gcgatcacca cactaatcaa    840
aatctttggg acaacttgaa cccacatttg acttttcttg gtcaaatatt ttggcatcat    900
gcatgatctt ctctataaaa accaaaaggc ctcaacgaca ttcataaact cagtcattat    960
atttattttt gttgtatttc aacgttcaat ctctgaaaac cattgcactg ggatccaaca   1020
atgtcctccg actcgtccaa gatcaagagg aagcggaacc gcatcccgct c            1071
```

<210> SEQ ID NO 54
<211> LENGTH: 1191
<212> TYPE: DNA
<213> ORGANISM: Oryza sativa
<220> FEATURE:
<221> NAME/KEY: misc_feature
<222> LOCATION: (1)..(1191)
<223> OTHER INFORMATION: Ceres Promoter construct pCRS-HT2-pGluB-1 as
      found in Promoter Report #58
<220> FEATURE:
<221> NAME/KEY: misc_feature
<222> LOCATION:
<223> OTHER INFORMATION: T2 Seedling Expression: GFP expression
      observed in the Epidermis (Ep) and Vasculature (Vs) of the
      cotyledon, the Epidermis (Ep) and Mesophyll (Me) of the primary
      leaf, the Lateral root (Lr), lateral root initial and lateral root
      primordia
<220> FEATURE:
<221> NAME/KEY: misc_feature
<222> LOCATION:
<223> OTHER INFORMATION: T2 Mature Plant Expression: GFP expression
      observed in the silique primordia, the Cortex (Cr) and Stigma (Sg)
      of the developing and fertilized silique, the Vasculature (Vs) of
      the sepal, mature embryo and the leaf

<400> SEQUENCE: 54

```
gatctcgatt tttgaggaat tttagaagtt gaacagagtc aatcgaacag acagttgaag      60
agatatggat tttctaagat cggggggaccg agtggaccgg acgaggatgt ggcctaggac    120
gagtgcacaa ggctagtgga ctcggtcccc gcgcggtatc ccgagtggtc cactgtctgc    180
aaacacgatt cacatagagc gggcagacgc gggagccgtc ctaggtgcac cggaagcaaa    240
tccgtcgcct gggtggattt gagtgacacg gcccacgtgt agcctcacag ctctccgtgg    300
tcagatgtgt aaaattatca taatatgtgt ttttcaaata gttaaataat atatataggc    360
aagttatatg ggtcaataag cagtaaaaag gcttatgaca tggtaaaatt acttacacca    420
atatgcctta ctgtctgata tattttacat gacaacaaag ttacaagtac gtcatttaaa    480
aatacaagtt acttatcaat tgtagtgtat caagtaaatg acaacaaacc tacaaatttg    540
ctattttgaa ggaacactta aaaaaatcaa taggcaagtt atatagtcaa taaactgcaa    600
gaaggcttat gacatggaaa aattacatac accaatatgc tttattgtcc ggtatatttt    660
```

-continued

```
acaagacaac aaagttataa gtatgtcatt taaaaataca agttacttat caattgtcaa      720
gtaaatgaaa acaaacctac aaatttgtta ttttgaagga acacctaaat tatcaaatat      780
agcttgctac gcaaaatgac aacatgctta caagttatta tcatcttaaa gttagactca      840
tcttctcaag cataagagct ttatggtgca aaaacaaata taatgacaag gcaaagatac      900
atacatatta agagtatgga cagacatttc tttaacaaac tccatttgta ttactccaaa      960
agcaccagaa gtttgtcatg gctgagtcat gaaatgtata gttcaatctt gcaaagttgc     1020 ctttccttt gtactgtgtt ttaacactac aagccatata ttgtctgtac gtgcaacaaa     1080
ctatatcacc atgtatccca agatgctttt ttattgctat ataaactagc ttggtctgtc     1140
tttgaactca catcaattag cttaagtttc cataagcaag tacaaatagc t             1191
```

<210> SEQ ID NO 55
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct YP0008 as found in
      Promoter Report #60
<220> FEATURE:
<221> NAME/KEY: misc_feature
<222> LOCATION:
<223> OTHER INFORMATION: T1 Mature Plant Expression: GFP expression
      observed in the Endothelium (Ed) of the mature seed
<220> FEATURE:
<221> NAME/KEY: misc_feature
<222> LOCATION:
<223> OTHER INFORMATION: T2 Seedling Expression: GFP expression
      observed in the Cortex (Cr) of the seedling

<400> SEQUENCE: 55

```
ctcgagagat gaagtcttag taatgtttga acaaacaata atcacgtttt ccatcaaatt       60
cgagcattta aagtttatat tactacatgc cccaagatga taccgtccat ctcatccgaa      120
aatatttctg aaattgcgct aagacaacaa tgtttgctca aattcgatca tttaaagttt      180
acaaatctct catcaatctt acaaacttct cacactaaac agaggtacat attttcttat      240
aaagacaaaa ggttcgaaca gctggcttct caactcgagt tgtttgtcag ggcctctctt      300
cactaactac aagttggtac ttcaaatatt ggtggctagc ttcacgtgat attgtctaca      360
aattaaaccc atgaaaaagc tgcattaatt gttccaagtg aaccctgagg agtgtcaata      420
gtctttgctt tagtgtgatc attaaaccaa atctctaaat tcctaatttg tactaacatt      480
tggaacgtat ttcctactct tctccctgct ccaactccca aaaataagat tagttagatt      540
tctataacta atatacatgt atactcccaa aaacagtaaa accatattaa taaagctaat      600
tttgcataga tttatttcgg taaaccggcg gttcaagttg gggaaaaaaa agacaaacgg      660
tctaaagtca tccaaagaca aaaaaccaaa gacaagttga gagagacgag accaatcaca      720
acattgcttc gtagattgcg tgacatcatc cttgacggct actttcattt gtgtcttatt      780
tggataaaac gcacgtgttt aattcacgaa ccttctagc aataagaaat ttccattact      840
ttcatatttt caactttttt tattacccat tacatgctta aaatattaat tcacaagtct      900
ttgtcaaaat tcaatatttt ccaggttcat gaaccctttt tatctcaatc tactctataa      960
tatctcccta taaattacaa caaaacctct ttattttca                           1000
```

<210> SEQ ID NO 56
<211> LENGTH: 1000
<212> TYPE: DNA

```
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct YP0009 as found in
      Promoter Report #61
<220> FEATURE:
<221> NAME/KEY: misc_feature
<222> LOCATION:
<223> OTHER INFORMATION: T2 Seedling Expression:  GFP expression
      observed in the Epidermis (Ep) and Cortex (Cr) of the hypocotyl
      root zone, the Epidermis (Ep), Cortex (Cr) Pericycle (Pr) and
      Vasculature (Vs) of the root
<220> FEATURE:
<221> NAME/KEY: misc_feature
<222> LOCATION:
<223> OTHER INFORMATION: T2 Mature Plant Expression:  GFP expression
      observed in the Guard cell (Gc), Epidermis (Ep) and Vasculature
      (Vs) of the leaf, the  Vascular bundle (Vb) of the stem

<400> SEQUENCE: 56
aattcgtttt ttatactccc tctgttccaa gatacttgat attttgggtt tttgcacaag      60
aattaagaaa agtaactttt atattttttaa ttattctttt agttagttta ataatattaa   120
ttttacttct ctcatttcat tattggttac aaacaaaaat aataatgata gttttttcaaa   180 acatcaattt tggtggaaca aataaaaaaa ctcaaaatat caaataactt gaaacagagg   240
gagtagttaa ttaaaaaaag atatttcaca ctttgacttg gcgaagcctc ataacaatga   300
agttatgtat gaactatata tgaagttaga acaatggaa aacagcttgt aaatattcat    360
tgttgtatat atgttttttt gggtcaattt ggtgcatgaa caaaaataaa aacgtagatg   420
aaaaccggat attttggtgt taacatttgc atttgaactt cgtgaaagac ggataaaagc    480 tcattttgt tttttattat atggctgcta ttagtacaca gagttgaact ttagaatact    540
aaaaatctcg acatctttta ttttattttt gtcaagcatc gacatctttt ctgttcaaga   600
aaacgaccgc aatagtcgaa taatataact cttggactag ttaatatata tttgcgatag   660
attttcgatc tcacttatat cttataacca agagacaaaa acaatattgc agtcaagtac    720
aaaacgaaaa caatcacaat gtcgactata gatgagtcgg tcattcgatc caacggctct   780
gagtccacga aacacgcaac caagtggtgc tctcttttac accaaatcat attatataaa   840
acttaaaaga aagagaggat ggttcgttgg ctccttcttg ttccttaatt aattcaaatt   900
atattcatca cctccattga ataagtccat ttcacgacaa agtcaccaat gcttcttta    960 catgtatata tacttcttc cactccctct tctctactca                        1000

<210> SEQ ID NO 57
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct YP0010 as found in
      Promoter Report #62
<220> FEATURE:
<221> NAME/KEY: misc_feature
<222> LOCATION:
<223> OTHER INFORMATION: T2 Seedling Expression:  GFP expression
      observed in the Phloem (Ph) of the root
<220> FEATURE:
<221> NAME/KEY: misc_feature
<222> LOCATION:
<223> OTHER INFORMATION: T2 Mature Plant Expression:  GFP expression
      observed in the Guard cell (Gc) of the Pedicel (Pd) and Sepal (Se)
      of the flower, the Guard cell (Gc) and Vasculature (Vs) of the
      silique and pre-fertilized silique, the Carpel (Ca), Stigma (Sg)
      and Style (Sy) of the mature silique, the Septum (Sp) of the
``` silique, the Hydathode (Hd) of the leaf, the Mesophyll (Me) of the
adax the Vasculature (Vs) and Hydathode (Hd) of the abaxial leaf

<400> SEQUENCE: 57

```
aattcgtctt gcattggtaa tccaatattc catgtgatgc ttttctttct aactgaaggt      60
attcgtgaaa acgaattcaa gattgtggga gataattagg gtttcgtcaa aagcatgaat     120
taggaaaatt tgggattgat ttttttgaatt tgggaaaagt cctaatttta attcgatcaa    180
agcttaaatg atgtcgtttt gggctgacta acgaagtcgt taacaggtgc caacgagtgt    240
taaaaatctg ttatcgcttg ataactcttt ggttttttag tctaatcaac acattctcat    300
gtttcaaaca gttaatcaac atattgttca tgttaaaaaa ttaacacatg tgaaattgat    360
atataaaaat atcatatatt ttcaaaagtt ggatcattaa ataaaaattt tccctatttt    420
tgaaataatt ctaaaacagt attaaagata tttcctgaaa ttgtttgcat gtgatcggtt    480
ttggaccgaa actaaaaaac ttagaaacta tattaacttt gagttgtcga gatgaagatg    540
tgaaatagaa ataggatc aatggttaga attttggcaa atgtatgaag gtgtgtttga      600
ttgaatattc caagtccttt gccttttgga ataggcataa ctactacaac aaagttttga    660
taggttttcc gaattctta aactccttaa attttaata catctcaatc aaactccact      720
tatactaaaa ataatccata ttgcatttt aaaaatccta aaagaagaat cacatgataa     780
cttgataagc acttttaaat gatagatgtc cacgtagagg aataagacaa aaagacaaaa    840
taaagaaaaa ggacgaaatc taaagagaga aaataagtaa caagtccaag aaaaggtagt    900
atgatctttc tcggtccgat cctcgaaact ccctcgaagg ctcgaaccct ctctttgttt    960
ttttaccact atataagaaa gtccgattcc tcgtcactct                         1000
```

<210> SEQ ID NO 58
<211> LENGTH: 1054
<212> TYPE: DNA
<213> ORGANISM: Arabidopsis thaliana
<220> FEATURE:
<221> NAME/KEY: misc_feature
<222> LOCATION: (1)..(1054)
<223> OTHER INFORMATION: Ceres Promoter construct YP0039 as found in
   Promoter Report #64
<220> FEATURE:
<221> NAME/KEY: misc_feature
<222> LOCATION:
<223> OTHER INFORMATION: T1 Mature Plant Expression: GFP expression
   observed in the Antipodal cells (Ap), Central cell (Cc), Central
   cell vacuole (Cv)and Egg cell (Ec) of the pre-fertilized ovule,
   the globular stage, heart stage and torpedo stage embryo in the
   ovule, the Cotyledon (Co) of the ovule, the mature pollen, the
   fertilized ovule and embryo
<220> FEATURE:
<221> NAME/KEY: misc_feature
<222> LOCATION:
<223> OTHER INFORMATION: T2 Seedling Expression: GFP expression
   observed in the lateral root primordial, the lateral root, the
   Cortex (Cr) of the root and the root tip

<400> SEQUENCE: 58

```
ccgttcgagt atttgaaaat ttcgggtaca cccgcctaaa taggcggacc ttatctagta     60
tatatataca tttgaactat attgtttact ttttagttga tttaggctat gtcatgacat    120
tgacataaat ctacctgtta tttatcacgt gtaattcgtg taaagtgtaa actagaaagt    180
tcaaatacgt atttgttttt gttctgttat ataggattgt catagttgta aatctacaat    240
ttattacaac atgaataagt acacaagcaa tgtaattgga tttaattgct aaactcttta    300
catggtcaat ctaaatttga taagaaatac gtcacatatt actaagactg atagtttttt    360
```

```
tgttgtcacc aattatttttt gttaaattga cgaaaacaat tccaaaaact caaatgtaca    420
aaatcataca gtctcacaaa catctcatag agaaagatat aaatctccca tatgggaacg    480
ataacacgag gtcgaaatac tattcgtaaa actaaaacgc cttagttata aatcgttagt    540
tgtaaccgcg gtcgagaata catacagatc cacgaaacta ctactacaca tgctgctgaa    600
ttggaatttg gaaaagacca tcttctttag gaagagctca cccaatgagt gacaaaggtg    660
tcggtggctt gttttctacc catatgtata catcaaatgg tagtttcatt aacgtttggt    720
tttgagaaaa gtaagacttt ggctagtagc taggttcgta tataataaac tcttttgaga    780
aagttcatca ctggtggaaa atgttaaacc ggttttttct cattttttcc gccatgttaa    840
ccaccggttt aaaagaccg taacacattg aaagattaat aagggtatat ttgtaattac    900
ggtttgctgg caatttttaa ttattatttt aattagagaa aatagagaag ccctatcaat    960
gtacatggta tatatataaa aggcaaaacc ctagaaaacg atactattcg actcagccgt   1020
cctttcgcaa gaaaccattt ggagttggag cttt                               1054

<210> SEQ ID NO 59
<211> LENGTH: 1007
<212> TYPE: DNA
<213> ORGANISM: Arabidopsis thaliana
<220> FEATURE:
<221> NAME/KEY: misc_feature
<222> LOCATION: (1)..(1007)
<223> OTHER INFORMATION: Ceres Promoter construct YP0070 as found in
      Promoter Report #66
<220> FEATURE:
<221> NAME/KEY: misc_feature
<222> LOCATION:
<223> OTHER INFORMATION: T1 Mature Plant Expression:  GFP expression
      observed in the Funiculus (Fn), the Chalaza (Ch) of the mature
      ovule
<220> FEATURE:
<221> NAME/KEY: misc_feature
<222> LOCATION:
<223> OTHER INFORMATION: T2 Seedling Expression:  GFP expression
      observed in the Epidermis (Ep) of the petiole, the Hypocotyl (Hy),
      the Rooot hair (Rh) of the hypocotyl

<400> SEQUENCE: 59
ttggcgttaa tcgttaagaa aaaaacgtgc ctacctagcc aaatgacatc ttcctctttt     60
gtgtttagca caagtgaatg atccaaatat catctaccta atatgaccca taaaatagta    120
tgtgattgtc tttggatgtt atcccataac ataacttaaa tttgggatgc atgcatatat    180
tatatacttc atataaaatg agtggaccct ataagttgcg gtttcgattt ttatcaaaaa    240
caacagttgt ccactttttg attttgacac acacccacat tcaagcatct cctttcttct    300
atattattac tcaaagaata acacccccta aggataacac cattcacaca atcaattctc    360
agttaatcat ttgtttcaat atatgttagt acttaagaaa tattcgaata gttttacgta    420
ttcaaatttt ataaattcag tgaatgttta attaccaagt cattttggct tggaatctat    480
tcaattattc aaaaaaataa ataaataata ctgcatttta acgtatcagc cagtcaatat    540
attacacgtg tcataaagca ttacccacac gtttctcctg cctcttttcc tttcattttt    600
ttttttcatt ttttttgttt cttctcttgt tgttgttatc ttcttctagc tagctctgtg    660
aaacacttca aatgaacaaa tatatcaaat aataatagtg taattaagtc ggaggaaaac    720
aacaagaacc cagaaagagg aacgaagaaa ctaattcaaa ggtatgatct tttattcttt    780
gagagaatta tgttttcttt gtagcaaatc ctctggtctt acgtttagtc actgaatttg    840
ttccacttct ggaaaaatct agacaccaaa agcaatctat gaactttaat ttccaatcac    900
```

-continued

```
taccgtcttt tgaggttgta aaatcggtaa atggcagatt tttcactctc attcctttgt    960
ggtgatagga tcaagttcac cgcttcattt tagtcattaa acaaaga                 1007
```

<210> SEQ ID NO 60
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter construct YP0086 as found in
      Promoter Report #68
<220> FEATURE:
<221> NAME/KEY: misc_feature
<222> LOCATION:
<223> OTHER INFORMATION: T2 Mature Plant Expression:  GFP expression
      observed in the Shoot apical meristem (SAM), Silique (Si), Stamen
      (St) and Sepal (Se) of the, the Placenta Silique (Si), Stamen
      (St), Sepal (Se), Abscision zone (Az) and Nectary (Ne) of the, the
      Carpel (Ca), Ovule (Ov) and Stigma (Sg) of the immature silique,
      Carpel (Ca), Ovule (Ov) and Placenta (Pl), of the ovary, the
      Filament (Fi) of the Anther (An) in the stamen, the Cortex (Cr) of
      the silique, the Outer integument (Oi) and Funiculus (Fn) of the
      pre-fertilized and fertilized ovule, the Embryo (Em), Suspensor
      (Su) and Micropyle (Mp) of the ovule, the Pollen (Po), the
      Hyphosis (Hp) and Suspensor (Su) of the embryo, the Cotyledon (Co)
      and Root (Rt) of the mature embryo, the Epidermis (Ep), Pith (Pi)
      and Vascular bundle (Vb) of the stem, the Epidermis (Ep),
      Mesophyll (Me) and Vascular bundle (Vs) of the leaf
<220> FEATURE:
<221> NAME/KEY: misc_feature
<222> LOCATION:
<223> OTHER INFORMATION: T3 Seedling Expression:  GFP expression
      observed in the Hypocotyl (Hy) and Rosette leaf (Rl) in the
      seedling, the of the cotyledon, the Epidermis (Ep), Mesophyll (Me)
      and Vasculature (Vs) of the rosette leaf, the Epidermis (Ep),
      Vasculature (Vs)  and Root hair (Rh) in the hypocotyl root, the
      Vasculature bundle (Vb), Cortex (Cr) and Epidermis (Ep) of the
      root

<400> SEQUENCE: 60

```
cttatccttt aacaatgaac aggttttag aggtagcttg atgattcctg cacatgtgat    60
cttggcttca ggcttaattt tccaggtaaa gcattatgag atactcttat atctcttaca   120 tactttgag ataatgcaca agaacttcat aactatatgc tttagtttct gcatttgaca   180
ctgccaaatt cattaatctc taatatcttt gttgttgatc tttggtagac atgggtacta   240
gaaaaagcaa actacaccaa ggtaaaatac ttttgtacaa acataaactc gttatcacgg   300
aacatcaatg gagtgtatat ctaacggagt gtagaaacat ttgattattg caggaagcta   360
tctcaggata ttatcggttt atatggaatc tcttctacgc agagtatctg ttattcccct   420
tcctctagct ttcaatttca tggtgaggat atgcagtttt cttgtatat cattcttctt    480 cttctttgta gcttggagtc aaaatcggtt ccttcatgta catacatcaa ggatatgtcc   540
ttctgaattt ttatatcttg caataaaaat gcttgtacca attgaaacac cagcttttg    600 agttctatga tcactgactt ggttctaacc aaaaaaaaaa aaatgtttaa tttacatatc   660
taaaagtagg tttagggaaa cctaaacagt aaaatatttg tatattattc gaatttcact   720
catcataaaa acttaaattg caccataaaa ttttgtttta ctattaatga tgtaatttgt    780
gtaacttaag ataaaaataa tattccgtaa gttaaccggc taaaccacg tataaaccag    840 ggaacctgtt aaaccggttc tttactggat aaagaaatga agcccatgt agacagctcc    900 attagagccc aaaccctaaa tttctcatct atataaaagg agtgacatta gggttttgt    960 tcgtcctctt aaagcttctc gttttctctg ccgtctctc                         999
```

<210> SEQ ID NO 61
<211> LENGTH: 1106
<212> TYPE: DNA
<213> ORGANISM: Arabidopsis thaliana
<220> FEATURE:
<221> NAME/KEY: misc_feature
<222> LOCATION: (1)..(1106)
<223> OTHER INFORMATION: Ceres Promoter construct YP0088 as found in Promoter Report #69
<220> FEATURE:
<221> NAME/KEY: misc_feature
<222> LOCATION:
<223> OTHER INFORMATION: T1 Mature Plant Expression: GFP expression observed in the Hypophysis (Hp) and Suspensor (Su) of the heart stage embryo, the torpedo stage embryo, the Root apical meristem (RAM) of the mature embryo, the mature embryo
<220> FEATURE:
<221> NAME/KEY: misc_feature
<222> LOCATION:
<223> OTHER INFORMATION: T2 Seedling Expression: GFP expression observed in the rosette leaf, the Lateral root (Lr), the Epidermis (Ep) of the root, the Lateral root tip and the root timp

<400> SEQUENCE: 61

```
tcgattggga ttactacttc atctagtaag gttctgaaaa cgtttgttgt tgataaggaa    60
gattcgtctc aggttattac tgttgatctt caaggtttgt gattgtgacg cttatacatg   120
tgctgaaact gtggtgttta tttattgaaa acaaaaaaaa agtctctctt gtagtttcat   180
tgtactaaat agaaacaag aaacgttttt ttctttaatc ttctacattg ataatattgg    240
atcaaaggat tgtttctgca agacacaaca caaacatact tatactagtt tacttctact   300
aagtactaac tacataccca tacacacact tgcacctaga ctttacttct agacatcatt   360
accctaaggt agaaccaagc ttacaagcaa gttttaccga caactcttac attacaactc   420
tagtctgtag tctttaacgt agacttacta actagtcatt agtggtttaa ttttttaaat   480
tttcatccat atgttttttgt tgtagatata aactaaagtc ggtcacattt aataattgtc   540
attatgtccg cgtaaaagtc aattcagcta ttggacattt atgaaatgta agattttctc   600
tctcatttcc ccgtgcgtga agacatgcat tggttttttct gtaataatca acaaatccaa   660
acccctttc gatctttatt tggacattgt tagagacaaa atttctctat agtcttttc    720
ctaatttgat accatgtttt tgtttctgca caaatttact cactggttta actaactatc   780
cacttattta tgattttacc attaggcgtc agctagccct agtcaaattt gtaaacaagc   840
caagctatct acataaatcg agatgtcatt aacgttaatc gtcgttaatt cgaatttgaa   900
aacatagata gctttagcag tacaatgggc aatggtaaga agaatagcaa aaggcccaat   960
atttggtttg cagaaattaa agccttaaaa aaaagcccac agatatttgt caaagaaccc  1020
taataacctt tcggtgctc aagcgccgtt tctagggttt ttctctgagg aagaaagcgt  1080
ttcatttctc tgaatttcat cgaaaa                                       1106
```

<210> SEQ ID NO 62
<211> LENGTH: 1004
<212> TYPE: DNA
<213> ORGANISM: Arabidopsis thaliana
<220> FEATURE:
<221> NAME/KEY: misc_feature
<222> LOCATION: (1)..(1004)
<223> OTHER INFORMATION: Ceres Promoter construct YP0101 as found in Promoter Report #70
<220> FEATURE:
<221> NAME/KEY: misc_feature
<222> LOCATION:
<223> OTHER INFORMATION: T1 Mature Plant Expression: GFP expression observed in the Chalaza (Ch), Female gametophyte (Fgm), Funiculus (Fn) and Micropyle (Mp) of the, the Embryo (Es), the Mesophyll

```
        (Me) of the leaf
<220> FEATURE:
<221> NAME/KEY: misc_feature
<222> LOCATION:
<223> OTHER INFORMATION: T2 Seedling Expression:  GFP expression
      observed in the Hypocotyl (Hy) root, the Hypocotyl (Hy) root zone,
      the Root hair (Rh), the Cortex (Cr) and Epidermis (Ep) of the
      root, the Epidermis (Ep) and Root hair (Rh) of the lateral root,
      the Epidermis (Ep) of the root tip

<400> SEQUENCE: 62
ttctcgttct ctagaatatt gctggaccgg attaggtcaa tattattggg ccagattaga     60
tattgaattg tcgacgttgc ttacgttacg ttatatcttg tttaagaatt aaacctatcg    120
acttagtctt aattaagaaa acattgcctt aaattctctg gtctgcgacc gttttttga     180 ccgttaaccc ctaattaaag aaacaaaata attatagaaa gagcactgaa atgtgattat    240
tttaacagta ctcttatgag aaaattcgta cttttagtt ttttttttgt acaaatctct     300 aagaaaaca ctactactaa ttaagaaacg tttcaaacaa ttttattttc gttggctcat    360
aatctttctt tctcggtccg ggactaaccg ttggcaaaaa aaaaaaaaa gttgacaata    420 attattaaag cgtaaatcat acctctcaaa taaaaacttg aatttggaaa caaagacaac    480
taaaaaactc gaatttaaga gaattcctaa aatcaagtga agtatcatca cttggtaaaa    540
tttcataacc gttggcttct atttctatgt gtgccttggt ttgcaggaga taatatttca    600
tttccaacca atgatattcg tacacatagt caaacaaatg tttgtctttg ttattatatt    660
gagaaagaaa caagaaagag agagagagat agataagacg aaggaagtga agcttccaag    720
cgcccaccgt taaaatctc gtgtgcaagt ttcaaataca agtggccggt ggtctccata    780
atttgatcgt catccaatta aaaggaaga aaaagcgtgt tttatacaag aaaactcatt    840
aaaatagcaa gtctagaaat atctcaacac taatctacca cgtctattac acacacacac    900
acacacactt gatcttaatt tattttcaag attcaagaaa atacccattc cattaccaca    960
acttgaccac acgcctatat ataaaacata aaagcccttt cccc                    1004

<210> SEQ ID NO 63
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct YP0115 as found in
      Promoter Report #71
<220> FEATURE:
<221> NAME/KEY: misc_feature
<222> LOCATION:
<223> OTHER INFORMATION: T1 Mature Plant Expression:  GFP expression
      observed in the Funiculus (Fn), Inner integument (Ii), Megaspore
      mother cell (Mmc) and Outer, the Funiculus (Fn) and Outer
      integument (Oi) of the pre-fertilized ovule, the Seed coat (Sc) of
      the developing seed
<220> FEATURE:
<221> NAME/KEY: misc_feature
<222> LOCATION:
<223> OTHER INFORMATION: T2 Seedling Expression:  GFP expression
      observed in the Epidermis (Ep) of the hypocotyl, root and root
      tip, the Root hair (Rh) of the hypocotyl-root transition zone, the
      Vascular (Vs) of the cotyledon

<400> SEQUENCE: 63
atgatgaaca ttctacatat ataattatta tgtttaagca cttagacagc ataaattctt     60
tctaattata taaatctaac cttgttacat tgtacatcta taaattactt gaagaaataa    120
cgagttctat ttcttttaa aaattaaaaa tactatacca tatctcagtg attaagttga    180
```

```
accaaaaggt acggaggaga aacaagcatt tgattcttcc ttattttatt ttattcatct     240
ctcactaatg atggtggaga aaaaagaaa atacctaaca aacaaatata tattgtcata      300
caaaaatatt tctatatttt tagttaatta gtttatattc ctcacttttc agggcttata    360
taagaaagtg agcaaacaca aatcaaaatg cagcagcaaa tactatcatc acccatctcc    420
ttagttctat tttataattc ctcttctttt tgttcatagc tttgtaatta tagtcttatt    480
tctctttaag gctcaataag aggaggtact attactacac ttctctctac ttttacttgt    540
attttagcat taaaatccta aaatccgttt taaattcaaa ataaacttag agatgttta     600 atctcgattc ggttttttcgg ctttaggaga ataattatat gaaattagta tggatatctt   660
tactagtttc cattcaaatg attctgattt caatctaata ctctcactct ttaattaaac   720
tatatgtagt gtaatttcac actgttaaat ttctaccatg tcatgtatat tagagttgca   780
tagaaaattg taaacatcc atttgaattc gaatgaaaca aaatgttta aaataaaatt     840 ttggttttta aagaaaaat ctaaaactga attatatcgt ttaaccaagt tgtaaaagtc     900
ataaaacgta gtatcttgta aatcgctctt ccacggtcca aatagacttc tagtaataaa   960
caagtaaaac taatttttggt ttcttactaa ttttcacaga                        1000
```

<210> SEQ ID NO 64
<211> LENGTH: 1009
<212> TYPE: DNA
<213> ORGANISM: Arabidopsis thaliana
<220> FEATURE:
<221> NAME/KEY: misc_feature
<222> LOCATION: (1)..(1009)
<223> OTHER INFORMATION: Ceres Promoter construct YP0133 as found in
      Promoter Report #72
<220> FEATURE:
<221> NAME/KEY: misc_feature
<222> LOCATION:
<223> OTHER INFORMATION: T1 Mature Plant Expression: GFP expression
      observed in the Guard cell (Gc)
<220> FEATURE:
<221> NAME/KEY: misc_feature
<222> LOCATION:
<223> OTHER INFORMATION: T2 Seedling Expression: GFP expression
      observed in the Epidermis (Ep) of the Rosette leaf (Rl) and
      Petiole (Pt) in the seedling, the Epidermis (Ep) and Root hair
      (Rh), of the root

<400> SEQUENCE: 64

```
gtcgattggt attagtccaa taactttcac agtttactta taatataata ttgaaagtat   60
ggttaattga caatagggta tttccactga taatcagtca ccagtaataa taatttgttg   120
ggactagaat caatcacttg agttttaaat tgatatatgc ctagatggtt gttaggacca    180
atattcctaa acaataccaa attttaatat agaaatgtaa ataattcgc cgacacatta    240 tttcgttatt gacattgaat atttcaatga tatcaactct gtttatttac atctatttag    300
tataatttct tgagcaacaa aaaagtagt tttaaagtta ttttccctag attttttctat    360 tgtaaaagcc tatatatcac aacaaaaatt aaccattttc tcttttggca agtttaaaat    420
ttttataatg aatataccat tttaaaaaaa aaattatcca aactaaatta accatttttct   480 cttttggcaa caaaattaa ccattttaaaa aaaaaaaaaa aaaaaagtt taaaattttt    540 ataacaacag aaagtaatat tatccaaact atgaataatt aaaaaatctg tccacatacg    600
atcatatatt tctctccacc gacagccgaa aacactgtca atggcccacg ttcctctaaa    660
agctgtcgtc ttcggtaata ttttccggta ataaactaac ttccgatcac aattacacaa    720
aagccccttt ctcgtttata atcataggct atgattcata gcaaacttac agagttggtt   780
```

```
attaagaagt caaaatacag gattccttaa aatattttt ttctgttcat atattttta      840 tcgagaaaca attacttaaa cataagaagc aagacaagaa ttaatgttct tattaacatg     900
atgctaatat aatcggaaaa caaatcaaa tcatgataga agggtaaaat ggtcaaatca     960
tcgttcccgg ctcaaatttt actaaaacag ccactagcca gccagatcc              1009
```

<210> SEQ ID NO 65
<211> LENGTH: 1001
<212> TYPE: DNA
<213> ORGANISM: Arabidopsis thaliana
<220> FEATURE:
<221> NAME/KEY: misc_feature
<222> LOCATION: (1)..(1001)
<223> OTHER INFORMATION: Ceres Promoter construct YP0137 as found in
      Promoter Report #73
<220> FEATURE:
<221> NAME/KEY: misc_feature
<222> LOCATION:
<223> OTHER INFORMATION: T1 Mature Plant Expression: GFP expression
      observed in the Egg apparatus (Ea ) of the ovule and fertilized
      ovule, the Antipodal cells (Ap), Central cell (Cc), Synergid cell
      (Sn), Egg sac (Es), Egg, the Antipodal cells (Ap), Central cell
      (Cc), Synergid cell (Sn) and Egg apparatus, the Antipodal cells
      (Ap), Central cell (Cc), Cv, Sc and Micropyle (Mp) in an abnormal
<220> FEATURE:
<221> NAME/KEY: misc_feature
<222> LOCATION:
<223> OTHER INFORMATION: T2 Seedling Expression: GFP expression
      observed in the Root hair (Rh) of the root, the Epidermis (Ep) of
      the root and Lateral root (Lr), the upper and lower portions of
      the root, the Endodermis (Ed) of the root

<400> SEQUENCE: 65

```
gtggcacatg ctgaaacccc gagcatctct ccggaagaca cgcgtcgttc gctccaaaga      60
aaacagtcac agctgccgga gaatctccgc cgtcttcttc tgccaccgga aaaactctct     120
ccaccacttt cagtgcccac ctcgtgttat atccactgta tcctcgtagc accatatcag     180
cctaataaaa ttttatgtat caaattttaa gacatagccg aaactacact atactagaca     240
ataataatat gatttgtttc ctgaaaaatt atggtttcat gagaaacatt aatcatctat     300
aaaacaaatt agctatggca tcgaagagtt atcaatcaaa actgatgaat ctttacttaa     360
tatatacaac atatctttac cttgcggcgg agaagatcgg cgagagaagc accccagcca     420
ccgtcactaa aggattcttc agtgatggaa tcaccaaaga gaaaaacctt ccgtctcatc     480
atcttccaca caatcttctt gagaaaatct gagagataag aaaggtgtag tggttttgct     540
gaagtgatcg tgtttgattt agtaaagaaa tgctttattt attgttgggg gaaacataaa     600
taaataaagt aaaagtggat gcactaaatg ctttcaccca ctaatcaccg accttttcatg     660 gtttattgtg aaatacactc atagatagac atacaatacc ttatgtacgt aaataacatt     720
ttatttgtcg acacttatgt aagtaacgca tagattattt tctatgtgat tgccactctc     780
agactctcag tttcaaccaa taataacaat aactacaaca acattaatca taaacatatg     840
ctctggttta caattaaagc ttagattaag aaactgtaac aacgttacag aaaaaaaatg     900
ttatttacgt tttgtaagat tagtctctag aatcatcacc gttttttata tattaatgat     960
tctttcttat atataaaacc tttctcgaaa tacccatgaa a                        1001
```

<210> SEQ ID NO 66
<211> LENGTH: 1003
<212> TYPE: DNA
<213> ORGANISM: Arabidopsis thaliana
<220> FEATURE:
<221> NAME/KEY: misc_feature

```
<222> LOCATION: (1)..(1003)
<223> OTHER INFORMATION: Ceres Promoter construct YP0144 as found in
      Promoter Report #74
<220> FEATURE:
<221> NAME/KEY: misc_feature
<222> LOCATION:
<223> OTHER INFORMATION: T1 Mature Plant Expression: GFP expression
      observed in the flower, the Carpel (Ca), Stigma (Sg) and Style
      (Sy) of the Silique (Si), the Cortex (Co) and Epidermis (Ep) of
      the carpel, the Guard cell (Gc) of the carpel, the Epidermis (Ep)
      and Mesophyll (Me) of the leaf, the Vasculature of the leaf, the
      Cortex (Cr) and Epidermis (Ep) of the stem
<220> FEATURE:
<221> NAME/KEY: misc_feature
<222> LOCATION:
<223> OTHER INFORMATION: T2 Seedling Expression: GFP expression
      observed in the Cotyledon (Co), Hypocotyl (Hy) and Rosette leaf
      (Rl) of the seedling, the Epidermis (Ep) of the seedling Cotyledon
      (Co), Hypocotyl (Hy) and Rosette leaf (Rl)

<400> SEQUENCE: 66
aaacgttgca agattattga ttgtgagaaa gagtgctcaa ggtagtactg atttctgtaa      60
agctcacggt ggtgggaaac gatgttcttg gggagatggg aaatgtgaga aaatttgcta     120
gaggaaagaa gcggtttatg cgctgcgcat aacactatta tgtctcggga gaacaaagat    180
ggaagcaaga gcggtttgat tggaccggga ctctttagtg gccttgtttt tggctctact    240
tctgatcatt ctcagtctgg agctagcgct gtctctgatt gtactgattc tgttgaacga    300
atacagtttg agaataggca gaagaacaag aagatgatga taccgatgca ggttctagta    360
ccttcatcaa tgaaatctcc aagtaattca catgaaggag aaacaaacat ctatgacttc    420
atggttccgg aggagagagt tcacggcggt gggctagtaa tgtctttact tggtggctcc    480
attgatcgaa actgaaagcc atttatggta aaagtgtcac attctcagca aaaacctgtg    540
taaagctgta aaatgtgtgg gaatctccga atctgtttgt agccggttac gttatgctgg    600
atcaaaaact caagatttgt tggatattgt tatgctggat cggtggtgaa accacttccc    660
ggttgctaaa taaataaacg ttttttgtttt ataatctttt tcactaaacg gcagtatggg    720
cctttagtgg gcttcccttta agcgaccaat acaatcgtcg caccggaatc tactaccatt    780 tataggtttta ttcatgtaaa acctcggaaa atttgagagc cacaacggtc aagagacaaa    840
aacaacttga agataaaggg ataaggaagg cttcctacat gatggacaac atttctttcc    900
acacaaattc tcataataaa aatcttataa tacaaatact tacgtcataa tcattcaatc    960
tagtccccat gttttaaggt cctgtttctt gtctgataca aat                     1003

<210> SEQ ID NO 67
<211> LENGTH: 1001
<212> TYPE: DNA
<213> ORGANISM: Arabidopsis thaliana
<220> FEATURE:
<221> NAME/KEY: misc_feature
<222> LOCATION: (1)..(1001)
<223> OTHER INFORMATION: Ceres Promoter construct YP0143 as found in
      Promoter Report #75
<220> FEATURE:
<221> NAME/KEY: misc_feature
<222> LOCATION:
<223> OTHER INFORMATION: T1 Mature Plant Expression: GFP expression
      observed in the flower Guard cells and Guard cells of the Sepal
      (Se), the stem Guard cells, the Cotyledon (Co) and Radicle (Rd) of
      the ovule, the Radicle (Rd) of the torpedo stage embryo, the
      Cotyledon (Co) and Radicle (Rd) of the embryo, the Root cap (Rc)
      of the mature embryo, the Cotyledon (Co)

<400> SEQUENCE: 67
atacaacaga tggcagatat cgagttaaat acgtgaatca gccgttacga tattttaaaa      60
```

-continued

```
ctagaaaatt atttaaaaat attgcaaaat accatttaat ttcattgttc ataaaaaaaa      120
gaaattcaaa aacttaaaaa ctgattcaaa aatttggatt aattctcatt aacagtcttc      180
aacactacaa caacatgttt ctaatttatt ttatatttta ataattaaac aatatatacg      240
tctgcacatt gttgctccga cataatctag tataaaaata gttgcagcat atgtgaaaag      300
caagcagcat ttatcactca atacttttaa ttttatctgt tgtatgtatt aaggttttgt      360
agctttaaga aaacgcttat aatataaaat aacttctaaa agatatttca tgcgtataca      420
ataaatattt gtgaaaaaac atttcgaaaa cgtgtacaat atataaacta ttgtgttatc      480
ttttgacatt caaacaaatg ttgacaatgt aattttatcc atgatatgat tggccaatta      540
gctgcgaggt aaaaatccgt atacgagtaa aagtaagata aaatttcgca agaagatttt      600
tagcaggaaa tctaagacaa gtgtcatgaa cgtgtcaatc aacaaacgaa aaggagaatt      660
atagaatcca gattcgacgt accacattaa taaaatatcaa aacatttat gttattttat       720 ttttgctctg gcagttacac tcttttttcat tgctccaata aaaaaatcac tcgcatgcat      780
gcatatatat acaccatagt aaactccgcc tcttcttcat tttaaaagta tcagtttaca      840
ctgacacaat ccttaactat tttcctttgt tcttcttcat ctttattaca cattttttc       900 aaggtaacaa ataatctttt taagtcactt ttatactctt taaatcttag attgatatat      960
gaatgcatgt taatatttca agatttatag gtctaccaaa c                          1001
```

<210> SEQ ID NO 68
<211> LENGTH: 1004
<212> TYPE: DNA
<213> ORGANISM: Arabidopsis thaliana
<220> FEATURE:
<221> NAME/KEY: misc_feature
<222> LOCATION: (1)..(1004)
<223> OTHER INFORMATION: Ceres Promoter construct YP0156 as found in
      Promoter Report #76
<220> FEATURE:
<221> NAME/KEY: misc_feature
<222> LOCATION:
<223> OTHER INFORMATION: T2 Seedling Expression: GFP expression
      observed in the root, the Epidermis (Ep) and Root hair (Rh) of the
      root, the lateral root primordial and lateral root tip, the root
      tip

<400> SEQUENCE: 68

```
ttggtttgca ttgtgaagat ttgtattaac tatagaacat tgaattgatg gtgttaagtt       60
cttacacaag cgtgcttctc ggtttgaact gtttcttttg tatgttgaat cagagcttag      120
tttataggaa ccagagtatc tacttagtca ttctctgatg ctaagtgcta aggttctacc      180
tagttgccct ctaggccctt atgttattga taacttatga agctatttga acacttgatt      240
cttaggagac ctaagttggt acagccagat agagtgtatg ttcttgttct ctatgtgaca      300
ggatcaagct gccacacata gttcaagggt atgctctgtg tgggtttgct cagattgagg      360
acaaatctat acaaggaagt agagtctttg acattttgat gttgtatgat aagaagaaga      420 aggagagta ataagaaag agaaaaggga aacagaaaca cgtgggagaa catcccaaag       480
aggaagcaca cgcggatctt catgcaaagc tccccgattc tcccatgtgg tcccttcctc      540
cctttgtccc cctcctcttt cttcttttct catttactc ttttttttac cattatacaa       600
cgaatctttt ttatcataat ttttttggttt tggttttattt tccaataaca ctttcttggt      660
tacttcccat tctcacttt tcatataaga aactcacttt gggaaactta tgtttgagaa       720
tgacaagtct ttttagagaa agtgatgtaa caaatctaaa gtgattatat aataaccttg     780
```

-continued

```
cacaatgttt ttgattttt  gtaagattcg aatattaggt ttattattcg tagggaataa        840
acttactttc aaaagcgttc ataagttaat actttcatat atgatcataa gtacggacac        900
tattgttttt tgtttgtttg tgtttattct aaaagaaagt agctttaat  tgaaatgtcc        960 tcggaggcac agtttaaagt tcgagtgtaa cagtttctaa ggca                        1004
```

<210> SEQ ID NO 69
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct YP0158 as found in
      Promoter Report #77
<220> FEATURE:
<221> NAME/KEY: misc_feature
<222> LOCATION:
<223> OTHER INFORMATION: T1 Mature Plant Expression: GFP expression
      observed in the Epidermis (Ep) and Vasculature (Vs) of the
      flower/pedicle, the Vasculature (Vs) of the flower petal, the
      Epidermis (Ep) and Cortex (Cr) of the stem
<220> FEATURE:
<221> NAME/KEY: misc_feature
<222> LOCATION:
<223> OTHER INFORMATION: T2 Seedling Expression: GFP expression
      observed in the Shoot apical meristem (SAM) of the inflorescence
      meristem, the Epidermis (Ep) and Vasculature (Vs) of the rosette
      leaf and root, the Hydothode (Hd), Epidermis (Ep) and Vasculature
      (Vs) of the cotyledon, the seedling, the Epidermis (Ep) and
      Vasculature (Vs) of the hypocotyl, the Epidermis (Ep) and Root
      hair (Rh) hypocotyl/root

<400> SEQUENCE: 69

```
ttattagatt aatagattgc attgcattgc ttgtgctttc aatttacaaa ttgtctccca         60
actccatcga cacatctctt tttgtgtata taagattcag acttgttata tttttttat         120 aaatatgtta ttagcatctt aagttaaatt gattttttat atctgcatta aggattacac        180
gactatattt gcgattgtgt gttggttaaa atataattta ggattgtctt taactacatt        240
taggattata tgactatatt tggttaaata taaaatctag ctgtgattat tagtattcaa        300
aaataagtag cctaaccaat taaaacaacg gctattgggg caaattagaa catttagtg         360 tgtccaaaat ataatggtca ttaggtcata ttcctcctag cttcatcgca gcataattga        420
atgattgcct tattagaag  agcttttcca ctttcccaaa atctaggtgg gatcttttg         480 ttttgacctt cattttctt  gtttaccatt tttagctaaa ttatttacga ttacaaaaga        540
tatcaaaagt tggatcataa tacaatttat agacttactg tagaaaattc gtatgtacaa        600
gtacaacaaa ttcttcataa taatttga   aaattctatt acaatgttg  taagaaatag        660 aatttgaaat atatataaac taaggagaaa aaaaagaga  acatgcattg ctctagtcag        720
agtggaccaa catcaacgag ataagataac ataaaaacca actcaccata actaaaaaca        780
tcccaagaga tccaacgatt catatcaaac acaaaaacat cgaacgatca gatttaaacc        840
atctctggta tctccaaaac acaaacactt tttttttct  tttgtctgaa tggaacaaaa        900
gcatgcgaca tctctgtgtc tttatcttct ctctcctctt cttgaaaaac tgaacctta         960 attctttctt cacatctcct ttagctttct gaagctgcta                             1000
```

<210> SEQ ID NO 70
<211> LENGTH: 997
<212> TYPE: DNA
<213> ORGANISM: Arabidopsis thaliana
<220> FEATURE:
<221> NAME/KEY: misc_feature

```
<222> LOCATION: (1)..(997)
<223> OTHER INFORMATION: Ceres Promoter construct YP0164 as found in
      Promoter Report #79
<220> FEATURE:
<221> NAME/KEY: misc_feature
<222> LOCATION:
<223> OTHER INFORMATION: T1 Mature Plant Expression:  GFP expression
      observed in the Epidermis (Ep) and Vasculature (Vs) of the
      inflorescence, the Sepals (Se) and Shoot apical meristem (SAM),
      the Vasculature (Vs) of the stamen filament, the Nectary (Ne) and
      Ovule (Ov) of the flower, the Epidermis (Ep) and Cortex (Cr) of
      the silique, the Placenta (Pl), Ovule (Ov) and Funiculus (Fn) of
      the ovary., the Outer integument (Oi) of the ovule, the Embryo
      (Em) of the ovule at the globular stage, the Embryo (Em) and the
      Root apical meristem (RAM) of the embryo at the heart stage, the
      Embryo (Em) at the torpedo stage, the Root apical meristem (RAM)
      of the mature embryo, the root tip, the Pith (Pi), Cortex (Cr) and
      Vascular bundle (Vb) of the stem
<220> FEATURE:
<221> NAME/KEY: misc_feature
<222> LOCATION:
<223> OTHER INFORMATION: T2 Seedling Expression:  GFP expression
      observed in the Epidermis (Ep), of the hypocotyl, the Lateral root
      (Lr) and Vasculature (Vs) of the root, the lateral root tip, the
      Pericycle (Pr) and Vasculature (Vs) of the lateral root initial,
      the lateral root primordial, the Root apical meristem (RAM) of the
      tip

<400> SEQUENCE: 70
gtcgattggc attactagag ttttagattt cacagaattc ttttctttgt ttggtctgtt      60
cgtcctctac tgtgttttc ttttgttttg gctattttgc cgtctgttaa aaaattgggg     120
ttttccgata atgtattgta tatgcctgaa ttatggaaat atcactaaaa acacttttt     180 gcacttttgt atatattgca attaagattt aattttttcta ttttgaagac ttttttgttaa    240 aagagagatt tgctaactca aaattaccgg agtaataag ttcgttctca tcagattagc      300
aaaacattca tctttaaaga aatctgttta tctcacgtaa aattctacta attggcagca     360
gcacactact ttaatgggcc tattactatt tcaatatgca ctgaaaactt cattggactg     420
tccaataaca ttataacatt attaaaacta aactacattt gtatttgggt tacaattta     480 taaagagtaa gactcaagat actaattggg ctgcagacaa cttaaaagc cttactacaa     540 aaatcaaaac cattcttaat taactaacaa ccaggtaaaa atctcagtac aatatttaca     600
ctaaaaatag gtgccaccca ctatgcaaaa gtttagggcc acgaacaaaa aaacctgtaa     660
attgttatgt cttcacaata tgtgttttaa tacacatgaa ttttagctgc ggttaatgta     720
aattttgtag ttaaattaag gctaaacaat ctcaaatata aattggtcag gtccacagac     780
aacagcctgg caagtggcaa gcactaaaaa ttcgaccgtt attttttgcc ccttttttta     840
atatttcgaa attgtatctt ttagttttat tttaaagctt tttagcccgc tcctcctccg     900 ctccacctt aatttttca ccaattggat ttggatctgt caaaaatatt ggcctctttc      960
tctctttctc tcttgctctc tttctttgtt gggttga                             997

<210> SEQ ID NO 71
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct YP0119 as found in
      Promoter Report #80
<220> FEATURE:
<221> NAME/KEY: misc_feature
<222> LOCATION:
<223> OTHER INFORMATION: T1 Mature Plant Expression:  GFP expression
      observed in the silique, the Inner integument (Ii) of the ovule,
``` the Endosperm (En) and Inner integument (Ii) of the ovule ath the
torpedo stage, the Outer integument (Oi) of the ovule at the
zygote stage, the Inner integument (Ii) and Outer integument (Oi)
of the ovule, the Seed coat (Sc) of the seed

<400> SEQUENCE: 71

```
taccaaaaat aaggagtttc caaaagatgg ttctgatgag aaacagagcc catccctctc    60
cttttcccct tcccatgaaa gaaatcggat ggtcctcctt caatgtcctc cacctactct   120
tctcttcttt cttttttttct ttcttattat taaccattta attaatttcc ccttcaattt  180
cagtttctag ttctgtaaaa agaaaataca catctcactt atagatatcc atatctattt   240
atatgcatgt atagagaata aaaagtgtg agtttctagg tatgttgagt atgtgctgtt    300
tggacaattg ttagatgatc tgtccatttt tttcttttttt cttctgtgta taaatatatt  360
tgagcacaaa gaaaaactaa taaccttctg ttttcagcaa gtagggtctt ataaccttca   420
aagaaatatt ccttcaattg aaaacccata aaccaaaata gatattacaa aaggaaagag   480
agatattttc aagaacaaca taattagaaa agcagaagca gcagttaagt ggtactgaga   540
taaatgatat agtttctctt caagaacagt ttctcattac ccaccttctc ctttttgctg   600
atctatcgta atcttgagaa ctcaggtaag gttgtgaata ttatgcacca ttcattaacc   660
ctaaaaataa gagatttaaa ataaatgttt cttctttctc tgattcttgt gtaaccaatt   720
catgggtttg atatgtttct tggttattgc ttatcaacaa agagatttga tcattataaa   780
gtagattaat aactcttaaa cacacaaagt ttctttattt tttagttaca tccctaattc   840
tagaccagaa catggatttg atctatttct tggttatgta ttcttgatca ggaaaaggga   900
tttgatcatc aagattagcc ttctctctct ctctctagat atctttcttg aatttagaaa   960
tctttattta attatttggt gatgtcatat ataggatcaa                         1000
```

<210> SEQ ID NO 72
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct YP0171 as found in
      Promoter Report #82
<220> FEATURE:
<221> NAME/KEY: misc_feature
<222> LOCATION:
<223> OTHER INFORMATION: T1 Mature Plant Expression:  GFP expression
      observed in the Stigma (Sg) and Style (Sy) of the distal silique,
      the Carpel (Ca) of the proximal silique
<220> FEATURE:
<221> NAME/KEY: misc_feature
<222> LOCATION:
<223> OTHER INFORMATION: T2 Seedling Expression:  GFP expression
      observed in the Vasculature (Vs), Pericycle (Pr), Endothelium (Ed)
      and Epidermis (Ep) of the root

<400> SEQUENCE: 72

```
aatgaaaaca atgggagaag tacatgcttg tcctcacaca ctaatgccga tgaggaaagc    60
ctttaagggg acttttatct ccgcaggagg tttcacgagg gaagatggga atgaggctgt   120
gtcaaaggga agaactgatt tggtggctta tggtcgatgg tttctagcca acccggacct   180
gccaaagagg ttccaagtgg atgcaccgct gaataagtac gatagaccaa cgttttacac   240
ttctgatcca gtcgtcggtt acaccgatta cccttttcctc gaatcaacag cttaaaattg  300
ttatcaataa tgtaatgtag tgtgtttccc ttatataaga tgtaataagt ttctggcttt   360
tcatttatac ttttttaagtt taagtcataa aaccttcaca aaaatttcca cggacacatt   420
```

```
atcacaaaag cgctttctag agaccaacat aacttaactt gattgttgat ttctgtttga      480
tgtgatcatg ccgcaatcca gtgtgttctc atgatgctat cttccctcct ttcacatgct      540
gcacagaaca aaacagagca ttttcctccc aactatacct aattttttt ggtcggtggt      600 caaagttata catcggaaga atctgttgaa atcatattga ggcccctcat ttgttatgtt      660
atgtaatctc caatggatca aaagtagaat cccaactgta aagatgata ctatcatgct       720 aggtagaaga cagcatggaa tatggggtaa gttcaaagtg gttacactct aatgtcgtct      780
caacgaatac gtctttatga agaaataaaa aaatctaagt ggttggatgc gtcatcaatg      840
acgaccacgt cgttaaagac agaaagaaac acttgcgttc ctgattctct gatcaatcaa      900
tgtgtataaa tatgttcgga tatgtccatt atcttacgca atcttgaaaa gtgttttga      960 gagaaatata ggttttacaa aatccaccgt tgtgaattca                           1000
```

<210> SEQ ID NO 73
<211> LENGTH: 1005
<212> TYPE: DNA
<213> ORGANISM: Arabidopsis thaliana
<220> FEATURE:
<221> NAME/KEY: misc_feature
<222> LOCATION: (1)..(1005)
<223> OTHER INFORMATION: Ceres Promoter construct YP0188 as found in
      Promoter Report #84
<220> FEATURE:
<221> NAME/KEY: misc_feature
<222> LOCATION:
<223> OTHER INFORMATION: T1 Mature Plant Expression:  GFP expression
      observed in the Guard cell (Gc), of the Pedicel (Pd) and Sepal
      (Se), the Placenta (Pl) and Funiculus (Fn), the Suspensor (Su) of
      the early globular embryo, the Suspensor (Su), Embryo (Em),
      Hypocotyl (Hy) and Outer integument (Oi) of, the Suspensor (Su)
      and Embryo (Em) of the early heart stage embryo, the mid-heart,
      late heart and torpedo stage embryo, the leaf Epidermis (Ep),
      Mesophyll (Me) and Vasculature (Vs), the Cortex (Cr), Epidermis
      (Ep) and Guard cell (Gc) of the stem
<220> FEATURE:
<221> NAME/KEY: misc_feature
<222> LOCATION:
<223> OTHER INFORMATION: T2 Seedling Expression:  GFP expression
      observed in the Vasculature (Vs), Epidermis (Ep) and Root hair
      (Rh) of the hypocotyl-root transition, the Vasculature (Vs),
      Hydathode (Hd), Epidermis (Ep) and Mesophyll (Me) of the, the
      Epidermis (Ep) and Mesophyll (Me) of the rosette leaf, the
      Vasculature (Vs) and Epidermis (Ep) of the root, the Pericycle
      (Pr) of the Lateral root (Lr), the lateral root primordial

<400> SEQUENCE: 73

```
gattggtatg aaatttcgga gaccaacaaa aaaaacttta ttgagcttgg agtgaagcta       60
tatatatggg gcaagatcat aatatgttta tatcggcctt ttcgttaact gaaaataata     120
gttttgagaa atatatcaaa tggtaaacag acatcatctt tgaaaaatac catcaatgaa     180
gttaatattg ttattggcat atggtttacc catcttaatt ttaatgcaac caaacaaaca     240
agaaacaaaa actgtataag atacaaggtg ttttacgatt ttccgtctta aaaccgaaat     300 attttttgttc ctacgacttt aaacggactt tgcttaagtt gtgtgcatgt aagctcgtcg    360
tccctcgatt gtcatcaaca ttcaccaata tcagcctcta tcacacgagt gaaggtggtg     420
attcggctta atgaaaacag agaaatattt caatatgatt cctattaaat tttaaatctt     480
ttttctcaat ctctagattt tcattaaaag catcatgatt ttttttccact atgttcatat     540 atctctatca cagttttagg tacattgtag aaattggata agatacgtca tacgtctaac     600
atgaatttgg tctagcaagg aaggtttgag ataataagtg aaaagaaaac acaagataat     660
aaattataat ttataaatgc tttatagtat tgaaaaataa gatgattttt ttttttttta     720
```

-continued

```
ataccggatt ggctgatcca cttatgatga ctcaaatgtt attaagtttc aagacaattt    780
atgatgacac aaatcacaat gagtcaatag tagccacgaa gccagaaaaa aaaaatgtac    840
tacaaaaaga taatgatagt acaaaatgat acgtcgtact gccacatgta cgacacaact    900
cgattaccaa aaagcagagc catccaacca taaaactcaa aacacacaga ttccactggc    960
gtgtgctctc ctcacttcac tcgtccttga aacttgaggt actga                    1005
```

<210> SEQ ID NO 74
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct YP0258 as found in
      Promoter Report #85
<220> FEATURE:
<221> NAME/KEY: misc_feature
<222> LOCATION:
<223> OTHER INFORMATION: T1 Mature Plant Expression:  GFP expression
      observed in the Epidermis (Ep), Guard cell (Gc) and Vasculature
      (Vs) of the Sepal (Se) in developing
<220> FEATURE:
<221> NAME/KEY: misc_feature
<222> LOCATION:
<223> OTHER INFORMATION: T2 Seedling Expression:  GFP expression
      observed in the Epidermis (Ep), Hypocotyl (Hy) and Root hair (Rh)
      of the hypocotyl root transition, the Epidermis (Ep) of the root

<400> SEQUENCE: 74

```
taaataactt acttaaattt atattaaaac cgtttacatc tgatataatt taaaaggttt     60
tagacgaatt agtattagtg aaccattatc aagatgtatt tattcaaaaa tctataataa    120
taaaaacaaa actgggaaag caatgggaag aagatctgat tggctttgga agacttcgcg    180
tgttaataag attttttctca aaaagaaag atcggacggc aatgcgtggc aagtcgctta    240
tgacgtcgga agcttagctt gccacgtgta cggtcatcac catttaggtg accgatataa    300
tgtatttccc gtgacttgac aatctaatct cccaatttat cgtgctccag tgtctcaaga    360
gagaacttac tctattggtt acccaaaact cacataaaac gtggatttta tattttttt     420 tatcaaataa tttgatgtgc aatataaaca tatgtgatt attatcttgc atgttttaaaa    480 aatgctaact taaatttttc ttcaatgatt gagatttttc atacacatcc atcgagttca    540
cacttatgat taaacaaagt gtattgttac actaataacg gttctaagtt gtttcaatac    600
gtttatgata acggttctat actaatacta gtattcatac gtttatgaaa ctcgttaatt    660
atatatttaa ctttgtttag ctgtatcata acaagcgttt taagaaataa tttaataaaa    720
aatgagaaaa cgataagcga cgccttatcg cctatgtgta attatcgtgt caaaatatcg    780
tgataaggaa gctgtttcag aggagccttc tcgtttgttg cgtcgttgct ctgagccaac    840
aacgctaata taaaggaag ctcaagtctc tctgttttaa tctcggacca atatacaaaa    900
ccgtgtgttc ttctctgtat cttattaaat caaaaccaat tttgttcttc ttctttgatt    960 ctttttttcct tcatttttta acgtatcttg agagatcgac                        1000
```

<210> SEQ ID NO 75
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct YP0265 as found in

```
        Promoter Report #86
<220> FEATURE:
<221> NAME/KEY: misc_feature
<222> LOCATION:
<223> OTHER INFORMATION: T1 Mature Plant Expression:  GFP expression
      observed in the inflorescence meristem, the Epidermis (Ep) and
      Vasculature (Vs) in the Sepal (Se) of the inflorescence, the
      Epidermis (Ep) and Vasculature (Vs) in the Petal (Pe), the
      Vasculature (Vs) in the Filament (Fi) of the stamen, the Guard
      cell (Gc) and Vasculature (Vs) in the silique, the Guard cell (Gc)
      in the Style (Sy) of the silique, the Cortex (Cr), of the Carpel
      (Ca) in the silique, the Guard cell (Gc), Septum (Sp) and
      Vasculature (Vs) of the proximal silique, the Placenta (Pl), the
      Funiculus (Fn), the Placenta (Pl) of the ovary, the Outer
      integumen (Oi), Funiculus (Fn), Placenta (Pl) and Vasculature (Vs)
      of the pre-, the Embryo (Em) of the fertilized ovule, the
      Hypocotyl (Hy) of the heart stage embryo, the Outer integument
      (Oi) of the fertilized ovule, the adaxial and abaxial leaf, the
      Epidermis (Ep) and Vasculature (Vs) of the stem
<220> FEATURE:
<221> NAME/KEY: misc_feature
<222> LOCATION:
<223> OTHER INFORMATION: T2 Seedling Expression:  GFP expression
      observed in the Root hair (Rh) of the hypocotyl root transition
      zone, the Epidermis (Ep) of the cotyledon, the Epidermis (Ep) and
      Trichome (Tc) of the rosette leaf, the Epidermis (Ep) and Root
      hair (Rh) of the root, the root tip

<400> SEQUENCE: 75
gtcgattggt ttttttttta cggtttcctg caaattaatc catttttaaac aaatcctcca     60 ttgttttgta taatgttgga gattagtagg attagtcgga taatatggca taaacataat    120
atgatgctaa attctaaaga aacgatatga ataaataatg cagcagtata aaaactgtac    180
cattgcgtgg gtggaggatt ttaggtcatt gttagggcac tttcatgggg accatttccg    240
ccttaacgaa gacttattac acacaaccgt caatgtgggc tggaaacttg cagtgcaatc    300
cggtctggtc ctataattta tggccggtta gggtttacaa gttttttaatc tatcaattaa    360 atgagatgga cacaaaatgt aatcaccagt ggaaaagaaa acattacgag acttatacaa    420
tgtctacaag aagactcgag tggggcaaca tgttgtacat aatccgacgt cgttttggga    480
gtcagtaaat aaagttcgag aaatgacgtc gtttttgaagt catccgagag aaaatgactt    540
aaagtgaccg acgttgtttt gaagtcagcg gaagagtaaa gaagtaagaa acgaagtcgt    600
tttgaagtca tctcttcaga tatgtttgtt ctaattaaaa tttcccaagt gggaattagt    660
ttgtaattga aggtatgcac gatttttagt tacaatttta attcttcttc ttcagatcca    720
agaactctca gtctctgcgt tcacactctt tctttgaatc cttcatcatc ctaattcatc    780
tccaagaact gaatcagaag ttgtatttcg ctaattcaac ttttccaggt aattttccat    840
tcctcgatta ttcgaatttg ggtattaaat cataatgcat cgggaaattt ggattcttta    900
ggataatttt tccggcaaat ccgattattg agctagtttc tgaatgttta gattctcagt    960
gtctgtcaat taggttttga ttttggaagt agagaagtta                         1000

<210> SEQ ID NO 76
<211> LENGTH: 986
<212> TYPE: DNA
<213> ORGANISM: Arabidopsis thaliana
<220> FEATURE:
<221> NAME/KEY: misc_feature
<222> LOCATION: (1)..(986)
<223> OTHER INFORMATION: Ceres Promoter construct YP0071 as found in
      Promoter Report #99
<220> FEATURE:
<221> NAME/KEY: misc_feature
<222> LOCATION:
<223> OTHER INFORMATION: T1 Mature Plant Expression:  GFP expression
      observed in the flower bud and inflorescence meristem, the Cortex
```

(Cr) of the Receptacle (Re) and the Vasculature (Vs) of the Sepal
(Se) of the, the Vasculature (Vs) of the leaf and mid-vein rib
<220> FEATURE:
<221> NAME/KEY: misc_feature
<222> LOCATION:
<223> OTHER INFORMATION: T2 Seedling Expression: GFP expression
observed in the Vasculature (Vs) and Cortex (Cr) of the hypocotyl,
the Vasculature (Vs) and Guard cells (Gc) of the leaf, the
Epidermis (Ep) and Mesophyll (Me) of the rosette leaf, the
Vasculature (Vs) of the petiole, the Vasculature (Vs) of the root
transition zone

<400> SEQUENCE: 76

```
ataggcccta cttctaatta aagcccattt acttctctcc ttgtcttctt attcctcttt     60
tctccccatc acgtgacgac gatgctataa acgccgtcgg attatataac tggtgccgtt    120
gacaagacgg cgacagaaga aagaaagaag aaaccacagg ctctagggaa cgtaacgtta    180
tgtcctgtct atagcattta taacggtcag atcaacgccg tttagataaa gatctgtcaa    240
tgttaaagaa gagatgcatc tctacaccgt taaatttaaa acgccgtgaa cctcttatct    300
attgattttt gtttgatgaa gccaaaacaa atcgtgtcag aagacttatc agagaagaag    360
aaaacgacga cgttcccgtt tctccatgtc taataagtgt agtagtggcg gctactaaaa    420
actctaaagt ttgactccag taaaactgcc tttctagtgt aattccagtg attttagagt    480
ttgaatagtg tgtgaccaaa tttgaaagta caatctcagc aatattattg atcactcgtt    540 ataaagaat cgaatgtaaa aatagccaat gagagactga gacgtatgtg tttgaccata    600
agtcgtatag tttgtatcta tctacctgca agatcagcag atggttctct gatcaattgt    660
accttaatta tcttttattt tcgtaaaatt tctctattca caaatgataa atctacttaa    720
gacagtaacc ataacaagat ttacaagata atttgaaaaa tgaacacata aaagtatttt    780
ggcgcattat ttttaataat aacaatattt atgtaaagtc ataaaaagt atatattcgc    840 tcacaaagtc ttacggtatt tagaacagta gtaccacatc gattctcttc atcttcttct    900
tcataatatg ccattgttca tgtctctgtg tcctatcgca taacactcac gctatcttat    960
tattttctct cgctctttct cactga                                         986
```

<210> SEQ ID NO 77
<211> LENGTH: 1100
<212> TYPE: DNA
<213> ORGANISM: Arabidopsis thaliana
<220> FEATURE:
<221> NAME/KEY: misc_feature
<222> LOCATION: (1)..(1100)
<223> OTHER INFORMATION: Ceres Promoter construct YP0214 as found in
Promoter Report #100
<220> FEATURE:
<221> NAME/KEY: misc_feature
<222> LOCATION:
<223> OTHER INFORMATION: T1 Mature Plant Expression: GFP expression
observed in the Anther (An), Petal (Pe) and Sepal (Se) of the
inflorescence meristem, the Anther (An), Silique (Si), Ovule (Ov),
Placenta (Pl), Petal (Pe) and Sepal (Se) of the, the leaf, sepals
of floral primordial
<220> FEATURE:
<221> NAME/KEY: misc_feature
<222> LOCATION:
<223> OTHER INFORMATION: T2 Seedling Expression: GFP expression
observed in the Root hair (Rh) and Vasculature (Vs) of the
hypocotyl-root transition zone, the Epidermis (Ep) of the
hypocotyl, the Epidermis (Ep) and Vasculature (Vs) of the root,
the Epidermis (Ep) and Vasculature (Vs) of the cotyledon petiole,
the Epidermis (Ep), Mesophyll (Me) and Vasculature (Vs) of the
rosette leaf, the Epidermis (Ep), Vasculature (Vs) of the Cortex
(Cr), Endothelium (Ed), Pericycle, the primary root cap

<400> SEQUENCE: 77

-continued

```
ccagtcgatt ggcgcctcgc atgcctatca tatttaaccg tcaataatgg atttggcggt        60
tttggtaggc cgggtcaacc ggattaaaag aaaacggttt ggagtccttc cttgcaattg       120
aattttcaca cattcgggtt ttgtgatttc tctgtcataa tgggcccggc acatatggtt       180
cataacccat gtgggcctat ggtataattt ttccaattaa aactattgtt aggtcgataa       240
aacaaaaaac aataaaaacg agtggaatac acataccaaa aagaatgtga tgaacattag       300 taatttatt ttgatggtta atgaaaaaca aaataaatgc atcttggcat cttccgttgg        360
aaagcgcaaa tagggcagat tttcagacag atatcactat gatgggggt gagagaaaga       420 aaacgaggcg tacctaatgt aacactactt aattagtcgt tagttatagg actttttttt       480
tgtttgggcc tagttatagg atcataaggt aaaaatgaag aatgaatatt agattagtag       540
gagctaatga tggagttaag tatgcacgtg taagaactgg gaagtgaaac ctcctgtatg       600
gtgaagaaac tatacaacaa agcccttttgt tggtgtatac gtattaattt ttattctttt       660
atcacaagcg atacgtatct aagacataa taaatatata tcttactcat aataaatatc        720
ttaagatata tatacagtat acacctgtat atatataata aataggcata tagtagaaat       780
taatatgagt tgttgttgtt gcaaatatat aaatcaatca aaagatttaa aacccaccat       840
tcaatcttgg taagtaacga aaaaaaaggg aagcaagaag aaccacagaa aagggggcta       900
acaactagac acgtagatct tcatctgccc gtccatctaa cctaccacac tctcatcttc       960
tttttcccgt gtcagtttgt tatataagct ctcactctcc ggtatatttc cccattgcac      1020
tggacactct catcttcttt ttcccgtgtc agtttgttat ataagctctc actctccggt      1080
atatttcccc attgcactgg                                                  1100
```

<210> SEQ ID NO 78
<211> LENGTH: 990
<212> TYPE: DNA
<213> ORGANISM: Arabidopsis thaliana
<220> FEATURE:
<221> NAME/KEY: misc_feature
<222> LOCATION: (1)..(990)
<223> OTHER INFORMATION: Ceres Promoter construct YP0216 as found in Promoter Report #101
<220> FEATURE:
<221> NAME/KEY: misc_feature
<222> LOCATION:
<223> OTHER INFORMATION: T1 Mature Plant Expression: GFP expression observed in the Epidermis (Ep) of the inflorescence meristem, the Embryo (Em) and Placenta (Pl) of the ovule, the Vascular bundle (Vb) of the stem
<220> FEATURE:
<221> NAME/KEY: misc_feature
<222> LOCATION:
<223> OTHER INFORMATION: T2 Seedling Expression: GFP expression observed in the Epidermis (Ep), Mesophyll (Me), Hydathode (Hd) and Vasculature (Vs) of the, the Epidermis (Ep), Mesophyll (Me) and Vasculature (Vs) of the rosette leaf, (Cr), Lateral root (Lr), Rosette leaf (Rl)
<220> FEATURE:
<221> NAME/KEY: misc_feature
<222> LOCATION: (453)..(453)
<223> OTHER INFORMATION: n is a, c, t, g, unknown, or other

<400> SEQUENCE: 78

```
ttttgttttct aatagtttga tgtttatatc aacattatta tttactttca tttgttaccg        60
atagaaagag gagaaaattg ttgacaaaaa caaagataaa agtaaaatta atattattaa       120
attaataaaa ataacaaact gtaaaagcta tttttttaaa aattttgtgt aaaacatcta       180
aaaattattc ttttagaaac agaagaatat cattgaagat aatagtgtga aattatatat       240
```

```
atatatagaa atatataaag taggattttt ttctgtatac aaatatacgt ttccaatttt        300
atcaaaaact gtaaagattt ttttctttgt cagtacctgc taaacttgtt aattttttta        360
ttaaaaaaaa atcaaattac aattcttcta taatcatttt aaattccatt tctttatacc        420
acaaaagatt atattgcctt tatcgtcttt ggnatgtatg cgtgaatata tttatttatt        480
ttcttttctt tcattttctt tttaaagaac tttataaatg aaataaggaa caaacaatat        540
acatatgtac taacgtatat aaataaatatc atcaatatct atccaaaact tggatttcat        600
ggttgacgtg gcccaaccaa aatctcaagt tctctgcgga tgacgaacca tctccaccatc       660 tcttttttttc tctctctttt ttttttttaat atcatcagca cggttacata aaattcgtga      720
tccatgaagt tggctttctt gtcgttttac ttcatcaccc cattttttaa aagtctccat        780
ctttatactt cttcaactct ccaccaccac cattgtcacc accacattta aacacacact        840
ttcacttgta gtgggattag aaagtgcgtt ttattcattt gttttactgt ttttgataac        900
ctcaaaattt gcctaaattt tattctctat aaatccttat atgttttact tacattccta       960
aagttttcaa ctttcctgag cttcaaaaag                                          990
```

<210> SEQ ID NO 79
<211> LENGTH: 984
<212> TYPE: DNA
<213> ORGANISM: Arabidopsis thaliana
<220> FEATURE:
<221> NAME/KEY: misc_feature
<222> LOCATION: (1)..(984)
<223> OTHER INFORMATION: Ceres Promoter construct YP0271 as found in Promoter Report #102
<220> FEATURE:
<221> NAME/KEY: misc_feature
<222> LOCATION:
<223> OTHER INFORMATION: T1 Mature Plant Expression: GFP expression observed in the Megaspore mother cell (Mmc), Outer integument (Oi) and Funiculus (Fn) of the ovule, the Suspensor cells (Su) of the globular embryo stage in the ovule, the Suspensor apparatus. After first asymmetrical cell division of zygote, the larger basal, the Suspensor cells (Su) of the heart stage embryo, the Micopyle (Mp)

<400> SEQUENCE: 79

```
atctctgatt tttttttatca ggaacaagta aataaatagc tttgagtttt tgttttttt         60 ctacattctt cgcccaaaag atgtaagaaa ataaaggatt tgaaaccttg ttctgttgtt       120
actcctttaa attcttagaa actataaatc attatatctt tgatctgttt cacaaactaa       180
tcatattcgt tgcaaagtga gaattcgtcc cactttactc tttacaccga tactagtatt       240
atagatgtac agcatagtat tccatatcta gttatttagt caaaactcta tatattaaga       300
ggtaggttaa ttaattaagg agtaattgaa gattatagaa agaataaaaa ataccattta       360
atggacagaa ccaaagataa ctaactatca tactataatg ttgaatttct tccacgatcc       420
aatgcatgga taacaacatc aatcaaatca tacattcatg ctatataaca tagttttcag       480
ttacaaactc tcttttttat ttatttcagt tgttcctttt catgaccata ttaacatcaa       540
ataatgcatt tttttcaacg tctcttgact tacacccact aatattgaca aattgaacat       600
ctatacgact atacgcacat aagttaaaaa tgcatgcaag tgctaaggga atttataaca       660
tctaaggtta ataagactaa gaaagtataa aataagaata cgtattatga atttatgata       720
tactttacta atcttttttga aaaatacttt aatttaatct actataggg gtaaaaagta       780 aaaaagaaat aaagatacgt ttatccgcat atagtacctg gaaataacag aaaataaaaa       840
cacaggtaag tactttgcct gagctagtat atgaacacta aagagataca cacacacaaa       900
aagagagcag aaacaaaaca cacacactta aagctttcgt ctttacctct tcccttctct       960
```

```
ctctctatct aaaaagagtt ccga                                           984
```

<210> SEQ ID NO 80
<211> LENGTH: 979
<212> TYPE: DNA
<213> ORGANISM: Arabidopsis thaliana
<220> FEATURE:
<221> NAME/KEY: misc_feature
<222> LOCATION: (1)..(979)
<223> OTHER INFORMATION: Ceres Promoter construct YP0279 as found in
      Promoter Report #103
<220> FEATURE:
<221> NAME/KEY: misc_feature
<222> LOCATION:
<223> OTHER INFORMATION: T1 Mature Plant Expression: GFP expression
      observed in the Embryo (Em), Embryo sack (Es) and Micropyle (Mp)
      of the fertilized ovule, the Embryo proper (Ep) and Suspensor (Su)
      of the zygote, the Micropyle (Mp) pole of the ovule, the
      fertilized ovule, the Radicle (Rd) and Root apical meristem (Ram)
      of the torpedo stage embryo
<220> FEATURE:
<221> NAME/KEY: misc_feature
<222> LOCATION:
<223> OTHER INFORMATION: T2 Seedling Expression: GFP expression
      observed in the Epidermis (Ep), Guard cells (Gc) and Mesophyll
      (Me) of the rosette leaf, the root and root transition zone, the
      Pericycle (Pr) of the lateral root initials, the lateral root
      primordia

<400> SEQUENCE: 80

```
cgctttatta taggtttaac aattgatttt tcattatttt gttttcaatc tccaaatcat    60
ttctcaataa ctctcaaaca ttgtttaaag cttttttttct taattaacat tataacaaaa  120
aaataaatag agaaatttac tttgattcaa acaccagtca ttgtagatta gccaagagtt   180
ttcagtaaca aaatttacct tataaaacctt ttgaatggct atttctgaaa tggaatagaa  240
atctttagtc gtggaagtat ctctatccat aagaaaactc gttttacaaa gtaattttaa   300
atcaatacaa aaaagtgaaa aaatccactg gtggaccccca ttcattccag aattgccgat  360
tacgagctat cttgtccctt cttcaccatt cgctcactct ctctctctct ctctcgtctt   420
cttcttccca ccactctctc tgtttctcca caacttctct tctcaaagtt aaaattaccc   480
ctaaaccaaa aaaaaaaaaa cgctcttcac tatttattta ctaaactctc ctttgtttgt   540
tactaagctc tcactaaaac cctaatcttt tcctcttat atatctcgtg actcttcttt   600
ctcctccaat ctctctctcc ctcttcacaa accaattagc ttctttctgt aaaacctcac   660
tcgttggcca attcttttgg ttttcataca cataaatctc agattccaaa tgggttttct   720
tagctctttc tttcaaatga tgaacatttg ttagcagaat cttcctcatt ccctaaagtt   780
ttgatctttt tttccccctt caattttgta ttttctcacc aaataaaaaa aggtttcttc   840
agtgggtttt aagggtttat tattatctta aaattaaaca caattcttta atcaaaaggc   900
aaaaatctta atttcatcac tctcttctca ctcacaaaag ttcttacaat cttcaaagtt   960
ttggtcttgt ttcttttcc                                                979
```

<210> SEQ ID NO 81
<211> LENGTH: 981
<212> TYPE: DNA
<213> ORGANISM: Arabidopsis thaliana
<220> FEATURE:
<221> NAME/KEY: misc_feature
<222> LOCATION: (1)..(981)
<223> OTHER INFORMATION: Ceres Promoter construct YP0285 as found in
      Promoter Report #105
<220> FEATURE:
<221> NAME/KEY: misc_feature

```
<222> LOCATION:
<223> OTHER INFORMATION: T1 Mature Plant Expression: GFP expression
      observed in the Vasculature (Vs) of the leaf, the Embryo sack (Es)
      of the pre-fertilized and fertilizad ovule
<220> FEATURE:
<221> NAME/KEY: misc_feature
<222> LOCATION:
<223> OTHER INFORMATION: T2 Seedling Expression: GFP expression
      observed in the Vasculature (Vs) of the hypocotyl, the Vasculature
      (Vs) and Epidermis (Ep) of the root transition zone, the Hydathode
      (Hd) and Vasculature (Vs) of the cotyledon, the Pericycle (Pr),
      Vasculature (Vs) and Epidermis (Ep) of the root

<400> SEQUENCE: 81
gggattatat atgatagacg attgtatttg cgggacattg agatgtttcc gaaaatagtc      60
atcaaatatc aaaccagaat ttgatgtgaa aacactaatt aaaacatata attgacaact     120
agactatatc atttgttaag ttgagcgttg aaagaaaatg aaagagtgta gactgtagta     180
cgtatgagtt tcccaaaaga tggtgcttga atattattgg gaagagactt tggttggttc     240
ggttgaatga agattttttac ctgccatgtt gatagagaaa ggcaaataaa tgtagggtc      300 gatgtctaac gtaaagactg gatcaaccaa gagtcctcct cctcgtcttc accaaaaaaa     360
aagagtcctc ctcgtggaaa cttatttctt ctccagccaa gatctcatct catctcttca     420
ctctatgaaa tataaaggaa tcttatggtt tttctaaaaa ctatagtacg tctatatacc     480
aaaggaaaca atataaaatc agttaatctg ataaattttg agtaaataat aaagttaact     540
ttgtacttac ctatatcaaa ctaattcaca aaataaagta ataataacaa agaatttta      600 gtagatccac aatatacaca cacactatga gaaatcataa tagagaattt taatgatttt     660
gtctaactca tagcaacaag tcgctttggc cgagtggtta aggcgtgtgc ctgctaagta     720
catgggctct gcccgcgaga gttcgaatct ctcaggcgac gtttcttttg ttttcggcca     780
taaaggaaaa agcccaatta acacgtctcg cttataagcc cataaagcaa acaatgggct     840
gtctctgtct cactcacaca cgcgttttcc tactttttga ctattttat aaccggcggg       900 tctgacttaa ttagggtttt ctttaataat cagacactct ctcactcgtt tcgtcaacat     960
tgaacacaga caaaaccgcg t                                                981

<210> SEQ ID NO 82
<211> LENGTH: 982
<212> TYPE: DNA
<213> ORGANISM: Arabidopsis thaliana
<220> FEATURE:
<221> NAME/KEY: misc_feature
<222> LOCATION: (1)..(982)
<223> OTHER INFORMATION: Ceres Promoter construct YP0080 as found in
      Promoter Report #106
<220> FEATURE:
<221> NAME/KEY: misc_feature
<222> LOCATION:
<223> OTHER INFORMATION: T1 Mature Plant Expression: GFP expression
      observed in the vasculature of the inflorescence meristem, the
      Petal (Pe) and Silique (Si) of the flower, the Medial vasculature
      (Mv) in the silique, the Vascular bundle (Vb) of the leaf and stem
<220> FEATURE:
<221> NAME/KEY: misc_feature
<222> LOCATION:
<223> OTHER INFORMATION: T2 Seedling Expression: GFP expression
      observed in the Rosette leaf (Rl), the Vascular(Vs) of the
      hypocotyly, leaf and root, the Pericycle (Pr) of the root and
      lateral root

<400> SEQUENCE: 82
aagcggcaat ttagtaagaa gtattcaatg tatcatttac caaaagtata tggttttggg      60
aagagttgtt agggatgtat tctttctaaa cagatgatat gacgatgttc ttgaaaacta     120
```

```
atgttaaaga cgggatctct cgcatcttca ctcgggagat atattaaacc gttgattgta    180
gttagccatg tacttagctt agtgcacaaa taatctgctg caagaaatct ttttctatta    240
taatatctct catttaaaca ttagaacata ttgtttaact tgttcttcta gaaataaaac    300
tgctaatttc ttatggtaaa ctattttcct ttagattgca caatcgaact cgaaaatcta    360
gtggagacta tgtgactatg tttatatata tgaaacctaa atcaaattat cccaataatt    420
gggagacaca aagaaaaaa agaaaacagg aaatcaaatc aaagataaa gagaaggtaa     480 aacaaaaggc aagaagcact aatgtttaat atttatagtt ttctccatta agaaaaaagc    540
gatgatgtgt gtgttctcat cttttgtgaa agtatatata ttgcttttgc tcttctcaaa    600
agcaaaagac tcatccaaca acaacaacaa aaaaaaacct aaagctcaat ccaaaagacg    660
aagaatgcat tggatactac aacttctttt tcacttttct ttcgaattta caattatgat    720
tttcacaata cagtgtattc aaaaataaat aaaaaaacga ggcatgaaaa taatgattat    780
cctcttcact tattaagcca ctcactataa gcagagcaac tccagaacat agtgagcccc    840
caaaacatta aagcatgatg atgtctaatg atgatgatct tcttcgttcc atttctctaa    900 attttttggga tttctgcgaa gaccttctt ctctttctct tctctgaact tcaagattcg    960
tgtcggacaa atttttgttt tt                                             982
```

<210> SEQ ID NO 83
<211> LENGTH: 987
<212> TYPE: DNA
<213> ORGANISM: Arabidopsis thaliana
<220> FEATURE:
<221> NAME/KEY: misc_feature
<222> LOCATION: (1)..(987)
<223> OTHER INFORMATION: Ceres Promoter construct YP0122 as found in Promoter Report #107
<220> FEATURE:
<221> NAME/KEY: misc_feature
<222> LOCATION:
<223> OTHER INFORMATION: T2 Seedling Expression: GFP expression observed in the Epidermis (Ep) of the root transition zone, the root and the cotyledon, the Vasculature (Vs) of the cotyledon

<400> SEQUENCE: 83

```
agtttaatta tttgttatct atccaatcaa ttttttttc taaactgttt ggaccaatgt     60
acgtacgtac catccttttt gattttttt gtaaactaaa ttttcggatt agcaggttct    120
taataattga acgaagaaaa taaagaatag aggtagacac ctgtagtatt tcttggtca    180 gaccaataat ttataattca acgtcaaaga agaagaaaaa tataaaccat tatttcatta    240
tgacttacgt ataccaaaat acacaaatta aatgtataat tgtgaggcat tttatatgcg    300
ggaaaaaata aaataaaaag aatattaata tttcttttga aaattgtaaa gcattttgac    360
ccacttgtga tatatatata tagatatata tagagagaga gattaaaaca ttgatggcta    420
gctatagagt ctatggcagg gtcatgatca cctatcttct gatctctgaa gagataccaa    480
tctgattttt tctcttccta ggtttaattt tattttacca ttttataatt ctttattttt    540
gcctgtagta caatttacag acccatacta aagaaaaat taaattttgt caaagtacaa    600
aacaaagaga gaggtgaagc cacacaatct cttttcttct ctctctctct gttatatctc    660
ttctgtttaa ttcttttatt cttcttcgtc tatcttctcc tataatctct tctctctccc    720
tcttcaccta aagaataaga agaaaaataa ttcacatctt tatgcaaact actttcttgt    780
agggttttag gagctatctc tattgtcttg gttctgatac aaagttttgt aattttcatg    840
gtatgagaar atttgccttt ctattttgtt tattggttct tttaactttt tcttggagaa    900
```

```
tgggttcttg tagatcttaa tgaaacttct gttttgtcc caaaagagt tttcttttt      960 cttctcttct tttttggttt tcaattc                                        987
```

<210> SEQ ID NO 84
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter construct YP0226 as found in
      Promoter Report #108
<220> FEATURE:
<221> NAME/KEY: misc_feature
<222> LOCATION:
<223> OTHER INFORMATION: T1 Mature Plant Expression: GFP expression
      observed in the Vasculature (Vs) of the flower and the Silique
      (Si)
<220> FEATURE:
<221> NAME/KEY: misc_feature
<222> LOCATION:
<223> OTHER INFORMATION: T2 Seedling Expression: GFP expression
      observed in the Vasculature (Vs) of the hypocotyl and root

<400> SEQUENCE: 84

```
ctccttgata atgatttga tcaaaagtgt aatttccaca aaccaattgc gcctgcaaaa      60
gttttcaaag gatcatcaaa cataatgatg aatatctcat caccacgatt ttataataat    120 gcatctttc ccaccatttt ttttccctca ctttctttta taatcttgtt cgacaacaat     180
catggtctaa ggaaaaagtt gaaaatatat attatcttag ttattagaaa agaaagataa    240
tcaaatggtc gatatgcaaa tggcatatga ccataaacga gtttgctagt ataaagaatg    300
atggccaacc tgttaaagag agactaaaat taggtctaaa atctaggagc aatgtaacca    360
atacatagta tatgaaatat aaagttaat ttagatttt tgattagccc aaattaaaga      420
aaaatggtat ttaaaacaga gactcttcat cctaaaggct aaagcaatac aattttggt     480 taagaaaaga aaaaaccac aagcggaaaa gaaaacaaaa aaactatat tatgatgcaa      540 cagcaacaca aagcaacacc ttgcacacac acatacaact gtaaacaagt ttcttgggac    600
tctctatttt ctcttgctgc ttgaaccaaa cacaacaacg atatcccaac gagagcacaa    660
caggtttgat tatgtcggaa gacaagtttt gagagaaaac aaacaatatt ttataacaaa    720
ggagaagact tttggttagg aaaaattggt atggccatta caagacatat gggtcccaat    780
tctcatcact ctctccacca ccaaaatcct cctctctctc tctctctttt actctgtttt    840
catcatctct ttctctcgtc tctctcaaac cctaaataca ctctttctct tcttgttgtc    900
tccattctct ctgtgtcatc aagcttcttt tttgtgtggg ttatttgaaa gacactttct    960
ctgctggtat cattggagtc tagggttttg ttattgaca                           999
```

<210> SEQ ID NO 85
<211> LENGTH: 1002
<212> TYPE: DNA
<213> ORGANISM: Arabidopsis thaliana
<220> FEATURE:
<221> NAME/KEY: misc_feature
<222> LOCATION: (1)..(1002)
<223> OTHER INFORMATION: Ceres Promoter construct YP0244 as found in
      Promoter Report #110
<220> FEATURE:
<221> NAME/KEY: misc_feature
<222> LOCATION:
<223> OTHER INFORMATION: T1 Mature Plant Expression: GFP expression
      observed in the pollen

<400> SEQUENCE: 85

```
ttgatttgat gtatagttac tatttaaagt cttatttgtg aaattttaca aatgttggaa        60
aaaagcattt tatggtgcta tatttgtcag tttcccttga ttatatatcc ttttgaaaag       120
taatgttttt tttatgtgtg tgtattcatg aaccttggaa aaactacaaa tcagatcatg       180
gtctgtttta ggtgaaaaat ttagaacaca gttacgcaag aaagatatcg gtaaatttt        240
gtttctttga atcgaaatta atcaaaaagt attttccatt atataacaac aactaatctc       300
tgttttttt tttttttttt aacaactaat ctcttatcaa aatgacacta cagaatcacg        360
attgtaaatc ttcaaaaggg cagtctgaaa aaatattcat gaggatgaga ttttattcat       420
tcatggttgt aagtaatcat tatgtaaagt ttaggataag gacgttcaaa atcatataaa       480
aaaactctac gaataaagtt tatagtctat catattgatt catatttcat agaaagttac       540
tggaaaacat tacacaagta ttctcgattt ttacgagttt gtttagtagt cgcaaaattt       600
tattttactt ttgagtatac gaacccataa gctgattttc tttccaagtt ccaataatga       660
tatcatagtg tactcttcat gaatgtttca agcatataat tataacgttc ataagtaaca       720
ttctactgca tgtttgttat tataaattaa ctaataatcg aacgtatgag ttttggttga       780
gattgttgtg ctcacgaaat gaaggactcg gtcaattcta aagcttaaaa taagaagctc       840
agatcttaaa actcgctttc gtcttcgtcc tccatttaag tttgcgattc ttttgctctt       900
ctttctctct cacattttg tcccaaaaca ataaaaagaa acaataatag aaagtgttac        960
agaaaaagaa agaaaactat cattgaagtt gggaaggaga aa                        1002
```

<210> SEQ ID NO 86
<211> LENGTH: 996
<212> TYPE: DNA
<213> ORGANISM: Arabidopsis thaliana
<220> FEATURE:
<221> NAME/KEY: misc_feature
<222> LOCATION: (1)..(996)
<223> OTHER INFORMATION: Ceres Promoter construct YP0286 as found in
      Promoter Report #111
<220> FEATURE:
<221> NAME/KEY: misc_feature
<222> LOCATION:
<223> OTHER INFORMATION: T1 Mature Plant Expression: GFP expression
      observed in the Pedicel (Pd) of the inflorescence meristem and the
      flower, the stem
<220> FEATURE:
<221> NAME/KEY: misc_feature
<222> LOCATION:
<223> OTHER INFORMATION: T2 Seedling Expression: GFP expression
      observed in the Epidermis (Ep) of the Hypocotyl (Hy), Rosette leaf
      (Rl), Cotyledon (Co), root, the Mesophyll (Me) and Vasculature
      (Vs) of the cotyledon

<400> SEQUENCE: 86

```
gaaaacaatc ataggttacg ctattatcat cgaaaggtat gtgatgcata ttcccattga        60
accagatttc catatatttt atttgtaaag tgataatgaa tcacaagatg attcaatatt       120
aaaaatgggt aactcacttt gacgtgtagt acgtggaaga atagttagct atcacgcata       180
catatatcta tgaataagtg tgtatgcat aagaaactaa aatatttacc taaagtccag        240
ttactcatac tgatttcatg catatatgta ttatttattt attttttaata aagaagcgat       300
tggtgttttc atagaaatca tgatagattg ataggtattt cagttccaca aatctagatc       360
tgtgtgctat acatgcatgt attaattttt tccccttaaa tcatttcagt tgataatatt       420
gctctttgtt ccaactttag aaaaggtatg aaccaacctg acgattaaca agtaaacatt       480
aattaatctt tatatgagat aaaaccgagg atatatatga ttgtgttgct gtctattgat       540
```

-continued

```
gatgtgtcga tattatgctt gttgtaccaa tgctcgagcc gagcgtgatc gatgccttga      600
caaactatat atgtttcccg aattaattaa gttttgtatc ttaattagaa taacattttt      660
atacaatgta atttctcaag cagacaagat atgtatccta tattaattac tatatatgaa      720
ttgccgggca cctaccagga tgtttcaaat acgagagccc attagtttcc acgtaaatca      780
caatgacgcg acaaaatcta gaatcgtgtc aaaactctat caatacaata atatatattt      840
caagggcaat ttcgacttct cctcaactca atgattcaac gccatgaatc tctatataaa      900
ggctacaaca ccacaaagga tcatcagtca tcacaaccac attaactctt caccactatc      960
tctcaatctc tcgtttcatt tcttgacgcg tgaaaa                               996
```

<210> SEQ ID NO 87
<211> LENGTH: 998
<212> TYPE: DNA
<213> ORGANISM: Arabidopsis thaliana
<220> FEATURE:
<221> NAME/KEY: misc_feature
<222> LOCATION: (1)..(998)
<223> OTHER INFORMATION: Ceres Promoter construct YP0289 as found in
      Promoter Report #112
<220> FEATURE:
<221> NAME/KEY: misc_feature
<222> LOCATION:
<223> OTHER INFORMATION: T1 Mature Plant Expression: GFP expression
      observed in the Endothelium (Ed), Stomium region (StR), Pollen
      (Po) of the developing, mature and dehiscing anther
<220> FEATURE:
<221> NAME/KEY: misc_feature
<222> LOCATION:
<223> OTHER INFORMATION: T2 Seedling Expression: GFP expression
      observed in the Epidermis (Ep) of the Cotyledon (Co), cotyledon
      petiole and root, the Guard Cells (Gc) of the coteledon, the
      Hypocotyl (Hy)-root transition zone, the Root hair (Rh), the
      Trichomes (Tc) of the Rosette leaf (Rl)

<400> SEQUENCE: 87

```
atggactttt cttctattat atggtcaaac aattactgct caatgtattt gcgtatagag       60
catgtccaat accatgcctc atgatgtgag attgcgaggc ggagtcagag aacgagttaa      120
agtgacgacg ttttttttgtt tttttttgggc atagtgtaaa gtgatattaa aatttcatgg    180
ttggcaggtg actgaaaata aaaatgtgta taggatgtgt ttatatgcta gacggaaaaa      240
tagttactca actaatacag atcttttataa agagtatata agtctatggt taatcatgaa    300
tggcaatata taagagtaga tgagatttat gtttatattg aaacaaggga aagatatgtg     360
taattgaaac aatggcaaaa tatatagtca aatcaaactg gtttctgata atatatgtgt     420
tgaatcaatg tatatcttgg tattcaaaac caaaacaact acaaccaatt tctttaaaaa     480
accagttgat ctaataacta cattttaata ctagtagcta ttagctgtat ttcataatca    540
atttcttgca ttaaaattttg aagtgggttt tgcatttaaa cttactcggt ttgtattaat    600
agactttcaa agattaaaag aaaactactg cattcagaga ataaagctat cttactaaac    660 actacttttta aagtttcttt tttcacttat taatcttctt atacaaatgg atctgtctct    720
ctgcatggca aaatacttac actaattttta ttttctttgt ttgataacaa atttatcggc    780
taagcatcac ttaaatttaa tacacgttat gaagactaaa accacgtcac actataagaa    840
ccttacaggc tgtcaaacac ccttccctac ccactcacat ctctccacgt ggcaatcttt    900
gatattgaca ccttagccac tacagctgtc acactcctct ctcggtttca aaacaacatc    960
tctggtataa atacctctgt atatctttat aaaccccca                            998
```

```
<210> SEQ ID NO 88
<211> LENGTH: 984
<212> TYPE: DNA
<213> ORGANISM: Arabidopsis thaliana
<220> FEATURE:
<221> NAME/KEY: misc_feature
<222> LOCATION: (1)..(984)
<223> OTHER INFORMATION: Ceres Promoter construct YP0015 as found in
      Promoter Report #116
<220> FEATURE:
<221> NAME/KEY: misc_feature
<222> LOCATION:
<223> OTHER INFORMATION: T1 Mature Plant Expression:  GFP expression
      observed in the Abscission zone (Ab), Cortex (Cr), Epidermis (Ep)
      and Guard cells (Gc) of the flower, the Guard cells (Gc) of the
      pedicle, and pre-fertilized silique, the Abscission zone (Ab) and
      Carpel (Ca) of the mature silique, the Cortex (Cr) and Epidermis
      (Ep) of the carple, the Mesophyll (Me), Vasculature (Vs) and
      Epidermis (Ep) of the leaf
<220> FEATURE:
<221> NAME/KEY: misc_feature
<222> LOCATION:
<223> OTHER INFORMATION: T2 Seedling Expression:  GFP expression
      observed in the Root hair (Rh) and Root transition (Rt) of the
      Hypocotyl (Hy)

<400> SEQUENCE: 88
ttgagcctta ttgttgttat tgactttag  ccaatagaaa gagatggaaa ttcaataatt      60
atccacaaaa ttccaaatca ttggtgtaca aaaagatcta aggctgttat atttccaaaa    120
aagaaagaaa agaaatgcaa caaatatgga ttaaactgtg gtttgtaaat tgagctttgc    180
atgaaaactt tatcactatg atttcactac tccatattta ttgactaaag tggcactaat    240
gaatttctta atcatgaaat cttgtatcaa aaagtactaa aataaacatg acattggcaa    300
ttaggaaaat tctaaattag aaattagtaa aaatgaaagg tgaaagggaa agatgatgat    360
atgaattggt tggtgaccag gagaaatgta tcccgatttt tgcagacact ttcagtgtcc    420
ccattcatat aattatggcc cacctcgtta agatttttca ttcaccacca taacaagatc    480
taagcttaga tttcatgtaa ttaaacatat aatatacttg ccaatactat ctaataaagt    540
atacttaagc aaaaattatt actctagtgt aaggcgatga aatataagtt tagttgaaaa    600
tttatgtcga tataacaaag tataatgaat taagaccttg gttttcgatt aacaaactaa    660
ttaaacacta gttttgccta ataaaaccgg gaatcgtatt caaaaccgaa cgacaaaaca    720
agggacaagt tgagagacaa aaccaaatca gcatctttct tccagaaatg tcatgaccac    780
atgacgtcat cttgacccct cttcattgtg atatctgtgg ataaagcgca cgtgtttaat    840
tcacgaacct tcgtagtaac gaaaaatcca caactttcat atttttttaat tacccactaa    900 actaaaacaa atttggaaaa acatgaaaaa cttttctttt ttttccaggt tcgtgaacct    960
cgtaccctct atataaacct ctta                                            984

<210> SEQ ID NO 89
<211> LENGTH: 970
<212> TYPE: DNA
<213> ORGANISM: Arabidopsis thaliana
<220> FEATURE:
<221> NAME/KEY: misc_feature
<222> LOCATION: (1)..(970)
<223> OTHER INFORMATION: Ceres Promoter construct YP0230 as found in
      Promoter Report #118
<220> FEATURE:
<221> NAME/KEY: misc_feature
<222> LOCATION:
<223> OTHER INFORMATION: T1 Mature Plant Expression:  GFP expression
      observed in the Vascular (Vs) of the Petal (Pe) in immature and
      mature flowers, the Guard cells (Gc) of immature flowers, the
      anther and pollen mother cells, the Pollen (Po) during attachment
```

("foot"), adhesion and hydration, the Seed coat (Sc) of the ovule, mature Embryo (Em), the heart stage Embryo (Em) of the ovule, the Embryo sack (Es) of the pre-fertilized ovule, the Guard cells (Gc), Trichomes (Tc) and Epidermis (Ep) of the stem, the Guard cells (Gc) of the leaf
<220> FEATURE:
<221> NAME/KEY: misc_feature
<222> LOCATION:
<223> OTHER INFORMATION: T2 Seedling Expression: GFP expression observed in the Epidermis (Ep) and Guard cells (Gc) of the hypocotyl apex, the Guard cells (Gc), Vascular (Vs) and Mesophyll (Me) of the cotyledon, the Epidermis (Ep) and Cortex (Cr) of the root transition zone, the Cortex (Cr) and Nucleus (Nu) of the root

<400> SEQUENCE: 89

```
aatcattaaa tctttgatga gaaatatcca atctactaat gtatatcgat gatttaaatg      60
aaattactta tttgaacaca aaaataaatg aatttactaa taaataaata gcgtagttgc     120
gagcaagtgg ctaaaaaaat tacaaatcta gtttccattc tcagcggcgg ggtgcttgga     180
acgtcaccgt ttttggaaa acgcaatctt cctcccttcc gggacgtctc accggaattt     240
tctcgctttt gtctactctc ctccatctcc gaggttctcc aagctcagct cctcttccca     300
tcattcatcc gaccgcctta tccggtcaga tcctttacgt atttctattt tcctgatcgt     360
cgattttga gaaatgtaaa aacagatcgt ataaggcctc gaagtttta atttgaaagt     420
ggtatcgaaa ttttttggtc tttgattagg ttagggcacc gtagctctgg gtattgaatt     480
tgtagggttt tcctctggtt attggtcttt ggagcttggt aatttctgct gaattgattg     540
atcccttttc catcttttga agtaaagtct cgagctttcg tgtctcgatg tagatgaatt     600
ctattttgaa tatgagattt gataagacgt caattgctga taatttggag tctttgtgtc     660
tgaatttgtt catatgaagt tttctgaggg atgtgaattt tattgtctgc taatttttgaa     720
acgttccttt tggaatttgg tttgtgagga gtcctagatc ttttttctgtt aagtttcttg     780
cttgtaagtt ttctggatca cttgattgag tctagaatct agatagatta catgttcggt     840
ttgattcctt tggctgattt tccaaagttt tgttcaaatt tcaggagaac tacaaagagg     900
aaaccaagat ggttttgttt tgttagactc taccccttt ccgattcaca tggtaaggac     960
attgaggtag                                                           970
```

<210> SEQ ID NO 90
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter construct YP0120 as found in Promoter Report #119
<220> FEATURE:
<221> NAME/KEY: misc_feature
<222> LOCATION:
<223> OTHER INFORMATION: T1 Mature Plant Expression: GFP expression observed in the ovules of the pre-fertilized and fertilized silique, the Outer integument (Oi) of the fertilized ovule, the maturing seed, the Seed coat (Sc) of the mature seed

<400> SEQUENCE: 90

```
tagttttga tttaatctac gtttttctta atcataaatg ggtaattatt agttttgca       60
aaatcaaaat ccaaaaattg ttctaaacac tgcaaccatt taaggcctat atcactcaga    120
aaatttctgg tgggagaact aatcgtttgt cctttctaaa tctcacatat tagaatttag    180
aattagtgtg ctacataaga atattagttc agctcggaac aactattttt tggtaaaaca    240
gagaacttaa acaaatgcat tattttatca acatgcattt tgaattgaat ataaaatttc    300
```

```
ataattgtaa agacataaat tacataaaat tttacatgaa aaaatagata tagaaagaaa      360
atgaaactaa ctgatgatat gctctctaaa ttttttaatc tcataacaag aattcaaatt      420
aattagttca tattttggt taatataaca tttacctgtc taagttggaa cttcattt       480 tttctgtttt gtttagtcag tattcttaat gtgaaacgga aagttgaatt tattcaaact      540
taaattcaat agcattaatt aaaggcgaaa gctattatct ctacatgtgg ttcaaactag      600
acatccaatt taattagctt attgacgttg aaatgttttc caaaactact atagtttggc      660
aatttgaaag atgcatcaga actactcaga caggtaaaag tagaacctct agctgtgtga      720
attgtatgtt agtccataaa gaacatcttg taaacttcat acttaagata tatattacaa      780
tatatacttg aatggtagat aaaaacgatt agtctgattg ctagcatact cacaactatt      840
tggaaatgag taagatattg gcattctaga gttactacta tggagacaaa agtcgaataa      900
aagagacctc acgtgaaaat gttacgagct agtaaaaaaa gcatttacac taacggtaaa      960
aaaagtatct ataaatgttt acacaaggta gtagtcatt                             999

<210> SEQ ID NO 91
<211> LENGTH: 989
<212> TYPE: DNA
<213> ORGANISM: Arabidopsis thaliana
<220> FEATURE:
<221> NAME/KEY: misc_feature
<222> LOCATION: (1)..(989)
<223> OTHER INFORMATION: Ceres Promoter construct YP0261 as found in
      Promoter Report #120
<220> FEATURE:
<221> NAME/KEY: misc_feature
<222> LOCATION:
<223> OTHER INFORMATION: T1 Mature Plant Expression: GFP expression
      observed in the Epidermis (Ep) and Vasculature (Vs) of the Petal
      (Pe)
<220> FEATURE:
<221> NAME/KEY: misc_feature
<222> LOCATION:
<223> OTHER INFORMATION: T2 Seedling Expression: GFP expression
      observed in the Epidermis (Ep) and Guard cells (Gc) of the rosette
      leaf primordia
<220> FEATURE:
<221> NAME/KEY: misc_feature
<222> LOCATION: (480)..(480)
<223> OTHER INFORMATION: n is a, c, t, g, unknown, or other

<400> SEQUENCE: 91
ttgtaaatta gttttatcgt agaagtacca aatcaagtga ttcatggtt aaattaaggt       60 attaagttac atttgatatt taaaagtatc cagaccttca ttatagctca taagggttaa     120
aattttgtcg ttctttgta tattcatggc aagctctaat tcatgactaa gtcacatttt     180
tcaaatatgt ttttagtttt tacttatgtt ggtaattagt ggatttatag ttaagttaaa     240
aagttggcga gttctagctt tgaaactcat ttagaaatat atatatat atatatattc      300 aattttagta aattgttaat ctattctaat ggtgtaactg taacaaatga gaatgaaaaa     360
aatatactat tgtgaataaa accccacaca acacattact ataataagtt aaacttcttt     420
ttttataggc gcctggaaaa aaagaaaag caacaagagg gstgtgagga cgcatcaccn     480
ggtttcgtag cacacatgtg catttgtctc tttgctttt cggtttttt cttgccaatc     540 aatttatttt gttcctcaga aaaagaaaa tctaaaacca aaatatatat tataacctca     600
tttaataaac aacaaaaatg tttgttgaaa aaaaaaagt tttatttat cttgacctta     660 tttctttgaa gaaataaag cttggttatt aagaagtcc aagttagttg ccaccatcag     720
tggcataacg gtaaattaaa gccaacttcc tctaactaaa gtttctata aattcaacca     780
```

-continued

```
ctcacctccc actctaaaac ccaacaacat aatttcacat atctctcttt ctttctcttg       840
aaggaaagac gaagatctcc aagtcccaag tacgtaacta ctttctccat ctacattcaa       900
ttgtttctcc ttaatttctc tagtacatat ttacttgtgc tataagtaat tgattttata       960
tcacccatgt gcaggttgtt aacacaaga                                         989
```

<210> SEQ ID NO 92
<211> LENGTH: 911
<212> TYPE: DNA
<213> ORGANISM: Arabidopsis thaliana
<220> FEATURE:
<221> NAME/KEY: misc_feature
<222> LOCATION: (1)..(911)
<223> OTHER INFORMATION: Ceres Promoter construct YP0263 as found in
      Promoter Report #121
<220> FEATURE:
<221> NAME/KEY: misc_feature
<222> LOCATION:
<223> OTHER INFORMATION: T1 Mature Plant Expression:  GFP expression
      observed in the Vasculature (Vs) of the inflorescence meristem and
      the Pedicel (Pd) and Receptacle, the Medial vasculature (Mv) of
      the leaf, the stem, the Medial vasculature (Mv) of the immature
      and mature silique, the Vasculature (Vs) of the Anther (An),
      Abscission zone (Az), Filament (Fi), Carpel (Ca), Filament (Fi),
      Funiculus (Fn), Ovule (Ov), Placenta (Pl), Root cap (Rc), Sepal
      (Se), Silique (Si)
<220> FEATURE:
<221> NAME/KEY: misc_feature
<222> LOCATION:
<223> OTHER INFORMATION: T2 Seedling Expression:  GFP expression
      observed in the Epidermis (Ep) of the Rosette leaf (Rl) of the
      seeding, the Cortex (Cr) of the root, the vasculature of the
      seedling and cotyledon, the root tip

<400> SEQUENCE: 92

```
atctagctgt ggattccacc aaaattctgg cagggccatg atctaaaaac tgagactgcg       60
cgtgttgttt tgcagtgatt tgtatttcat atttgcacca tcctacacag tccacttggt      120
atcgtaacca aacataagga gaacctaatt acattattgt tttaatttcg tcaaactggt      180
ttttaccttt tagttacata gttgattctt catttgtttt agtagttatg gagcacaata      240
atgtgcaaca aagaaagatc atagtggatt aatatgttga gaggtcagaa attcttggtt      300
aacaaaaaaa agttacaagg actgagattt tgggtgggag aaagccatag cttttaaaac      360
atgattgaac ttaaaagtga tgttatggtt tgaggggaaa aaggttgatg tcaactaaga      420
tagttgaagt aatgtcttaa actaaagtaa accaccggtc caaccgtggt ccggaagcat      480
ctctggtatg atttatccta aaaatcaaaa tagtagaaac atactttaaa tatatacatt      540
gatcggacga aaattgtaaa ctagtatagt ttcaaaaact agttgaacag gttatgtacc      600
ttaaacattt atttcaaact taaacactaa agaacatata tgaatagaag tttatataaa      660
ttactatata tctaccataa atctcttata attatgatgt cacgatgagg aagtgttgaa      720
acgttaaaat gccaaaatat aagcatgcga cggaattttg gcagaagatt gtagagttgt      780
aatctgtcgc aatcattact cgtgctagca ttttcattt tcccttcatt tgtggataac      840
gcacgatata acattctaca caccaacaag attctataaa aacgcaaagg ttgtctccat      900
agaatatcgt c                                                           911
```

<210> SEQ ID NO 93
<211> LENGTH: 863
<212> TYPE: DNA
<213> ORGANISM: Arabidopsis thaliana
<220> FEATURE:
<221> NAME/KEY: misc_feature -continued

```
<222> LOCATION: (1)..(863)
<223> OTHER INFORMATION: Ceres Promoter construct YP0003 as found in
      Promoter Report #123
<220> FEATURE:
<221> NAME/KEY: misc_feature
<222> LOCATION:
<223> OTHER INFORMATION: T1 Mature Plant Expression:  GFP expression
      observed in the Guard cells (Gc) of the flower, pedicel and
      silique, the Vasculature (Vs) of the mature embryo and the
      cotyledons
<220> FEATURE:
<221> NAME/KEY: misc_feature
<222> LOCATION:
<223> OTHER INFORMATION: T2 Seedling Expression:  GFP expression
      observed in the Root hair (Rh) of the Hypocotyl (Hy) and the root
      transition zone, the Epidermis (Ep) of the upper and lower Root
      (Rt), the Vascular (Vs) of the lower root

<400> SEQUENCE: 93
tggatctgct agatatatga gaacgaaaga accagaagct attagaggcg ggaggagata    60
tgtggggatg atttcagtgc aattccacga cgcaccattt ccactttcgt aacacctaaa   120
cgaccgcttc ggccgtataa aatcgcaaat gtttggtctc agtgtatttt tccaatttcc   180
aaatacatca attcaaatta tataatatct agtggcaatt ataagtatat catatatttt   240
caaaattaat taaaaagatt actaaattat gtttgactac aactattata atagttaaaa   300
acataaacaa aaacaaagaa actatttaa taaaaaaatc aagtaaacat taaaacataa   360
gcaaaaaata atgttaaaga aattattaat tattaattta ctaataatta atacctctat   420
aaattaattg ttagaggttt aacgtaattt ataaggaaaa ctaaagaaga ctttaaccca   480
taaagaaaaa aacaaagact gaattgaagg cccatattta gaagaagaga aagaagaccc   540
aaatatgata taaaatccag cccatttata tatttttatt ttgtttctgg aaggaaaata   600
agaaaatggc aaaaacgaaa taatctgaaa aagtaaggtc ttttaccaaa aaggatattt   660
tttttataaa cagagcataa agttttcact tttcttctgc tcctttctcg tctctgtctt   720
cttcgtcctc attcgttta aagcatcaaa atttcatcaa cccaaaatag attaaaaaaa   780
tctgtagctt tcgcatgtaa atctctcttt gaaggttcct aactcgttaa tcgtaactca   840
cagtgactcg ttcgagtcaa agt                                           863

<210> SEQ ID NO 94
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct YP0356 as found in
      Promoter Report #125
<220> FEATURE:
<221> NAME/KEY: misc_feature
<222> LOCATION:
<223> OTHER INFORMATION: T1 Mature Plant Expression:  GFP expression
      observed in the Pedicel (Pd) of the inflorescence meristem and the
      flower, the item below the inflorescence meristem, the Stigma (Sg)
      of the flower, the Petal (Pe) of the flower, the Style (Sy) and
      Carpel (Ca) of the silique, the Outer integument (Oi) of the
      ovule, Epidermis (Ep) of the stem
<220> FEATURE:
<221> NAME/KEY: misc_feature
<222> LOCATION:
<223> OTHER INFORMATION: T2 Seedling Expression:  GFP expression
      observed in the Epidermis (Ep) of the hypocotyl, the root
      transition zone, the cotyledon and the rosette, the Trichomes (Tc)
      of the rosette leave and trichome base cells

<400> SEQUENCE: 94
```

-continued

```
ttagttcatt gaaacgtcaa cttttttactt gcaaccactt tgtaggacca ttaactgcaa        60
aataagaatt ctctaagctt cacaaggggt tcgtttggtg ctataaaaac attgttttaa       120
gaactggttt actggttcta taaatctata aatccaaata tgaagtatgg caataataat       180
aacatgttag cacaaaaaat actcattaaa ttcctaccca aaaaaaatct ttatatgaaa       240
ctaaaactta tatacacaat aatagtgata caaagtaggt cttgatattc aactattcgg       300
gattttctgg tttcgagtaa ttcgtataaa aggtttaaga tctattatgt tcactgaaat       360
cttaactttg ttttgtttcc agttttaact agtagaaatt gaattttta  aaaattgtta       420 cttacaataa aatttgaatc aatatcctta atcaaaggat cttaagacta gcacaattaa       480
aacatataac gtagaatatc tgaaataact cgaaatatc  tgaactaagt tagtagtttt       540
aaaatataat cccggtttgg accgggcagt atgtacttca atacttgtgg gttttgacga       600
ttttggatcg gattgggcgg gccagccaga ttgatctatt acaaatttca cctgtcaacg       660
ctaactccga acttaatcaa agattttgag ctaaggaaaa ctaatcagtg atcacccaaa       720
gaaaacattc gtgaataatt gtttgctttc catggcagca aaacaaatag gacccaaata       780
ggaatgtcaa aaaaagaaa  gacacgaaac gaagtagtat aacgtaacac acaaaaataa       840
actagagata ttaaaaacac atgtccacac atggatacaa gagcatttaa ggagcagaag       900
gcacgtagtg gttagaaggt atgtgatata attaatcggc ccaaatagat tggtaagtag       960
tagccgtcta tatcatccat actcatcata acttcaacct                            1000
```

<210> SEQ ID NO 95
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct YP0374 as found in
      Promoter Report #126
<220> FEATURE:
<221> NAME/KEY: misc_feature
<222> LOCATION:
<223> OTHER INFORMATION: T1 Mature Plant Expression: GFP expression
      observed in the Chalaza (Ch), Funiculus (Fn) and Outer integument
      (Oi) of the ovule primordial, the Chalaza (Ch) in the
      pre-fertilized ovule, the Chalaza (Ch) and Micropyle (Mp) of the
      fertilized ovule and developing seed, the Chalaza (Ch) of the
      mature seed
<220> FEATURE:
<221> NAME/KEY: misc_feature
<222> LOCATION:
<223> OTHER INFORMATION: T2 Seedling Expression: GFP expression
      observed in the Epidermis (Ep) of the seedling root, the Vascular
      (Vs) of the Hypocotyl (Hy) and root transition zone, the Vascular
      (Vs) and Pericycle (Pr) of the root

<400> SEQUENCE: 95

```
aagacacccg taaatgttgt catgtagaag aaactagaaa cgttaaacgc atcaaatcaa        60
gaaattaaat tgaaggtaat ttttaacgcc gcctttcaaa tattcttcct aggagaggct       120
acaagacgcg tatttctttc gaattctcca aaccattacc attttgatat ataataccga       180
catgccgttg ataaagtttg tatgcaaatc gttcattggg tatgagcaaa tgccatccat       240
tggttcttgt aattaaatgg tccaaaaata gtttgttccc actactagtt actaatttgt       300
atcactctgc aaaataatca tgatataaac gtatgtgcta tttctaatta aaactcaaaa       360
gtaatcaatg tacaatgcag agatgaccat aaaagaacat taaaacacta cttccactaa       420
atctatgggg tgccttggca aggcaattga ataaggagaa tgcatcaaga tgatatagaa       480
```

-continued

```
aatgctattc agtttataac attaatgttt tggcggaaaa ttttctatat attagacctt      540
tctgtaaaaa aaaaaaaatg atgtagaaaa tgctattatg tttcaaaaat ttcgcactag      600
tataatacgg aacattgtag tttacactgc tcattaccat gaaaaccaag gcagtatata      660
ccaacattaa taaactaaat cgcgattcct agcaccccca ttaattaatt ttactattat      720
acattctctt tgcttctcga ataataaac ttctctatat cattctacat aataaataag       780
aaagaaatcg acaagatcta aatttagatc tattcagctt tttcgcctga gaagccaaaa     840
ttgtgaatag aagaaagcag tcgtcatctt cccacgtttg gacgaaataa aacataacaa     900
taataaaata ataaatcaaa tatataaatc cctaatttgt ctttattact ccacaatttt    960
ctatgtgtat atatataccc acctctctct tgtgtatttg                           1000
```

<210> SEQ ID NO 96
<211> LENGTH: 998
<212> TYPE: DNA
<213> ORGANISM: Arabidopsis thaliana
<220> FEATURE:
<221> NAME/KEY: misc_feature
<222> LOCATION: (1)..(998)
<223> OTHER INFORMATION: Ceres Promoter construct YP0377 as found in
      Promoter Report #127
<220> FEATURE:
<221> NAME/KEY: misc_feature
<222> LOCATION:
<223> OTHER INFORMATION: T1 Mature Plant Expression: GFP expression
      observed in the Petal (Pe), and Sepal (Se) of the flower, the
      flower bud
<220> FEATURE:
<221> NAME/KEY: misc_feature
<222> LOCATION:
<223> OTHER INFORMATION: T2 Seedling Expression: GFP expression
      observed in the Epidermis (Ep), Vasculature (Vs) and Guard cells
      (Gc) of the seedling apex, the Vasculature (Vs) of the Cotyledon
      (Co) petiole, Hypocotyl (Hy) and root, the Epidermis (Ep) of the
      root and Cotyledon (Co) petiole

<400> SEQUENCE: 96

```
tataaccat tcctataaca ccatatttaa acataacaat gaattgcttg gatttcaaac       60
tttattaaat ttggatttta aatttttaatt tgattgaatt atacccccctt aattggataa     120 attcaaatat gtcaactttt ttttgtaag atttttttat ggaaaaaaaa attgattatt       180
cactaaaaag atgacaggtt acttataatt taatatatgt aaaccctaaa aagaagaaaa     240
tagtttctgt tttcactta ggtcttatta tctaaacttc tttaagaaaa tcgcaataaa      300
ttggtttgag ttctaacttt aaacacatta atatttgtgt gctatttaaa aaataattta    360
caaaaaaaaa aacaaattga cagaaaatat caggttttgt aataagatat ttcctgataa    420
atatttaggg aatataacat atcaaaagat tcaaattctg aaaatcaaga atggtagaca    480
tgtgaaagtt gtcatcaata tggtccactt ttctttgctc tataacccaa aattgaccct    540
gacagtcaac ttgtacacgc ggccaaacct ttttataatc atgctattta tttccttcat   600
ttttattcta tttgctatct aactgatttt tcattaacat gataccagaa atgaatttag   660
atggattaat tcttttccat ccacgacatc tggaaacact tatctcctaa ttaaccttac   720
ttttttttta gtttgtgtgc tccttcataa aatctatatt gtttaaaaca aaggtcaata   780
aatataaata tggataagta taataaatct ttattggata tttctttttt taaaaagaa    840 ataaatcttt tttggatatt ttcgtggcag catcataatg agagactacg tcgaaaccgc    900
tggcaaccac ttttgccgcg tttaatttct ttctgaggct tatataaata gatcaaaggg   960
gaaagtgaga tataatacag acaaaacaag agaaaaga                            998
```

```
<210> SEQ ID NO 97
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter construct YP0380 as found in
      Promoter Report #128
<220> FEATURE:
<221> NAME/KEY: misc_feature
<222> LOCATION:
<223> OTHER INFORMATION: T1 Mature Plant Expression:  GFP expression
      observed in the Flower (Fl), of the inflorescence meristem, the
      Silique (Si), Stamen (St), Petal (Pe), and Sepal (Se) of the
      immature flower, the Silique (Si), Sepal (Se) and Receptacle (Re)
      of the mature flower, the Anther (An), the Valve margin (Vm) of
      the silique, the Funiculus (Fn) of the placenta and mature ovule,
      the ovule primordial and developing ovule, the Trichome (Tc),
      Epidermis (Ep), Nucleus (Nu) and Guard cells (Gc), the Epidermis
      (Ep), Mesophyll (Me) and Guard cells (Gc) of the abaxial leaf, the
      Mesophyll (Me) of the adaxial leaf, the Cortex (Cr), Epidermis
      (Ep) and Guard cells (Gc) of thestem
<220> FEATURE:
<221> NAME/KEY: misc_feature
<222> LOCATION:
<223> OTHER INFORMATION: T2 Seedling Expression:  GFP expression
      observed in the seedling, seedling apex, hypocotyl, cotyledon and
      root, the Rosette leaf (Rl), the Root (Rt),, the Mesophyll (Me),
      Epidermis (Ep) and Guard cells (Gc) of the leaf

<400> SEQUENCE: 97
acaagtacca ttcacttttt tactttttcaa tgtatacaat catcatgtga taaaaaaaaa      60
aatgtaacca atcaacacac tgagatacgg ccaaaaaatg gtaatacata aatgtttgta     120
ggttttgtaa tttaaatact ttagttaagt tatgatttta ttattttttgc ttatcactta     180 tacgaaatca tcaatctatt ggtatctctt aatcccgctt tttaatttcc accgcacacg     240
caaatcagca aatggttcca gccacgtgca tgtgaccaca tattgtggtc acagtactcg     300
tccttttttt ttcttttgta atcaataaat ttcaatccta aaacttcaca cattgagcac     360
gtcggcaacg ttagctccta aatcataacg agcaaaaaag ttcaaattag ggtatatgat     420
caattgatca tcactacatg tctacataat taatatgtat tcaaccggtc ggtttgttga     480
tactcatagt taagtatata tgtgctaatt agaattagga tgaatcagtt cttgcaaaca     540
actacggttt catataatat gggagtgtta tgtacaaaat gaaagaggat ggatcattct     600
gagatgttat gggctcccag tcaatcatgt tttgctcgca tatgctatct tttgagtctc     660
ttcctaaact catagaataa gcacgttggt tttttccacc gtcctcctcg tgaacaaaag     720
tacaattaca tttttagcaaa ttgaaaataa ccacgtggat ggaccatatt atatgtgatc     780
atattgcttg tcgtcttcgt tttcttttaa atgtttacac cactacttcc tgacacgtgt     840
ccctattcac atcatccttg ttatatcgtt ttacttataa aggatcacga acaccaaaac     900
atcaatgtgt acgtcttttg cataagaaga aacagagagc attatcaatt attaacaatt     960
acacaagaca gcgagattgt aaaagagtaa gagagagag                            999

<210> SEQ ID NO 98
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct YP0381 as found in
      Promoter Report #129
<220> FEATURE:
```

```
<221> NAME/KEY: misc_feature
<222> LOCATION:
<223> OTHER INFORMATION: T1 Mature Plant Expression: GFP expression
      observed in the Pedicel (Pd) of the inflorescence meristem, the
      lateral and medial Nectary (Ne) in the flower, the modified
      stomata opening in the lateral nectary
<220> FEATURE:
<221> NAME/KEY: misc_feature
<222> LOCATION:
<223> OTHER INFORMATION: T2 Seedling Expression: GFP expression
      observed in the Vasculature (Vs) of the Hypocotyl (Hy) and root

<400> SEQUENCE: 98
cacggtcaaa gtattgctaa catggtcatt acattgaaaa agaaaattaa ttgtctttac      60
tcatgtttat tctatacaaa taaaaatatt aaccaaccat cgcactaaca aaatagaaat     120
cttattctaa tcacttaatt gttgacaatt aaatcattga aaaatacact taaatgtcaa     180
atattcgttt tgcatacttt tcaatttaaa tacatttaaa gttcgacaag ttgcgtttac     240
tatcatagaa aactaaatct cctaccaaag cgaaatgaaa ctactaaagc gacaggcagg     300
ttacataacc taacaaatct ccacgtgtca attaccaaga gaaaaaaaga gaagataagc     360
ggaacacgtg gtagcacaaa aaagataatg tgatttaaat taaaaaacaa aaacaaagac     420
acgtgacgac ctgacgctgc aacatcccac cttacaacgt aataaccact gaacataaga     480
cacgtgtacg atcttgtctt tgttttctcg atgaaaacca cgtgggtgct caaagtcctt     540
gggtcagagt cttccatgat tccacgtgtc gttaatgcac caaacaaggg tactttcggt     600
attttggctt ccgcaaatta gacaaaacag ctttttgttt gattgatttt tctcttctct     660
ttttccatct aaattctctt tgggctctta atttcttttt gagtgttcgt tcgagatttg     720
tcggagattt tttcggtaaa tgttgaaatt ttgtgggatt ttttttttatt tctttattaa     780 actttttttt attgaattta taaaaaggga aggtcgtcat taatcgaaga aatggaatct     840
tccaaaattt gatattttgc tgttttcttg ggatttgaat tgctctttat catcaagaat     900
ctgttaaaat ttctaatcta aaatctaagt tgagaaaaag agagatctct aatttaaccg     960
gaattaatat tctccgaccg aagttattat gttgcaggct                         1000

<210> SEQ ID NO 99
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter construct YP0382 as found in
      Promoter Report #130
<220> FEATURE:
<221> NAME/KEY: misc_feature
<222> LOCATION:
<223> OTHER INFORMATION: T1 Mature Plant Expression: GFP expression
      observed in the Nectary (Ne) of the flower, the Vasculature (Vs)
      of the Sepal (Se)
<220> FEATURE:
<221> NAME/KEY: misc_feature
<222> LOCATION:
<223> OTHER INFORMATION: T2 Seedling Expression: GFP expression
      observed in the Vasculature (Vs) of the cotyledon and Rosette leaf
      (Rs), the Epidermis (Ep) and Root hair (Rh), of the root, the
      seedling root and root cap

<400> SEQUENCE: 99
gcaaacaata atttatcgta agagtttttt taaaattcgt tggaacttgg aagggatttt      60
aaatattatt ttgttttcct tcatttttat aggttaataa ttgtcaaaga tacaactcga     120
tggaccaaaa taaaataata aaattcgtcg aatttggtaa agcaaaacgg tcgaggatag     180
```

-continued

```
ctaatattta tgcgaaaccc gttgtcaaag cagatgttca gcgtcacgca catgccgcaa      240
aaagaatata catcaacctc ttttgaactt cacgccgttt tttaggccca caataatgct      300
acgtcgtctt ctgggttcac cctcgttttt tttttaaact tctaaccgat aaaataaatg      360
gtccactatt tcttttcttc tctgtgtatt gtcgtcagag atggtttaaa agttgaaccg      420
aactataacg attctcttaa aatctgaaaa ccaaactgac cgattttctt aactgaaaaa      480
aaaaaaaaaa aaactgaatt taggccaact tgttgtaata tcacaaagaa aattctacaa      540
tttaattcat ttaaaaataa agaaaaattt aggtaacaat ttaactaagt ggtctatcta      600
aatcttgcaa attctttgac tttgaccaaa cacaacttaa gttgacagcc gtctcctctc      660
tgttgtttcc gtgttattac cgaaatatca gaggaaagtc cactaaaccc caaatattaa      720
aaatagaaac attactttct ttacaaaagg aatctaaatt gatcccttc attcgtttca      780 ctcgtttcat atagttgtat gtatatatgc gtatgcatca aaaagtctct ttatatcctc      840
agagtcaccc aatcttatct ctctctcctt cgtcctcaag aaaagtaatt ctctgtttgt      900
gtagttttct ttaccggtga attttctctt cgttttgtgc ttcaaacgtc acccaaatca      960
ccaagatcga tcaaaatcga aacttaacgt ttcagaaga                            999
```

<210> SEQ ID NO 100
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct YP0388 as found in
      Promoter Report #131
<220> FEATURE:
<221> NAME/KEY: misc_feature
<222> LOCATION:
<223> OTHER INFORMATION: T1 Mature Plant Expression: GFP expression
      observed in the Guard cells (Gc) and Seed coat (Sc) of the
      inflorescence meristem, the Stamen (St) of the flower, the Seed
      coat (Sc) of the developing seed, the Chalaza (Ch) and Outer
      integument (Oi) of aborted ovules, the Guard cells (Gc) and
      Vasculature (Vs) of the leaf
<220> FEATURE:
<221> NAME/KEY: misc_feature
<222> LOCATION:
<223> OTHER INFORMATION: T2 Seedling Expression: GFP expression
      observed in the Epidermis (Ep) of the seedling root

<400> SEQUENCE: 100

```
agaagtattc acgcaccaag gttatatttg tagtgacata ttctacaatt atcacatttt       60
tctcttatgt ttcgtagtcg cagatggtca attttttcta taataatttg tccttgaaca      120
caccaaactt tagaaacgat gatatatacc gtattgtcac gctcacaatg aaacaaacgc      180
gatgaatcgt catccaccagc taaaagccta aaacaccatc ttagttttca ctcagataaa     240
aagattattt gtttccaacc tttctattga attgattagc agtgatgacg taattagtga      300
tagtttatag taaaacaaat ggaagtggta ataaatttac acaacaaaat atggtaagaa      360
tctataaaat aagaggttaa gagatctcat gttatattaa atgattgaaa gaaaacaaa      420 ctattggttg atttccatat gtaatagtaa gttgtgatga aagtgatgac gtaattagtt      480
gtatttatag taaaacaaat taaatggta aggtaaattt ccacaacaaa acttggtaaa       540
aatcttaaaa aaaaaaaag aggtttagag atcgcatgcg tgtcatcaaa ggttctttt        600 cactttaggt ctgagtagtg ttagactttg attggtgcac gtaagtgttt cgtatcgcga      660
tttaggagaa gtacgtttta cacgtggaca caatcaacgg tcaagatttc gtcgtccaga      720
```

-continued

```
tagaggagcg atacgtcacg ccattcaaca atctcctctt cttcattcct tcattttgat    780
tttgagtttt gatctgcccg ttcaaaagtc tcggtcatct gcccgtaaat ataaagatga    840
ttatatttat ttatatcttc tggtgaaaga agctaatata aagcttccat ggctaatctt    900
gtttaagctt ctcttcttct tctctctcct gtgtctcgtt cactagtttt ttttcggggg    960
agagtgatgg agtgtgtttg ttgaatagtt ttgacgatca                         1000
```

<210> SEQ ID NO 101
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct YP0396 as found in
      Promoter Report #133
<220> FEATURE:
<221> NAME/KEY: misc_feature
<222> LOCATION:
<223> OTHER INFORMATION: T1 Mature Plant Expression: GFP expression
      observed in the Style (Sy) of the Silique (Si), the Anther (An),
      Petal (Pe) and Sepal (Se) of the flower, the anther locules, the
      Outer integument (Oi) of the normal Ovule (Ov) and aborted ovule,
      the Hydathode (Hd) and Vasculature (Vs) of the leaf
<220> FEATURE:
<221> NAME/KEY: misc_feature
<222> LOCATION:
<223> OTHER INFORMATION: T2 Seedling Expression: GFP expression
      observed in the Epidermis (Ep) of the root

<400> SEQUENCE: 101

```
catagtaaaa gtgaatttaa tcatactaag taaaataaga taaacatgt tatttgaatt     60 tgaatatcgt gggatgcgta tttcggtatt tgattaaagg tctggaaacc ggagctccta    120
taacccgaat aaaaatgcat aacatgttct tccccaacga ggcgagcggg tcagggcact    180
agggtcattg caggcagctc ataaagtcat gatcatctag gagatcaaat tgtatgtcgg    240
ccttctcaaa attacctcta agaatctcaa acccaatcat agaacctcta aaaagacaaa    300
gtcgtcgctt tagaatgggt tcggttttg gaaccatatt tcacgtcaat ttaatgttta    360
gtataatttc tgaacaacag aattttggat ttatttgcac gtatacaaat atctaattaa    420
taaggacgac tcgtgactat ccttacatta agtttcactg tcgaaataac atagtacaat    480
acttgtcgtt aatttccacg tctcaagtct ataccgtcat ttacggagaa agaacatctc    540 tgttttcat ccaaactact attctcactt tgtctatata tttaaaatta agtaaaaaag    600
actcaatagt ccaataaaat gatgaccaaa tgagaagatg gttttgtgcc agattttagg    660
aaaagtgagt caaggtttca catctcaaat ttgactgcat aatcttcgcc attaacaacg    720
gcattatata tgtcaagcca attttccatg ttgcgtactt ttctattgag gtgaaaatat    780
gggtttgttg attaatcaaa gagtttgcct aactaatata actacgactt tttcagtgac    840
cattccatgt aaactctgct tagtgtttca tttgtcaaca atattgtcgt tactcattaa    900
atcaaggaaa aatatacaat tgtataattt tcttatattt taaaattaat tttgatgtat    960 tacccctta taaataggct atcgctacaa caccaataac                          1000
```

<210> SEQ ID NO 102
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)

```
<223> OTHER INFORMATION: Ceres Promoter construct PT0506 as found in
      Promoter Report #135
<220> FEATURE:
<221> NAME/KEY: misc_feature
<222> LOCATION:
<223> OTHER INFORMATION: T1 Mature Plant Expression: GFP expression
      observed in the Filament (Fi)

<400> SEQUENCE: 102
aggacttcca ctactctttc ccacacgctc cagaccactg tttgctttcc tctgattaac      60
caatctcaat taaactacta atttataatt caagataatt agataaccaa tcttaaaatt     120
tggaatcttc ttccctcact tgatattaca aaaaaaaaac tgatttatca tacggttaat     180
tcaagaaaac agcaaaaaaa ttgcactata atgcaaaaca tcaattaatt acattcgatt     240
aaaaaatcat cattgaatct aaaatggcct caaatctatt gagcatttgt catgtgccta     300
aaatggttca ggagttttac atctaatcac ataaaaagca aacaataacc aaaaaaattg     360
cattttagca aatcaaatac ttatatatat acgtatgatt aagcgtcatg actttaaaac     420
ctctgtaaaa ttttgattta tttttcgatg cttttatttt ttaaccaata gtaataaagt     480
ccaaatctta aatacgaaaa aatgtttctt tctaagcgac caacaaaatg gtccaaatca     540
cagaaaatgt tccataatcc aggcccatta agctaatcac caagtaatac attacacgtc     600
accaattaat acattacacg tacggccttc tctcttcacg agtaatatgc aaacaaacgt     660
acattagctg taatgtactc actcatgcaa cgtcttaacc tgccacgtat tacgtaatta     720
caccactcct tgttcctaac ctacgcattt cactttagcg catgttagtc aaaaaacaca     780
aacataaact acaaataaaa aaactcaaaa caaaacccaa tgaacgaacg gaccagcccc     840
gtctcgattg atggaacagt gacaacagtc ccgtttttctc gggcataacg gaaacggtaa     900
ccgtctctct gtttcatttg caacaacacc attttttataa ataaaaacac atttaaataa     960
aaaattatta aaacctcaaa aaatctctgt ttcttgttta                          1000

<210> SEQ ID NO 103
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct PT0511 as found in
      Promoter Report #136
<220> FEATURE:
<221> NAME/KEY: misc_feature
<222> LOCATION:
<223> OTHER INFORMATION: T1 Mature Plant Expression: GFP expression
      observed in the Anther (An) and Vascular (Vs) of the anther
<220> FEATURE:
<221> NAME/KEY: misc_feature
<222> LOCATION:
<223> OTHER INFORMATION: T2 Seedling Expression: GFP expression
      observed in the root and Vascular (Vs) of the Pedicle (Pd)

<400> SEQUENCE: 103
tttaattttg attctaaaga gttgtgacgg gtcatcacag attcttcgtt tttttataga      60
tagaaaagga ataacgttaa aagtatacaa attatatgca agagtcattc gaaagaatta     120
aataaagaga tgaactcaaa agtgatttta aattttaatg ataagaatat acatctcaca     180
gaaatctttt atttgacatg taaaatcttg ttttcaccta tcttttgtta gtaaacaaga     240
atatttaatt tgagcctcac ttggaacgtg ataataatat acatcttatc ataattgcat     300
attttgcgga tagttttttgc atggggagat taaaggctta ataaagcctt gaatttccga     360
```

-continued

```
ggggaggaat catgttttat acttgcaaac tatacaacca tctgcatcga taattggtgt      420
taatacatgc aaggattata cactaaaaca aatcatttat ttccttacaa aaagagagtc      480
gactgtgagt cacattctgt gacaaggaaa ggtcaagaac catcgctttt atcatcattc      540
tctttgctaa caacttacaa ccacacaaac gcaagagttc cattctcatg gagaagaaca      600
tattatgcaa aataatgtat gtcgatcgat agagaaaagg atccacaatt attgctccat      660
ctcaaaagct tctttagtac acgatacatg tatcatgtaa atagaaatat gaaagataca      720
atacacgacc cattctcata aagatagcaa catttcatgt tatgtaaaga gtcttcctta      780
ggacacatgc attaaaacta aggattacca acccacttac tcctcactcc aaccaaatat      840
caatcatcta ttttgggtcc ttcactcata agtcaactct catgccttcc tctataaata      900
ccgtacccta cgcatccctt agttctacat cacataaaaa caatcatagc aaaaacatat      960
atcctcaaat taattagatc tcatctatct ctaccctcga                          1000
```

<210> SEQ ID NO 104
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter construct YP0262 as found in
      Promoter Report #141
<220> FEATURE:
<221> NAME/KEY: misc_feature
<222> LOCATION:
<223> OTHER INFORMATION: T1 Mature Plant Expression: GFP expression
      observed in Guard Cells (GC) that define the stomate

<400> SEQUENCE: 104

```
tacttcgtaa ggttaatata tgatatagtg ggcctgacaa aaaatcatat gggcttgaca       60
aaatctatgt ttatatccag ttcggtccaa aattcgaaaa cataaacaat gtggaaagat      120
gtgttggcta atctgatacc atgtcaaaaa aacatagaag ttcttgtgag gtttcttgtt      180
tattcatgtg gaggcaattg cccttgtata caaggcttgt gaaagaagta aagaagataa      240
gtttaggaag aaggtggccc atgagggccc aatattcata tcattagtga aaagcatagg      300
aatttcaact tgtaatatta aaatcagtga taattgaata acattaatct ttttaagatt      360
tccaaattaa ttcaaatctt cattaagaaa taagatttag gaatactaaa aagctaaata      420
attatctaat tacttaaaat cagtaatgaa aattaatatt atactcccat agtatatttt      480
cttcactatg aatgaagttg agacttcaat tttgacaaat tcggtgttct ggaataacaa      540
aagaagtcaa agaaagaaaa ttagggagat agagtaaatt aaagttgaga caaatcagct      600
tcattttgtt tttcccaaat aataatatac agatagatct ttcggccccg gcgcattctc      660
tagatttgct catcaccacc tcgaaatttc tgctcgaagt tctccaaaac agttcattca      720
tctacattta ccagatcata ttcgtattca gtcgtctcta aattctcact aaatcaatcc      780
ttcctttgga taattccggt gtttgcgagg aatctgttga aatgattggt tagttcagtt      840
aaactctact tctaaaacta aatctgcatt caaatgtagt ctctagttct cgtacttgaa      900
gtagacttga ttcgatttga tttactgatt cgtggctttt gatttcacag gtcaattgga      960
aatctgagaa tccgtgtgac tattattgca gctggatcg                            999
```

<210> SEQ ID NO 105
<211> LENGTH: 999
<212> TYPE: DNA
<213> ORGANISM: Arabidopsis thaliana

```
<220> FEATURE:
<221> NAME/KEY: misc_feature
<222> LOCATION: (1)..(999)
<223> OTHER INFORMATION: Ceres Promoter construct YP0275 as found in
      Promoter Report #142
<220> FEATURE:
<221> NAME/KEY: misc_feature
<222> LOCATION:
<223> OTHER INFORMATION: T2 Seedling Expression:  GFP expression
      observed in the seedling root, Epidermis (Ep), Root cap (Rc) and
      Root hair (Rh) of the root

<400> SEQUENCE: 105
aaacattaat atgtagtaac tatgggcgta tgctttactt tttaaaatgg gcctatgcta      60
taattgaatg acaaggatta aacaactaat aaaattgtag atgggttaag atgacttatt     120
tttttactta ccaatttata aatgggcttc gatgtactga aatatatcgc gcctattaac     180
gaggccattc aacgaatgtt ttaagggccc tatttcgaca ttttaaagaa cacctaggtc     240
atcattccag aaatggatat tataggattt agataatttc ccacgtttgg tttatttatc     300 tatttttga cgttgaccaa cataatcgtg cccaaccgtt tcacgcaacg aatttatata     360
cgaaatatat atattttttca aattaagata ccacaatcaa aacagctgtt gattaacaaa     420 gagattttt ttttttggtt ttgagttaca ataacgttag aggataaggt ttcttgcaac     480
gattaggaaa tcgtataaaa taaaatatgt tataattaag tgttttattt tataatgagt     540
attaatataa ataaaacctg caaaaggata gggatattga ataataaaga gaaacgaaag     600
agcaatttta cttctttata attgaaatta tgtgaatgtt atgtttacaa tgaatgattc     660
atcgttctat atattgaagt aaagaatgag tttattgtgc ttgcataatg acgttaactt     720
cacatataca cttattacat aacatttatc acatgtgcgt cttttttttt ttttactttg     780
taaaatttcc tcacttttaa gacttttata acaattacta gtaaaataaa gttgcttggg     840
gctacaccct ttctccctcc aacaactcta tttatagata acattatatc aaaatcaaaa     900
catagtccct ttcttctata aaggttttt cacaaccaaa tttccattat aaatcaaaaa     960
ataaaaactt aattagtttt tacagaagaa aagaaaaca                           999

<210> SEQ ID NO 106
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct YP0337 as found in
      Promoter Report #143
<220> FEATURE:
<221> NAME/KEY: misc_feature
<222> LOCATION:
<223> OTHER INFORMATION: T2 Seedling Expression:  GFP expression
      observed in the Epidermis (Ep) and Root hair (Rh) of the seedling
      root

<400> SEQUENCE: 106
taattttttt attttggaa ctaacactta ttagtttagg tttccatcac ctatttaatt      60
cgtaattctt atacatgcat ataatagaga tacatatata caaatttatg atcatttttg     120
cacaacatgt gatctcattc attagtatgc attatgcgaa aacctcgacg cgcaaaagac     180
acgtaatagc taataatgtt actcattat aatgattgaa gcaagacgaa aacaacaaca     240
tatatatcaa attgtaaact agatatttct taaaagtgaa aaaaaacaaa gaaatataaa     300
ggacaatttt gagtcagtct cttaatatta aaacatatat acataaataa gcacaaacgt     360
```

```
ggttacctgt cttcatgcaa tgtggacttt agtttatcta atcaaaatca aaataaaagg      420
tgtaatagtt ctcgtcattt ttcaaatttt aaaaatcaga accaagtgat ttttgtttga      480
gtattgatcc attgtttaaa caatttaaca cagtatatac gtctcttgag atgttgacat      540
gatgataaaa tacgagatcg tctcttggtt ttcgaatttt gaactttaat agttttcttt      600
tttagggaaa ctttaatagt tgtttatcat aagattagtc acctaatggt tacgttgcag      660
taccgaacca attttttacc ctttttttcta aatgtggtcg tggcataatt tccaaaagag     720
atccaaaacc cggtttgctc aactgataag ccggtcggtt ctggtttgaa aaacaagaaa      780
taatctgaaa gtgtgaaaca gcaacgtgtc tcggtgtttc atgagccacc tgccacctca      840
ttcacgtcgg tcattttgtc gtttcacggt tcacgctcta gacacgtgct ctgtccccac      900
catgactttc gctgccgact cgcttcgctt tgcaaactca aacatgtgtg tatatgtaag      960
tttcatccta ataagcatct cttaccacat taattaaaaa                            1000
```

<210> SEQ ID NO 107
<211> LENGTH: 999
<212> TYPE: DNA
<213> ORGANISM: Arabidopsis thaliana
<220> FEATURE:
<221> NAME/KEY: misc_feature
<222> LOCATION: (1)..(999)
<223> OTHER INFORMATION: Ceres Promoter construct YP0384 as found in
      Promoter Report #144
<220> FEATURE:
<221> NAME/KEY: misc_feature
<222> LOCATION:
<223> OTHER INFORMATION: T2 Seedling Expression:  GFP expression
      observed in the seedling Root (Rt), the Epidermis (Ep) of the root

<400> SEQUENCE: 107

```
tttaaaaaat tggataaaac accgataaaa attcacattt gcaaatttta ttcagtcgga      60
atatatattt gaaacaagtt ttgaaatcca ttggacgatt aaaattcatt gttgagagga     120
taaatatgga tttgttcatc tgaaccatgt cgttgattag tgattgacta ccatgaaaaa     180
tatgttatga aaagtataac aacttttgat aaatcacatt tattaacaat aaatcaagac     240
aaaatatgtc aacaataata gtagtagaag atattaattc aaattcatcc gtaacaacaa     300
aaaatcatac cacaattaag tgtacagaaa aaccttttgg atatatttat tgtcgctttt     360
caatgatttt cgtgaaaagg atatatttgt gtaaaataag aaggatcttg acgggtgtaa      420
aaacatgcac aattcttaat ttagaccaat cagaagacaa cacgaacact tctttattat      480
aagctattaa acaaaatctt gcctattttg cttagaataa tatgaagagt gactcatcag      540
ggagtggaaa atatctcagg atttgctttt agctctaaca tgtcaaacta tctagatgcc      600
aacaacacaa agtgcaaatt cttttaatat gaaaacaaca ataatatttc taatagaaaa      660
ttaaaagggg aaataaaata tttttttaaa atatacaaaa gaagaaggaa tccatcatca      720
aagttttata aaattgtaat ataatacaaa cttgtttgct tccttgtctc tccctctgtc      780
tctctcatct ctcctatctt ctccatatat acttcatctt cacacccaaa actccacaca      840
aaatatctct ccctctatct gcaaatttttc caaagttgca tcctttcaat ttccactcct      900
ctctaatata attcacattt tcccactatt gctgattcat ttttttttgt gaattatttc      960
aaacccacat aaaaaaatct tgtttaaat ttaaaacca                              999
```

<210> SEQ ID NO 108
<211> LENGTH: 1000
<212> TYPE: DNA
<213> ORGANISM: Arabidopsis thaliana

```
<220> FEATURE:
<221> NAME/KEY: misc_feature
<222> LOCATION: (1)..(1000)
<223> OTHER INFORMATION: Ceres Promoter construct PT0535 as found in
      Promoter Report #145
<220> FEATURE:
<221> NAME/KEY: misc_feature
<222> LOCATION:
<223> OTHER INFORMATION: T1 Mature Plant Expression: GFP expression
      observed in the Stem (Sm) of the inflorescence meristem, the
      Pedicel (Pd), the Cortex (Cr) of the Pedicel (Pd), the Epidermis
      (Ep) and Guard cell (Gc) of the stem
<220> FEATURE:
<221> NAME/KEY: misc_feature
<222> LOCATION:
<223> OTHER INFORMATION: T2 Seedling Expression: GFP expression
      observed in the root transition zone of the Hypocotyle (Hy), the
      Epidermis (Ep) of the lower root

<400> SEQUENCE: 108
tatcattatt gtactgcctg tcaattttt gattgtatct tttattcagc agcatcacat     60
tctccttcag tgtccttctc ttcttttctt tttcttttct ttttctttcc tcattaaacc    120
catacaattc tacggtaaat attatggatt tgcatacaaa ctctctaatt gtttgtttgg    180
gtactataat atgggtccc tataatatgt gtagcttaac tttaagatag aactaagtca    240
acaagatccg gagacaccat gtcaaagttc tatgttctta tgattagatg aacaaagtta    300
tgatttattc aagattatca cgattcgaac tagttctaaa cttgtaaacg taaaataata    360
aataacgttt gcaactacaa cactgaacat aaattaatga agtttgcttg atgtgttggt    420
taaaatttgg aatgggacaa taaaagaag aagagaactg agagaagtgg tgggggaagt    480 gggaaccta acttccccac gtgacactaa cgagcaacgt taattgaata gtagtaggcc    540 cttttttgtag tacactcttt tatatatggt caccttttaa ttagtttgca aatcacatac    600
ttttaaaatc ataaaagcaa ttaacgttgc tcgttggtgt catatgcgat tgtagttagt    660
ataatcgatc ttaattaaaa caaagtccat attaaaatg accaaagtat gtaaaataa    720 aatgttgaat tagcatatgg tcactgatct tttctattt aagatttagt aaacctaaga    780
tgtatccgca agcctatagg gtttgatgtg gattactact agttactttt gtatgggctt    840
gaagaaactt cattgggcca caagaggga ggagtgagcg aagagcccaa attcaaacaa    900
aaggatatga gggttcaaat gttattataa aatatattgt ggccaatttg taaagaaact    960
tgataattac tttaaaagcc ccaacacaat tatctttaca                         1000

<210> SEQ ID NO 109
<211> LENGTH: 998
<212> TYPE: DNA
<213> ORGANISM: Arabidopsis thaliana
<220> FEATURE:
<221> NAME/KEY: misc_feature
<222> LOCATION: (1)..(998)
<223> OTHER INFORMATION: Ceres Promoter construct YP0385 as found in
      Promoter Report #146
<220> FEATURE:
<221> NAME/KEY: misc_feature
<222> LOCATION:
<223> OTHER INFORMATION: T1 Mature Plant Expression: GFP expression
      observed in the Abscission zone (Az) between the Pedicel (Pd) and
      Sepal (Se), the Abscission zone (Az) in the flower
<220> FEATURE:
<221> NAME/KEY: misc_feature
<222> LOCATION:
<223> OTHER INFORMATION: T2 Seedling Expression: GFP expression
      observed in the Epidermis (Ep) of the seedling root

<400> SEQUENCE: 109
```

```
actcaacaat aggacaagcc aaaaaaattc caattattgt gttactctat tcttctaaat      60
ttgaacacta atagactatg acatatgagt atataatgtg aagtcttaag atattttcat     120
gtgggagatg aataggccaa gttggagtct gcaaacaaga agctcttgag ccacgacata     180
agccaagttg atgaccgtaa ttaatgaaac taaatgtgtg tggttatata ttagggaccc     240
atggccatat acacaatttt tgtttctgtc gatagcatgc gtttatatat atttctaaaa     300
aaactaacat atttactgga tttgagttcg aatattgaca ctaatataaa ctacgtacca     360
aactacatat gttatctcat atttgattga tcgaagaatt ctgaactgtt ttagaaaatt     420
tcaatacact taacttcatc ttacaacggt aaaagaaatc accactagac aaacaatgcc     480
tcataatgtc tcgaaccctc aaactcaaga gtatacattt tactagatta gagaatttga     540
tatcctcaag ttgccaaaga attggaagct tttgttacca aacttagaaa cagaagaagc     600
cacaaaaaaa gacaagggag gttaaagatt gaagtgatgc atttgtctaa gtgtgaaagg     660
tctcaagtct caactttgaa ccataataac attactcaca ctccctttt tttttctttt      720 ttttcccaaa gtacccttt taattccctc tataacccac tcactccatt ccctctttct      780
gtcactgatt caacacgtgg ccacactgat gggatccacc tttcctctta cccacctccc     840
ggtttatata aaccctcac aacacttcat cgctctcaaa ccaactctct cttctctctt      900
ctctcctctc ttctcacaaga agaaaaaaaa cagagccttt acacatctca aaatcgaact     960
tactttaacc accaaatact gattgaacac acttgaaa                              998
```

<210> SEQ ID NO 110
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct YP0371 as found in
      Promoter Report #147
<220> FEATURE:
<221> NAME/KEY: misc_feature
<222> LOCATION:
<223> OTHER INFORMATION: T1 Mature Plant Expression:  GFP expression
      observed in the Guard cell (GC) of the flower
<220> FEATURE:
<221> NAME/KEY: misc_feature
<222> LOCATION:
<223> OTHER INFORMATION: T2 Seedling Expression:  GFP expression
      observed in the Epidermis (Ep) and Root hairs (Rh) of the seedling
      root

<400> SEQUENCE: 110

```
gatatatttg tttaataatg cctacgattc tgcgaagaca ggagaagcca taccttcaa       60 tctaagccgt caacttgttc ccttacgtgg gatcctatta tacaatccaa cggttctaaa     120
tgagccacgc cttccagatc taacacagtc atgccttcta cagtctgcac cccttttttt     180
tttagtgttt tatctcactt tttccttg tgtttaattt tgtgccaaca tctataactt      240 accctataa aaatattcaa ttatcacaga atacccacaa tcgaaaacaa aatttaccgg     300
aataatttaa ttaaagctgg actataatga caattccgaa actatcaagg ataaaattaa     360
agaaactaaa aaactaaagg gcattagagt aaagaagcgg caacatcaga attaaaaaac    420
tgccgaaaaa ccaacctagt agccgtttat atgacaacac gtacgcaaag tctcggtaat     480
gactcatcag ttttcatgtg caaacatatt accccatga aataaaaaag cagagaagcg      540
atcaaaaaaa tcttcattaa aagaacccta aatctctcat atccgccgcc gtctttgcct    600
cattttcaac accggtgatg acgtgtaaat agatctggtt ttcacggttc tcactactct     660
```

```
ctgtgatttt tcagactatt gaatcgttag gaccaaaaca agtacaaaga aactgcagaa      720
gaaaagattt gagagagata tcttacgaaa caaggtatat atttctcttg ttaaatcttt      780
gaaaatactt tcaaagtttc ggttggattc tcgaataagt taggttaaat agtcaatata      840
gaattataga taaatcgata ccttttgttt gttatcattc aatttttatt gttgttacga      900
ttagtaacaa cgtttagat cttgatctat atattaataa tactaatact ttgttttttt       960 ttgtttttt tttaatacat attttgcttt tggaagatca                            1000
```

<210> SEQ ID NO 111
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct PT0610 as found in
      Promoter Report #148
<220> FEATURE:
<221> NAME/KEY: misc_feature
<222> LOCATION:
<223> OTHER INFORMATION: T1 Mature Plant Expression: GFP expression
      observed in the flower, the silique, the pre-fertilized silique,
      the fertilized silique, the leaf, the stem

<400> SEQUENCE: 111

```
ttagtgaaat tatgacatta agtaaggttt tcttagttag ctaatgtatg gctattcaat       60
tgttatgtta ggctatttta gttagtatat gaatttaggc agtctatgca aatgatttcg      120
ttttcatttt ttcatatgta aacatcaaga tcaagtaacg ccattcgagt tgatattttt      180
tttttaaatt agtgtgtgta aattttggac cgcttatttg agtttgctaa tgaagttgca      240
tatatattac gttaaaccat aggcaaacta atttgaaaca tccgattcga tttcctgtaa      300
tttttcttgg ttaattgacc aaaatcaaga tcttcagaaa taaaataaaa gacgaaagaa      360
agctgtcgca aagcagattg tgttaaaaaa agtggattg ggctcaaacg caacttgtcc       420
agcccgtgac aattaccccta tacgcaagta agagtaacgt atcactggca aaagttggta     480
ttagttacga tatctttgtc atgggggcat gcatgggcat ggcttaagag ttaagcctta      540
agaagagtcc cacactcgtg actctcatga tcacttgttg tttcttacgg gcaaatacat      600
ttaactttat tcttcattta ttcacctata ttcttttgga taataacttt tctctatata      660
aaataacaaa catcgtacgt ttcatttatt tacaacaagc gatgagaatt aaaaggagac      720
cttaattgat gatactcttc ttttctctcg gttacaacgg gattattaca gataatgata      780
atctatatgg atgctgacgt ggaaaaacaa aatttggtga aacacgtcaa ttaagcacga      840
cttttccatg gctagtggct aagatcgttt catcacatgg ctatatcata taatacttgg      900
atgaattcaa aataaacgac tgagaaaatg tccacgtcac ggcgcaccgc tttggactta      960
agtctcctat aataaataca acaccaaaca ttgcattcca                           1000
```

<210> SEQ ID NO 112
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct PT0590 as found in
      Promoter Report #152
<220> FEATURE:
<221> NAME/KEY: misc_feature
<222> LOCATION:

```
<223> OTHER INFORMATION: T1 Mature Plant Expression: GFP expression
      observed in the flower bud, pedicel and silique
<220> FEATURE:
<221> NAME/KEY: misc_feature
<222> LOCATION:
<223> OTHER INFORMATION: T2 Seedling Expression: GFP expression
      observed in the seedling, the root transition zone, the rosette
      leaf, the lateral root, the root, lateral root initiation

<400> SEQUENCE: 112
attattcaat ttaataaaaa ttgagtcggc caatttaatg cgagacttct gtacaacgac      60
cctaaaagtg ggtttgataa atgaaacata ttgcaacaaa aaatactag taataatgat      120 aaaatagtaa catgtcatgg cgcattgaat atcctacgaa ggtttagtgt ttactttta      180 aaaatcctaa tatgatacta gtacatatag ctagcttgcc ttgcttatgc tattgcatag      240
tctgtattaa taaatgatgt tatacatttc gatagagtaa cattttggga acatgagtga      300
acgtgcttga atcttcgtgc ccttgacgtc agaagctagt aatttaaat actaattaac       360 attcatacaa attaacagat acaatgtact atatcataat tcgtttccgt aacacaacgc      420
aacaatttga agtagatgt actttagtac ttagttagtg tgcaccaaaa aaaaaagatg       480
tagttagtta gtaaggggtt aaatgttttta atttattaag aaaacttaaa ttcattaaat    540
gttagaaaaa gtctaattag tttatattcg aacactgtgc tcaaaattaa aaagtcaact     600
attttagact atagagttta ttaattaata ataaattcga taaatcaccg tattattttc    660
ttcaacgaca agtagccgtg aagacacggg agcgaagaga gataaacaga agatgaagaa    720
gaagatcaat gtcataatct tcagggagat aaatccgtaa tctttattaa tcaaggttaa    780
tccttttttt tttcttcatc ttaattcttt gcgtcttcct tttctattta tcacgagatc     840
tgtctttctt tttcctcttc tttctctctc ttctctctga agacagtact tgtttctgtc     900
cggcgttaaa agcttcggtg gtggtctctt gacttctctg agaagaagaa aaggaagctg     960
agtctcattt tagattcagc tcacgaggaa gtgacgacga                          1000

<210> SEQ ID NO 113
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct PT0629 as found in
      Promoter Report #154
<220> FEATURE:
<221> NAME/KEY: misc_feature
<222> LOCATION:
<223> OTHER INFORMATION: T1 Mature Plant Expression: GFP expression
      observed in the Guard cells (Gc) of the pedicel and leaf,, the
      Root apical meristem (RAM) and Suspensor (Su) of the late torpedo
      stage in the ovule, the Suspensor (Su) of the ovule
<220> FEATURE:
<221> NAME/KEY: misc_feature
<222> LOCATION:
<223> OTHER INFORMATION: T2 Seedling Expression: GFP expression
      observed in the Guard cells (Gc) and Vasculature (Vs) of the
      seedling, the Vasculature (Vs) of the cotyledon and root, the
      root transition zone, the Root Cap (Rc) of the root tip

<400> SEQUENCE: 113
tttaagcata tcaaatgtga aaattggtct taggttatga tgtatatcct tatatagtaa     60
aagtatatta gtctaaaaat ttagatttaa aaagtgaact aaaatttaaa agcaagctga    120
attacataaa tcaagtgaca attgtaattt ggtgtgacat ttgtaagttc ataatggtac    180
gtgtcacgct atgttaatta agtttgaaat atgagatgta agaaaaaagt gatcaaaaat    240
```

```
taagttctttt tggagcgtta agtccaaagg tcaattagag cgcaatatca gtccagaaaa      300
gtggatgaaa aatgtccatc catccatcga gaaatatgct taaagtaaac gcttactttt      360
caagcgacct tcacggtatt gccgcagtca aaaatacgcg gcgactgttt ggttggtata      420
gtgacgaccc actctcacgc ggattcatta atttcctatc acaaataaga aaaagaaac       480 gtgaaattaa tttgttaagt aacaaaaaca aagaaaaag gaaactgaca agaaacgcta       540
aagtggttcc ttccttgtac tcaaaaaaac gttaatttac agctcagaat aagttttcct      600
gtttaccgta atttcgaccc aatattttta cgaataacaa tttagtccaa aacctctttg      660
atatattgca atttaatacc ctaattaagt cttcttatct agtaatttgg ttttatttcc      720
atgacctaca atataagata atagtcatta gtgctagata taaagactga attagggtat      780
ataagatata tggaatgcta agattacaaa gagatagaga atcaaaaaaa ggaaagaatt      840
aaggggcaaa tatgaaataa ttaaaaacaa gggagccaaa ggaacaatgt aagaaaagca      900
ataaaattaa aaacaaaacc ctcaaaaaga agaaagcgga gactcgttag cttttcctg      960 cctcctataa attgaacgcg acttgcagaa cctttcctca                           1000
```

<210> SEQ ID NO 114
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct PT0642 as found in
      Promoter Report #160
<220> FEATURE:
<221> NAME/KEY: misc_feature
<222> LOCATION:
<223> OTHER INFORMATION: T1 Mature Plant Expression: GFP expression
      observed in the Endosperm (En) of the ovules at torpedo stage of
      the embryo and in mature ovules
<220> FEATURE:
<221> NAME/KEY: misc_feature
<222> LOCATION:
<223> OTHER INFORMATION: T2 Seedling Expression: GFP expression
      observed in the Epidermis (Ep) of the seedling, hypocotyl,
      cotyledon and Root (Rt)

<400> SEQUENCE: 114

```
ttgaacatcc ttaatttgaa ccataaaaaa tatgacatta actatctgat taattttcac       60
ttaagggatg gttagttaag ttacattgga ttaaaaatgg tattagtaga ccaattagaa      120
catgtatgcc atttttttgtt tacaaaaacc ttttttaagtg gtatttataa gacttgctca    180
atttcattca aaagaacatg aaatggatgg actagtttta atggcaataa cccacacaat     240
tactcatatt tggttcaaca aacttctatt tcggttcact tattaatttt ccatctatat     300
atgaatcata taatatgatt aatttacaca agttcacacg gccacgtaaa atgtaactgt     360
cttcaagttg tgcacataaa gagggtagtt tcgaagataa cgggtcaacg aaagggtaaa    420
agagtaaatt gcatagaacg cggccaaatt aaaagccccc aattgggata aaagtcatcg    480
ccgtctctta ggtgtcaaat ctcaactgtc taaaaacatt aaaagcttcg ttggggtagt   540
tgcatcttcc ctctctaata caaaacttat tttatccagt tttagtttcg attttttcatt  600 tgttaacatg ttttcatttt tcttttaatg ttaatagcct tttatttgg aaaatgaaaa    660 caatttcaca atttaattct aaattaccat ttctaaaaaa tagaaataat ataaataata    720
atattgaata atacatggac taaaaaatta tagtactgtc ctaaacaaaa ttgcttgact    780
agattgaaca gaaaatgttt ttgatgtctt actagtttga acaatttatt tgctaacatt   840
```

```
attctctttg tatatttctt aaaaacccat attttttcct taaatatttc ccatttcccc      900
taactacatt caatagctaa gtctctctct ccctctctct ttctctctca ctcaaaaatt      960
tcccattaaa ttctcaaatt ttctccaact ttttaggcca                           1000
```

<210> SEQ ID NO 115
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct PT0623 as found in
      Promoter Report #161
<220> FEATURE:
<221> NAME/KEY: misc_feature
<222> LOCATION:
<223> OTHER INFORMATION: T1 Mature Plant Expression: GFP expression
      observed in the inflorescence meristem, the inflorescence
      meristem, the flower, the stamen, the pre-fertilized silique, the
      unfertilized stigma, the pre-fertilized ovule, the fertilized
      ovule, the developing seed, the developing seed, the early mature
      seed coat (Sc), the seed coat, the embryo, the Leaf, the stem
<220> FEATURE:
<221> NAME/KEY: misc_feature
<222> LOCATION:
<223> OTHER INFORMATION: T2 Seedling Expression: GFP expression
      observed in the leaf, the leaf, the seedling, the root tip

<400> SEQUENCE: 115

```
aaagttattg acattttgaa aggaccgtaa atattaccaa aaaactgacg gagttaggat        60
cggccacgta gaaagggaca aagagagaac agtcacggac tcggccagac taagtatggg       120
cctgtctgaa tccaaactca gctaagttcc aaaagcataa agagagatgt gtaatgaaat       180
gaacgtattc tagaaacgaa agcaatgtta tgctttgttt ttgagccaca tgttttttggg      240 agatggagag aatcttttttt acgtttttaa cctaacccac ttggcacttg gccaaaaaag      300
tgagaagaaa ctgtggcgaa tgagtaggcc acgccatgga ctttgttcct tgtccttcaa       360
aagttaaatt tatgttatgc gtggggacaa tctaagcaac gtggttcctt taaatatcgc       420
agcttcctct tttacacttt tggagcctac gtgttttgtt ttggaccggc caaatacacg       480
agtcagtcag tttagaaata atttggatgt ccaaaaatct tggagatcca aataaaataa       540
ttagcatgtt ttagttcata agaatatgaa atgtagataa actgtctata ttaatttttc       600
catagaattg gctttttatc gaggtgatgt acttaatgac tttgttgatt actactcgta       660
taacaataaa gaatatgata ctatgtgaga cttataatga atttggtgtg tgttaattaa       720
tccagttgaa acagtttaat aacaaatcag aataaaaatt gtagtaagaa aatttgaacg       780
ctgatccttc aacctagata gtgaaccttt caaatactat atgattcacg tgtaatgttt       840
ttgaccgttg gttatttttg tgtgaactat attaacttat caatatcgaa aggctaaata       900
agtaaataac taaagaaag ttcaggaaac aactcgacct aatgacctat catttctgat        960
cacccgtcct ataaatacat acgtaagatc attcgttact                           1000
```

<210> SEQ ID NO 116
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct PT0613 as found in
      Promoter Report #163
<220> FEATURE:

```
<221> NAME/KEY: misc_feature
<222> LOCATION:
<223> OTHER INFORMATION: T1 Mature Plant Expression: GFP expression
      observed in the silique, the pollen, the embryo, the embryo, the
      stem,
<220> FEATURE:
<221> NAME/KEY: misc_feature
<222> LOCATION:
<223> OTHER INFORMATION: T2 Seedling Expression: GFP expression
      observed in the Epidermis (Ep), Root hair (Rh), Cortex (Cr) and
      Hypocotyl (Hy) in the root tip

<400> SEQUENCE: 116
ttaatactaa cattgtagaa agccacaaaa aagaaattga aatgtgagta gatgctgagt      60
cagaggtttg gtcaatacac aacagctaat tgagataata ttatacacgt cacgatgact    120
tgttttttct cctcccaact tgttaatttc tttattctta aaattaaacc atcgcaaaaa    180
cagaagaaca cagctgtttt tctcgactcc caatttctat tttgctgcta aggacatttc    240
atttcattat ttcccaattc aggactcctt agattttcct aaatttgttt tcctaacttg    300
ctctctctca ttctaacatt ttctcatttt tttagattat cttgtacttt ttagtagatt    360
attttatcag gttttacaaa catacattga cattctaaaa agggcttcta aaaattcagt    420
gtggaatgct gatatactaa aaaaaggtca tgcaaaatta tctacgattt atctaaaatt    480
agataatttg ccatatataa ctattaacta ataatcgatc ctttgatttt ttgtttagat    540
aaaacgaaac agctatatct tttttttttg ttatcggatt ttaatcgaat aaaagctgaa    600
aaataacagt tatatcttct tcttttttaa ctaatgaaac agttatatct taaacaaaca    660
acagaaacag taaaatatta atgcaaatcc gcgtcaagag ataaatttta acaaactaat    720
aacaattgag ataagattag cgcaaaagaa actctaattt tagagcgtgt aaacacaaac    780
acgtcttgaa agtaaacgtg aattacacgc ttctaaaacg agcgtgagtt ttggttataa    840
cgaagatacg gtgaagtgtg acacctttct acgttaattt cagtttgagg acacaactca    900
agttatgttt gatatctaag gacttgcact gtctccaaat ctgcaggaag gacttttga     960 ttggatcaat ataaatacca tctccattct cgtctccttc                         1000

<210> SEQ ID NO 117
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter construct YP0093 as found in
      Promoter Report #261
<220> FEATURE:
<221> NAME/KEY: misc_feature
<222> LOCATION:
<223> OTHER INFORMATION: T1 Mature Plant Expression: GFP expression
      observed in Chalaza (Ch), Funiculus (Fn), Petals (Pe), Receptacle
      (Rc), Sepals (Se), Silique (Si), Stamen (St), Placenta (Pl),
      Micropyle (Mp).
<220> FEATURE:
<221> NAME/KEY: misc_feature
<222> LOCATION:
<223> OTHER INFORMATION: T2 Seedling Expression: GFP expression
      observed in Cotyledons (Co), Hypocotyl (Hy), Root Hair (Rh),
      Vascular bundle (Vb), Vascular (Vs)

<400> SEQUENCE: 117
atgatgaaca ttctacatat ataattatta tgtttaagca cttagacagc ataaattctt      60
tctaattata taaatctaac cttgttacat tgtacatcta taaattactt gaagaaataa    120
cgagttctat ttcttttttaa aaattaaaaa tactatacca tatctcagtg attaagttga    180
```

-continued

```
accaaaaggt acggaggaga aacaagcatt tgattcttcc ttattttatt ttattcatct      240
ctcactaatg atggtggaga aaaaaagaaa atacctaaca aacaaatata tattgtcata      300
caaaaatatt tctatatttt tagttaatta gtttatattc ctcacttttc agggcttata      360
taagaaagtg agcaaacaca aatcaaaatg cagcagcaaa tactatcatc acccatctcc      420
ttagttctat tttataattc ctcttctttt tgttcatagc tttgtaatta tagtcttatt      480
tctctttaag gctcaataag aggaggtact attactacac ttctctctac ttttacttgt      540
attttagcat taaaatccta aaatccgttt taaattcaaa aataaactta gagatgttta      600
atctcgattc ggtttttcgg ctttaggaga ataattatat gaaattagta tggatatctt      660
tactagtttc cattcaaatg attctgattt caatctaata ctctcactct ttaattaaac      720
tatatgtagt gtaatttcac actgttaaat ttctaccatg tcatgtatat tagagttgca      780
tagaaaattg taaaacatcc atttgaattc gaatgaaaca aaatgttta aaataaaatt       840 ttggttttta aagaaaaat ctaaaactga attatatcgt ttaaccaagt tgtaaaagtc       900
ataaaacgta gtatcttgta aatcgctctt ccacggtcca aatagacttc tagtaataaa      960
caagtaaaac taattttggt ttcttactaa ttttcacaga                           1000
```

What is claimed is:

1. An isolated vector construct comprising:
   a. a first nucleic acid molecule capable of modulating transcription, wherein said first nucleic acid molecule has the sequence set forth in SEQ ID NO: 111; and
   b. a second nucleic acid operably linked to said first nucleic acid molecule,
      wherein said first and second nucleic acid molecules are heterologous to each other.

2. A host cell comprising:
   a. a first nucleic acid molecule capable of modulating transcription, wherein said first nucleic acid molecule has the sequence set forth in SEQ ID NO: 111; and
   b. a second nucleic acid molecule operably linked to said first nucleic acid molecule, wherein said first and second nucleic acid molecules are heterologous to each other.

3. A plant comprising
   a. a first nucleic acid molecule capable of modulating transcription wherein said first nucleic acid molecule has the sequence set forth in SEQ ID NO: 111; and
   b. a second nucleic acid molecule operably linked to said first nucleic acid molecule, wherein said first and second nucleic acid molecules are heterologous to each other.

4. A progeny of the plant according to claim 3, said progeny comprising:
   a. a first nucleic acid molecule capable of modulating transcription wherein said first nucleic acid molecule has the sequence set forth in SEQ ID NO: 111; and
   b. a second nucleic acid molecule operably linked to said first nucleic acid molecule,
      wherein said first and second nucleic acid molecules are heterologous to each other.

5. Seed of the plant according to claim 3, said seed comprising:
   a. a first nucleic acid molecule capable of modulating transcription wherein said first nucleic acid molecule has the sequence set forth in SEQ ID NO: 111; and
   b. a second nucleic acid molecule operably linked to said first nucleic acid molecule, wherein said first and second nucleic acid molecules are heterologous to each other.

6. A cell from the plant according to claim 3, said cell comprising:
   a. a first nucleic acid molecule capable of modulating transcription wherein said first nucleic acid molecule has the sequence set forth in SEQ ID NO: 111; and
   b. a second nucleic acid molecule operably linked to said first nucleic acid molecule,
      wherein said first and second nucleic acid molecules are heterologous to each other.

* * * * *